US012503444B2

(12) United States Patent
Lou et al.

(10) Patent No.: US 12,503,444 B2
(45) Date of Patent: Dec. 23, 2025

(54) COMPOUND CONTAINING BENZENE RING AND APPLICATION THEREOF

(71) Applicant: WUHAN LL SCIENCE AND TECHNOLOGY DEVELOPMENT CO., LTD., Hubei (CN)

(72) Inventors: Jun Lou, Hubei (CN); Yongkai Chen, Hubei (CN); Yihan Zhang, Hubei (CN); Xiaodan Guo, Hubei (CN); Lina Qian, Hubei (CN); Li Liu, Hubei (CN); Wei Peng, Hubei (CN); Fei Rong, Hubei (CN); Chaodong Wang, Hubei (CN)

(73) Assignee: WUHAN LL SCIENCE AND TECHNOLOGY DEVELOPMENT CO., LTD., Hubei (CN)

( * ) Notice: Subject to any disclaimer, the term of this patent is extended or adjusted under 35 U.S.C. 154(b) by 703 days.

(21) Appl. No.: 17/756,705

(22) PCT Filed: Nov. 27, 2020

(86) PCT No.: PCT/CN2020/132418
§ 371 (c)(1),
(2) Date: May 31, 2022

(87) PCT Pub. No.: WO2021/104486
PCT Pub. Date: Jun. 3, 2021

(65) Prior Publication Data

US 2023/0183182 A1 Jun. 15, 2023

(30) Foreign Application Priority Data

Nov. 29, 2019 (CN) ........................ 201911203127.2

(51) Int. Cl.

| | |
|---|---|
| ***C07D 231/56*** | (2006.01) |
| ***C07D 209/44*** | (2006.01) |
| ***C07D 235/24*** | (2006.01) |
| ***C07D 401/06*** | (2006.01) |
| ***C07D 405/04*** | (2006.01) |
| ***C07D 405/06*** | (2006.01) |

(52) U.S. Cl.
CPC ......... *C07D 231/56* (2013.01); *C07D 209/44* (2013.01); *C07D 235/24* (2013.01); *C07D 401/06* (2013.01); *C07D 405/04* (2013.01); *C07D 405/06* (2013.01)

(58) Field of Classification Search
CPC .................................................... C07D 231/56
See application file for complete search history.

(56) References Cited

U.S. PATENT DOCUMENTS

| | | | |
|---|---|---|---|
| 8,008,313 | B2 | 8/2011 | Broka et al. |
| 8,524,725 | B2 | 9/2013 | Broka et al. |
| 9,657,033 | B2 | 5/2017 | Aicher et al. |
| 10,377,768 | B2 | 8/2019 | Aicher et al. |
| 2007/0037974 | A1 | 2/2007 | Brotherton-Pleiss et al. |
| 2007/0049609 | A1 | 3/2007 | Broka et al. |
| 2010/0144758 | A1 | 6/2010 | Dillon et al. |
| 2010/0324070 | A1 | 12/2010 | Dillon et al. |
| 2012/0122859 | A1 | 5/2012 | Broka et al. |
| 2013/0225570 | A1 | 8/2013 | Broka et al. |
| 2013/0267529 | A1 | 10/2013 | Dillon et al. |
| 2015/0111877 | A1 | 4/2015 | Aicher et al. |
| 2016/0271131 | A1 | 9/2016 | Broka et al. |
| 2016/0362395 | A1 | 12/2016 | Dillon et al. |
| 2017/0313722 | A1 | 11/2017 | Aicher et al. |
| 2018/0311240 | A1 | 11/2018 | Broka et al. |
| 2018/0338980 | A1 | 11/2018 | Werner et al. |
| 2019/0119210 | A1 | 4/2019 | Werner et al. |
| 2022/0324807 | A1 | 10/2022 | Werner et al. |

FOREIGN PATENT DOCUMENTS

| | | | |
|---|---|---|---|
| CN | 104812393 | A | 7/2015 |
| CN | 107848974 | A | 3/2018 |
| CN | 109415321 | A | 3/2019 |
| JP | 2009504705 | A | 2/2009 |
| JP | 2012532832 | A | 12/2012 |
| JP | 2019519484 | A | 7/2019 |
| WO | 2010066629 | A2 | 6/2010 |

(Continued)

OTHER PUBLICATIONS

Sorrell, Thomas N.; "Organic Chemistry", University Science Books, 1999, pp. 1-982.

(Continued)

*Primary Examiner* — Golam M Shameem
(74) *Attorney, Agent, or Firm* — NKL Law; Allen Xue

(57) ABSTRACT

A compound containing a benzene ring as shown in formula I, a pharmaceutically acceptable salt thereof, a stereoisomer thereof, a tautomer thereof, an isotopic compound thereof, a crystal form thereof, a nitrogen oxide thereof, and a solvate thereof or a solvate of the pharmaceutically acceptable salt thereof are provided. The compound has high P2X4 antagonistic activity, good selectivity, low toxicity and good metabolic stability.

I

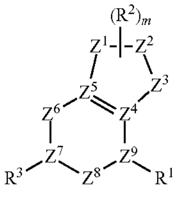

10 Claims, No Drawings

(56) References Cited

FOREIGN PATENT DOCUMENTS

| | | | |
|---|---|---|---|
| WO | 2010149634 | A1 | 12/2010 |
| WO | 2013169704 | A2 | 11/2013 |
| WO | 2016198374 | A1 | 12/2016 |
| WO | 2017191000 | A1 | 11/2017 |

OTHER PUBLICATIONS

Smith, Michael B. et al.; "March's Advanced Organic Chemistry", John Wiley&Sons, New York; 2007, 1-2374.

Berge, Stephen M. et al.; "Pharmaceutical Salts", Journal of Pharmaceutical Science; Jan. 1977, vol. 66, No. 1; pp. 1-19.

Stahl, P. Heinrich et al.; "Handbook of Pharmaceutical Salts: Properties,Selection, and Use"; International Union of Pure and Applied Chemistry, Wiley-VCH; 2002; pp. 1-376.

Deady, Leslie W.; "Synthetic Communications: An International Journal for Rapid Communication of Synthetic Organic Chemistry", Ring Nitrogen Oxidation of Amino Substituted Nitrogen Heterocycles With m-Chmroperbenzoic Acid; Advanced Organic Chemistry, Wiley Interscience; vol. 7, No. 8; 1977, pp. 509-514.

IUP AC-IUB Commission on Biochemical Nomenclature Abbreviated Nomenclature of Synthetic Polypeptides (Polymerized Amino Acids) Revised Recommendations ( 1971); Biochemistry, 1972, vol. 11, No. 5; pp. 942-944.

COMPOUND CONTAINING BENZENE RING AND APPLICATION THEREOF

CROSS-REFERENCE TO RELATED APPLICATIONS

This application is a U.S. national stage entry of PCT International Application No. PCT/CN2020/132418. filed on November 27, 2020. which claims priority to Chinese Patent Application No. 201911203127.2, filed on Nov. 29, 2019, the content of which is incorporated herein by reference in its entirety.

TECHNICAL FIELD

The present invention relates to a compound containing a benzene ring and use thereof.

BACKGROUND

ATP receptors are classified into two main families, the P2Y-purinoreceptors and P2X-purinoreceptors, based on molecular structure, transduction mechanism and pharmacological properties. The P2X-purinoreceptors are a family of ATP-gated cation channels, and several subtypes have been cloned, including six homomeric receptors (P2X1, P2X2, P2X3, P2X4, P2X5 and P2X7) and three heteromeric receptors (P2X2/3, P2X4/6 and P2X1/5). The P2X4 receptor is the only subtype in the current P2X family whose crystal structure was resolved with the resolution as high as 2.8 Å, and P2X4 was found to be the most permeable P2X subtype to $Ca^{2+}$.

Cough is the main symptom of respiratory diseases, and is observed in 70%-80% of patients in outpatients of the respiratory department. With increasing prevalence of COPD, IPF, etc., there's also an increasing demand for treatment of cough as it is the main symptom of most respiratory tract diseases. Cough, as a defensive nervous reflex of the body, is beneficial to the removal of respiratory secretions and harmful factors. However, frequent and violent cough will seriously affect the work, life and social activities of patients.

The indications of the currently researched drugs related to the P2X4 target are mostly neuropathic pain or inflammation, and no information is researched on the drugs related to cough indications. In addition, no drugs are available on the market that inhibit the pathway of P2X4 for the treatment of numerous conditions, including chronic cough. Therefore, the development of new compounds capable of inhibiting the activity of P2X4 is of great significance for treating diseases.

SUMMARY

The technical problem to be solved in the disclosure is that the existing P2X4 antagonist has a monotonous structure, accordingly, the disclosure provides a compound containing a benzene ring and use thereof. The compound possesses high P2X4 antagonistic activity, relatively good selectivity, low toxicity and good metabolic stability.

The disclosure provides a compound containing a benzene ring represented by formula I, or a pharmaceutically acceptable salt thereof, a stereoisomer thereof, a tautomer thereof or an isotopic compound thereof;

I

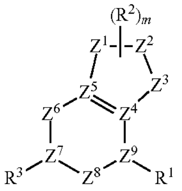

wherein,

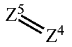

is a single bond or a double bond;

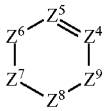

is a benzene ring, a "6 membered heteroalkyl ring containing 1, 2 or 3 heteroatoms selected from one or more of N, O and S", a "6 membered heteroalkenyl ring containing 1, 2 or 3 heteroatoms selected from one or more of N, O and S", or a "6 membered heteroaryl ring containing 1, 2 or 3 heteroatoms selected from one or more of N, O and S";

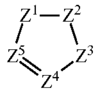

is a "5 membered heteroaryl ring containing 1, 2 or 3 heteroatoms selected from one or more of N, O and S" or a "5 membered heteroalkenyl ring containing 1, 2 or 3 heteroatoms selected from one or more of N, O and S";

$R^1$ is

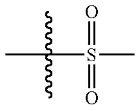

,

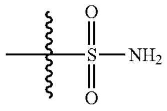

or

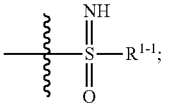

$R^{1-1}$ is halogen, hydroxyl, amino, —$NHR^{1-1-4}$, —$N(R^{1-1-5})(R^{1-1-6})$, $C_1$-$C_6$ alkyl, $C_3$-$C_6$ cycloalkyl, $C_1$-$C_6$alkyl substituted with one or more $R^{1-1-1}$, $C_3$-$C_6$ cycloalkyl substituted with one or more $R^{1-1-2}$, or "4-7 membered heterocycloalkyl containing 1, 2 or 3 heteroatoms selected from one or more of N, O and S" substituted with one or more $R^{1-1-3}$;

$R^{1-1-1}$, $R^{1-1-2}$, $R^{1-1-3}$, $R^{1-1-4}$, $R^{1-1-5}$ and $R^{1-1-6}$ are independently halogen, hydroxyl, $C_1$-$C_6$ alkyl, $C_3$-$C_6$ cycloalkyl, $C_1$-$C_6$ alkoxy or "4-7 membered heterocycloalkyl containing 1, 2 or 3 heteroatoms selected from one or more of N, O and S";

$R^3$ is

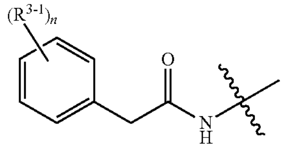

or

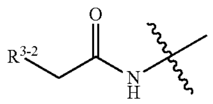

;

n is 0, 1, 2 or 3;

$R^{3-1}$ is independently halogen, hydroxyl, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, "5-6 membered heterocycloalkyl containing 1, 2 or 3 heteroatoms selected from one or more of N, O and S" substituted with one or more $R^{3-2-2}$, or "5-6 membered heteroaryl containing 1, 2 or 3 heteroatoms selected from one or more of N, O and S" substituted with one or more $R^{3-1-3}$;

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or $C_1$-$C_6$ alkoxy substituted with $C_1$-$C_6$ alkoxy;

m is 0, 1 or 2;

$R^2$ is oxo, halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-7}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl, phenyl substituted with one or more $R^{2-4}$, "5-6 membered heteroaryl containing 1, 2 or 3 heteroatoms selected from one or more of N, O and S", "5-6 membered heteroaryl containing 1, 2 or 3 heteroatoms selected from one or more of N, O and S" substituted with one or more $R^{2-5}$, or —(C=O)—$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, "4-6 membered heterocycloalkyl containing 1, 2 or 3 heteroatoms selected from one or more of N, O and S", "4-6 membered heterocycloalkyl containing 1, 2 or 3 heteroatoms selected from one or more of N, O and S" substituted with one or more $R^{2-1-7}$, phenyl, phenyl substituted with one or more $R^{2-1-1}$, "5-6 membered heteroaryl containing 1, 2 or 3 heteroatoms selected from one or more of N, O and S", "5-6 membered heteroaryl containing 1, 2 or 3 heteroatoms selected from one or more of N, O and S" substituted with one or more $R^{2-1-6}$, —$OR^{2-1-2}$, —$N(R^{2-1-3})(R^{2-1-4})$, or —$S(=O)_2$—$R^{2-1-5}$;

$R^{2-1-1}$, $R^{2-1-6}$, $R^{2-1-7}$ and $R^{2-1-8}$ are independently oxo, hydroxyl, amino, carboxyl, halogen, —CN, $C_1$-$C_6$ alkyl, $C_1$-$C_6$ alkyl substituted with one or more halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ and $R^{2-6}$ are independently $C_1$-$C_6$ alkyl;

$R^{2-4}$ and $R^{2-5}$ are independently halogen, hydroxyl, —$N(R^{2-4-1})(R^{2-4-2})$ or $C_1$-$C_6$ alkoxy; $R^{2-4-1}$ and $R^{2-4-2}$ are independently hydrogen, $C_1$-$C_6$ alkyl or $C_3$-$C_6$ cycloalkyl;

$R^{2-7}$ is independently halogen;

$R^{2-2}$ is $C_1$-$C_6$ alkyl, $C_3$-$C_6$ cycloalkyl, phenyl or phenyl substituted with one or more $R^{2-2-1}$, $R^{2-2-1}$ is independently halogen.

In a certain embodiment, in the above-mentioned compound containing a benzene ring represented by formula I, or a pharmaceutically acceptable salt thereof, a stereoisomer thereof, a tautomer thereof or an isotopic compound thereof, some groups have the following definitions, and the definitions of the non-mentioned groups are as described in any of the above embodiments (hereinafter, referred to as "in a certain embodiment" in this paragraph):

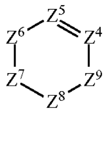

is a benzene ring or a "6 membered heteroaryl ring containing 1, 2 or 3 heteroatoms selected from N".

In a certain embodiment.

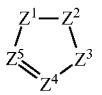

is a "5 membered heteroaryl ring containing 1 or 2 heteroatoms selected from one or more of N, O and S" or a "5 membered heteroalkenyl ring containing 1 or 2 heteroatoms selected from one or more of N, O and S".

In a certain embodiment:

I

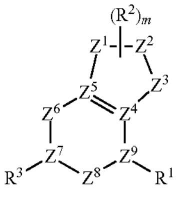

is

I-1

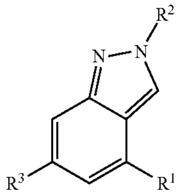

or

I-2

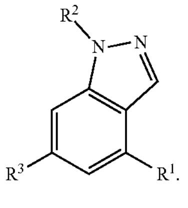

.

In a certain embodiment: $R^1$ is

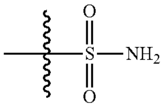

or

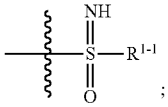

;

$R^{1-1}$ is $C_1$-$C_6$ alkyl.

In a certain embodiment:

$R^1$ is

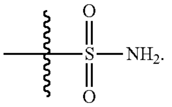 [SMILES: *S(N)(=O)=O]

In a certain embodiment: $R^3$ is

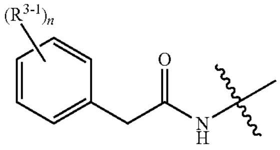

or

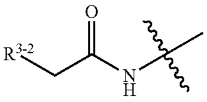

;

n is 1;

$R^{3-1}$ is halogen, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, or "5-6 membered heteroaryl containing 1, 2 or 3 heteroatoms selected from one or more of N, O and S" substituted with one or more $R^{3-2-3}$;

$R^{3-2-1}$ and $R^{3-2-3}$ are independently halogen or hydroxyl.

In a certain embodiment:

$R^3$ is

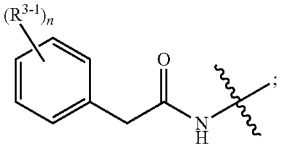

n is 1;

$R^{3-1}$ is halogen.

In a certain embodiment:

m is 0 or 1.

In a certain embodiment:

$R^2$ is halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-4}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl substituted with one or more $R^{2-4}$, or —(C═O)—$R^{2-2}$;

$R^{2-1}$ is independently hydroxyl, halogen, $C_3$-$C_6$ cycloalkyl, "4-6 membered heterocycloalkyl containing 1, 2 or 3 heteroatoms selected from one or more of N, O and S", phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —$N(R^{2-1-3})(R^{2-1-4})$, or —$S(═O)_2$—$R^{2-1-5}$;

$R^{2-1-1}$ and $R^{2-1-6}$ are independently hydroxyl, amino, halogen, —CN, $C_1$-$C_6$ alkyl, $C_1$-$C_6$ alkyl substituted with one or more halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ and $R^{2-6}$ are independently $C_1$-$C_6$ alkyl;

$R^{2-4}$ is independently halogen;

$R^{2-7}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment:

$R^2$ is $C_1$-$C_{10}$ alkyl, $C_1$-$C_{10}$ alkyl substituted with one $R^{2-1}$, or $C_3$-$C_6$ cycloalkyl;

$R^{2-1}$ is independently halogen, $C_3$-$C_6$ cycloalkyl, phenyl substituted with one or more $R^{2-1-1}$, or —$OR^{2-1-2}$; $R^{2-1-1}$ is independently amino, halogen, —CN, $C_1$-$C_6$ alkyl, $C_1$-$C_6$ alkyl substituted with one or more halogen, or —$OR^{2-1-1-1}$; $R^{2-1-1-1}$ is independently $C_1$-$C_6$ alkyl; $R^{2-1-2}$ is $C_1$-$C_6$ alkyl.

In a certain embodiment:

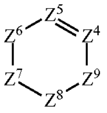

is a benzene ring or a "6 membered heteroaryl ring containing 1, 2 or 3 heteroatoms selected from N";

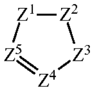

is a "5 membered heteroaryl ring containing 1 or 2 heteroatoms selected from one or more of N, O and S" or a "5 membered heteroalkenyl ring containing 1 or 2 heteroatoms selected from one or more of N, O and S";

$R^1$ is

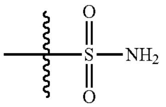

or

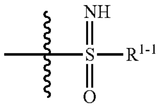

;

$R^{1-1}$ is $C_1$-$C_6$ alkyl;

$R^3$ is

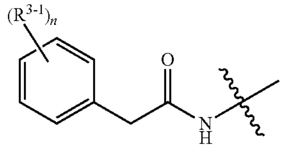 or 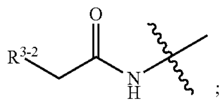 ;

n is 1;

$R^{3-1}$ is halogen, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, or "5-6 membered heteroaryl containing 1, 2 or 3 heteroatoms selected from one or more of N, O and S" substituted with one or more $R^{3-2-3}$;

$R^{3-2-1}$ and $R^{3-2-3}$ are independently halogen or hydroxyl;

m is 0, 1 or 2;

$R^2$ is halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-7}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl substituted with one or more $R^{2-4}$, or —(C═O)—$R^{2-2}$;

$R^{2-1}$ is independently hydroxyl, halogen, $C_3$-$C_6$ cycloalkyl, "4-6 membered heterocycloalkyl containing 1, 2 or 3 heteroatoms selected from one or more of N, O and S", phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —$N(R^{2-1-3})(R^{2-1-4})$, or —$S(═O)_2$—$R^{2-1-5}$;

$R^{2-1-1}$ and $R^{2-1-6}$ are independently hydroxyl, amino, halogen, —CN, $C_1$-$C_6$ alkyl, $C_1$-$C_6$ alkyl substituted with one or more halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ and $R^{2-6}$ are independently $C_1$-$C_6$ alkyl;

$R^{2-4}$ is independently halogen;

$R^{2-7}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment:

I-1

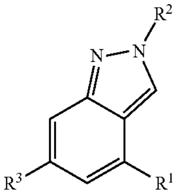 or

-continued

I-2

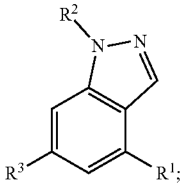

$R^1$ is

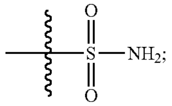 [SMILES: *S(N)(=O)=O]

$R^3$ is

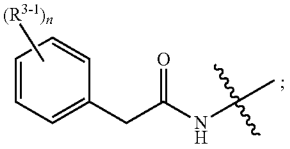

n is 1;

$R^{3-1}$ is halogen, m is 0 or 1;

$R^2$ is $C_1$-$C_{10}$ alkyl, $C_1$-$C_{10}$ alkyl substituted with one $R^{2-1}$, or $C_3$-$C_6$ cycloalkyl;

$R^{2-1}$ is independently halogen, $C_3$-$C_6$ cycloalkyl, phenyl substituted with one or more $R^{2-1-1}$, or —$OR^{2-1-2}$; $R^{2-1-1}$ is independently amino, halogen, —CN, $C_1$-$C_6$ alkyl, $C_1$-$C_6$ alkyl substituted with one or more halogen or —$OR^{2-1-1-1}$; $R^{2-1-1-1}$ is independently $C_1$-$C_6$ alkyl; $R^{2-1-2}$ is $C_1$-$C_6$ alkyl.

In a certain embodiment: $Z^4$ is carbon.

In a certain embodiment: $Z^5$ is carbon.

In a certain embodiment:

When

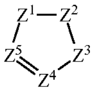

is a "5 membered heteroaryl ring containing 1 or 2 heteroatoms selected from one or more of N, O and S", the "5 membered heteroaryl ring containing 1 or 2 heteroatoms selected from one or more of N, O and S" is, for example, a "5 membered heteroaryl ring containing 1 or 2 heteroatoms selected from N", and for another example, a pyrrole ring, a pyrazole ring or an imidazole ring.

In a certain embodiment:

When

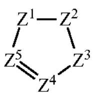

is a "5 membered heteroalkenyl ring containing 1, 2 or 3 heteroatoms selected from one or more of N, O and S", the "5 membered heteroalkenyl ring containing 1, 2 or 3 heteroatoms selected from one or more of N, O and S" is, for example, a "5 membered heteroalkenyl ring containing 1 or 2 heteroatoms selected from N", and for another example, a 2,5-dihydropyrrole ring.

In a certain embodiment:

I

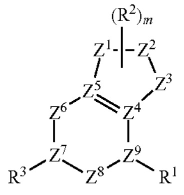

is, for example,

I-1

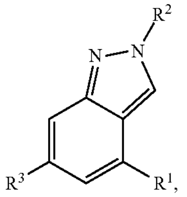

I-2

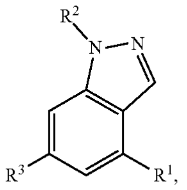

I-3

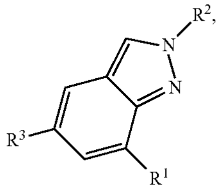

I-4

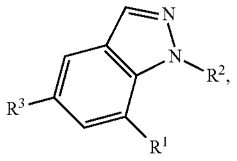

I-5

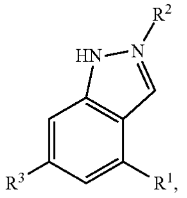

I-6

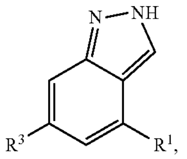

-continued

I-7

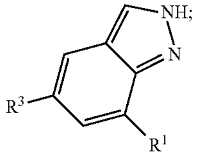

I-8

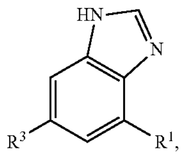

I-9

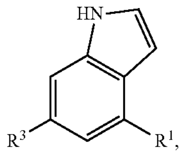

I-10

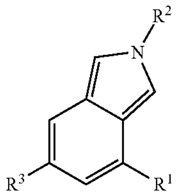

or

I-11

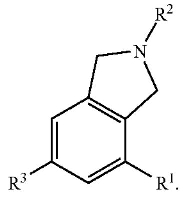

In a certain embodiment:

When $R^{1-1}$ is $C_1$-$C_6$ alkyl, the $C_1$-$C_6$ alkyl is, for example, $C_1$-$C_4$ alkyl, and for another example, methyl, ethyl, n-propyl, isopropyl, n-butyl, isobutyl, sec-butyl or tert-butyl.

In a certain embodiment:

When n is 1 or 2, $R^{3-1}$ can be independently located in the ortho-, meta- or para-position relative to

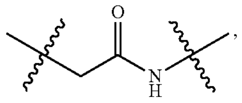 [SMILES: *CC(=O)N*]

and can also be independently located in the ortho-position relative to

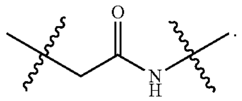 [SMILES: *CC(=O)N*]

In a certain embodiment:

When $R^{3-1}$ is halogen, the halogen is, for example, fluorine, chlorine, bromine or iodine, and for another example, chlorine.

In a certain embodiment:

When $R^{3-1}$ is $C_1$-$C_6$ alkyl, the $C_1$-$C_6$ alkyl is, for example, $C_1$-$C_4$ alkyl, and for another example, methyl, ethyl, n-propyl, isopropyl, n-butyl, isobutyl, sec-butyl or tert-butyl.

In a certain embodiment:

When $R^{3-1}$ is $C_1$-$C_6$ alkoxy, the $C_1$-$C_6$ alkoxy is, for example, $C_1$-$C_4$ alkoxy, and for another example, methoxy, ethoxy, n-propoxy, isopropoxy, n-butoxy, isobutoxy, sec-butoxy or tert-butoxy.

In a certain embodiment:

When $R^{3-1}$ is $C_1$-$C_6$ alkoxy substituted with $C_1$-$C_6$ alkoxy, the $C_1$-$C_6$ alkoxy is, for example, $C_1$-$C_4$ alkoxy, and for another example, methoxy, ethoxy, n-propoxy, isopropoxy, n-butoxy, isobutoxy, sec-butoxy or tert-butoxy.

In a certain embodiment:

When $R^{3-1}$ is $C_1$-$C_6$ alkoxy substituted with $C_1$-$C_6$ alkoxy, the $C_1$-$C_6$ alkoxy substituted with $C_1$-$C_6$ alkoxy is, for example,

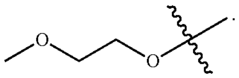 [SMILES: *OCCOC]

In a certain embodiment:

When $R^{3-2}$ is $C_3$-$C_6$ cycloalkyl substituted with one or more $R^{3-2-1}$, the $C_3$-$C_6$ cycloalkyl is, for example, cyclopropyl, cyclobutyl, cyclopentyl or cyclohexyl.

When $R^{3-2}$ is $C_3$-$C_6$ cycloalkyl substituted with one or more $R^{3-2-1}$, the $C_3$-$C_6$ cycloalkyl substituted with one $R^{3-2-1}$ is, for example,

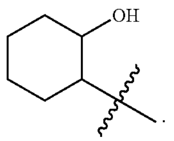 [SMILES: *C1CCCCC1O]

In a certain embodiment:

When $R^{3-2-3}$ is halogen, the halogen is, for example, fluorine, chlorine, bromine or iodine, and for another example, chlorine.

In a certain embodiment:

When $R^{3-2}$ is "5-6 membered heteroaryl containing 1, 2 or 3 heteroatoms selected from one or more of N, O and S" substituted with one or more $R^{3-2-3}$, the "5-6 membered heteroaryl containing 1, 2 or 3 heteroatoms selected from one or more of N, O and S" is, for example, "5-6 membered heteroaryl containing 1 or 2 heteroatoms selected from N", and for another example, pyridinyl.

In a certain embodiment:

When $R^{3-2}$ is "5-6 membered heteroaryl containing 1, 2 or 3 heteroatoms selected from one or more of N, O and S" substituted with one or more $R^{3-2-3}$, the "5-6 membered heteroaryl containing 1, 2 or 3 heteroatoms selected from one or more of N, O and S" substituted with one $R^{3-2-3}$ is, for example,

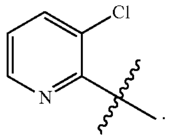 [SMILES: *c1ncccc1Cl]

In a certain embodiment:

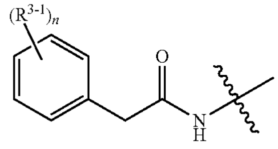

can be

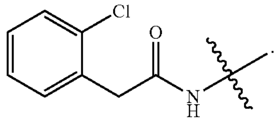 [SMILES: *NC(=O)Cc1ccccc1Cl]

In a certain embodiment:

When $R^2$ is halogen, the halogen is, for example, fluorine, chlorine, bromine or iodine, and for another example, chlorine.

In a certain embodiment:

When $R^2$ is $C_1$-$C_{10}$ alkyl, the $C_1$-$C_{10}$ alkyl is, for example, $C_1$-$C_6$ alkyl, for another example, $C_1$-$C_5$ alkyl, and for still another example, methyl, ethyl, n-propyl, isopropyl, n-butyl, isobutyl, sec-butyl, tert-butyl, n-pentyl, isopentyl or

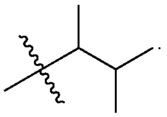

In a certain embodiment:

When $R^2$ is $C_1$-$C_{10}$ alkyl substituted with one or more $R^{2-1}$, the $C_1$-$C_{10}$ alkyl is, for example, $C_1$-$C_6$ alkyl, for another example, $C_1$-$C_4$ alkyl, for still another example, methyl, ethyl, n-propyl, isopropyl, n-butyl, isobutyl, sec-butyl or tert-butyl, and for yet another example, methyl, ethyl, isopropyl or isobutyl.

In a certain embodiment:

When $R^{2-1}$ is halogen, the halogen is, for example, fluorine, chlorine, bromine or iodine, and for another example, fluorine.

In a certain embodiment:

When $R^{2-1}$ is $C_3$-$C_6$ cycloalkyl, the $C_3$-$C_6$ cycloalkyl is, for example, cyclopropyl, cyclobutyl, cyclopentyl or cyclohexyl.

In a certain embodiment:

When $R^{2-1}$ is "4-6 membered heterocycloalkyl containing 1, 2 or 3 heteroatoms selected from one or more of N, O and S", the "4-6 membered heterocycloalkyl containing 1, 2 or 3 heteroatoms selected from one or more of N, O and S" is, for example, "5 or 6 membered heterocycloalkyl containing 1 or 2 heteroatoms selected from one or more of N, O and S", for another example, tetrahydrofuranyl, morpholinyl or tetrahydropyranyl, and for still another example, tetrahydrofuranyl-2-yl, tetrahydrofuranyl-3-yl, morpholin-1-yl or tetrahydropyranyl-4-yl.

In a certain embodiment:

When $R^{2-1}$ is "5-6 membered heteroaryl containing 1, 2 or 3 heteroatoms selected from one or more of N, O and S" substituted with one or more $R^{2-1}$, the "5-6 membered heteroaryl containing 1, 2 or 3 heteroatoms selected from one or more of N, O and S" is, for example, 5-6 membered heteroaryl containing 1 heteroatom selected from one or more of N, O and S, for another example, pyridinyl, and for still another example, pyridin-3-yl or pyridin-4-yl.

In a certain embodiment:

$R^{2-1-1}$ can be independently located in the ortho-, meta- or para-position relative to phenyl.

In a certain embodiment:

$R^{2-1-1}$ can be independently located in the ortho-, meta- or para-position relative to 6 membered heteroaryl.

In a certain embodiment:

$R^{2-1-6}$ can be independently located in the ortho- or meta-position relative to 5 membered heteroaryl.

In a certain embodiment:

When $R^{2-1-1}$ is halogen, the halogen is, for example, fluorine, chlorine, bromine or iodine, and for another example, fluorine or chlorine.

In a certain embodiment:

When $R^{2-1-1}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-1}$ is $C_1$-$C_6$ alkyl substituted with one or more halogen, the halogen is, for example, fluorine, chlorine, bromine or iodine, and for another example, fluorine.

In a certain embodiment:

When $R^{2-1-1}$ is $C_1$-$C_6$ alkyl substituted with one or more halogen, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-1}$ is $C_1$-$C_6$ alkyl substituted with one or more halogen, the $C_1$-$C_6$ alkyl substituted with a plurality of halogen is, for example, trifluoromethyl.

In a certain embodiment:

When $R^{2-1-6}$ is halogen, the halogen is, for example, fluorine, chlorine, bromine or iodine, and for another example, fluorine.

In a certain embodiment:

When $R^{2-1-1-1}$, $R^{2-1-1-2}$ and $R^{2-1-1-3}$ are $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl.

In a certain embodiment:

When $R^{2-1-2}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-2}$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-1-3}$ and $R^{2-1-4}$ are $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-3}$ and $R^{2-1-4}$ are $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-1-5}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-5}$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^2$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-3}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl, ethyl or isopropyl.

In a certain embodiment:

When $R^2$ is $C_3$-$C_6$ cycloalkyl substituted with one or more $R^{2-3}$, the $C_3$-$C_6$ cycloalkyl is, for example, cyclopropyl, cyclobutyl, cyclopentyl or cyclohexyl, and for another example, cyclopropyl.

In a certain embodiment:

When $R^2$ is $C_2$-$C_6$ alkenyl, the $C_2$-$C_6$ alkenyl is, for example, $C_2$-$C_4$ alkenyl, and for another example, vinyl or propenyl.

In a certain embodiment:

When $R^2$ is $C_2$-$C_6$ alkenyl substituted with one or more $R^{2-7}$, the $C_2$-$C_6$ alkenyl is, for example, $C_2$-$C_4$ alkenyl, and for another example, vinyl or propenyl.

In a certain embodiment:

When $R^{2-7}$ is halogen, the halogen is, for example, fluorine, chlorine, bromine or iodine, and for another example, fluorine.

In a certain embodiment:

When $R^2$ is "4 membered heterocycloalkyl containing 1 heteroatom selected from one of N, O and S", the "4 membered heterocycloalkyl containing 1 heteroatom selected from one of N, O and S" is, for example, oxetanyl, and for another example, oxetan-3-yl.

In a certain embodiment:

When $R^2$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl.

In a certain embodiment:

When $R^2$ is "4-6 membered heterocycloalkyl containing 1, 2 or 3 heteroatoms selected from one or more of N, O and S" substituted with one or more $R^{2-6}$, the "4-6 membered heterocycloalkyl containing 1, 2 or 3 heteroatoms selected from one or more of N, O and S" is, for example, "4-6 membered heterocycloalkyl containing 1 heteroatom selected from one of N, O and S", for another example, oxetanyl, and for still another example, oxetan-3-yl.

In a certain embodiment:

$R^{2-4}$ can be independently located in the ortho-, meta- or para-position relative to phenyl.

In a certain embodiment:

When $R^{2-4}$ is halogen, the halogen is, for example, fluorine, chlorine, bromine or iodine, and for another example, fluorine or chlorine.

In a certain embodiment:

When $R^{2-2}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, isopropyl.

In a certain embodiment:

When $R^{2-2}$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

$R^{2-2-1}$ can be independently located in the ortho-, meta- or para-position relative to phenyl.

In a certain embodiment:

When $R^{2-2-1}$ is halogen, the halogen is, for example, fluorine, chlorine, bromine or iodine, and for another example, fluorine.

In a certain embodiment:

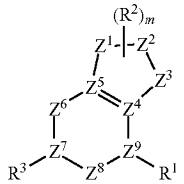

I wherein,

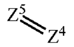

is a single bond or a double bond;

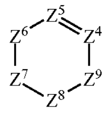

is a benzene ring, a "6 membered heteroalkyl ring containing 1, 2 or 3 heteroatoms selected from one or more of N, O and S", a "6 membered heteroalkenyl ring containing 1, 2 or 3 heteroatoms selected from one or more of N, O and S", or a "6 membered heteroaryl ring containing 1, 2 or 3 heteroatoms selected from one or more of N, O and S";

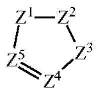

is a "5 membered heteroaryl ring containing 1, 2 or 3 heteroatoms selected from one or more of N, O and S" or a "5 membered heteroalkenyl ring containing 1, 2 or 3 heteroatoms selected from one or more of N, O and S";

$R^1$ is

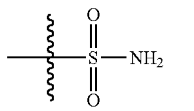 or 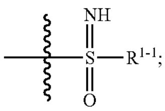;

$R^{1-1}$ is halogen, hydroxyl, amino, —$NHR^{1-1-4}$, —$N(R^{1-1-5})(R^{1-1-6})$, $C_1$-$C_6$ alkyl, $C_3$-$C_6$ cycloalkyl, $C_1$-$C_6$ alkyl substituted with one or more $R^{1-1-1}$, $C_3$-$C_6$ cycloalkyl substituted with one or more $R^{1-1-2}$, or "4-7 membered heterocycloalkyl containing 1, 2 or 3 heteroatoms selected from one or more of N, O and S" substituted with one or more $R^{1-1-3}$;

$R^{1-1-1}$, $R^{1-1-2}$, $R^{1-1-3}$, $R^{1-1-4}$, $R^{1-1-5}$ and $R^{1-1-6}$ are independently halogen, hydroxyl, $C_1$-$C_6$ alkyl, $C_3$-$C_6$ cycloalkyl, $C_1$-$C_6$ alkoxy or "4-7 membered heterocycloalkyl containing 1, 2 or 3 heteroatoms selected from one or more of N, O and S";

$R^3$ is H or H;

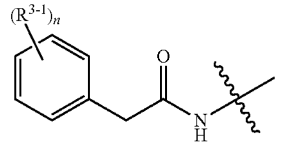 or 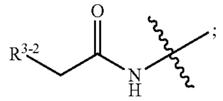;

n is 0, 1, 2 or 3;

$R^{3-1}$ is independently halogen, hydroxyl, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, "5-6 membered heterocycloalkyl containing 1, 2 or 3 heteroatoms selected from one or more of N, O and S" substituted with one or more $R^{3-2-2}$, or "5-6 membered heteroaryl containing 1, 2 or 3 heteroatoms selected from one or more of N, O and S" substituted with one or more $R^{3-2-3}$;

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or $C_1$-$C_6$ alkoxy substituted with $C_1$-$C_6$ alkoxy;

m is 0 or 1;

$R^2$ is oxo, cyano, $C_1$-$C_{10}$ alkyl, $C_1$-$C_{10}$ alkyl substituted with one or more $R^{2-1}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", phenyl, phenyl substituted with one or more $R^{2-4}$, "5-6 membered heteroaryl containing 1, 2 or 3 heteroatoms selected from one or more of N, O and S", "5-6 membered heteroaryl containing 1, 2 or 3 heteroatoms selected from one or more of N, O and S" substituted with one or more $R^{2-5}$, or —(C═O)—$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, "4-6 membered heterocycloalkyl containing 1, 2 or 3 heteroatoms selected from one or more of N, O and S", "4-6 membered heterocycloalkyl containing 1, 2 or 3 heteroatoms selected from one or more of N, O and S" substituted with one or more $R^{2-1-7}$, phenyl, phenyl substituted with one or more $R^{2-1-1}$, "5-6 membered heteroaryl containing 1, 2 or 3 heteroatoms selected from one or more of N, O and S", "5-6 membered heteroaryl containing 1, 2 or 3 heteroatoms selected from one or more of N, O and S" substituted with one or more $R^{2-1-6}$, —$OR^{2-1-2}$, —$N(R^{2-1-3}(R^{2-1-4})$, or —$S(═O)_2$—$R^{2-1-5}$;

$R^{2-1-1}$, $R^{2-1-6}$, $R^{2-1-7}$ and $R^{2-1-8}$ are independently oxo, hydroxyl, amino, carboxyl, halogen, —CN, $C_1$-$C_6$ alkyl, $C_1$-$C_6$ alkyl substituted with one or more halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ and $R^{2-5}$ are independently halogen, hydroxyl, —N($R^{2-4-1}$))($R^{2-4-2}$) or $C_1$-$C_6$ alkoxy; $R^{2-4-1}$ and $R^{2-4-2}$ are independently hydrogen, $C_1$-$C_6$ alkyl or $C_3$-$C_6$ cycloalkyl;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment, in the above-mentioned compound containing a benzene ring represented by formula I, or a pharmaceutically acceptable salt thereof, a stereoisomer thereof, a tautomer thereof or an isotopic compound thereof, some groups have the following definitions, and the definitions of the non-mentioned groups are as described in any of the above embodiments (hereinafter, referred to as "in a certain embodiment" in this paragraph):

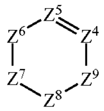

is a benzene ring or a "6 membered heteroaryl ring containing 1, 2 or 3 heteroatoms selected from N".

In a certain embodiment:

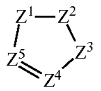

is a "5 membered heteroaryl ring containing 1 or 2 heteroatoms selected from one or more of N, O and S".

In a certain embodiment:

The compound of formula I is

I-1

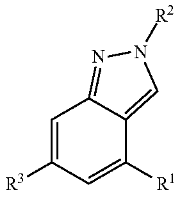

or

I-2

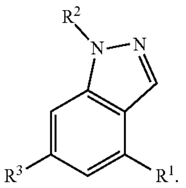

In a certain embodiment:

$R^1$ is

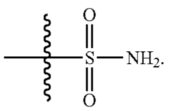 [SMILES: *S(N)(=O)=O]

In a certain embodiment:

$R^3$ is

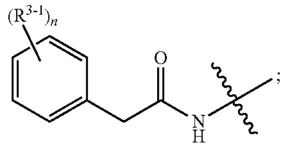

n is 1; $R^{3-1}$ is halogen.

In a certain embodiment:

$R^2$ is cyano, $C_1$-$C_{10}$ alkyl, $C_1$-$C_{10}$ alkyl substituted with one or more $R^{2-1}$, $C_3$-$C_6$ cycloalkyl, $C_3$-$C_6$ cycloalkyl substituted with one or more $R^{2-3}$, phenyl substituted with one or more $R^{2-4}$, or —(C═O)—$R^{2-2}$.

In a certain embodiment:

$R^2$ is $C_1$-$C_{10}$ alkyl, $C_1$-$C_{10}$ alkyl substituted with one $R^{2-1}$, or $C_3$-$C_6$ cycloalkyl.

In a certain embodiment:

$R^{2-1}$ is independently hydroxyl, halogen, $C_3$-$C_6$ cycloalkyl, phenyl substituted with one or more $R^{2-1-1}$, "5-6 membered heteroaryl containing 1, 2 or 3 heteroatoms selected from one or more of N, O and S" substituted with one or more $R^{2-1-6}$, —O$R^{2-1-2}$, —N($R^{2-1-3}$)($R^{2-1-4}$), or —S(═O)$_2$—$R^{2-1-5}$;

$R^{2-1-1}$ and $R^{2-1-6}$ are independently hydroxyl, halogen, —O$R^{2-1-1-1}$, or —N($R^{2-1-1-2}$)($R^{2-1-1-3}$); $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl.

In a certain embodiment:

$R^{2-1}$ is independently halogen, $C_3$-$C_6$ cycloalkyl, phenyl substituted with one or more $R^{2-1-1}$, or —O$R^{2-1-2}$; $R^{2-1-1}$ is halogen; $R^{2-1-2}$ is $C_1$-$C_6$ alkyl.

In a certain embodiment:

$R^{2-3}$ is independently $C_1$-$C_6$ alkyl.

In a certain embodiment:

$R^{2-4}$ is independently halogen.

In a certain embodiment:

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment:

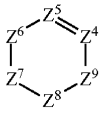

is a benzene ring or a "6 membered heteroaryl ring containing 1, 2 or 3 heteroatoms selected from N".

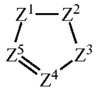

is a "5 membered heteroaryl ring containing 1 or 2 heteroatoms selected from one or more of N, O and S";

$R^1$ is

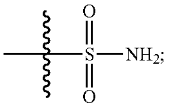 [SMILES: *S(N)(=O)=O]

$R^3$ is

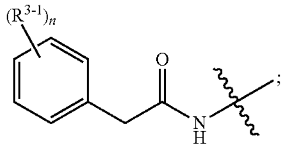

n is 1;

$R^{3-1}$ is halogen;

m is 0 or 1;

$R^2$ is cyano, $C_1$-$C_{10}$ alkyl, $C_1$-$C_{10}$ alkyl substituted with one or more $R^{2-1}$, $C_3$-$C_6$ cycloalkyl, $C_3$-$C_6$ cycloalkyl substituted with one or more $R^{2-3}$, phenyl substituted with one or more $R^{2-4}$, or —(C═O)—$R^{2-2}$;

$R^{2-1}$ is independently hydroxyl, halogen, $C_3$-$C_6$ cycloalkyl, phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —$N(R^{2-1-3})(R^{2-1-4})$, or —$S(═O)_2$—$R^{2-1-5}$;

$R^{2-1-1}$ and $R^{2-1-6}$ are independently hydroxyl, halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment:

I-1

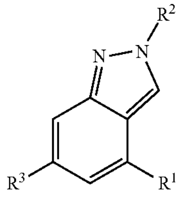

or

I-2

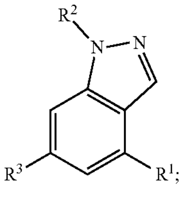

$R^1$ is

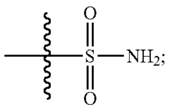 [SMILES: *S(N)(=O)=O]

$R^3$ is

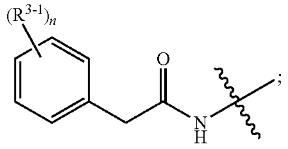

n is 1;

$R^{3-1}$ is halogen;

m is 0 or 1;

$R^2$ is $C_1$-$C_{10}$ alkyl, $C_1$-$C_{10}$ alkyl substituted with one $R^{2-1}$, or $C_3$-$C_6$ cycloalkyl;

$R^{2-1}$ is independently halogen, $C_3$-$C_6$ cycloalkyl, phenyl substituted with one or more $R^{2-1-1}$, or —$OR^{2-1-2}$; $R^{2-1-1}$ is halogen; $R^{2-1-2}$ is $C_1$-$C_6$ alkyl.

In a certain embodiment:

When

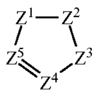

is a "5 membered heteroaryl ring containing 1 or 2 heteroatoms selected from one or more of N, O and S", the "5 membered heteroaryl ring containing 1 or 2 heteroatoms selected from one or more of N, O and S" is, for example, a "5 membered heteroaryl ring containing 1 or 2 heteroatoms selected from N", and for another example, a pyrrole ring, a pyrazole ring or an imidazole ring.

In a certain embodiment:

I

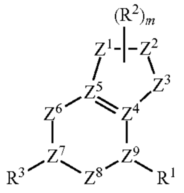

is, for example,

I-1

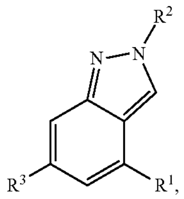

-continued

I-2

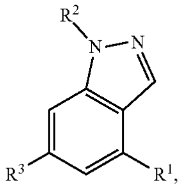

I-3

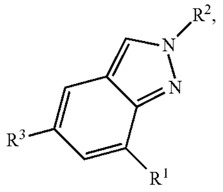

I-4

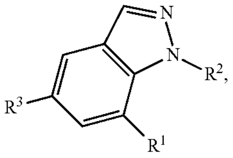

I-5

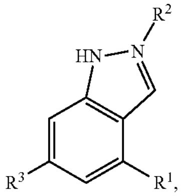

I-6

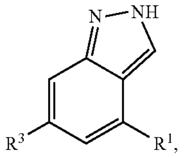

I-7

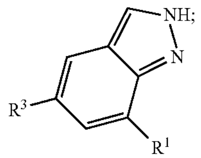

I-8

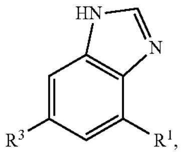

I-9

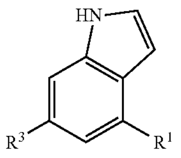

or

-continued

I-10

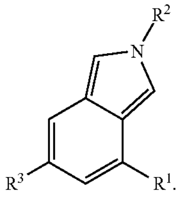

In a certain embodiment:

When $R^{3-1}$ is independently halogen, the halogen is, for example, fluorine, chlorine, bromine or iodine, and for another example, chlorine.

In a certain embodiment:

When n is 1 or 2, $R^{3-1}$ can be independently located in the ortho-, meta- or para-position relative to

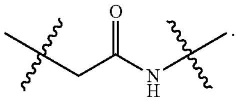 [SMILES: *CC(=O)N*]

In a certain embodiment:

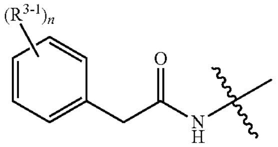

is

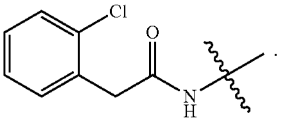

In a certain embodiment:

When $R^2$ is $C_1$-$C_{10}$ alkyl, the $C_1$-$C_{10}$ alkyl is, for example, $C_1$-$C_6$ alkyl, for another example, $C_1$-$C_5$ alkyl, and for still another example, methyl, ethyl, n-propyl, isopropyl, n-butyl, isobutyl, sec-butyl, tert-butyl, n-pentyl, isopentyl or

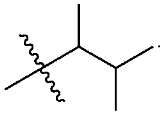

In a certain embodiment:

When $R^2$ is $C_1$-$C_{10}$ alkyl substituted with one or more $R^{2-1}$, the $C_1$-$C_{10}$ alkyl is, for example, $C_1$-$C_6$ alkyl, for another example, $C_1$-$C_4$ alkyl, for still another example, methyl, ethyl, n-propyl, isopropyl, n-butyl, isobutyl, sec-butyl or tert-butyl, and for yet another example, methyl, ethyl, isopropyl or isobutyl.

In a certain embodiment:

When $R^{2-1}$ is independently halogen, the halogen is, for example, fluorine, chlorine, bromine or iodine, and for another example, fluorine.

In a certain embodiment:

When $R^{2-1}$ is independently $C_3$-$C_6$ cycloalkyl, the $C_3$-$C_6$ cycloalkyl is, for example, cyclopropyl, cyclobutyl, cyclopentyl or cyclohexyl.

In a certain embodiment:

When $R^{2-1}$ is independently "5-6 membered heteroaryl containing 1, 2 or 3 heteroatoms selected from one or more of N, O and S" substituted with one or more $R^{2-1-6}$, the "5-6 membered heteroaryl containing 1, 2 or 3 heteroatoms selected from one or more of N, O and S" is, for example, 5-6 membered heteroaryl containing 1 heteroatom selected from one or more of N, O and S, for another example, pyridinyl, and for still another example, pyridin-4-yl.

In a certain embodiment:

$R^{2-1-1}$ can be independently located in the ortho-, meta- or para-position relative to phenyl.

In a certain embodiment:

$R^{2-1-6}$ can be independently located in the ortho-, meta- or para-position relative to 6 membered heteroaryl.

In a certain embodiment:

$R^{2-1-6}$ can be independently located in the ortho- or meta-position relative to 5 membered heteroaryl.

In a certain embodiment:

When $R^{2-1-1}$ is independently halogen, the halogen is, for example, fluorine, chlorine, bromine or iodine, and for another example, fluorine.

In a certain embodiment:

When $R^{2-1-6}$ is independently halogen, the halogen is, for example, fluorine, chlorine, bromine or iodine, and for another example, fluorine.

In a certain embodiment:

When $R^{2-1-1-1}$, $R^{2-1-1-2}$ and $R^{2-1-1-3}$ are independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl.

In a certain embodiment:

When $R^{2-1-2}$ is independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-2}$ is independently $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-1-3}$ and $R^{2-1-4}$ are independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-3}$ and $R^{2-1-4}$ are independently $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-1-5}$ is independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-5}$ is independently $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^2$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^2$ is $C_3$-$C_6$ cycloalkyl substituted with one or more $R^{2-3}$, the $C_3$-$C_6$ cycloalkyl is, for example, cyclopropyl, cyclobutyl, cyclopentyl or cyclohexyl, and for another example, cyclopropyl.

In a certain embodiment:

When $R^{2-3}$ is independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl, ethyl or isopropyl.

In a certain embodiment:

$R^{2-4}$ can be independently located in the ortho-, meta- or para-position relative to phenyl.

In a certain embodiment:

when $R^{2-1}$ is independently halogen, the halogen is, for example, fluorine, chlorine, bromine or iodine, and for another example, fluorine or chlorine.

In a certain embodiment:

when $R^{2-2}$ is independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, isopropyl.

In a certain embodiment:

when $R^{2-2}$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

$R^{2-2-1}$ can be independently located in the ortho-, meta- or para-position relative to phenyl.

In a certain embodiment:

when $R^{2-2-1}$ is independently halogen, the halogen is, for example, fluorine, chlorine, bromine or iodine, and for another example, fluorine.

In a certain embodiment, the compound containing a benzene ring represented by formula I is any one of the following compounds:

1

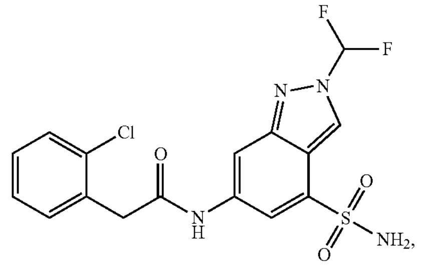

2

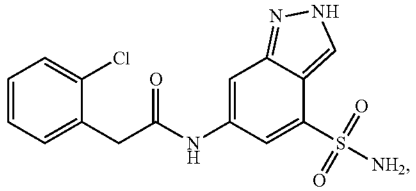

3-A

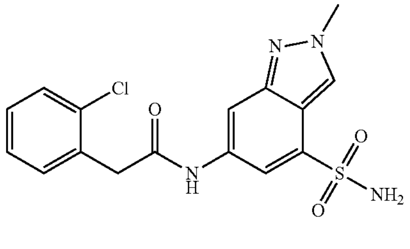

-continued
3-B
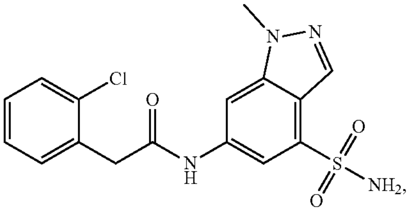
4-A
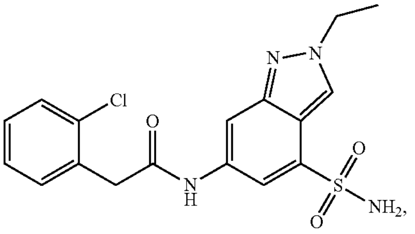
4-B
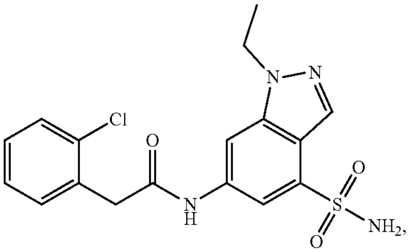
5-A
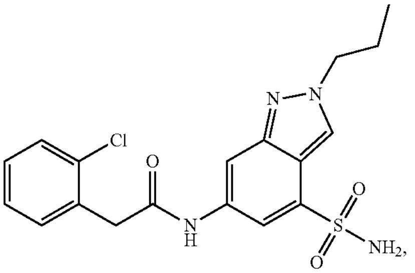
5-B
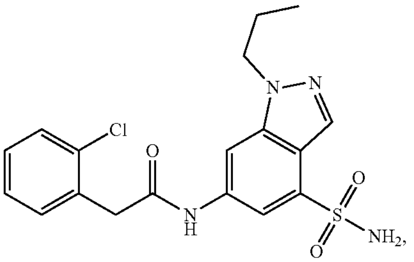
6-A
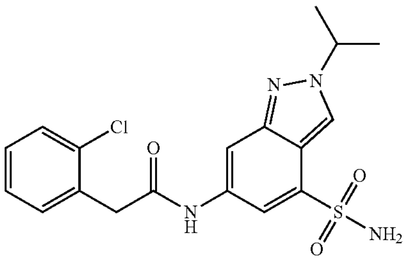
-continued
6-B
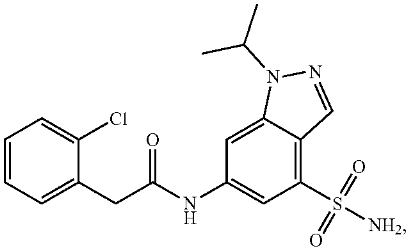
7-A
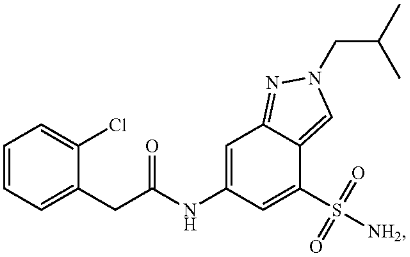
7-B
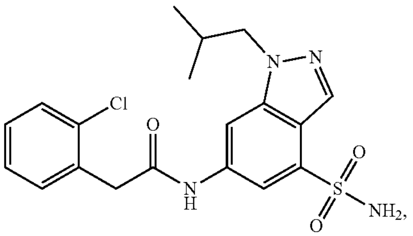
8-A
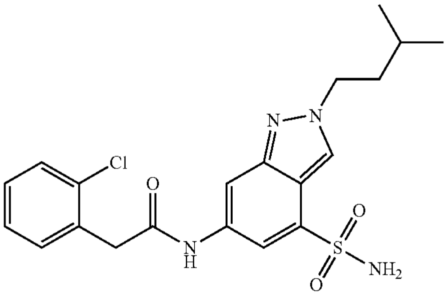
,
8-B
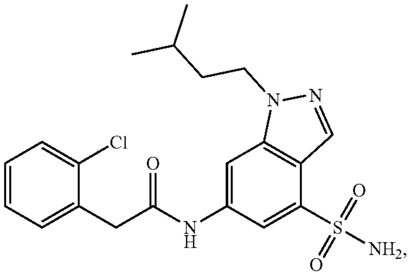
9
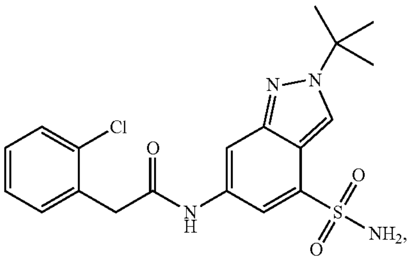

-continued
10
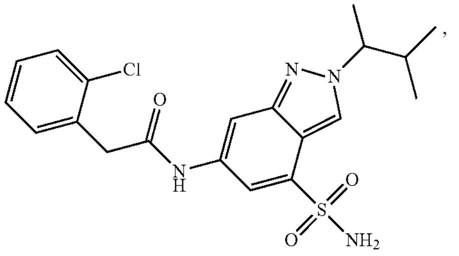
11
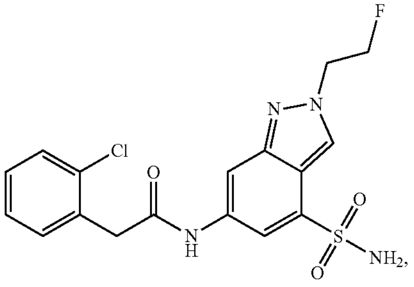
12-A
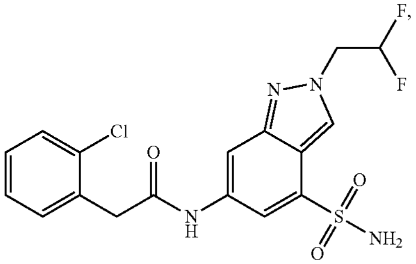
12-B
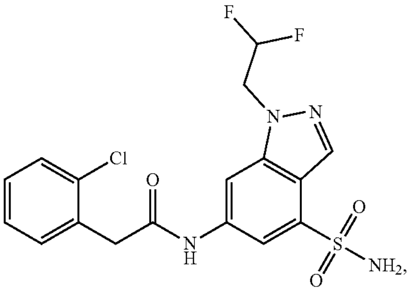
13
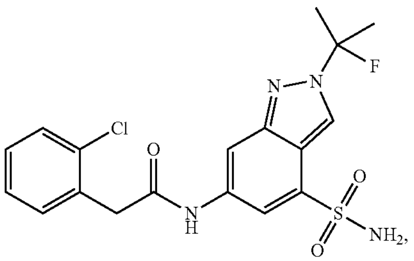
-continued
14-A
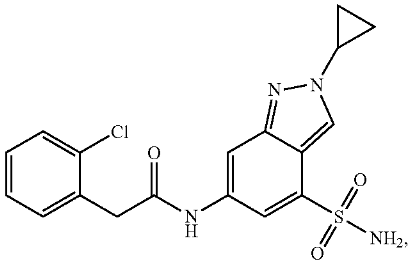
14-B
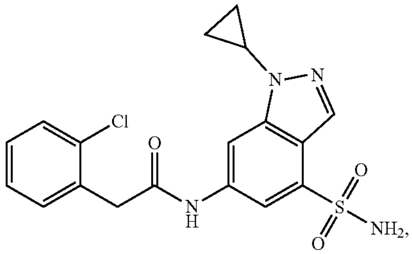
15-A
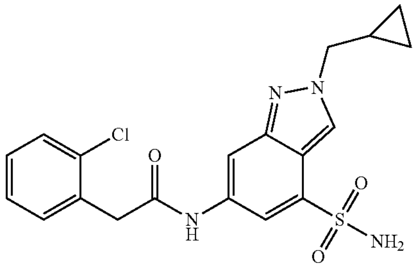
15-B
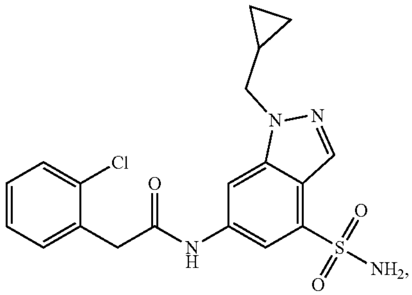
16-A
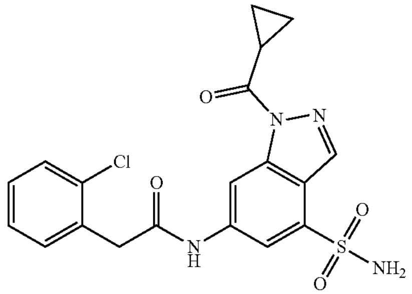

16-B
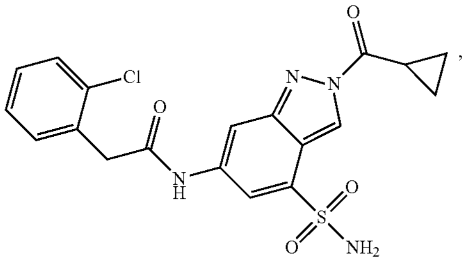
17
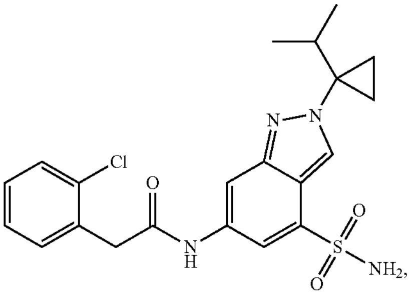
18
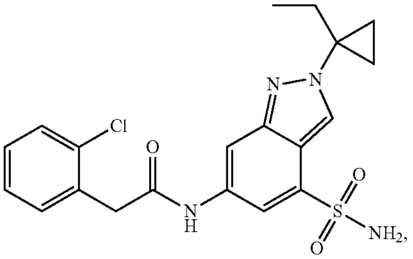
19
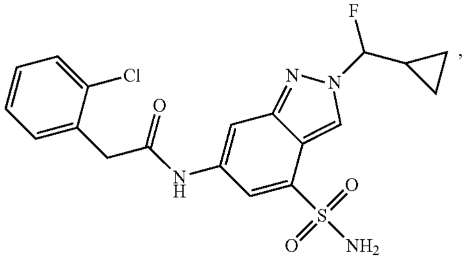
20
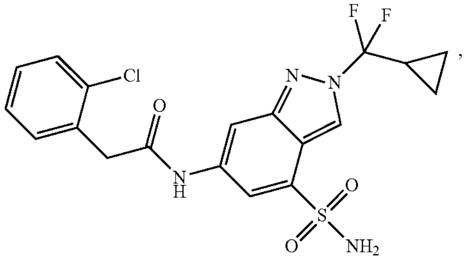
21
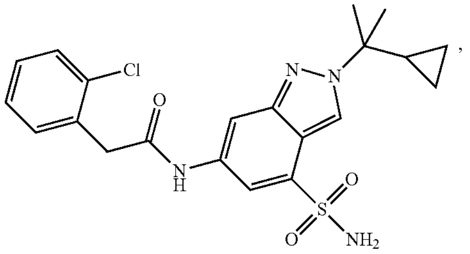
22
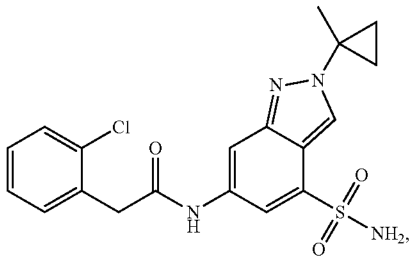
23
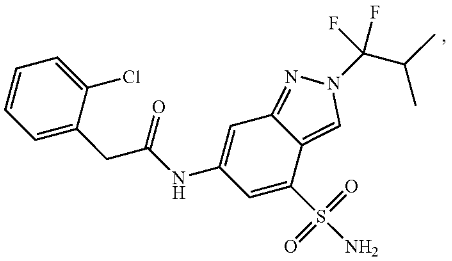
24-A
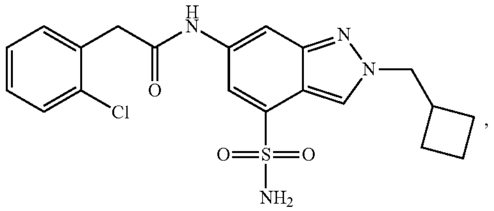
24-B
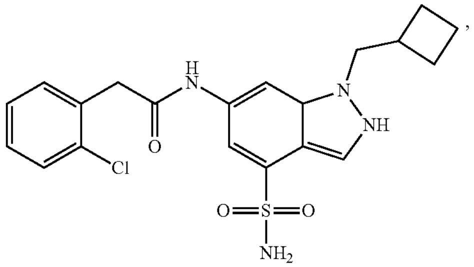
25
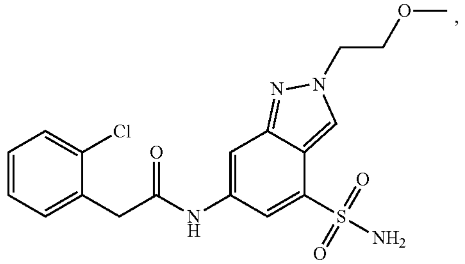

-continued
25A
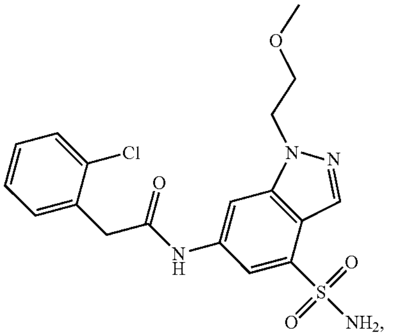
26-A
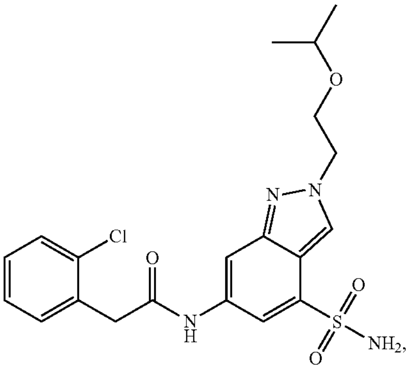
26-B
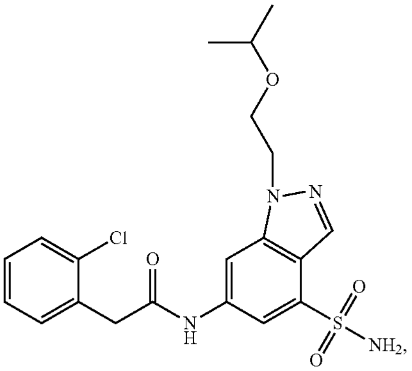
27-A
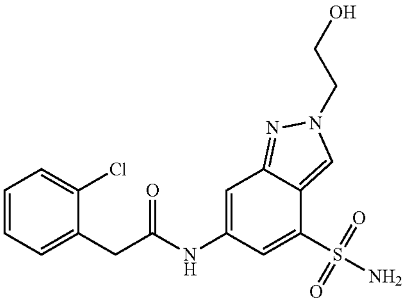
27-B
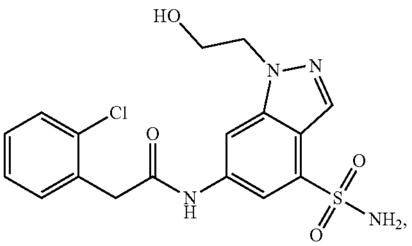
-continued
28
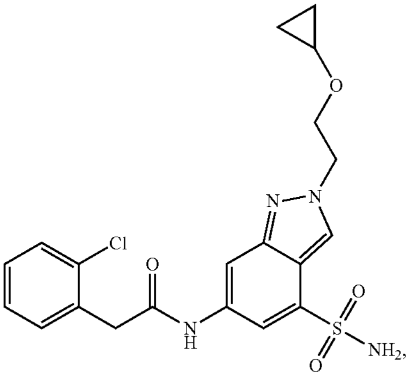
29
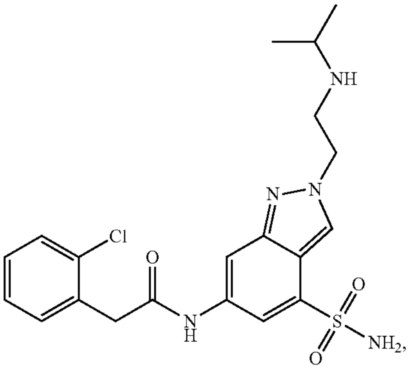
30
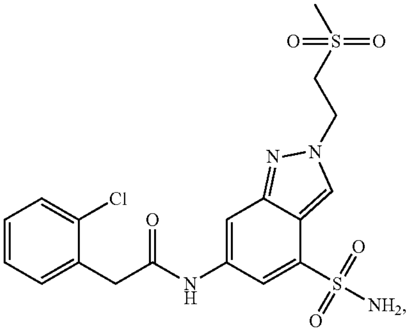
31-A
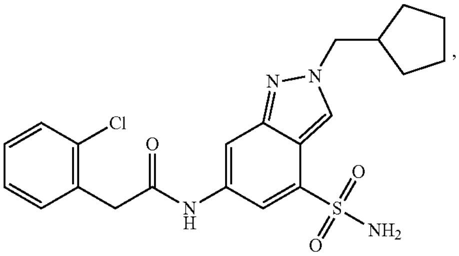

-continued
31-B
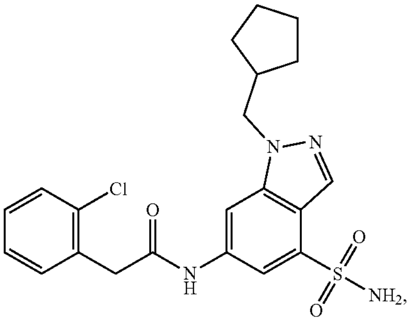
32-A
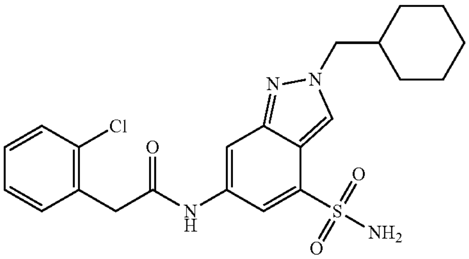
,
32-B
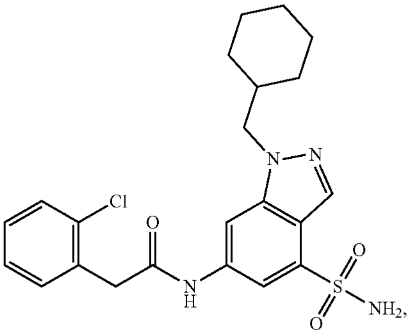
33
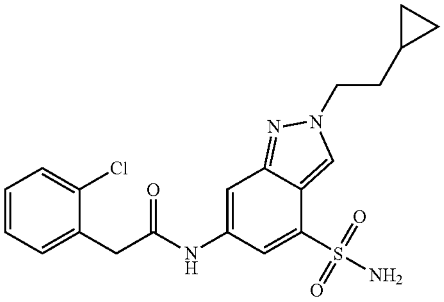
,
34
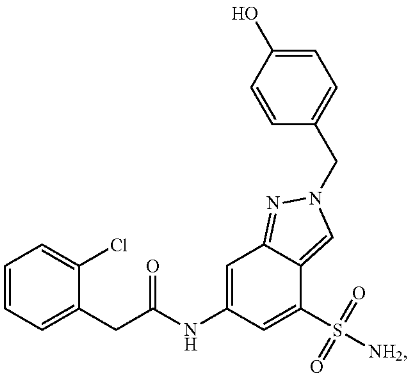
-continued
35-A
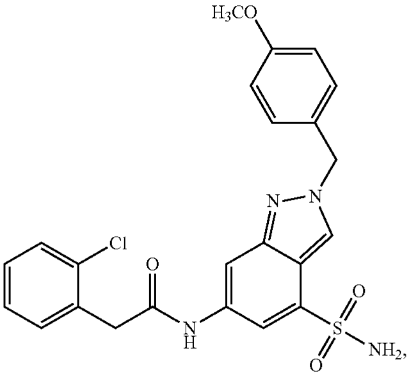
35-B
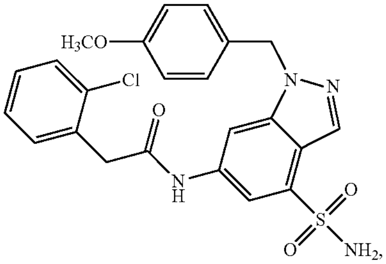
36-A
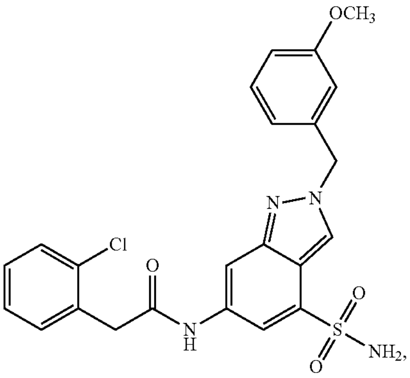
36-B
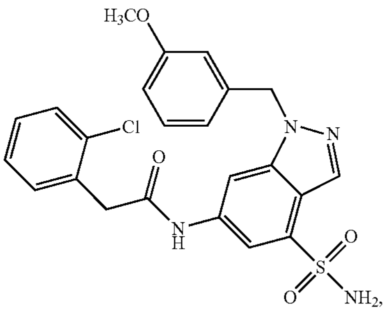

-continued
37-A
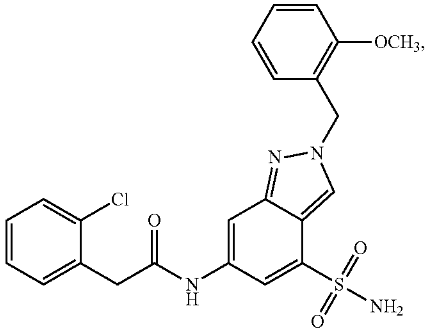
37-B
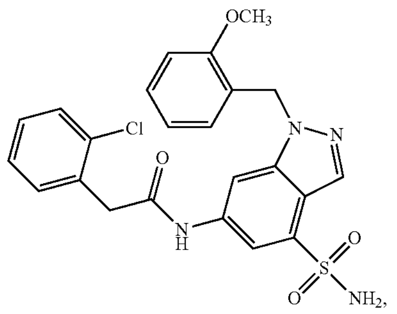
38
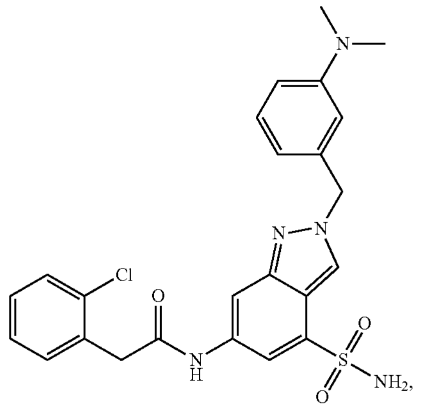
39
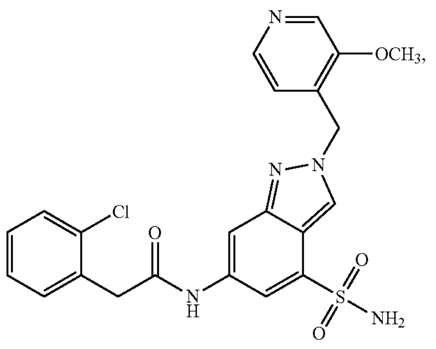
-continued
40-A
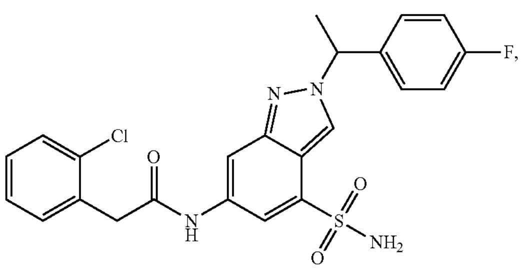
40-B
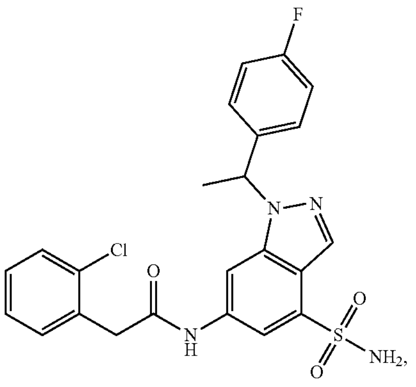
41
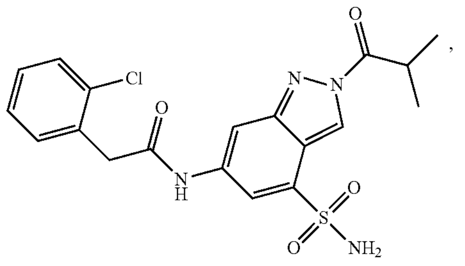
42-A
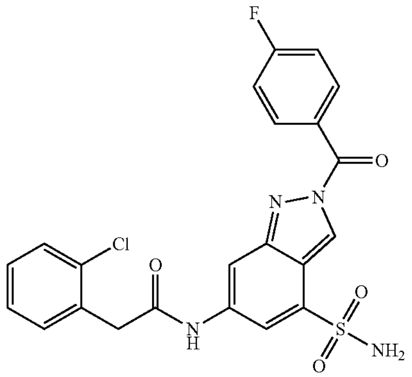
42-B
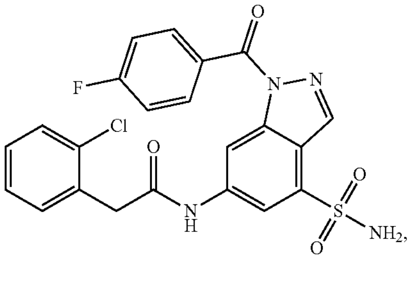

-continued
43
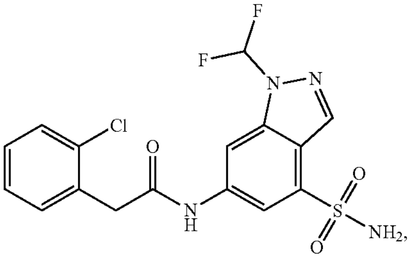
44
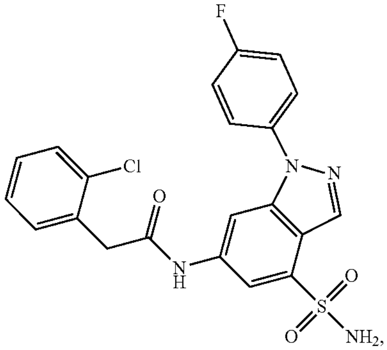
45
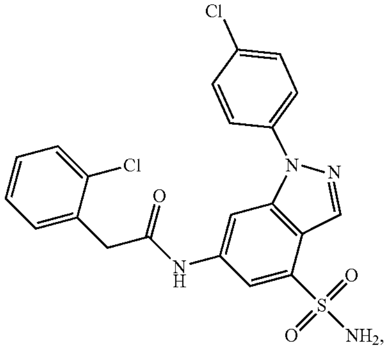
46
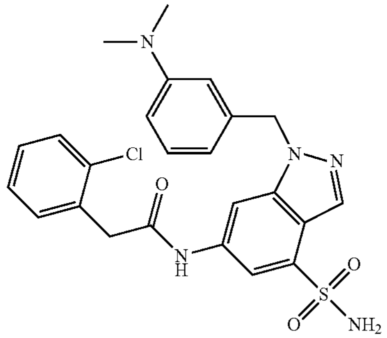
47
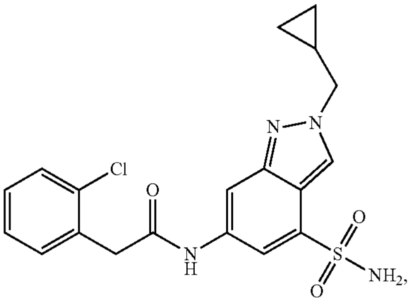
-continued
48-A
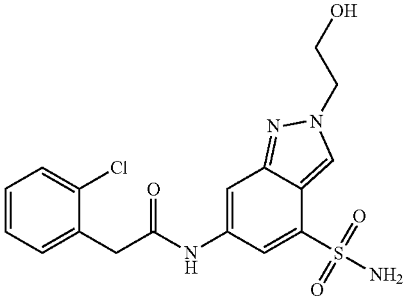
48-B
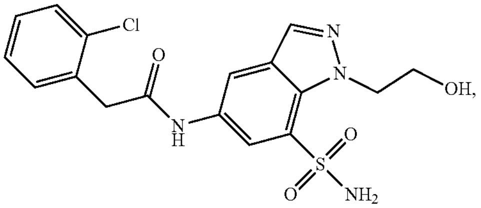
49
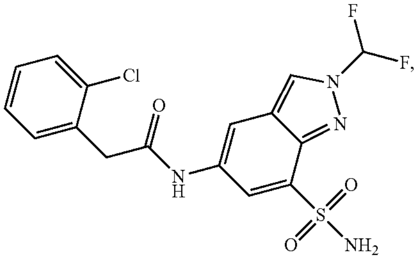
50
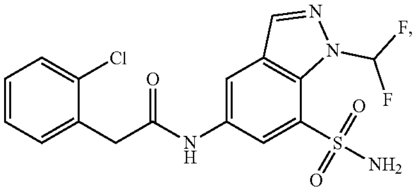
51
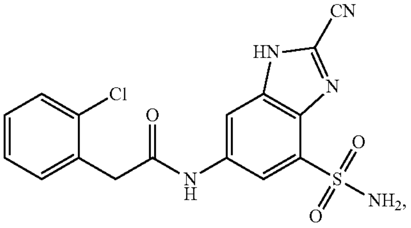
52
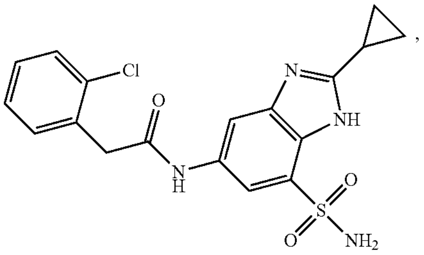

-continued
53
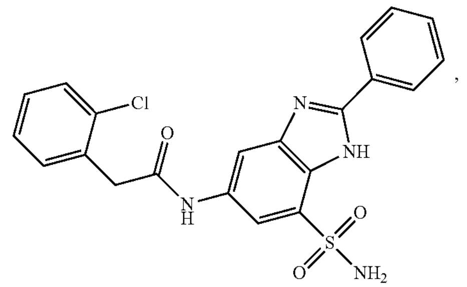
55
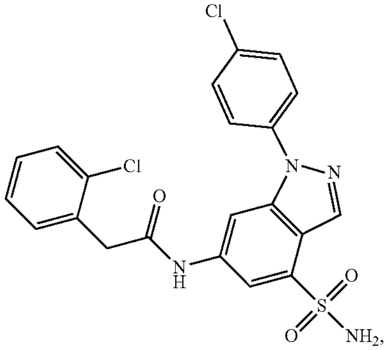
54
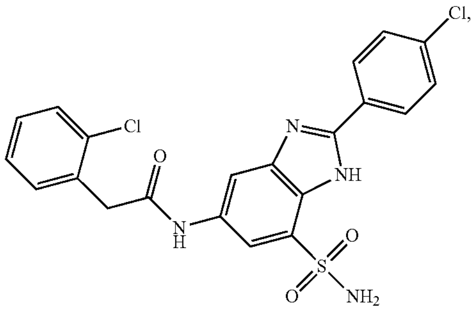
56
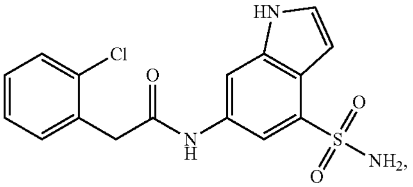
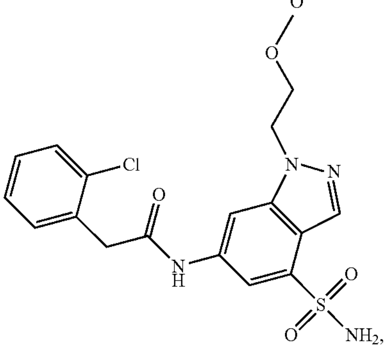
-continued
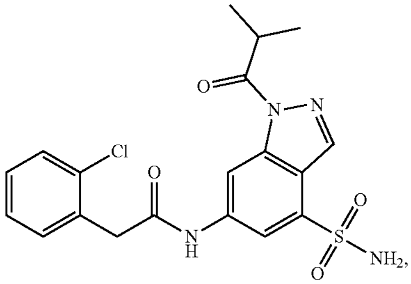
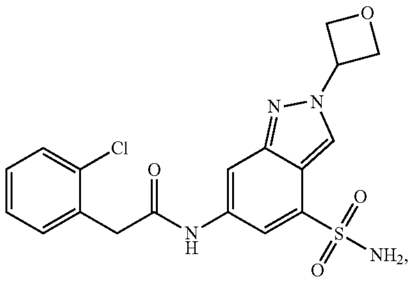
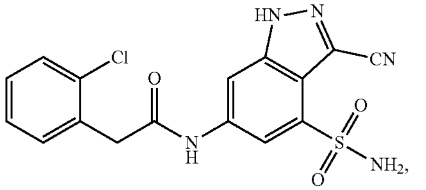
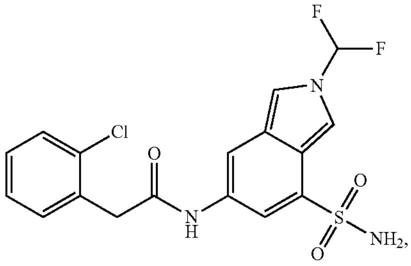
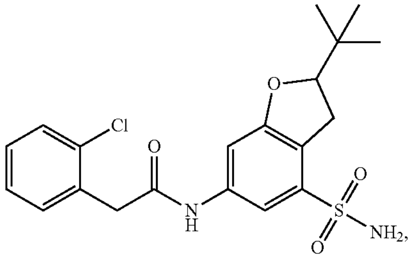
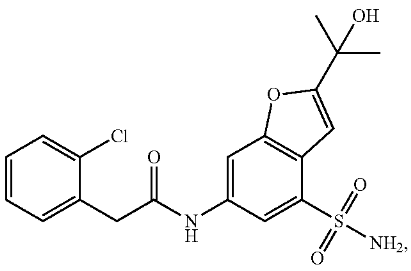

-continued
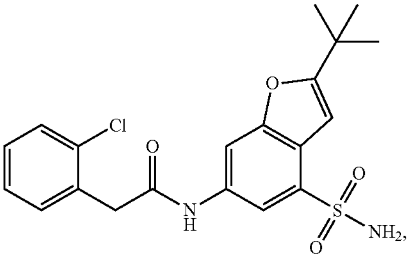
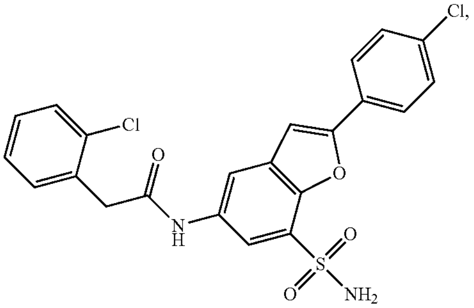
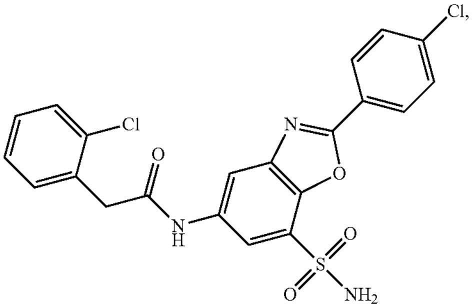
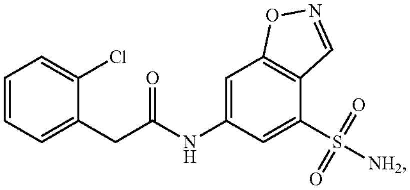
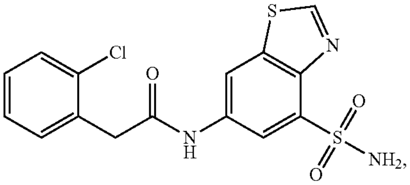
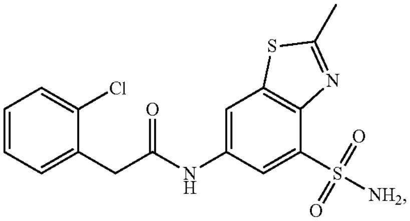
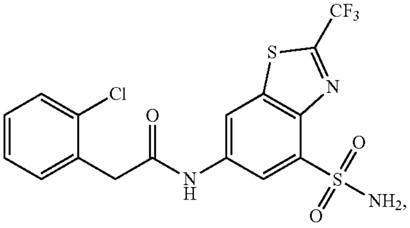
-continued
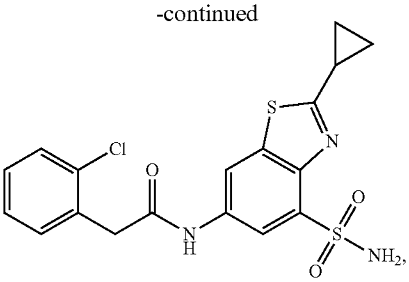
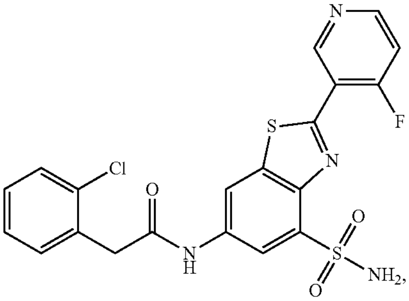
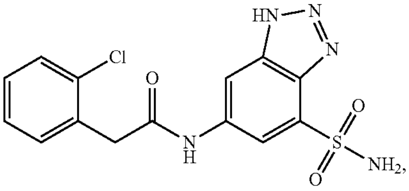
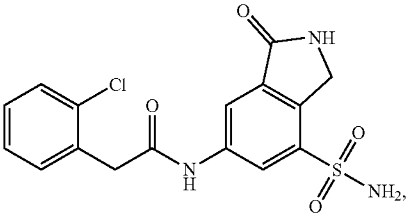
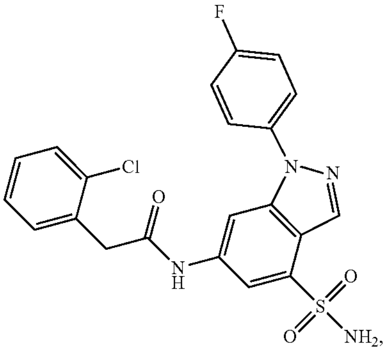
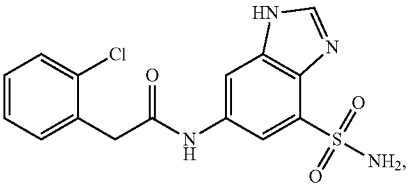
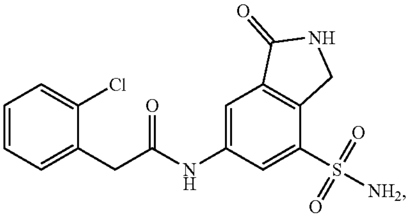

-continued
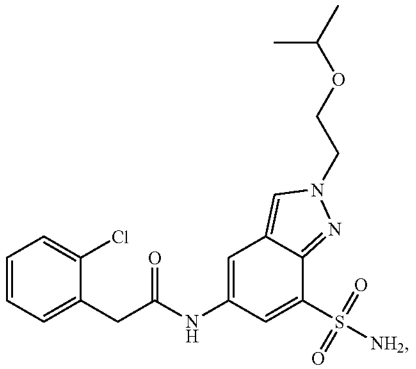
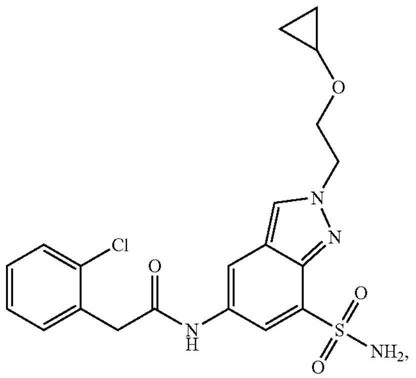
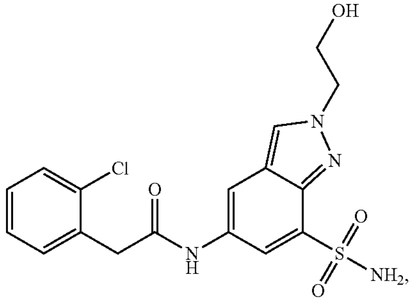
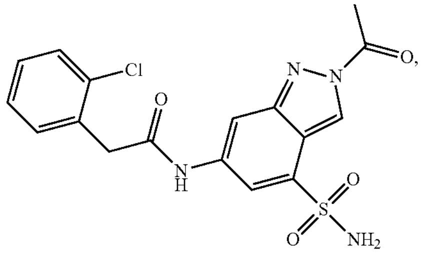
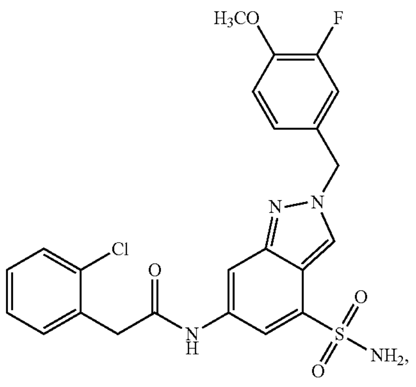
-continued
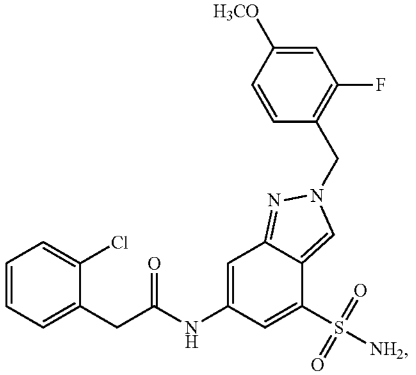
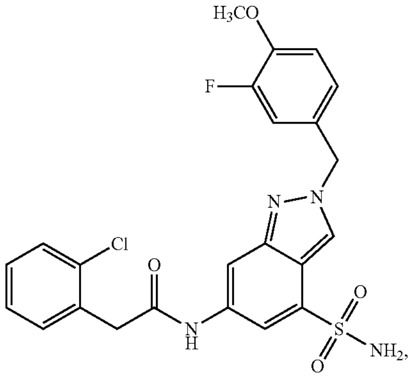
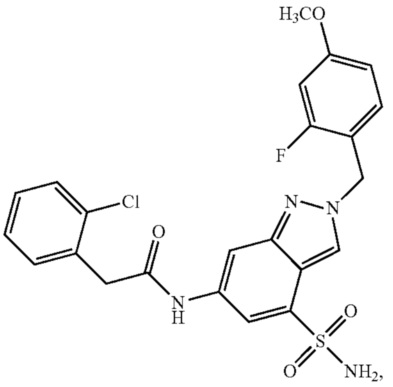
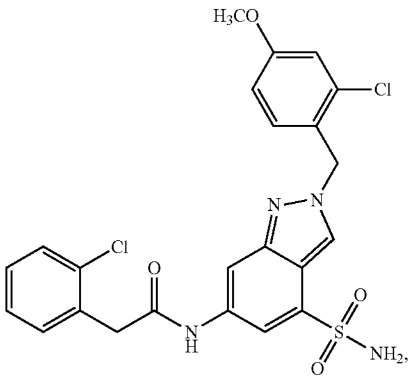

-continued
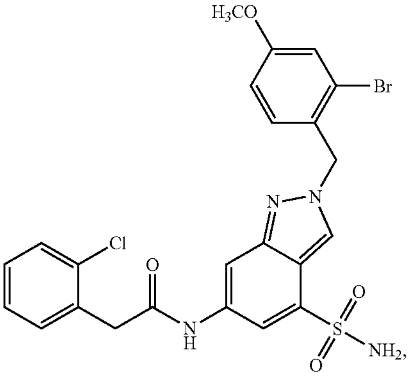
,
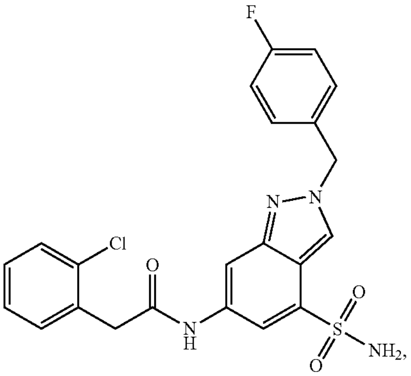
,
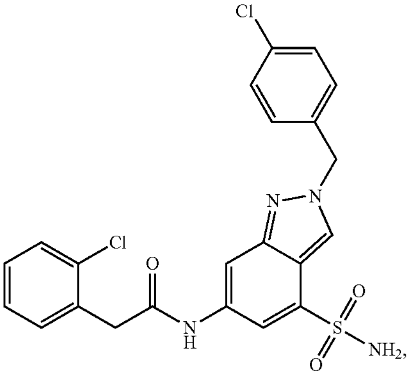
,
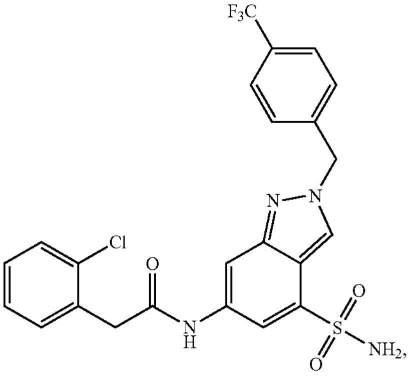
,
-continued
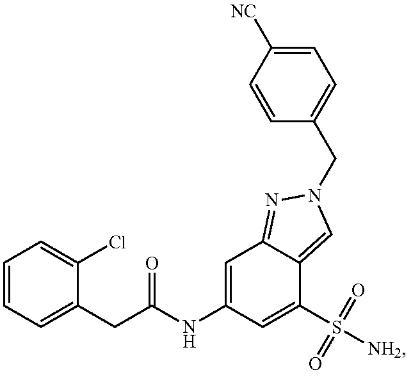
,
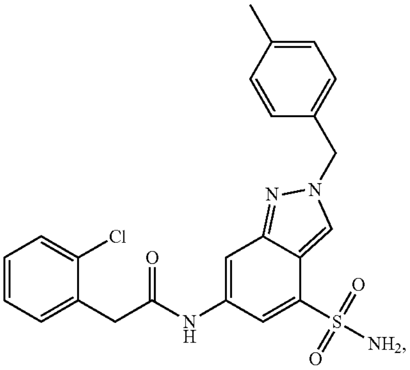
,
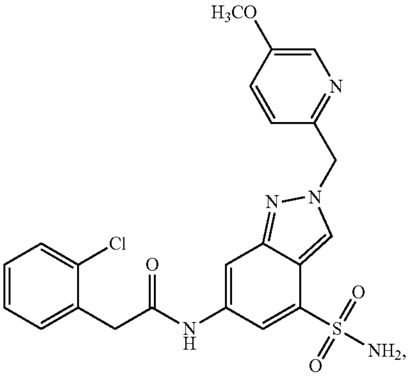
,
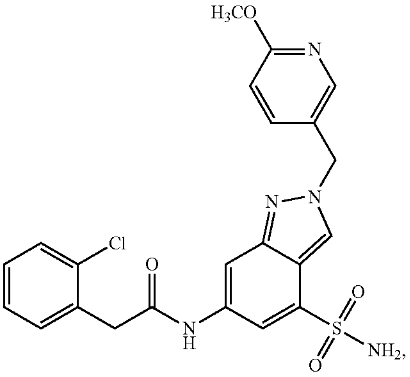
, -continued
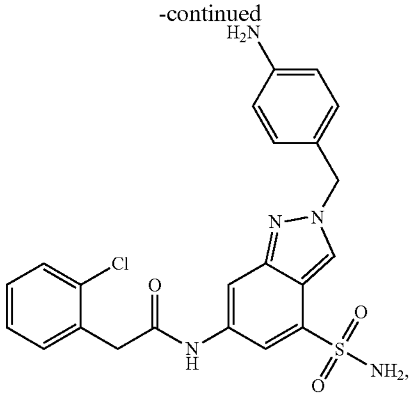
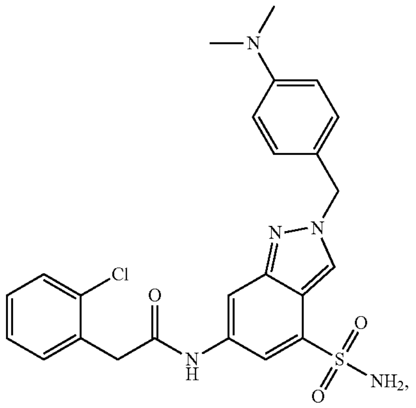
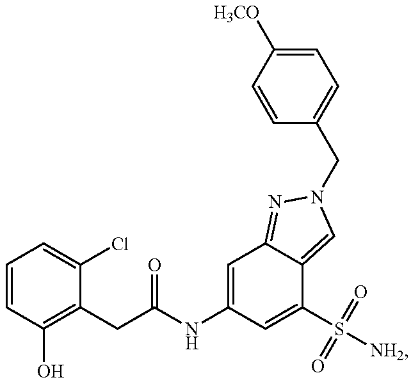
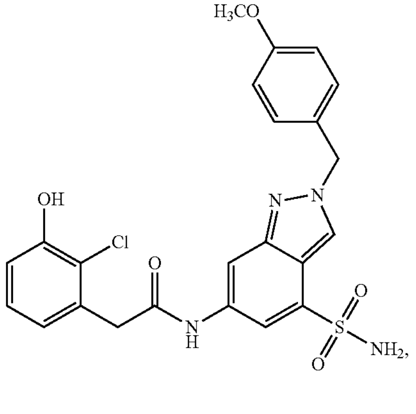
-continued
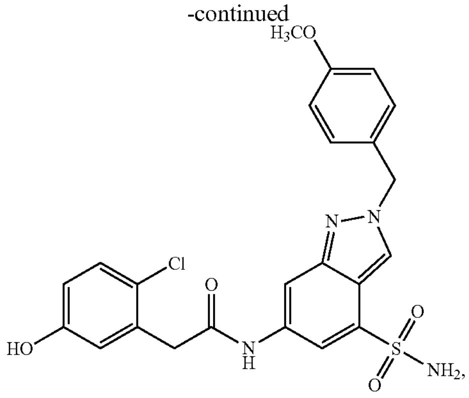
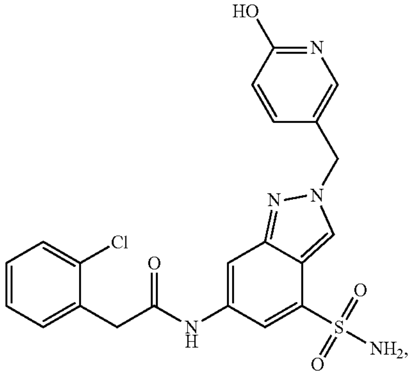
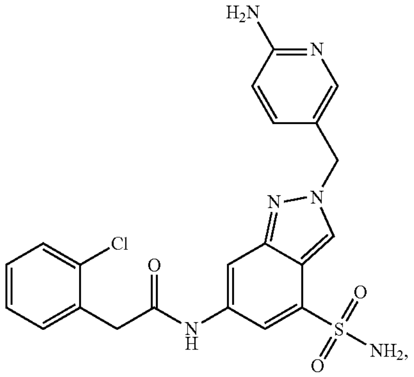
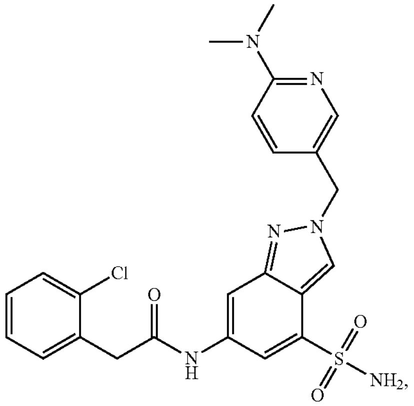

-continued
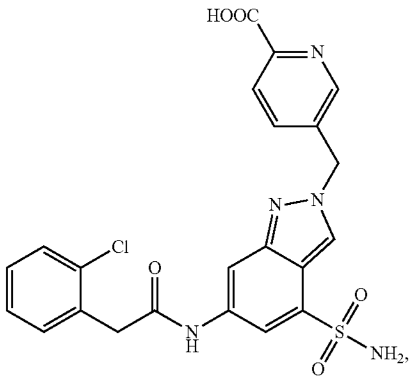
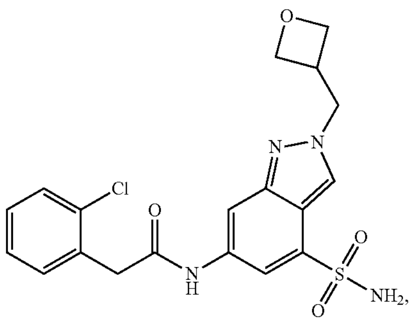
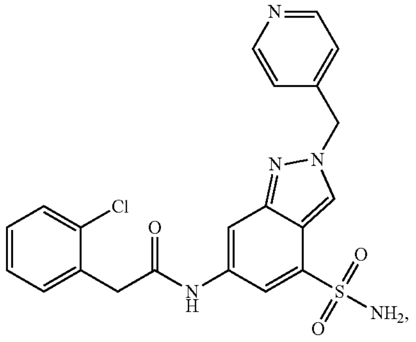
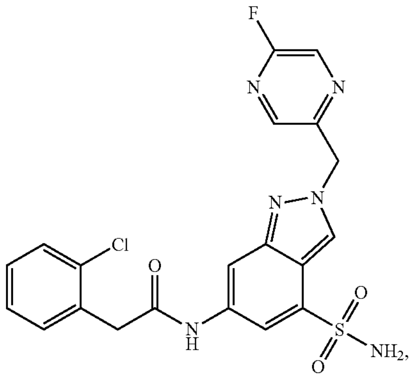
-continued
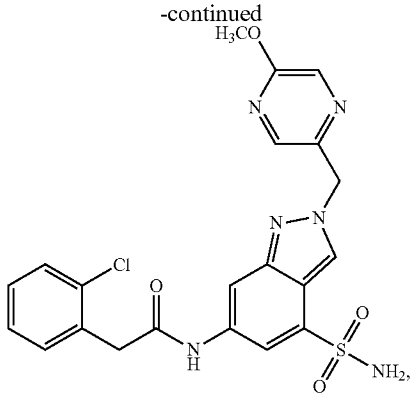
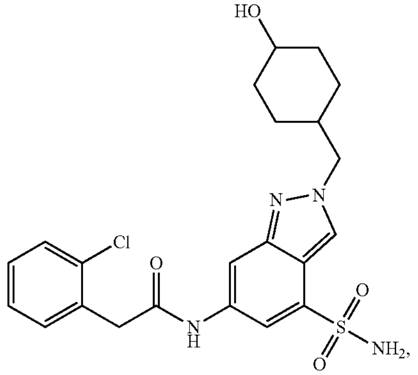
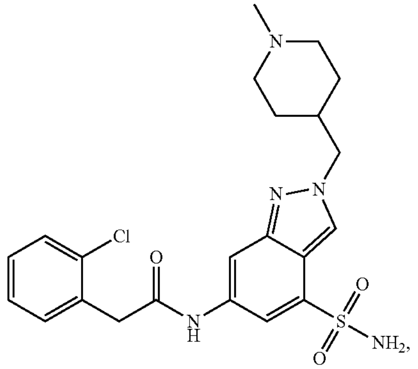
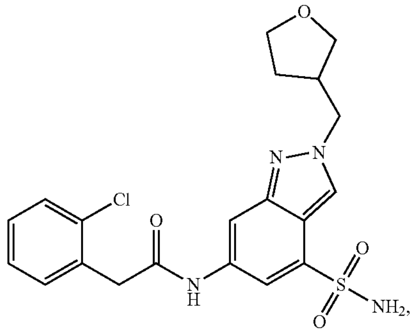
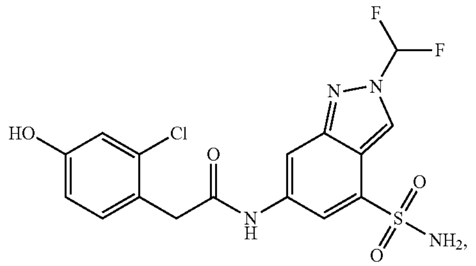

-continued
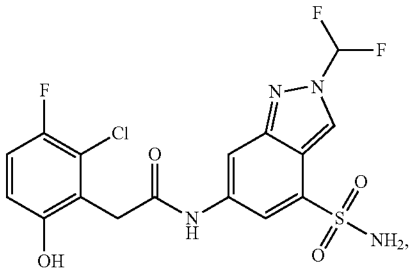
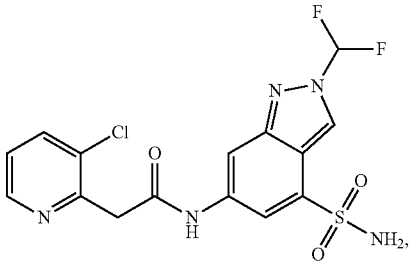
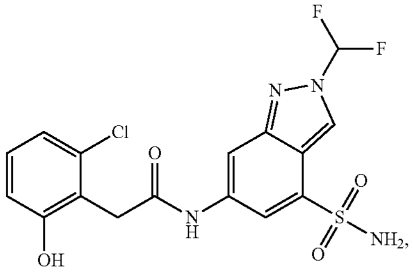
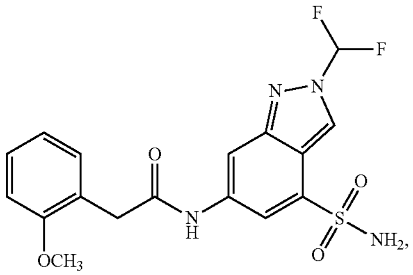
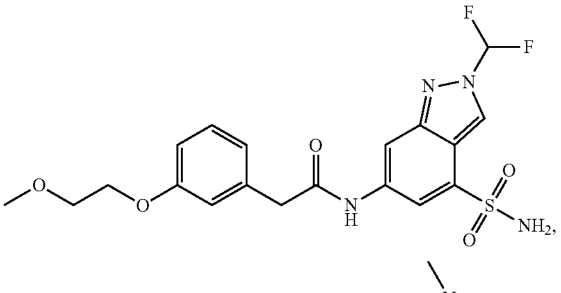
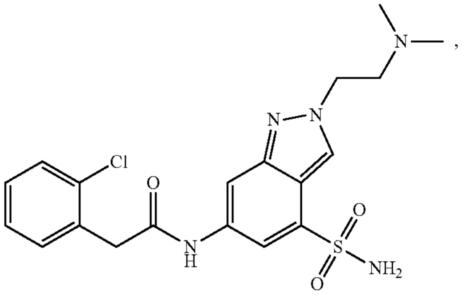
-continued
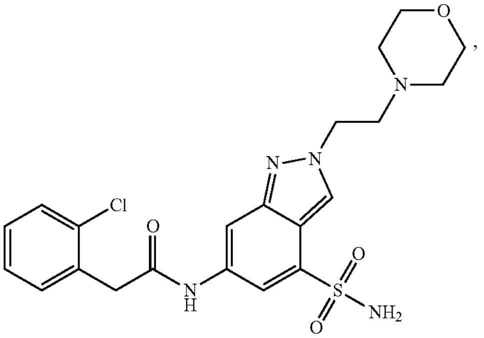
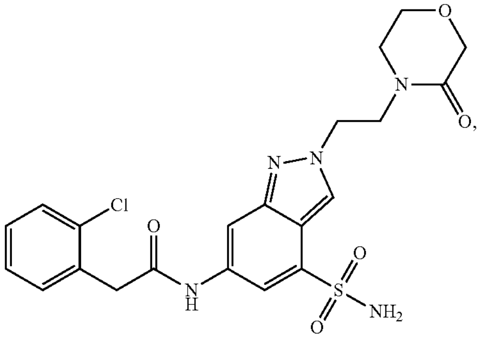
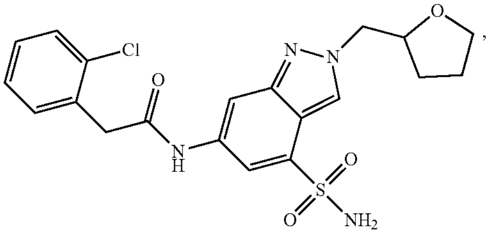
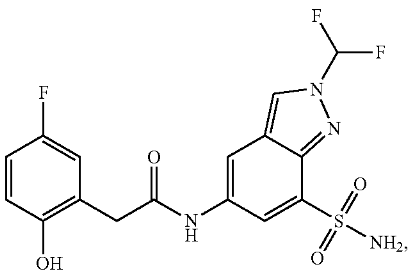
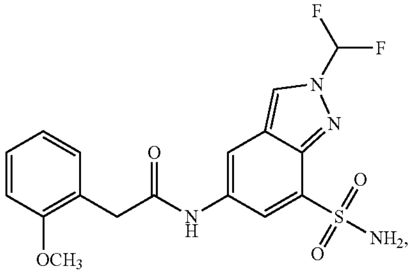

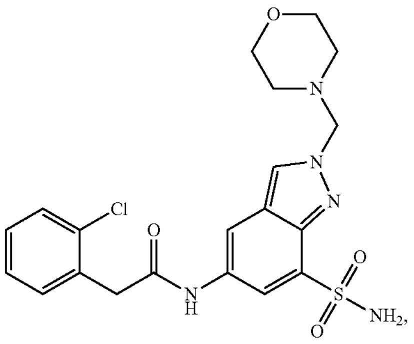
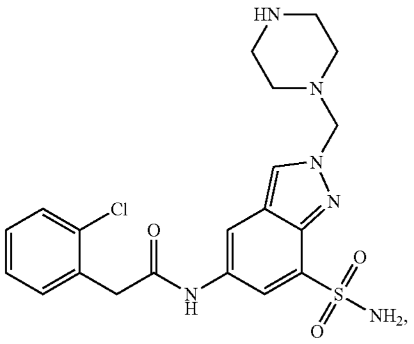
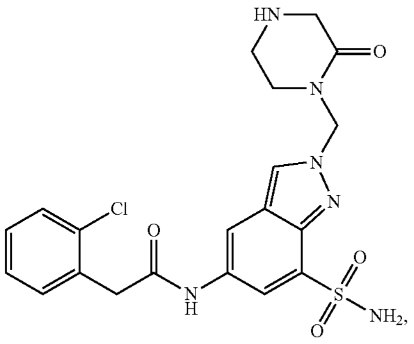
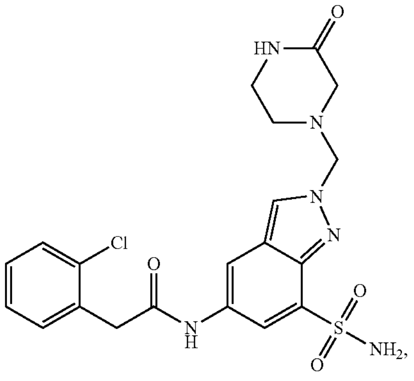
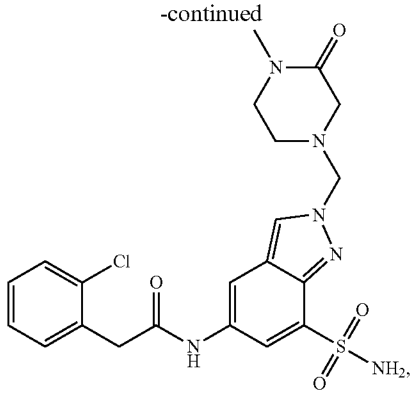
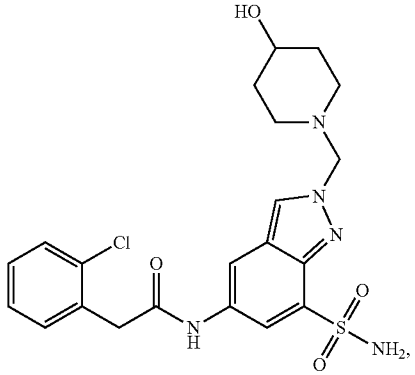
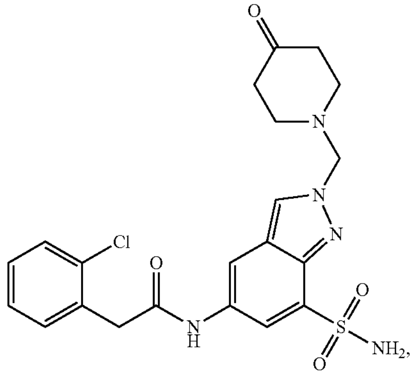
58
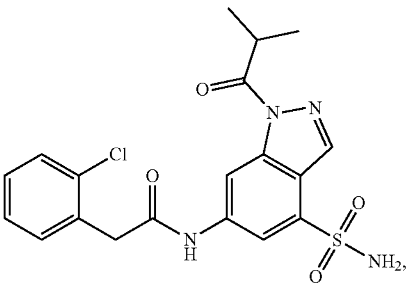
59
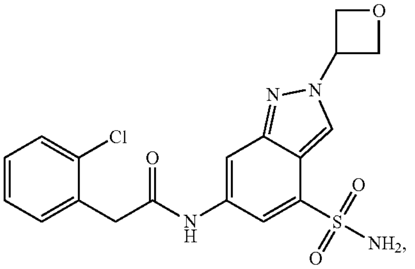

-continued
75
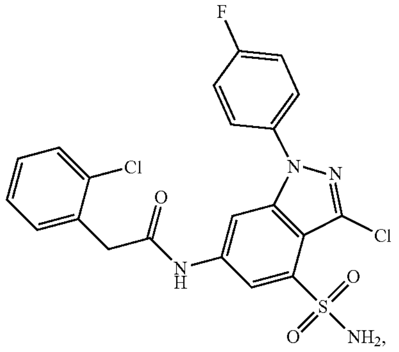
83
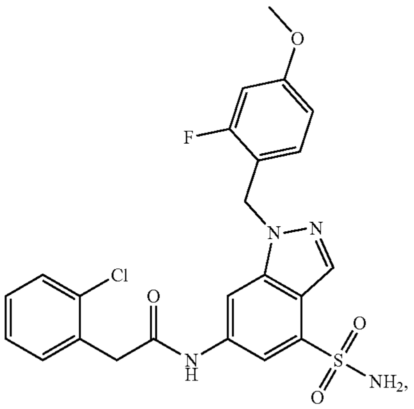
88
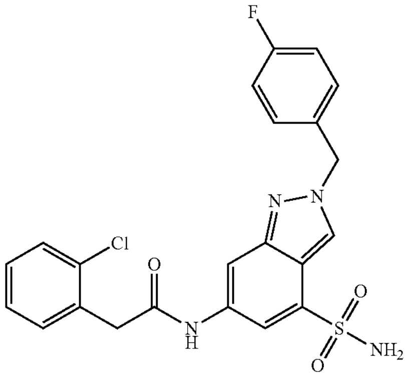
88A
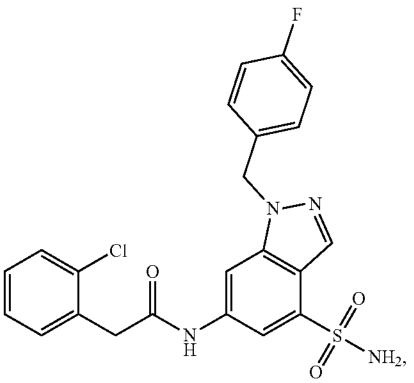
-continued
89
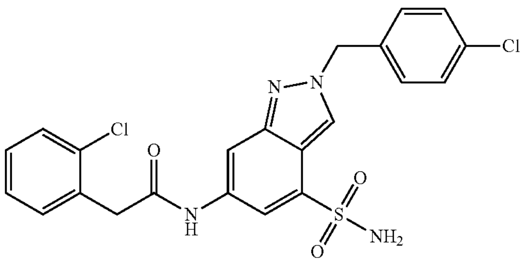
89A
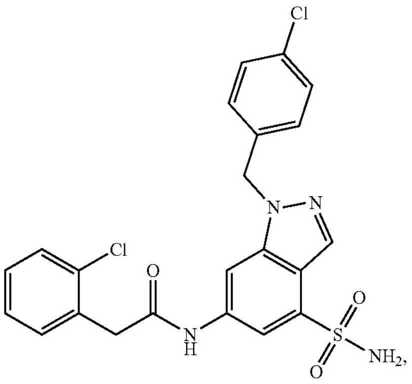
90
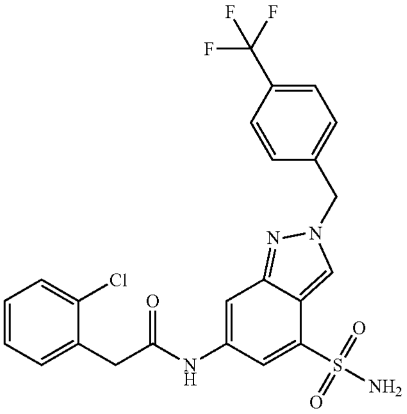
90A
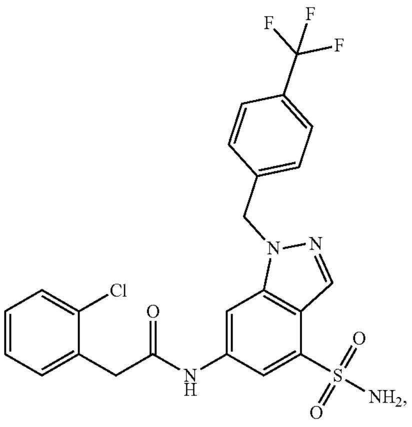

-continued
91
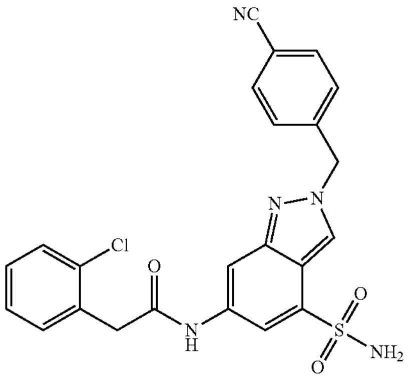
91A
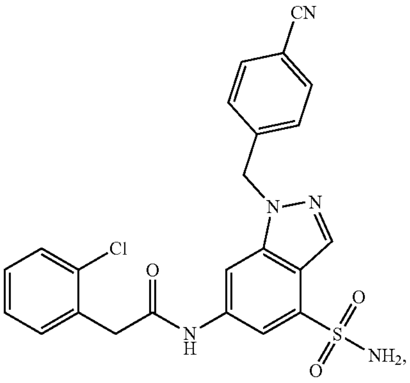
92
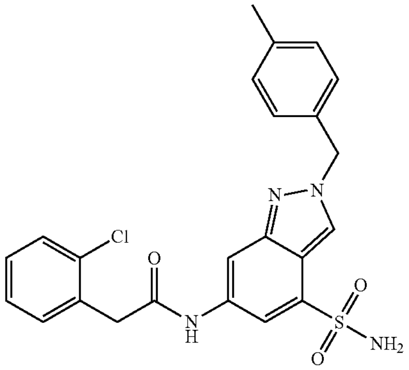
92A
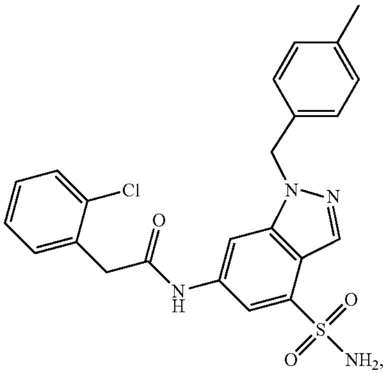
-continued
95
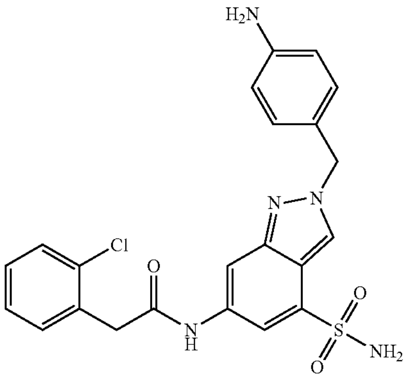
95A
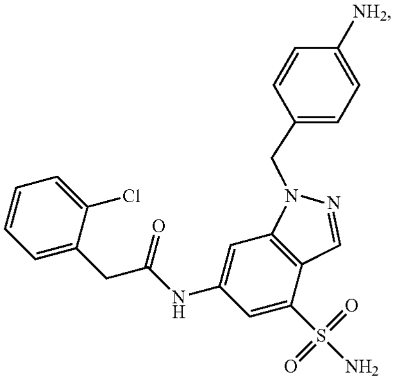
101
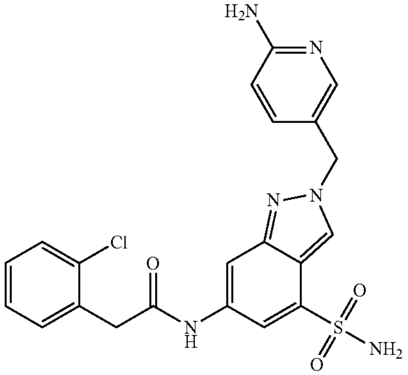
101A
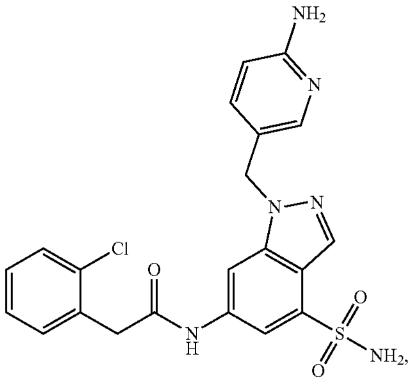

-continued
110
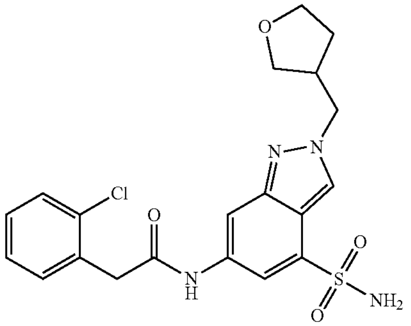
110A
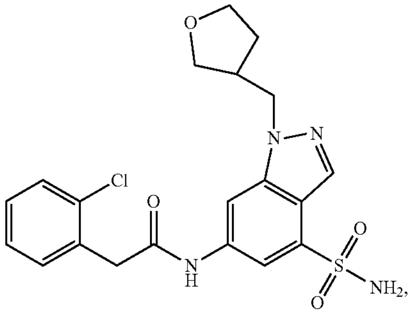
113
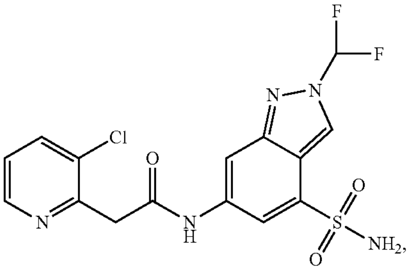
115
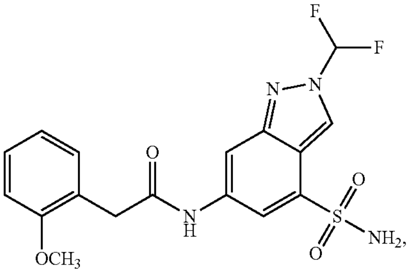
116
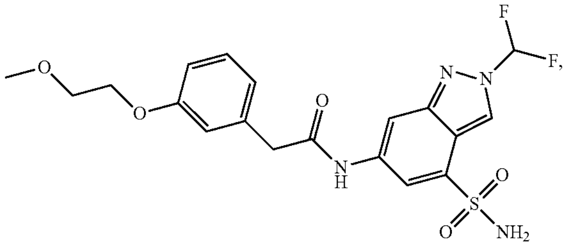
-continued
118
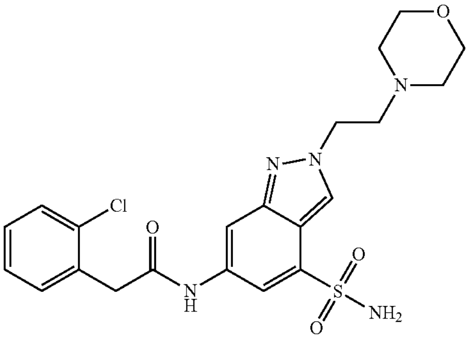
118A
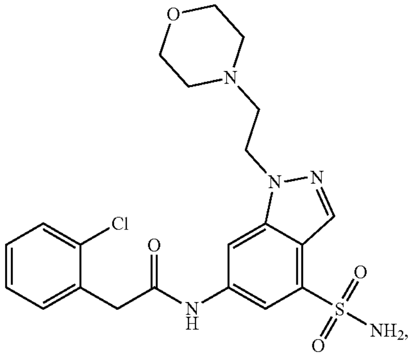
120
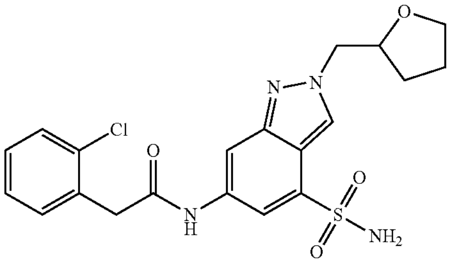
12A
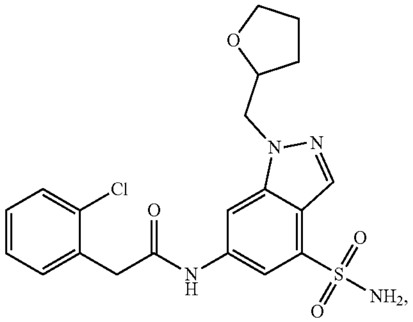
130
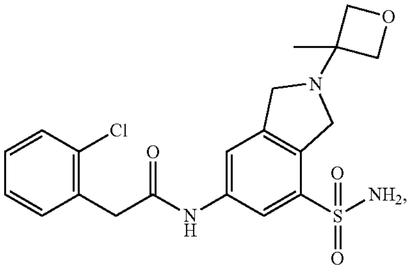

-continued
131
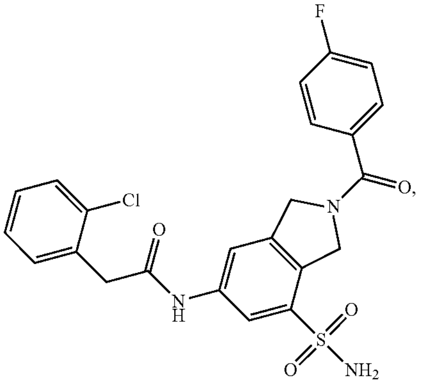
132
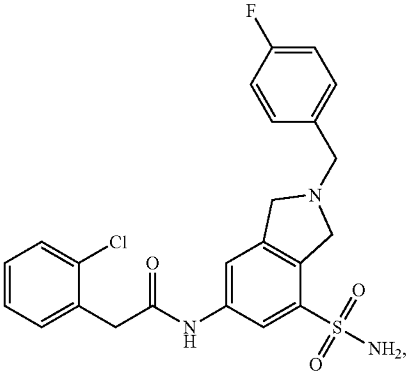
133
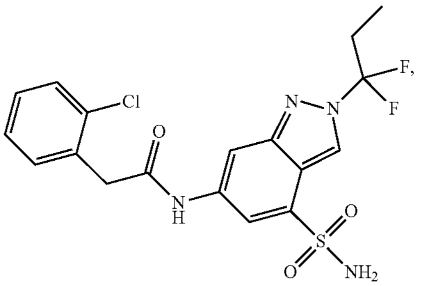
134
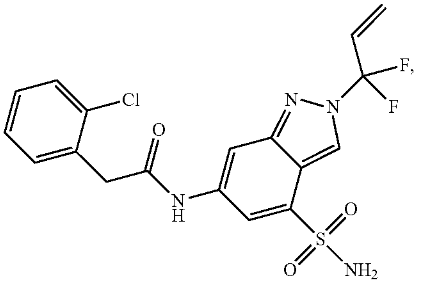
136
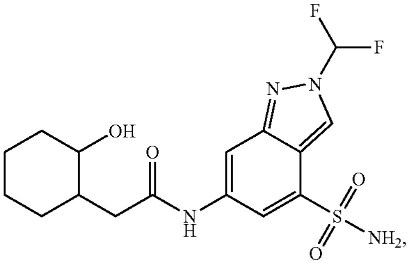
-continued
137
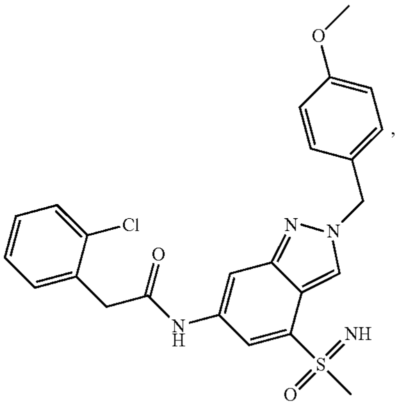
138
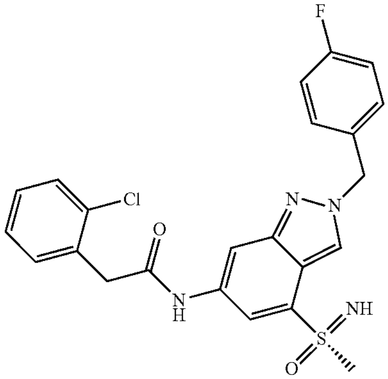
138A
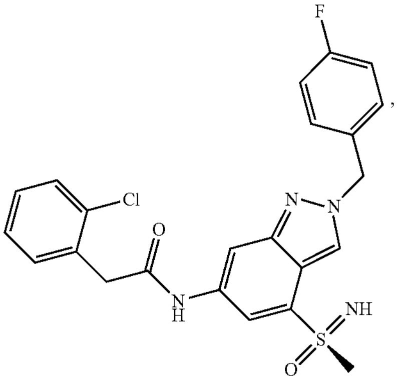
139
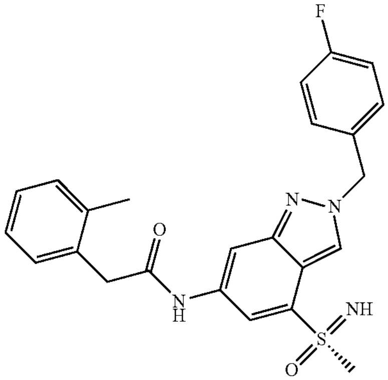

139A
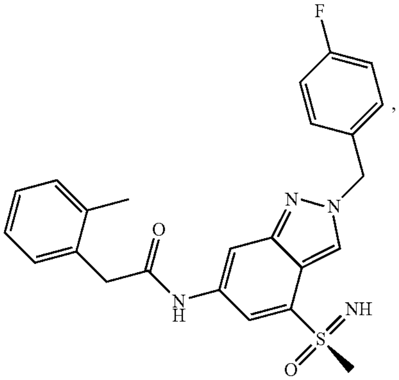
140
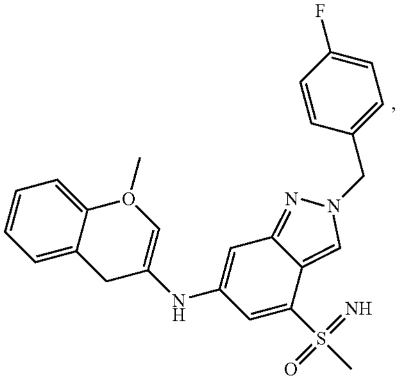
141
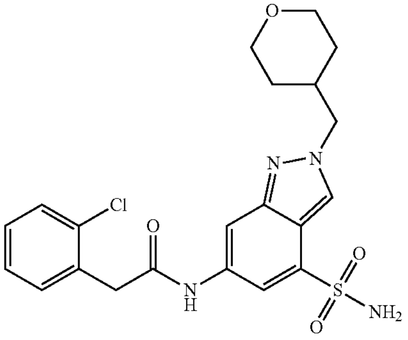
141A
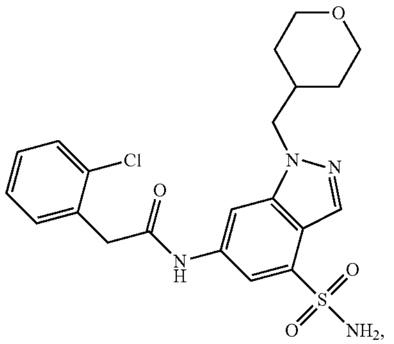
82
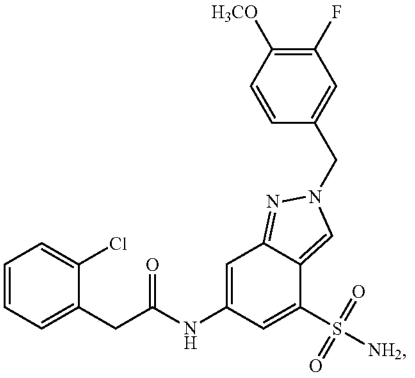
85
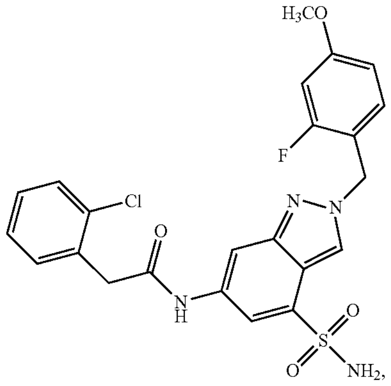
86
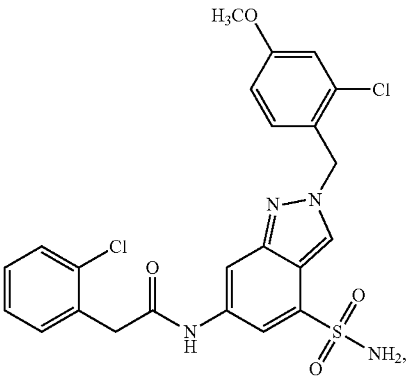
87
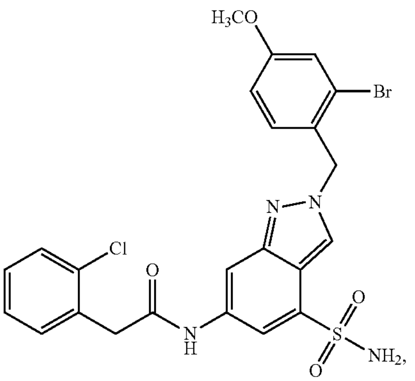

-continued

93

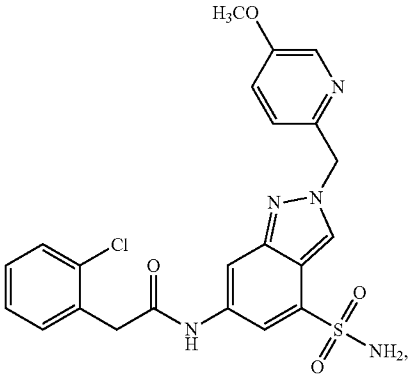

94

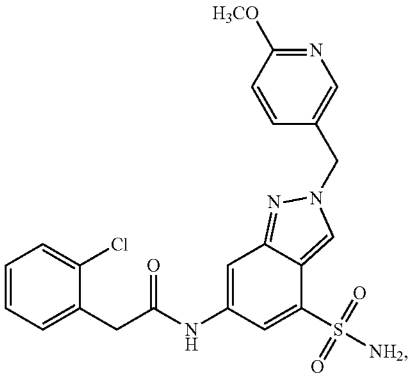

108

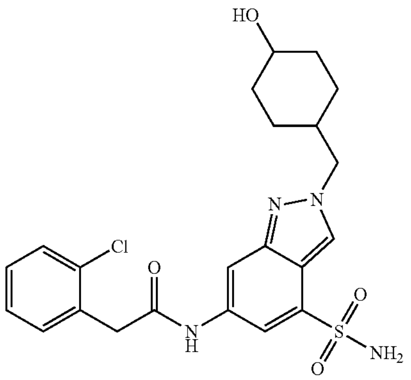

and

135

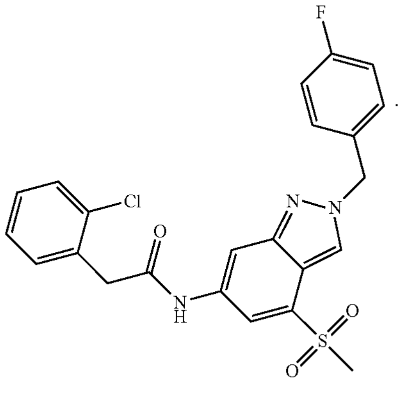

The compound containing a benzene ring represented by formula I, or the pharmaceutically acceptable salt thereof, the stereoisomer thereof, the tautomer thereof or the isotopic compound thereof can be synthesized by methods similar to those known in the chemical field, and can also be synthesized by the method described herein.

The disclosure further provides a pharmaceutical composition comprising substance A and at least one pharmaceutically acceptable excipient;

substance A is the compound containing a benzene ring represented by formula I, or the pharmaceutically acceptable salt thereof, the stereoisomer thereof, the tautomer thereof or the isotope compound thereof.

In the pharmaceutical composition, the dosage of substance A may be a therapeutically effective amount.

The disclosure further provides use of substance A in the preparation of a P2X4 receptor antagonist or drug;

substance A is the compound containing a benzene ring represented by formula I, or the pharmaceutically acceptable salt thereof, the stereoisomer thereof, the tautomer thereof or the isotope compound thereof.

In a certain embodiment, the P2X4 receptor antagonist is used in vitro.

In a certain embodiment, the drug may be used for the treatment or prevention of urinary tract diseases, respiratory diseases, pain, autoimmune diseases, inflammation, Alzheimer's disease, Parkinson's disease, sleep disorders, epilepsy, psychiatric disorders, arthritis, neurodegeneration, traumatic brain injury, myocardial infarction, rheumatoid arthritis, cerebral stroke, thrombosis, atherosclerosis, colon syndrome, inflammatory bowel disease, digestive tract diseases, gastrointestinal dysfunction, respiratory failure, sexual dysfunction, cardiovascular diseases, heart failure, hypertension, urinary incontinence, cystitis, arthritis, endometriosis, hematological diseases, musculoskeletal and connective tissue developmental disorders, or systemic disorder diseases in an animal (e.g., a human). The urinary tract diseases are, for example, urinary incontinence, overactive bladder, dysuria or cystitis. The respiratory diseases are, for example, respiratory disorders including idiopathic pulmonary fibrosis, chronic obstructive pulmonary disease, asthma, bronchospasm, or cough (e.g., chronic cough). The pain is, for example, inflammatory pain, surgical pain, visceral pain, dental pain, premenstrual pain, central pain, pain resulting from burns, migraine, cluster headache or chronic pain.

In a certain embodiment, the drug can be used for the prevention or treatment of diseases mediated at least in part by P2X4 in an animal (e.g., a human).

The diseases mediated at least in part by P2X4 are, for example, urinary tract diseases, respiratory diseases, pain, autoimmune diseases, inflammation, Alzheimer's disease, Parkinson's disease, sleep disorders, epilepsy, psychiatric disorders, arthritis, neurodegeneration, traumatic brain injury, myocardial infarction, rheumatoid arthritis, cerebral stroke, thrombosis, atherosclerosis, colon syndrome, inflammatory bowel disease, digestive tract diseases, gastrointestinal dysfunction, respiratory failure, sexual dysfunction, cardiovascular diseases, heart failure, hypertension, urinary incontinence, cystitis, arthritis, endometriosis, hematological diseases, musculoskeletal and connective tissue developmental disorders, or systemic disorder diseases. The urinary tract diseases are, for example, urinary incontinence, overactive bladder, dysuria or cystitis. The respiratory diseases are, for example, respiratory disorders including idiopathic pulmonary fibrosis, chronic obstructive pulmonary disease, asthma, bronchospasm, or cough (e.g., chronic cough). The pain is, for example, inflammatory pain, surgical pain, visceral pain, dental pain, premenstrual pain, central pain, pain resulting from burns, migraine, cluster headache or chronic pain.

The disclosure provides a compound containing a benzene ring represented by formula I, or a pharmaceutically acceptable salt thereof, a stereoisomer thereof, a tautomer thereof, an isotopic compound thereof, a crystalline form thereof, a nitrogen oxide thereof or a solvate thereof, or a solvate of a pharmaceutically acceptable salt thereof;

I

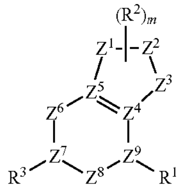

wherein,

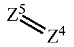

is a single bond or a double bond;

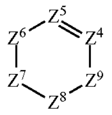

is a benzene ring, a "6 membered heteroalkyl ring containing 1, 2 or 3 heteroatoms selected from one or more of N, O and S", a "6 membered heteroalkenyl ring containing 1, 2 or 3 heteroatoms selected from one or more of N, O and S", or a "6 membered heteroaryl ring containing 1, 2 or 3 heteroatoms selected from one or more of N, O and S";

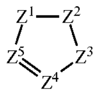

is a "5 membered heteroaryl ring containing 1, 2 or 3 heteroatoms selected from one or more of N, O and S" or a "5 membered heteroalkenyl ring containing 1, 2 or 3 heteroatoms selected from one or more of N, O and S";

$R^1$ is

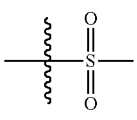

,

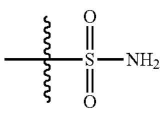

or

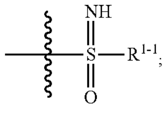

;

$R^{1-1}$ is halogen, hydroxyl, amino, —$NHR^{1-1-4}$, —$N(R^{1-1-5})(R^{1-1-6})$, $C_1$-$C_6$ alkyl, $C_3$-$C_6$ cycloalkyl, $C_1$-$C_6$alkyl substituted with one or more $R^{1-1-1}$, $C_3$-$C_6$ cycloalkyl substituted with one or more $R^{1-1-2}$, or "4-7 membered heterocycloalkyl containing 1, 2 or 3 heteroatoms selected from one or more of N, O and S" substituted with one or more $R^{1-1-3}$;

$R^{1-1-1}$, $R^{1-1-2}$, $R^{1-1-3}$, $R^{1-1-4}$, $R^{1-1-5}$ and $R^{1-1-6}$ are independently halogen, hydroxyl, $C_1$-$C_6$ alkyl, $C_3$-$C_6$ cycloalkyl, $C_1$-$C_6$ alkoxy or "4-7 membered heterocycloalkyl containing 1, 2 or 3 heteroatoms selected from one or more of N, O and S";

$R^3$ is

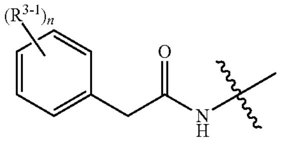

or

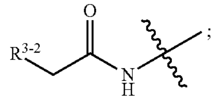

;

n is 0, 1, 2 or 3;

$R^{3-1}$ is independently halogen, hydroxyl, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy, $R^{3-2}$ is $C_3$-$C_6$ cycloalkyl substituted with one or more $R^{3-2-1}$, "5-6 membered heterocycloalkyl containing 1, 2 or 3 heteroatoms selected from one or more of N, O and S" substituted with one or more $R^{3-2-2}$, or "5-6 membered heteroaryl containing 1, 2 or 3 heteroatoms selected from one or more of N, O and S" substituted with one or more $R^{3-2-3}$;

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or $C_1$-$C_6$ alkoxy substituted with $C_1$-$C_6$ alkoxy;

m is 0, 1 or 2;

$R^2$ is oxo, halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-7}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl, phenyl substituted with one or more $R^{2-4}$, "5-6 membered heteroaryl containing 1, 2 or 3 heteroatoms selected from one or more of N, O and S", "5-6 membered heteroaryl containing 1, 2 or 3 heteroatoms selected from one or more of N, O and S" substituted with one or more $R^{2-5}$, or —(C═O)—$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, "4-6 membered heterocycloalkyl containing 1, 2 or 3 heteroatoms selected from one or more of N, O and S", "4-6 membered heterocycloalkyl containing 1, 2 or 3 heteroatoms selected from one or more of N, O and S" substituted with one or more $R^{2-7}$, phenyl, phenyl substituted with one or more $R^{2-1-1}$, "5-6 membered heteroaryl containing 1, 2 or 3 heteroatoms selected from one or more of N, O and S", "5-6 membered heteroaryl containing 1, 2 or 3 heteroatoms selected from one or more of N, O and S" substituted with one or more $R^{2-1-6}$, —$OR^{2-1-2}$, —$N(R^{2-1-3})(R^{2-1-4})$, or —$S(═O)_2$—$R^{2-1-5}$;

$R^{2-1-1}$, $R^{2-1-6}$, $R^{2-1-7}$ and $R^{2-1-8}$ are independently oxo, hydroxyl, amino, carboxyl, halogen, —CN, $C_1$-$C_6$ alkyl, $C_1$-$C_6$ alkyl substituted with one or more halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ and $R^{2-6}$ are independently $C_1$-$C_6$ alkyl;

$R^{2-4}$ and $R^{2-5}$ are independently halogen, hydroxyl, —$N(R^{2-4-1})(R^{2-4-2})$ or $C_1$-$C_6$ alkoxy; $R^{2-4-1}$ and $R^{2-4-2}$ are independently hydrogen, $C_1$-$C_6$ alkyl or $C_3$-$C_6$ cycloalkyl;

$R^{2-7}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment, in the compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof, some groups have the following definitions, and the definitions of the non-mentioned groups are as described in any of the above embodiments (hereinafter, referred to as "in a certain embodiment" in this paragraph):

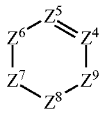

is a benzene ring or a "6 membered heteroaryl ring containing 1, 2 or 3 heteroatoms selected from N".

In a certain embodiment:

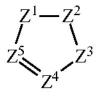

is a "5 membered heteroaryl ring containing 1 or 2 heteroatoms selected from one or more of N, O and S" or a "5 membered heteroalkenyl ring containing 1 or 2 heteroatoms selected from one or more of N, O and S".

In a certain embodiment:

I

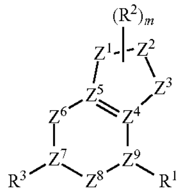

is

I-1

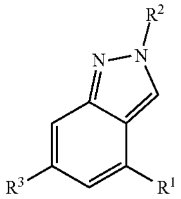 or

-continued

I-2

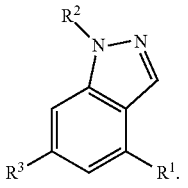

In a certain embodiment:

$R^1$ is

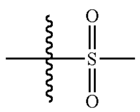, 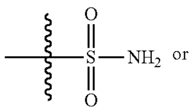 or 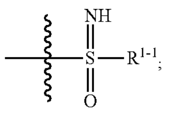

$R^{1-1}$ is $C_1$-$C_6$ alkyl.

In a certain embodiment:

$R^1$ is

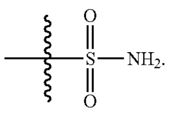 [SMILES: *S(N)(=O)=O]

In a certain embodiment:

$R^3$ is

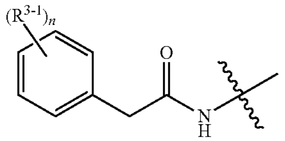 or

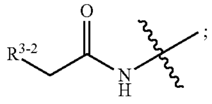

n is 1;

$R^{3-1}$ is halogen, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, or "5-6 membered heteroaryl containing 1, 2 or 3 heteroatoms selected from one or more of N, O and S" substituted with one or more $R^{3-2-3}$ $R^{3-2-1}$ and $R^{3-2-3}$ are independently halogen or hydroxyl.

In a certain embodiment:

$R^3$ is

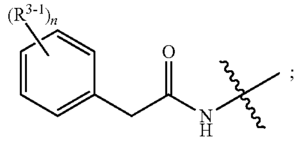

n is 1;

$R^{3-1}$ is halogen.

In a certain embodiment:

m is 0 or 1.

In a certain embodiment:

$R^2$ is halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-7}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl substituted with one or more $R^{2-1}$, or —(C═O)—$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, "4-6 membered heterocycloalkyl containing 1, 2 or 3 heteroatoms selected from one or more of N, O and S", phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —$N(R^{2-1-3})(R^{2-1-4})$, or —$S(═O)_2$—$R^{2-1-5}$;

$R^{2-1-1}$, $R^{2-1-6}$ and $R^{2-1-8}$ are independently hydroxyl, amino, halogen, —CN, $C_1$-$C_6$ alkyl, $C_1$-$C_6$ alkyl substituted with one or more halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ and $R^{2-6}$ are independently $C_1$-$C_6$ alkyl;

$R^{2-4}$ is independently halogen;

$R^{2-7}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment:

$R^2$ is $C_1$-$C_{10}$ alkyl, $C_1$-$C_{10}$ alkyl substituted with one $R^{2-1}$, or $C_3$-$C_6$ cycloalkyl;

$R^{2-1}$ is independently halogen, $C_3$-$C_6$ cycloalkyl, phenyl substituted with one or more $R^{2-1-1}$, "5-6 membered heteroaryl containing 1, 2 or 3 heteroatoms selected from one or more of N, O and S" substituted with one or more $R^{2-1-6}$, or —$OR^{2-1-2}$; $R^{2-1-1}$ and $R^{2-1-6}$ are independently amino, halogen, —CN, $C_1$-$C_6$ alkyl, $C_1$-$C_6$ alkyl substituted with one or more halogen, or —$OR^{2-1-1-1}$; $R^{2-1-1-1}$ is independently $C_1$-$C_6$ alkyl; $R^{2-1-2}$ is $C_1$-$C_6$ alkyl.

In a certain embodiment:

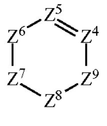

is a benzene ring or a "6 membered heteroaryl ring containing 1, 2 or 3 heteroatoms selected from N";

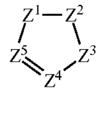

is a "5 membered heteroaryl ring containing 1 or 2 heteroatoms selected from one or more of N, O and S" or a "5 membered heteroalkenyl ring containing 1 or 2 heteroatoms selected from one or more of N, O and S";

$R^1$ is

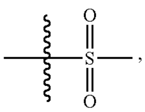,

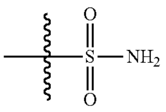 or

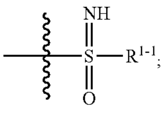

$R^{1-1}$ is $C_1$-$C_6$ alkyl;

$R^3$ is

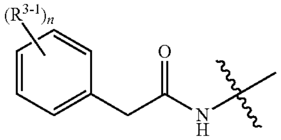 or

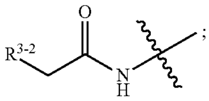

n is 1;

$R^{3-1}$ is halogen, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, or "5-6 membered heteroaryl containing 1, 2 or 3 heteroatoms selected from one or more of N, O and S" substituted with one or more $R^{3-2-3}$;

$R^{3-2-1}$ and $R^{3-2-3}$ are independently halogen or hydroxyl;

m is 0, 1 or 2;

$R^2$ is halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-7}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl substituted with one or more $R^{2-4}$, or —(C═O)—$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, "4-6 membered heterocycloalkyl containing 1, 2 or 3 heteroatoms selected from one or more of N, O and S", phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —$N(R^{2-1-3})(R^{2-1-4})$, or —$S(═O)_2$—$R^{2-1-5}$;

$R^{2-1-1}$, $R^{2-1-6}$ and $R^{2-1-8}$ are independently hydroxyl, amino, halogen, —CN, $C_1$-$C_6$ alkyl, $C_1$-$C_6$ alkyl substituted with one or more halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ and $R^{2-6}$ are independently $C_1$-$C_6$ alkyl;

$R^{2-4}$ is independently halogen;

$R^{2-7}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment:

I-1

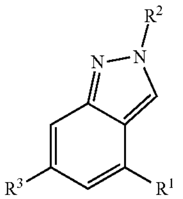

or

I-2

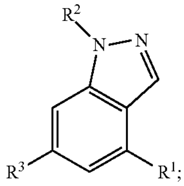

$R^1$ is

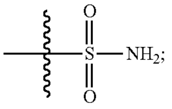 [SMILES: *S(N)(=O)=O]

$R^3$ is

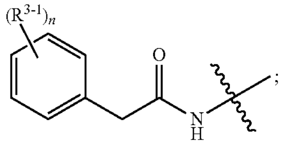

n is 1;

$R^{3-1}$ is halogen;

m is 0 or 1;

$R^2$ is $C_1$-$C_{10}$ alkyl, $C_1$-$C_{10}$ alkyl substituted with one $R^{2-1}$, or $C_3$-$C_6$ cycloalkyl;

$R^{2-1}$ is independently halogen, $C_3$-$C_6$ cycloalkyl, phenyl substituted with one or more $R^{2-1-1}$, "5-6 membered heteroaryl containing 1, 2 or 3 heteroatoms selected from one or more of N, O and S" substituted with one or more $R^{2-1-6}$, or —$OR^{2-1-2}$; $R^{2-1-1}$ and $R^{2-1-6}$ are independently amino, halogen, —CN, $C_1$-$C_6$ alkyl, $C_1$-$C_6$ alkyl substituted with one or more halogen, or —$OR^{2-1-1-1}$; $R^{2-1-1-1}$ is independently $C_1$-$C_6$ alkyl; $R^{2-1-2}$ is $C_1$-$C_6$ alkyl.

In a certain embodiment: $Z^4$ is carbon.

In a certain embodiment: $Z^5$ is carbon.

In a certain embodiment:

When

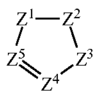

is a "5 membered heteroaryl ring containing 1 or 2 heteroatoms selected from one or more of N, O and S", the "5 membered heteroaryl ring containing 1 or 2 heteroatoms selected from one or more of N, O and S" is, for example, a "5 membered heteroaryl ring containing 1 or 2 heteroatoms selected from N", and for another example, a pyrrole ring, a pyrazole ring or an imidazole ring.

In a certain embodiment:

When

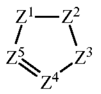

is a "5 membered heteroalkenyl ring containing 1, 2 or 3 heteroatoms selected from one or more of N, O and S", the "5 membered heteroalkenyl ring containing 1, 2 or 3 heteroatoms selected from one or more of N, O and S" is, for example, a "5 membered heteroalkenyl ring containing 1 or 2 heteroatoms selected from N", and for another example, a 2,5-dihydropyrrole ring.

In a certain embodiment:

I

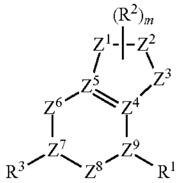

is, for example,

I-1

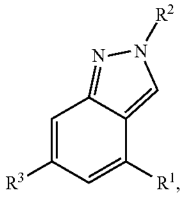

,

I-2

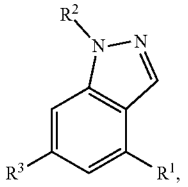

,

I-3

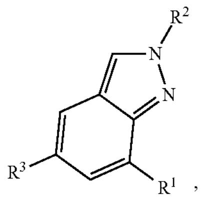

,

I-4

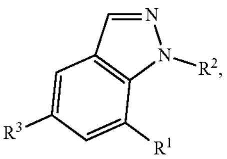

-continued

I-5

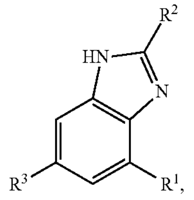

I-6

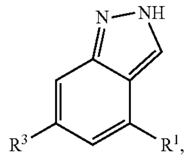

I-7

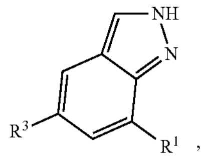

I-8

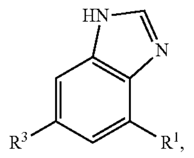

I-9

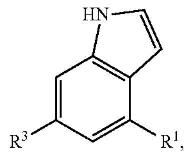

I-10

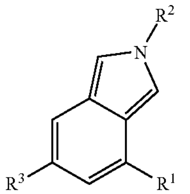

or

I-11

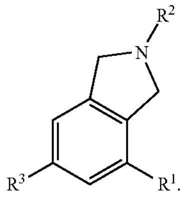

In a certain embodiment:

When $R^{1-1}$ is $C_1$-$C_6$ alkyl, the $C_1$-$C_6$ alkyl is, for example, $C_1$-$C_4$ alkyl, and for another example, methyl, ethyl, n-propyl, isopropyl, n-butyl, isobutyl, sec-butyl or tert-butyl.

In a certain embodiment:

When n is 1 or 2, $R^{3-1}$ can be independently located in the ortho-, meta- or para-position relative to

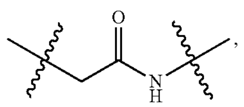

and can also be independently located in the ortho-position relative to

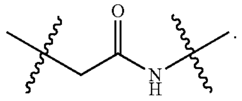 [SMILES: *CC(=O)N*]

In a certain embodiment:

When $R^{3-1}$ is halogen, the halogen is, for example, fluorine, chlorine, bromine or iodine, and for another example, chlorine.

In a certain embodiment:

When $R^{3-1}$ is $C_1$-$C_6$ alkyl, the $C_1$-$C_6$ alkyl is, for example, $C_1$-$C_4$ alkyl, and for another example, methyl, ethyl, n-propyl, isopropyl, n-butyl, isobutyl, sec-butyl or tert-butyl.

In a certain embodiment:

When $R^{3-1}$ is $C_1$-$C_6$ alkoxy, the $C_1$-$C_6$ alkoxy is, for example, $C_1$-$C_4$ alkoxy, and for another example, methoxy, ethoxy, n-propoxy, isopropoxy, n-butoxy, isobutoxy, sec-butoxy or tert-butoxy.

In a certain embodiment:

When $R^{3-1}$ is $C_1$-$C_6$ alkoxy substituted with $C_1$-$C_6$ alkoxy, the $C_1$-$C_6$ alkoxy is, for example, $C_1$-$C_4$ alkoxy, and for another example, methoxy, ethoxy, n-propoxy, isopropoxy, n-butoxy, isobutoxy, sec-butoxy or tert-butoxy.

In a certain embodiment:

When $R^{3-1}$ is $C_1$-$C_6$ alkoxy substituted with $C_1$-$C_6$ alkoxy, the $C_1$-$C_6$ alkoxy substituted with $C_1$-$C_6$ alkoxy is, for example,

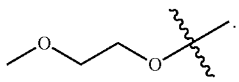

In a certain embodiment:

When $R^{3-2}$ is $C_3$-$C_6$ cycloalkyl substituted with one or more $R^{3-2-1}$, the $C_3$-$C_6$ cycloalkyl is, for example, cyclopropyl, cyclobutyl, cyclopentyl or cyclohexyl.

When $R^{3-2}$ is $C_3$-$C_6$ cycloalkyl substituted with one or more $R^{3-2-1}$, the $C_3$-$C_6$ cycloalkyl substituted with one $R^{3-2-1}$ is, for example,

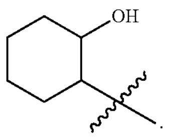 [SMILES: *C1CCCCC1O]

In a certain embodiment:

When $R^{3-2-3}$ is halogen, the halogen is, for example, fluorine, chlorine, bromine or iodine, and for another example, chlorine.

In a certain embodiment:

When $R^{3-2}$ is "5-6 membered heteroaryl containing 1, 2 or 3 heteroatoms selected from one or more of N, O and S" substituted with one or more $R^{3-2-3}$, the "5-6 membered heteroaryl containing 1, 2 or 3 heteroatoms selected from one or more of N, O and S" is, for example, "5-6 membered heteroaryl containing 1 or 2 heteroatoms selected from N", and for another example, pyridinyl.

In a certain embodiment:

When $R^{3-2}$ is "5-6 membered heteroaryl containing 1, 2 or 3 heteroatoms selected from one or more of N, O and S" substituted with one or more $R^{3-2-3}$, the "5-6 membered heteroaryl containing 1, 2 or 3 heteroatoms selected from one or more of N, O and S" substituted with one $R^{3-2-3}$ is, for example,

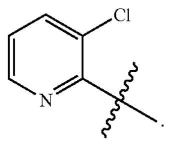 [SMILES: *c1ncccc1Cl]

In a certain embodiment:

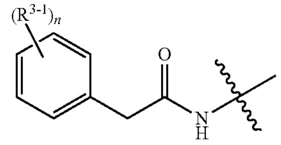

can be

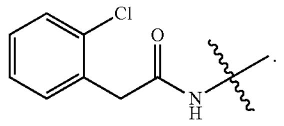 [SMILES: *NC(=O)Cc1ccccc1Cl]

In a certain embodiment:

When $R^2$ is halogen, the halogen is, for example, fluorine, chlorine, bromine or iodine, and for another example, chlorine.

In a certain embodiment:

When $R^2$ is $C_1$-$C_{10}$ alkyl, the $C_1$-$C_{10}$ alkyl is, for example, $C_1$-$C_6$ alkyl, for another example, $C_1$-$C_5$ alkyl, and for still another example, methyl, ethyl, n-propyl, isopropyl, n-butyl, isobutyl, sec-butyl, tert-butyl, n-pentyl, isopentyl or

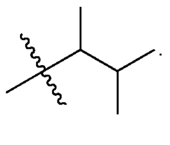 [SMILES: *C(C)C(C)C]

In a certain embodiment:

When $R^2$ is $C_1$-$C_{10}$ alkyl substituted with one or more $R^{2-1}$, the $C_1$-$C_{10}$ alkyl is, for example, $C_1$-$C_6$ alkyl, for another example, $C_1$-$C_4$ alkyl, for still another example, methyl, ethyl, n-propyl, isopropyl, n-butyl, isobutyl, sec-butyl or tert-butyl, and for yet another example, methyl, ethyl, isopropyl or isobutyl.

In a certain embodiment:

When $R^{2-1}$ is halogen, the halogen is, for example, fluorine, chlorine, bromine or iodine, and for another example, fluorine.

In a certain embodiment:

When $R^{2-1}$ is $C_3$-$C_6$ cycloalkyl, the $C_3$-$C_6$ cycloalkyl is, for example, cyclopropyl, cyclobutyl, cyclopentyl or cyclohexyl.

In a certain embodiment:

When $R^{2-1}$ is $C_3$-$C_6$ cycloalkyl substituted with one or more $R^{2-1-8}$, the $C_3$-$C_6$ cycloalkyl is, for example, cyclopropyl, cyclobutyl, cyclopentyl or cyclohexyl.

In a certain embodiment:

When $R^{2-1}$ is "4-6 membered heterocycloalkyl containing 1, 2 or 3 heteroatoms selected from one or more of N, O and S", the "4-6 membered heterocycloalkyl containing 1, 2 or 3 heteroatoms selected from one or more of N, O and S" is, for example, "5 or 6 membered heterocycloalkyl containing 1 or 2 heteroatoms selected from one or more of N, O and S", for another example, tetrahydrofuranyl, morpholinyl or tetrahydropyranyl, and for still another example, tetrahydrofuranyl-2-yl, tetrahydrofuranyl-3-yl, morpholin-1-yl or tetrahydropyranyl-4-yl.

In a certain embodiment:

When $R^{2-1}$ is "5-6 membered heteroaryl containing 1, 2 or 3 heteroatoms selected from one or more of N, O and S" substituted with one or more $R^{2-1-6}$, the "5-6 membered heteroaryl containing 1, 2 or 3 heteroatoms selected from one or more of N, O and S" is, for example, 5-6 membered heteroaryl containing 1 heteroatom selected from one or more of N, O and S, for another example, pyridinyl, and for still another example, pyridin-3-yl or pyridin-4-yl.

In a certain embodiment:

$R^{2-1-1}$ can be independently located in the ortho-, meta- or para-position relative to phenyl.

In a certain embodiment:

$R^{2-1-6}$ can be independently located in the ortho-, meta- or para-position relative to 6 membered heteroaryl.

In a certain embodiment:

$R^{2-1-6}$ can be independently located in the ortho- or meta-position relative to 5 membered heteroaryl.

In a certain embodiment:

When $R^{2-1-1}$ is halogen, the halogen is, for example, fluorine, chlorine, bromine or iodine, and for another example, fluorine or chlorine.

In a certain embodiment:

When $R^{2-1-1}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-1}$ is $C_1$-$C_6$ alkyl substituted with one or more halogen, the halogen is, for example, fluorine, chlorine, bromine or iodine, and for another example, fluorine.

In a certain embodiment:

When $R^{2-1-1}$ is $C_1$-$C_6$ alkyl substituted with one or more halogen, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-1}$ is $C_1$-$C_6$ alkyl substituted with one or more halogen, the $C_1$-$C_6$ alkyl substituted with a plurality of halogen is, for example, trifluoromethyl.

In a certain embodiment:

When $R^{2-1-6}$ is halogen, the halogen is, for example, fluorine, chlorine, bromine or iodine, and for another example, fluorine.

In a certain embodiment:

When $R^{2-1-1-1}$, $R^{2-1-1-2}$ and $R^{2-1-1-3}$ are $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl.

In a certain embodiment:

When $R^{2-1-2}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-2}$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-1-3}$ and $R^{2-1-4}$ are $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-3}$ and $R^{2-1-4}$ are $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-1-5}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-5}$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^2$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-3}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl, ethyl or isopropyl.

In a certain embodiment:

When $R^2$ is $C_3$-$C_6$ cycloalkyl substituted with one or more $R^{2-3}$, the $C_3$-$C_6$ cycloalkyl is, for example, cyclopropyl, cyclobutyl, cyclopentyl or cyclohexyl, and for another example, cyclopropyl.

In a certain embodiment:

When $R^2$ is $C_2$-$C_6$ alkenyl, the $C_2$-$C_6$ alkenyl is, for example, $C_2$-$C_4$ alkenyl, and for another example, vinyl or propenyl.

In a certain embodiment:

When $R^2$ is $C_2$-$C_6$ alkenyl substituted with one or more $R^{2-7}$, the $C_2$-$C_6$ alkenyl is, for example, $C_2$-$C_4$alkenyl, and for another example, vinyl or propenyl.

In a certain embodiment:

When $R^{2-7}$ is halogen, the halogen is, for example, fluorine, chlorine, bromine or iodine, and for another example, fluorine.

In a certain embodiment:

When $R^2$ is "4 membered heterocycloalkyl containing 1 heteroatom selected from one of N, O and S", the "4 membered heterocycloalkyl containing 1 heteroatom selected from one of N, O and S" is, for example, oxetanyl, and for another example, oxetan-3-yl.

In a certain embodiment:

When $R^2$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl.

In a certain embodiment:

When $R^2$ is "4-6 membered heterocycloalkyl containing 1, 2 or 3 heteroatoms selected from one or more of N, O and S" substituted with one or more $R^{2-6}$, the "4-6 membered heterocycloalkyl containing 1, 2 or 3 heteroatoms selected from one or more of N, O and S" is, for example, "4-6 membered heterocycloalkyl containing 1 heteroatom selected from one of N, O and S", for another example, oxetanyl, and for still another example, oxetan-3-yl.

In a certain embodiment:

$R^{2-4}$ can be independently located in the ortho-, meta- or para-position relative to phenyl.

In a certain embodiment:

When $R^{2-4}$ is halogen, the halogen is, for example, fluorine, chlorine, bromine or iodine, and for another example, fluorine or chlorine.

In a certain embodiment:

When $R^{2-2}$ is $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, isopropyl.

In a certain embodiment:

When $R^{2-2}$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

$R^{2-2-1}$ can be independently located in the ortho-, meta- or para-position relative to phenyl.

In a certain embodiment:

When $R^{2-2-1}$ is halogen, the halogen is, for example, fluorine, chlorine, bromine or iodine, and for another example, fluorine.

In a certain embodiment:

I

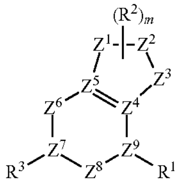

wherein

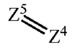

is a single bond or a double bond;

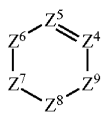

is a benzene ring, a "6 membered heteroalkyl ring containing 1, 2 or 3 heteroatoms selected from one or more of N, O and S", a "6 membered heteroalkenyl ring containing 1, 2 or 3 heteroatoms selected from one or more of N, O and S", or a "6 membered heteroaryl ring containing 1, 2 or 3 heteroatoms selected from one or more of N, O and S";

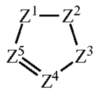

is a “5 membered heteroaryl ring containing 1, 2 or 3 heteroatoms selected from one or more of N, O and S” or a “5 membered heteroalkenyl ring containing 1, 2 or 3 heteroatoms selected from one or more of N, O and S”;

$R^1$ is

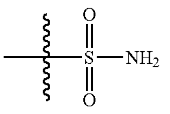

or

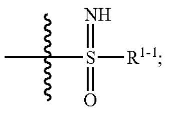

$R^{1-1}$ is halogen, hydroxyl, amino, —$NHR^{1-1-4}$, —$N(R^{1-1-5})(R^{1-1-6})$, $C_1$-$C_6$ alkyl, $C_3$-$C_6$ cycloalkyl, $C_1$-$C_6$ alkyl substituted with one or more $R^{1-1-1}$, $C_3$-$C_6$ cycloalkyl substituted with one or more $R^{1-1-2}$, or “4-7 membered heterocycloalkyl containing 1, 2 or 3 heteroatoms selected from one or more of N, O and S” substituted with one or more $R^{1-1-3}$;

$R^{1-1-1}$, $R^{1-1-2}$, $R^{1-1-3}$, $R^{1-1-4}$, $R^{1-1-5}$ and $R^{1-1-6}$ are independently halogen, hydroxyl, $C_1$-$C_6$ alkyl, $C_3$-$C_6$ cycloalkyl, $C_1$-$C_6$ alkoxy or “4-7 membered heterocycloalkyl containing 1, 2 or 3 heteroatoms selected from one or more of N, O and S”;

$R^3$ is

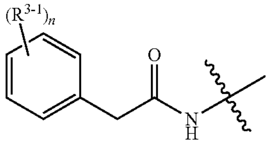

or

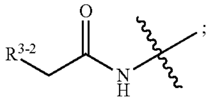

n is 0, 1, 2 or 3;

$R^{3-1}$ is independently halogen, hydroxyl, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, “5-6 membered heterocycloalkyl containing 1, 2 or 3 heteroatoms selected from one or more of N, O and S” substituted with one or more $R^{3-2-2}$, or “5-6 membered heteroaryl containing 1, 2 or 3 heteroatoms selected from one or more of N, O and S” substituted with one or more $R^{3-2-3}$;

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or $C_1$-$C_6$ alkoxy substituted with $C_1$-$C_6$ alkoxy;

m is 0 or 1;

$R^2$ is oxo, cyano, $C_1$-$C_{10}$ alkyl, $C_1$-$C_{10}$ alkyl substituted with one or more $R^{2-1}$, $C_3$-$C_6$ cycloalkyl, $C_3$-$C_6$ cycloalkyl substituted with one or more $R^{2-3}$, “5-6 membered heterocycloalkyl containing 1, 2 or 3 heteroatoms selected from one or more of N, O and S”, phenyl, phenyl substituted with one or more $R^{2-4}$, “5-6 membered heteroaryl containing 1, 2 or 3 heteroatoms selected from one or more of N, O and S”, “5-6 membered heteroaryl containing 1, 2 or 3 heteroatoms selected from one or more of N, O and S” substituted with one or more $R^{2-5}$, or —(C═O)—$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, “4-6 membered heterocycloalkyl containing 1, 2 or 3 heteroatoms selected from one or more of N, O and S”, “4-6 membered heterocycloalkyl containing 1, 2 or 3 heteroatoms selected from one or more of N, O and S” substituted with one or more $R^{2-1-7}$, phenyl, phenyl substituted with one or more $R^{2-1-4}$, “5-6 membered heteroaryl containing 1, 2 or 3 heteroatoms selected from one or more of N, O and S”, “5-6 membered heteroaryl containing 1, 2 or 3 heteroatoms selected from one or more of N, O and S” substituted with one or more $R^{2-1-6}$, —$OR^{2-1-2}$, —$N(R^{2-1-3})(R^{2-1-4})$, or —S(═O)$_2$—$R^{2-1-5}$;

$R^{2-1-1}$, $R^{2-1-6}$, $R^{2-1-7}$ and $R^{2-1-8}$ are independently oxo, hydroxyl, amino, carboxyl, halogen, —CN, $C_1$-$C_6$alkyl, $C_1$-$C_6$ alkyl substituted with one or more halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ and $R^{2-5}$ are independently halogen, hydroxyl, —$N(R^{2-4-1})(R^{2-4-2})$ or $C_1$-$C_6$ alkoxy; $R^{2-4-1}$ and $R^{2-4-2}$ are independently hydrogen, $C_1$-$C_6$ alkyl or $C_3$-$C_6$ cycloalkyl;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment, in the compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof, some groups have the following definitions, and the definitions of the non-mentioned groups are as described in any of the above embodiments (hereinafter, referred to as “in a certain embodiment” in this paragraph):

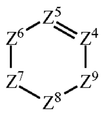

is a benzene ring or a “6 membered heteroaryl ring containing 1, 2 or 3 heteroatoms selected from N”.

In a certain embodiment:

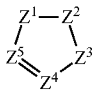

is a “5 membered heteroaryl ring containing 1 or 2 heteroatoms selected from one or more of N, O and S”.

In a certain embodiment:

The compound of formula I is

I-1

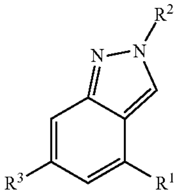

or

I-2

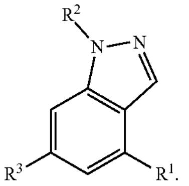

In a certain embodiment:

$R^1$ is

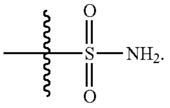

In a certain embodiment:

$R^3$ is

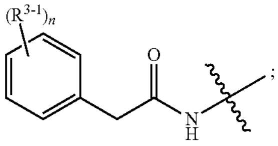

n is 1; $R^{3-1}$ is halogen.

In a certain embodiment:

$R^2$ is cyano, $C_1$-$C_{10}$ alkyl, $C_1$-$C_{10}$ alkyl substituted with one or more $R^{2-1}$, $C_3$-$C_6$ cycloalkyl, $C_3$-$C_6$ cycloalkyl substituted with one or more $R^{2-3}$, phenyl substituted with one or more $R^{2-4}$, or —(C═O)—$R^{2-2}$.

In a certain embodiment:

$R^2$ is $C_1$-$C_{10}$ alkyl, $C_1$-$C_{10}$ alkyl substituted with one $R^{2-1}$, or $C_3$-$C_6$ cycloalkyl.

In a certain embodiment:

$R^{2-1}$ is independently hydroxyl, halogen, $C_3$-$C_6$ cycloalkyl, phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —N($R^{2-1-3}$)($R^{2-1-4}$), or —S(═O)$_2$—$R^{2-1-5}$;

$R^{2-1-1}$ and $R^{2-1-6}$ are independently hydroxyl, halogen, —$OR^{2-1-1-1}$, or —N($R^{2-1-1-2}$)($R^{2-1-1-3}$); $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl.

In a certain embodiment:

$R^{2-1}$ is independently halogen, $C_3$-$C_6$ cycloalkyl, phenyl substituted with one or more $R^{2-1-1}$, or —$OR^{2-1-2}$; $R^{2-1-1}$ is halogen; $R^{2-1-2}$ is $C_1$-$C_6$ alkyl.

In a certain embodiment:

$R^{2-3}$ is independently $C_1$-$C_6$ alkyl.

In a certain embodiment:

$R^{2-4}$ is independently halogen.

In a certain embodiment:

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment:

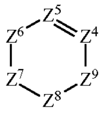

is a benzene ring or a "6 membered heteroaryl ring containing 1, 2 or 3 heteroatoms selected from N";

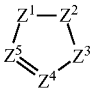

is a "5 membered heteroaryl ring containing 1 or 2 heteroatoms selected from one or more of N, O and S";

$R^1$ is

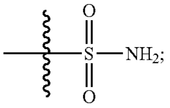 [SMILES: *S(N)(=O)=O]

$R^3$ is

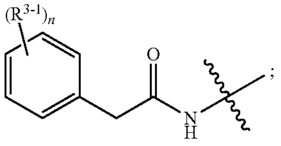

n is 1;

$R^{3-1}$ is halogen;

m is 0 or 1;

$R^2$ is cyano, $C_1$-$C_{10}$ alkyl, $C_1$-$C_{10}$ alkyl substituted with one or more $R^{2-1}$, $C_3$-$C_6$ cycloalkyl, $C_3$-$C_6$ cycloalkyl substituted with one or more $R^{2-3}$, phenyl substituted with one or more $R^{2-4}$, or —(C═O)—$R^{2-2}$;

$R^{2-1}$ is independently hydroxyl, halogen, $C_3$-$C_6$ cycloalkyl, phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —N($R^{2-1-3}$)($R^{2-1-4}$), or —S(═O)$_2$—$R^{2-1-5}$;

$R^{2-1-1}$ and $R^{2-1-6}$ are independently hydroxyl, halogen, —$OR^{2-1-1-1}$, or —N($R^{2-1-1-2}$)($R^{2-1-1-3}$); $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

In a certain embodiment:

I-1

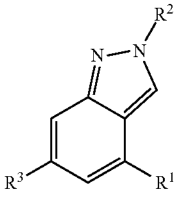

or

I-2

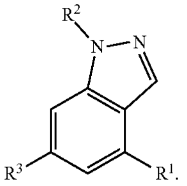

$R^1$ is

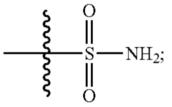 [SMILES: *S(N)(=O)=O]

$R^3$ is H;

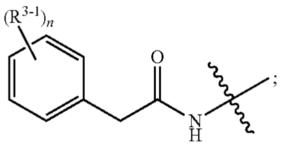

n is 1;

$R^{3-1}$ is halogen;

m is 0 or 1;

$R^2$ is $C_1$-$C_{10}$ alkyl, $C_1$-$C_{10}$ alkyl substituted with one $R^{2-1}$, or $C_3$-$C_6$ cycloalkyl;

$R^{2-1}$ is independently halogen, $C_3$-$C_6$ cycloalkyl, phenyl substituted with one or more $R^{2-1-1}$, or —$OR^{2-1-2}$; $R^{2-1-1}$ is halogen; $R^{2-1-2}$ is $C_1$-$C_6$ alkyl.

In a certain embodiment:

When

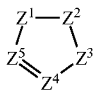

is a "5 membered heteroaryl ring containing 1 or 2 heteroatoms selected from one or more of N, O and S", the "5 membered heteroaryl ring containing 1 or 2 heteroatoms selected from one or more of N, O and S" is, for example, a "5 membered heteroaryl ring containing 1 or 2 heteroatoms selected from N", and for another example, a pyrrole ring, a pyrazole ring or an imidazole ring.

In a certain embodiment:

I

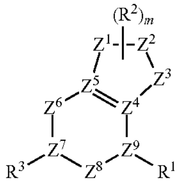

is, for example,

I-1

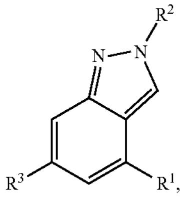

I-2

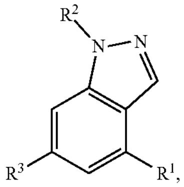

I-3

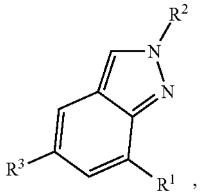

I-4

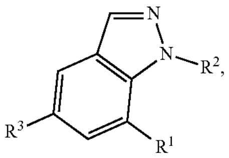

I-5

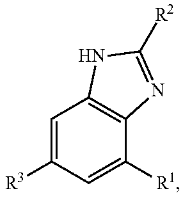

I-6

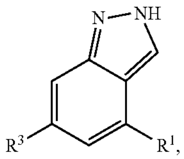

-continued

I-7

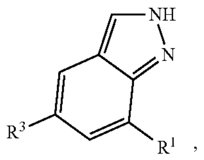

I-8

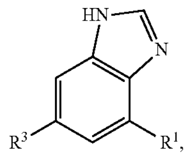

I-9

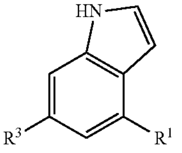

or

I-10

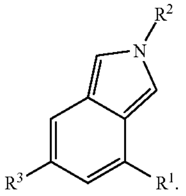

In a certain embodiment:

When $R^{3-1}$ is independently halogen, the halogen is, for example, fluorine, chlorine, bromine or iodine, and for another example, chlorine.

In a certain embodiment:

When n is 1 or 2, $R^{3-1}$ can be independently located in the ortho-, meta- or para-position relative to

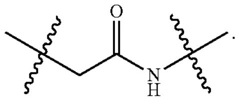 [SMILES: *CC(=O)N*]

In a certain embodiment:

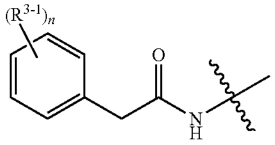

is

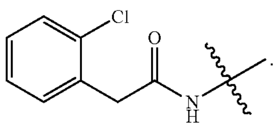 [SMILES: *NC(=O)Cc1ccccc1Cl]

In a certain embodiment:

When $R^2$ is $C_1$-$C_{10}$ alkyl, the $C_1$-$C_{10}$ alkyl is, for example, $C_1$-$C_6$ alkyl, for another example, $C_1$-$C_5$ alkyl, and for still another example, methyl, ethyl, n-propyl, isopropyl, n-butyl, isobutyl, sec-butyl, tert-butyl, n-pentyl, isopentyl or

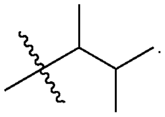 [SMILES: *C(C)C(C)C]

In a certain embodiment:

When $R^2$ is $C_1$-$C_{10}$ alkyl substituted with one or more $R^{2-1}$, the $C_1$-$C_{10}$ alkyl is, for example, $C_1$-$C_6$ alkyl, for another example, $C_1$-$C_4$ alkyl, for still another example, methyl, ethyl, n-propyl, isopropyl, n-butyl, isobutyl, sec-butyl or tert-butyl, and for yet another example, methyl, ethyl, isopropyl or isobutyl.

In a certain embodiment:

When $R^{2-1}$ is independently halogen, the halogen is, for example, fluorine, chlorine, bromine or iodine, and for another example, fluorine.

In a certain embodiment:

When $R^{2-1}$ is independently $C_3$-$C_6$ cycloalkyl, the $C_3$-$C_6$ cycloalkyl is, for example, cyclopropyl, cyclobutyl, cyclopentyl or cyclohexyl.

In a certain embodiment:

When $R^{2-1}$ is independently "5-6 membered heteroaryl containing 1, 2 or 3 heteroatoms selected from one or more of N, O and S" substituted with one or more $R^{2-1-6}$, the "5-6 membered heteroaryl containing 1, 2 or 3 heteroatoms selected from one or more of N, O and S" is, for example, 5-6 membered heteroaryl containing 1 heteroatom selected from one or more of N, O and S, for another example, pyridinyl, and for still another example, pyridin-4-yl.

In a certain embodiment:

$R^{2-1-1}$ can be independently located in the ortho-, meta- or para-position relative to phenyl.

In a certain embodiment:

$R^{2-1-6}$ can be independently located in the ortho-, meta- or para-position relative to 6 membered heteroaryl.

In a certain embodiment:

$R^{2-1-6}$ can be independently located in the ortho- or meta-position relative to 5 membered heteroaryl.

In a certain embodiment:

When $R^{2-1-1}$ is independently halogen, the halogen is, for example, fluorine, chlorine, bromine or iodine, and for another example, fluorine.

In a certain embodiment:

When $R^{2-1-6}$ is independently halogen, the halogen is, for example, fluorine, chlorine, bromine or iodine, and for another example, fluorine.

In a certain embodiment:

When $R^{2-1-1-1}$, $R^{2-1-1-2}$ and $R^{2-1-1-3}$ are independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl.

In a certain embodiment:

When $R^{2-1-2}$ is independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-2}$ is independently $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-1-3}$ and $R^{2-1-4}$ are independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-3}$ and $R^{2-1-4}$ are independently $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^{2-1-5}$ is independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl or isopropyl.

In a certain embodiment:

When $R^{2-1-5}$ is independently $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^2$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

When $R^2$ is $C_3$-$C_6$ cycloalkyl substituted with one or more $R^{2-3}$, the $C_3$-$C_6$ cycloalkyl is, for example, cyclopropyl, cyclobutyl, cyclopentyl or cyclohexyl, and for another example, cyclopropyl.

In a certain embodiment:

When $R^{2-3}$ is independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, methyl, ethyl or isopropyl.

In a certain embodiment:

$R^{2-4}$ can be independently located in the ortho-, meta- or para-position relative to phenyl.

In a certain embodiment:

When $R^{2-4}$ is independently halogen, the halogen is, for example, fluorine, chlorine, bromine or iodine, and for another example, fluorine or chlorine.

In a certain embodiment:

When $R^{2-2}$ is independently $C_1$-$C_6$ alkyl, the $C_1$-$C_6$ alkyl is, for example, $C_1$-$C_4$ alkyl, for another example, methyl, ethyl, n-propyl, isopropyl, n-butyl, isobutyl, sec-butyl or tert-butyl, and for still another example, isopropyl.

In a certain embodiment:

When $R^{2-2}$ is $C_3$-$C_6$ cycloalkyl, the $C_3$-$C_6$ cycloalkyl is, for example, cyclopropyl, cyclobutyl, cyclopentyl or cyclohexyl, and for another example, cyclopropyl.

In a certain embodiment:

$R^{2-2-1}$ can be independently located in the ortho-, meta- or para-position relative to phenyl.

In a certain embodiment:

When $R^{2-2-1}$ is independently halogen, the halogen is, for example, fluorine, chlorine, bromine or iodine, and for another example, fluorine.

In a certain embodiment, the compound containing a benzene ring represented by formula I is any one of the following compounds:

1

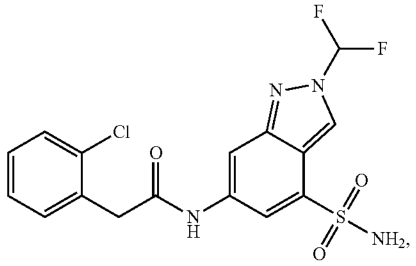

2

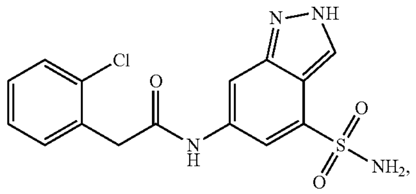

3-A

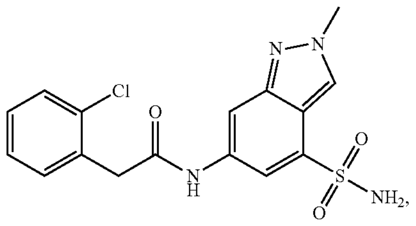

3-B

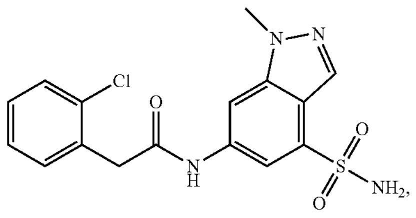

4-A

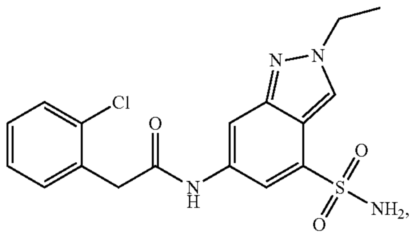

4-B

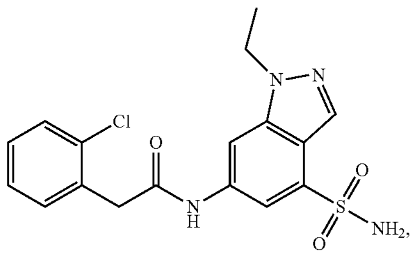

-continued
5-A
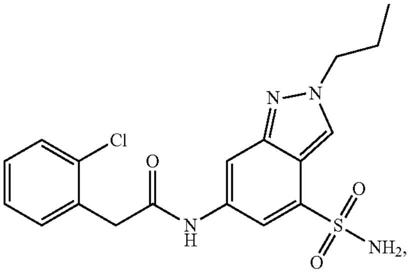
,
5-B
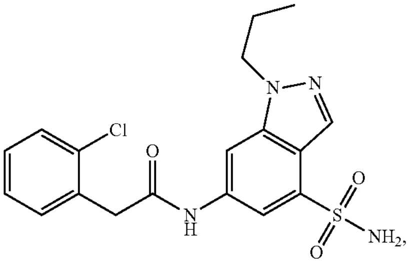
,
6-A
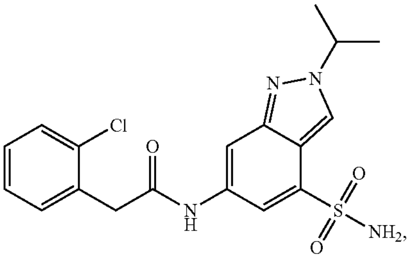
,
6-B
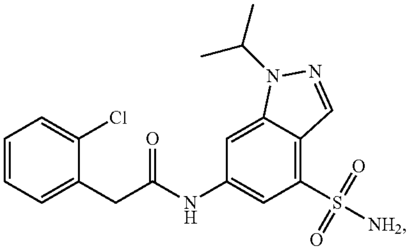
,
7-A
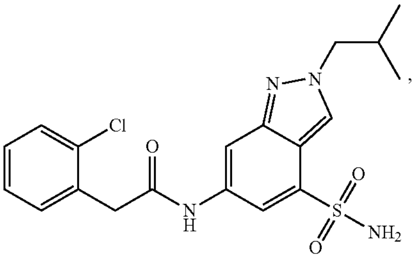
,
7-B
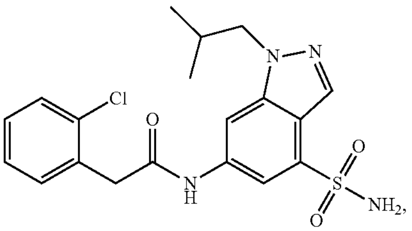
,
-continued
8-A
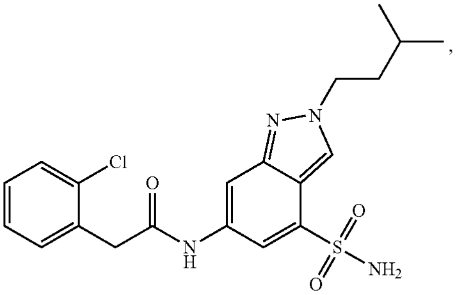
,
8-B
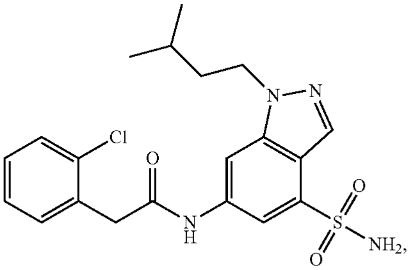
,
9
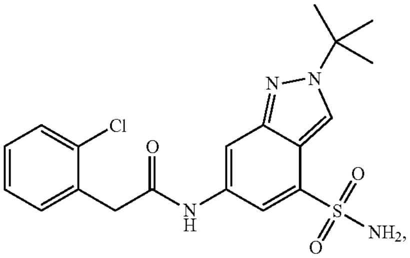
,
10
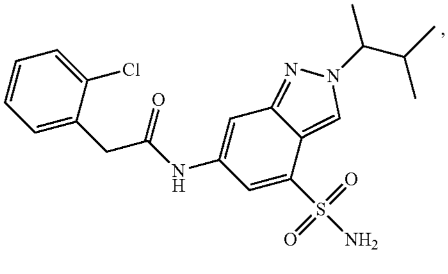
,
11
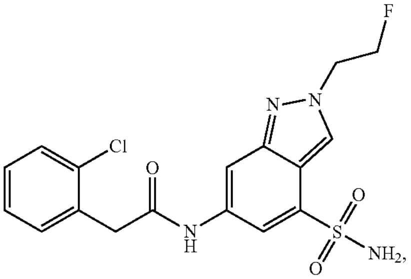
, -continued
12-A
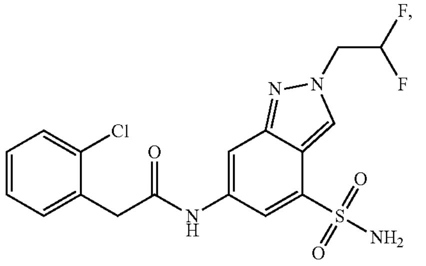
12-B
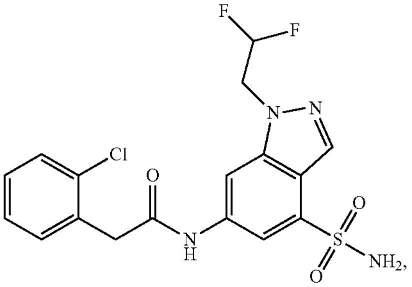
13
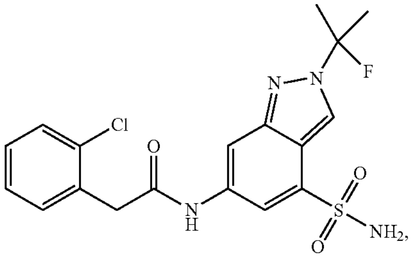
14-A
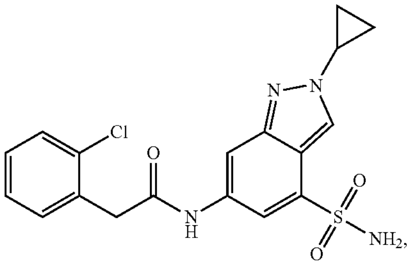
14-B
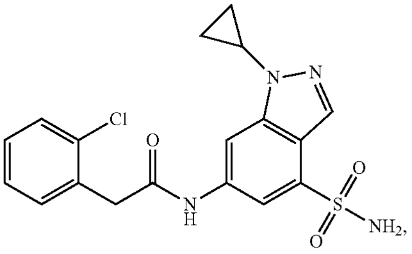
15-A
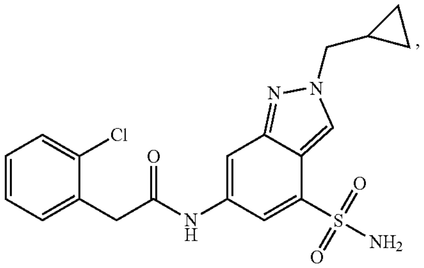
-continued
15-B
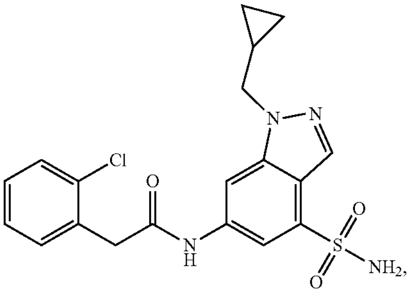
16-A
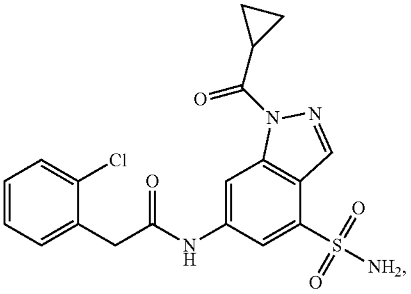
16-B
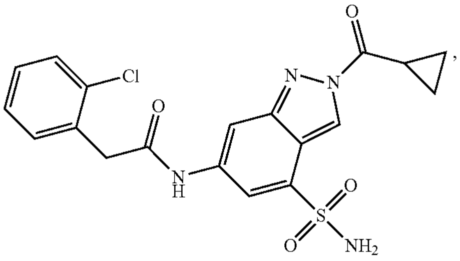
17
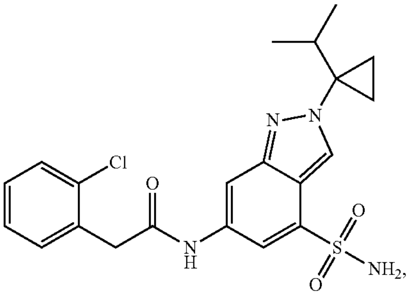
18
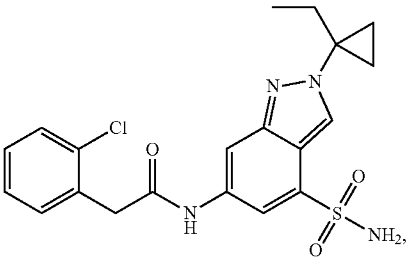

-continued
19
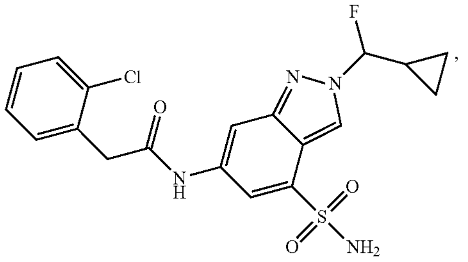
20
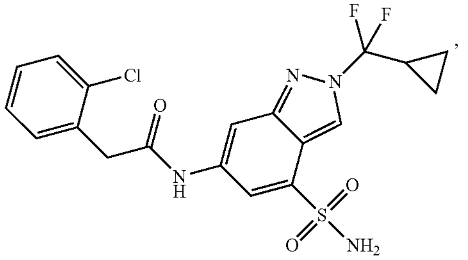
21
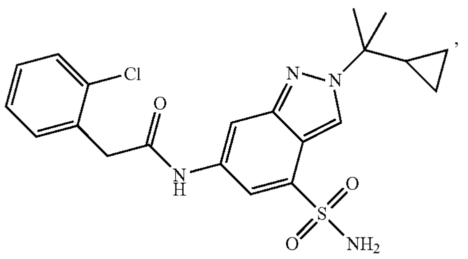
22
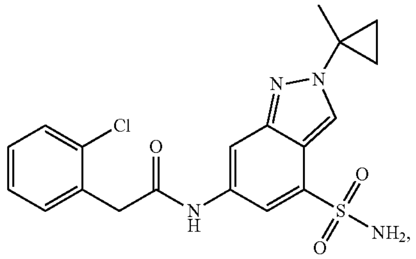
23
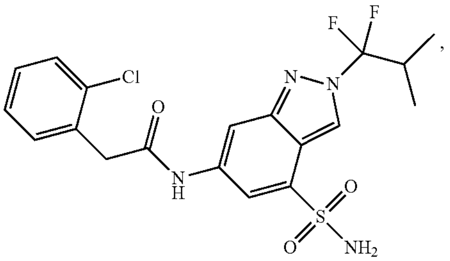
24-A
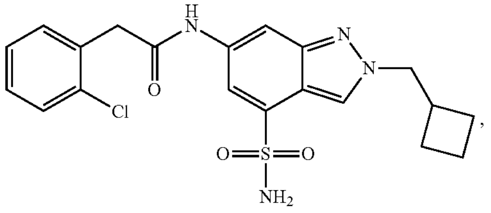
-continued
24-B
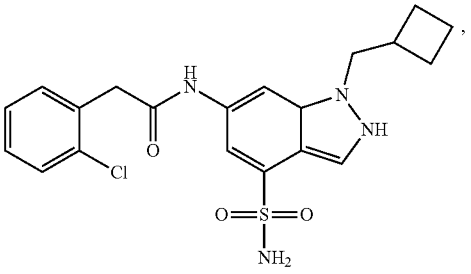
25
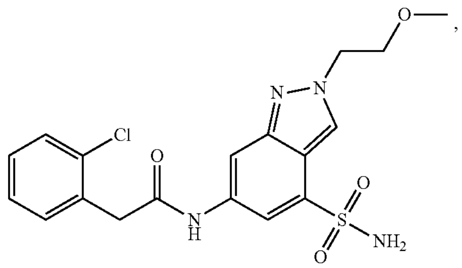
25A
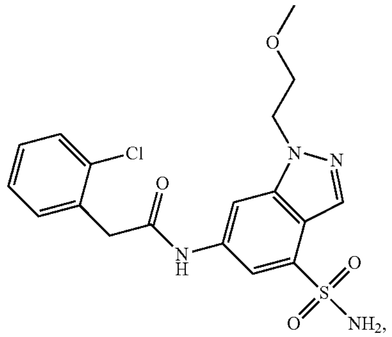
26-A
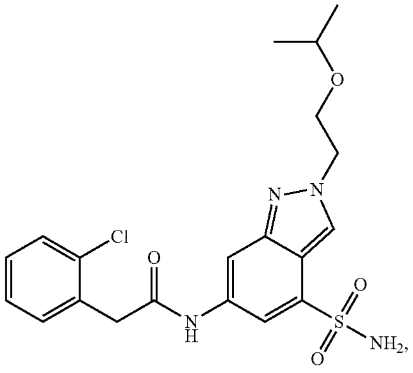
26-B
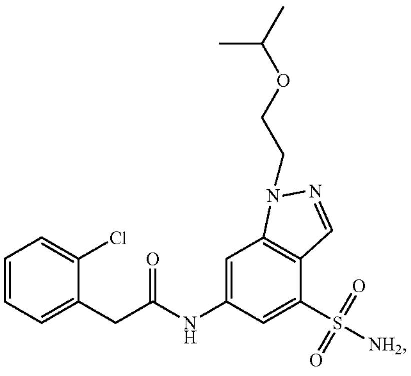

-continued
27-A
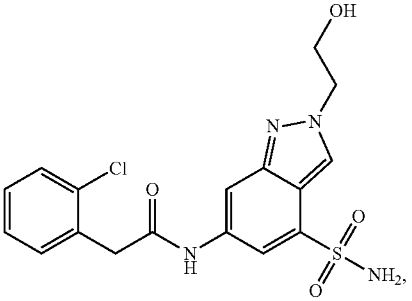
27-B
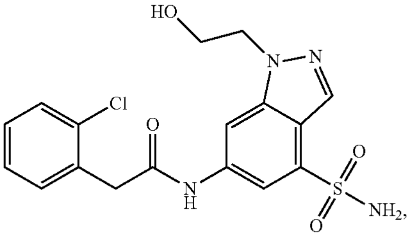
28
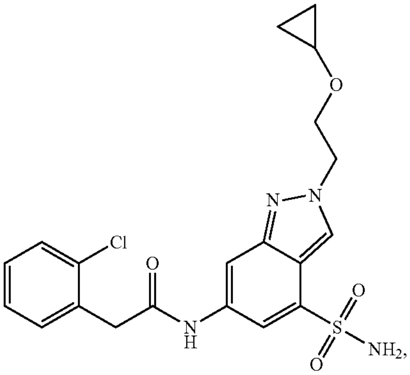
29
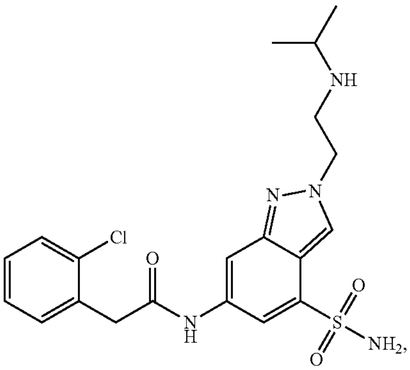
30
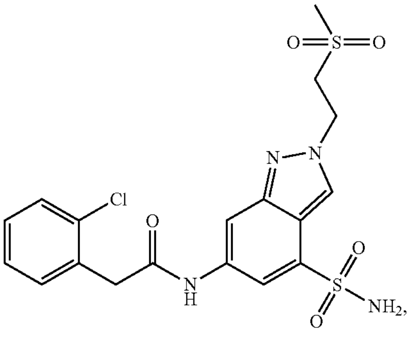
-continued
31-A
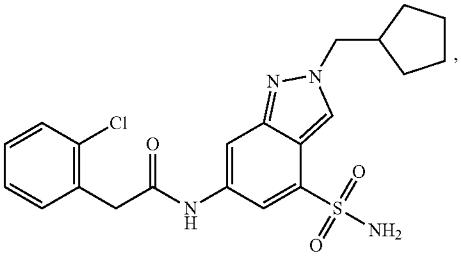
31-B
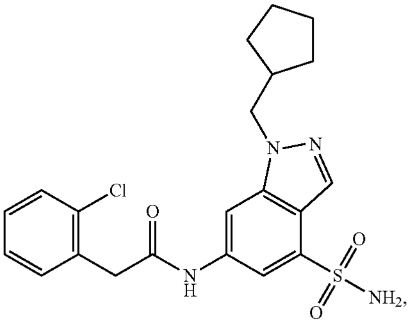
32-A
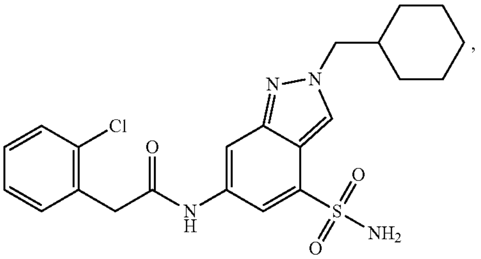
32-B
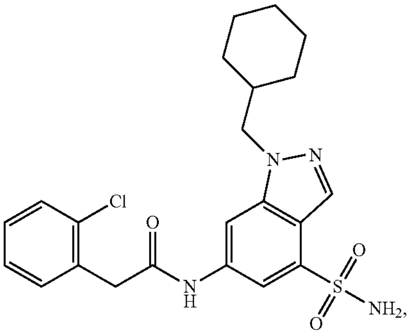
33
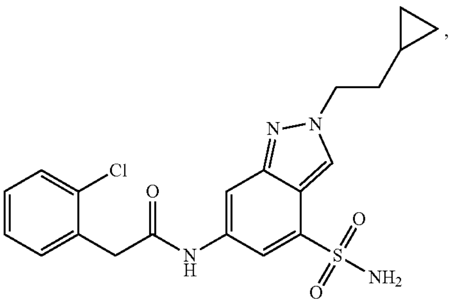

-continued
34
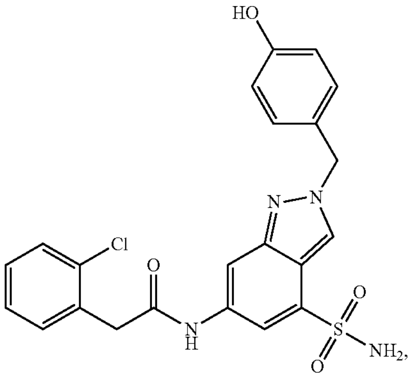
35-A
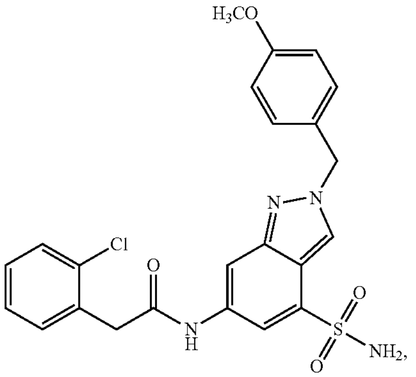
35-B
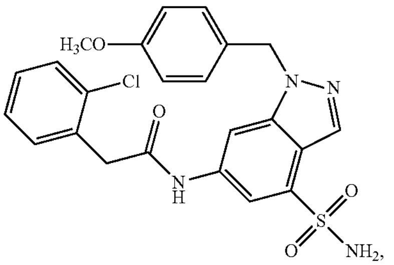
36-A
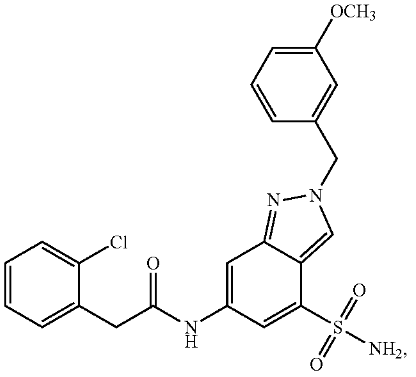
-continued
36-B
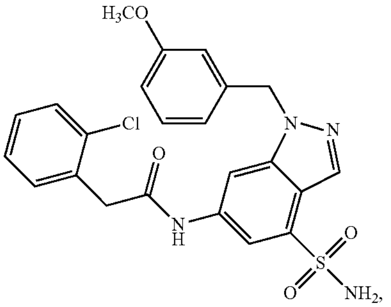
37-A
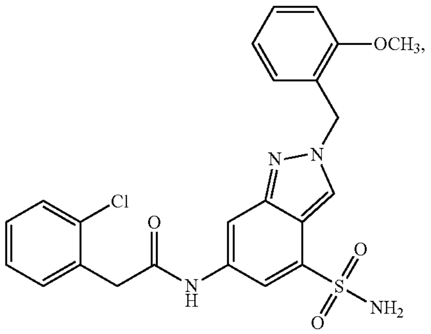
37-B
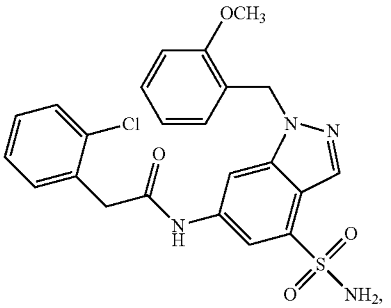
38
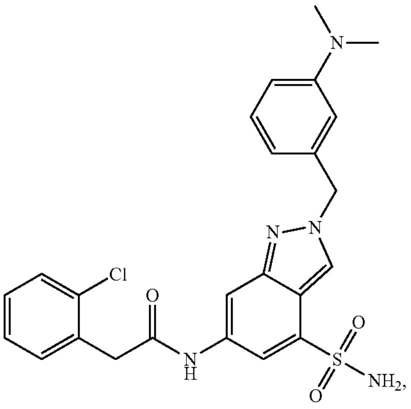

-continued
39
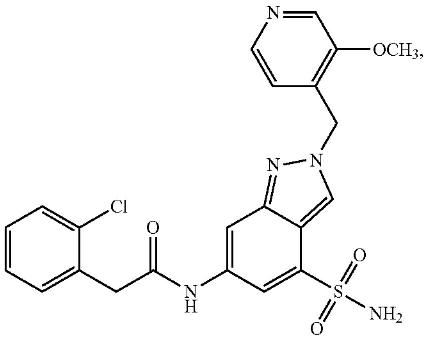
40-A
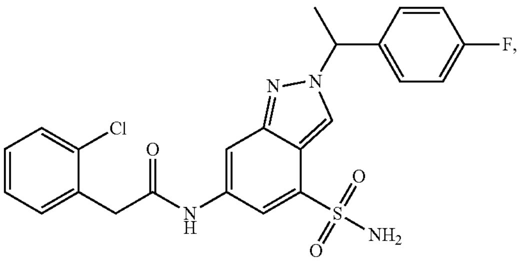
40-B
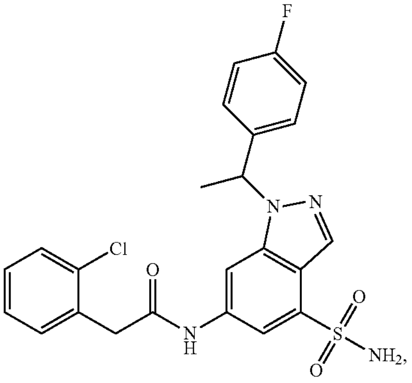
41
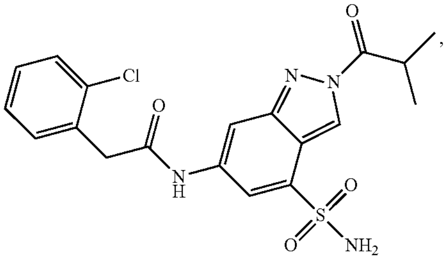
-continued
42-A
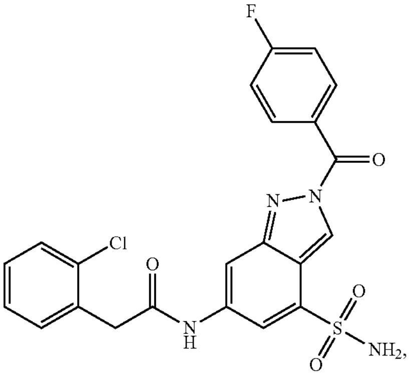
42-B
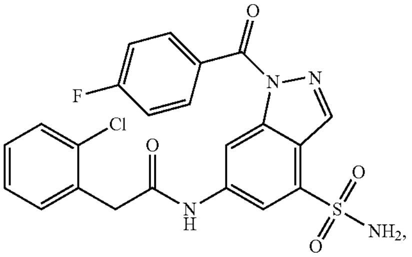
43
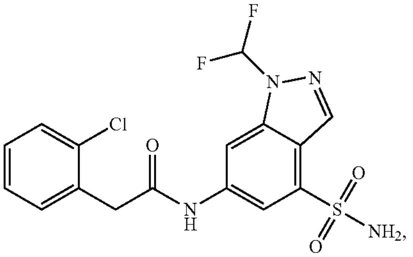
44
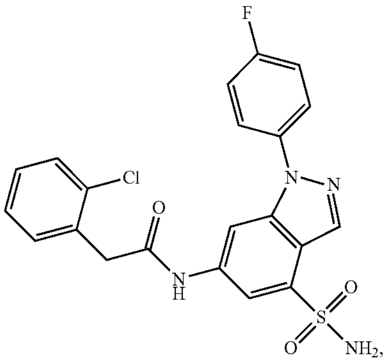
45
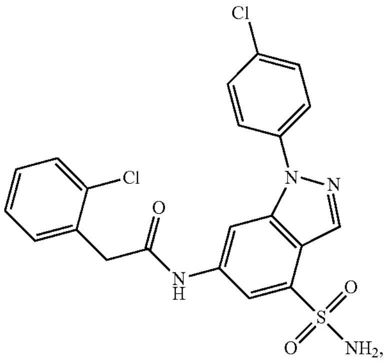

-continued
46
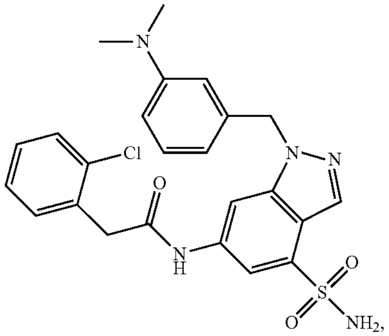
47
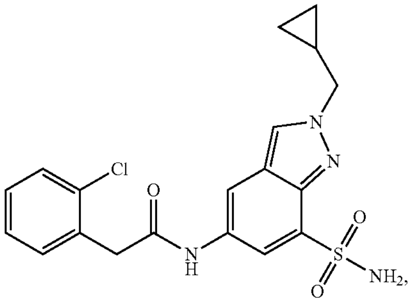
48-A
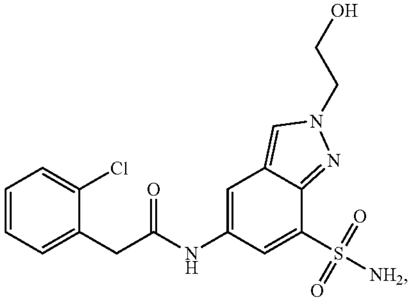
48-B
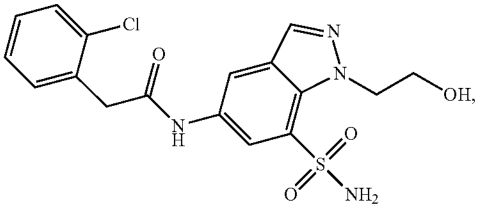
49
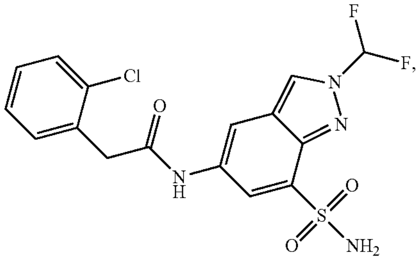
50
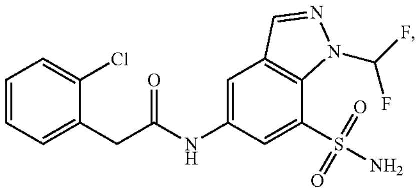
-continued
51
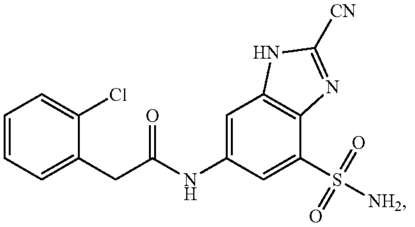
52
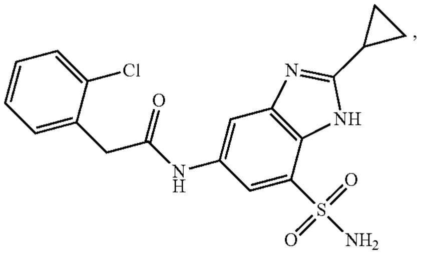
53
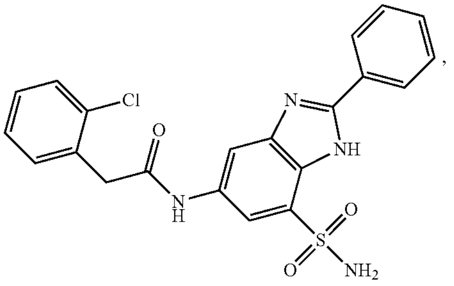
55
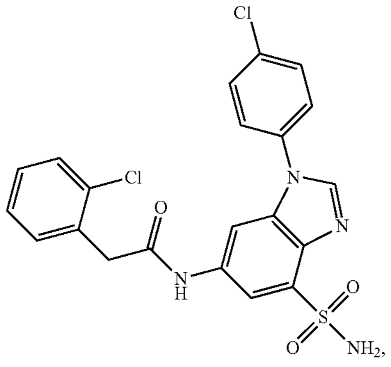
54
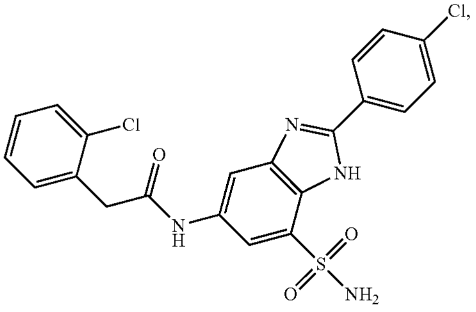

56
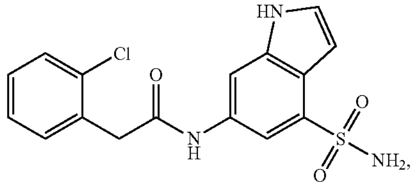
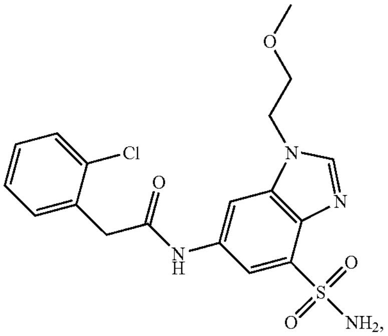
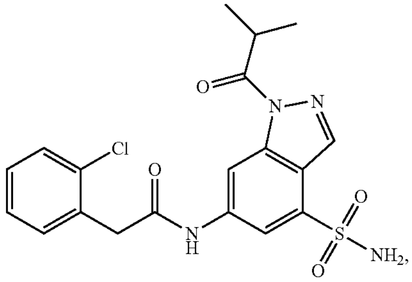
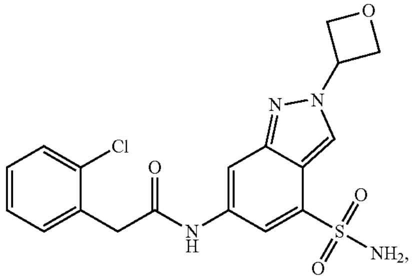
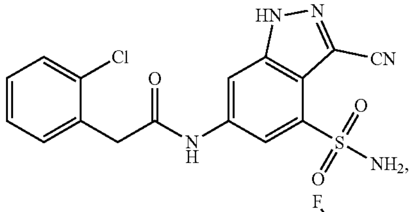
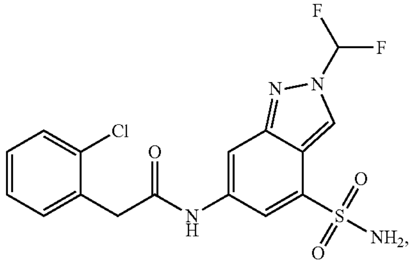
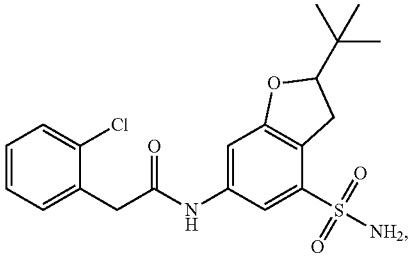
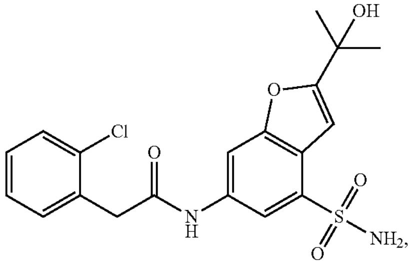
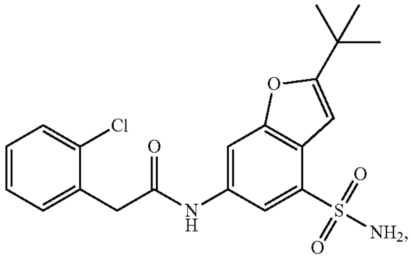
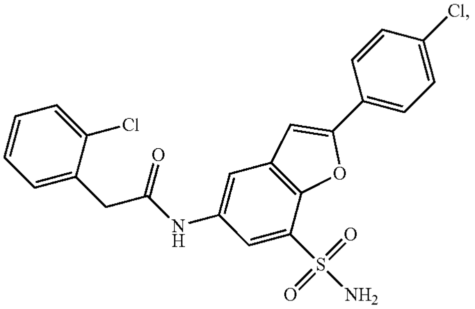
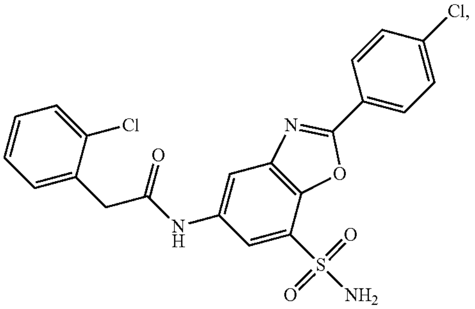
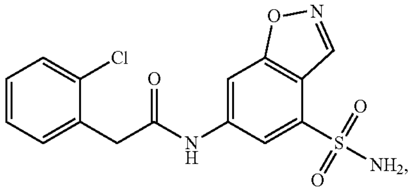

-continued
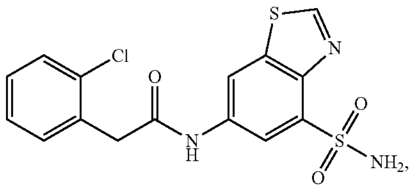
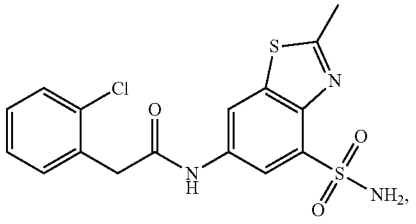
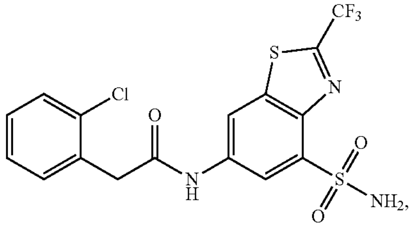
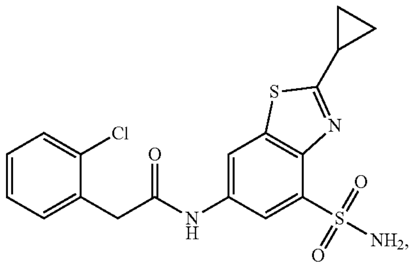
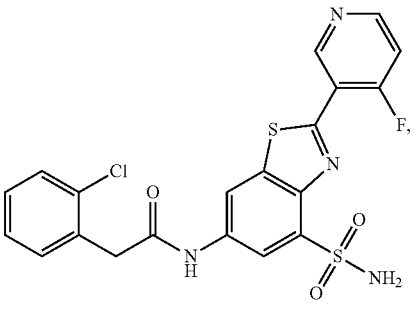
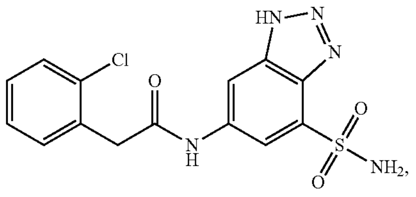
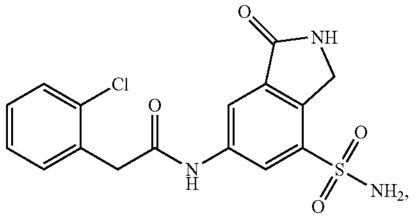
-continued
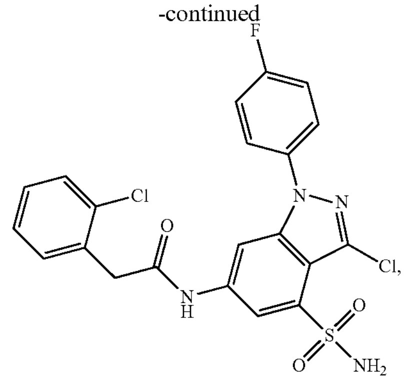
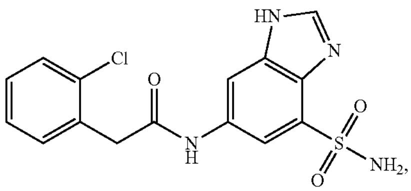
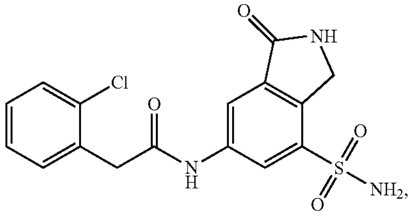
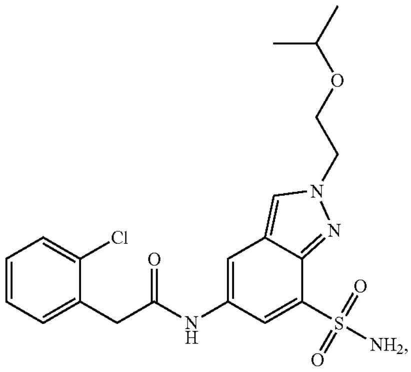
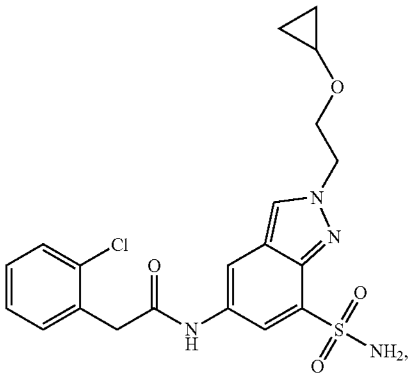

-continued
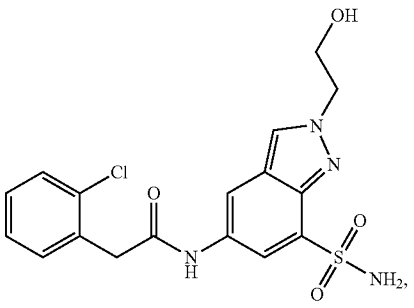
,
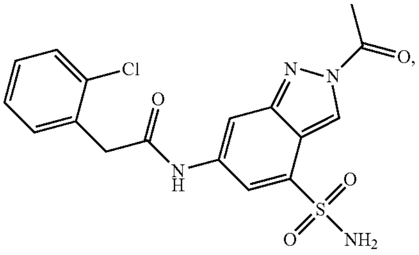
,
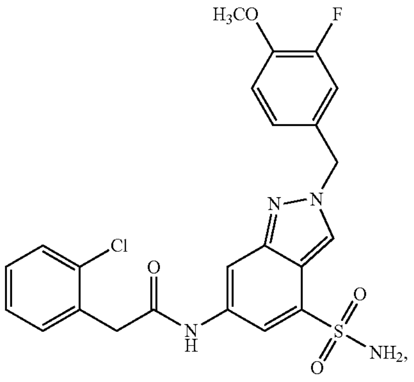
,
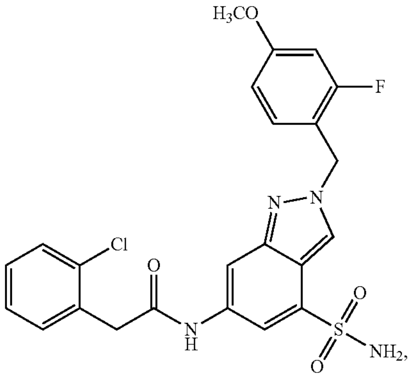
,
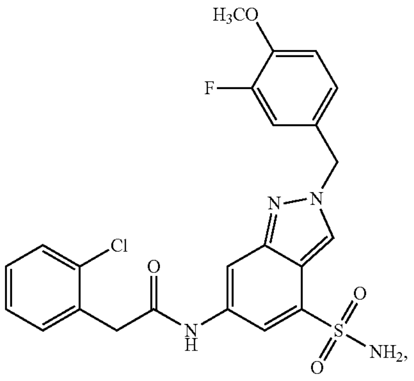
,
-continued
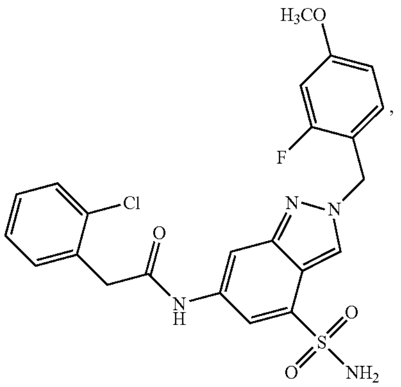
,
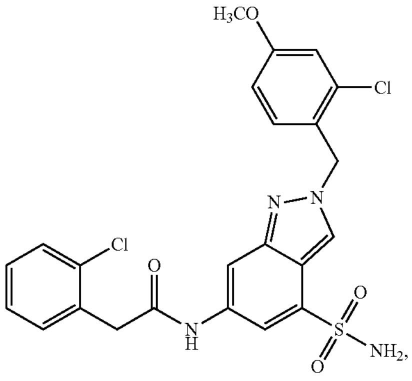
,
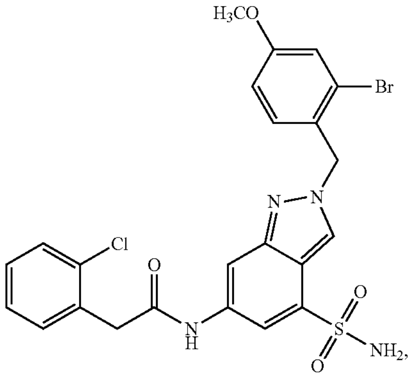
,
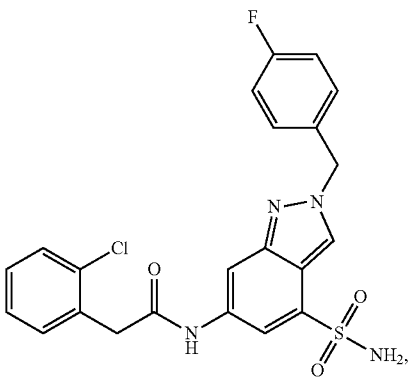
, -continued
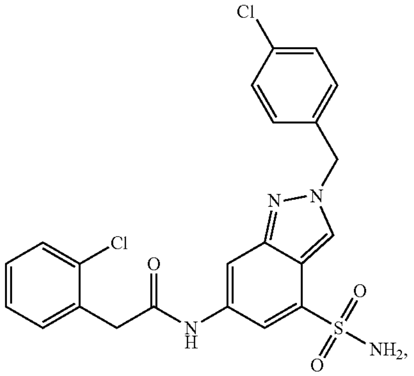
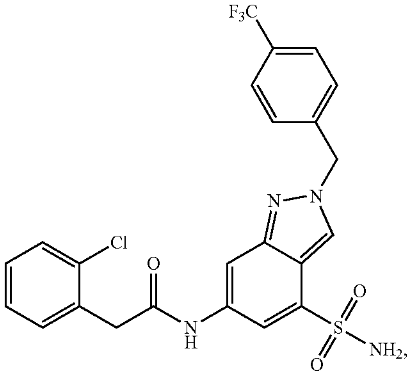
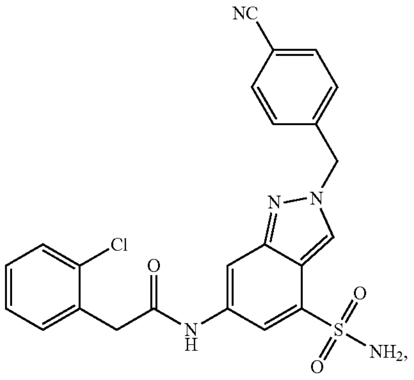
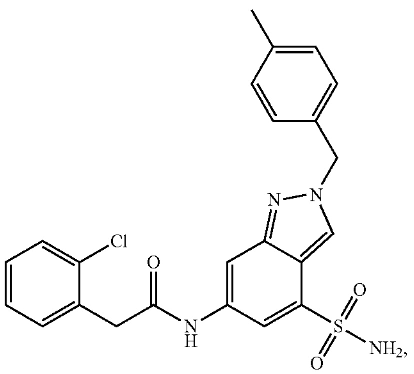
-continued
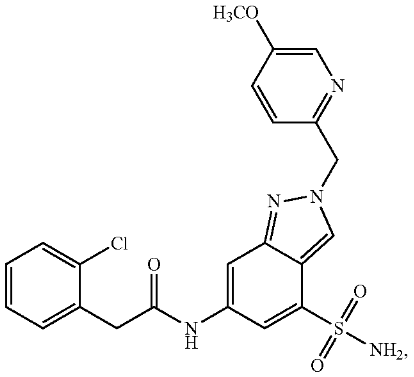
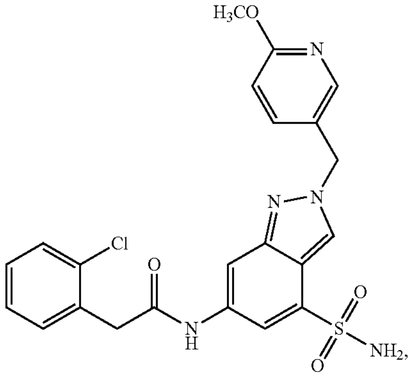
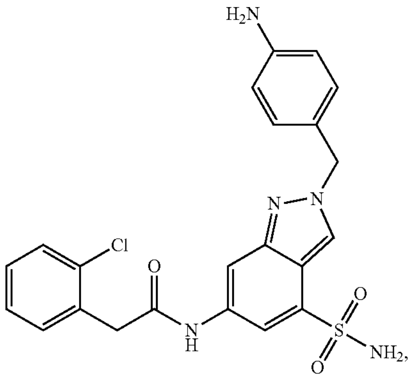
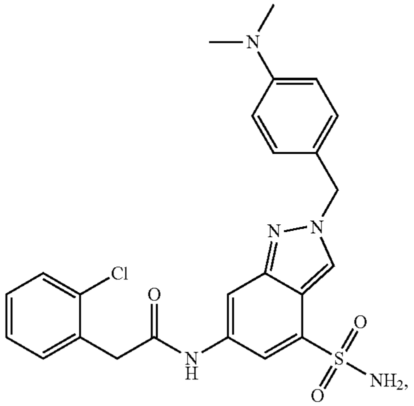

-continued
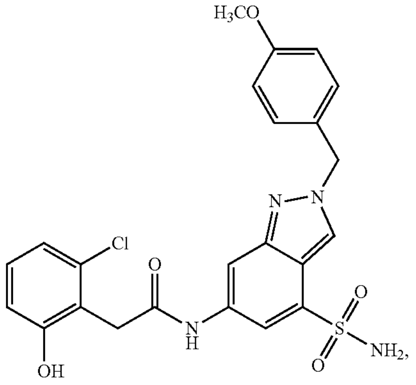
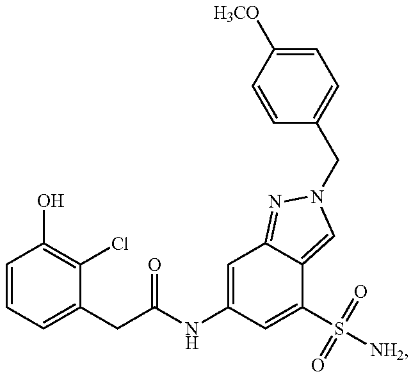
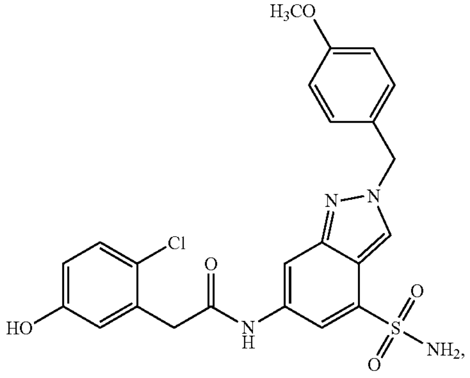
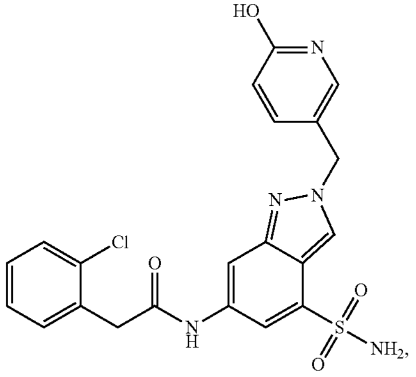
-continued
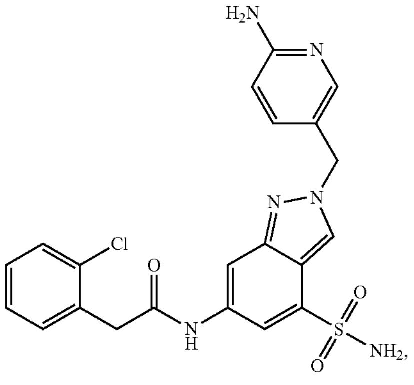
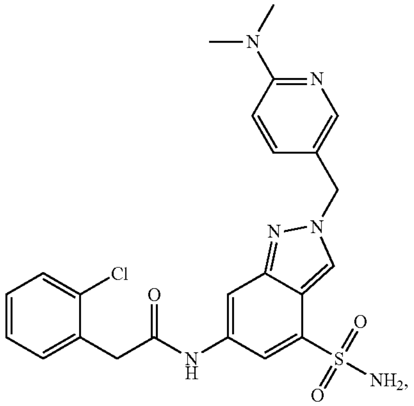
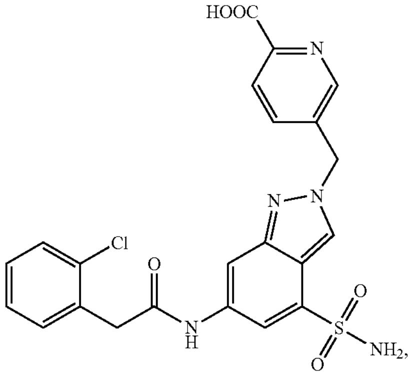
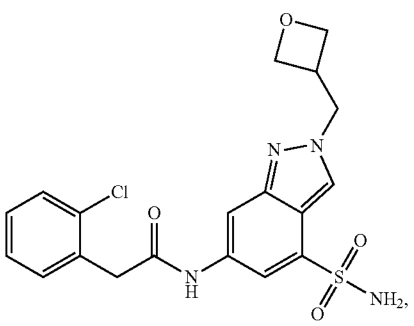

-continued
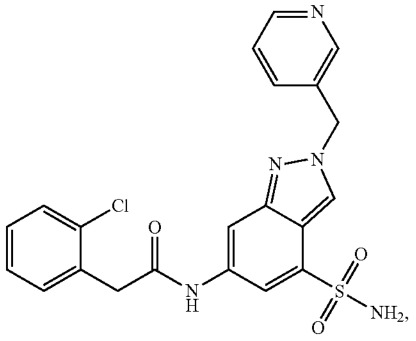
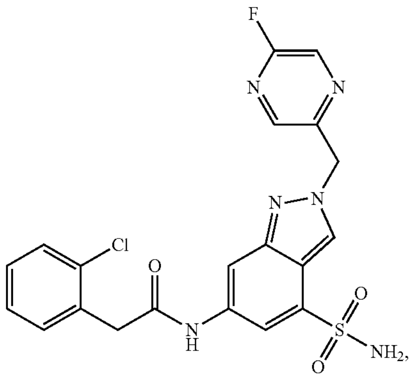
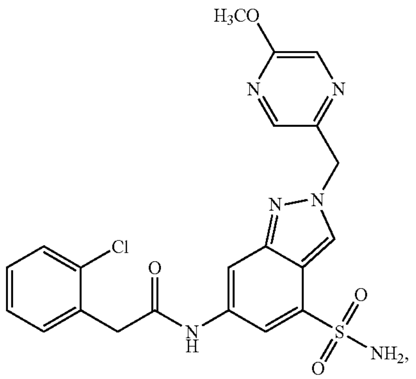
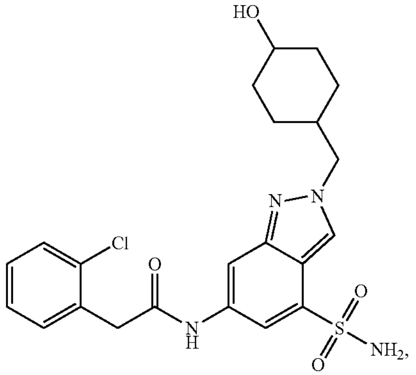
-continued
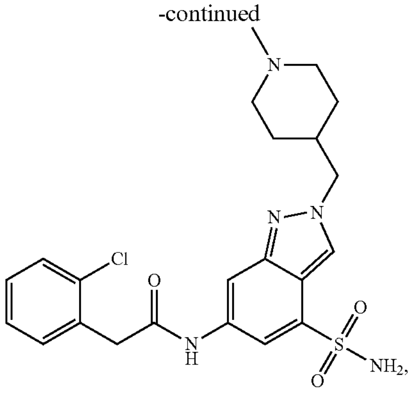
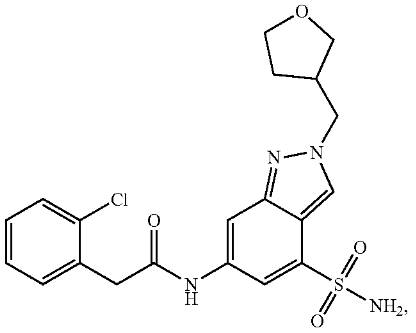
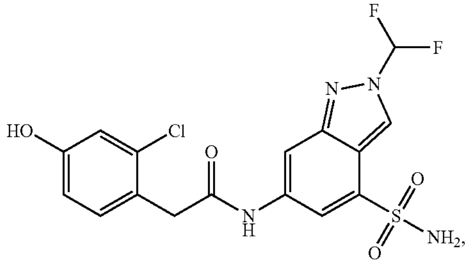
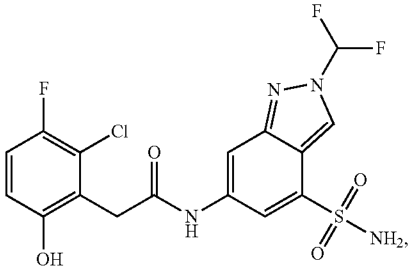
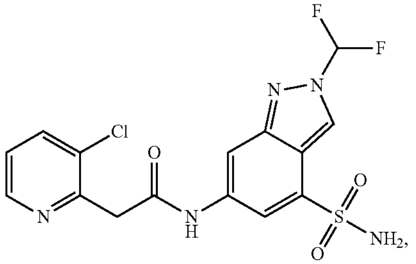

-continued
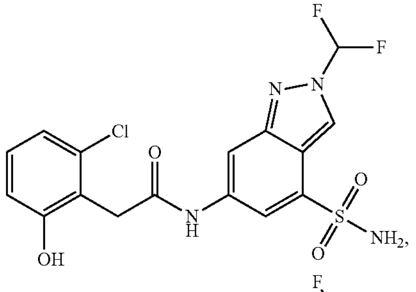
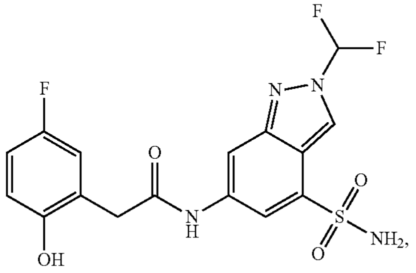
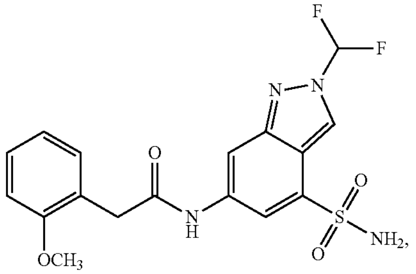
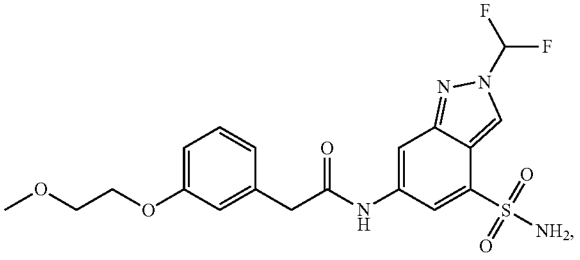
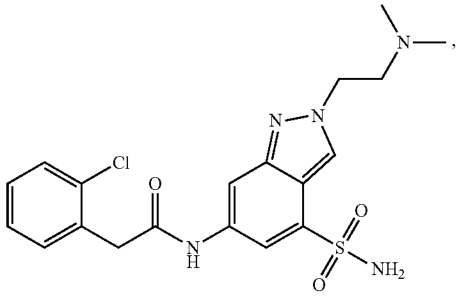
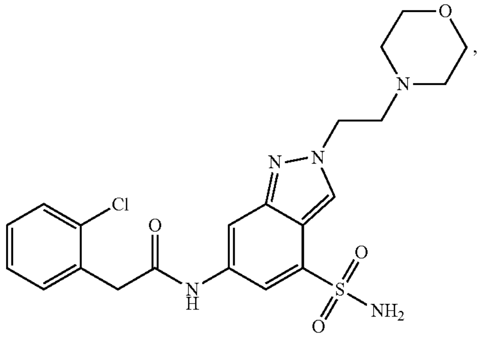
-continued
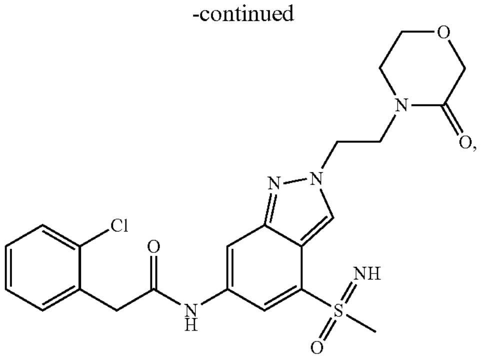
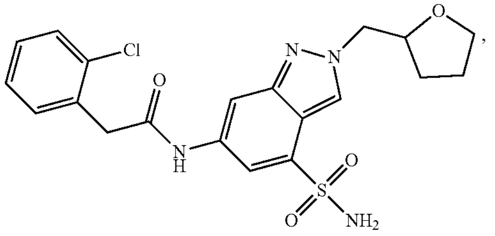
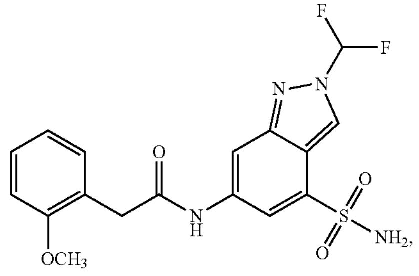
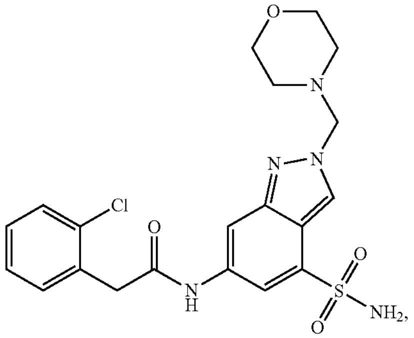
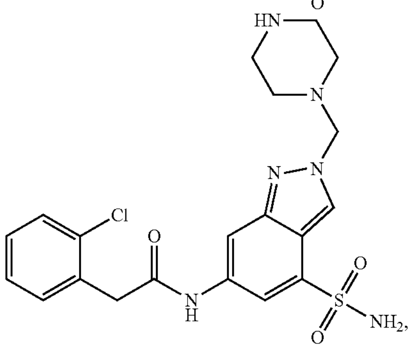

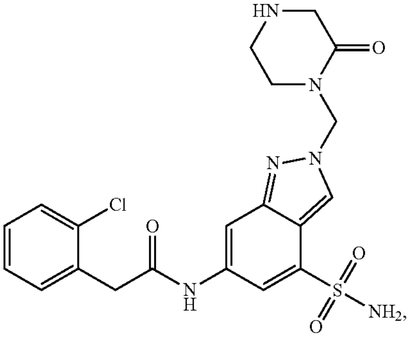
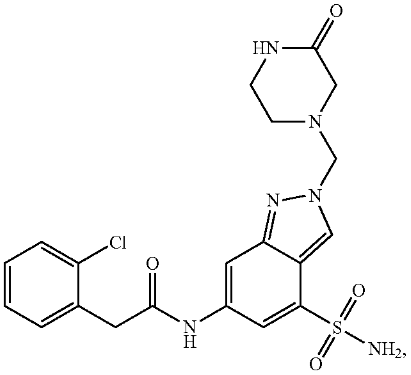
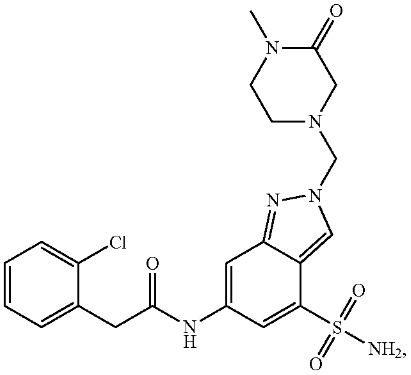
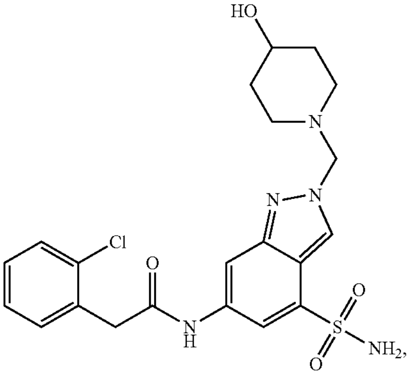
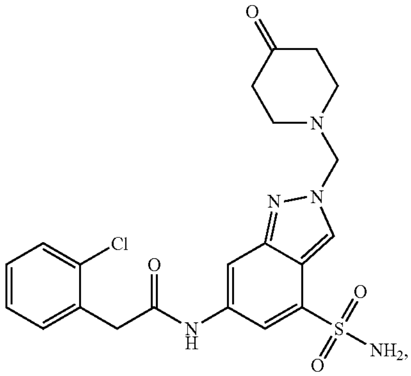
58
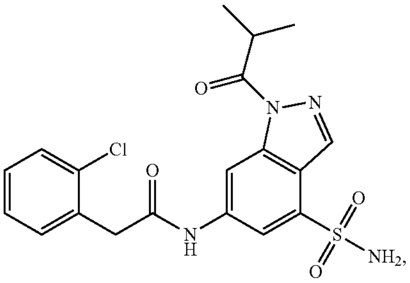
59
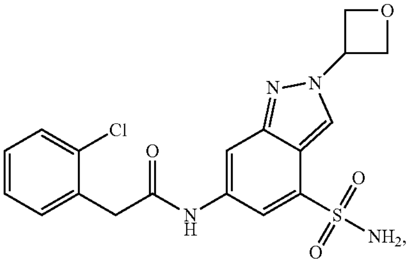
75
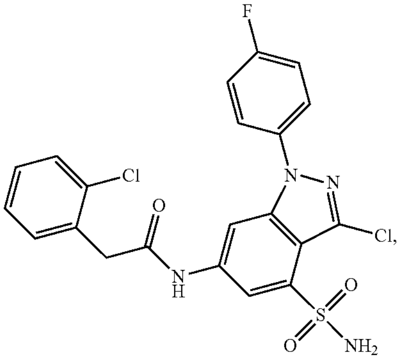

-continued
83
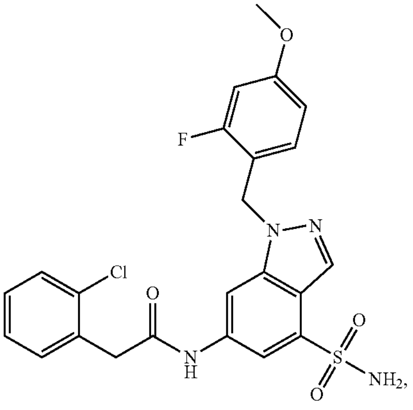
88
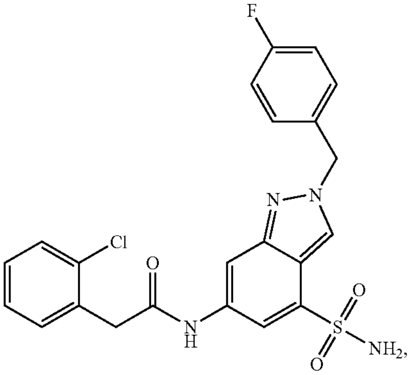
88A
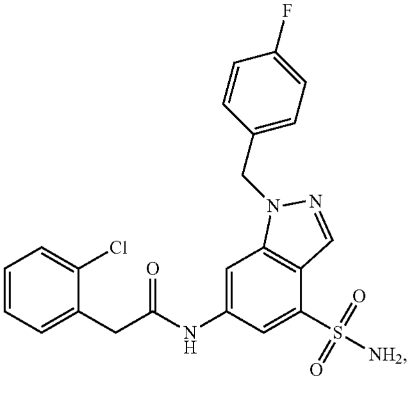
89
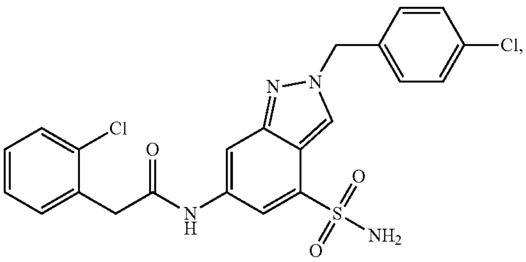
-continued
89A
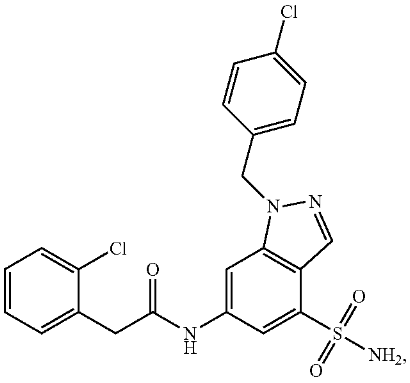
90
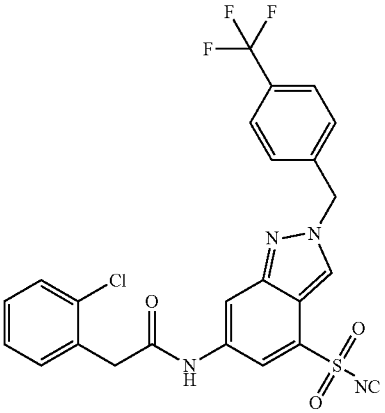
90A
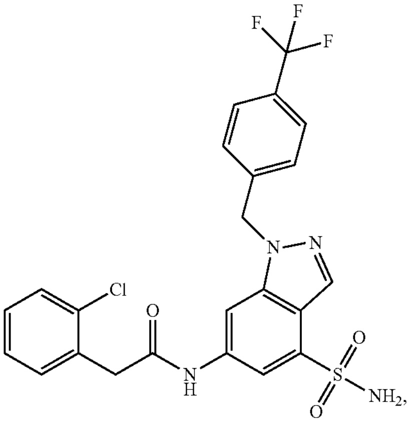
91
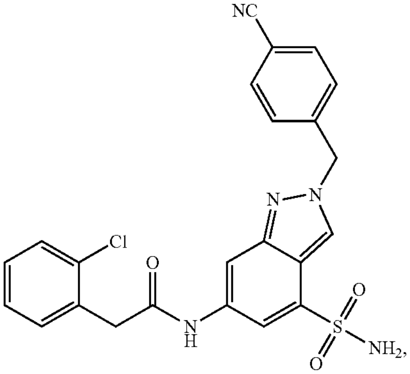

-continued
91A
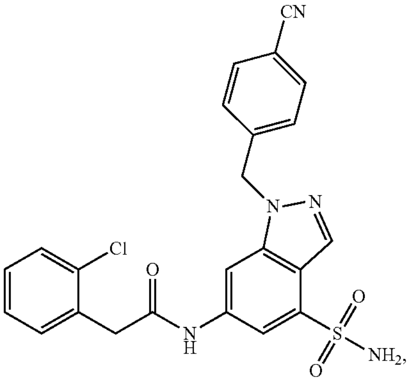
92
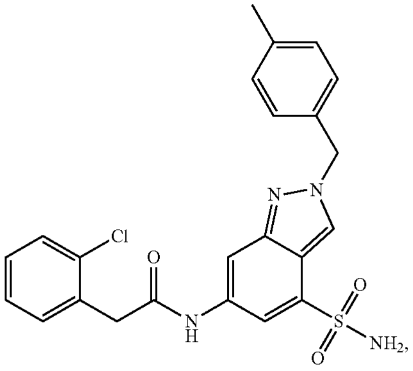
92A
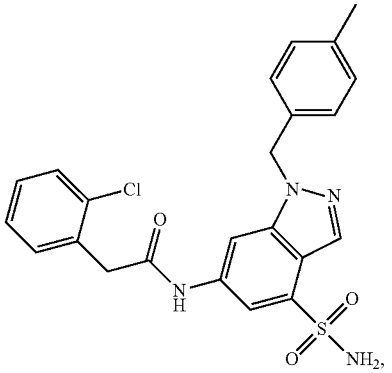
95
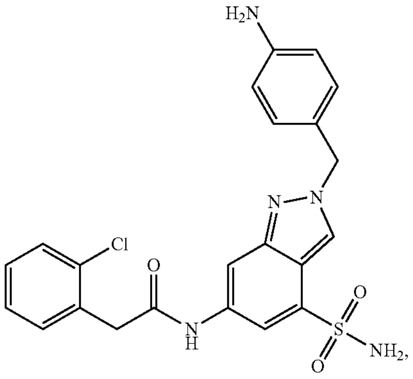
-continued
95A
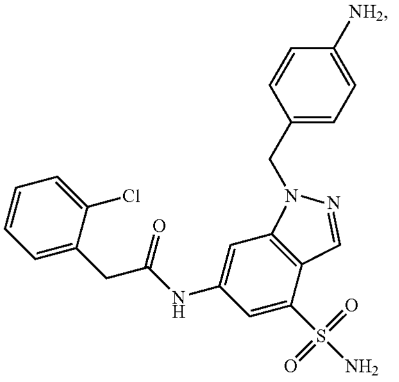
101
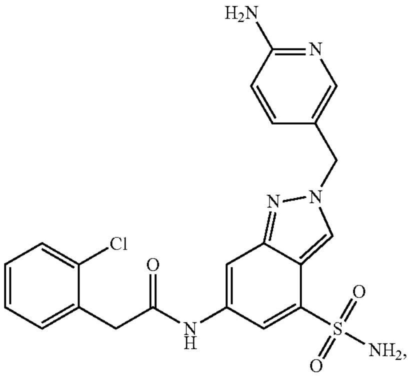
101A
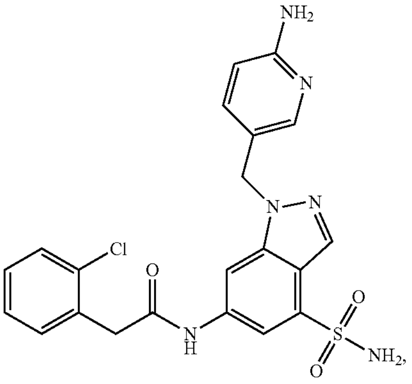
110
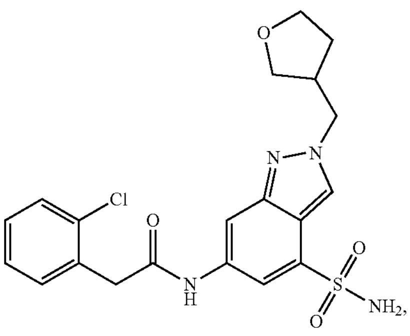

110A
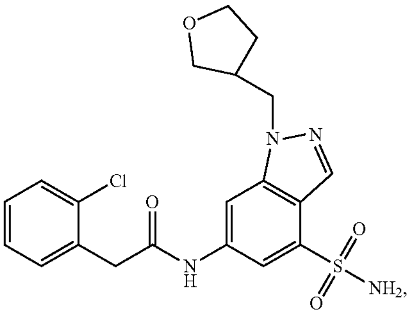
,
113
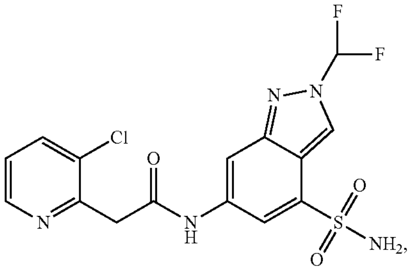
,
115
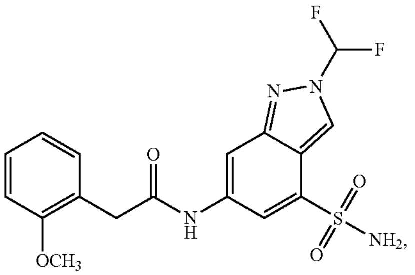
,
116
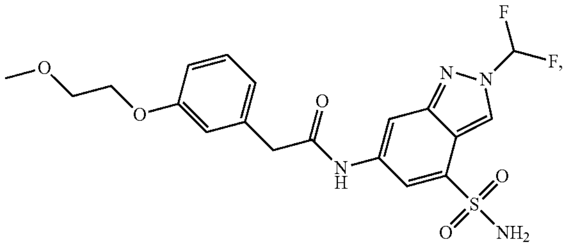
,
118
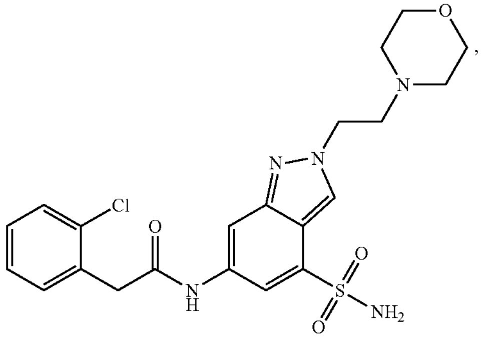
,
118A
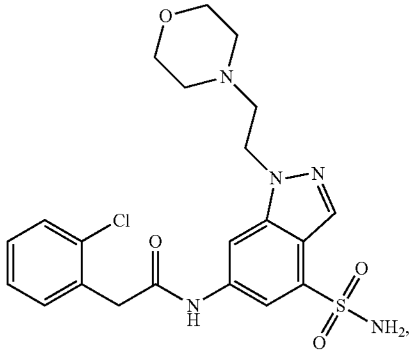
,
120
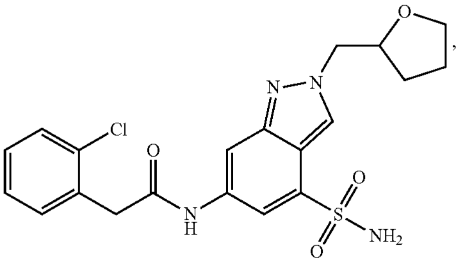
,
120A
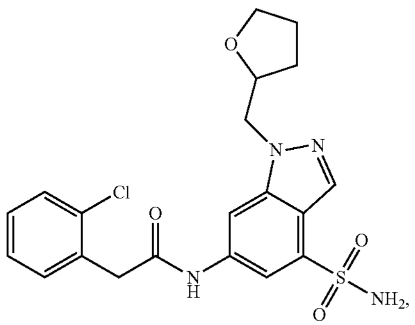
,
130
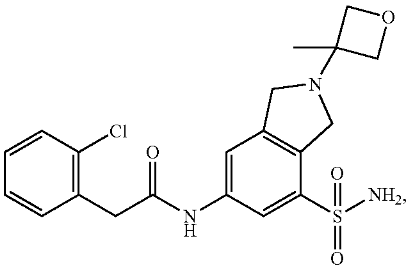
,
131
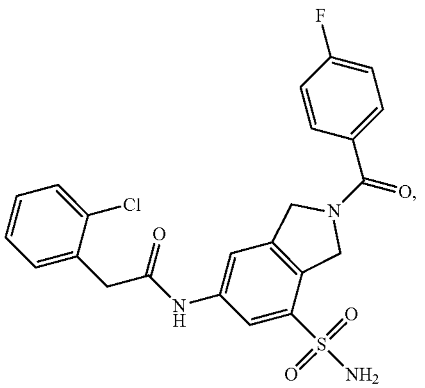
, -continued
132
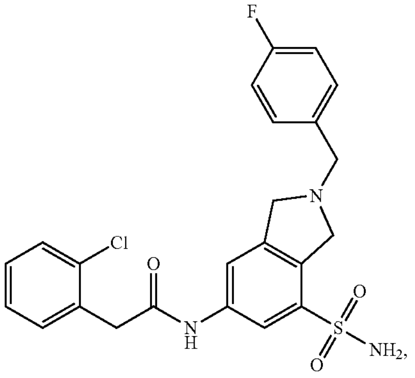
133
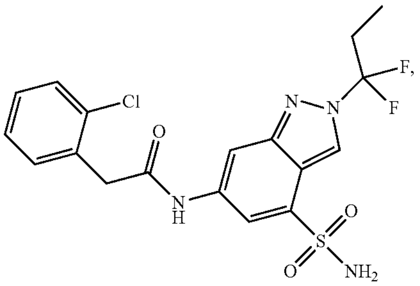
134
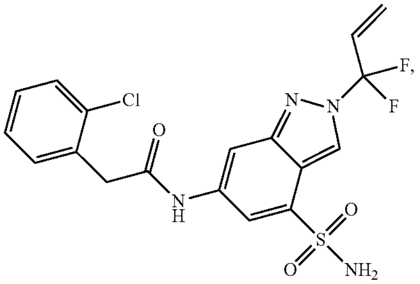
136
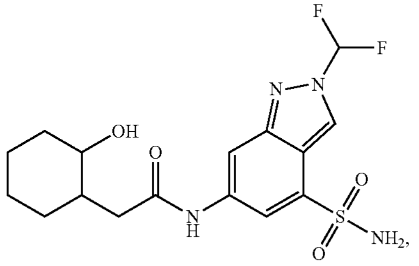
137
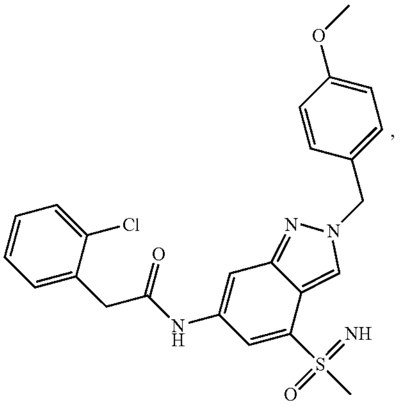
-continued
138
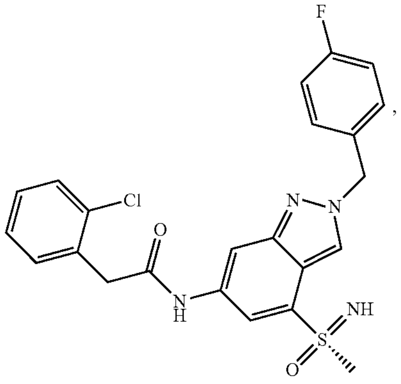
138A
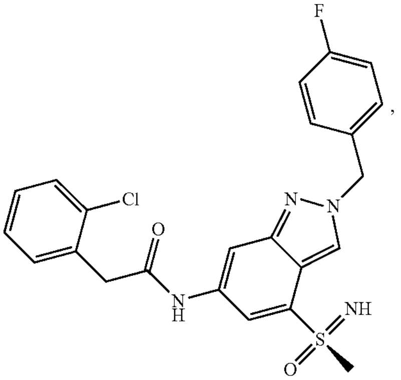
139
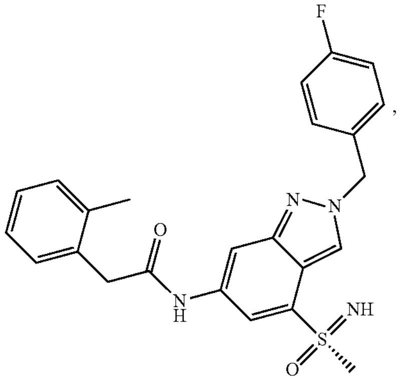
139A
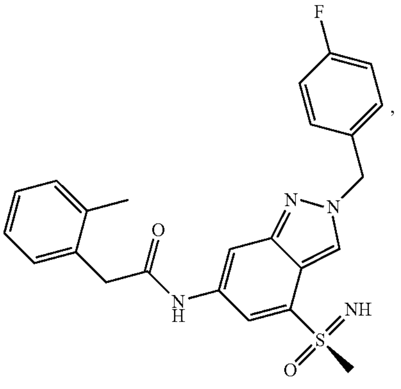

140
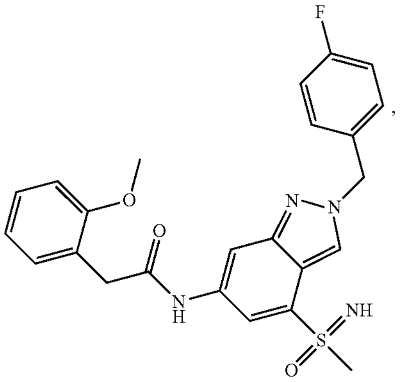
141
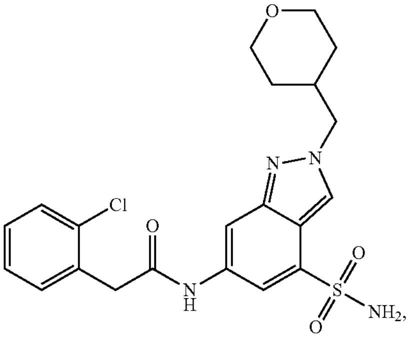
141A
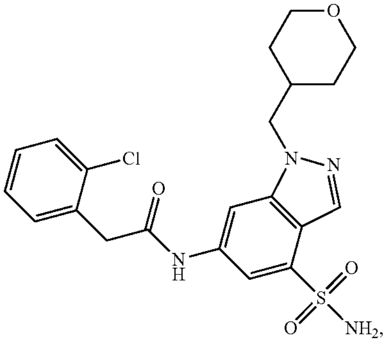
82
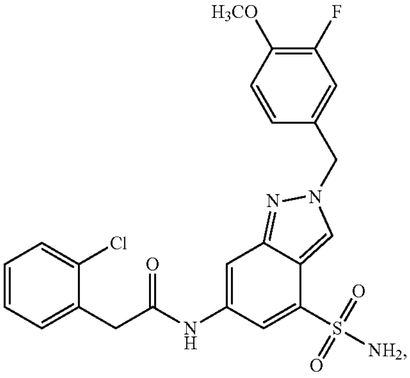
85
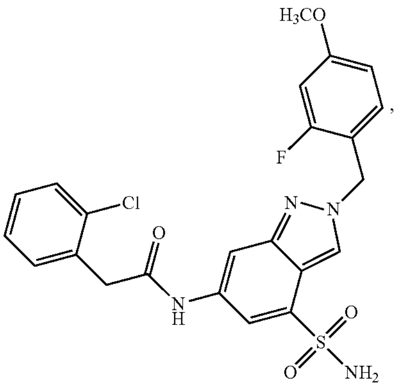
86
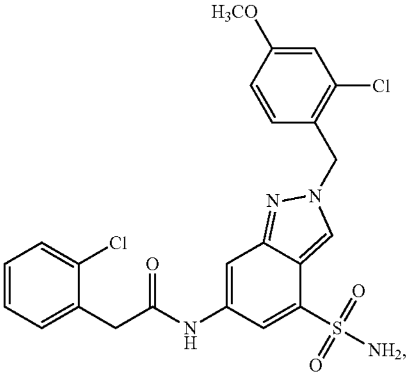
87
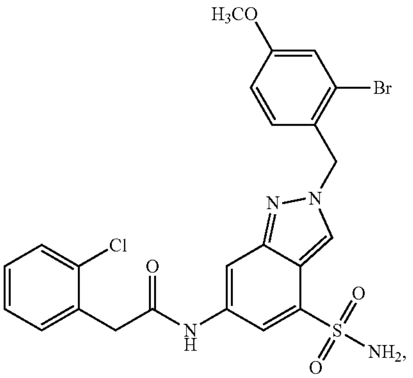
93
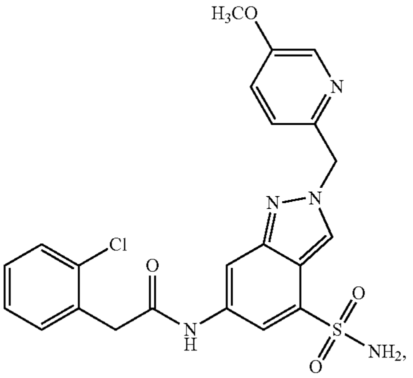

-continued

94

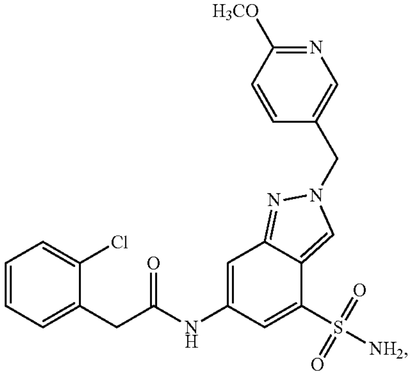

108

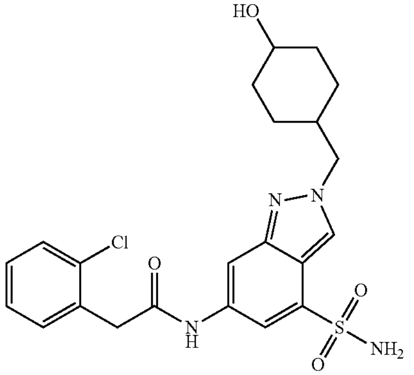

and

135

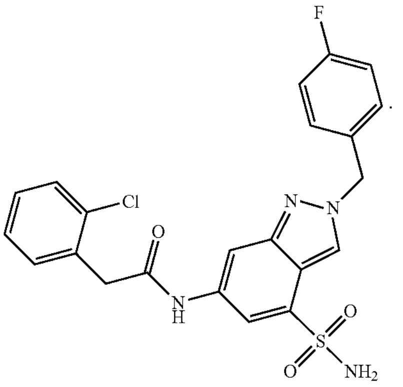

The compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof can be synthesized by methods similar to those known in the chemical field, and can also be synthesized by the method described herein.

The disclosure further provides a pharmaceutical composition comprising substance A and at least one pharmaceutically acceptable excipient;

substance A is the compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof.

In the pharmaceutical composition, the dosage of substance A may be a therapeutically effective amount.

The disclosure further provides use of substance A in the preparation of a P2X4 receptor antagonist or drug;

substance A is the compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof.

In a certain embodiment, the P2X4 receptor antagonist is used in vitro.

In a certain embodiment, the drug may be used for the treatment or prevention of urinary tract diseases, respiratory diseases, pain, autoimmune diseases, inflammation, Alzheimer's disease, Parkinson's disease, sleep disorders, epilepsy, psychiatric disorders, arthritis, neurodegeneration, traumatic brain injury, myocardial infarction, rheumatoid arthritis, cerebral stroke, thrombosis, atherosclerosis, colon syndrome, inflammatory bowel disease, digestive tract diseases, gastrointestinal dysfunction, respiratory failure, sexual dysfunction, cardiovascular diseases, heart failure, hypertension, urinary incontinence, cystitis, arthritis, endometriosis, hematological diseases, musculoskeletal and connective tissue developmental disorders, or systemic disorder diseases in an animal (e.g., a human). The urinary tract diseases are, for example, urinary incontinence, overactive bladder, dysuria or cystitis. The respiratory diseases are, for example, respiratory disorders including idiopathic pulmonary fibrosis, chronic obstructive pulmonary disease, asthma, bronchospasm, or cough (e.g., chronic cough). The pain is, for example, inflammatory pain, surgical pain, visceral pain, dental pain, premenstrual pain, central pain, pain resulting from burns, migraine, cluster headache or chronic pain.

In a certain embodiment, the drug can be used for the prevention or treatment of diseases mediated at least in part by P2X4 in an animal (e.g., a human).

The diseases mediated at least in part by P2X4 are, for example, urinary tract diseases, respiratory diseases, pain, autoimmune diseases, inflammation, Alzheimer's disease, Parkinson's disease, sleep disorders, epilepsy, psychiatric disorders, arthritis, neurodegeneration, traumatic brain injury, myocardial infarction, rheumatoid arthritis, cerebral stroke, thrombosis, atherosclerosis, colon syndrome, inflammatory bowel disease, digestive tract diseases, gastrointestinal dysfunction, respiratory failure, sexual dysfunction, cardiovascular diseases, heart failure, hypertension, urinary incontinence, cystitis, arthritis, endometriosis, hematological diseases, musculoskeletal and connective tissue developmental disorders, or systemic disorder diseases. The urinary tract diseases are, for example, urinary incontinence, overactive bladder, dysuria or cystitis. The respiratory diseases are, for example, respiratory disorders including idiopathic pulmonary fibrosis, chronic obstructive pulmonary disease, asthma, bronchospasm, or cough (e.g., chronic cough). The pain is, for example, inflammatory pain, surgical pain, visceral pain, dental pain, premenstrual pain, central pain, pain resulting from burns, migraine, cluster headache or chronic pain.

The disclosure further provides a method for treating or preventing diseases comprising administering to a patient (e.g., a human) a therapeutically effective amount of substance A; wherein the diseases are urinary tract diseases, respiratory diseases, pain, autoimmune diseases, inflammation, Alzheimer's disease, Parkinson's disease, sleep disorders, epilepsy, psychiatric disorders, arthritis, neurodegeneration, traumatic brain injury, myocardial infarction, rheumatoid arthritis, cerebral stroke, thrombosis, atherosclerosis, colon syndrome, inflammatory bowel disease, digestive tract diseases, gastrointestinal dysfunction, respiratory failure, sexual dysfunction, cardiovascular diseases, heart failure, hypertension, urinary incontinence, cystitis, arthritis, endometriosis, hematological diseases, musculoskeletal and connective tissue developmental disorders, or systemic disorder diseases;

substance A is the compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof.

In a certain embodiment, the urinary tract diseases are, for example, urinary incontinence, overactive bladder, dysuria or cystitis.

In a certain embodiment, the respiratory diseases are, for example, respiratory disorders including idiopathic pulmonary fibrosis, chronic obstructive pulmonary disease, asthma, bronchospasm, or cough (e.g., chronic cough).

In a certain embodiment, the pain is, for example, inflammatory pain, surgical pain, visceral pain, dental pain, premenstrual pain, central pain, pain resulting from burns, migraine, cluster headache or chronic pain.

The disclosure further provides a method for treating or preventing diseases mediated at least in part by P2X4 comprising administering to a patient (e.g., a human) a therapeutically effective amount of substance A;

substance A is the compound containing a benzene ring represented by formula I, or the pharmaceutically acceptable salt, the stereoisomer, the tautomer, the isotopic compound, the crystalline form, the nitrogen oxide or the solvate thereof, or the solvate of the pharmaceutically acceptable salt thereof.

In a certain embodiment, the diseases may be urinary tract diseases, respiratory diseases, pain, autoimmune diseases, inflammation, Alzheimer's disease, Parkinson's disease, sleep disorders, epilepsy, psychiatric disorders, arthritis, neurodegeneration, traumatic brain injury, myocardial infarction, rheumatoid arthritis, cerebral stroke, thrombosis, atherosclerosis, colon syndrome, inflammatory bowel disease, digestive tract diseases, gastrointestinal dysfunction, respiratory failure, sexual dysfunction, cardiovascular diseases, heart failure, hypertension, urinary incontinence, cystitis, arthritis, endometriosis, hematological diseases, musculoskeletal and connective tissue developmental disorders, or systemic disorder diseases.

In a certain embodiment, the urinary tract diseases are, for example, urinary incontinence, overactive bladder, dysuria or cystitis.

In a certain embodiment, the respiratory diseases are, for example, respiratory disorders including idiopathic pulmonary fibrosis, chronic obstructive pulmonary disease, asthma, bronchospasm, or cough (e.g., chronic cough).

In a certain embodiment, the pain is, for example, inflammatory pain, surgical pain, visceral pain, dental pain, premenstrual pain, central pain, pain resulting from burns, migraine, cluster headache or chronic pain.

All patents and publications referred to herein are incorporated herein by reference in their entirety. General principles of organic chemistry can be found in *Organic Chemistry*, Thomas Sorrell, University Science Books, Sausalito: 1999, and *March's Advanced Organic Chemistry* by Michael B. Smith and Jerry March, John Wiley & Sons, New York: 2007, which are incorporated herein by reference in their entirety.

Unless otherwise stated, terms used herein have the following definitions, and the definitions of terms not mentioned hereinafter are as commonly understood by those skilled in the art to which the disclosure pertains.

The term "a plurality of" refers to 2, 3, 4 or 5.

The term "pharmaceutically acceptable salt" refers to a salt of the compound of the disclosure which is prepared with a relatively nontoxic, pharmaceutically acceptable acid or base. When the compound disclosed herein contains a relatively acidic functional group, a base addition salt can be obtained by contacting the neutral form of such a compound with a sufficient amount of pharmaceutically acceptable base in a pure solution or a suitable inert solvent. Pharmaceutically acceptable base addition salts include, but are not limited to: lithium salt, sodium salt, potassium salt, calcium salt, aluminum salt, magnesium salt, zinc salt, bismuth salt, ammonium salt, and diethanolamine salt. When the compound disclosed herein contains a relatively basic functional group, an acid addition salt can be obtained by contacting the neutral form of such a compound with a sufficient amount of pharmaceutically acceptable acid in a pure solution or a suitable inert solvent. The pharmaceutically acceptable acid includes inorganic acids including, but not limited to: hydrochloric acid, hydrobromic acid, hydroiodic acid, nitric acid, carbonic acid, phosphoric acid, phosphorous acid, sulfuric acid, and the like. The pharmaceutically acceptable acid includes organic acids including, but not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acidic citric acid, oleic acid, tannic acid, pantothenic acid, bitartrate, ascorbic acid, gentisic acid, fumaric acid, gluconic acid, saccharic acid, formic acid, ethanesulfonic acid, pamoic acid (i.e., 4,4'-methylene-bis(3-hydroxy-2-naphthoic acid)), amino acids (e.g., glutamic acid, arginine), and the like. When the compound of the disclosure contains relatively acidic and relatively basic functional groups, they may be converted to base addition salts or acid addition salts. Details can be found in Berge et al., "*Pharmaceutical Salts*", *Journal of Pharmaceutical Science* 66: 1-19 (1977), or, *Handbook of Pharmaceutical Salts: Properties, Selection, and Use* (P. Heinrich Stahl and Camile G. Wermuth, ed., Wiley-VCH, 2002).

The term "solvate" refers to a substance formed by combining a compound of the disclosure with a stoichiometric or non-stoichiometric amount of a solvent. The solvent molecules in the solvate may be present in ordered or unordered arrangements. Such solvents include, but are not limited to: water, methanol, ethanol, and the like.

The terms "pharmaceutically acceptable salt" and "solvate" in the "solvate of a pharmaceutically acceptable salt" as described above refer to: 1. substances of the compound of the disclosure which are prepared with relatively nontoxic, pharmaceutically acceptable acids or bases, and 2. substances formed by combining the compound of the disclosure with a stoichiometric or non-stoichiometric amount of a solvent. The "solvate of a pharmaceutically acceptable salt" includes, but is not limited to, the hydrochloride monohydrate of the compound of the disclosure.

The term "stereoisomer" refers to an isomer caused by the same order of connection of atoms or groups of atoms to each other but different in spatial arrangement in a molecule, such as cis-trans isomer, optical isomer, or atropisomer. These stereoisomers can be separated, purified and enriched by asymmetric synthesis method or chiral separation method (including, but not limited to, thin layer chromatography, rotary chromatography, column chromatography, gas chromatography, high pressure liquid chromatography, etc.), and can also be obtained by chiral resolution by bonding (chemical bonding, etc.) or salt formation (physical bonding, etc.) with other chiral compounds.

The term "tautomer" refers to functional isomers resulting from the rapid movement of an atom in a molecule between two positions. For example, acetone and 1-propen-2-ol can be converted into one another by the rapid movement of hydrogen atoms on oxygen and α-carbon.

The term "isotopic compound" means that one or more atoms in the compound are substituted with one or more atoms having a specific atomic mass or mass number. Examples of isotopes capable of being incorporated into the compound of the disclosure include, but are not limited to, isotopes of hydrogen, carbon, nitrogen, oxygen, fluorine, sulfur, and chlorine (e.g., 2H, 3H, 13C, 14C, 15N, 18O, 17O, 18F, 35S, and 36Cl). The isotopic compound disclosed herein can generally be prepared by substituting isotopically-labeled reagents for non-isotopically-labeled reagents according to the methods described herein.

The term "crystalline form" refers to a form in which ions or molecules are arranged strictly periodically in a three-dimensional space in a defined manner and have a periodic recurring pattern at certain intervals; due to the above different periodic arrangements, various crystalline forms, i.e., polymorphism, may exist.

The term "nitrogen oxide" refers to an N-oxide formed by oxidizing one or more nitrogen atoms when the compound contains several amine functional groups. Specific examples of N-oxides are N-oxides of tertiary amines or N-oxides of a nitrogen atom of a nitrogen-containing heterocycle. The corresponding amines can be treated with an oxidant such as hydrogen peroxide or peracid (e.g., peroxycarboxylic acid) to form N-oxides (see *Advanced Organic Chemistry*, Wiley Interscience, 4th edition, Jerry March, pages). In particular, N-oxides may be prepared by the method of L. W. Deady (*Syn. Comm.* 1977, 7,509-514) in which an amine compound is reacted with m-chloroperoxybenzoic acid (MCPBA), for example, in an inert solvent such as dichloromethane.

When any variable (e.g., $R^{1-1-1}$) occurs multiple times in the definition of the compound, the definition of the occurrence of this variable at each position is independent of the definition of the occurrence of this variable at the remaining positions, and their meanings are independent of one another and do not affect one another. Thus, if a certain group is substituted with 1, 2 or 3 $R^{1-1-1}$, that is, this group may be substituted with up to 3 $R^{1-1-1}$, the definition of $R^{1-1-1}$ at this position is independent of the definition of $R^{1-1-1}$ at the remaining positions. In addition, combinations of substituents and/or variables are permissible only if such combinations result in stable compounds.

used in the structural formula describing groups herein means that the corresponding groups are connected to other fragments and groups in the compound through this site.

In each part of the disclosure, connecting substituents are described. When a connecting group is clearly required to a structure, the Markush variables listed for the group should be understood as a connecting group. For example, $C_1$-$C_6$ alkyl in the group "$C_1$-$C_6$ haloalkyl" should be understood as $C_1$-$C_6$ alkylene.

Unless otherwise indicated, abbreviations for any of protective groups, amino acids and other compounds used herein are provided based on their commonly used and accepted abbreviations, or by referring to *IUPAC-IUB Commission on Biochemical Nomenclature* (see *Biochem.* 1972, 11:942-944).

The term "oxo" means that two hydrogens on methylene are substituted with oxygen, i.e., methylene is substituted with carbonyl.

The term "halogen" refers to fluorine, chlorine, bromine or iodine.

The term "alkyl" refers to linear or branched alkyl having the indicated number of carbon atoms.

Examples of alkyl include methyl, ethyl, n-propyl, isopropyl, n-butyl, tert-butyl, isobutyl, sec-butyl, n-pentyl, n-hexyl, n-heptyl, n-octyl, and the like.

The term "alkoxy" refers to the group —O-Rx, wherein RX is alkyl as defined above.

The term "cycloalkyl" refers to monovalent saturated cyclic alkyl, preferably monovalent saturated cyclic alkyl having 3 to 7 ring carbon atoms, and more preferably monovalent saturated cyclic alkyl having 3 to 6 carbon atoms, such as cyclopropyl, cyclobutyl, cyclopentyl or cyclohexyl.

The term "heterocycloalkyl" or "heteroalkyl ring" refers to a saturated monocyclic group having heteroatoms, and preferably 3-7 membered saturated monocyclic ring containing 1, 2 or 3 ring heteroatoms independently selected from N, O and S. Examples of heterocycloalkyl are: pyrrolidinyl, tetrahydrofuranyl, tetrahydropyranyl, tetrahydrothienyl, tetrahydropyridinyl, tetrahydropyrrolyl, azetidinyl, thiazolidinyl, oxazolidinyl, piperidyl, morpholinyl, thiomorpholinyl, piperazinyl, azepanyl, diazepanyl, oxazepanyl, and the like.

The term "heterocycloalkenyl" or "heteroalkenyl ring" refers to a monocyclic group having heteroatoms (this monocyclic group has double bonds without aromaticity), and preferably a 3-7 membered monocyclic ring containing 1, 2 or 3 ring heteroatoms independently selected from N, O and S. Examples of heterocycloalkenyl are: dihydrofuranyl, dihydrothienyl, dihydropyrrolyl, dioxolyl, dihydroimidazolyl, dihydropyrazolyl, dihydrothiazolyl, dihydroisothiazolyl, dihydrooxadiazolyl, dihydrothiadiazolyl, dihydrotriazolyl, dihydrotetrazolyl, tetrahydropyridinyl, 3,4-dihydro-2H-pyran, pyranyl, thiopyranyl, dihydropyridinyl, dihydropyrazinyl, dihydropyrimidinyl, oxazinyl, dihydrotetrazolyl, and the like.

The term "heteroaryl" or "heteroaryl ring" refers to an aromatic group containing heteroatoms, and preferably an aromatic 5-6 membered monocyclic ring containing 1, 2 or 3 heteroatoms independently selected from nitrogen, oxygen and sulfur, for example, furanyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, and thiadiazolyl.

The term "pharmaceutically acceptable excipients" refers to excipients and additives used in the manufacture of pharmaceutical products and in the formulation of pharmaceutical formulations, and are all the substances contained in pharmaceutical preparations, except for the active ingredients. It can be found in the *Chinese Pharmacopoeia* (Volume IV, 2015 Edition), or *Handbook of Pharmaceutical Excipients* (Raymond C Rowe, 2009, Sixth Edition)

The term "treatment" refers to therapeutic therapy. Where specific conditions are involved, the treatment refers to: (1) relieving one or more of biological manifestations of a disease or condition, (2) interfering with (a) one or more of points in a biological cascade that causes or contributes to a condition or (b) one or more of biological manifestations of a condition, (3) ameliorating one or more of symptoms, effects, or side effects associated with a condition, or one or more of symptoms, effects, or side effects associated with a condition or treatment thereof, or (4) slowing the progression of a condition or one or more of biological manifestations of a condition.

The term "prevention" refers to a reduced risk of acquiring or developing a disease or disorder.

The term "therapeutically effective amount" refers to an amount of a compound that, when administered to a patient, is sufficient to effectively treat diseases or conditions described herein.

The "therapeutically effective amount" varies depending on the compound, the condition and its severity, and the age of the patient to be treated, but can be adjusted as desired by those skilled in the art.

The term "patient" refers to any animal, preferably a mammal, and most preferably a human, that is to receive or has received administration of the compound or composition according to the embodiments of the disclosure. The term "mammal" includes any mammal. Examples of mammals include, but are not limited to, cows, horses, sheep, pigs, cats, dogs, mice, rats, rabbits, guinea pigs, monkeys, humans, and the like, with humans being most preferred.

The biological activity of the compounds disclosed herein can be assessed by using any conventionally known method. Appropriate detection methods are well known in the art. For example, the compound disclosed herein can be tested for inhibitory activity against P2X4, pharmacokinetic activity, and/or liver microsomal stability, etc., by an appropriate conventional method. The detection methods provided by the disclosure are presented as examples only and do not limit the disclosure. The compounds disclosed herein are active in at least one of the detection methods provided by the disclosure.

The above preferred conditions may be combined arbitrarily to obtain preferred embodiments of the disclosure without departing from the general knowledge in the art.

The reagents and starting materials used in the disclosure are commercially available.

The positive progress effects of the disclosure are as follows: the compound has high P2X4 antagonistic activity, good selectivity, low toxicity and good metabolic stability.

DETAILED DESCRIPTION

The disclosure is further illustrated by the following examples; however, these examples should not be construed as limiting the disclosure. Experimental procedures without specified conditions in the following examples are conducted in accordance with conventional procedures and conditions, or in accordance with the manufacturer's manual.

In the disclosure, the following abbreviations have parenthesized meanings.

DPPA (diphenylphosphoryl azide), TEMPO (2,2,6,6-tetramethyl-1-piperidone), LDA (lithium diisopropylamide), DMF (N,N-dimethylformamide), DMA (N,N-dimethylacetamide), DCM (dichloromethane), DME (dimethoxyethane), PE (petroleum ether), EA (ethyl acetate), DIPEA (N,N-diisopropylethylamine), THF (tetrahydrofuran), Ac (acetyl), MeOH (methanol), Boc(tert-butoxycarbonyl), $B_2Pin_2$ (bis (pinacolato)diboron), rt (room temperature), HATU (2-(7-azabenzotriazol-1-yl)-N,N,N',N'-tetramethyluronium hexafluorophosphate), reflux (refluxing conditions), eq (equivalent), $R_f$ (retardation factor), g (gram), mg (milligram), mol (mole), mmol (millimole), h (hour), min (minute), mL (milliliter), μL (microliter).

Overnight refers to 8-15 h, for example 12 h; the room temperature refers to 10-30° C.; solvent ratio (such as PE/EA) refers to the volume ratio.

Unless otherwise indicated, all temperatures in the examples described below are given in Celsius degrees. Unless otherwise indicated, reagents are purchased from commercial suppliers such as Aldrich Chemical Company, Arco Chemical Company and Alfa Chemical Company, and used without further purification. General reagents are purchased from Shantou Xilong Chemical Plant Co. Ltd., Guangdong Guanghua Sci-Tech Co., Ltd., Guangzhou Chemical Reagent Factory, Tianjin Yuyu Fine Chemical Co., Ltd., Qingdao Tenglong Chemical Reagent Co., Ltd., or Qingdao Haiyang Chemical Co., Ltd.

Anhydrous tetrahydrofuran, dioxane, toluene and diethyl ether are obtained by refluxing and drying with sodium metal. Anhydrous dichloromethane and chloroform are obtained by refluxing and drying with calcium hydride. Ethyl acetate, petroleum ether, i-hexane, N,N-dimethylacetamide and N,N-dimethylformamide are pre-dried over anhydrous sodium sulfate.

The following reactions are generally preformed under a positive pressure of nitrogen or argon or by placing a drying tube over an anhydrous solvent (unless otherwise indicated), the reaction vial is stoppered with a suitable rubber stopper and the substrate is driven in by a syringe. Each piece of glassware is dried.

Chromatographic column is a silica gel column. Silica gel (300-400 mesh) is purchased from Qingdao Haiyang Chemical Co., Ltd. NMR spectral data are measured on a Bruker Avance 400 NMR spectrometer or a BrukerAvance IIIHD600 NMR spectrometer using $CDCl_3$, DMSO-$d_6$, $CD_3OD$ or Acetone-$d_6$ as solvents (reported in ppm) and TMS (0 ppm) or chloroform (7.25 ppm) as reference standards. When multiple peaks are present, the following abbreviations will be used: s (singlet): d (doublet): t (triplet); m (multiplet); br (broadened); dd (doublet of doublets); dt (doublet of triplets); ddd (doublet of doublet of doublets); ddt (doublet of doublet of triplets); dddd (doublet of doublet of doublet of doublets). Coupling constants are expressed in hertz (Hz).

Low-Resolution Mass Spectrometry (MS) data are determined on an Agilent 6320 series LC-MS spectrometer equipped with a G1312A binary pump and an aG1316ATCC (column temperature maintained at 30° C.), with a G1329A autosampler and G1315BDAD detector applied to the analysis and an ESI source applied to the LC-MS spectrometer.

The above two spectrometers are equipped with an Agilent Zorbax SB-$C_{18}$ column (2.1×30 mm, 5 μm). The injection volume is determined by the sample concentration; the flow rate is 0.6 mL/min; peak values of HPLC are recorded at UV-Vis wavelength of 210 nm and 254 nm.

Example 1
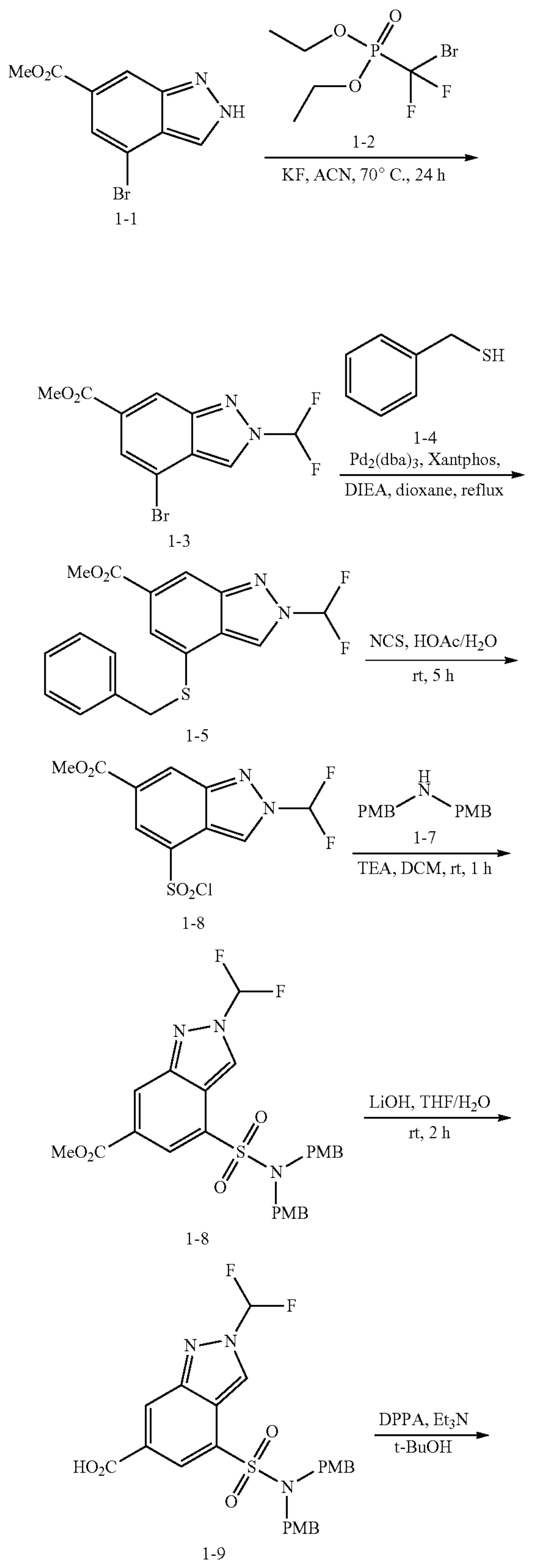
-continued
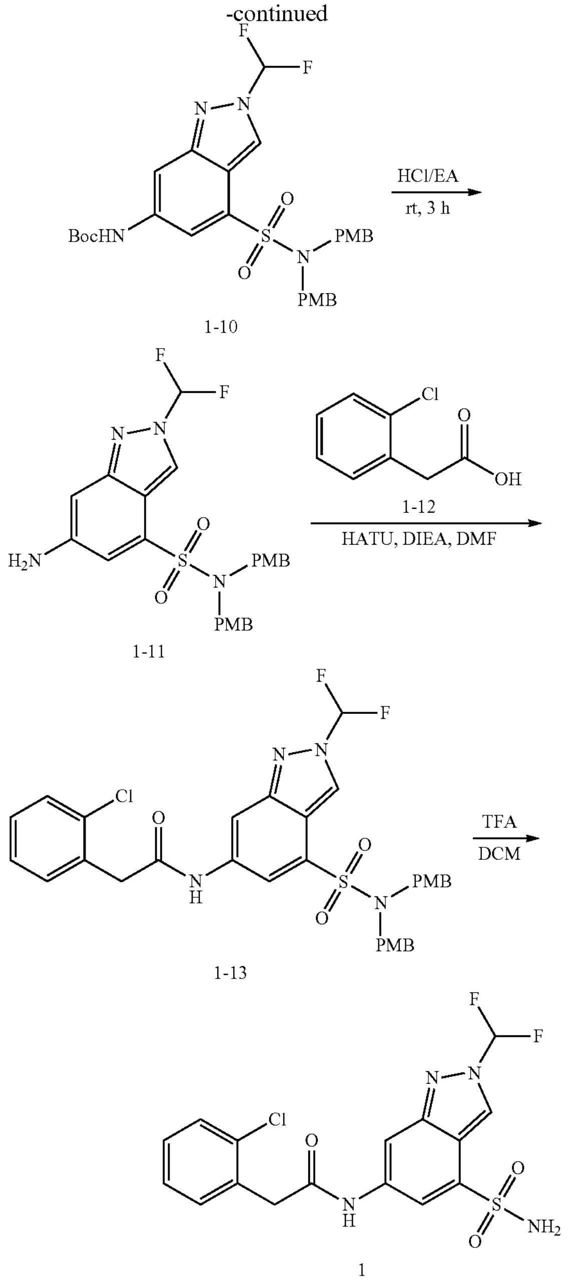
Step (1) Preparation of methyl 4-bromo-2-(difluoromethyl)-2H-indazole-6-carboxylate
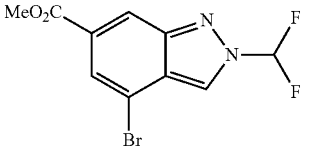
1-3
Compound 1-1 (20.0 g, 78.4 mmol) was dissolved in acetonitrile (250 mL), followed by the addition of KF (18.3 g, 314.9 mmol) and intermediate 1-2 (bromodifluoromethane diethyl phosphate, 62.9 g, 235.6 mmol), and after the addition was completed, the mixture was heated to 60° C. for 24 h under nitrogen atmosphere. After the reaction starting material was completely reacted as indicated by thin-layer chromatography, the reaction solution was filtered, the filter cake was washed with EA (250 mL), the filtrate was concentrated under reduced pressure, and the concentrate was stirred with silica gel and purified by column chromatography to give intermediate 1-3 (6.0 g, 25.3% yield) in the form of a white solid. LC-MS: $[M+H]^+=304.9$.

Step (2) Preparation of methyl 4-(benzylthio)-2-(difluoromethyl)-2H-indazole-6-carboxylate 1-5

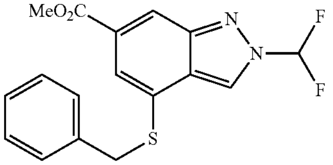

To a reaction flask were added intermediate 1-3 (19.0 g, 62.3 mmol), dioxane (380 mL), $Pd_2(dba)_3$ (5.7 g, 6.2 mmol), Xantphos (1.8 g, 3.1 mmol), intermediate 1-4 (benzyl mercaptan, 23.2 g, 186.8 mmol) and DIEA (32.3 g, 249.9 mmol), and the mixture was heated to reflux overnight under nitrogen atmosphere. After the reaction starting material was completely reacted as indicated by thin-layer chromatography, the reaction solution was filtered, the filter cake was washed with EA, and the filtrate was concentrated by rotary evaporation, stirred with silica gel and purified by column chromatography to give intermediate 1-5 (19.2 g, 88.5% yield) in the form of a yellow solid. LC-MS: $[M+H]^+=349.0$.

Step (3) Preparation of methyl 4-(chlorosulfonyl)-2-difluoromethyl)-2H-indazole-6-carboxylate 1-6

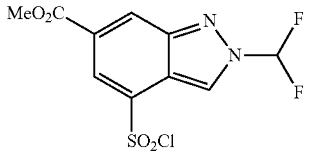

Intermediate 1-5 (21.0 g, 60.3 mmol) was dissolved in a mixed solution of glacial acetic acid (180 mL) and water (60 mL), NCS (32.2 g, 241.1 mmol) was added in portions, and after the addition was completed, the reaction solution was reacted overnight at room temperature. The solid was precipitated, the reaction starting material was completely reacted as indicated by thin-layer chromatography, then the reaction solution was filtered, and the solid was washed with water (50 mL×2) and concentrated by rotary evaporation to give a pure product; the filtrate was extracted twice with EA, and the organic phase was concentrated by rotary evaporation, stirred with silica gel and purified by column chromatography and then concentrated by rotary evaporation to give intermediate 1-6 (19.0 g, 97% yield) in the form of a white solid together with the filter cake. LC-MS: $[M+H]^+=324.9/326.9$.

Step (4) Preparation of methyl 4-(N,N-bis(4-methoxybenzyl)sulfamoyl)-2-(difluoromethyl)-2H-indazole-6-carboxylate 1-8

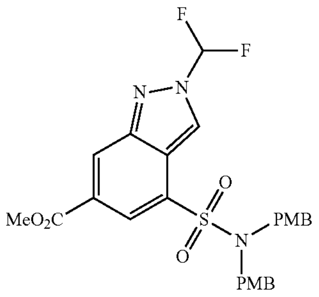

Intermediate 1-7 (bis-(4-methoxybenzyl)-amine, 18.1 g, 70.2 mmol) was dissolved in dichloromethane (250 mL), followed by the addition of TEA (17.8 g, 175.6 mmol), and after stirring at room temperature for 10 min, the mixture was added with intermediate 1-6 (19.0 g, 58.5 mmol) and reacted at room temperature for 1 h; after the reaction starting material was completely reacted as indicated by thin-layer chromatography, the reaction solution was concentrated, stirred with silica gel and purified by column chromatography to give intermediate 1-8 (18.0 g, 57.1% yield) in the form of a yellow solid. LC-MS: $[M-H]^+=546.2$.

Step (5) Preparation of 4-(N,N-bis(4-methoxybenzyl)sulfamoyl)-2-(difluoromethyl)-2H-indazole-6-carboxylic acid 1-9

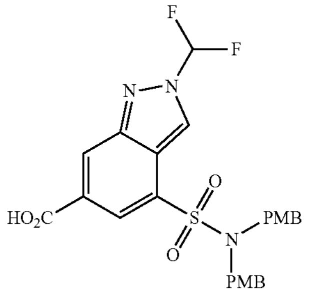

Intermediate 1-8 (17.5 g, 32.1 mmol) was dissolved in a mixed solution of tetrahydrofuran (300 mL) and water (75 mL), followed by the addition of lithium hydroxide monohydrate (6.8 g, 160.1 mmol), then the mixture was reacted at room temperature for 2 h, and after the reaction starting material was completely reacted as indicated by thin-layer chromatography, the reaction solution was concentrated by rotary evaporation and added with water (100 mL), and pH was adjusted to 4-5 with HCl (1 N); the solid was precipitated and filtered, the filter cake was washed for 3 times with water, and concentrated by rotary evaporation to give a product intermediate 1-9 (17.0 g, 99% yield) in the form of a light yellow solid. LC-MS: $[M-H]^+=532.1$.

Step (6) Preparation of tert-butyl (4-(N,N-bis(4-methoxybenzyl)sulfamoyl)-2-(difluoromethyl)-2H-indazol-6-yl)carbamate 1-10

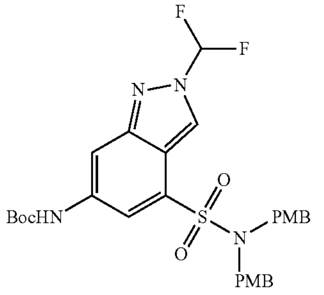

Intermediate 1-9 (16.6 g, 31.2 mmol) was dissolved in tert-butanol (320 mL), followed by the addition of DPPA (12.9 g, 46.9 mmol), and the mixture was stirred at room temperature for 10 min under $N_2$ atmosphere, added with triethylamine (12.7 g, 124.9 mmol), stirred at room temperature for 0.5 h, and heated to reflux at 90° C. for 3 h. After the reaction starting material was completely reacted as indicated by thin-layer chromatography, the reaction solution was added with water and extracted 2 times with EA, the organic phase was washed with saturated brine, dried over sodium sulfate, concentrated, stirred with silica gel and purified by column chromatography to give intermediate 1-10 (5.0 g, 27% yield) in the form of a yellow solid. LC-MS: $[M-H]^+$=603.2.

Step (7) Preparation of 6-amino-2-(difluoromethyl)-N,N-bis(4-methoxybenzyl)-2H-indazole-4-sulfonamide 1-11

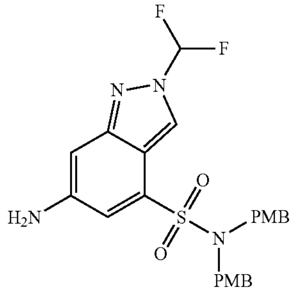

Intermediate 1-10 (5.0 g, 8.3 mmol) was dissolved in EA (40 mL), followed by the addition of a solution of HCl in EA (3.0 M, 40 mL), the mixture was reacted at room temperature for 2 h, and the solid was precipitated; after the reaction starting material was completely reacted as indicated by thin-layer chromatography, the reaction solution was directly concentrated by rotary evaporation, and the resulting solid was slurried with a mixed solution (PE/EA=5/1), filtered and concentrated by rotary evaporation to give intermediate 1-11 (4.2 g, 99.0% yield) in the form of a light yellow solid. LC-MS: $[M-H]^+$=503.1.

Step (8) Preparation of N-(4-(N,N-bis(4-methoxybenzyl)sulfamoyl)-2-(difluoromethyl)-2H-indazol-6-yl)-2-(2-chlorophenyl)acetamide 1-13

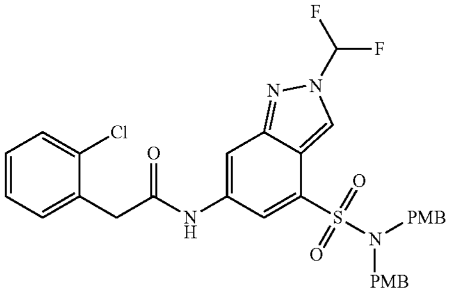

Intermediate 1-12 (2-chlorophenylacetic acid, 2.14 g, 12.536 mmol) was dissolved in DMF (50 mL), followed by the addition of HATU (4.77 g, 12.536 mmol), and the mixture was stirred at room temperature for 30 min under $N_2$ atmosphere, added with DIEA (4.3 g, 33.430 mmol) and intermediate 1-11 (4.2 g, 8.358 mmol), and reacted at room temperature for 2 h; after the reaction starting material was completely reacted as indicated by thin-layer chromatography, the reaction solution was added with water and extracted 2 times with EA, the organic phase was washed with saturated brine, dried over sodium sulfate, concentrated, stirred with silica gel and purified by column chromatography to give intermediate 1-13 (3.4 g, 62% yield) in the form of a light yellow solid. LC-MS: $[M-H]^+$=655.10.

Step (9) Preparation of 2-(2-chlorophenyl)-N-(2-(difluoromethyl)-4-sulfamoyl-2H-indazol-6-yl)acetamide

1

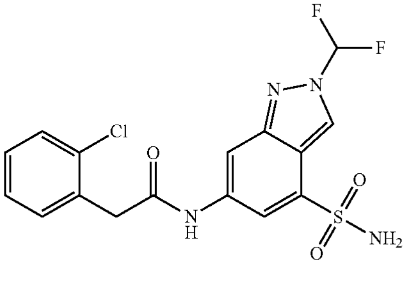

Intermediate 1-13 (3.4 g, 5.198 mmol) was dissolved in dichloromethane (60 mL), followed by the addition of TFA (60 mL), and the mixture was reacted at 40° C. for 3 h; after the reaction starting material was completely reacted as indicated by thin-layer chromatography, the reaction solution was concentrated by rotary evaporation, stirred with silica gel and purified by column chromatography to give compound 1 (1.7 g, 79% yield) in the form of a white solid. LC-MS: $[M-H]^+$=415.0.

$^1$H NMR (400 MHz, d-DMSO): δ10.70 (s, 21H), 10.70 (s, 21H), 8.96 (d, J=0.9 Hz, 21H), 8.96 (d, J=0.9 Hz, 21H), 8.36 (s, 18H), 8.35 (d, J=9.0 Hz, 25H), 8.33 (s, 5H), 8.19 (s, 11H), 8.19 (s, 10H), 8.04 (s, 6H), 8.04 (s, 5H), 7.84 (d, J=1.6 Hz, 21H), 7.84 (d, J=1.6 Hz, 20H), 7.66 (s, 40H), 7.66 (s, 41H), 7.46 (ddd, J=7.4, 3.9, 1.9 Hz, 42H), 7.46 (ddd, J=7.4, 3.9, 1.9 Hz, 40H), 7.39-7.27 (m, 43H), 7.36-7.29 (m, 42H), 3.91 (s, 40H), 3.91 (s, 41H), 3.33 (s, 26H), 2.50 (dt, J=3.6, 1.8 Hz, 29H), 2.07 (s, 6H).

Example 2

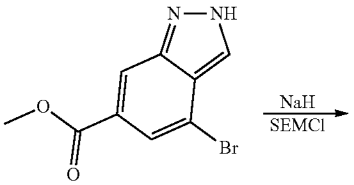

1-1

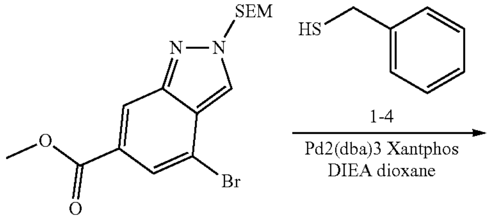

2-1

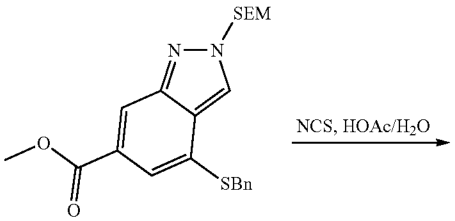

2-2

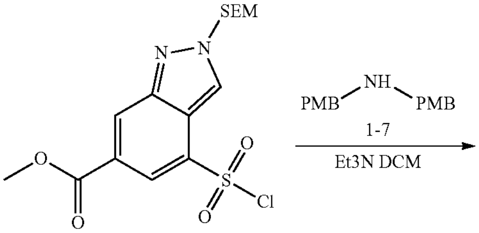

2-3

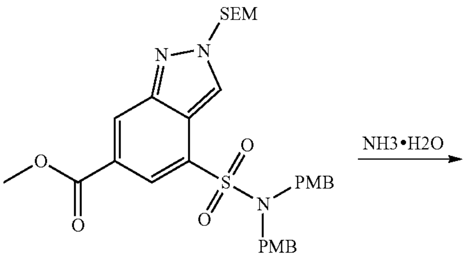

2-4

-continued

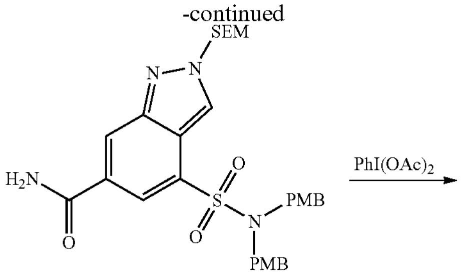

2-5

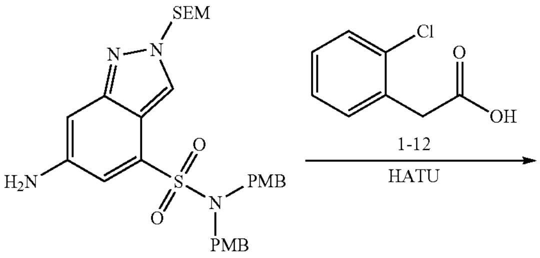

2-6

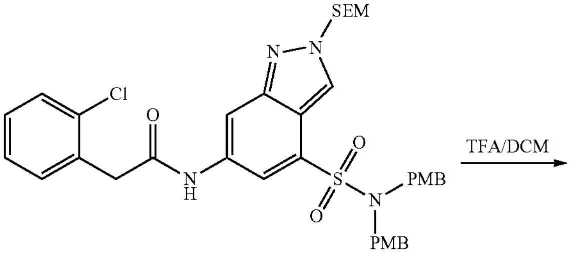

2-7

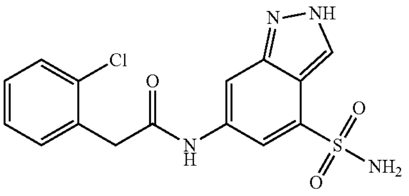

2

Step (1) Preparation of methyl-4-bromo-2((2-(trimethylsilyl)ethoxy)methyl)-2H-indazole-6-carboxylic acid 2-1

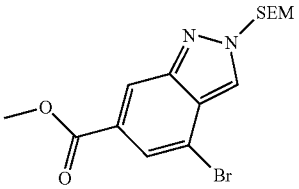

To a three-necked flask was added compound 1-1 (20 g, 78.41 mmol), followed by the addition of DMF (300 mL), and the mixture was added with NaH (4.08 g, 60% purity, 101.93 mmol) in portions in an ice-water bath, reacted at room temperature for 30 min, added dropwise with SEMCl (16.99 g, 101.93 mmol) in an ice-water bath, and then reacted overnight at room temperature after the dropwise addition was completed. After the reaction was completed as detected by TLC the next day, the reaction solution was poured into 500 mL (0.2 M) of citric acid in ice water, and the resulting solution was extracted with EA (300 mL×3), washed with saturated NaCl solution (20 mL), dried over $Na_2SO_4$, and concentrated and purified by column chromatography to give intermediate 2-1 (37.5 g, 70.7% purity, 87.7% yield) in the form of a yellow oil. LC-MS: $[M+H]^+$=385.1.

Step (2) Preparation of methyl-4-benzylthio-2((2-(trimethylsilyl)ethoxy)methyl)-2H-indazole-6-carboxylic acid 2-2

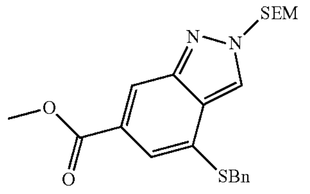

To a single-necked flask were added intermediate 2-1 (4.8 g, 12.46 mmol), benzylthiol (4.6 g, 37.4 mmol), DIEA (7.1 g, 49.8 mmol), $Pd_2(dba)_3$ (1.1 g, 1.25 mmol) and Xantphos (360 mg, 0.6 mmol), and the mixture was reacted at 85° C. overnight under $N_2$ atmosphere. After the reaction was completed as detected by TLC the next day, the reaction solution was directly stirred with silica gel and purified by column chromatography to give intermediate 2-2 (5.6 g) in the form of a light yellow liquid. LC-MS: $[M+H]^+$=429.2.

Step (3) Preparation of methyl-4-chlorosulfonyl-2((2-(trimethylsilyl)ethoxy)methyl)-2H-indazole-6-carboxylic acid 2-3

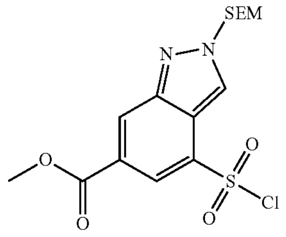

To a single-necked flask was added intermediate 2-2 (5.6 g, 13.1 mmol), followed by the addition of HOAc (50 mL) and $H_2O$ (10 mL), NCS (13.9 g, 104.5 mmol) was added in portions after the dissolution was completed, and after the addition was completed, the reaction solution was reacted overnight at room temperature; After the reaction was completed as detected by TLC the next day, the reaction solution was added with $H_2O$ (150 mL), extracted with EA, washed with saturated NaCl solution, dried over $Na_2SO_4$, concentrated, and purified by column chromatography to give intermediate 2-3 (3.3 g) in the form of a yellow oil. LC-MS: $[M+H]^+$=405.1.

Step (4) Preparation of methyl-4-(N,N-bis(4-methoxybenzyl)aminesulfonyl-2((2-(trimethylsilyl)ethoxy)methyl)-2H-indazole-6-carboxylic acid 2-4

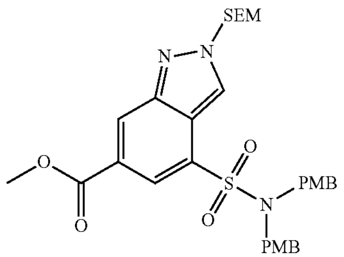

To a three-necked flask were sequentially added $NH(PMB)_2$ (2.3 g, 8.9 mmol) and $Et_3N$ (1.2 g, 12.2 mmol), followed by the addition of DCM (40 mL), intermediate 2-3 (3.3 g, 8.2 mmol) was added in portions in an ice bath, and after the addition was completed, the mixture was reacted at room temperature for 1 h. After the reaction was completed as detected by TLC, the reaction solution was added with $H_2O$ (80 mL), extracted with DCM (30 mL×2), washed with saturated NaCl, dried over $Na_2SO_4$, concentrated, and purified by column chromatography to give intermediate 2-4 (1.7 g) in the form of a yellow oil. LC-MS: $[M+H]^+$=626.2.

Step (5) Preparation of 4-(N,N-bis(4-methoxybenzyl)aminesulfonyl-2((2-(trimethylsilyl)ethoxy)methyl)-2H-indazole-6-carboxamide 2-5

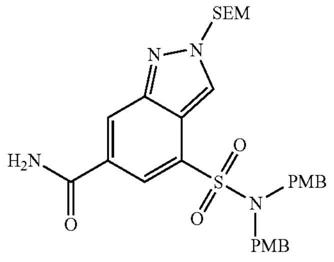

To a closed container was added intermediate 2-4 (1.5 g, 2.4 mmol), followed by the addition of aqueous ammonia (4 mL) and dioxane (4 mL), and the closed container was sealed and reacted in an oil bath at 110° C. for 5 h; after the reaction was completed as detected by TLC, the reaction solution was extracted with DCM (10 mL×2), dried over $Na_2SO_4$, concentrated, and purified by column chromatography to give intermediate 2-5 (0.5 g) in the form of a yellow oil. LC-MS: $[M+H]^+$=611.2.

Step (6) Preparation of 6-amino-4-(N,N-bis(4-methoxybenzyl)-2((2-(trimethylsilyl)ethoxy)methyl)-2H-indazole-4-sulfonamide 2-6

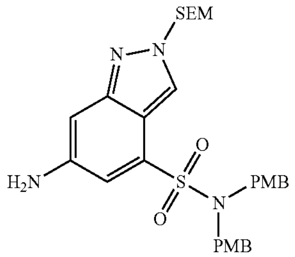

To a single-necked flask were added intermediate 2-5 (300 mg, 491.2 μmol) and DBU (149.5 mg, 982.3 μmol), followed by the addition of THF (2 mL) and $H_2O$ (0.7 mL), $PhI(OAc)_2$ (189.8 mg, 589.4 μmol) was added in an ice bath, and after the addition was completed, the mixture was reacted in an ice bath for 5 min. After the reaction was completed as detected by TLC, the reaction solution was added with $Na_2SO_3$ to quench the reaction, added with water (5 mL), extracted with EA (10 mL/2), dried, concentrated and purified by column chromatography to give intermediate 2-6 (232.0 mg). LC-MS: $[M+H]^+$=583.2.

Step (7) Preparation of N-(4-(N,N-bis(4-methoxybenzyl)sulfamoyl-2((2-(trimethylsilyl)ethoxy)methyl)-2H-indazol-6-yl)-2-(2-chlorophenyl)acetamide 2-7

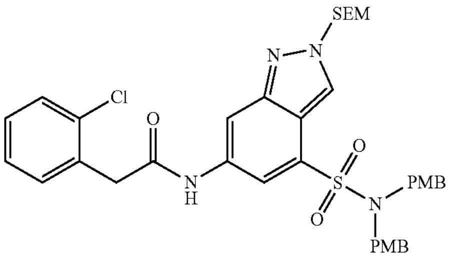

To a single-necked flask were added intermediate 2-6 (300 mg, 514.7 μmol), o-chlorophenylacetic acid (131.7 mg, 772.2 μmol), $Et_3N$ (156.3 mg, 1.5 mmol) and HATU (293.6 mg, 772.2 μmol), followed by the addition of DMF (2 mL), and after the addition was completed, the mixture was reacted at room temperature overnight; after the reaction was completed as detected by TLC the next day, the reaction solution was added with water (10 mL), extracted with EA (5 mL×2), washed with saturated brine, dried over $Na_2SO_4$, concentrated, and purified by column chromatography to give intermediate 2-7 (320.0 mg) in the form of a brown oil. LC-MS: $[M+H]^+$=735.2.

Step (8) Preparation of 2-(2-chlorophenyl)-N-(4-sulfamoyl-2H-indazol-6-yl)acetamide

2

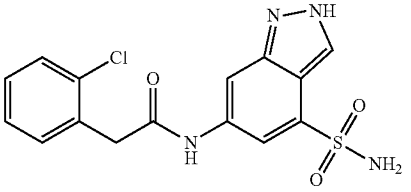

To a single-necked flask was added intermediate 2-7 (60.0 mg, 81.6 μmol), followed by the addition of TFA (2 mL) and DCM (2 mL), and the mixture was reacted at room temperature overnight; after the reaction was completed as detected by TLC the next day, the reaction solution was concentrated, the crude product was separated by prep-HPLC and lyophilized to give compound 2 (6.1 mg, 96.9% purity) in the form of a white solid. LC-MS: $[M+H]^+$=365.0.

$^1H$ NMR (400 MHz, $d_6$-DMSOmso): δ 13.31 (s, 1H), 10.66 (s, 1H), 8.31 (s, 1H), 8.26 (s, 1H), 7.70 (d, J=1.4 Hz, 1H), 7.55 (s, 2H), 7.48-7.42 (m, 2H), 7.35-7.29 (m, 2H), 3.89 (s, 2H).

Example 3

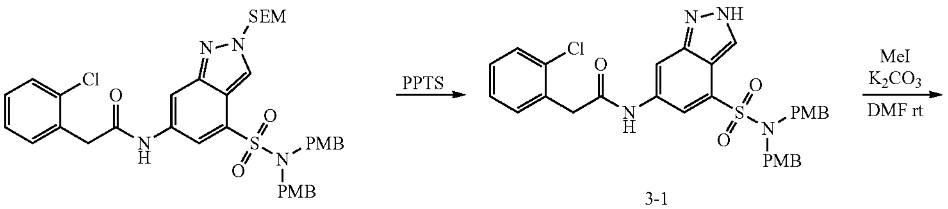

2-7

3-1

-continued

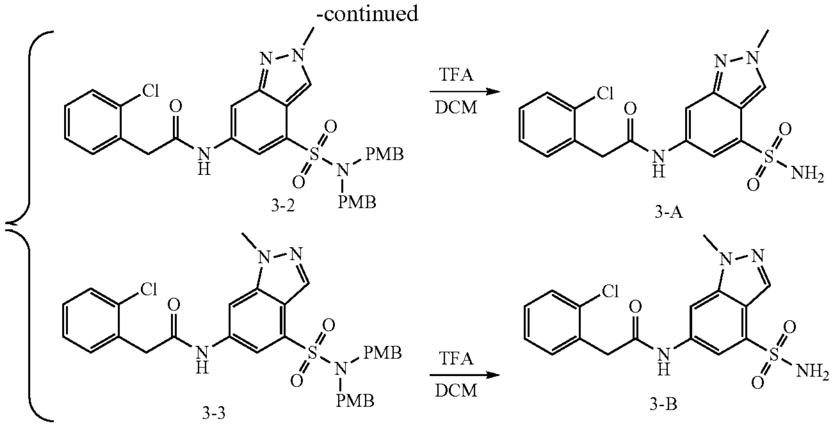

3-2 3-A 3-3 3-B

Step (1) Preparation of N-(4-(N,N-bis(4-methoxybenzyl)sulfamoyl-2H-indazol-6-yl)-2-(2-chlorophenyl)

3-1

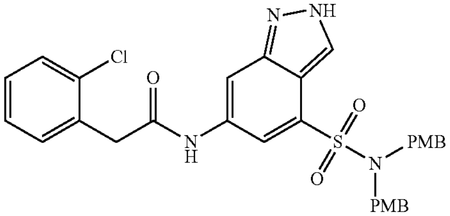

To a single-necked flask were added intermediate 2-7 (1.7 g, 2.3 mmol), PPTS (2.9 g, 11.6 mmol) and NMP (15 mL), the mixture was reacted at 135° C. overnight under $N_2$ atmosphere, and after the reaction was completed as detected by TLC, the reaction solution was added with water (100 mL), extracted with EA (30 mL×3), washed with saturated brine, dried over $Na_2SO_4$, concentrated, and purified by column chromatography to give intermediate 3-1 (3.0 g, crude) in the form of a yellow oil. LC-MS: $[M+H]^+$=605.1.

Step (2) Preparation of Intermediate 3-2 (N-(4-(N,N-bis(4-methoxybenzyl)sulfamoyl)-2-methyl-2H-indazol-6-yl)-2-(2-chlorophenyl)acetamide) and Intermediate 3-3 (N-(4-(N,N-bis(4-methoxybenzyl)sulfamoyl)-1-methyl-1H-indazol-6-yl)-2-(2-chlorophenyl)acetamide)

3-A

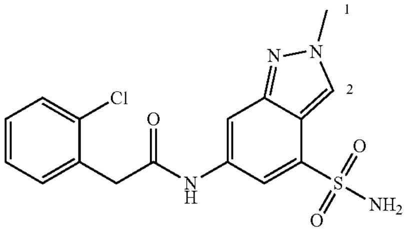

-continued

3-B

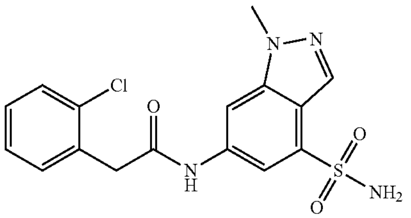

Intermediate 3-1 (300.0 mg, 0.5 mmol), iodomethane (510.0 mg, 1.5 mmol) and $K_2CO_3$ (414.0 mg, 1.5 mmol) were dissolved in DMF and stirred at room temperature overnight for reaction. After the reaction starting material was completely reacted as indicated by thin-layer chromatography, the reaction solution was added with water (5 mL) and extracted three times with EA, the EA phases were combined, washed with saturated brine, and dried over sodium sulfate, and the crude product was purified by column chromatography to give intermediate 3-2 (220.0 mg, yellow oil) and intermediate 3-3 (30.0 mg, yellow oil) according to different chromatographic solutions. LC-MS: $[M+H]^+$=619.0.

Step (3) Preparation of Compound 3-A (2-(2-chlorophenyl)-N-(2-methyl-4-sulfamoyl-2H-indazol-6-yl)acetamide) and Compound 3-B (2-(2-chlorophenyl)-N-(1-methyl-4-sulfamoyl-1H-indazol-6-yl) acetamide)

3-A

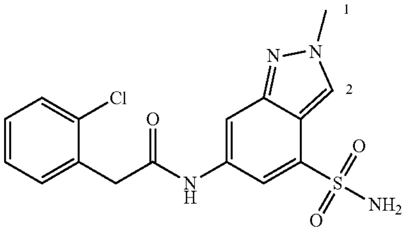

-continued

3-B

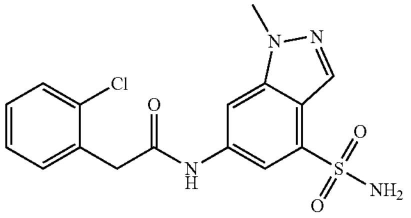

Intermediate 3-2 (200 mg, 0.3 mmol) was dissolved in DCM (3 mL), followed by the addition of an equal volume of TFA, and the mixture was stirred and reacted at room temperature overnight. After the reaction starting material was completely reacted as indicated by thin-layer chromatography, the reaction solution was concentrated by rotary evaporation, purified by preparative chromatography, and lyophilized to give compound 3-A (6.1 mg, 96.9% purity) in the form of a white solid. LC-MS: $[M+H]^+$=379.1.

$^1$H NMR (400 MHz, DMSO): δ 8.23 (d, J=1.3 Hz, 1H), 8.17 (d, J=0.9 Hz, 1H), 7.70 (d, J=1.6 Hz, 1H), 7.39-7.33 (m, 2H), 7.28-7.19 (m, 2H), 3.95 (s, 3H), 3.87 (s, 2H).

2D-HNMR (NOE) results showed that No. 1 hydrogen and No. 2 hydrogen in compound 3-A are correlated.

Intermediate 3-3 (30 mg, 0.045 mmol) was dissolved in DCM (1 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 3-B (6.1 mg, 96.5% purity) in the form of a white solid. LC-MS: $[M+H]^+$=379.1.

Example 4

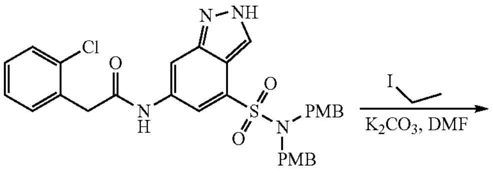

3-1

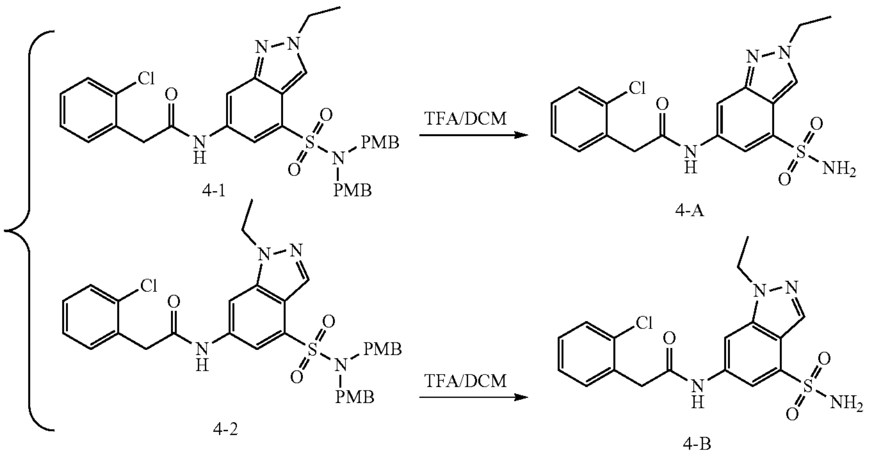

4-1 4-A 4-2 4-B

Step (1) Preparation of Intermediate 4-1 (4-(N,N-bis(4-methoxybenzyl)sulfonamide-6-N-(2-chlorophenylacetyl)-2-ethyl)-indazole) and Intermediate 4-2 (4-(N,N-bis(4-methoxybenzyl)sulfonamide-6-N-(2-chlorophenylacetyl)-1-ethyl)-indazole)

4-1

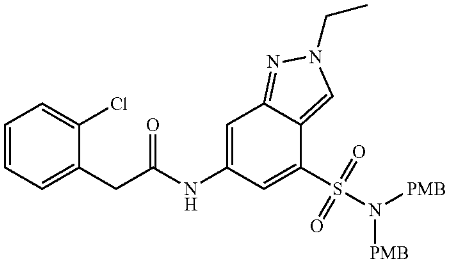

4-2

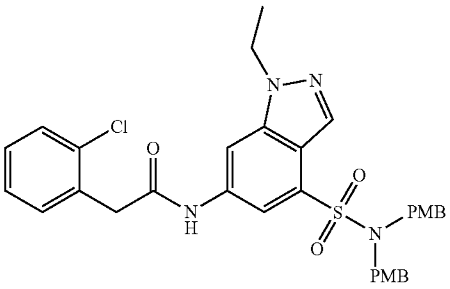

Intermediate 3-1 (180 mg, 298.0 μmol) and iodoethane (186 mg, 1.2 mmol) were dissolved in DMF (3 mL), followed by the addition of $K_2CO_3$, and then the mixture was stirred at room temperature for 3 h. After the reaction was completed, the reaction solution was poured into water, the resulting solution was extracted with EtOAc, the organic phase was dried over anhydrous sodium sulfate and filtered, and the filtrate was concentrated by rotary evaporation to obtain a crude product which was purified by silica gel column chromatography to give intermediate 4-1 (30.0 mg, yellow oil) and intermediate 4-2 (60.0 mg, yellow oil) from different chromatographic solutions. LC-MS: $[M+H]^+$=633.0.

Step (2) Preparation of Compound 4-A ((4-sulfonamide-6-N-(2-chlorophenylacetyl)-2-ethyl)-indazole) and Compound 4-1B((4-sulfonamide-6-N-(2-chlorophenylacetyl)-1-ethyl)-indazole)

4-B

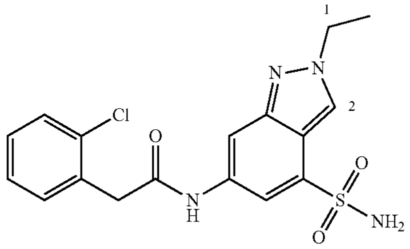

4-B

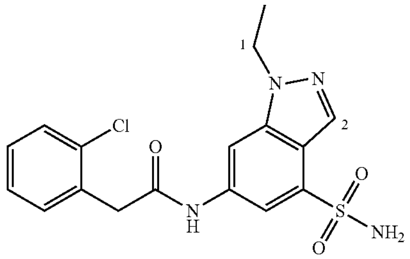

Intermediate 4-1 (30.0 mg, 47.4 μmol) was dissolved in DCM (0.5 mL), followed by the addition of TFA (0.5 mL), and the reaction solution was stirred at room temperature overnight. After the reaction was completed, the reaction solution was concentrated under reduced pressure at room temperature to give a crude product which was purified by prep-HPLC to give compound 4-A (5.0 mg) in the form of a white solid powder. LC-MS: $[M+H]^+$=393.0. $^1H$ NMR (400 MHz, MeOD): δ 8.46 (s, 1H), 8.24 (s, 1H), 7.83 (d, J=1.5 Hz, 1H), 7.43 (dd, J=5.2, 2.4 Hz, 2H), 7.34-7.27 (m, 2H), 4.51 (q, J=7.3 Hz, 3H), 3.93 (s, 2H), 1.61 (t, J=7.3 Hz, 3H).

Intermediate 4-2 (60.0 mg, 94.8 μmol) was dissolved in THF (1 mL), followed by the addition of TFA (1 mL), the reaction solution was stirred at room temperature overnight, and after the reaction was completed, the reaction solution was concentrated under reduced pressure at room temperature to give a crude product which was purified by prep-HPLC to give compound 4-B (4.6 mg) in the form of a white solid powder. LC-MS: $[M+H]^+$=393.1. $^1H$ NMR (400 MHz, DMSO): δ 10.70 (s, 1H), 8.32 (s, 1H), 8.22 (s, 1H), 7.68 (d, J=1.2 Hz, 1H), 7.56 (s, 2H), 7.47-7.40 (m, 2H), 7.34-7.26 (m, 2H), 4.37 (q, J=7.2 Hz, 2H), 3.89 (s, 2H), 1.35 (t, J=7.2 Hz, 3H).

2D-HNMR (NOE) results showed that No. 1 hydrogen and No. 2 hydrogen in compound 4-A are correlated, and No. 1 hydrogen and No. 2 hydrogen in compound 4-B are not correlated.

Example 5

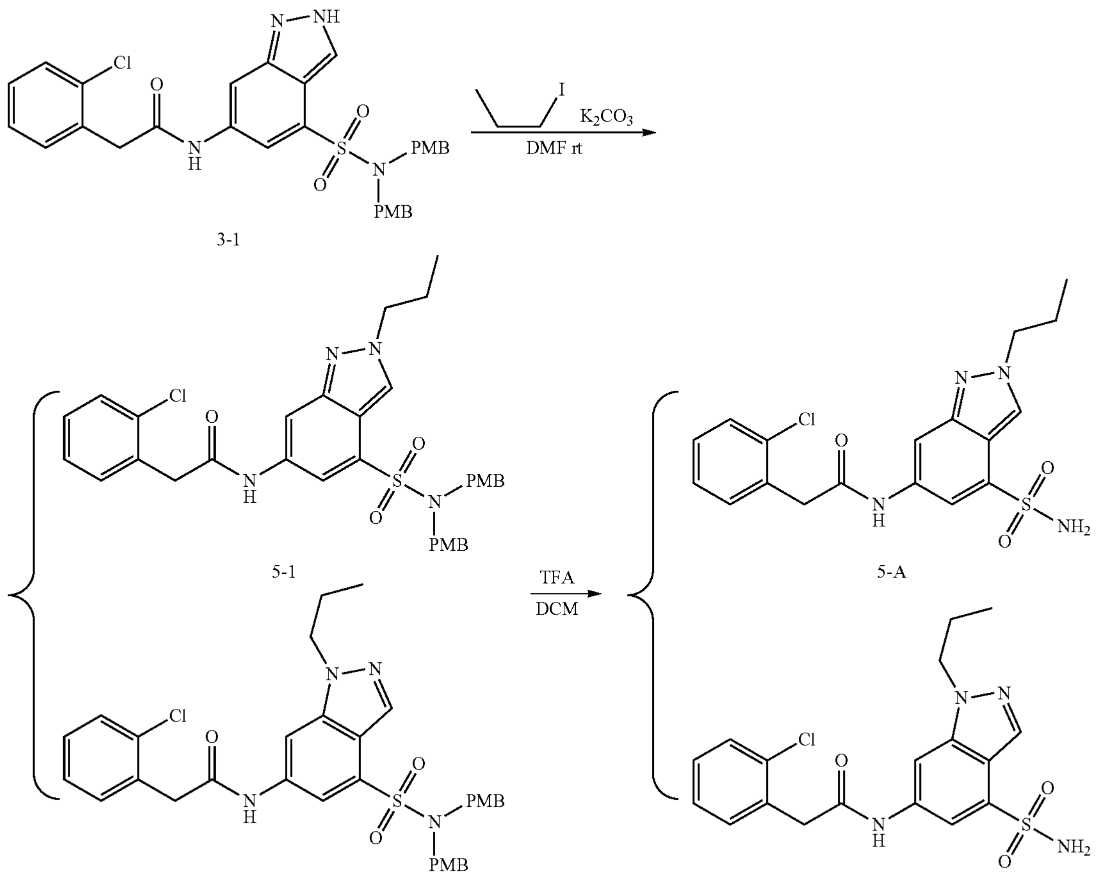

3-1

5-1

5-2

5-A

5-B

Step (1) Preparation of Intermediate 5-1 (N-(4-(N,N-bis(4-methoxybenzyl)sulfonamide)-2-propyl-2H-indazol-6-yl)-2-(2-chlorophenyl)acetamide) and Intermediate 5-2 (N-(4-(N,N-bis(4-methoxybenzyl)sulfon amide)-1-propyl-1H-indazol-6-yl)-2-(2-chlorophenyl)acetamide)

5-1

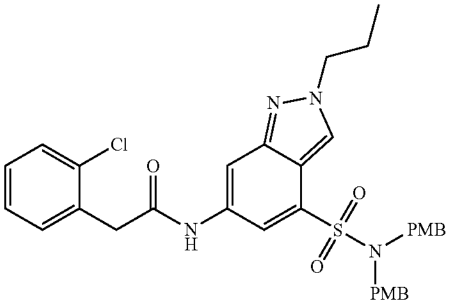

-continued 5-2

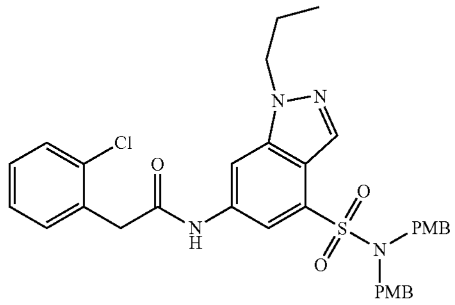

Intermediate 3-1 (300.0 mg, 0.5 mmol), iodopropane (510.0 mg, 1.5 mmol) and $K_2CO_3$ (414.0 mg, 1.5 mmol) were dissolved in DMF and stirred at room temperature overnight for reaction. After the reaction starting material was completely reacted as indicated by thin-layer chromatography, the reaction solution was added with water (5 mL) and extracted three times with EA, the EA phases were combined, washed with saturated brine, dried over sodium sulfate, filtered and concentrated to give a mixture (212.0 mg) of intermediate 5-1 and intermediate 5-2 in the form of a yellow oil. LC-MS: $[M+H]^+$=647.1.

Step (2) Preparation of Compound 5-A (2-(2-chlorophenyl)-N-(2-propyl-4-sulfonylamino-2H-indazol-6-yl)acetamide) and Compound 5-B (2-(2-chlorophenyl)-N-(1-propyl-4-sulfonylamino-1H-indazol-6-yl)acetamide)

5-A

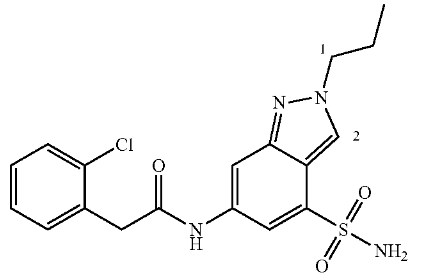

5-B

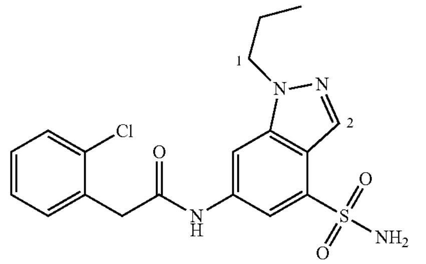

A mixture (200.0 mg, 0.31 mmol) of intermediate 5-1 and intermediate 5-2 was dissolved in DCM (3 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 5-A (13.0 mg, white solid) and compound 5-B (10.5 mg, white solid). LC-MS: $[M+H]^+$=407.1.

Compound 5-A: $^1H$ NMR (400 MHz, $CDCl_3$) δ 9.13 (s, 1H), 8.25 (s, 2H), 7.73 (d, J=1.2 Hz, 1H), 7.33 (d, J=6.8 Hz, 2H), 7.19 (s, 2H), 6.17 (s, 2H), 4.28 (t, J=7.0 Hz, 2H), 3.81 (s, 2H), 0.87 (s, 3H).

Compound 5-B: $^1H$ NMR (400 MHz, $CDCl_3$) δ 10.24 (s, 1H), 8.47 (s, 1H), 8.25 (d, J=0.8 Hz, 1H), 7.57 (d, J=1.6 Hz, 1H), 7.32 (dd, J=6.8, 2.4 Hz, 2H), 7.19 (dt, J=4.8, 4.0 Hz, 2H), 6.81 (s, 2H), 4.21 (t, J=7.0 Hz, 2H), 3.83 (s, 2H), 1.80 (dt, J=14.6, 7.4 Hz, 2H), 0.80 (t, J=7.4 Hz, 3H).

2D-HNMR (NOE) results showed that No. 1 hydrogen and No. 2 hydrogen in compound 5-A are correlated, and No. 1 hydrogen and No. 2 hydrogen in compound 5-B are not correlated.

Example 6

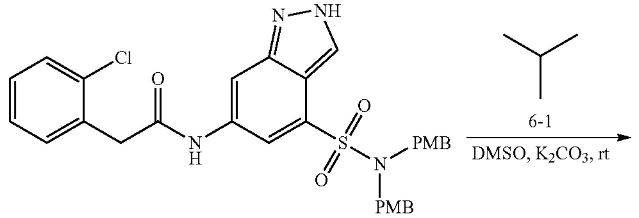

3-1

-continued

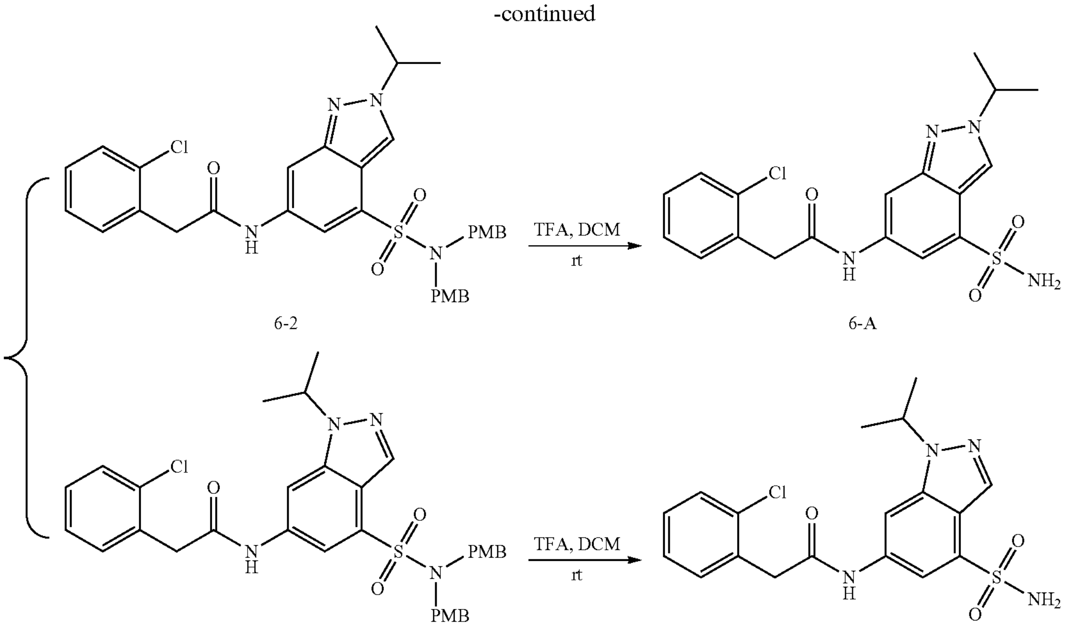

6-2 6-A 6-3 6-B

Step (1) Preparation of Intermediate 6-2 (N-(4-(N,N-bis(4-methoxybenzyl)sulfamoyl)-2-isopropyl-2H-indazol-6-yl)-2-(2-chlorophenyl)acetamide) and Intermediate 6-3 (N-(4-(N,N-bis(4-methoxybenzyl)sulfamoyl)-1-isopropyl-1H-indazol-6-yl)-2-(2-chlorophenyl)acetamide)

6-2

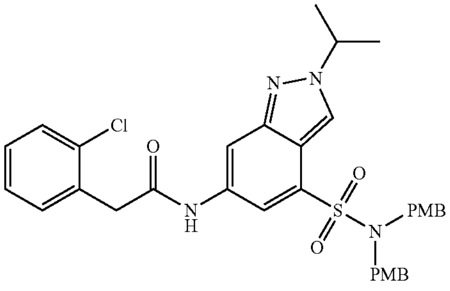

6-3

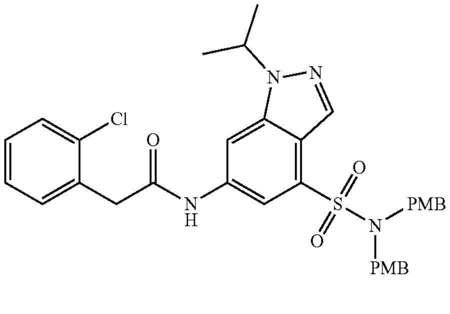

Intermediate 3-1 (210.0 mg, 347.1 μmmol) was dissolved in DMSO (10 mL), followed by the addition of intermediate 6-1 (118.0 g, 694.1 μmmol) and $K_2CO_3$ (95.9 mg, 694.1 μmmol), and the mixture was stirred at room temperature overnight. After the reaction starting material was completely reacted as detected by TLC, the reaction solution was added with water (30 mL) and ethyl acetate (30 mL) for dilution, followed by liquid separation. The organic phase was collected, the aqueous phase was extracted with EA (30 mL×3), the organic phases were combined, washed with saturated brine, and dried over anhydrous $Na_2SO_4$, and the crude product was purified by silica gel column chromatography to give intermediate 6-2 (120.0 mg, yellow oil) and intermediate 6-3 (30.0 mg, yellow oil) according to different chromatographic solutions. LC-MS: $[M+H]^+$=647.1.

Step (2) Preparation of Compound 6-A (2-(2-chlorophenyl)-N-(2-isopropyl-4-sulfamoyl-2H-indazol-6-yl)acetamide) and Compound 6-B (2-(2-chlorophenyl)-N-(1-isopropyl-4-sulfamoyl-1H-indazol-6-yl)acetamide)

6-A

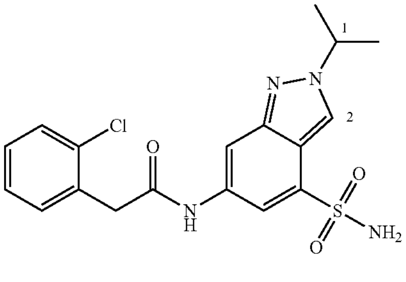

6-B

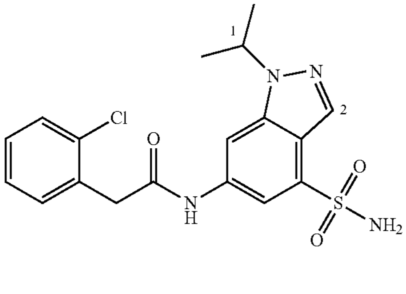

Intermediate 6-2 (100.0 mg, 154.5 μmmol) was dissolved in DCM (3 mL), followed by the addition of TFA (3 mL), and the mixture was stirred at room temperature overnight. After the reaction starting material was completely reacted as detected by TLC, the reaction was stopped.

The solvent was concentrated by rotary evaporation to give a crude product which was separated by prep-HPLC using a $H_2O$/ACN system and lyophilized to give compound 6-A (35.0 mg, 95.9% purity) in the form of a white solid. LC-MS: $[M+H]^+$=407.1.

$^1$H NMR (400 MHz, DMSO-$d_6$): δ 10.73 (s, 1H), 8.38 (s, 1H), 8.26 (s, 1H), 7.70 (d, J=1.4 Hz, 1H), 7.58 (s, 2H), 7.48-7.44 (m, 2H), 7.35-7.30 (m, 2H), 4.90-4.83 (m, 1H), 3.91 (s, 2H), 1.47 (s, 3H), 1.46 (s, 3H).

Intermediate 6-3 (30.0 mg, 46.5 μmmol) was dissolved in DCM (1 mL), followed by the addition of TFA (1 mL), and the mixture was stirred at room temperature overnight. After the reaction starting material was completely reacted as detected by TLC, the reaction was stopped. The solvent was concentrated by rotary evaporation to give a crude product which was separated by prep-HPLC using a $H_2O$/ACN system and lyophilized to give compound 6-B (5.0 mg, 95.9% purity) in the form of a white solid. LC-MS: $[M+H]^+$= 407.1.

2D-HNMR (NOE) results showed that No. 1 hydrogen and No. 2 hydrogen in compound 6-A are correlated, and No. 1 hydrogen and No. 2 hydrogen in compound 6-B are not correlated.

Example 7

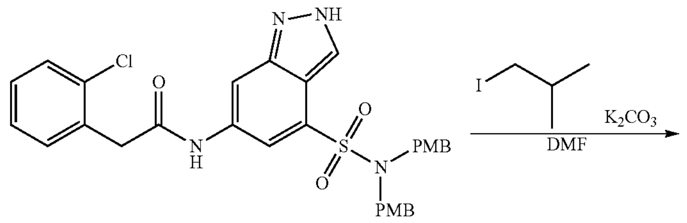

3-1

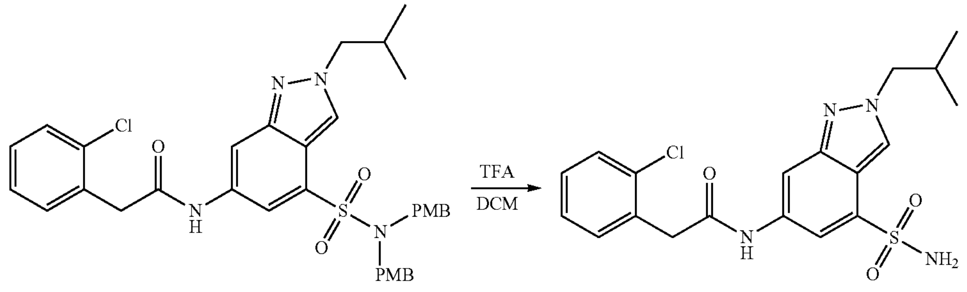

7-1 7-A

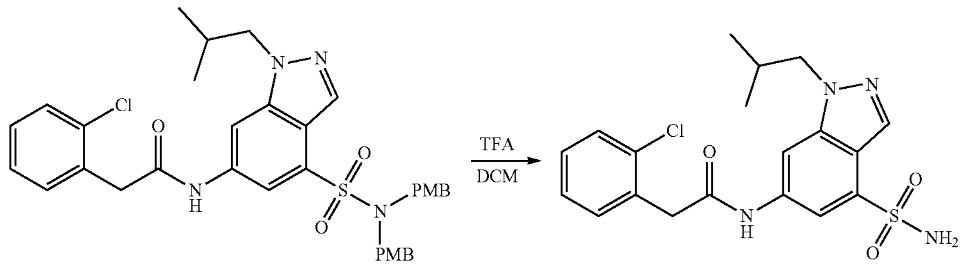

7-2 7-B

Step (1) Preparation of Intermediate 7-1 (N-(4-(N,N-bis(4-methoxybenzyl)sulfamoyl(-2-isobutyl-2H-indazol-6-yl)-2-(2-chlorophenyl) acetamide) and Intermediate 7-2 (N-(4-(N,N-bis(4-methoxybenzyl) sulfamoyl)-1-isobutyl-1H-indazol-6-yl)-2-(2-chlorophenyl)acetamide)

7-1

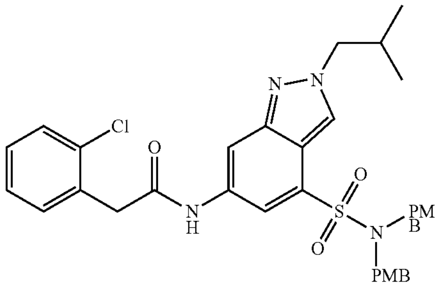

7-2

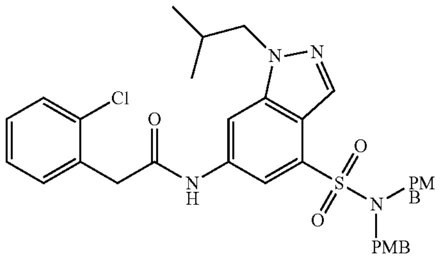

Intermediate 3-1 (600 mg, 1.0 mmol), 1-iodo 2-methylpropane (913.9 mg, 5.0 mmol) and potassium carbonate (274.6 mg, 2.0 mmol) were sequentially added to DMF (5 mL), the mixture was stirred at room temperature overnight (for 14 h), and after the reaction was completed as detected by LC-MS, the reaction solution was added with water (25 mL), and extracted with ethyl acetate (100 mL×3). The oil phases were combined, washed 3 times with saturated brine, dried over anhydrous sodium sulfate, and filtered, and the filtrate was concentrated under reduced pressure to give a crude product which was purified by silica gel column chromatography to give intermediate 7-1 (white solid, 80.0 mg, 81.2% purity) and intermediate 7-2 (white solid, 1.3 g, 86.9% purity). LC-MS: $[M+H]^+$=661.2.

Step (2) Preparation of Compound 7-A (2-(2-chlorophenyl)-N-(2-isobutyl-4-sulfamoyl-2H-indazol-6-yl)acetamide) and Compound 7-B (2-(2-chlorophenyl)-N-(1-isobutyl-4-sulfamoyl-2H-indazol-6-yl) acetamide)

7-A

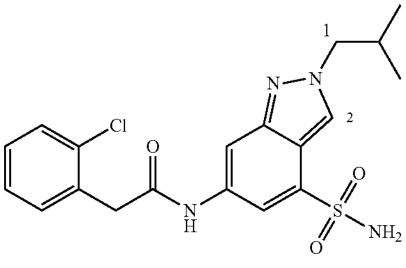

7-B

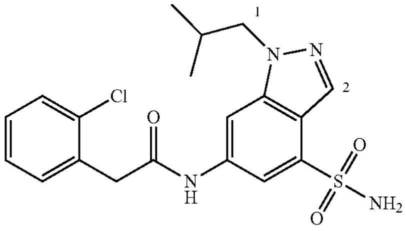

Intermediate 7-1 (80.0 mg, 0.1 mmol) was dissolved in dichloromethane (1.5 mL), the reaction solution was added with TFA (1 mL) and then stirred at room temperature overnight (for 14 h). After the reaction was completed as detected by TLC, the reaction solution was concentrated to dryness to give a reddish solid (54.0 mg) which was purified by preparative chromatography to give compound 7-A (14.5 mg, 99.6% purity) in the form of a white solid. LC-MS: $[M+H+2]^+$=421.1.

$^1$H NMR (400 MHz, dmso) δ 10.73 (s, 1H), 8.34 (s, 1H), 8.25 (s, 1H), 7.71 (d, J=1.4 Hz, 1H), 7.60 (s, 2H), 7.48-7.42 (m, 2H), 7.35-7.28 (m, 2H), 4.16 (d, J=7.2 Hz, 2H), 3.91 (s, 2H), 2.19 (dp, J=13.6, 6.8 Hz, 1H), 0.84 (d, J=6.7 Hz, 6H).

Intermediate 7-2 (64.0 mg, 0.097 mmol) was dissolved in dichloromethane (1.5 mL), the reaction solution was added with TFA (1 mL) and then stirred at room temperature overnight (for 14 h). After the reaction was completed as detected by TLC, the reaction solution was concentrated to dryness to give a reddish solid (44.0 mg, 75.0% purity) which was purified by preparative chromatography to give compound 7-B (6.3 mg, 98.7% purity) in the form of a white solid. LC-MS: $[M+H+2]^+$=421.1.

$^1$H NMR (400 MHz, dmso) δ 10.52 (s, 1H), 8.46 (s, 1H), 8.22 (s, 1H), 7.72 (s, 1H), 7.50 (s, 2H), 7.48-7.43 (m, 2H), 7.35-7.27 (m, 2H), 4.24 (d, J=7.2 Hz, 2H), 3.88 (s, 2H), 2.29 (td, J=13.5, 6.7 Hz, 1H), 0.87 (d, J=6.7 Hz, 6H).

2D-HNMR (NOE) results showed that No. 1 hydrogen and No. 2 hydrogen in compound 7-A are correlated, and No. 1 hydrogen and No. 2 hydrogen in compound 7-B are not correlated.

Example 8

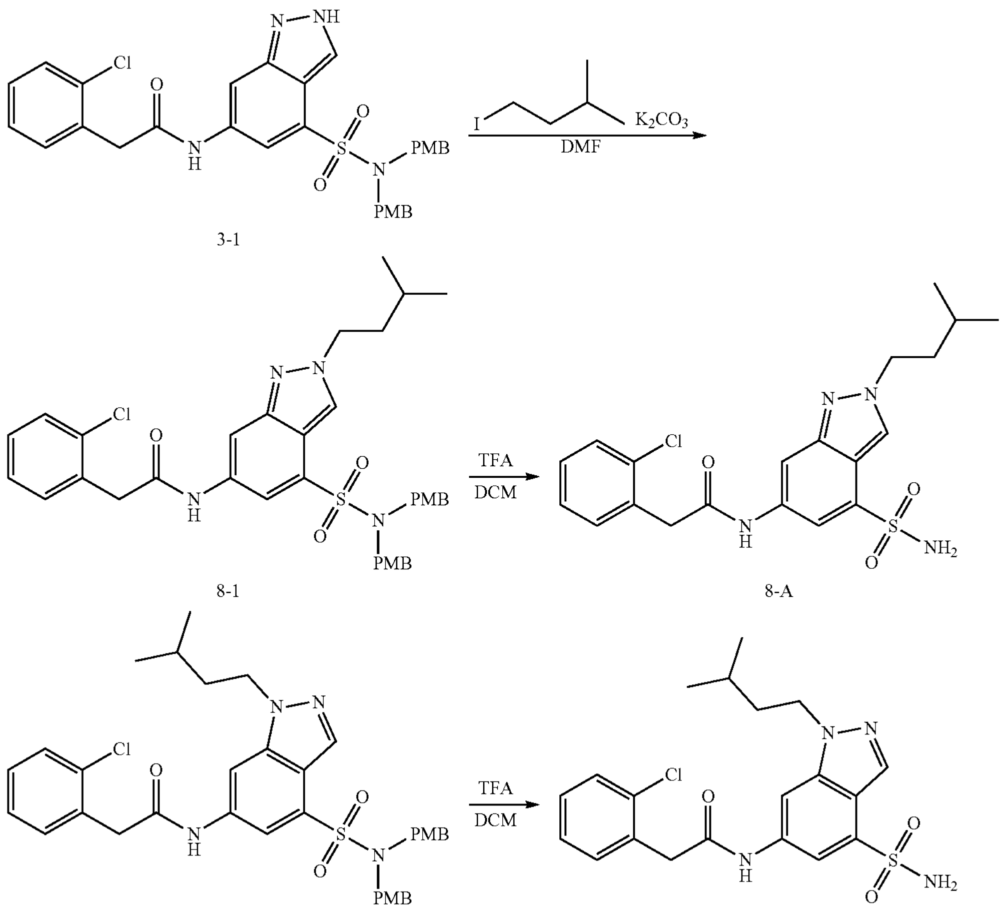

3-1

8-1 8-A 8-2 8-B

Step (1) Preparation of Intermediate 8-1 (N-(4-(N,N-bis(4-methoxybenzyl)sulfamoyl)-2-isopentyl-2H-indazol-6-yl)-2-(2-chlorophenyl) acetamide) and Intermediate 8-2 (N-(4-(N,N-bis(4-methoxybenzyl) sulfamoyl)-1-isopentyl-2H-indazol-6-yl)-2-(2-chlorophenyl)acetamide)

8-1

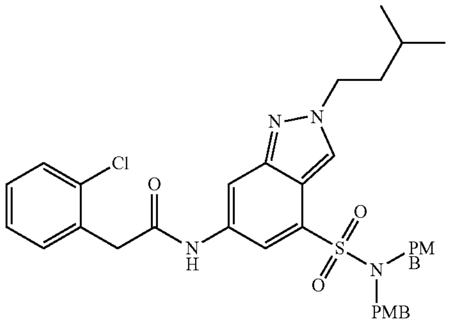

-continued 8-2

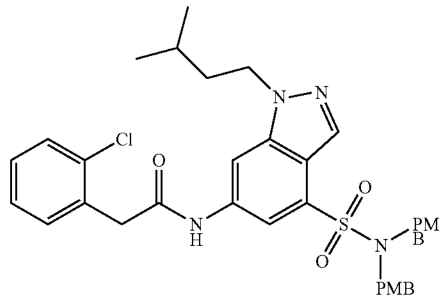

Intermediate 3-1 (600 mg, 1.0 mmol), 1-iodo-3-methylbutane (983.7 mg, 5.0 mmol) and potassium carbonate (274.6 mg, 2.0 mmol) were sequentially added to DMF (5 mL), the mixture was stirred at room temperature overnight (for 14 h), and after the reaction was completed as detected by LCMS, the reaction solution was added with water (25 mL), and extracted with ethyl acetate (100 mL×3). The oil phases were combined, washed 3 times with saturated brine, dried over anhydrous sodium sulfate, and filtered, and the filtrate was concentrated under reduced pressure to give a crude product which was purified by silica gel column chromatography to give intermediate 8-1 (white solid, 29.0 mg, 96.1% purity) and intermediate 8-2 (white solid, 47.0 mg, 81.4% purity). LC-MS: $[M+H]^+$=675.2.

Step (2) Preparation of Compound 8-A (2-(2-chlorophenyl)-N-(2-isopentyl-4-sulfamoyl-2H-indazol-6-yl)acetamide) and Compound 8-B (2-(2-chlorophenyl)-N-(1-isopentyl-4-sulfamoyl-2H-indazol-6-yl) acetamide)

8-A

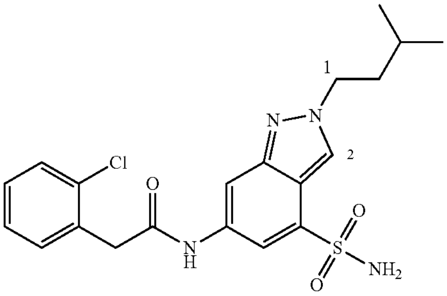

8-B

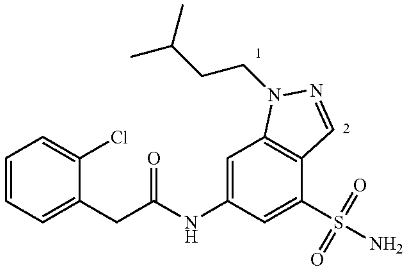

Intermediate 8-1 (29.0 mg, 43.0 μmol) was dissolved in dichloromethane (1.5 mL), and the reaction solution was added with TFA (1 mL) and then stirred at room temperature overnight (for 14 h). After the reaction was completed as detected by TLC, the reaction solution was concentrated to dryness to give a reddish solid (24.0 mg) which was purified by preparative chromatography to give compound 8-A (5.1 mg, 99.4% purity) in the form of a white solid. LC-MS: $[M+H+2]^+$=435.1.

$^1$H NMR (400 MHz, dmso) δ 10.70 (s, 1H), 8.31 (s, 1H), 8.22 (s, 1H), 7.70 (s, 1H), 7.57 (s, 2H), 7.43 (s, 2H), 7.35-7.26 (m, 2H), 4.35 (t, J=7.0 Hz, 2H), 3.89 (s, 2H), 1.67 (q, J=7.0 Hz, 2H), 1.42 (dt, J=13.3, 6.5 Hz, 1H), 0.87 (d, J=6.6 Hz, 6H).

Intermediate 8-2 (47.0 mg, 70.0 μmol) was dissolved in dichloromethane (1.5 mL), the reaction solution was added with TFA (1 mL) and then stirred at room temperature overnight (for 14 h).

After the reaction was completed as detected by TLC, the reaction solution was concentrated to dryness to give a reddish solid (35.0 mg) which was purified by preparative chromatography to give compound 8-B (7.2 mg, 99.4% purity) in the form of a white solid. LC-MS: $[M+H+2]^+$=435.10. $^1$H NMR (400 MHz, dmso) δ 10.52 (s, 1H), 8.50 (s, 1H), 8.22 (s, 1H), 7.72 (s, 1H), 7.49 (s, 2H), 7.44 (s, 2H), 7.36-7.29 (m, 2H), 4.45 (t, J=7.2 Hz, 2H), 3.88 (s, 2H), 1.81 (q, J=7.0 Hz, 2H), 1.52 (dt, J=13.3, 6.7 Hz, 1H), 0.92 (d, J=6.5 Hz, 6H).

2D-HNMR (NOE) results showed that No. 1 hydrogen and No. 2 hydrogen in compound 8-A are correlated, and No. 1 hydrogen and No. 2 hydrogen in compound 8-B are not correlated.

Example 9

Preparation of 2-(2-chlorophenyl)-N-(2-(tert-butyl)-4-sulfamoyl-2H-indazol-6-yl)acetamide

9

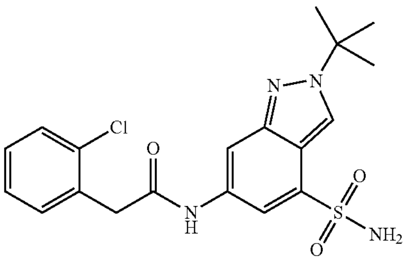

The compound was prepared using the preparation method described in Example 4. LC-MS: $[M+H]^+$=421.1.

Example 10

Preparation of 2-(2-chlorophenyl)-N-(2-(3-methylbutan-2-yl)-4-sulfamoyl-2H-indazol-6-yl)acetamide

10

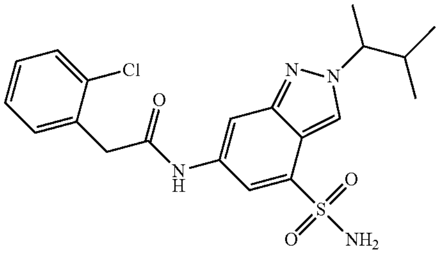

The compound was prepared using the preparation method described in Example 4. LC-MS: $[M+H]^+$=435.1.

Example 10-1

Compound Nos. 10+10A

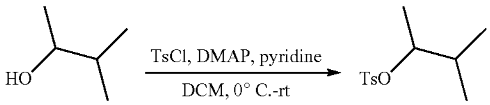

10-1 10-2

-continued

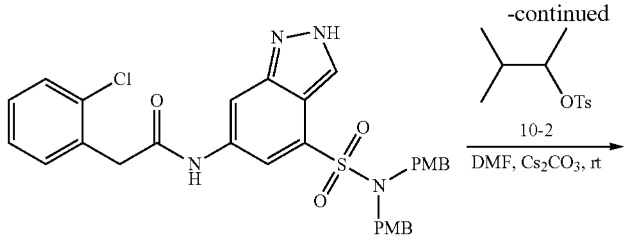

3-1

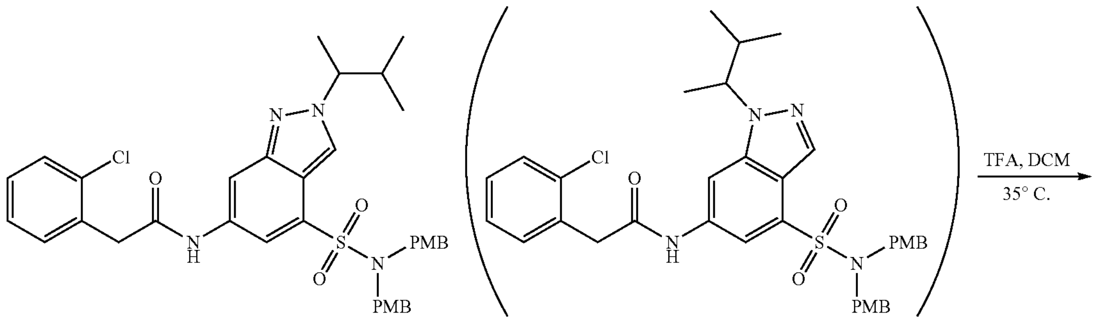

10-3 10-4

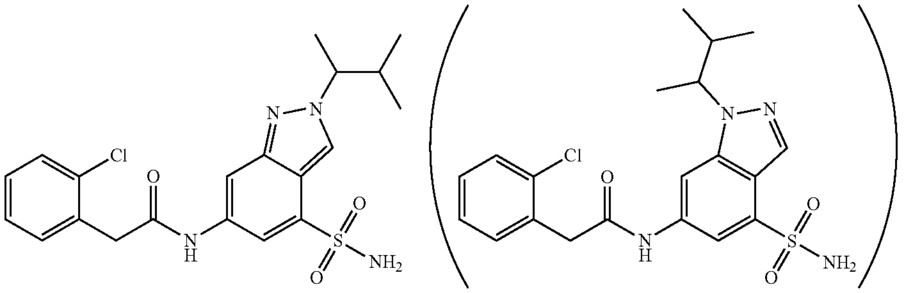

10 10A

Step (1) Preparation of 3-methylbutan-2-yl 4-methylbenzenesulfonate 10-2

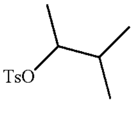

Intermediate 10-1 (3-methylbutan-2-ol) (1.0 g, 11.34 mmol) was dissolved in DCM (15 mL), followed by the addition of DMAP (138.6 mg, 1.13 mmol) and pyridine (1.79 g, 22.69 mmol). The system was cooled to 0° C., added with TsCl (2.81 g, 14.75 mmol), heated to room temperature, and stirred overnight. After the reaction starting material was completely reacted as detected by TLC (EA:PE=1:5), the reaction solution was added with 50 mL of water and 50 mL of dichloromethane for dilution, followed by liquid separation. The organic phase was collected, and the solvent was concentrated by rotary evaporation to give intermediate 10-2 (920 mg) in the form of a yellow oil. LC-MS: $[M+H]^+$=243.

Step (2) Preparation of N-(4-(N,N-bis(4-methoxybenzyl)sulfamoyl)-2-(3-methylbutan-2-yl)-2H-indazol-6-yl)-2-(2-chlorophenyl)acetamide (N-(4-(N,N-bis(4-methoxybenzyl)sulfamoyl)-1-(3-methylbutan-2-yl)-1H-indazol-6-yl)-2-(2-chlorophenyl) acetamide)

10-3

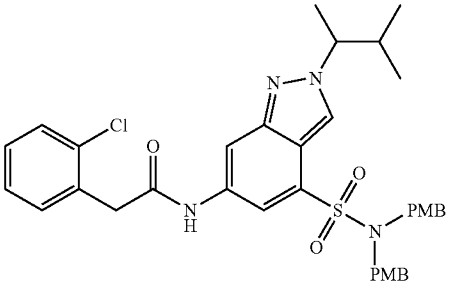

-continued 10-4

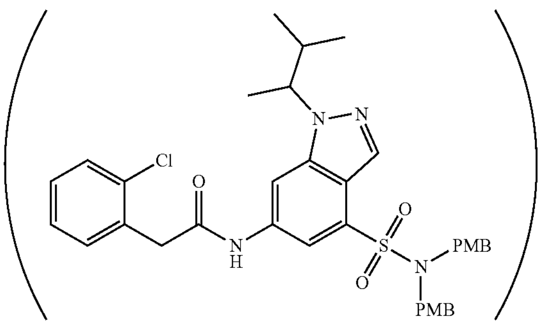

Intermediate 3-1 (700.0 mg, 1.16 mmol) was dissolved in DMF (15 mL), followed by the addition of intermediate 10-2 (420.5 mg, 1.74 mmol) and $Cs_2CO_3$ (753.8 mg, 2.31 mmol), and the mixture was heated to 50° C. and stirred overnight. After the reaction starting material was completely reacted as detected by TLC (EA:PE=1:2), the reaction solution was added with 50 mL of water and 50 mL of ethyl acetate for dilution, followed by liquid separation. The organic phase was collected, the aqueous phase was extracted with ethyl acetate (50 mL×3), the organic phases were combined, washed with saturated brine, and dried over anhydrous $Na_2SO_4$, and the solvent was concentrated by rotary evaporation to give a mixture (700.2 mg) of intermediate 10-3 (intermediate 10-4) in the form of a brown oil. LC-MS: $[M+H]^+$=675.

Step (3) Preparation of 2-(2-chlorophenyl)-N-(2-(3-methylbutan-2-yl)-4-sulfamoyl-2H-indazol-6-yl) acetamide and (2-(2-chlorophenyl)-N-(1-(3-methylbutan-2-yl)-4-sulfamoyl-1H-indazol-6-yl) acetamide)

10

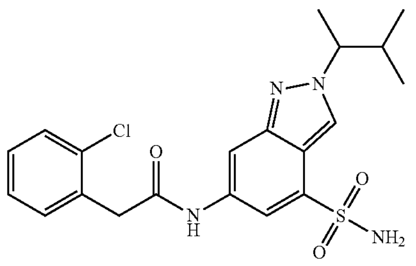

-continued

10A

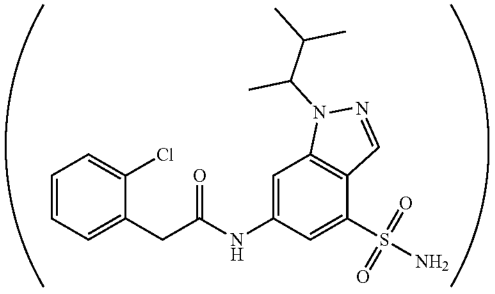

A mixture (670.2 mg, 992.53 μmol) of intermediate 10-3 (intermediate 10-4) was dissolved in DCM (7 mL), followed by the addition of TFA (7 mL), and the mixture was stirred at 35° C. overnight. After the reaction starting material was completely reacted as detected by TLC (MeOH:DCM=1:10), the reaction was stopped. The solvent was concentrated by rotary evaporation to give a crude product which was separated by prep-HPLC using a $H_2O$/ACN system and lyophilized to give compound 10 (40.5 mg, 99.73% purity) in the form of a beige solid and compound 10A (55.6 mg, 99.55% purity) in the form of a beige solid. LC-MS: $[M+H]^+$=435.05.

$^1H$ NMR (400 MHz, DMSO-$d_6$) δ (ppm): 10.50 (s, 1H), 8.49 (s, 1H), 8.23 (s, 1H), 7.72 (d, J=1.5 Hz, 1H), 7.50 (s, 2H), 7.48-7.43 (m, 2H), 7.36-7.28 (m, 2H), 4.40 (p, J=6.8 Hz, 1H), 3.88 (s, 2H), 2.22-2.13 (m, 1H), 1.54 (d, J=6.8 Hz, 3H), 0.95 (d, J=6.7 Hz, 3H), 0.67 (d, J=6.7 Hz, 3H).

LC-MS: $[M+H]^+$=435.05.

$^1H$ NMR (400 MHz, DMSO-$d_6$) δ (ppm): 10.71 (s, 1H), 8.39 (s, 1H), 8.28 (s, 1H), 7.69 (d, J=1.4 Hz, 1H), 7.58 (s, 2H), 7.49-7.42 (m, 2H), 7.36-7.29 (m, 2H), 4.39-4.31 (m, 1H), 3.91 (s, 2H), 2.22-2.12 (m, 1H), 1.47 (d, J=6.7 Hz, 3H), 0.97 (d, J=6.7 Hz, 3H), 0.61 (d, J=6.6 Hz, 3H).

Example 11

Preparation of 2-(2-chlorophenyl)-N-(2-(2-fluoroethyl)-4-sulfamoyl-2H-indazol-6-yl)acetamide

11

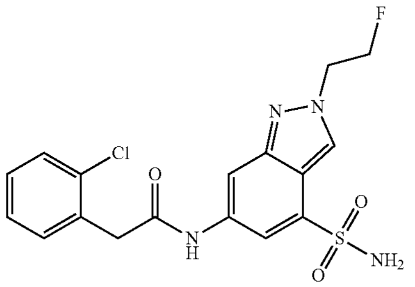

The compound was prepared using the preparation method described in Example 4. LC-MS: $[M+H]^+$=411.1.

Example 12

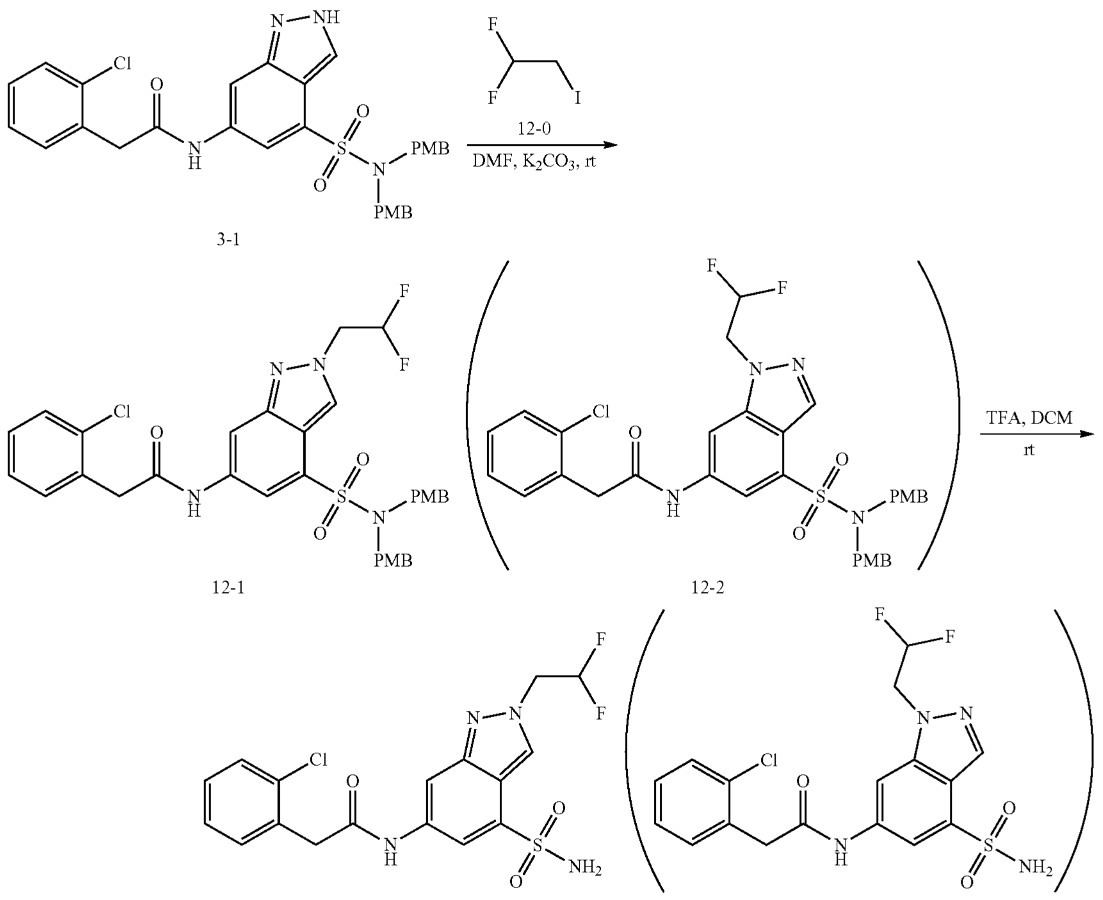

3-1

12-1

12-2

12-A

12-B

Step (1) Preparation of Intermediate 12-1 (N (4-(N, N-bis(4-methoxybenzyl)sulfamoyl)-2-(2,2-difluoroethyl)-2H-indazol-6-yl)-2-(2-chlorophenyl)acetamide) and Intermediate 12-2 (N-(4-(N,N-bis(4-methoxybenzyl)sulfamoyl)-1-(2,2-difluoroethyl)-1H-indazol-6-yl)-2-(2-chlorophenyl)acetamide)

12-1

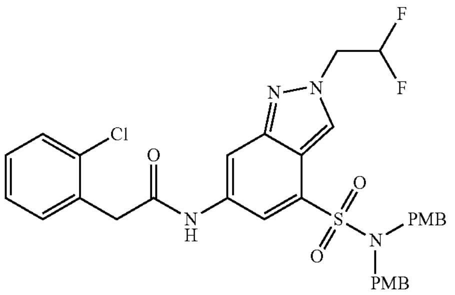

-continued 12-2

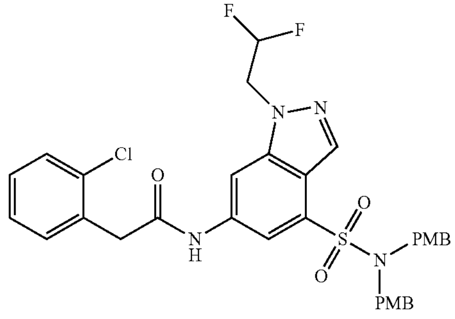

Intermediate 3-1 (180.0 mg, 297.5 μmmol) was dissolved in DMF (5 mL), followed by the addition of intermediate 12-0 (85.7 mg, 446.2 μmmol) and $K_2CO_3$ (61.7 mg, 446.2 μmmol), and the mixture was stirred at room temperature overnight. After the reaction starting material was completely reacted as detected by TLC, the reaction solution was added with water (50 mL) and ethyl acetate (50 mL) for dilution, followed by liquid separation. The organic phase was collected, washed with saturated brine (2 mL×3), and dried over anhydrous $Na_2SO_4$, and the solvent was concentrated by rotary evaporation to give a mixture (190.0 mg) of intermediate 12-1 and intermediate 12-2 in the form of a brown solid. LC-MS: $[M+H]^+$=669.10.

Step (2) Preparation of Compound 12-A (2-(2-chlorophenyl)-N-(2-(2,2-difluoroethyl)-4-sulfamoyl-2H-indazol-6-yl)acetamide) and Compound 12-B (2-(2-chlorophenyl)-N-(1-(2,2-difluoroethyl)-4-sulfamoyl-1H-indazol-6-yl)acetamide)

12-A

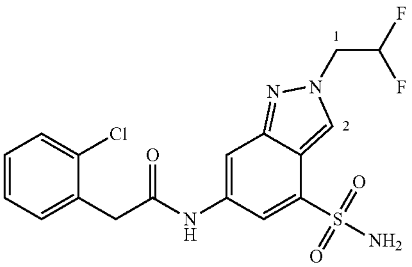

12-B

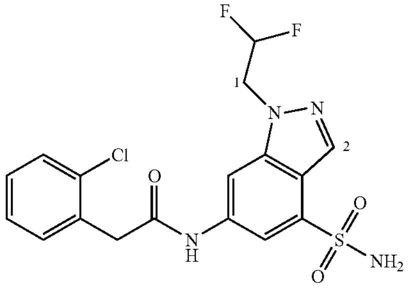

A mixture (180.0 mg, 269.0 μmmol) of intermediate 12-1 and intermediate 12-2 was dissolved in DCM (5 mL), followed by the addition of TFA (5 mL), and the mixture was stirred at room temperature overnight. After the reaction starting material was completely reacted as detected by TLC, the reaction was stopped. The solvent was concentrated by rotary evaporation to give a crude product which was separated by prep-HPLC using a $H_2O$/ACN system and lyophilized to give compound 12-A (4.1 mg, 94.8% purity) in the form of a beige solid and compound 12-B (16.2 mg, 98.610% purity) in the form of a white solid.

Compound 12-A: LC-MS: $[M+H]^+$=429.05. $^1$H NMR (400 MHz, DMSO) δ 10.58 (s, 1H), 8.58 (s, 1H), 8.27 (s, 1H), 7.76 (s, 1H), 7.56 (s, 2H), 7.49-7.42 (m, 2H), 7.36-7.28 (m, 2H), 6.68 (t, J=3.5 Hz, 1H), 6.54 (t, J=3.6 Hz, 1H), 6.41 (t, J=3.6 Hz, 1H), 5.07-4.95 (m, 2H), 3.89 (s, 2H).

Compound 12-B: LC-MS: $[M+H]^+$=429.00. $^1$H NMR (400 MHz, DMSO) δ 10.73 (s, 1H), 8.36 (s, 1H), 8.31 (s, 1H), 7.75 (d, J=0.9 Hz, 1H), 7.61 (s, 2H), 7.47-7.40 (m, 2H), 7.34-7.27 (m, 2H), 6.53 (t, J=3.1 Hz, 1H), 6.39 (t, J=3.1 Hz, 1H), 6.26 (t, J=3.2 Hz, 1H), 4.94-4.82 (m, 2.9 Hz, 2H), 3.89 (s, 2H).

2D-HNMR (NOE) results showed that No. 1 hydrogen and No. 2 hydrogen in compound 12-A are correlated, and No. 1 hydrogen and No. 2 hydrogen in compound 12-B are not correlated.

Example 13

Preparation of 2-(2-chlorophenyl)-N-(2-(2-fluoropropan-2-yl)-4-sulfamoyl-2H-indazol-6-yl)acetamide

13

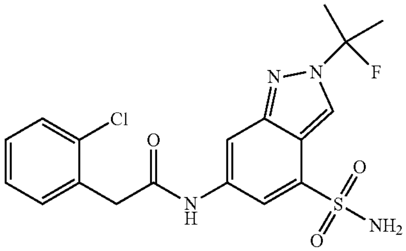

The compound was prepared using the preparation method described in Example 4. LC-MS: $[M+H]^+$=425.08.

Example 14

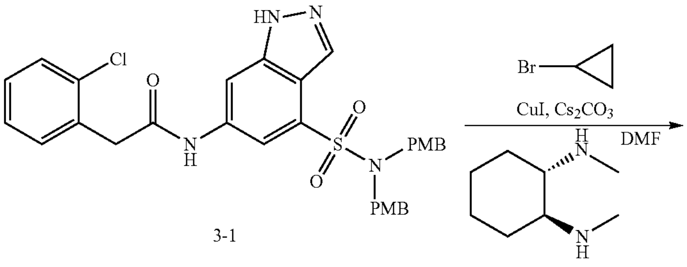

3-1

-continued

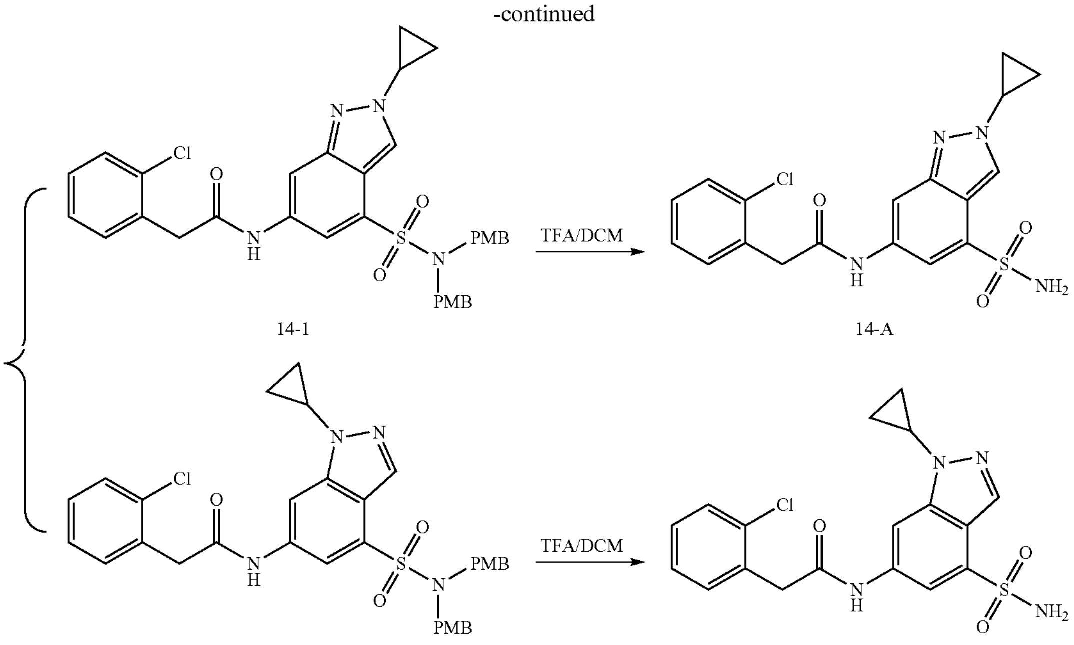

14-1 14-A 14-2 14-B

Step (1) Preparation of Intermediate 14-1 (4-(N,N-bis(4-methoxybenzyl)sulfonamide-6-N-(2-chlorophenylacetyl)-2-cyclopropyl)-indazole) and Intermediate 14-2 (4-(N,N-bis(4-methoxybenzyl) sulfonamide-6-N-(2-chlorophenylacetyl)-1-cyclopropyl)-indazole)

14-1

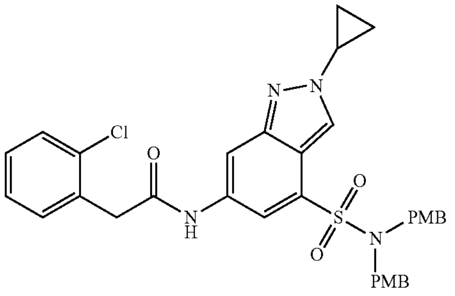

14-2

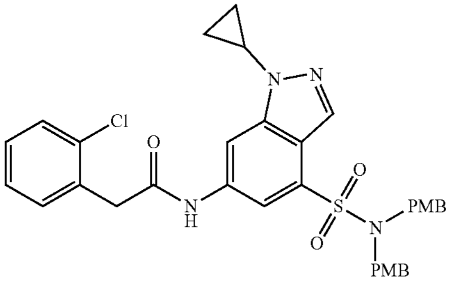

Intermediate 3-1 (400 mg, 0.66 mmol) and bromocyclopropane were dissolved in DMF (5 mL), followed by the addition of $Cs_2CO_3$ (424 mg, 1.3 mmol), CuI (12.5 mg, 66 μmol) and trans-N,N'-dimethyl-1,2-cyclohexanediamine (18.5 mg, 130.0 μmol). The reaction solution was stirred at 110° C. overnight under $N_2$ atmosphere. After the reaction was completed, the reaction solution was cooled to room temperature, and then poured into water, and the resulting solution was extracted with EtOAc. The organic phase was dried over anhydrous $Na_2SO_4$ and filtered, and the filtrate was concentrated to give a crude product which was purified by silica gel column chromatography to give intermediate 14-1 (140.0 mg, yellow oil) and intermediate 14-2 (100.0 mg, yellow oil). LC-MS: $[M+H]^+$=645.

Step (2) Preparation of Compound 14-A (2-(2-chlorophenyl)-N-(2-cyclopropyl-4-sulfamoyl-2H-indazol-6-yl)acetamide)

14-A

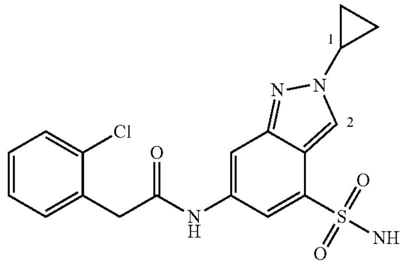

Intermediate 14-1 (140.0 mg, 220.0 μmol) was dissolved in DCM (2 mL), followed by the addition of TFA (2 mL), and the reaction solution was stirred at room temperature overnight. After the reaction was completed, the reaction solution was added to saturated aqueous $NaHCO_3$ solution, and the resulting solution was extracted with EtOAC. The organic phase was dried over anhydrous $Na_2SO_4$ and filtered, and the filtrate was concentrated to give a crude product which was purified by prep-HPLC to give compound 14-A (20.7 mg) in the form of a white solid powder. LC-MS: $[M+H]^+$=405.1. $^1$H NMR (400 MHz, DMSO-$d_6$) δ 10.53 (s, 1H), 8.48 (s, 1H), 8.24 (s, 1H), 7.74 (d, J=1.0 Hz, 1H), 7.51 (s, 2H), 7.48-7.41 (m, 2H), 7.35-7.27 (m, 2H), 6.18-6.07 (m, 1H), 5.33-5.24 (m, 2H), 5.10 (d, J=6.0 Hz, 2H), 3.88 (s, 2H).

Step (3) Preparation of Compound 14-B (2-(2-chlorophenyl)-N-(1-cyclopropyl-4-sulfamoyl-1H-indazol-6-yl)acetamide)

14-B

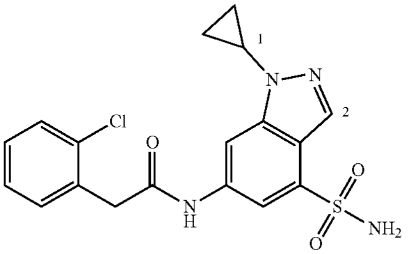

Intermediate 14-2 (100.0 mg, 150.0 μmol) was dissolved in DCM (2 mL), followed by the addition of TFA (2 mL), and the reaction solution was stirred at room temperature overnight. After the reaction was completed, the reaction solution was added to saturated aqueous $NaHCO_3$ solution, and the resulting solution was extracted with EtOAC. The organic phase was dried over anhydrous $Na_2SO_4$ and filtered, and the filtrate was concentrated to give a crude product which was purified by prep-HPLC to give compound 14-B (13.7 mg) in the form of a white solid powder. LC-MS: $[M+H]^+$=405.0. $^1$H NMR (400 MHz, DMSO-$d_6$): δ 10.73 (s, 1H), 8.29 (s, 1H), 8.26 (d, J=0.7 Hz, 1H), 7.73 (d, J=1.5 Hz, 1H), 7.60 (s, 2H), 7.47-7.42 (m, 2H), 7.35-7.29 (m, 2H), 6.05-5.92 (m, 2H), 5.16 (dd, J=10.3, 1.4 Hz, 1H), 5.03 (d, J=5.3 Hz, 2H), 4.97 (dd, J=17.1, 1.5 Hz, 1H), 3.90 (s, 2H).

2D-HNMR (NOE) results showed that No. 1 hydrogen and No. 2 hydrogen in compound 14-A are correlated, and No. 1 hydrogen and No. 2 hydrogen in compound 14-B are not correlated.

Example 15

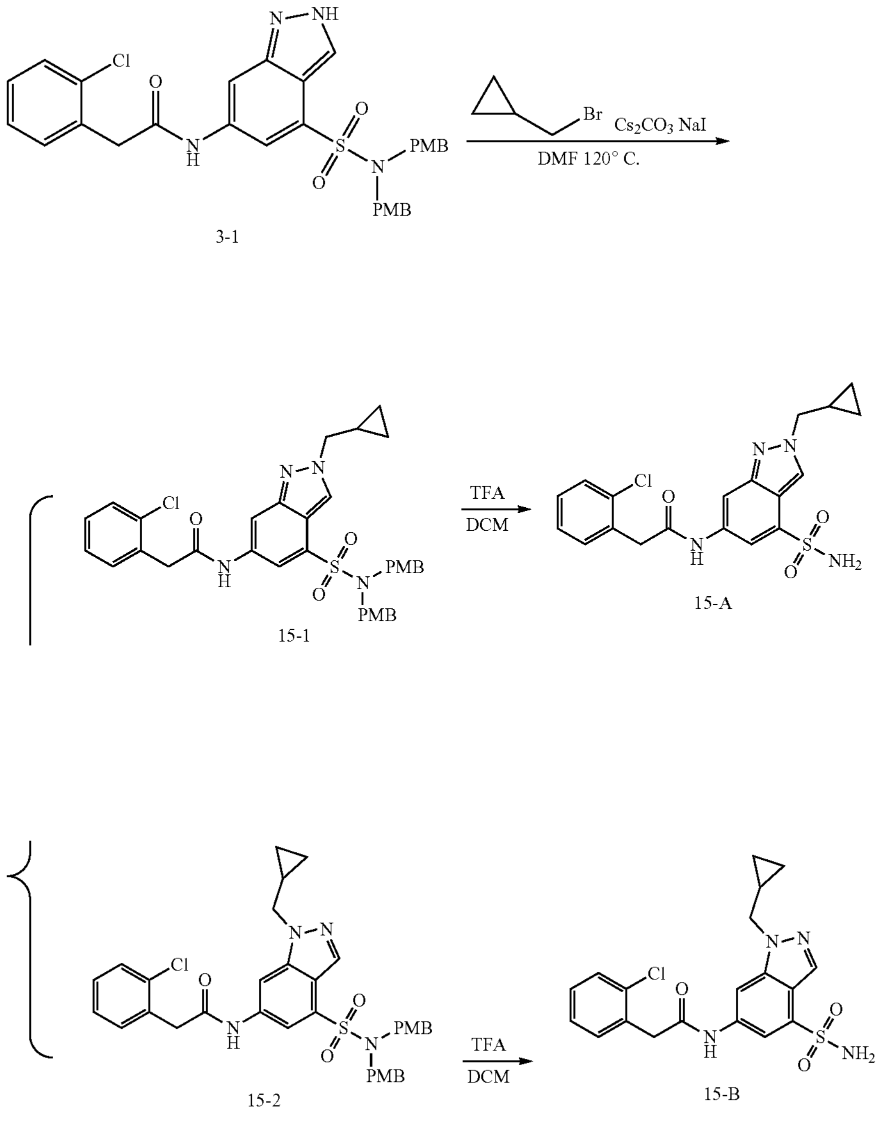

Step (1) Preparation of Intermediate 15-1 (N-(4-(N,N-bis(4-methoxybenzyl)sulfonamide)-2-(cyclopropylmethyl)-2H-indazol-6-yl)-2-(2-chlorophenyl)acetamide) and Intermediate 15-1 (N-(4-(N,N-bis(4-methoxybenzyl)sulfamoyl)-1-(cyclopropylmethyl)-1H-indazol-6-yl)-2-(2-chlorophenyl)acetamide)

15-1

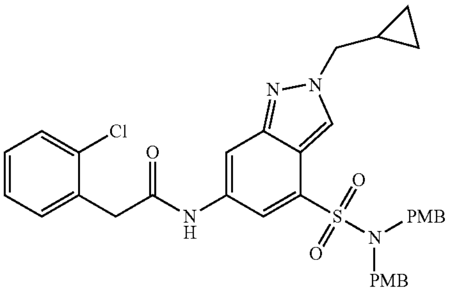

15-2

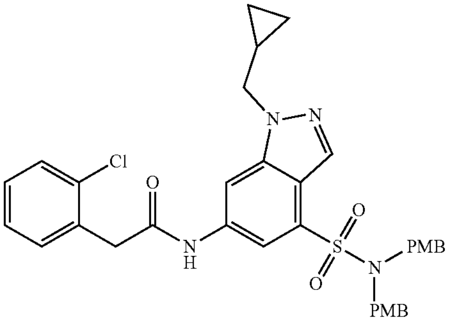

Intermediate 3-1 (300.0 mg, 0.5 mmol), bromomethylcyclopropane (201.0 mg, 1.5 mmol), $Cs_2CO_3$ (525.0 mg, 1.5 mmol) and NaI (225.0 mg, 1.5 mmol) were dissolved in DMF and stirred at 120° C. overnight for reaction. After the reaction starting material was completely reacted as indicated by thin-layer chromatography, the reaction solution was added with water (5 mL) and extracted three times with EA, and the EA phases were combined, washed with saturated brine, dried over sodium sulfate, filtered and concentrated to give a crude product which was purified by column chromatography to give intermediate 15-1 (220.0 mg) and intermediate 15-2 (30.0 mg). LC-MS: $[M+H]^+$=659.

Step (2) Preparation of Compound 15-A (2-(2-chlorophenyl)-N-(2-(cyclopropylmethyl)-4-sulfonamido-2H-indazol-6-yl)acetamide) and Compound 15-B (2-(2-chlorophenyl)-N-(1-(cyclopropylmethyl)-4-sulfamoyl-1H-indazol-6-yl)acetamide)

15-A

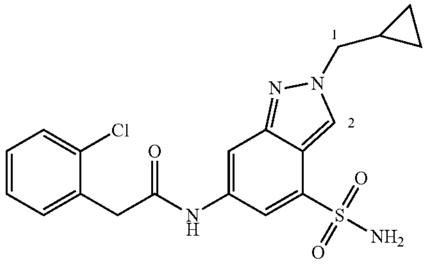

-continued

15-B

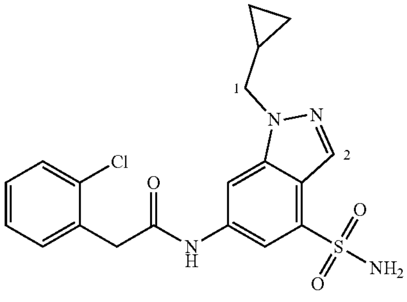

Intermediate 15-1 (200.0 mg, 0.30 mmol) was dissolved in DCM (3 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 15-A (12.0 mg) in the form of a white powder solid. LC-MS: $[M+H]^+$=419.1.

$^1H$ NMR (400 MHz, DMSO-d6): δ 10.71 (s, 1H), 8.38 (s, 1H), 8.24 (s, 1H), 7.69 (s, 1H), 7.58 (s, 2H), 7.48-7.42 (m, 2H), 7.35-7.30 (m, 2H), 3.91 (s, 2H), 3.67-3.61 (m, 1H), 1.28-1.17 (m, 2H), 0.52-0.44 (m, 2H), 0.40-0.33 (m, 2H).

Intermediate 15-2 (30.0 mg, 0.045 mmol) was dissolved in DCM (1 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 15-B (3.0 mg) in the form of a white powder solid. LC-MS: $[M+H]^+$=419.1.

2D-HNMR (NOE) results showed that No. 1 hydrogen and No. 2 hydrogen in compound 15-A are correlated, and No. 1 hydrogen and No. 2 hydrogen in compound 15-B are not correlated.

Example 16

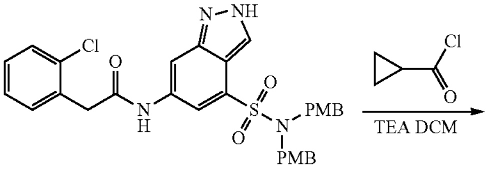

3-1

-continued

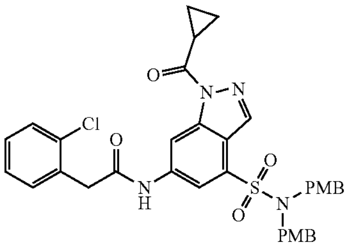

16-1

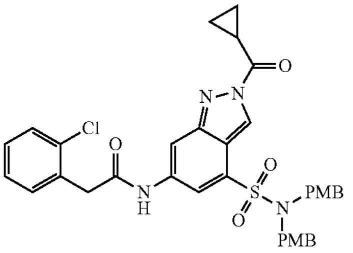

16-2

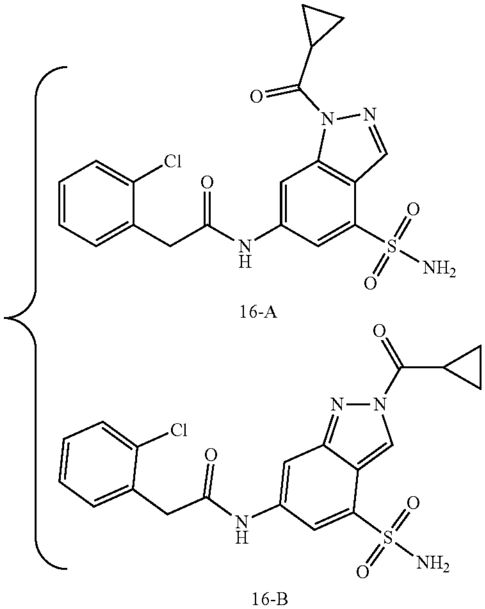

16-A

16-B

Step (1) Preparation of Intermediate 16-1 (N-(4-(N,N-bis(4-methoxybenzyl)sulfamoyl)-1-(cyclopropylcarbonyl)-1H-indazol-6-yl)-2-(2-chlorophenyl)acetamide) and Intermediate 16-2 (N-(4-(N,N-bis(4-methoxybenzyl)sulfamoyl)-2-(cyclopropylcarbonyl)-2H-indazol-6-yl)-2-(2-chlorophenyl)acetamide)

16-1

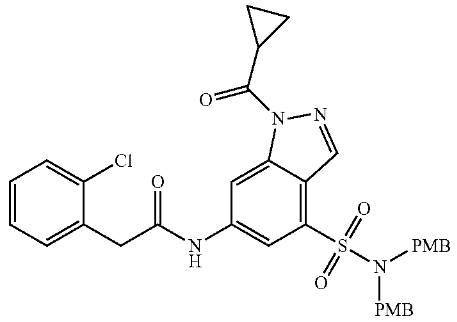

16-2

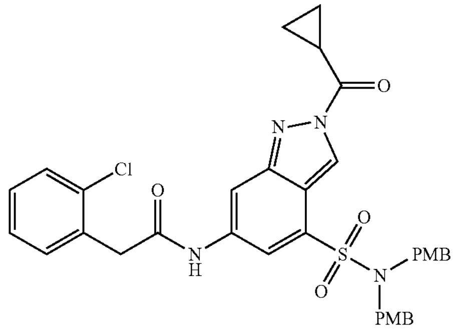

Intermediate 3-1 (800 mg, 1.34 mmol), cyclopropanecarbonyl chloride (45.9 mg, 0.34 mmol) and triethylamine (400 mg, 3.96 mmol) were sequentially dissolved in DCM (16 mL), followed by the dropwise addition of cyclopropanecarbonyl chloride (165.6 mg, 1.6 mmol) in an ice bath, and after the addition was completed, the mixture was slowly heated to room temperature and stirred for 2 h. After the reaction was completed as detected by TLC, the reaction solution was added with water (10 mL) to quench the reaction, and extracted twice with DCM (5 mL). The organic phases were combined, washed with saturated brine, dried over anhydrous sodium sulfate, and filtered, the filtrate was concentrated under reduced pressure, and the crude product was purified by column chromatography to give a mixture (1.0 g) of intermediate 16-1 and intermediate 16-2 in the form of a light yellow oil. LC-MS: $[M]^+$=673.

Step (2) Preparation of Compound 16-A (2-(2-chlorophenyl)-N-(1-(cyclopropylcarbonyl)-4-sulfamoyl-1H-indazol-6-yl)acetamide) and Compound 16-B (2-(2-chlorophenyl)-N-(2-(cyclopropylcarbonyl)-4-sulfamoyl-2H-indazol-6-yl)acetamide)

16-A

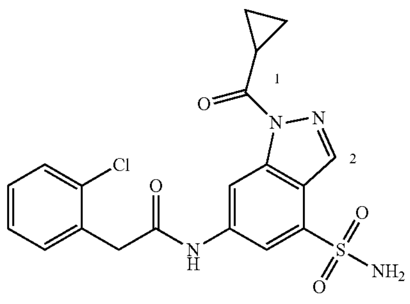

16-B

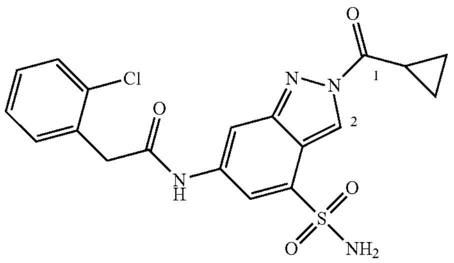

A mixture (900 mg, 1.34 mmol) of intermediate 16-1 and intermediate 16-2 was dissolved in DCM (18 mL), followed by the addition of TFA (36 mL), and the mixture was stirred at 45° C. overnight. After the reaction starting material was completed as detected by LCMS, the reaction solution was concentrated under reduced pressure to give a crude product, pH was adjusted to 8 with saturated sodium bicarbonate, and the crude product was extracted twice with (10 mL, DCM/DMF=10/1) and concentrated to give an oil (2.1 g, crude) which was purified by column chromatography to give a crude product (1.3 g, DMF) which was separated by prep-HPLC using a $H_2O$/CAN system and lyophilized to give compound 16-A (51.6 mg, 96.8% purity) in the form of a white solid and compound 16-B (11.6 mg, 96.9% purity) in the form of a white solid.

Wherein, for compound 16-A, LC-MS: $[M]^+$=433. $^1$H NMR (400 MHz, DMSO) δ 10.87 (s, 1H), 8.98 (d, J=0.8 Hz, 1H), 8.61 (d, J=0.7 Hz, 1H), 8.12 (d, J=1.7 Hz, 1H), 7.76 (s, 2H), 7.43 (td, J=5.2, 2.3 Hz, 2H), 7.35-7.23 (m, 2H), 3.89 (s, 2H), 3.14 (dq, J=7.5, 5.1 Hz, 1H), 1.28-1.00 (m, 4H).

2D-HNMR (HMBC) results showed that No. 1 hydrogen and No. 2 hydrogen in compound 16-A are not correlated, and No. 1 hydrogen and No. 2 hydrogen in compound 16-B are correlated.

Example 17

Preparation of 2-(2-chlorophenyl)-N-(2-(1-isopropylcyclopropyl)-4-sulfamoyl-2H-indazol-6-yl)acetamide

17

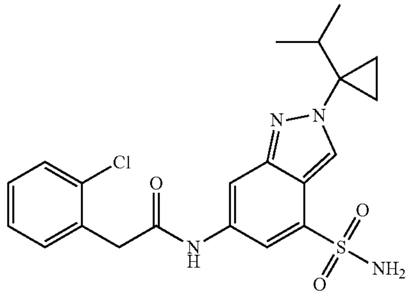

The compound was prepared using the preparation method described in Example 14. LC-MS: $[M+H]^+$=447.1.

Example 18

Preparation of 2-(2-chlorophenyl)-N-(2-(1-ethylcyclopropyl)-4-sulfamoyl-2H-indazol-6-yl)acetamide

18

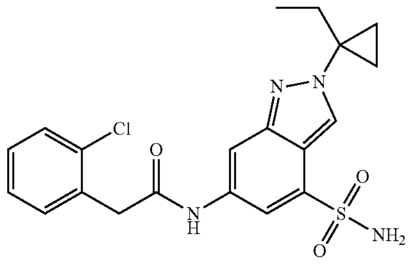

The compound was prepared using the preparation method described in Example 14. LC-MS: $[M+H]^+$=433.1.

Example 19

Preparation of 2-(2-chlorophenyl)-N-(2-(cyclopropylfluoromethyl)-4-sulfamoyl-2H-indazol-6-yl)acetamide

19

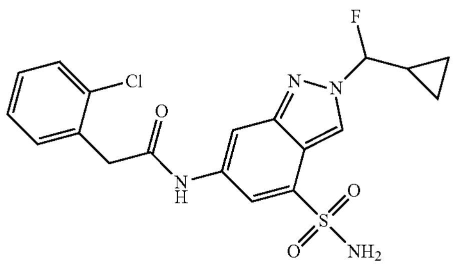

The compound was prepared using the preparation method described in Example 14. LC-MS: $[M+H]^+=437.1$.

Example 20

Preparation of 2-(2-chlorophenyl)-N-(2-(cyclopropyldifluoromethyl)-4-sulfamoyl-2H-indazol-6-yl) acetamide

20

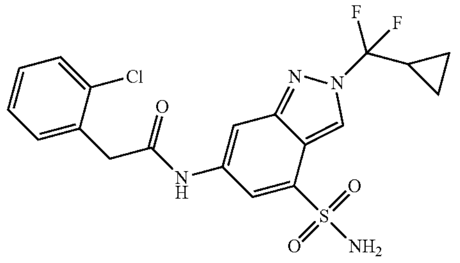

The compound was prepared using the preparation method described in Example 14. LC-MS: $[M+H]^+=455.1$.

Example 21

Preparation of 2-(2-chlorophenyl)-N-(2-(2-cyclopropylpropan-2-yl)-4-sulfamoyl-2H-indazol-6-yl)acetamide

21

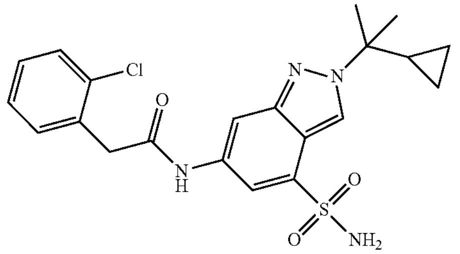

The compound was prepared using the preparation method described in Example 14. LC-MS: $[M+H]^+=447.1$.

Example 22

Preparation of 2-(2-chlorophenyl)-N-(2-(1-methylcyclopropyl)-4-sulfamoyl-2H-indazol-6-yl)acetamide

22

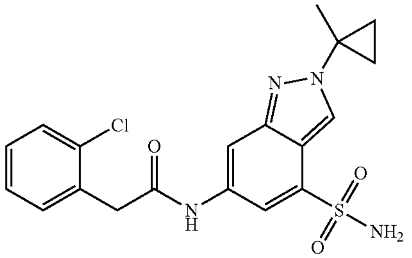

The compound was prepared using the preparation method described in Example 14. LC-MS: $[M+H]^+=419.1$.

Example 23

Preparation of 2-(2-chlorophenyl)-N-(2-(1,1-difluoro-2-methylpropyl)-4-sulfamoyl-2H-indazol-6-yl) acetamide

23

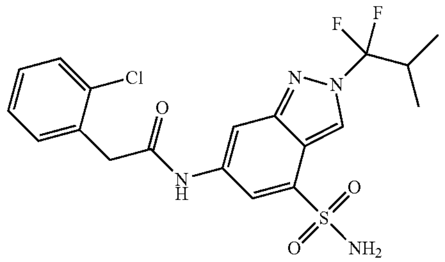

The compound was prepared using the preparation method described in Example 14. LC-MS: $[M+H]^+=457.1$.

Example 24

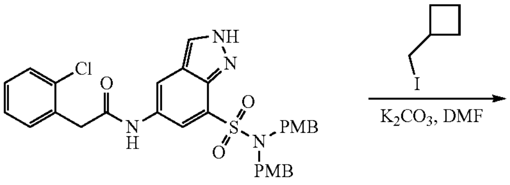

3-1

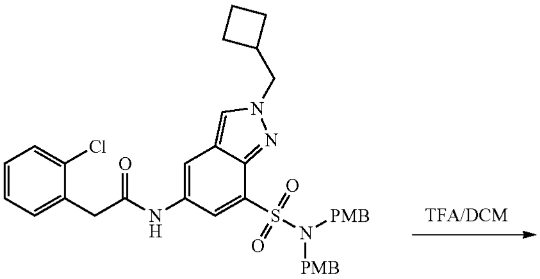

24-1

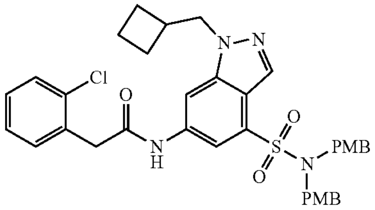

24-2

-continued

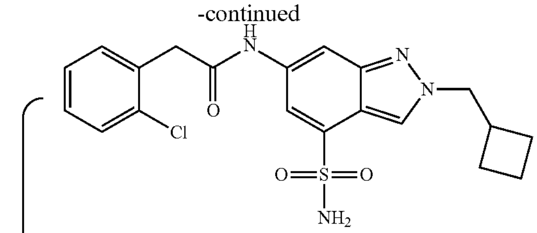

24-A

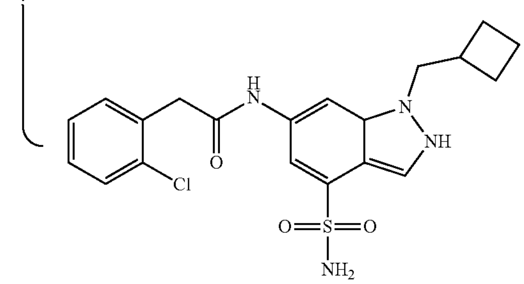

24-B

Step (1) Preparation of Intermediate 24-1 (N-(4-(N,N-bis(4-methoxybenzyl)sulfamoyl)-2-(cyclobutylmethyl)-2H-indazol-6-yl-2-(2-chlorophenyl)acetamide)) and Intermediate 24-2 (N-(4-(N,N-bis(4-methoxybenzyl)sulfamoyl)-1-(cyclobutylmethyl)-2H-indazol-6-yl-2-(2-chlorophenyl)acetamide))

24-1

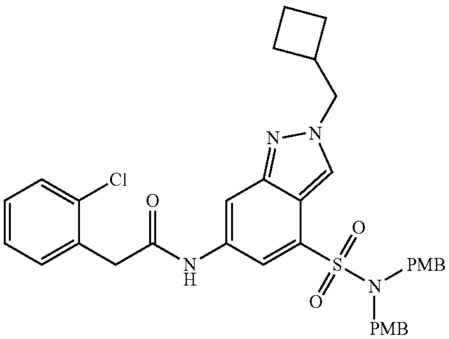

24-2

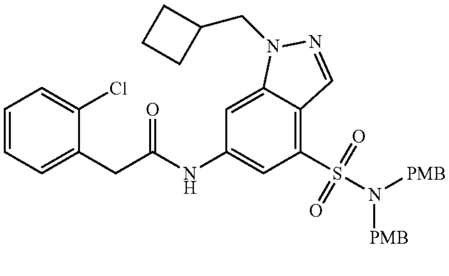

Intermediate 3-1 (180.0 mg, 30.0 μmol) was sequentially dissolved in DMF (5 mL), followed by the addition of cyclobutyliodomethane (61.0 mg, 31.0 μmol) and potassium carbonate (82.0 mg, 60.0 μmol), and the mixture was purged three times with $N_2$, stirred at room temperature for 16 h, and sampled; after the reaction starting material was completed as detected by LCMS, the reaction solution was diluted with EA (20 mL), washed with water (10 mL), stirred for 10 min, and left to stand to separate the organic phase. The organic phase was sequentially washed with saturated aqueous ammonium chloride solution and saturated brine, dried over anhydrous sodium sulfate, and filtered, and the filtrate was concentrated under reduced pressure to give a mixture of intermediate 24-1 and intermediate 24-2 in the form of a red oil (200.0 mg, crude). LC-MS: $[M+H]^+$=673.2.

Step (2) Preparation of Compound 24-A (2-(2-chlorophenyl)-N-(2-(cyclobutylmethyl)-4-sulfamoyl-2H-indazol-6-yl)acetamide) and Compound 24-B (2-(2-chlorophenyl)-N-(1-(cyclobutylmethyl)-4-sulfamoyl-1H-indazol-6-yl)acetamide)

24-A

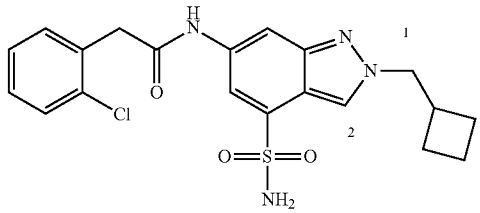

24-B

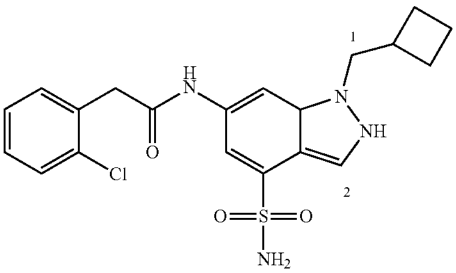

A mixture of intermediate 24-1 and intermediate 24-2 (0.2 g, 30.0 μmol, crude) was dissolved in DCM (5 mL), followed by the addition of TFA (10 mL), and the mixture was reacted at room temperature for 16 h and sampled; after the reaction was completed as detected by LCMS, the reaction solution was diluted with DCM (50 mL), and pH was adjusted to 8-9 with $Na_2CO_3$ solid, and the system was stirred and left to stand to separate the DCM phase. The aqueous phase was extracted twice with DCM (20 mL). The DCM phases were combined, dried over anhydrous sodium sulfate, and filtered, the filtrate was concentrated under reduced pressure to give a crude product which was separated by prep-HPLC using a $H_2O/CH_3CN$ system and lyophilized to give compound 24-A (3.2 mg, 98.4% purity) in the form of a white solid and compound 24-B (7.4 mg, 99.2% purity) in the form of a white solid. LC-MS: $[M+H]^+$= 433.1.

Compound 24-A: $^1$H NMR (400 MHz, DMSO) δ 10.51 (s, 1H), 8.45 (d, J=0.7 Hz, 1H), 8.22 (s, 1H), 7.71 (d, J=1.6 Hz, 1H), 7.49 (s, 2H), 7.47-7.43 (m, 2H), 7.34-7.30 (m, 2H), 4.46 (d, J=7.3 Hz, 2H), 3.88 (s, 2H), 2.92-2.87 (m, 1H), 2.02-1.96 (m, 2H), 1.88-1.79 (m, 4H).

Compound 24-B: $^1$H NMR (400 MHz, DMSO) δ 10.72 (s, 1H), 8.37 (s, 1H), 8.23 (s, 1H), 7.69 (d, J=1.4 Hz, 1H), 7.58 (s, 2H), 7.48-7.43 (m, 2H), 7.35-7.30 (m, 2H), 4.37 (d, J=7.1 Hz, 2H), 3.91 (s, 2H), 2.82-2.77 (m, 1H), 1.95-1.89 (m, 2H), 1.84-1.75 (m, 4H).

2D-HNMR (NOE) results showed that No. 1 hydrogen and No. 2 hydrogen in compound 24-A are correlated, and No. 1 hydrogen and No. 2 hydrogen in compound 24-B are not correlated.
Example 25
Preparation of 2-(2-chlorophenyl)-N-(2-(2-methoxyethyl)-4-sulfamoyl-2H-indazol-6-yl)acetamide
25
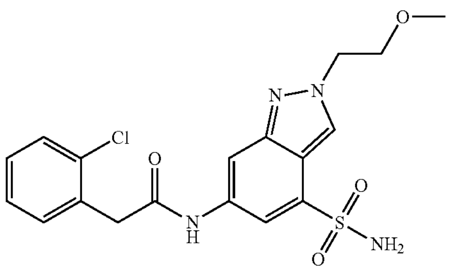
The compound was prepared using the preparation method described in Example 4. LC-MS: $[M+H]^+$=423.1.
Example 26
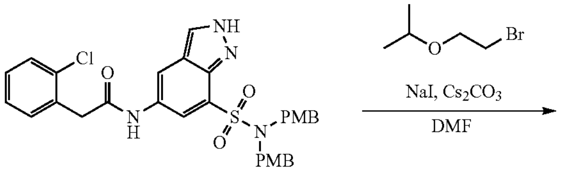
3-1
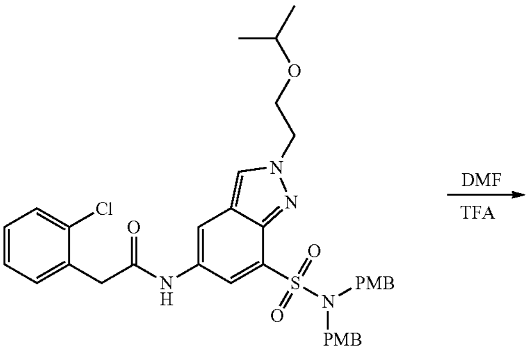
26-1
+
-continued
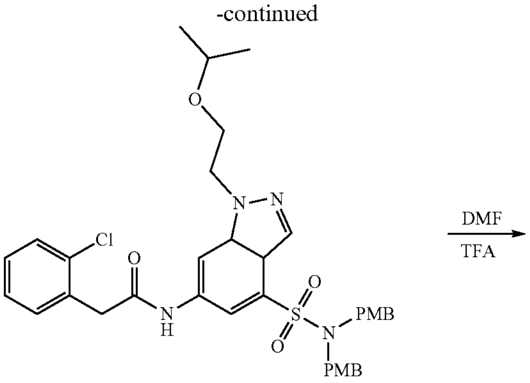
26-2
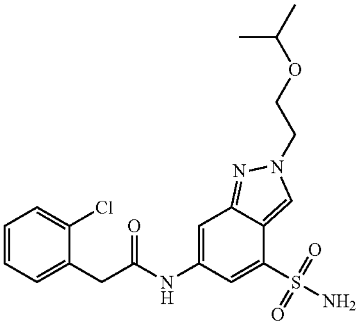
26-A
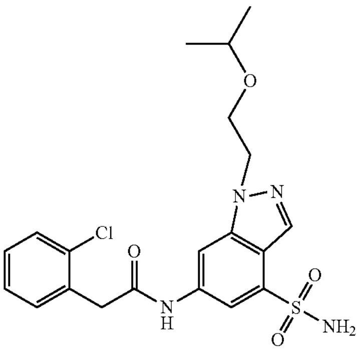
26-B Step (1) Preparation of Intermediate 26-1 (N-(4-(N,N-bis-(4-methoxybenzyl)sulfamoyl)-2-(2-isopropoxyethyl)-2H-indazol-6-yl)-2-(2-chlorophenyl)acetamide) and Intermediate 26-2 (N-(4-(N,N-bis-(4-methoxybenzyl)sulfamoyl)-1-(2-isopropoxyethyl)-1H-indazol-6-yl)-2-(2-chlorophenyl) acetamide)

26-1

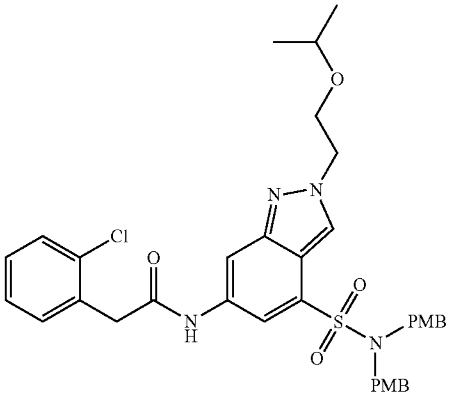

26-2

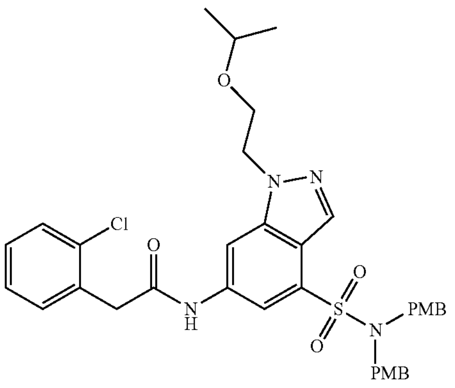

Intermediate 3-1 (200.0 mg, 330.0 μmol), 2-bromoethanol (110.0 mg, 660.0 μmol), NaI (50 mg, 330 μmol) and $Cs_2CO_3$ (161.0 mg, 500.0 μmol) were dissolved in DMF (5 mL), and the reaction solution was stirred at 70° C. for 24 h. After the reaction starting material was completely reacted as detected by TLC, the reaction solution was cooled to room temperature and added with water (50 mL), the aqueous phase was extracted with EA (100 mL×3), the organic phases were combined, dried over anhydrous sodium sulfate, and filtered, and the filtrate was concentrated to give a crude product which was subjected to silica gel column chromatography to give a mixture (100 mg) of intermediate 26-1 and intermediate 26-2 in the form of a yellow solid.

Step (2) Preparation of Compound 26-A (2-(2-chlorophenyl)-N-(2-(2-isopropoxyethyl)-4-sulfamoyl-2H-indazol-6-yl)acetamide) and Compound 26-B (2-(2-chlorophenyl)-N-(1-(2-isopropoxyethyl)-4-sulfamoyl-1H-indazol-6-yl)acetamide)

26-A

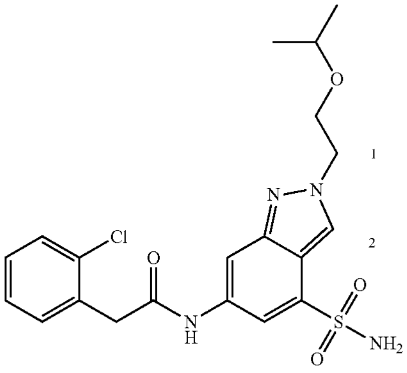

26-B

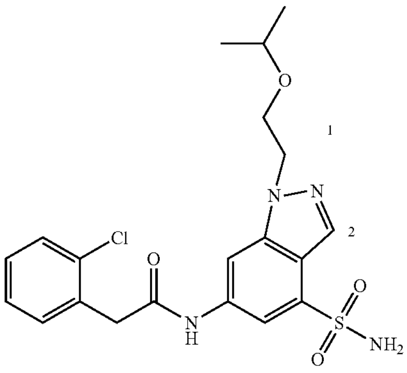

Intermediate 26-1 and intermediate 26-2 (100.0 mg, 145.0 μmol) were dissolved in DCM (1.0 mL), and the reaction solution was slowly added with TFA (1.0 mL), heated to room temperature and reacted overnight. After the reaction was completed as detected by TLC and the reaction starting material was completely reacted as detected by LCMS, the reaction solution was directly separated by prep-HPLC using a $H_2O$/MeCN system and lyophilized to give target products of compound 26-A (white solid, 2 mg, 96.8% purity) and compound 26-B (white solid, 1 mg, 97.6% purity). LC-MS: $[M+H]^+=451.1$.

Compound 26-A: $^1H$ NMR (400 MHz, DMSO) δ 10.52 (s, 1H), 8.49 (d, J=0.6 Hz, 1H), 8.24 (s, 1H), 7.72 (d, J=1.6 Hz, 1H), 7.51 (s, 2H), 7.47-7.41 (m, 2H), 7.32 (s, 2H), 4.54 (t, J=5.4 Hz, 2H), 3.88 (d, J=2.6 Hz, 2H), 3.87 (d, J=5.6 Hz, 2H), 3.51 (s, 1H), 1.01 (d, J=6.0 Hz, 6H).

Compound 26-B: $^1H$ NMR (400 MHz, DMSO) δ 10.66 (s, 1H), 8.33 (s, 1H), 8.23 (t, J=4.0 Hz, 1H), 7.70 (d, J=1.6 Hz, 1H), 7.56 (s, 2H), 7.47-7.39 (m, 2H), 7.34-7.26 (m, 2H), 4.45 (dd, J=14.4, 9.0 Hz, 2H), 3.88 (s, 2H), 3.73 (t, J=5.2 Hz, 2H), 3.46-3.40 (m, 1H), 0.92 (t, J=4.8 Hz, 6H).

2D-HNMR (NOE) results showed that No. 1 hydrogen and No. 2 hydrogen in compound 26-A are correlated, and No. 1 hydrogen and No. 2 hydrogen in compound 26-B are not correlated.

Example 27

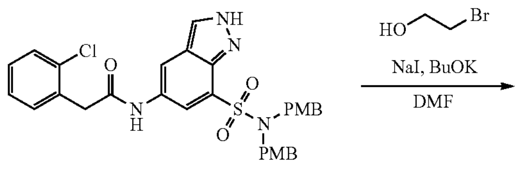

3-1

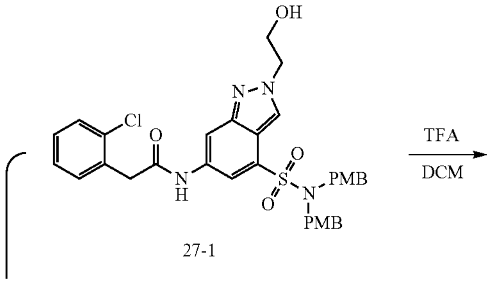

27-1

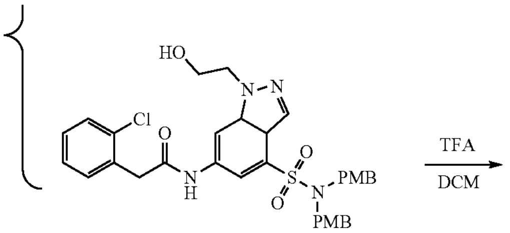

27-2

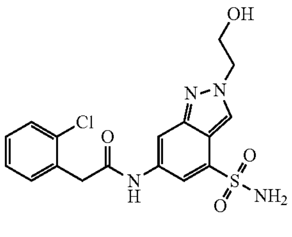

27-A

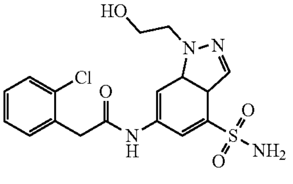

27-B

Step (1) Preparation of Intermediate 27-1 (N-(4-(N,N-bis-(4-methoxybenzyl)sulfamoyl)-2-(2-hydroxyethyl)-2H-indazol-6-yl)-2-(2-chlorophenyl)acetamide) and Intermediate 27-2 (N-(4-(N,N-bis(4-methoxybenzyl)sulfamoyl)-1-(2-hydroxyethyl)-1H-indazol-6-yl)-2-(2-chlorophenyl)acetamide)

27-1

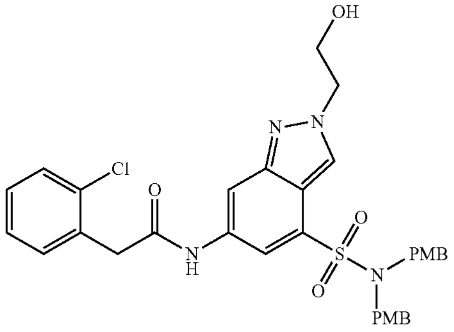

27-2

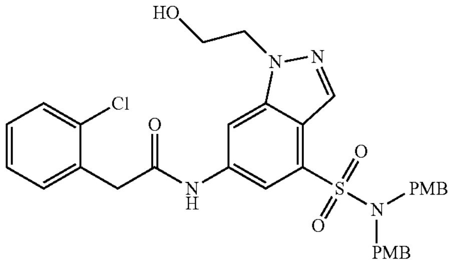

Intermediate 3-1 (400 mg, 0.66 mmol), 2-bromoethanol (110 mg, 1.32 mmol), NaI (100 mg, 0.66 mmol) and BuOK (110 mg, 0.66 mmol) were dissolved in DMF (5 mL), and the reaction solution was stirred at 140° C. for 24 h. After the reaction starting material was completely reacted as detected by TLC, the reaction solution was cooled to room temperature and added with water (50 mL), the aqueous phase was extracted with EA (100 mL×3), the organic phases were combined, dried over anhydrous sodium sulfate, and filtered, and the filtrate was concentrated to give a crude product which was subjected to silica gel column chromatography to give intermediate 27-1 (150 mg) in the form of a yellow solid and intermediate 27-2 (30 mg) in the form of a yellow solid. LC-MS: $[M+H]^+$=409.1.

Step (2) Preparation of Compound 27-A (2-(2-chlorophenyl)-N-(2-(2-hydroxyethyl)-4-sulfamoyl-2H-indazol-6-yl)acetamide) and Compound 27-B (2-(2-chlorophenyl)-N-(1-(2-hydroxyethyl)-4-sulfamoyl-2H-indazol-6-yl)acetamide)

27-A

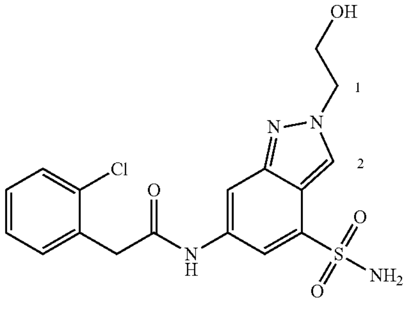

27-B

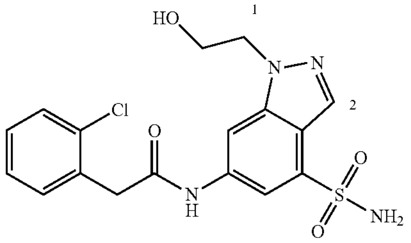

Intermediate 27-1 (150 mg, 0.23 mmol) was dissolved in DCM (0.5 mL), and the reaction solution was slowly added with TFA (0.5 mL), heated to room temperature and reacted overnight. After the reaction was completed as detected by TLC and the reaction starting material was completely reacted as detected by LCMS, the reaction solution was directly separated by prep-HPLC using a $H_2O$/MeCN system and lyophilized to give compound 27-A (18.6 mg, 98.35% purity) in the form of a white solid. LC-MS: $[M+H]^+$=409.05.

$^1$H NMR (400 MHz, DMSO) δ10.51 (s, 1H), 8.49 (d, J=0.7 Hz, 1H), 8.23 (s, 1H), 7.72 (d, J=1.6 Hz, 1H), 7.50 (s, 2H), 7.48-7.38 (m, 2H), 7.38-7.28 (m, 2H), 5.01 (t, J=5.4 Hz, 1H), 4.46 (t, J=5.4 Hz, 2H), 3.88 (p, J=5.6 Hz, 3H).

2D-HNMR (NOE) results showed that No. 1 hydrogen and No. 2 hydrogen in compound 27-A are correlated.

Intermediate 27-2 (30 mg, 0.04 mmol) was dissolved in DCM (0.5 mL), and the reaction solution was slowly added with TFA (0.5 mL), heated to room temperature and reacted overnight. After the reaction was completed as detected by TLC and the reaction starting material was completely reacted as detected by LCMS, the reaction solution was directly separated by prep-HPLC using a $H_2O$/MeCN system and lyophilized to give compound 27-B (3.6 mg, 98.3% purity) in the form of a white solid. LC-MS: $[M+H]^+$=409.05.

Example 28

Preparation of 2-(2-chlorophenyl)-N-(2-(2-cyclopropyloxyethyl)-4-sulfamoyl-2H-indazol-6-yl)acetamide

28

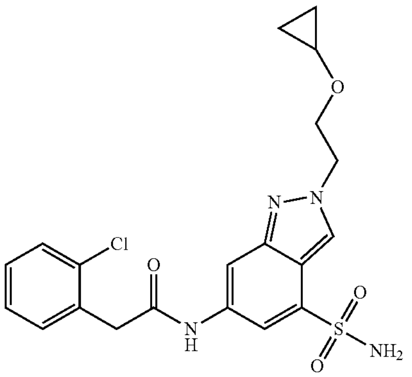

The compound was prepared using the preparation method described in Example 26. LC-MS: $[M+H]^+$=449.1.

Example 29

Preparation of 2-(2-chlorophenyl)-N-(2-(2-(isopropylamino)ethyl)-4-sulfamoyl-2H-indazol-6-yl)acetamide

29

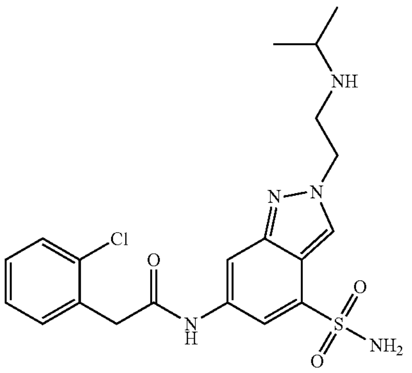

The compound was prepared using the preparation method described in Example 26. LC-MS: $[M+H]^+$=449.2.

Example 30
Preparation of 2-(2-chlorophenyl)-N-(2-(2-(methyl-sulfonyl)ethyl)-4-sulfamoyl-2H-indazol-6-yl)acetamide
30
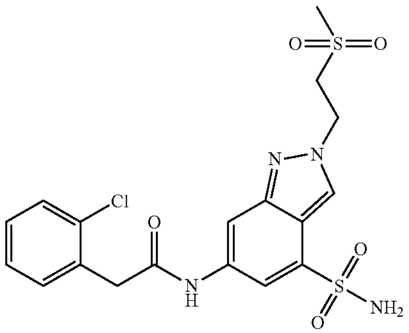
The compound was prepared using the preparation method described in Example 26. LC-MS: $[M+H]^+$=471.1.
Example 31

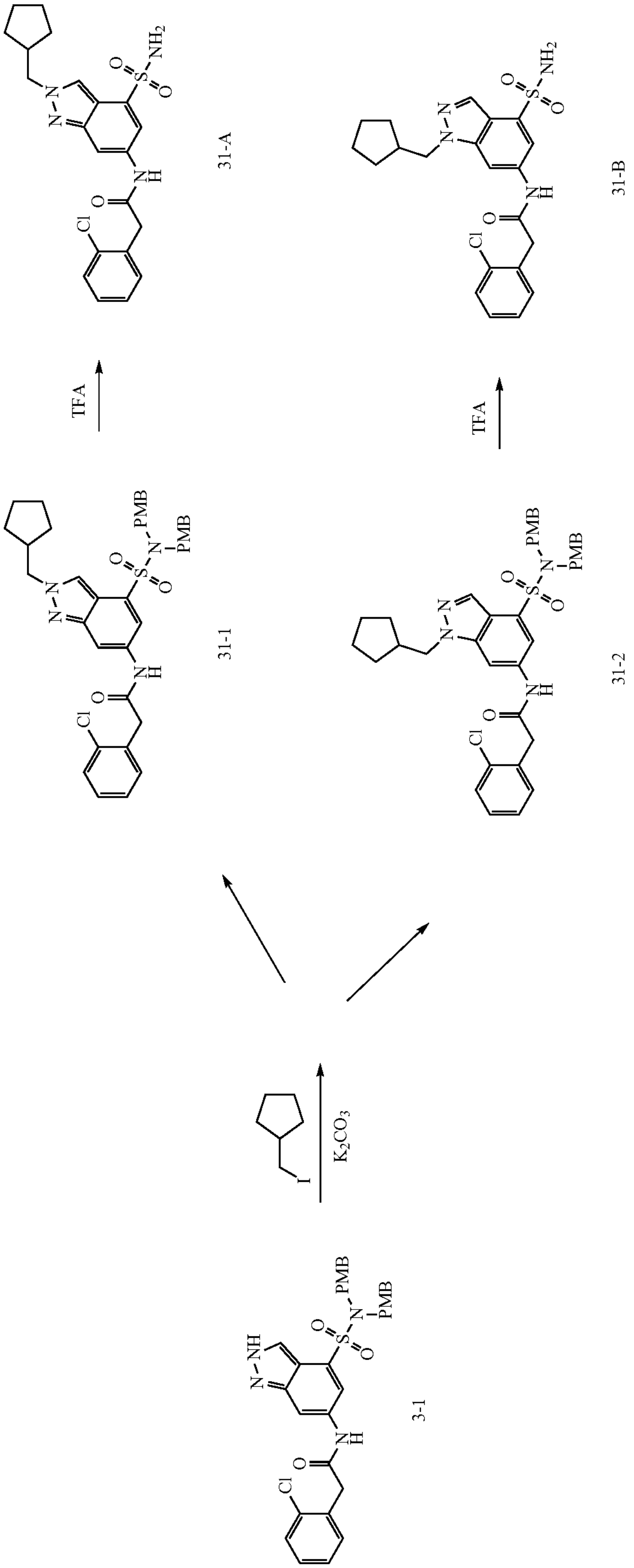
3-1
$K_2CO_3$
31-1
31-2
TFA
TFA
31-A
31-B

Step (1) Preparation of Intermediate 31-1 (N-(4-(N,N-bis(4-methoxybenzyl)sulfamoyl)-2-(cyclopentylmethyl)-2H-indazol-6-yl)-2-(2-chlorophenyl)acetamide) and Intermediate 31-2 (N-(4-(N,N-bis(4-methoxybenzyl)sulfamoyl)-1-(cyclopentylmethyl)-1H-indazol-6-yl)-2-(2-chlorophenyl)acetamide)

31-1

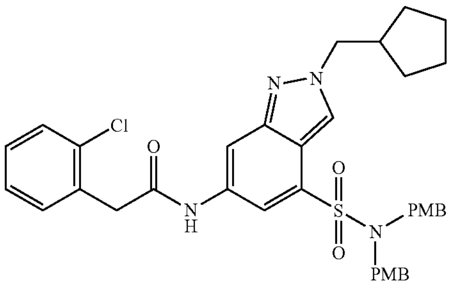

31-2

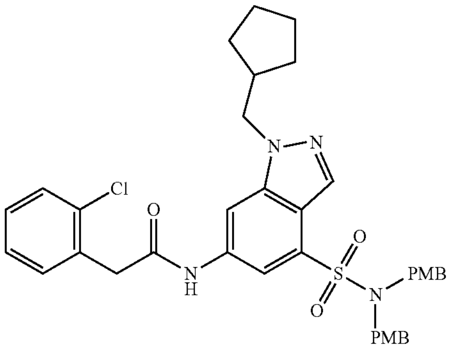

To a single-necked flask were added intermediate 3-1 (400 mg, 661 μmol), $K_2CO_3$ (182.7 mg, 1.32 mmol) and iodomethylcyclopentane (208.3 mg, 991.6 μmol), followed by the addition of DMF (2 mL), and the mixture was reacted at room temperature overnight. After the reaction was completed as detected by TLC, the reaction solution was poured into water (10 mL), extracted with EA, washed with water, concentrated and purified by column chromatography to give intermediate 31-1 (yellow solid, 100 mg) and intermediate 31-2 (yellow liquid, 150 mg). LC-MS: $[M+H]^+$=687.2.

Step (2) Preparation of Compound 31-A (2-(2-chlorophenyl)-N-(2-(cyclopentylmethyl)-4-sulfamoyl-2H-indazol-6-yl)acetamide) and Compound 31-B (2-(2-chlorophenyl)-N-(1-(cyclopentylmethyl)-4-sulfamoyl-1H-indazol-6-yl)acetamide)

31-A

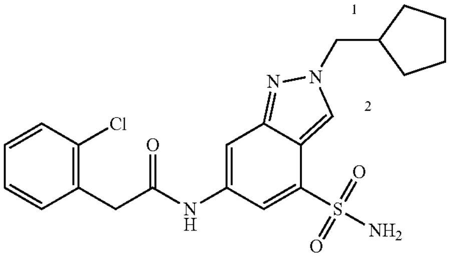

31-B

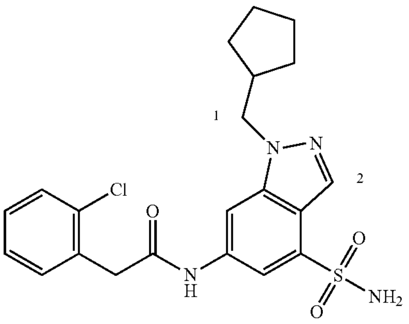

To a single-necked flask was added intermediate 31-1 (100 mg, 145.5 μmol), followed by the addition of TFA (3 mL) and DCM (3 mL), and the mixture was stirred at room temperature overnight. After the reaction was completed as detected by TLC, the reaction solution was concentrated, purified by prep-HPLC, and lyophilized to give compound 31-A (22 mg, 97.38% purity, 34.74% yield) in the form of a white solid. LC-MS: $[M+H]^+$=447.0. $^1$H NMR (400 MHz, DMSO) δ 10.51 (s, 1H), 8.48 (s, 1H), 8.23 (s, 1H), 7.72 (d, J=1.2 Hz, 1H), 7.55-7.41 (m, 4H), 7.36-7.27 (m, 2H), 4.35 (d, J=7.5 Hz, 2H), 3.88 (s, 2H), 2.57-2.51 (m, 1H), 1.68-1.48 (m, 6H), 1.34-1.25 (m, 2H).

To a single-necked flask was added intermediate 31-2 (150 mg, 218.2 μmol), followed by the addition of TFA (3 mL) and DCM (3 mL), and the mixture was stirred at room temperature overnight. After the reaction was completed as detected by TLC, the reaction solution was concentrated, purified by prep-HPLC, and lyophilized to give compound 31-B (72 mg, 99.86% purity, 73.91% yield) in the form of a white solid. LC-MS: $[M+H]^+$=447.0. $^1$H NMR (400 MHz, DMSO) δ 10.72 (s, 1H), 8.36 (s, 1H), 8.24 (s, 1H), 7.70 (s, 1H), 7.59 (s, 2H), 7.50-7.41 (m, 2H), 7.38-7.28 (m, 2H), 4.27 (d, J=7.4 Hz, 2H), 3.91 (s, 2H), 2.42 (dt, J=14.6, 7.4 Hz, 1H), 1.71-1.39 (m, 6H), 1.26 (dd, J=12.0, 5.6 Hz, 2H).

2D-HNMR (NOE) results showed that No. 1 hydrogen and No. 2 hydrogen in compound 31-A are correlated, and No. 1 hydrogen and No. 2 hydrogen in compound 31-B are not correlated.

Example 32

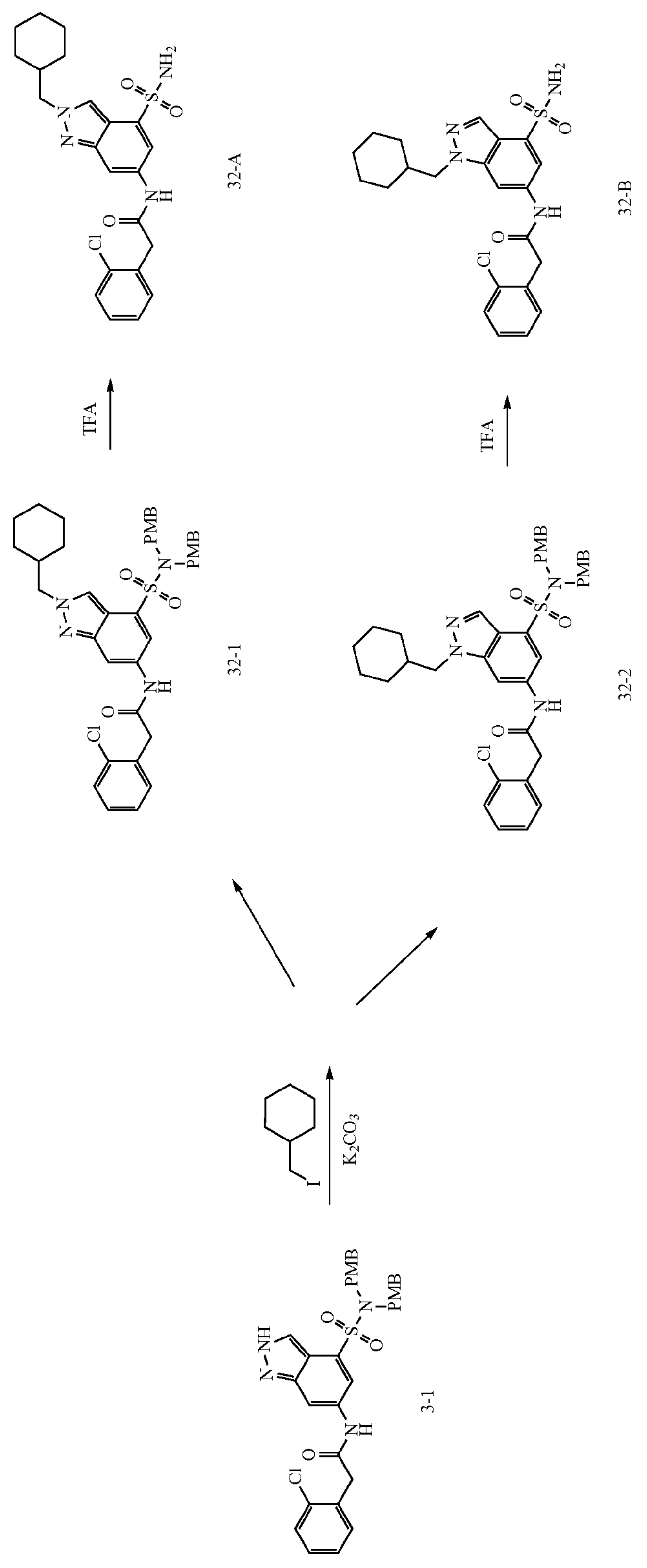
3-1
32-1
32-2
32-A
32-B

Step (1) Preparation of Intermediate 32-1 (N-(4-(N,N-bis(4-methoxybenzyl)sulfamoyl)-2-(cyclohexylmethyl)-2H-indazol-6-yl)-2-(2-chlorophenyl)acetamide) and Intermediate 32-2 (N-(4-(N,N-bis(4-methoxybenzyl)sulfamoyl)-1-(cyclohexylmethyl)-1H-indazol-6-yl)-2-(2-chlorophenyl)acetamide)

32-1

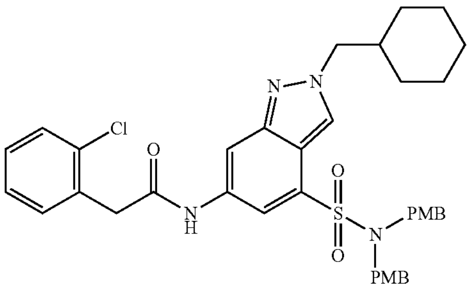

32-2

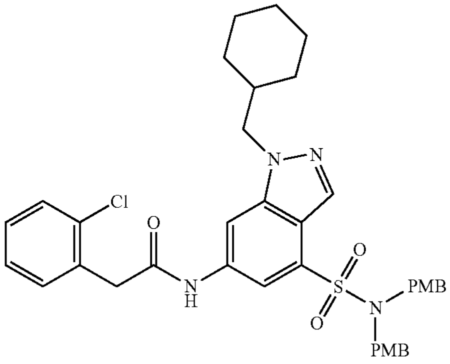

To a single-necked flask were added intermediate 3-1 (400 mg, 661 μmol), $K_2CO_3$ (182.7 mg, 1.32 mmol) and iodomethylcyclohexane (222.2 mg, 991.6 μmol), followed by the addition of DMF (2 mL), and the mixture was reacted at room temperature overnight. After the reaction was completed as detected by TLC, the reaction solution was poured into water (10 mL), extracted with EA, washed with water, concentrated and purified by column chromatography to give intermediate 32-1 (yellow liquid, 110 mg) and intermediate 32-1 (yellow liquid, 170 mg). LC-MS: $[M+H]^+$=687.2.

Step (2) Preparation of Compound 32-A (2-(2-chlorophenyl)-N-(2-(cyclohexylmethyl)-4-sulfamoyl-2H-indazol-6-yl)acetamide) and Compound 32-B (2-(2-chlorophenyl)-N-(1-(cyclohexylmethyl)-4-sulfamoyl-1H-indazol-6-yl)acetamide)

32-A

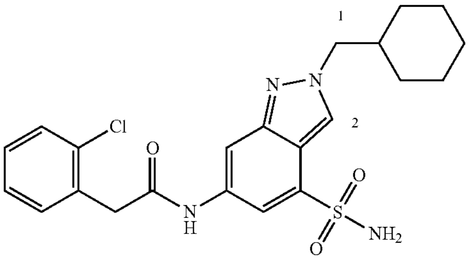

-continued

32-B

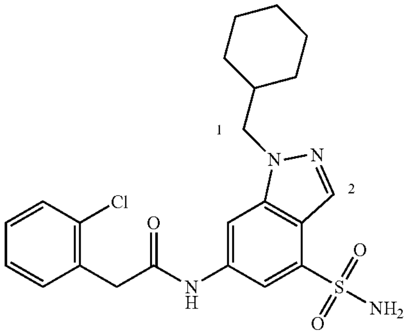

To a single-necked flask was added intermediate 32-1 (110 mg, 156.8 μmol), followed by the addition of TFA (3 mL) and DCM (3 mL), and the mixture was stirred at room temperature overnight. After the reaction was completed as detected by TLC, the reaction solution was concentrated, purified by prep-HPLC, and lyophilized to give compound 32-A (21 mg, 99.31% purity, 29.56% yield) in the form of a light yellow solid. LC-MS: $[M+H]^+$=461.0. $^1H$ NMR (400 MHz, DMSO): δ10.51 (s, 1H), 8.44 (s, 1H), 8.23 (s, 1H), 7.72 (s, 1H), 7.56-7.40 (m, 4H), 7.36-7.28 (m, 2H), 4.27 (d, J=7.1 Hz, 2H), 3.88 (s, 2H), 1.96 (ddd, J=10.9, 7.4, 3.5 Hz, 1H), 1.69-1.47 (m, 5H), 1.23-0.95 (m, 5H).

To a single-necked flask was added intermediate 32-2 (170 mg, 242.4 μmol), followed by the addition of TFA (3 mL) and DCM (3 mL), and the mixture was stirred at room temperature overnight. After the reaction was completed as detected by TLC, the reaction solution was concentrated, purified by prep-HPLC, and lyophilized to give compound 32-B (30.2 mg, 96.12% purity, 28.42% yield) in the form of a white solid. LC-MS: $[M+H]^+$=461.0. $^1H$ NMR (400 MHz, DMSO): δ 10.71 (s, 1H), 8.32 (s, 1H), 8.24 (s, 1H), 7.71 (s, 1H), 7.58 (s, 2H), 7.49-7.42 (m, 2H), 7.34 (dd, J=8.9, 5.1 Hz, 2H), 4.19 (d, J=7.1 Hz, 2H), 3.91 (s, 2H), 1.91-1.82 (m, 1H), 1.60 (d, J=18.4 Hz, 3H), 1.46 (d, J=12.3 Hz, 2H), 1.12 (t, J=8.5 Hz, 3H), 1.04-0.93 (m, 2H).

2D-HNMR (NOE) results showed that No. 1 hydrogen and No. 2 hydrogen in compound 32-A are correlated, and No. 1 hydrogen and No. 2 hydrogen in compound 32-B are not correlated.

Example 33

Preparation of 2-(2-chlorophenyl)-N-(2-(2-cyclopropylethyl)-4-sulfamoyl-2H-indazol-6-yl)acetamide

33

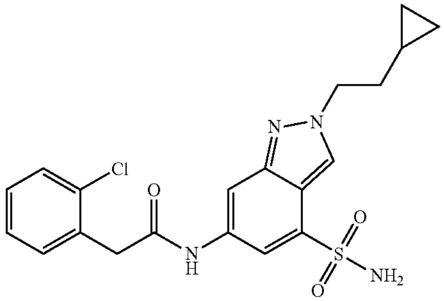

The compound was prepared using the preparation method described in Example 4. LC-MS: $[M+H]^+=433.1$.
Example 34
Preparation of 2-(2-chlorophenyl)-N-(2-(4-hydroxybenzyl)-4-sulfamoyl-2H-indazol-6-yl)acetamide
34
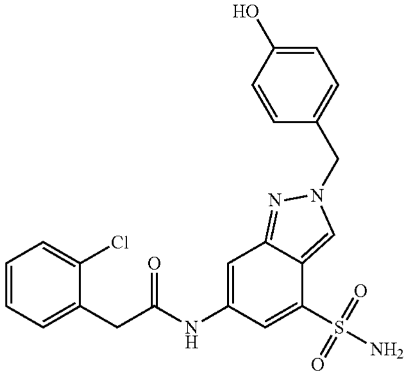
The compound was prepared using the preparation method described in Example 4. LC-MS: $[M+H]^+=471.1$.
Example 35
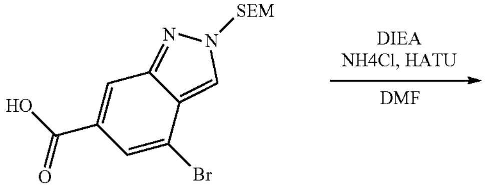
35-1
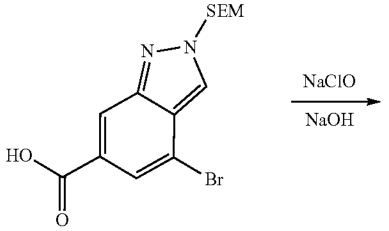
35-2
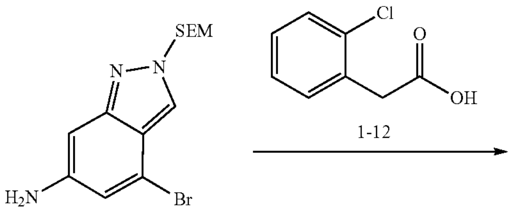
35-3 1-12
-continued
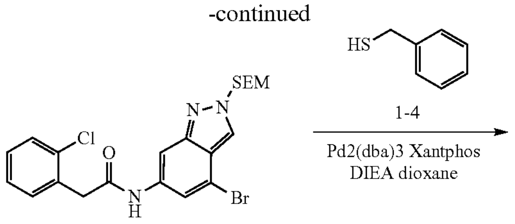
35-4
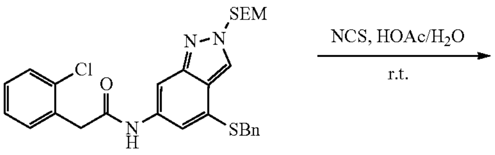
35-5
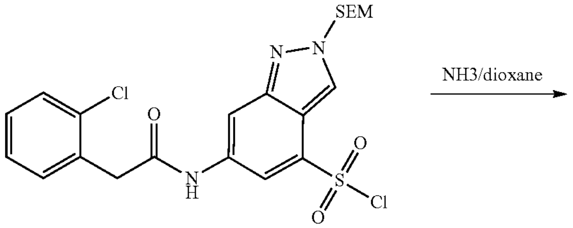
35-6
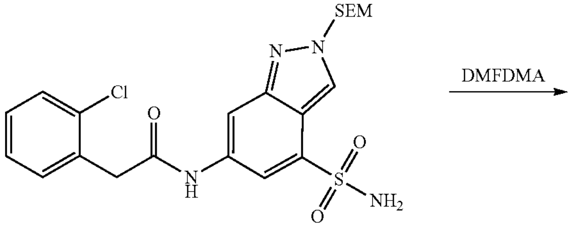
35-7
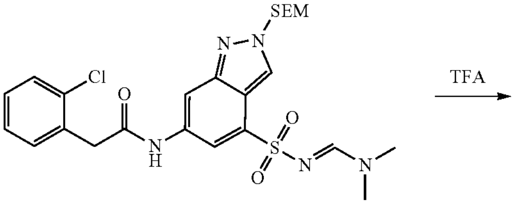
35-8
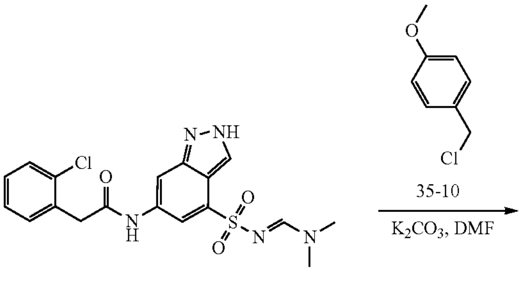
35-9

-continued

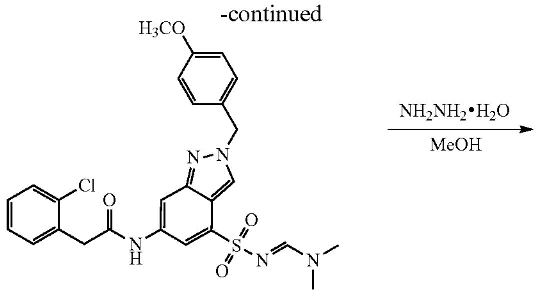

35-11

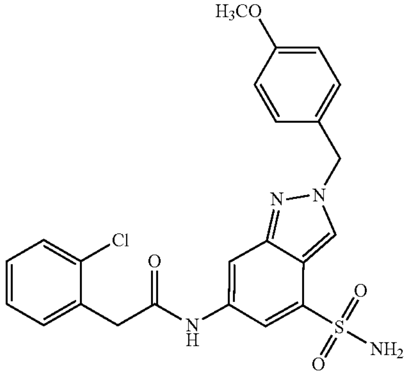

+

35-A

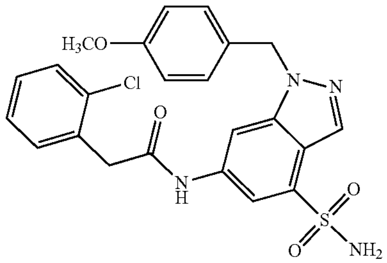

35-B

Step (1) Preparation of 4-bromo-2-((2-(trimethylsilyl)ethoxy)methyl)-2H-indazole-6-carboxamide 35-2

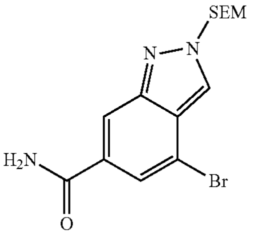

Compound 35-1 (23 g, 61.94 mmol), ammonium chloride (9.94 g, 123.8 mmol), HATU (30.61 g, 80.53 mmol) and DIEA (16.01 g, 185.83 mmol) were dissolved in DMF (200 mL), and the mixture was stirred at room temperature overnight. After the reaction was completed as detected by TLC, the reaction solution was added with water (1000 mL), and extracted twice with ethyl acetate (300 mL). The organic phases were combined, dried, concentrated under reduced pressure and purified by column chromatography to give intermediate 35-2 (15 g) in the form of a light yellow oil. LC-MS: $[M+2]^+$=372.3.

Step (2) Preparation of 4-bromo-2-((2-(trimethylsilyl)ethoxy)methyl)-2H-indazol-6-amine 35-3

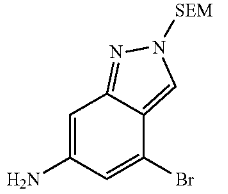

NaOH (1.35 g, 33.87 mmol) was dissolved in THF/$H_2O$ (120/80 mL), NaClO solution (13 mL, 20.3 mmol, 12%) was added at 0° C. and stirred for 5 min, and then intermediate 35-2 (5.0 g, 13.55 mmol) was added and stirred at 50° C. for 1.5 h. After the reaction was completed as detected by TLC, the reaction solution was concentrated under reduced pressure and purified by column chromatography to give intermediate 35-3 (4.2 g) in the form of a yellow solid. LC-MS: $[M+2]^+$=344.2.

Step (3) Preparation of N-(4-bromo-2-((2-(trimethylsilyl)ethoxy)methyl)-2H-indazol-6-y)-2-(2-chlorophenyl)acetamide 35-4

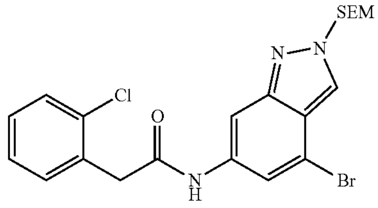

Intermediate 35-3 (5.05 g, 14.7 mmol), 2-chlorophenylacetic acid (3.75 g, 22.1 mmol), HATU (8.4 g, 22.1 mmol) and DIEA (8.1 mL, 44.1 mmol) were dissolved in DMF (44 mL) and stirred at room temperature for 2 h. After the reaction was completed as detected by TLC, the reaction solution was added with water (100 mL), and extracted twice with ethyl acetate (30 mL). The organic phases were combined, dried, concentrated under reduced pressure and purified by column chromatography to give intermediate 35-4 (6.5 g) in the form of a light yellow solid. LC-MS: $[M+2]^+$=496.1.

Step (4) Preparation of N-(4-(benzylthio)-2-((2-(trimethylsilyl)ethoxy)methyl)-2H-indazol-6-yl)-2-(2-chlorophenyl)acetamide 35-5

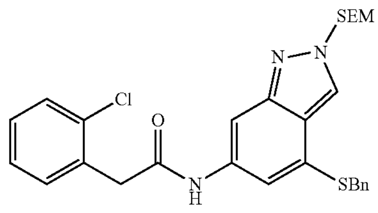

Intermediate 35-4 (6.5 g, 13.1 mmol), benzylthiol (4.9 g, 39.5 mmol), $Pd_2(dba)_3$ (1.2 g, 1.3 mmol), DIEA (6.8 g, 52.4 mmol) and Xantphos (0.37 g, 0.65 mmol) were dissolved in dioxane (81 mL) and stirred at room temperature for 4 h. After the reaction was completed as detected by TLC, the reaction solution was concentrated under reduced pressure and purified by column chromatography to give intermediate 35-5 (6.0 g) in the form of a yellow solid. LC-MS: $[M]^+$=538.1.

Step (5) Preparation of 6-(2-(2-chlorophenyl)acetamide)-2-((2-(trimethylsilyl)ethoxy)methyl)-2H-indazole-4-sulfonyl chloride 35-6

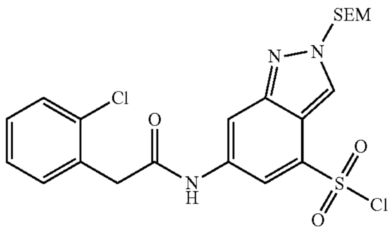

Intermediate 35-5 (6.0 g, 11.1 mmol) was added to $HOAc/H_2O$ (100/30 mL), and NCS (7.4 g, 55.5 mmol) was added to the cloudy solution in portions and stirred at room temperature for 30 min. After the reaction solution was clear and the reaction was completed as detected by TLC, the reaction solution was added with water (100 mL), and extracted twice with ethyl acetate (50 mL), the organic phases were combined, pH was adjusted to 8-9 with saturated sodium bicarbonate, and the organic phases were separated, dried and concentrated to give intermediate 35-6 (8.2 g, crude) in the form of a yellow oil which was directly used in the next step without purification. LC-MS: $[M]^+$=515.2.

Step (6) Preparation of 2-(2-chlorophenyl)-N-(4-sulfamoyl-2-((2-(trimethylsilyl)ethoxy)methyl)-2H-indazol-6-yl)acetamide 35-7

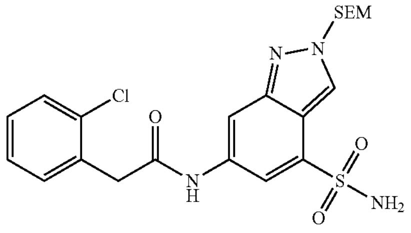

Intermediate 35-6 (8.2 g, crude) was dissolved in THF (10 mL), and the reaction solution was slowly added with a solution of ammonia in dioxane (300 mL, 0.4 M) and stirred at room temperature overnight. After the reaction was completed as detected by TLC, the reaction solution was concentrated under reduced pressure and purified by column chromatography to give intermediate 35-7 (4.0 g) in the form of a yellow solid. LC-MS: $[M]^+$=495.1.

Step (7) Preparation of (E)-2-(2-chlorophenyl)-N-(4-(N-((dimethylamino)methylene)sulfamoyl)-2-((2-(trimethylsilyl)ethoxy)methyl)-2H-indazol-6-yl)acetamide 35-8

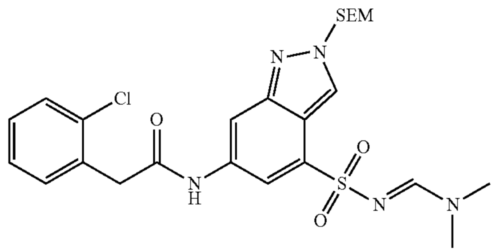

Intermediate 35-7 (3.8 g, 7.67 mmol) was dissolved in DMF (55 mL), followed by the dropwise addition of DMF-DMA (1.5 g, 12.2 mmol), and the mixture was stirred at 60° C. for 1.5 h. After the reaction was completed as detected by TLC, the reaction solution was cooled and added with water (200 mL) and extracted twice with ethyl acetate, the organic phase was dried and concentrated to give an oil (6.1 g, crude) which was purified by column chromatography to give intermediate 35-8 (3.8 g) in the form of a yellow oil. LC-MS: $[M]^+$=550.2.

Step (8) Preparation of (L)-2-(2-chlorophenyl)-N-(4-(N-((dimethylamino)methylene)sulfamoyl)-2H-indazol-6-yl)acetamide 35-9

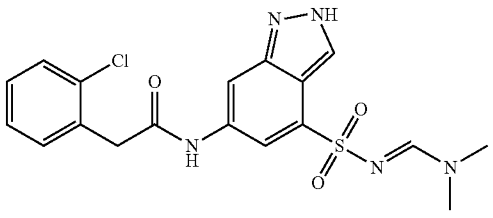

Intermediate 35-8 (3.8 g, 8.18 mmol) was dissolved in DCM (30 mL), followed by the addition of TFA (30 mL) in an ice bath, and the reaction solution was stirred at room temperature for 1 h. After the reaction was completed as detected by TLC, the reaction solution was concentrated to give a crude product, into which water was added, then pH was adjusted to about 8 with saturated sodium bicarbonate, the reaction solution was extracted twice with ethyl acetate and concentrated, the solid was precipitated, filtered and dried to give intermediate 35-9 (1.5 g, 86.2% yield) in the form of a light red solid. LC-MS: $[M]^+$=420.

Step (9) Preparation of (E)-2-(2-chlorophenyl)-N-(4-(N-((dimethylamino)methylene)sulfamoyl)-2-(4-methoxybenzyl)-2H-indazol-6-yl)acetamide 35-11

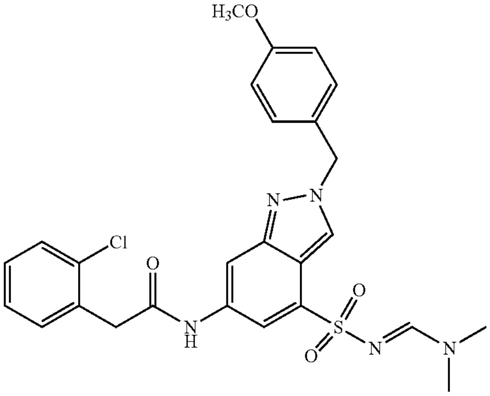

Intermediate 35-9 (300 mg, 0.716 mmol), PMBCl (167 mg, 1.07 mmol) and potassium carbonate (295.3 mg, 2.14 mmol) were sequentially dissolved in DMF (5 mL) and stirred at room temperature for 2 h. After the reaction was completed as detected by TLC, the reaction solution was diluted with water (15 mL), added with ethyl acetate (5 mL) and stirred for 10 min, and then left to stand to separate the ethyl acetate phase. The aqueous phase was extracted once with ethyl acetate (5 mL), the organic phases were combined, washed with saturated brine, dried over anhydrous sodium sulfate, and filtered, and the filtrate was concentrated under reduced pressure and purified by column chromatography to give intermediate 35-11 (210 mg) in the form of a white solid. LC-MS: $[M]^+$=540.

Step (10) Preparation of Compound 35-A (2-(2-chlorophenyl)-N-(2-(4-methoxybenzyl)-4-sulfamoyl-2H-indazol-6-yl)acetamide) and Compound 35-B (2-(2-chlorophenyl)-N-(1-(4-methoxybenzyl)-4-sulfamoyl-1H-indazol-6-yl)acetamide)

35-A

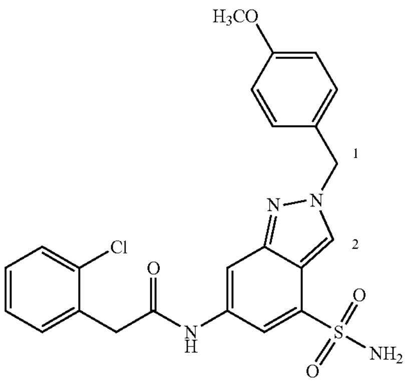

35-B

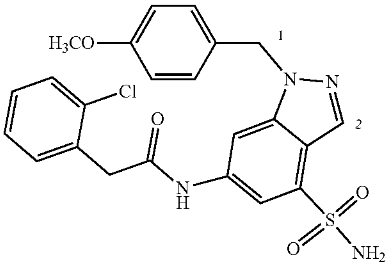

Intermediate 35-11 (210 mg, 0.38 mmol) was dissolved in methanol (0.6 mL), and the reaction solution was added dropwise with a hydrazine hydrate solution (0.5 mL, 85%) and stirred at room temperature for 30 min. After the reaction was completed as detected by LCMS, the reaction solution was concentrated under reduced pressure to give a crude product which was separated by prep-HPLC using a $H_2O$/CAN system and lyophilized to give compound 35-A (white solid, 25.8 mg, 97.89% purity, 13.7% yield) and compound 35-B (white solid, 32.6 mg, 98.08% purity, 17.3% yield).

Compound 35-A: LC-MS: $[M+1]^+$=485. $^1$H NMR (400 MHz, DMSO) δ 8.51 (s, 1H), 8.20 (s, 1H), 7.71 (d, J=1.5 Hz, 1H), 7.48 (s, 2H), 7.45-7.40 (m, 2H), 7.35-7.28 (m, 4H), 6.91 (dd, J=6.8, 4.8 Hz, 2H), 5.56 (s, 2H), 3.86 (s, 2H), 3.71 (s, 3H).

Compound 35-B: LC-MS: $[M+1]^+$=485. $^1$H NMR (400 MHz, dmso) δ 10.71 (s, 1H), 8.31 (s, 1H), 8.26 (s, 1H), 7.72 (s, 1H), 7.58 (s, 2H), 7.43 (dd, J=9.1, 5.0 Hz, 2H), 7.31 (dd, J=9.1, 4.8 Hz, 2H), 7.11 (d, J=8.5 Hz, 2H), 6.84 (d, J=8.5 Hz, 2H), 5.53 (s, 2H), 3.87 (s, 2H), 3.67 (s, 3H).

2D-HNMR (NOE) results showed that No. 1 hydrogen and No. 2 hydrogen in compound 35-A are correlated, and No. 1 hydrogen and No. 2 hydrogen in compound 35-B are not correlated.

Example 36

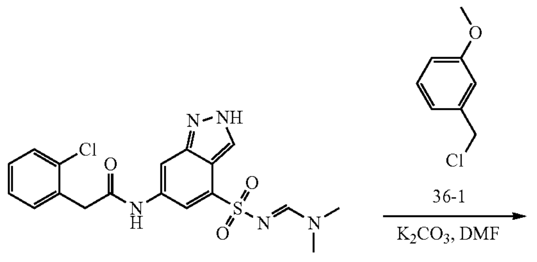

35-8

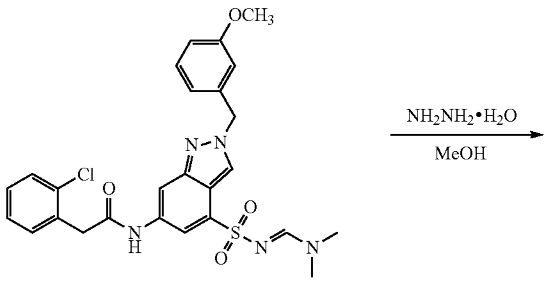

36-2

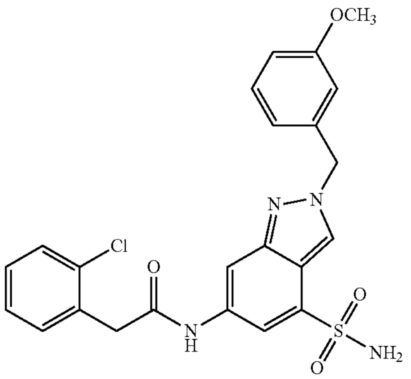

36-A

+

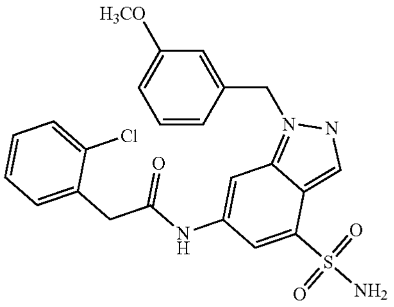

36-B

Step (1) Preparation of (E)-2-(2-chlorophenyl)-N-(4-(N-((dimethylamino)methylene)sulfamoyl)-2-(3-methoxybenzyl)-2H-indazol-6-yl)acetamide 36-2

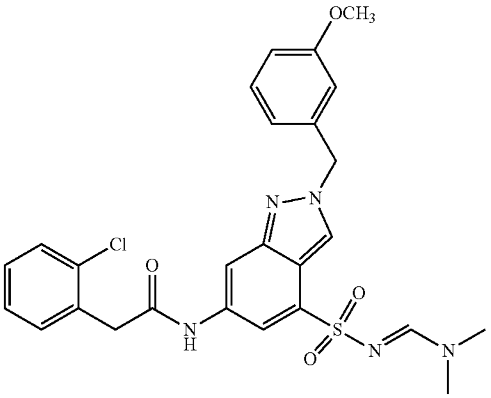

Intermediate 35-9 (300 mg, 0.716 mmol), 3-methoxybenzyl chloride (167 mg, 1.07 mmol) and potassium carbonate (295.3 mg, 2.14 mmol) were sequentially dissolved in DMF (5 mL) and stirred at room temperature for 2 h. After the reaction was completed as detected by TLC, the reaction solution was diluted with water (15 mL), added with ethyl acetate (5 mL) and stirred for 10 min, and then left to stand to separate the ethyl acetate phase. The aqueous phase was extracted once with ethyl acetate (5 mL), the organic phases were combined, washed with saturated brine, dried over anhydrous sodium sulfate, and filtered, and the filtrate was concentrated under reduced pressure and purified by column chromatography to give intermediate 36-2 (230 mg) in the form of a white solid. LC-MS: $[M]^+$=540.

Step (2) Preparation of Compound 36-A (2-(2-chlorophenyl)-N-(2-(3-methoxybenzyl)-4-sulfamoyl-2H-indazol-6-yl)acetamide) and Compound 36-B (2-(2-chlorophenyl)-N-(1-(3-methoxybenzyl)-4-sulfamoyl-1H-indazol-6-yl)acetamide)

36-A

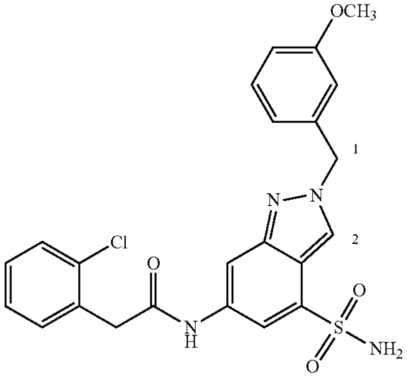

-continued

36-B

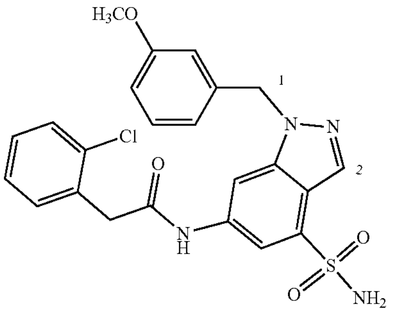

Intermediate 36-2 (230 mg, 0.42 mmol) was dissolved in methanol (0.65 mL), and the reaction solution was added dropwise with a hydrazine hydrate solution (0.5 mL, 85%) and stirred at room temperature for 30 min. After the reaction was completed as detected by LCMS, the reaction solution was concentrated under reduced pressure to give a crude product which was separated by prep-HPLC using a $H_2O$/CAN system and lyophilized to give compound 36-A (white solid, 44.6 mg, 99.50% purity, 21.6% yield) and compound 36-B (white solid, 57.8 mg, 98.19% purity, 28% yield).

Compound 36-A: LC-MS: [M+1]+=485. $^1$H NMR (400 MHz, DMSO) δ 10.52 (s, 1H), 8.56 (s, 1H), 8.21 (s, 1H), 7.72 (d, J=1.5 Hz, 1H), 7.49 (s, 2H), 7.45-7.40 (m, 2H), 7.34-7.20 (m, 3H), 6.97-6.82 (m, 3H), 5.61 (s, 2H), 3.86 (s, 2H), 3.71 (s, 3H).

Compound 36-B: LC-MS: $[M+1]^+$=485. $^1$H NMR (400 MHz, DMSO) δ 10.69 (s, 1H), 8.31 (s, 1H), 8.28 (s, 1H), 7.73 (d, J=1.3 Hz, 1H), 7.59 (s, 2H), 7.46-7.38 (m, 2H), 7.34-7.26 (m, 2H), 7.19 (t, J=7.9 Hz, 1H), 6.80 (dd, J=8.1, 2.4 Hz, 1H), 6.72 (s, 1H), 6.65 (d, J=7.6 Hz, 1H), 5.58 (s, 2H), 3.87 (s, 2H), 3.66 (s, 3H).

2D-HNMR (NOE) results showed that No. 1 hydrogen and No. 2 hydrogen in compound 36-A are correlated, and No. 1 hydrogen and No. 2 hydrogen in compound 36-B are not correlated.

Example 37

-continued

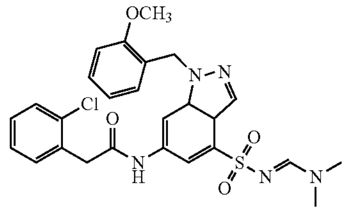

37-3

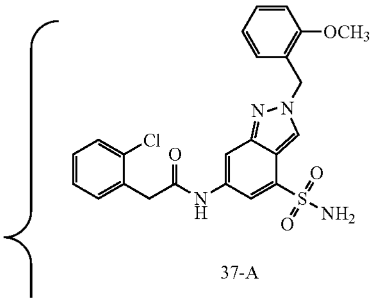

37-A

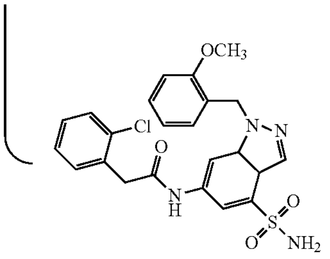

37-B

Step (1) Preparation of Intermediate 37-2 ((E)-2-(2-chlorophenyl)-N-(4-(N-((dimethylamino)methylene) sulfonamide)-2-(2-methoxybenzyl)-2H-indazol-6-yl) acetamide) and Intermediate 37-3 ((E)-2-(2-chlorophenyl)-N-(4-(N-((dimethylamino)methylene) sulfonamide)-1-(2-methoxybenzyl)-2H-indazol-6-yl) acetamide)

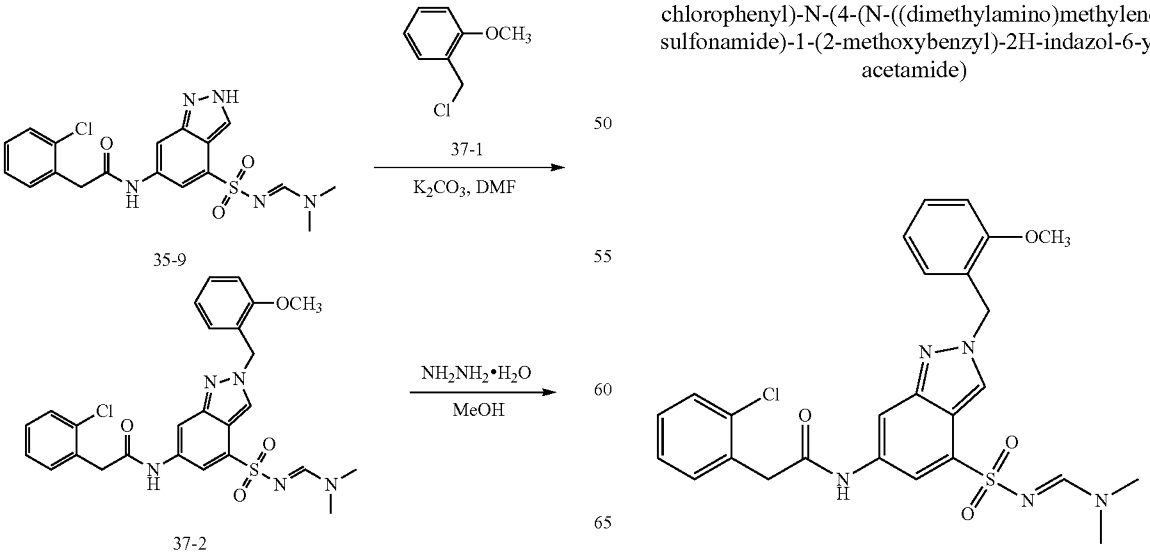

35-9

37-2

37-2

-continued 37-3

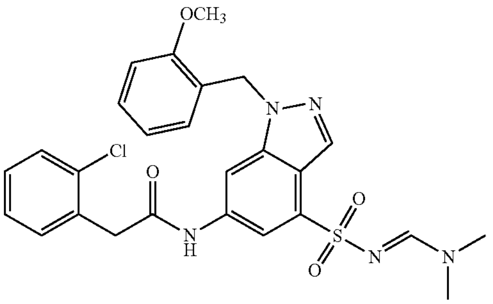

Intermediate 35-9 (300 mg, 0.716 mmol), 2-methoxybenzyl chloride (167 mg, 1.07 mmol) and potassium carbonate (295.3 mg, 2.14 mmol) were sequentially dissolved in DMF (5 mL) and stirred at room temperature for 2 h. After the reaction was completed as detected by TLC, the reaction solution was diluted with water (15 mL), added with ethyl acetate (5 mL) and stirred for 10 min, and then left to stand to separate the ethyl acetate phase. The aqueous phase was extracted once with ethyl acetate (5 mL), the organic phases were combined, washed with saturated brine, dried over anhydrous sodium sulfate, and filtered, and the filtrate was concentrated under reduced pressure and purified by column chromatography to give a mixture (190 mg, white solid) of intermediate 37-2 and intermediate 37-3. LC-MS: $[M]^+=540$.

Step (2) Preparation of Compound 37-A (2-(2-chlorophenyl)-N-(2-(2-methoxybenzyl)-4-sulfamoyl-2H-indazol-6-yl)acetamide) and Compound 37-B (2-(2-chlorophenyl)-N-(1-(2-methoxybenzyl)-4-sulfamoyl-1H-indazol-6-yl)acetamide)

37-A

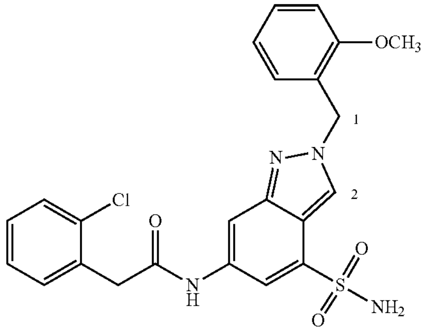

37-B

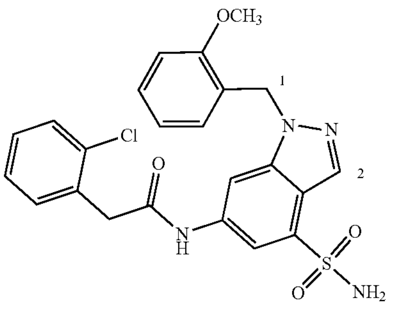

A mixture (190 mg, 0.35 mmol) of intermediate 37-2 and intermediate 37-3 was dissolved in methanol (0.55 mL), and the reaction solution was added dropwise with a hydrazine hydrate solution (0.5 mL, 85%) and stirred at room temperature for 30 min. After the reaction was completed as detected by LCMS, the reaction solution was concentrated under reduced pressure to give a crude product which was separated by prep-HPLC using a $H_2O$/CAN system and lyophilized to give compound 37-A (white solid, 40.0 mg, 99.65% purity, 23.5% yield) and compound 37-B (white solid, 49.3 mg, 99.70% purity, 28.9% yield).

Compound 37-A: LC-MS: $[M+1]^+=485$. $^1H$ NMR (400 MHz, DMSO) δ 10.52 (s, 1H), 8.43 (s, 1H), 8.20 (s, 1H), 7.72 (d, J=1.4 Hz, 1H), 7.51 (s, 2H), 7.46-7.39 (m, 2H), 7.31 (ddd, J=9.1, 6.5, 1.8 Hz, 3H), 7.11-7.01 (m, 2H), 6.91 (t, J=7.4 Hz, 1H), 5.59 (s, 2H), 3.86 (s, 2H), 3.80 (s, 3H).

Compound 37-B: LC-MS: [M+1]+=485. $^1H$ NMR (400 MHz, DMSO) δ 10.68 (s, 1H), 8.37 (s, 1H), 8.26 (s, 1H), 7.71 (d, J=1.4 Hz, 1H), 7.57 (s, 2H), 7.46-7.39 (m, 2H), 7.34-7.27 (m, 2H), 7.26-7.19 (m, 1H), 6.97 (d, J=8.2 Hz, 1H), 6.81 (q, J=7.2 Hz, 2H), 5.51 (s, 2H), 3.88 (s, 2H), 3.77 (s, 3H).

2D-HNMR (NOE) results showed that No. 1 hydrogen and No. 2 hydrogen in compound 37-A are correlated, and No. 1 hydrogen and No. 2 hydrogen in compound 37-B are not correlated.

Example 38

Preparation of 2-(2-chlorophenyl)-N-(2-(3-(dimethylamino)benzyl)-4-sulfamoyl-2H-indazol-6-yl)acetamide

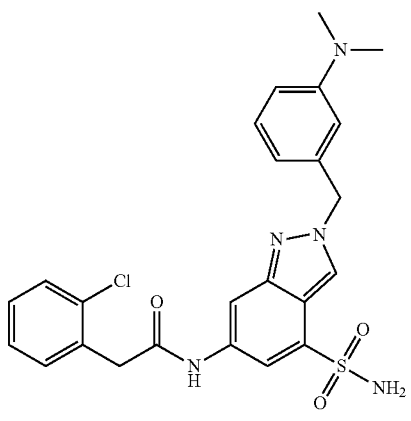 [SMILES: CN(C)c1cccc(Cn2cc3c(S(N)(=O)=O)cc(NC(=O)Cc4ccccc4Cl)cc3n2)c1]

The compound was prepared using the preparation method described in Example 4. LC-MS: $[M+H]^+=498.1$.

Example 39

Preparation of 2-(2-chlorophenyl)-N-(2-((3-methoxypyridin-4-yl)methyl)-4-sulfamoyl-2H-indazol-6-yl)acetamide

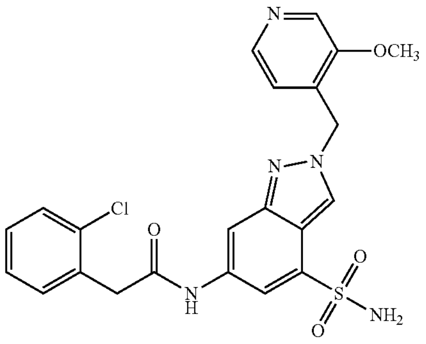 [SMILES: COc1cnccc1Cn1cc2c(S(N)(=O)=O)cc(NC(=O)Cc3ccccc3Cl)cc2n1]

The compound was prepared using the preparation method described in Example 4. LC-MS: $[M+H]^+$=486.1.

Example 40

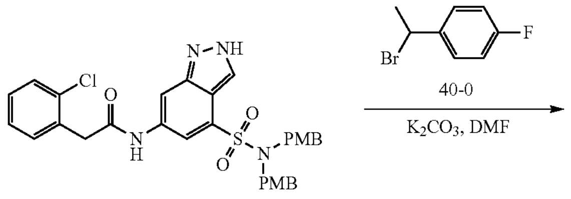

3-1

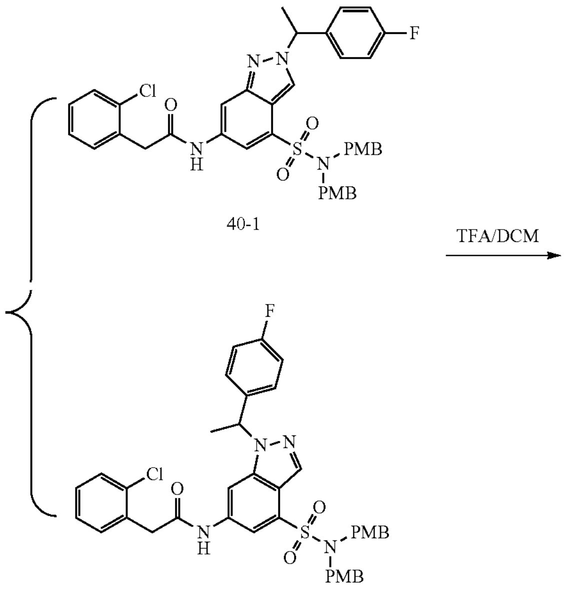

40-2

-continued

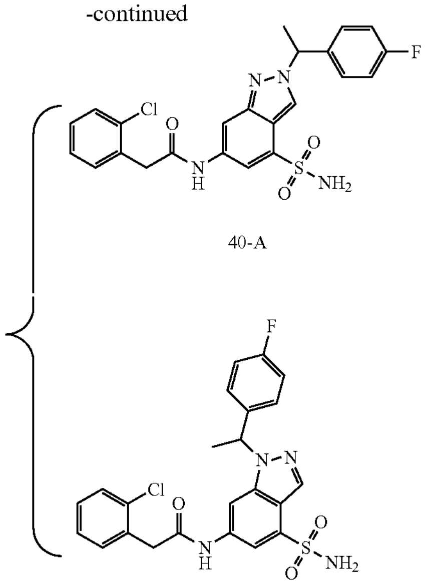

40-B

Step (1) Preparation of Intermediate 40-1 (4-(N,N-bis(4-methoxybenzyl)sulfonamide-6-N-(2-chlorophenylacetyl)-2-(1-(4-fluorophenyl)ethyl)-indazole) and Intermediate 40-2 (4-(N,N-bis(4-methoxybenzyl)sulfonamide-6-N-(2-chlorophenylacetyl)-1-(I-(4-fluorophenyl)ethyl)-indazole)

40-1

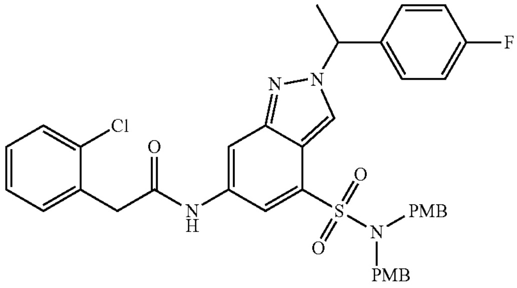

40-2

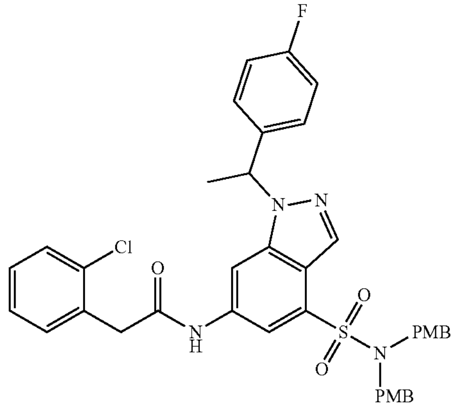

Intermediate 3-1 (350.0 mg, 578.0 μmol) and intermediate 40-0 (235.0 mg, 1.2 mmol) were dissolved in DMF (5 mL), $K_2CO_3$ (160.0 mg, 1.2 mmol) was added, and the mixture was stirred at room temperature overnight. After the reaction was completed, the reaction solution was poured into water, the resulting solution was extracted with EtOAc, the organic phase was dried over anhydrous sodium sulfate and filtered, and the filtrate was concentrated by rotary evaporation to give a mixture (400.0 mg, yellow oil, crude) of intermediate 40-1 and intermediate 40-2; LC-MS: $[M+H]^+$=727.

Step (2) Preparation of Compound 40-A (2-(2-chlorophenyl)-N-(2-(1-(4-fluorophenyl)ethyl)-4-sulfamoyl-2H-indazol-6-yl)acetamide) and Compound 40-B (2-(2-chlorophenyl)-N-(1-(1-(4-fluorophenyl)ethyl)-4-sulfamoyl-1H-indazol-6-yl)acetamide)

40-A

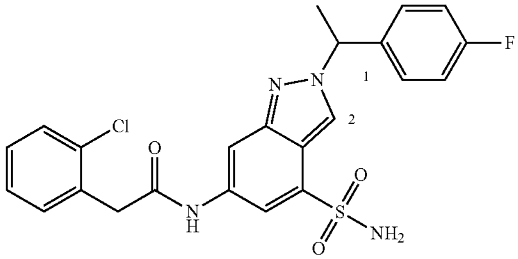

40-B

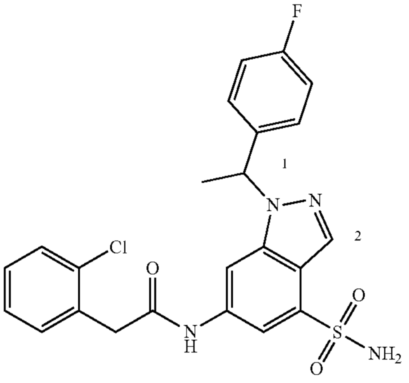

A mixture (390.0 mg, 536.0 μmol) of intermediate 40-1 and intermediate 40-2 was dissolved in DCM (5 mL), TFA (5 mL) was added, and the reaction solution was stirred at room temperature overnight. After the reaction was completed, the reaction solution was concentrated under reduced pressure at room temperature to give a crude product which was purified by prep-HPLC to give compound 40-A (white solid powder, 28.8 mg) and compound 40-B (white solid powder, 26.5 mg).

Compound 40-A: LC-MS: $[M+H]^+$=487. $^1H$ NMR (400 MHz, DMSO-$d_6$) δ 10.53 (s, 1H), 8.63 (s, 1H), 8.23 (s, 1H), 7.74 (d, J=1.4 Hz, 1H), 7.51 (s, 2H), 7.47-7.39 (m, 4H), 7.36-7.28 (m, 2H), 7.18 (t, J=8.9 Hz, 2H), 6.01 (q, J=7.0 Hz, 1H), 3.88 (s, 2H), 1.94 (d, J=7.0 Hz, 3H).

Compound 40-B: LC-MS: $[M+H]^+$=487. $^1H$ NMR (400 MHz, DMSO-$d_6$) δ 10.69 (s, 1H), 8.34 (s, 1H), 8.31 (s, 1H), 7.73 (s, 1H), 7.60 (s, 2H), 7.48-7.40 (m, 2H), 7.34-7.22 (m, 4H), 7.12 (t, J=8.6 Hz, 2H), 6.00 (q, J=6.8 Hz, 1H), 3.88 (s, 2H), 1.90 (d, J=6.9 Hz, 3H).

2D-HNMR (NOE) results showed that No. 1 hydrogen and No. 2 hydrogen in compound 40-A are correlated, and No. 1 hydrogen and No. 2 hydrogen in compound 40-B are not correlated.

Example 41

Preparation of 2-(2-chlorophenyl)-N-(2-isobutyryl-4-sulfamoyl-2H-indazol-6-yl)acetamide

41

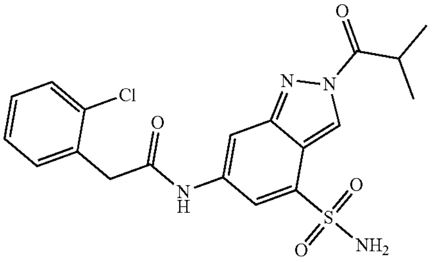

The compound was prepared using the preparation method described in Example 40. LC-MS: $[M+H]^+$=435.1.

Example 42

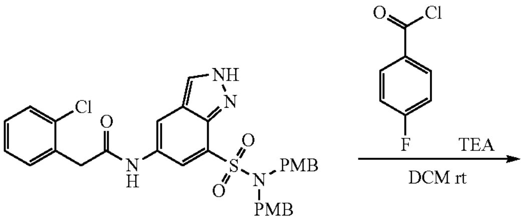

3-1

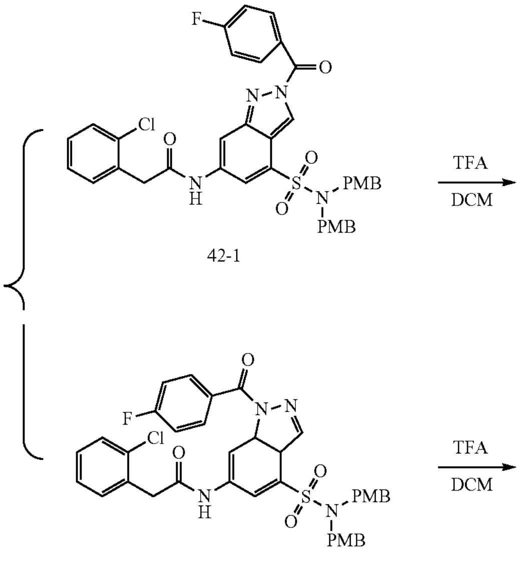

42-1

42-2

-continued

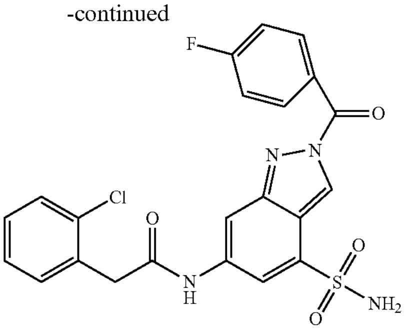

42-A

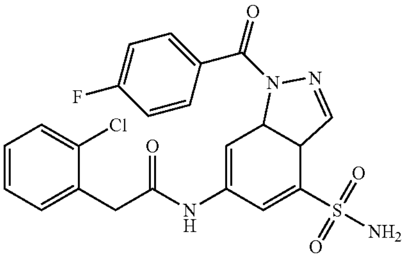

42-B

Step (1) Preparation of Intermediate 42-1 (N-(4-(N,N-bis(4-methoxybenzyl)sulfamoyl)-2-(4-fluorobenzoyl)-2H-indazol-6-yl)-2-(2-chlorophenyl) acetamide) and Intermediate 42-2 (N-(4-(N,N-bis(4-methoxybenzyl)sulfamoyl)-1-(4-fluorobenzoyl)-1H-indazol-6-y)-2-(2-chlorophenyl)acetamide)

42-1

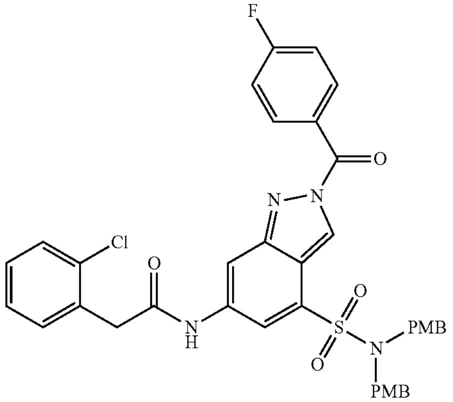

42-2

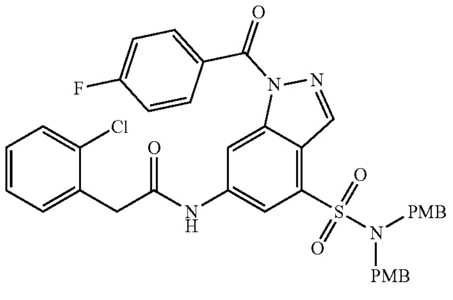

Intermediate 3-1 (375 mg, 0.62 mmol), p-fluorobenzoyl chloride (98 mg, 0.62 mmol) and triethylamine (125 mg, 1.24 mmol) were dissolved in DCM and stirred at room temperature overnight. After the reaction starting material was completely reacted as indicated by thin-layer chromatography, the reaction solution was added with water (5 mL) and extracted three times with EA, and the EA phases were combined, washed with saturated brine, dried over sodium sulfate, filtered and concentrated to give a crude product which was purified by column chromatography to give intermediate 42-1 (220 mg) in the form of a yellow oil and intermediate 42-2 (30 mg) in the form of a yellow oil. LC-MS: $[M+H]^+$=727.

Step (2) Preparation of Compound 42-A (2-(2-chlorophenyl)-N-(2-(4-fluorobenzoyl)-4-sulfamoyl-2H-indazol-6-yl)acetamide) and Compound 42-B (2-(2-chlorophenyl)-N-(1-(4-fluorobenzoyl)-4-sulfamoyl-1H-indazol-6-yl)acetamide)

42-A

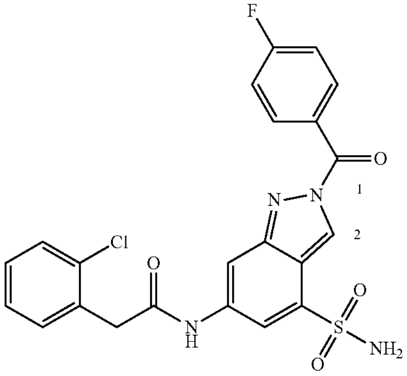

42-B

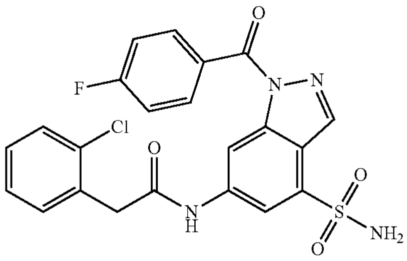

Intermediate 42-1 (200 mg, 0.28 mmol) was dissolved in DCM (3 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 42-A (6 mg) in the form of a white solid; LC-MS: $[M+H]^+$=487.1.

$^1H$ NMR (400 MHz, DMSO) S: 10.94 (s, 1H), 9.07 (s, 1H), 8.60 (s, 1H), 8.20 (d, J=1.6 Hz, 1H), 8.08 (dd, J=8.8, 5.6 Hz, 2H), 7.79 (s, 2H), 7.43 (dt, J=17.8, 7.6 Hz, 4H), 7.32 (dd, J=6.6, 2.6 Hz, 2H), 3.93 (s, 2H).

2D-HNMR (HMBC) results showed that No. 1 hydrogen and No. 2 hydrogen in compound 42-A are correlated.

Intermediate 42-2 (30 mg, 0.04 mmol) was dissolved in DCM (1 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 42-B (6 mg) in the form of a white solid. LC-MS: $[M+H]^+$=487.1.

Example 43

Preparation of 2-(2-chlorophenyl)-N-(1-(difluoromethyl)-4-sulfamoyl-1H-indazol-6-yl)acetamide

43

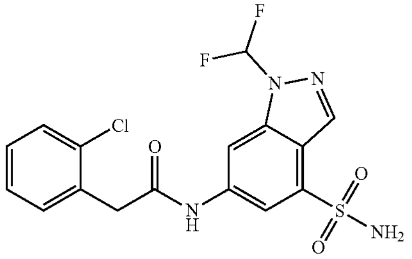

The compound was prepared using the preparation method described in Example 4. LC-MS: $[M+H]^+$=415.0.

Example 44

Preparation of 2-(2-chlorophenyl)-N-(1-(4-fluorophenyl)-4-sulfamoyl-1H-indazol-6-yl)acetamide

44

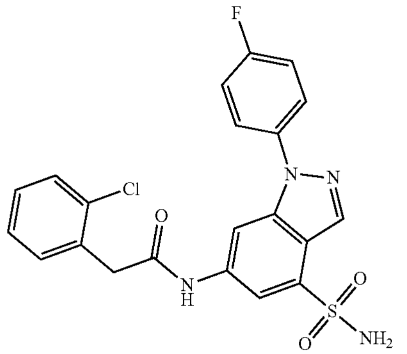

The compound was prepared using the preparation method described in Example 14. LC-MS: $[M+H]^+$=459.1.

Example 44-1

Preparation of 2-(2-chlorophenyl)-N-(1-(4-fluorophenyl)-4-sulfamoyl-1H-indazol-6-yl)acetamide

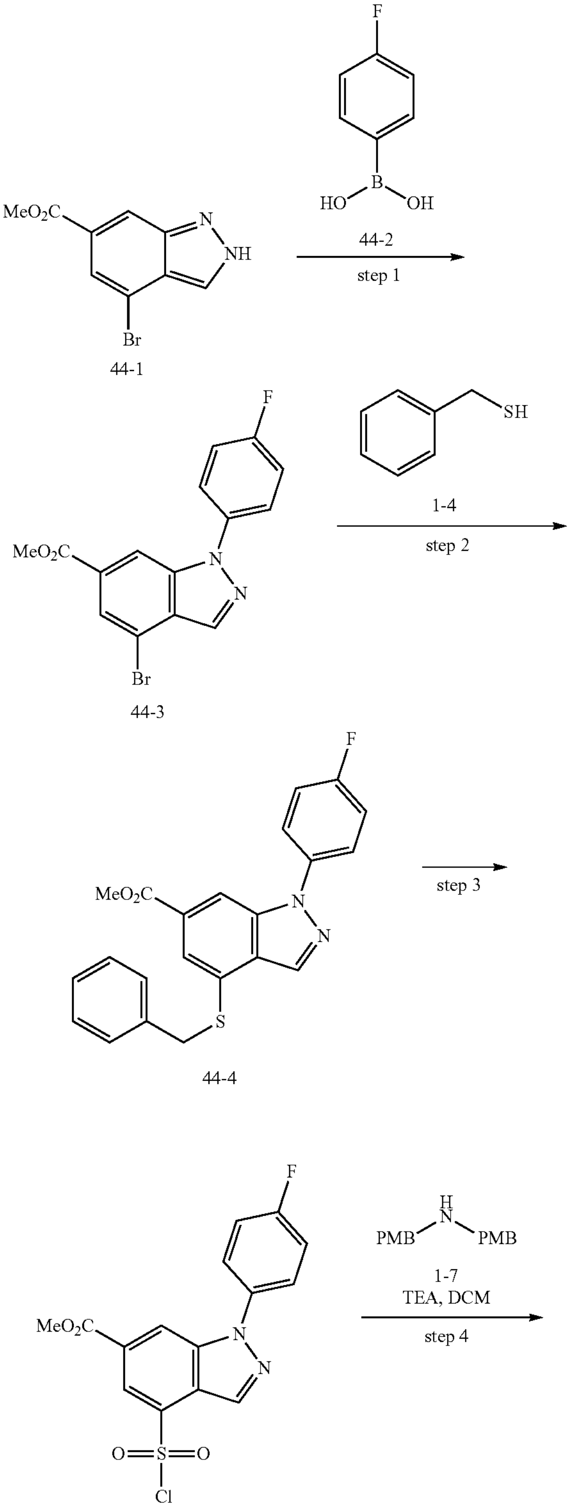

44-1
44-3
44-4
44-5

-continued

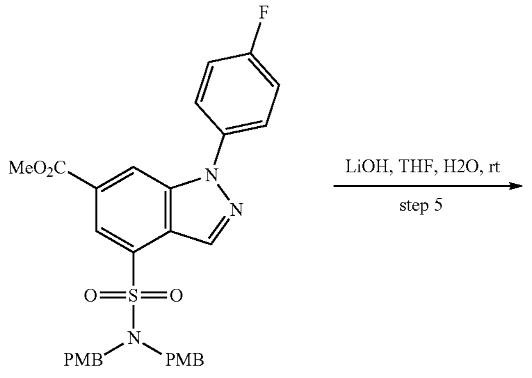

44-6

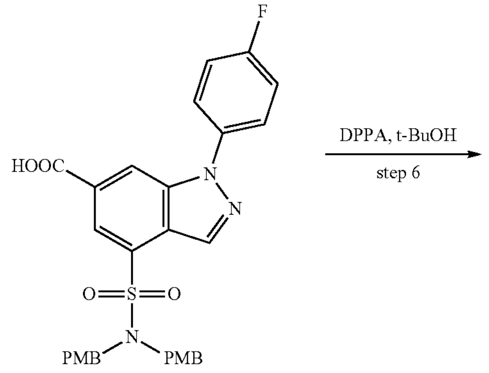

44-7

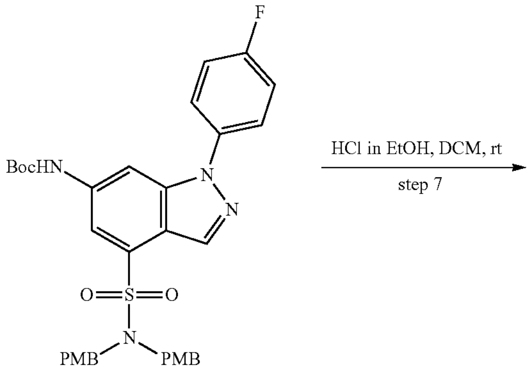

44-8

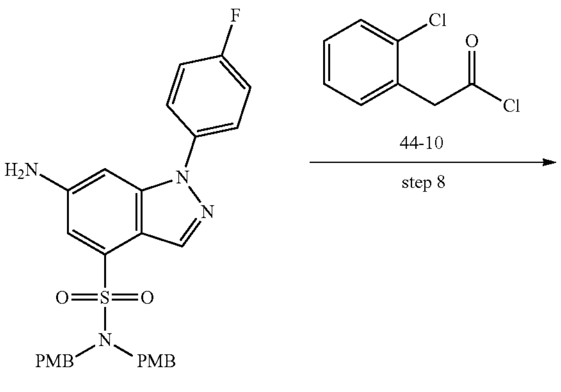

44-10

44-9

-continued

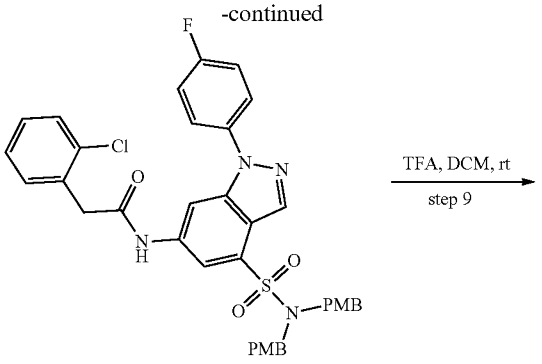

44-11

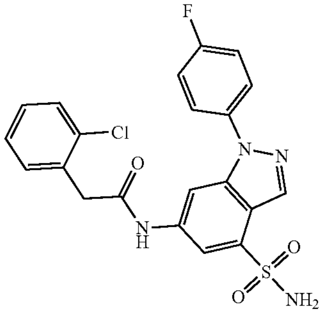

44

Step (1) Preparation of Intermediate 44-3 (methyl 4-bromo-1-(4-fluorophenyl)-1H-indazole-6-carboxylate)

T44-3

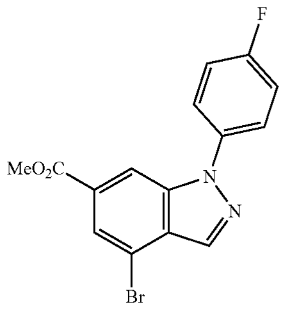

Intermediate 44-1 (methyl-4-bromo-2H-indazole-6-carboxylate) (4.00 g, 15.68 mmol), intermediate 44-2 ((4-fluorophenyl)boronic acid) (4.39 g, 31.36 mmol) and pyridine (3.73 g, 47.05 mmol) were added to dichloromethane (8 mL), followed by the addition of copper acetate (4.28 g, 23.50 mmol), and the mixture was reacted at room temperature in air for 16 h. The reaction solution was concentrated and purified by silica gel column chromatography (DCM/EA=4/5) to give intermediate 44-3 (0.75 g, 12.1% yield) in the form of a yellow solid. LC-MS: $[M+H]^+=350$.

Step (2) Preparation of Intermediate 44-4 (methyl 4-(benzylthio)-1-(4-fluorophenyl)-1H-indazole-6-carboxylate)

T44-4

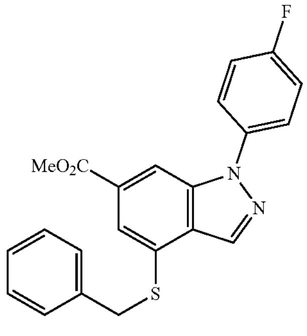

Intermediate 44-3 (750 mg, 2.15 mmol), tris(dibenzylideneacetone)dipalladium (187 mg, 0.21 mmol), intermediate 1-4 (benzylthiol) (800 mg, 6.44 mmol) and 4,5-bis-diphenylphosphino-9,9-dimethylxanthene (63 mg, 0.11 mmol) were dissolved in 1,4-dioxane (20 mL) under nitrogen atmosphere, N,N-diisopropylethylamine (1110 mg, 8.59 mmol) was added, and the reaction solution was stirred at 120° C. overnight, concentrated and purified by silica gel column chromatography (PE/EA=10/1) to give intermediate 44-4 (810 mg, 91.3% yield) in the form of a yellow solid. LC-MS: $[M+H]^+$=393.

Step (3) Preparation of Intermediate 44-5 (methyl-4-(chlorosulfonyl)-1-(4-fluorophenyl)-1H-indazole-6-carboxylate)

T44-5

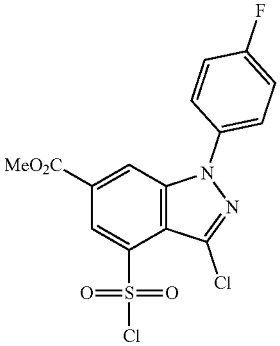

Intermediate 44-4 (810 mg, 2.06 mmol) was dissolved in acetonitrile (20 mL) and water (0.58 mL), 1,3-dichloro-5,5'-methylhydantoin (810 mg, 4.12 mmol) and acetic acid (0.89 mL) were added at 0° C., and the reaction solution was stirred at 0° C. for 1 h, concentrated at low temperature and purified by silica gel column chromatography (PE/EA=5/1) to give intermediate 44-5 (650 mg, 62.6% yield) in the form of a yellow solid. LC-MS: $[M+H]^+$=404.

Step (4) Preparation of Intermediate 44-6 (methyl-4-(N,N-bis(4-methoxybenzyl)sulfamoyl)-1-(4-fluorophenyl)-1H-indazole-6-carboxylate)

T44-6

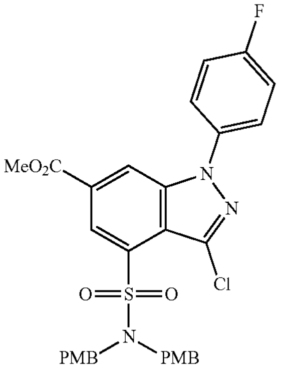

intermediate 44-5 (635 mg, 1.72 mmol) and triethylamine (523 mg, 5.16 mmol) were dissolved in dichloromethane (5 mL), bis-(4-methoxybenzyl)-amine (890 mg, 3.45 mmol) was added, and the reaction solution was stirred at room temperature overnight, concentrated under reduced pressure and purified by silica gel column chromatography (DCM/EA=5/1) to give a yellow solid (600 mg, 38.9% yield). LC-MS: $[M+H]^+$=625.

Step (5) Preparation of Intermediate 44-7 (4-(N,N-bis(4-methoxybenzyl)sulfamoyl)-1-(4-fluorophenyl)-1H-indazole-6-carboxylic acid)

T44-7

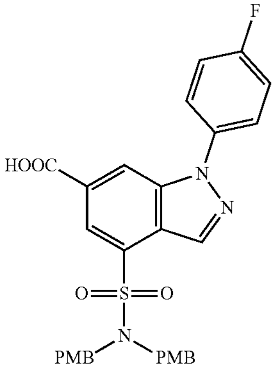

Intermediate 44-6 (600 mg, 1.02 mmol) and an aqueous lithium hydroxide solution (6 mL, 3 mol/L) were dissolved in tetrahydrofuran (3 mL) and stirred at room temperature overnight, pH was adjusted to 3 with diluted hydrochloric acid, and the reaction solution was diluted with ethyl acetate (30 mL), washed with saturated brine (15 mL), dried over anhydrous sodium sulfate, filtered, and concentrated to give a crude product (520 mg) in the form of a yellow solid. LC-MS: $[M-1]^-$=611.

Step (6) Preparation of Intermediate 44-8 (tert-butyl (4-(N,N-bis(4-methoxybenzyl)sulfamoyl)-1-(4-fluorophenyl)-1H-indazol-6-yl)carbamate)

T44-8

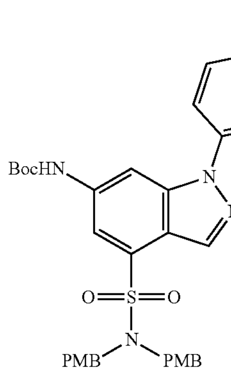

Intermediate 44-7 (500 mg, 0.82 mmol) and triethylamine (335 mg, 3.28 mmol) were dissolved in tert-butanol (3 mL), diphenylphosphine azide (320 mg, 1.16 mmol) was added, and the reaction solution was stirred at room temperature for 3 h and then heated to 85° C. and reacted for 12 h, concentrated, diluted with water (20 mL), and extracted with ethyl acetate (20 mL×3). The organic phases were combined, dried over anhydrous sodium sulfate, filtered, concentrated and purified by silica gel column chromatography (PE/EA=4/1) to give a yellow solid (140 mg, 19.8% yield). LC-MS: $[M+H]^+$=682.

Step (7) Preparation of Intermediate 44-9 (6-amino-1-(4-fluorophenyl)-N,N-bis(4-methoxybenzyl)-1H-indazole-4-sulfonamide)

T44-9

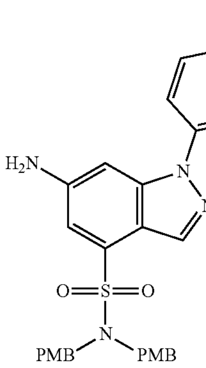

Intermediate 44-8 (140 mg, 0.19 mmol) was dissolved in dichloromethane (2 mL), a solution of hydrogen chloride in ethanol (1.5 mL, 4 N) was added, and the reaction solution was stirred at room temperature for 3 h, and concentrated to give a crude product (120 mg) in the form of a yellow solid. LC-MS: $[M+H]^+$=581.

Step (8) Preparation of Intermediate 44-11 (N-(4-(N,N-bis(4-methoxybenzyl)sulfamoyl)-1-(4-fluorophenyl)-1H-indazol-6-yl)-2-(2-chlorophenyl)acetamide)

T44-11

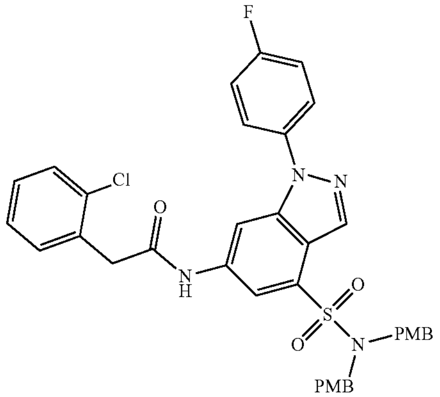

Intermediate 44-9 (120 mg, 0.21 mmol) and triethylamine (84 mg, 0.82 mmol) were dissolved in dichloromethane (3 mL), intermediate 44-10 (2-(2-chlorophenyl)acetyl chloride) (78 mg, 0.41 mmol) was added dropwise, the reaction solution was stirred at room temperature for 12 h, concentrated and purified by silica gel column chromatography (DCM/EA=4/1), and the residue was concentrated to give a yellow oil (140 mg, 82.3% yield). LC-MS: $[M+H]^+$=734.

Step (9) Preparation of Compound 44 (2-(2-chlorophenyl)-N-(1-(4-fluorophenyl)-4-sulfamoyl-1H-indazol-6-yl)acetamide)

T44

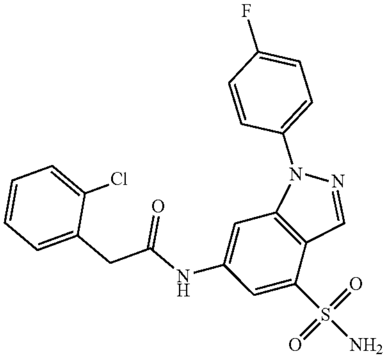

Intermediate 44-11 (140 mg, 0.19 mmol) was dissolved in dichloromethane (2 mL), trifluoroacetic acid (2 mL) was added, and the reaction solution was stirred at room temperature for 6 h, concentrated and purified by preparative chromatography, and then separated by a chiral column (SP-120-10-C18-BIO-C18 250×50 mm, 10 μm (pH 8-10), flow rate: 12.5 g/min, mobile phase B: $CO_2$-EtOH (DEA) (0.1% DEA), mobile phase A: ETOH (DEA), retention time: 10.97 min). The product was collected, concentrated and lyophilized to give a white solid (9.6 mg). LC-MS: $[M+H]^+$= 459.

$^1$H NMR (400 MHz, MeOD) δ 8.96 (s, 1H), 8.38 (s, 1H), 8.04 (dd, J=8.8, 4.6 Hz, 2H), 7.83 (s, 1H), 7.48-7.43 (m, 2H), 7.41-7.23 (m, 4H), 3.96 (s, 2H).

Example 45

Preparation of 2-(2-chlorophenyl)-N-(1-(4-chlorophenyl)-4-sulfamoyl-1H-indazol-6-yl)acetamide

45

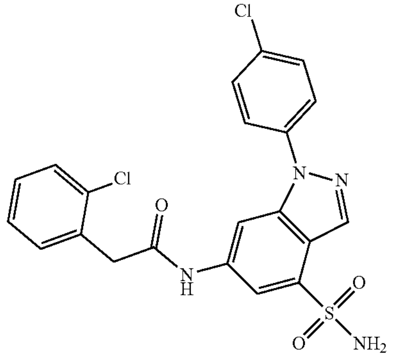

The compound was prepared using the preparation method described in Example 14. LC-MS: $[M+H]^+$=475.0.

Example 46

Preparation of 2-(2-chlorophenyl)-N-(1-(3-(dimethylamino)benzyl)-4-sulfamoyl-1H-indazol-6-yl)acetamide

46

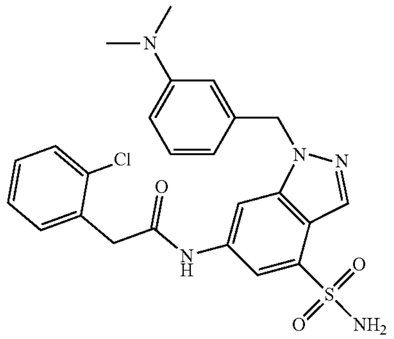

The compound was prepared using the preparation method described in Example 4. LC-MS: $[M+H]^+$=498.1.

Example 47

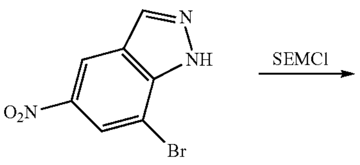

47-1

-continued

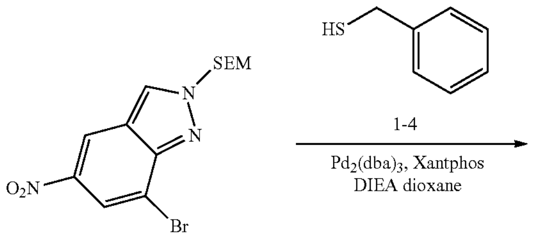

47-2

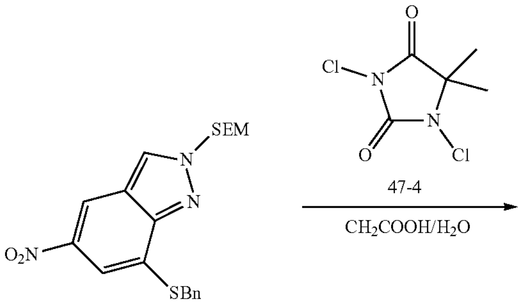

47-3

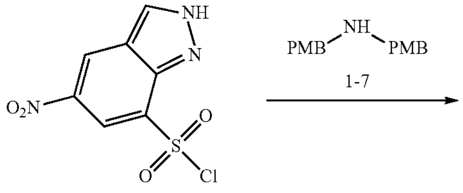

47-5

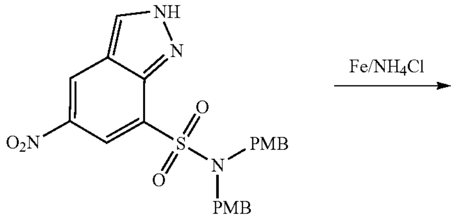

47-6

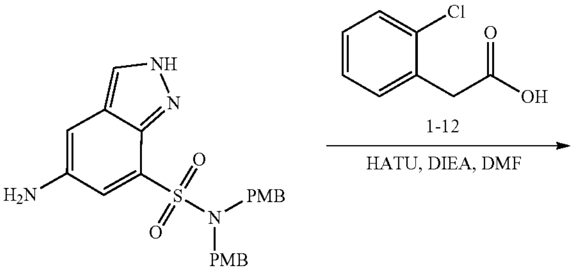

47-7

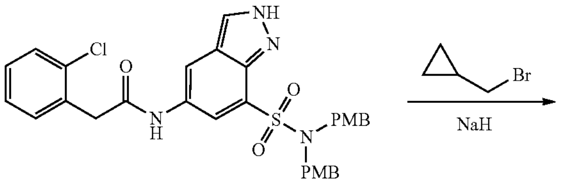

47-8

-continued

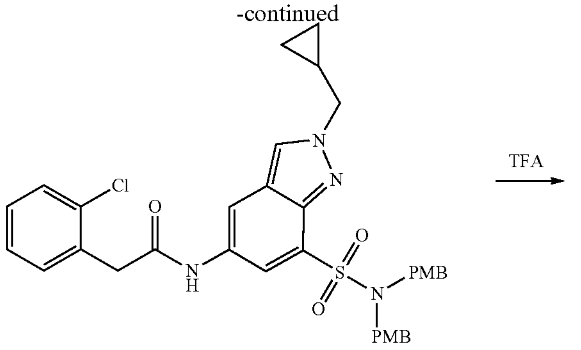

47-9

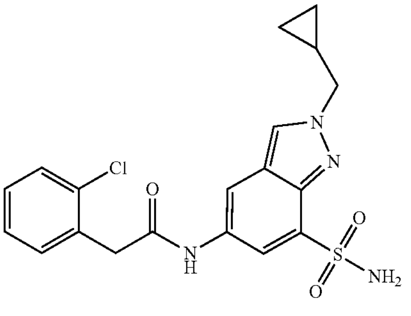

47

Step (1) Preparation of 7-bromo-5-nitro-2-((2-(trimethylsilyl)ethoxy)methyl)-2H-indazole 47-2

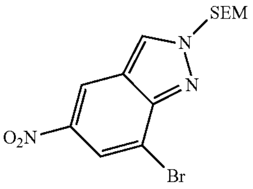

Intermediate 47-1 (8.0 g, 14 mmol) was dissolved in DMF (50 mL), NaH (1.7 g) was added in portions at 0° C., and the reaction solution was heated to room temperature and reacted for 0.5 h, then cooled to 0° C. again and slowly added with SEMCl (8.3 g) for 2 h. After the reaction was completed as detected by TLC, the reaction solution was added with water (200 mL) and EA (300 mL), and then washed three times with saturated brine, the organic phases were combined, dried over anhydrous sodium sulfate, and filtered, and the filtrate was concentrated to give a crude product which was subjected to silica gel column chromatography to give intermediate 47-2 (11.2 g) in the form of a yellow solid. LC-MS: $[M+H]^+$=372.3.

Step (2) Preparation of 7-(benzylthio)-5-nitro-2-((2-(trimethylsilyl)ethoxy)methyl)-2H-indazole 47-3

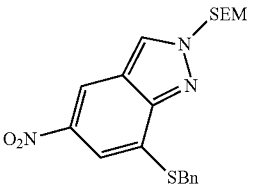

Intermediate 47-2 (11.0 g, 29.6 mmol) was dissolved in dioxane (100 mL), 1-4 (11.0 g, 88.6 mmol), $Pd_2(dba)_3$ (2.9 g, 8.9 mmol), Xantphos (1.8 g, 8.9 mmol) and DIEA (14.7 g, 118.2 mmol) were added, and the reaction solution was purged three times with $N_2$ and reacted at 85° C. overnight. After the reaction was completed as detected by TLC, the reaction solution was added with water (100 mL), extracted with EA (100 mL×3), and then washed three times with saturated brine. The organic phases were combined, dried over anhydrous sodium sulfate, and filtered, and the filtrate was concentrated to give a crude product which was subjected to silica gel column chromatography to give intermediate 47-3 (16.2 g) in the form of a yellow solid. LC-MS: $[M+H]^+$=416.1.

Step (3) Preparation of 5-nitro-2H-indazole-7-sulfonyl chloride 47-5

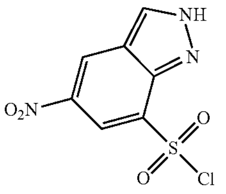

Intermediate 47-3 (6.0 g, 14 mmol) was dissolved in acetonitrile (50 mL), $CH_3COOH$ and $H_2O$ were added at room temperature, intermediate 47-4 (8.5 g, 43 mmol) was added at 0° C., and the reaction solution was reacted at room temperature for 24 h. After the reaction was completed as detected by TLC, the reaction solution was added with water (20 mL) and EA (100 mL), the aqueous phase was extracted with EA (100 mL×3), the organic phases were combined, dried over anhydrous sodium sulfate, and filtered, and the filtrate was concentrated to give a crude product which was subjected to silica gel column chromatography to give intermediate 47-5 (1.7 g) in the form of a yellow solid. LC-MS: $[M+H]^+$=261.9.

Step (4) Preparation of N,N-bis-(4-methoxybenzyl)-5-nitro-2H-indazole-7-sulfonamide 47-6

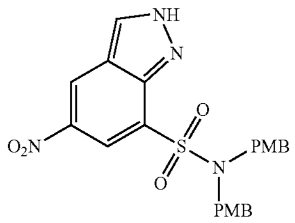

Intermediate 1-7 (2.0 g, 7.8 mmol) and $Et_3N$ (1.9 g, 19.5 mmol) were dissolved in DCM (20 mL), and the reaction solution was stirred at room temperature for 0.5 h, then cooled to 0° C., added with intermediate 47-5 (1.7 g, 6.5 mmol), and heated to room temperature and reacted for 2 h. After the reaction was completed as detected by TLC, the reaction solution was added with water (100 mL), the aqueous phase was extracted with DCM (100 mL×3), the organic phases were combined, dried over anhydrous sodium sulfate, and filtered, and the filtrate was concentrated to give a crude product which was subjected to silica gel column chromatography to give intermediate 47-6 (1.2 g) in the form of a yellow solid. LC-MS: $[M+H]^+$=483.1.

Step (5) Preparation of N,N-bis-(4-methoxybenzyl)-5-amino-2H-indazole-7-sulfonamide 47-7

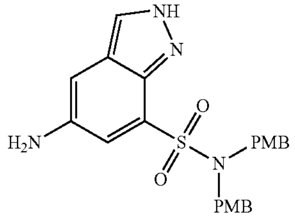

Intermediate 47-6 (1.2 g, 2.49 mmol) and $NH_4Cl$ (660.0 mg, 12.4 mmol) were dissolved in EtOH (20 mL) and $H_2O$ (2 mL), and the reaction solution was heated to 70° C., then added with Fe (0.7 g, 12.4 mmol), and reacted at 70° C. for 2 h. After the reaction was completed as detected by TLC, the reaction solution was filtered, the filtrate was extracted with EA (100 mL×3), the organic phases were combined, dried over anhydrous sodium sulfate, and filtered, and the filtrate was concentrated to give intermediate 47-7 (1.0 g) in the form of a light yellow solid. LC-MS: $[M+H]^+$=453.1.

Step (6) Preparation of N-(7-(N,N-bis-(4-methoxybenzyl)-2H-indazol-5-yl)-2-(2-chlorophenyl)acetamide 47-8

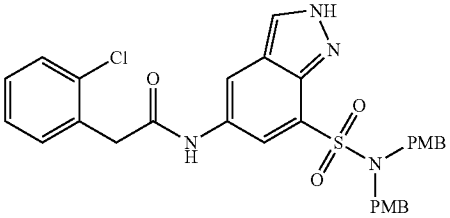

The intermediate 1-12 (1.0 g, 2.2 mmol), DIEA (850.0 mg, 6.6 mmol) and HATU (1.2 g, 3.3 mmol) were dissolved in DMF (10 mL), and the reaction solution was stirred at room temperature for 0.5 h, then cooled to 0° C., added with intermediate 47-7 (1.0 g, 2.21 mmol), and heated to room temperature and reacted overnight. After the reaction was completed as detected by TLC, the reaction solution was added with water (100 mL), the aqueous phase was extracted with EA (100 mL×3), the organic phases were combined, dried over anhydrous sodium sulfate, and filtered, and the filtrate was concentrated to give a crude product which was subjected to silica gel column chromatography to give intermediate 47-8 (0.8 g) in the form of a light yellow solid. LC-MS: $[M+H]^+$=605.1.

Step (7) Preparation of N-(7-(N,N-bis-(4-methoxybenzyl)aminosulfonyl)-2-(cyclopropylmethyl)-2H-indazol-5-yl)-2-(2-chlorophenyl)acetamide 47-9

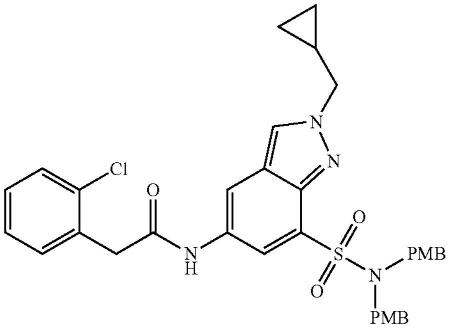

Intermediate 47-8 (150.0 mg, 240.0 μmol) was dissolved in DMF (0.5 mL), and the reaction solution was cooled to 0° C., slowly added with NaH (12.0 mg, 300.0 μmmol), stirred at 0° C. for 0.5 h, then added with cyclopropyl bromoethane (50.0 mg, 370.0 μmol), and heated to room temperature and reacted overnight. After the reaction was completed as detected by TLC, the reaction solution was added with water (50 mL), the aqueous phase was extracted with EA (100 mL×3), the organic phases were combined, dried over anhydrous sodium sulfate, and filtered, and the filtrate was concentrated to give a crude product which was subjected to silica gel column chromatography to give intermediate 47-9 (50.0 mg) in the form of a light yellow solid. LC-MS: $[M+H]^+$=659.2.

Step (8) Preparation of 2-(2-chlorophenyl)-N-(2-(cyclopropylmethyl)-7-sulfamoyl-2H-indazol-5-yl) acetamide

47

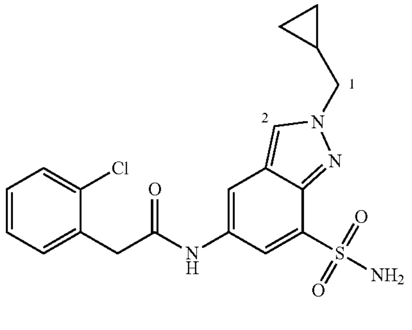

Intermediate 47-9 (50.0 mg, 76.0 μmol) was dissolved in DCM (0.5 mL), and the reaction solution was slowly added with TFA (0.5 mL), and heated to room temperature and reacted for 4 h. After the reaction was completed as detected by TLC and the reaction starting material was completely reacted as detected by LCMS, the reaction solution was directly separated by prep-HPLC using a $H_2O$/MeCN system and lyophilized to give compound 47 (20.0 mg, 99.8% purity) in the form of a white solid. LC-MS: $[M+H]^+$=419.1.

$^1$H NMR (400 MHz, DMSO) δ8.43 (s, 1H), 8.34 (t, J=3.4 Hz, 1H), 7.93 (d, J=2.0 Hz, 1H), 7.42 (ddd, J=6.4, 4.0, 2.0 Hz, 2H), 7.38-7.25 (m, 2H), 4.35 (d, J=7.4 Hz, 2H), 3.91 (s, 2H), 1.53-1.44 (m, 1H), 0.73-0.63 (m, 2H), 0.57-0.46 (m, 2H).

2D-HNMR (NOE) results showed that No. 1 hydrogen and No. 2 hydrogen in compound 47 are correlated.

Example 48

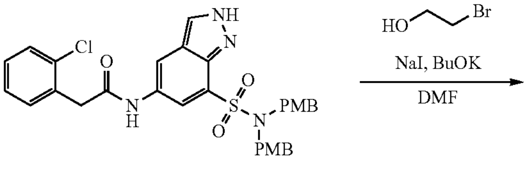

47-8

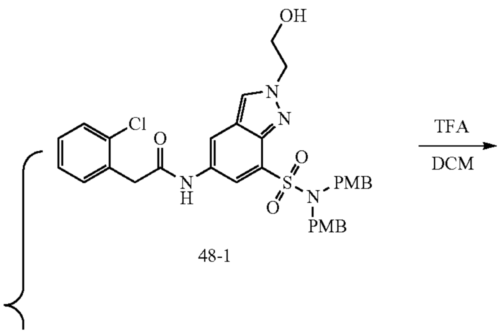

48-1

-continued

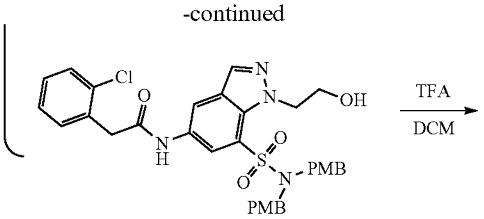

48-2

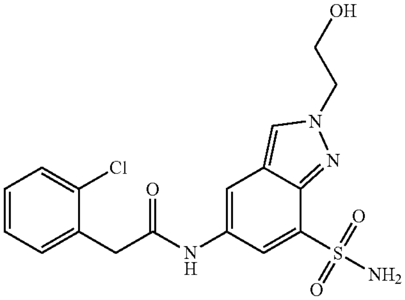

48-A

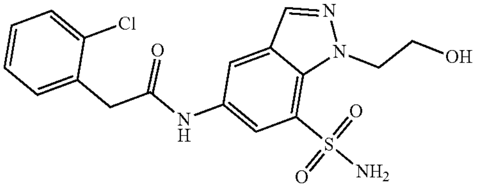

48-B

Step (1) Preparation of Intermediate 48-1 (N-(7-(N,N-bis-(4-methoxybenzyl)sulfamoyl)-2-(hydroxyethyl)-2H-indazol-5-yl)-2-(2-chlorophenyl)acetamide) and Intermediate 48-2 (N-(7-(N,N-bis(4-methoxybenzyl)sulfamoyl)-1-(2-hydroxyethyl)-1H-indazol-5-yl)-2-(2-chlorophenyl)acetamide)

48-1

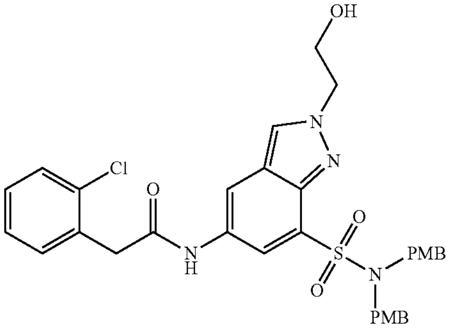

48-2

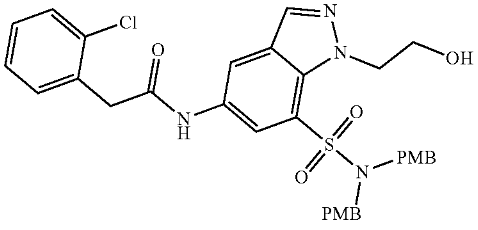

Intermediate 47-8 (150.0 mg, 250.0 μmol), 2-bromoethanol (62 mg, 500.0 μmol), NaI (37 mg, 250.0 μmol) and BuOK (42.0 mg, 370.0 μmol) were dissolved in DMF (1.5 mL), and the reaction solution was stirred at 120° C. for 24 h. After some reaction starting materials were not completely reacted as detected by TLC, the reaction solution was cooled to room temperature and added with water (50 mL), the aqueous phase was extracted with EA (100 mL×3), the organic phases were combined, dried over anhydrous sodium sulfate, and filtered, and the filtrate was concentrated to give a crude product which was subjected to silica gel column chromatography to give intermediate 48-1 (50.0 mg) in the form of a yellow solid and intermediate 48-2 (50.0 mg) in the form of a yellow solid. LC-MS: $[M+H]^+$=648.2.

Step (2) Preparation of Compound 48-A (2-(2-chlorophenyl)-N-(2-(2-hydroxyethyl)-7-sulfamoyl-2H-indazol-5-yl)acetamide) and Compound 48-A (2-(2-chlorophenyl)-N-(1-(2-hydroxyethyl)-7-sulfamoyl-1H-indazol-5-yl)acetamide)

48-A

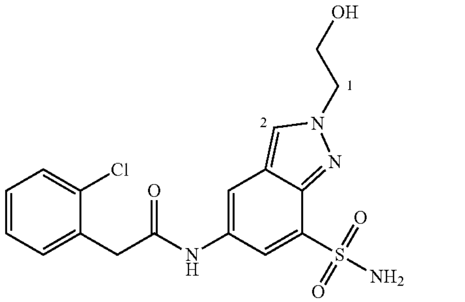

48-B

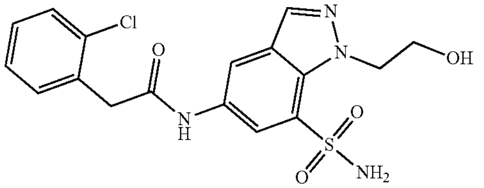

Intermediate 48-1 (40.0 mg, 74.0 μmol) was dissolved in DCM (0.5 mL), and the reaction solution was slowly added with TFA (0.5 mL), heated to room temperature and reacted overnight. After the reaction was completed as detected by TLC and the reaction starting material was completely reacted as detected by LCMS, the reaction solution was directly separated by prep-HPLC using a $H_2O$/MeCN system and lyophilized to give compound 48-A (4.8 mg, 98.7% purity) in the form of a white solid. LC-MS: $[M+H]^+$=409.1.

$^1$H NMR (400 MHz, DMSO): δ 8.37 (s, 1H), 8.33 (d, J=2.0 Hz, 1H), 7.94 (d, J=2.0 Hz, 1H), 7.41 (s, 2H), 7.29 (dd, J=6.4, 2.8 Hz, 2H), 4.59-4.56 (m, 2H), 4.07-4.03 (m, 2H), 3.91 (s, 2H).

2D-HNMR (NOE) results showed that No. 1 hydrogen and No. 2 hydrogen in compound 48-A are correlated.

Intermediate 48-2 (40.0 mg, 74.0 μmol) was dissolved in DCM (0.5 mL), and the reaction solution was slowly added with TFA (0.5 mL), heated to room temperature and reacted overnight. After the reaction was completed as detected by TLC and the reaction starting material was completely reacted as detected by LCMS, the reaction solution was directly separated by prep-HPLC using a $H_2O$/MeCN system and lyophilized to give compound 48-B (4.6 mg, 98.7% purity) in the form of a white solid. LC-MS: $[M+H]^+$=409.1.

Example 49

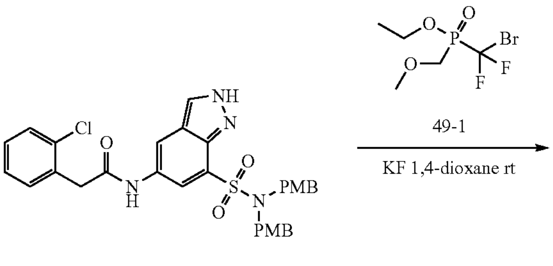

47-8

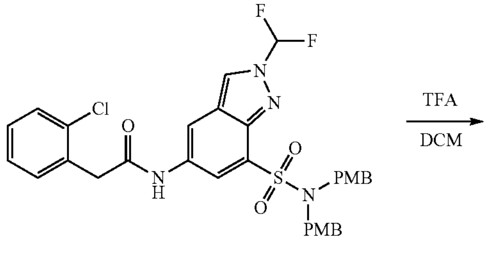

49-2

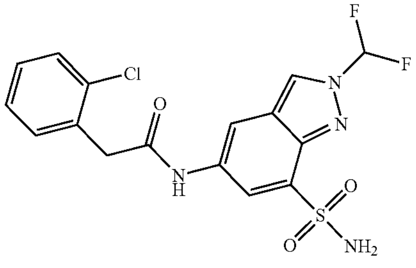

49

Step (1) Preparation of N-(7-(N,N-bis(4-methoxybenzyl)sulfamoyl)-2-(difluoromethyl)-2H-indazol-5-yl)-2-(2-chlorophenyl)acetamide

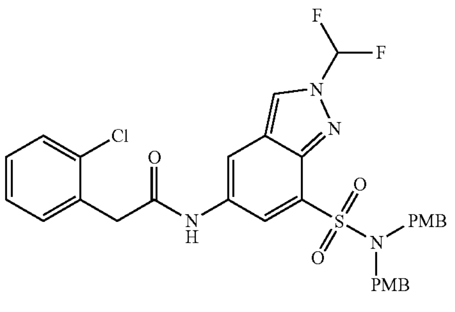

49-2

Intermediate 47-8 (30.0 mg, 50.0 μmol), KF (12.0 mg, 200.0 μmol) and intermediate 49-1 (40.0 mg, 0.15 mmol) were dissolved in dioxane, and the reaction solution was stirred at room temperature for 5 h. After the reaction starting material was completely reacted as indicated by thin-layer chromatography, the reaction solution was added with water (5 mL) and extracted three times with EA, the EA phases were combined, washed with saturated brine, dried over sodium sulfate, and filtered, and the filtrate was concentrated to give the product (12.0 mg). LC-MS: $[M+H]^+$= 655.1.

Step (2) Preparation of 2-(2-chlorophenyl)-N-(2-(difluoromethyl)-7-sulfamoyl-2H-indazol-5-yl)acetamide

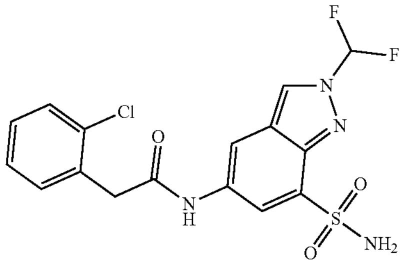

49 intermediate 49-2 (12.0 mg, 18.0 μmol) was dissolved in DCM (0.2 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 49. LC-MS: $[M+H]^+$=415.0.

$^1$H NMR (400 MHz, DMSO-d6): δ 10.71 (s, 1H), 8.38 (s, 1H), 8.24 (s, 1H), 7.69 (s, 1H), 7.58 (s, 2H), 7.48-7.42 (m, 2H), 7.35-7.30 (m, 2H), 3.91 (s, 2H), 3.67-3.61 (m, 1H), 1.28-1.17 (m, 2H), 0.52-0.44 (m, 2H), 0.40-0.33 (m, 2H).

Example 50

Preparation of 2-(2-chlorophenyl)-N-(1-(difluoromethyl)-7-sulfamoyl-1H-indazol-5-yl)acetamide

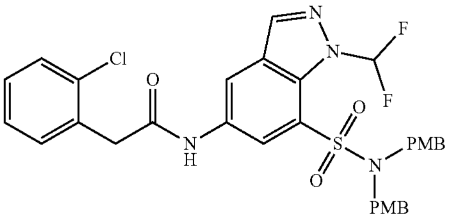

50

The compound was prepared using the preparation method described in Example 49. LC-MS: $[M+H]^+$=415.0.

Example 51

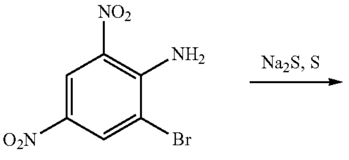

51-1

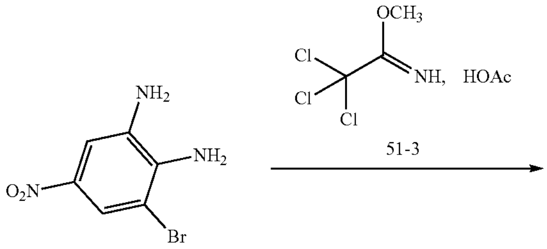

51-3

51-2

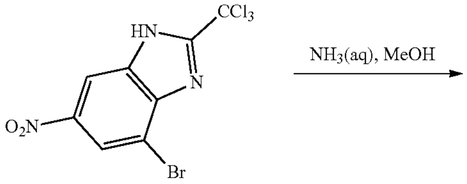

51-4

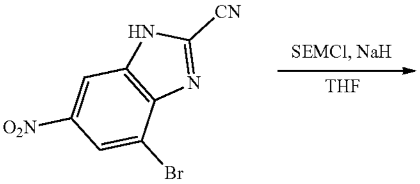

51-5

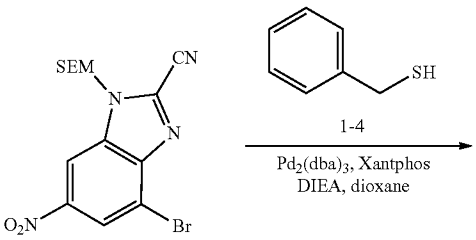

51-6

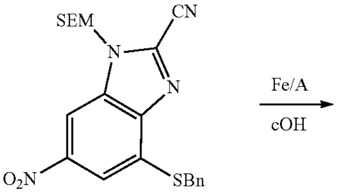

51-7

-continued

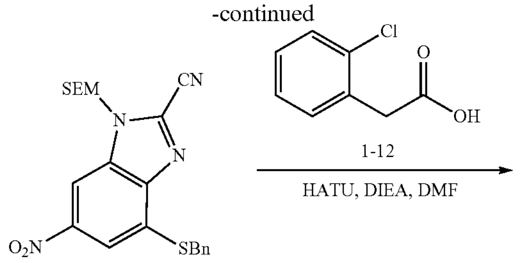

51-8

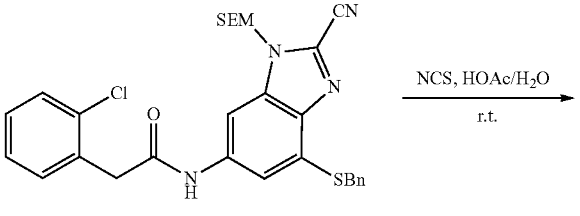

51-9

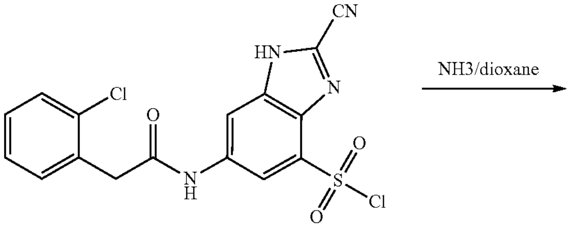

51-10

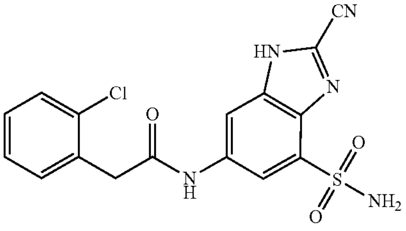

51

Step (1) Preparation of 3-bromo-5-nitro-1,2-phenylenediamine

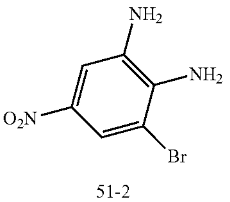 [SMILES: Nc1cc([N+](=O)[O-])cc(Br)c1N]

51-2

$Na_2S\cdot9H_2O$ (25.4 g, 105.9 mmol) and powdered sulfur (3.4 g, 105.9 mmol) were dissolved in EtOH (30 mL) and $H_2O$ (60 mL), and the reaction solution was stirred at 80° C. for 1 h under $N_2$ atmosphere. The above reaction solution was cooled to room temperature and added to a mixed solution of intermediate 51-1 (18.5 g, 70.6 mmol) and $NH_4Cl$ (5.5 g, 105.9 mmol) in EtOH (90 mL)/$H_2O$ (60 mL). The reaction system was stirred at 80° C. for 0.5 h under $N_2$ atmosphere, and finally added with an aqueous NaOH solution (74 mL, 2 M) and stirred at 80° C. for 0 h. After the reaction starting material was completely reacted as detected by TLC, product spots having slightly high polarity were formed. The reaction solution was neutralized with HCl (2 M) at 0° C. to pH=7, and then poured into water, and the solid was precipitated and filtered to give intermediate 51-2 (18.0 g) in the form of a dark red solid. LC-MS: $[M+H]^+$=232.0/234.0. $^1H$ NMR (400 MHz, $CDCl_3$) δ 8.00 (d, J=2.4 Hz, 1H), 7.58 (d, J=2.4 Hz, 1H), 4.50 (br.s, 2H), 3.57 (br.s, 2H).

Step (2) Preparation of 4-bromo-6-nitro-2-trifluoromethyl-1-hydro-benzimidazole

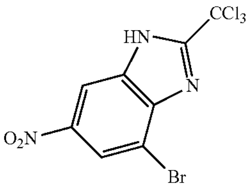

51-4

Intermediate 51-2 (11.0 g, 47.4 mmol) was dissolved in HOAc (100 mL), and the reaction solution was reacted at room temperature overnight. After a small amount of reaction starting material was reserved as detected by TLC, product spots having slight low polarity were formed. After the reaction was completed, the reaction solution was also poured into water, the yellow solid was precipitated and filtered to give a filter cake, and the filtrate was concentrated by rotary evaporation and purified by column chromatography to give intermediate 51-4 (10.0 g) in the form of a yellow solid. LC-MS: $[M+H]^+$=358.0/360.0.

Step (3) Preparation of 4-bromo-6-nitro-1-hydro-benzimidazole-2-carbonitrile

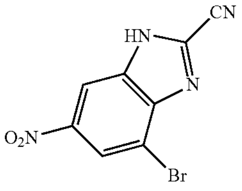

51-5

Intermediate 51-4 (8.0 g, 22.3 mmol) was dissolved in THF (30 mL), the reaction solution was added dropwise to $NH_3$/MeOH (7 M, 160 mL) at room temperature, after the dropwise addition was completed, the reaction solution was stirred at room temperature for 2 h. After the reaction was completed, the reaction solution was concentrated by rotary evaporation at room temperature to give a crude product which was purified by silica gel column chromatography to give intermediate 51-5 (4.0 g) in the form of a yellow solid. LC-MS: $[M+H]^+$=267.0/269.0.

Step (4) Preparation of 4-bromo-6-nitro-1-((2-(trimethylsilyl)ethoxy)methyl)-benzimidazole-2-carbonitrile

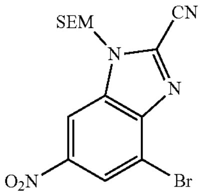

51-6

Intermediate 51-5 (4.0 g, 15.0 mmol) was dissolved in THF (80 mL), NaH (60%, 900.0 mg, 22.5 mmol) was added in portions at 0° C., and then stirred for 0.5 h. The reaction solution was added dropwise with SEMCl (3.7 g, 22.5 mmol) at a temperature controlled to be lower than 10° C., and after the dropwise addition was completed, the reaction solution was slowly heated to room temperature, and stirred for 2 h under $N_2$ atmosphere. After the reaction was completed, the reaction solution was diluted with EtOAc and then slowly poured into an excess of saturated aqueous $NH_4Cl$ solution at 0° C. with stirring. After the reaction was quenched, the reaction solution was extracted with EtOAc, the organic phase was dried over anhydrous $Na_2SO_4$ and filtered, and the filtrate was concentrated by rotary evaporation to give a crude product which was purified by silica gel column chromatography to give intermediate 51-6 (3.2 g) in the form of a light yellow solid. LC-MS: $[M+H]^+$=397.0/399.0.

$^1$H NMR (400 MHz, $CDCl_3$): δ 8.73 (d, J=2.0 Hz, 1H), 8.58 (d, J=2.0 Hz, 1H), 8.54 (d, J=2.0 Hz, 1H), 8.53 (d, J=2.0 Hz, 1H), 6.06 (s, 2H), 5.79 (s, 2H), 3.71-3.58 (m, 4H), 1.00-0.91 (m, 4H), −0.02-−0.05 (m, 18H).

Step (5) Preparation of 4-benzylthio-6-nitro-1-((2-(trimethylsilyl)ethoxy)methyl)-benzimidazole-2-carbonitrile

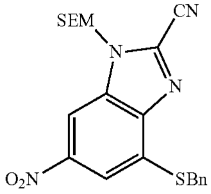

51-7

Intermediate 51-6 (3.2 g, 12 mmol) was dissolved in dioxane (60 mL), Pd(dppf)$Cl_2$ (550.0 mg, 0.6 mmol), Xantphos (694.0 mg, 1.2 mmol) and DIEA (4.6 g, 36 mmol) were added sequentially, and benzylmercaptan (2.2 g, 18 mmol) was finally added. The reaction solution was stirred at 80° C. for 3 h under $N_2$ atmosphere. After the reaction was completed, the reaction solution was cooled to room temperature and poured into water, the resulting solution was extracted with EtOAc, the organic phase was dried over anhydrous $Na_2SO_4$ and filtered, and the filtrate was concentrated by rotary evaporation to give a crude product which was purified by column chromatography to give intermediate 51-7 (2.0 g) in the form of a yellow oil. LC-MS: $[M+H]^+$=441.0.

Step (6) Preparation of 4-benzylthio-6-amino-1-((2-(trimethylsilyl)ethoxy)methyl)-benzimidazole-2-carbonitrile

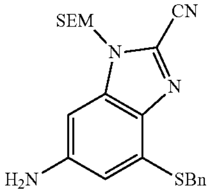

51-8

Intermediate 51-7 (2.0 g, 4.5 mmol) was dissolved in AcOH (40 mL), reduced Fe powder (2.5 g, 45 mmol) was added, and then the reaction solution was stirred at 45° C. for 2 h under $N_2$ atmosphere. After the reaction was completed, the reaction solution was cooled to room temperature, the white solid was precipitated and filtered, the filter residue was removed, the filtrate was slowly poured into an excess of saturated aqueous $NaHCO_3$ solution at 0° C., the resulting solution was extracted with EtOAc, the organic phase was dried over anhydrous $Na_2SO_4$ and filtered, and the filtrate was concentrated by rotary evaporation to give a crude product which was purified by silica gel column chromatography to give intermediate 51-8 (1.5 g) in the form of a yellow oil. LC-MS: $[M+H]^+$=411.0.

Step (7) Preparation of N-(4-(benzylthio)-2-cyano-1-((2-(trimethylsilyl)ethoxy)methyl)-benzimidazole-6-(2-chloro-phenylacetamide)

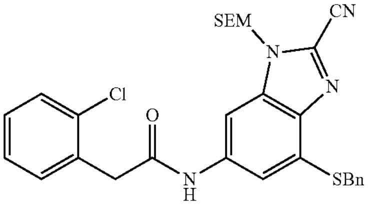

51-9

Intermediate 51-8 (1.3 g, 3.16 mmol) and o-chlorophenylacetic acid were dissolved in DMF (20 mL), HATU (1.8 g, 4.74 mmol) and DIEA (1.2 g, 9.48 mmol) were added, and the reaction solution was stirred at room temperature for 2 h. After the reaction was completed, the reaction solution was poured into water, the resulting solution was extracted with EtOAc, the organic phase was dried over $Na_2SO_4$ and filtered, and the filtrate was concentrated by rotary evaporation to give a crude product which was purified by silica gel column chromatography to give intermediate 51-9 (1.5 g) in the form of a yellow oil. LC-MS: $[M+H]^+$=563.0/565.0.

Step (8) Preparation of 6-(2-chloro-phenylacetamide)-2-cyano-benzimidazole-4-sulfonyl chloride

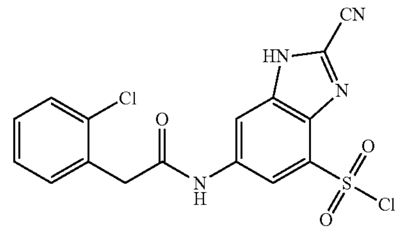

51-10

Intermediate 51-9 (1.5 g, 2.7 mmol) was added to a mixed solution of HOAc (20 mL) and $H_2O$ (5 mL), NCS was finally added, and the reaction solution was stirred at room temperature for 16 h. After the reaction was completed, the reaction solution was poured into an excess of a mixed solution of saturated aqueous $NaHCO_3$ and EtOAc at 0° C., followed by layer separation, the organic phase was dried over anhydrous $Na_2SO_4$ and filtered, and the filtrate was concentrated by rotary evaporation to give intermediate 51-10 (1.3 g, crude) in the form of a yellow oil. LC-MS: $[M+H]^+$=409.0.

Step (9) Preparation of 6-(2-chlorophenylacetamide)-2-nitrile-4-sulfonamide benzimidazole

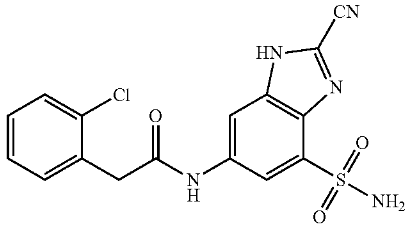

51

Intermediate 51-10 was dissolved in THF (2 mL), then $NH_3$/dioxane (0.4 M, 5 mL) was added, and the reaction solution was stirred at room temperature for 2 h. After the reaction was completed, the reaction solution was concentrated by rotary evaporation to give a crude product which was purified by prep-HPLC to give compound 51 (30.0 mg) in the form of a white solid. LC-MS: $[M+H]^+$=390/392.

$^1H$ NMR (400 MHz, dmso) δ 10.75 (br.s, 1H), 8.40 (s, 1H), 8.12 (br.s, 1H), 7.91 (s, 1H), 7.66 (br.s, 1H), 7.55-7.40 (m, 3H), 7.38-7.25 (m, 2H), 3.90 (s, 2H).

Example 52

Preparation of 2-(2-chlorophenyl)-N-(2-cyclopropyl-7-sulfamoyl-1H-benzo[d]imidazol-5-yl)acetamide

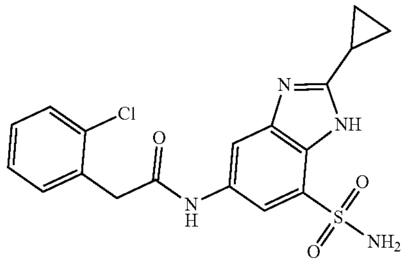

52

The compound was prepared using the preparation method described in Example 51. LC-MS: $[M+H]^+$=405.1.

Example 53

Preparation of 2-(2-chlorophenyl)-N-(2-phenyl-7-sulfamoyl-1H-benzo[d]imidazol-5-yl)acetamide

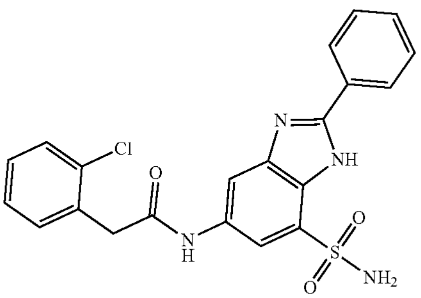

53

The compound was prepared using the preparation method described in Example 51. LC-MS: $[M+H]^+$=441.1.

Example 53-1

Preparation of 2-(2-chlorophenyl)-N-(2-phenyl-7-sulfamoyl-1H-benzo[d]imidazol-5-yl)acetamide

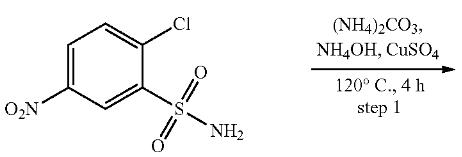

53-1

-continued

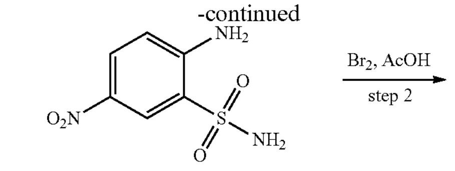

53-2

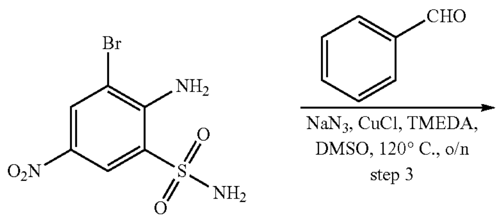

53-3

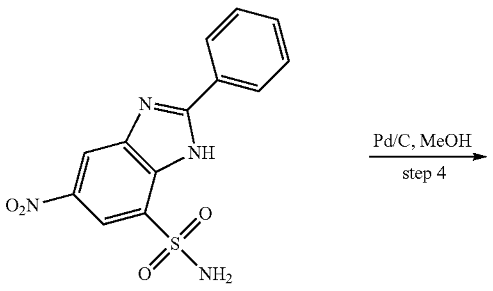

53-4

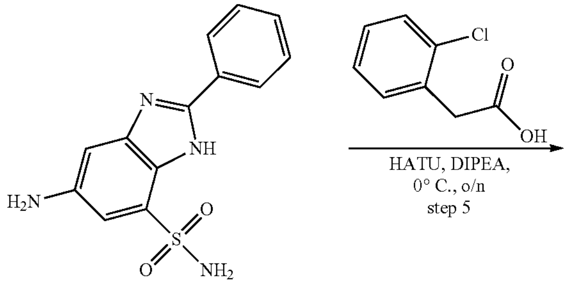

53-5

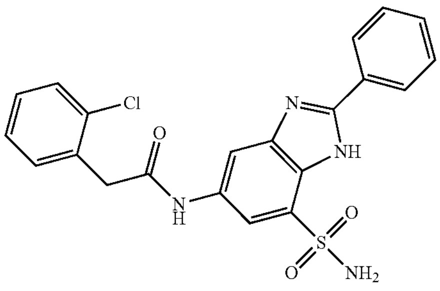

53

Step (1) Preparation of Intermediate 53-2 (2-amino-5-nitrobenzenesulfonamide)

53-2

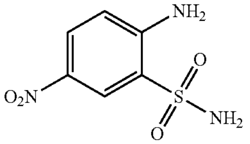

Intermediate 53-1 (2-chloro-5-nitrobenzenesulfonamide) (3.0 g, 12.68 mmol) was dissolved in strong ammonia (15 mL) in a closed container, ammonium carbonate (3.0 g, 31.23 mmol) and copper sulfate pentahydrate (0.6 g, 3.74 mmol) were added, and the reaction solution was stirred at 120° C. for 4 h and filtered, the filter cake was collected, and intermediate 53-2 (4.0 g, 45.8% yield, crude) was given in the form of a yellow solid. LC-MS $[M+H]^+$: 217.8.

Step (2) Preparation of Intermediate 53-3 (2-amino-3-bromo-5-nitrobenzenesulfonamide)

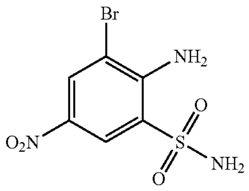

53-3

Under nitrogen atmosphere, intermediate 53-2 (800 mg, 3.68 mmol) was dissolved in glacial acetic acid (8 mL), the reaction system was added with the prepared bromine-acetic acid solution (156 mg/mL, 4 mL), heated to 80° C. and reacted for 2 h, then cooled to room temperature after the reaction was completed, added with water (10 mL) to quench the reaction, and filtered, the filter cake was collected and washed with water, and the resulting crude product was purified by silica gel column chromatography (dichloromethane:ethyl acetate=1:1) to give intermediate 53-3 (525 mg, 45.7% yield) in the form of a light yellow solid. MS $[M+H]^+$=295.6.

Step (3) Preparation of Intermediate 53-4 (5-nitro-2-phenyl-1H-benzo[d]imidazole-7-sulfonamide)

53-4

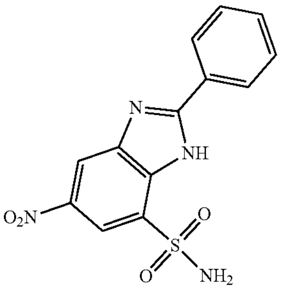

Intermediate 53-3 (500 mg, 1.70 mmol) was dissolved in dimethyl sulfoxide (10 mL), benzaldehyde (200 mg, 2.0 mmol), cuprous chloride (10 mg, 0.09 mmol), sodium azide (220 mg, 3.4 mmol) and tetramethylethylenediamine (0.5 mL) were added, and the reaction solution was stirred at 120° C. overnight. After the reaction was completed, the reaction solution was cooled to room temperature and added with water (20 mL) to quench the reaction, and extracted with ethyl acetate (15 mL×3). The organic phases were combined, washed with saturated brine (30 mL), dried over anhydrous sodium sulfate, filtered and concentrated, and the crude product was purified by silica gel column chromatography (4 g, dichloromethane:methanol=10:1) to give intermediate 53-4 (300 mg, 44.7% yield) in the form of a brown oil. MS $[M+H]^+$=318.7.

Step (4) Preparation of Intermediate 53-5 (5-amino-2-phenyl-1H-benzo[d]imidazole-7-sulfonamide)

53-5

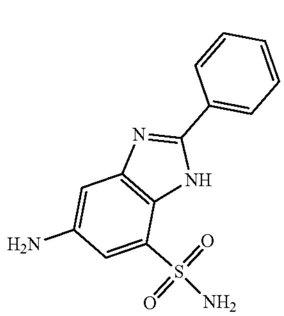

Intermediate 53-4 (280 mg, 0.88 mmol) was dissolved in methanol (10 mL), palladium on carbon catalyst (10%, 60 mg) was added, the reaction solution was purged with hydrogen and then stirred at room temperature for 5 h, and after the reaction was completed, filtration was carried out and the filtrate was concentrated by rotary evaporation to give intermediate 53-5 (170 mg, 53.6% yield, crude) in the form of a brown oil. MS $[M+H]^+$=288.7.

Step (5) Preparation of 2-(2-chlorophenyl)-N-(2-phenyl-7-sulfamoyl-1H-benzo[d]imidazol-5-yl)acetamide

53

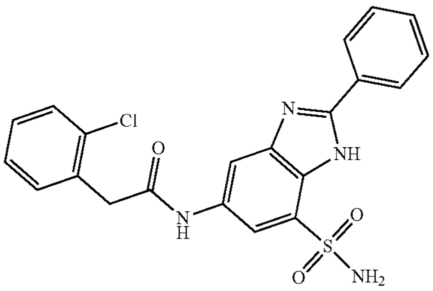

o-chlorophenylacetic acid (200 mg, 1.18 mmol) was dissolved in N,N-dimethylformamide (5 mL), and the reaction system was added with HATU (672 mg, 1.77 mmol), stirred at room temperature for 20 min, then added with intermediate 53-5 (170 mg, 0.59 mmol) and diisopropylethylamine (456 mg, 3.54 mmol), and stirred at room temperature overnight. After the reaction was completed, the reaction system was cooled to room temperature and added with water (20 mL) to quench the reaction, and extracted with ethyl acetate (15 mL×3). The organic phases were combined, washed with saturated brine (20 mL), dried over anhydrous sodium sulfate, filtered and concentrated to give a crude product which was purified by silica gel column chromatography (dichloromethane:methanol=10:1) and then purified by preparative reverse phase chromatography (column: -Gemini-C18 150×21.2 mm, 5 μm, mobile phase: ACN-$H_2O$ (0.1% FA), gradient: 40-50) to give compound 53 (211 mg, 4.0% yield) in the form of a white solid. MS $[M+H]^+$=440.6.

$^1H$ NMR (300 MHz, DMSO, 80° C.) δ 10.13 (s, 1H), 8.22-8.15 (m, 3H), 7.82 (s, 1H), 7.58-7.48 (m, 3H), 7.48-7.38 (m, 2H), 7.33-7.23 (m, 2H), 3.88 (s, 2H).

Example 54

Preparation of 2-(2-chlorophenyl)-N-(2-(4-chlorophenyl)-7-sulfamoyl-1H-benzo[d]imidazol-5-yl) acetamide

54

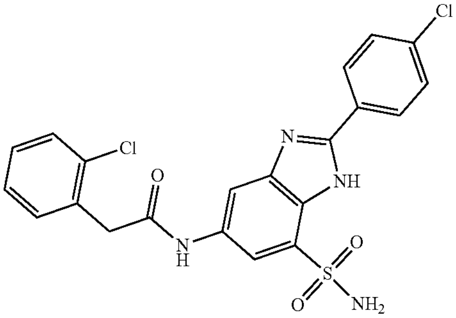

The compound was prepared using the preparation method described in Example 51. LC-MS: $[M+H]^+$=475.0.

Example 55

Preparation of 2-(2-chlorophenyl)-N-(1-(4-chlorophenyl)-4-sulfamoyl-1H-benzo[d]imidazol-6-yl) acetamide

55

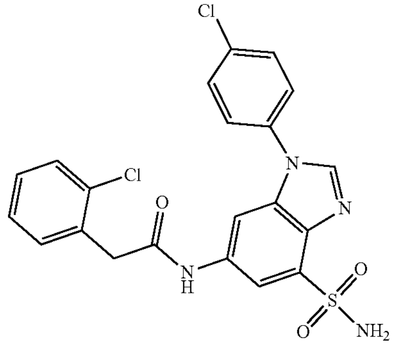

The compound was prepared using the preparation method described in Example 51. LC-MS: $[M+H]^+$=475.0.

Example 56

Preparation of 2-(2-chlorophenyl)-N-(4-sulfamoyl-1H-indol-6-yl)acetamide

56

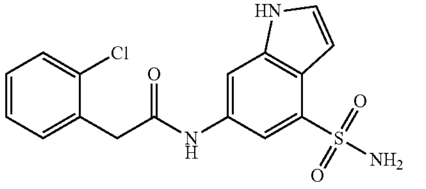

The compound was prepared using the preparation method described in Example 1. LC-MS: $[M+H]^+$=364.0.

Example X1: Preparation of Intermediate XX

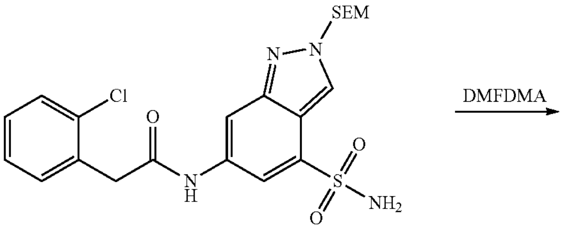

35-7

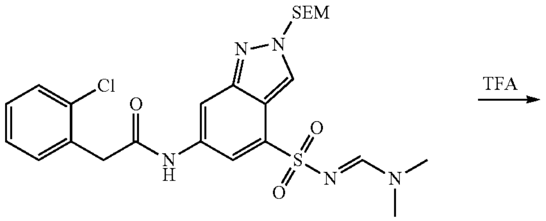

intermediate 19

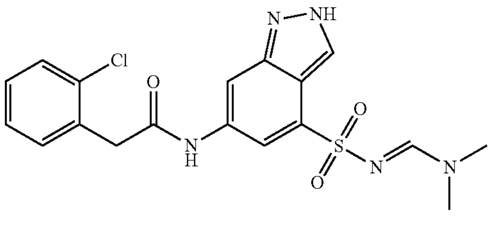

intermediate XX

Step (7) Preparation of Intermediate XX ((E)-2-(2-chlorophenyl)-N-(4-(N-((dimethylamino)methylene) sulfonamide)-2-((2-(trimethylsilyl)ethoxy)methyl)-2H-indazol-6-yl)acetamide)

Intermediate 35-7 (3.8 g, 7.67 mmol) was dissolved in DMF (55 mL), DMF-DMA (1.5 g, 12.2 mmol) was added dropwise, and the reaction solution was stirred at 60° C. for 1.5 h. After the reaction was completed as detected by TLC, the reaction solution was cooled and added with water (200 mL) and extracted twice with ethyl acetate, the organic phase was dried and concentrated to give an oil (6.1 g, crude) which was purified by column chromatography to give intermediate XX (3.8 g) in the form of a yellow oil. LC-MS: $[M]^+$=550.2.

Step (8) Preparation of Intermediate XX

Intermediate XX (3.8 g, 8.18 mmol) was dissolved in DCM (30 mL), TFA (30 mL) was added in an ice bath, and the reaction solution was stirred at room temperature for 1 h. After the reaction was completed as detected by TLC, the reaction solution was concentrated to give a crude product, water was added, then pH was adjusted to about 8 with saturated sodium bicarbonate, the reaction solution was extracted twice with ethyl acetate and concentrated, and the solid was precipitated, filtered and dried to give a product (1.5 g, 97% purity) in the form of a light red solid. Batch No.: NB190070-17-P1, LC-MS: $[M]^+$=420. The mother liquor was concentrated and then purified by column chromatography to give a product (1.0 g, 91% purity, 86.2% yield) in the form of a white solid. Batch No.: NB190070-17-P2, LC-MS: $[M]^+$=420.

Example 58

Compound No. 58

2-(2-chlorophenyl)-N-(1-isobutyryl-4-sulfamoyl-1H-indazol-6-yl)acetamide

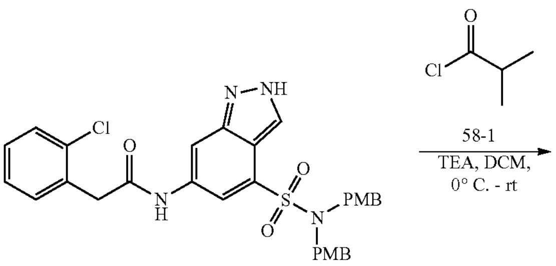

3-1

-continued

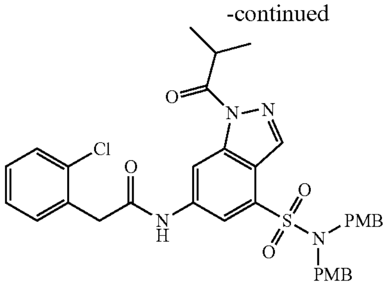

58-2

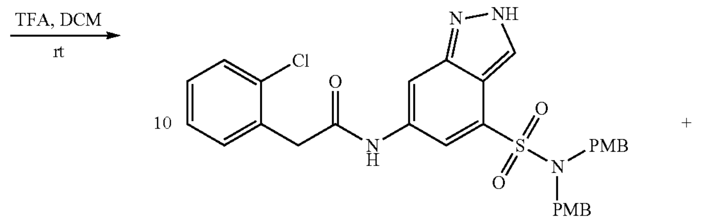

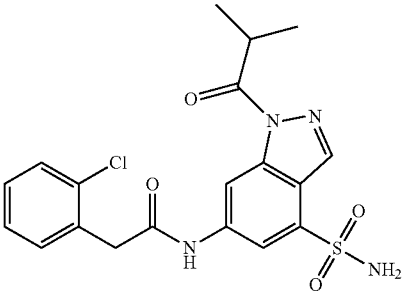

58

Step (1) Intermediate 58-2: preparation of N-(4-(N,N-bis(4-methoxybenzyl)sulfamoyl)-1-isobutyryl-1H-indazol-6-yl)-2-(2-chlorophenyl)acetamide Intermediate 3-1 (420.0 mg, 694.09 μmol) was dissolved in DCM (15 mL), TEA (140.5 mg, 1.39 mmol) was added, the system was cooled to 0° C., added with intermediate 58-1 (isobutyryl chloride) (110.9 mg, 1.04 mmol), and heated to room temperature and stirred for 0.5 h. After the reaction starting material was completely reacted as detected by TLC (EA:PE=1:1). The reaction solution was added with 50 mL of water and 50 mL of dichloromethane for dilution, followed by liquid separation, the organic phase was collected, and the solvent was concentrated by rotary evaporation to give intermediate 58-2 (220.0 mg) in the form of a yellow oil. LC-MS: $[M+H]^+$=675.05.

Step (2) Preparation of 2-(2-chlorophenyl)-N-(1-isobutyryl-4-sulfamoyl-1H-indazol-6-yl)acetamide Intermediate 58-2 (220.0 mg, 325.83 μmol) was dissolved in DCM (9 mL), TFA (3 mL) was added, and the reaction solution was stirred at room temperature overnight. After the reaction starting material was completely reacted as detected by TLC (EA:PE=1.1), the reaction was stopped. The solvent was concentrated by rotary evaporation to give a crude product which was separated by prep-HPLC using a $H_2O$/ACN system and lyophilized to give compound 58 (35.0 mg, 98.912% purity) in the form of a white solid. LC-MS: $[M+H]^+$=435.00.

$^1$H NMR (400 MHz, DMSO-$d_6$) δ (ppm): 10.90 (s, 1H), 9.02 (d, J=0.8 Hz, 1H), 8.59 (d, J=0.7 Hz, 1H), 8.13 (d, J=1.7 Hz, 1H), 7.76 (s, 2H), 7.50-7.42 (m, 2H), 7.37-7.29 (m, 2H), 3.92 (s, 2H), 3.87 (q, J=6.9 Hz, 1H), 1.26 (s, 3H), 1.25 (s, 3H).

Example 59

Compound 59

3-1

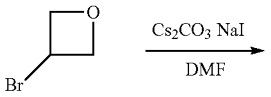

59-1

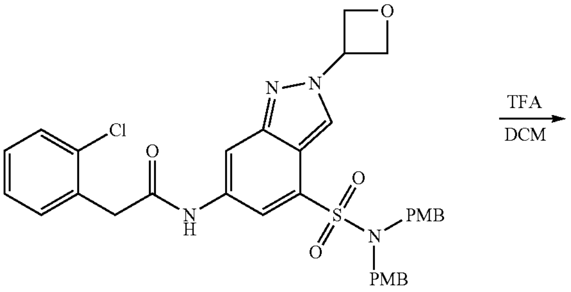

59-2

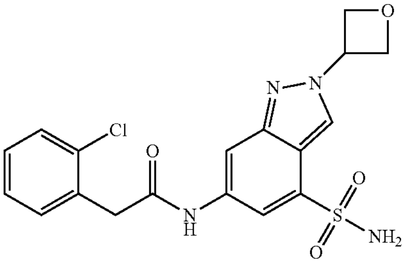

59

Step (1) Preparation of Intermediate 59-2 ((N-(4-(N,N-bis(4-methoxybenzyl)sulfamoyl)-2-(oxetan-3-yl)-2H-indazol-6-yl)-2-(2-chlorophenyl)acetamide))

Intermediate 3-1 (300 mg, 0.50 mmol), intermediate 59-1 (3-bromooxetane) (81 mg, 0.60 mmol), $Cs_2CO_3$ (492 mg, 1.5 mmol) and NaI (75 mg, 0.5 mmol) were weighed accurately and dissolved in DMF, and the reaction solution was stirred at room temperature overnight. After the reaction starting material was completely reacted as indicated by thin-layer chromatography, post-treatment was carried out, that is, the reaction solution was added with water and EA and fully stirred, then the EA phase was separated, the aqueous phase was extracted twice with EA, the EA phases were combined, dried, concentrated by rotary evaporation and purified by thin layer chromatography to give the product. The reaction was completed successfully and 220 mg of a yellow oily liquid was given. LC-MS $[M+H]^+$=661.

Step (2) Preparation of Compound 59 (2-(2-chlorophenyl)-N-(2-(oxetan-3-yl)-4-sulfamoyl-2H-indazol-6-yl)acetamide)

Intermediate 59-2 (220 mg, 0.333 mmol) was weighed accurately and dissolved in DCM, a few drops of TFA were added dropwise, and the reaction solution was stirred at room temperature for 1 h. After the reaction starting material was completely reacted as indicated by thin-layer chromatography, the reaction solution was concentrated by rotary evaporation, purified by preparative chromatography, and lyophilized to give the product. The reaction was completed successfully and 36 mg of a white foamy solid was given. LC-MS $[M+H]^+$=421.

$^1$H NMR (400 MHz, dmso) δ 10.55 (s, 1H), 8.64 (s, 1H), 8.28 (s, 1H), 7.75 (d, J=1.1 Hz, 1H), 7.50 (s, 2H), 7.46-7.40 (m, 2H), 7.35-7.28 (m, 2H), 5.95-5.85 (m, 1H), 5.01 (dt, J=13.4, 6.9 Hz, 4H), 3.88 (s, 2H).

Example 75

Compound 75

N-(3-chloro-1-(4-fluorophenyl)-4-sulfamoyl-1H-indazol-6-yl)-2-(2-chlorophenyl)acetamide

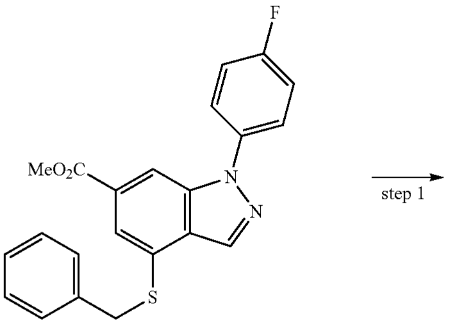

44-4

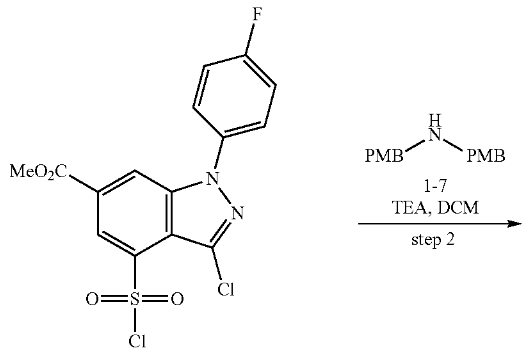

75-1

-continued

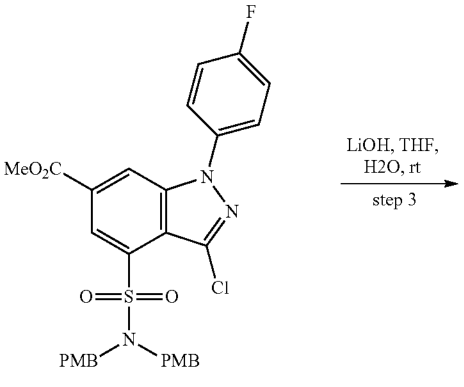

75-2

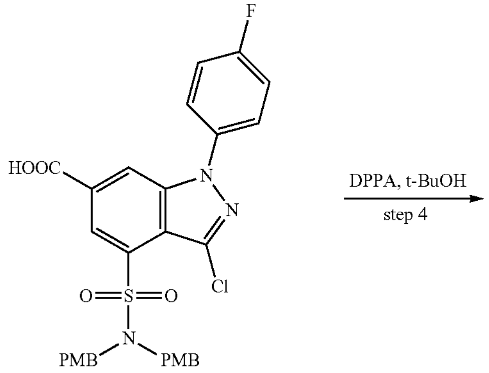

75-3

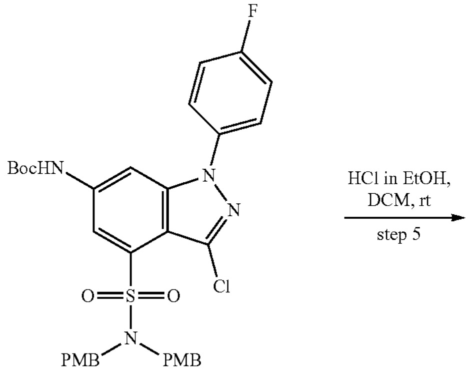

75-4

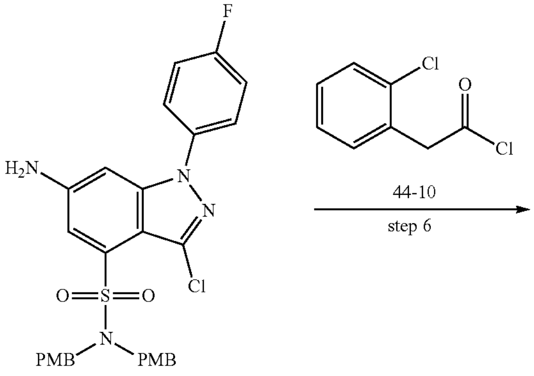

75-5

-continued

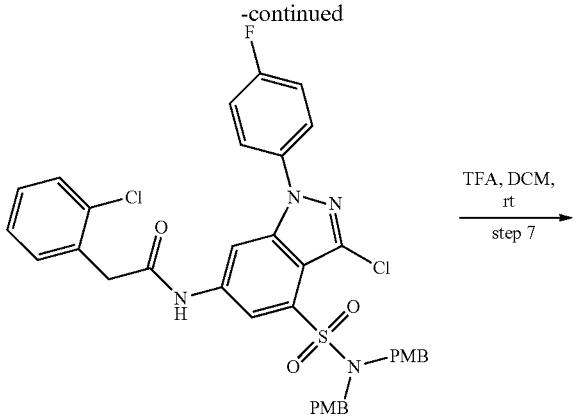

75-6

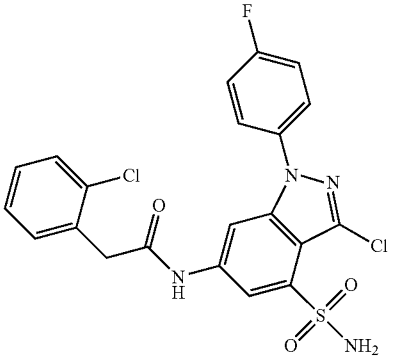

75

Step (1) Preparation of Intermediate 75-1 (methyl-3-chloro-4-(chlorosulfonyl)-1-(4-fluorophenyl)-1H-indazole-6-carboxylate)

Intermediate 44-4 (methyl-4-(benzylthio)-1-(4-fluorophenyl)-1H-indazole-6-carboxylate) (810 mg, 2.06 mmol) was dissolved in acetonitrile (20 mL) and water (0.58 mL), 1,3-dichloro-5,5'-methylhydantoin (810 mg, 4.12 mmol) and acetic acid (0.89 mL) were added at 0° C., and the reaction solution was stirred at 0° C. for 1 h, concentrated at low temperature and purified by silica gel column chromatography (PE/EA=5/1) to give intermediate 75-1 (650 mg, 62.6% yield) in the form of a yellow solid. LC-MS: [M+H]+= 404.

Step (2) Preparation of Intermediate 75-2 (methyl-4-(N,N-bis(4-methoxybenzyl)sulfamoyl)-3-chloro-1-(4-fluorophenyl)-1H-indazole-6-carboxylate)

Intermediate 75-1 (635 mg, 1.72 mmol) and triethylamine (523 mg, 5.16 mmol) were dissolved in dichloromethane (5 mL), intermediate 1-7 (bis-(4-methoxybenzyl)-amine) (890 mg, 3.45 mmol) was added, and the reaction solution was stirred at room temperature overnight, concentrated under reduced pressure and purified by silica gel column chromatography (DCM/EA=5/1) to give intermediate 75-2 (600 mg, 38.9% yield) in the form of a yellow solid. LC-MS: $[M+H]^+$=625.

Step (3) Preparation of Intermediate 75-3 (4-(N,N-bis(4-methoxybenzyl)sulfamoyl)-3-chloro-1-(4-fluorophenyl)-1H-indazole-6-carboxylic acid)

Intermediate 75-2 (600 mg, 1.02 mmol) and an aqueous lithium hydroxide solution (6 mL, 3 mol/L) were dissolved in tetrahydrofuran (3 mL) and stirred at room temperature overnight, pH was adjusted to 3 with diluted hydrochloric acid, and the reaction solution was diluted with ethyl acetate (30 mL), washed with saturated brine (15 mL), dried over anhydrous sodium sulfate, filtered, and concentrated to give intermediate 75-3 (520 mg, crude) in the form of a yellow solid. LC-MS: $[M-1]^-$=611.

Step (4) Preparation of Intermediate 75-4 (tert-butyl (4-(N,N-bis(4-methoxybenzyl)sulfamoyl)-3-chloro-1-(4-fluorophenyl)-11H-indazol-6-yl)carbamate)

Intermediate 75-3 (500 mg, 0.82 mmol) and triethylamine (335 mg, 3.28 mmol) were dissolved in tert-butanol (3 mL), diphenylphosphine azide (320 mg, 1.16 mmol) was added, and the reaction solution was stirred at room temperature for 3 h and then heated to 85° C. and reacted for 12 h, concentrated, diluted with water (20 mL), and extracted with ethyl acetate (20 mL×3). The organic phases were combined, dried over anhydrous sodium sulfate, filtered, concentrated and purified by silica gel column chromatography (PE/EA=4/1) to give intermediate 75-4 (140 mg, 19.8% yield) in the form of a yellow solid. LC-MS: $[M+H]^+$=682.

Step (5) Preparation of Intermediate 75-5 (6-amino-3-chloro-1-(4-fluorophenyl)-N,N-bis(4-methoxybenzyl)-1H-indazole-4-sulfonamide)

Intermediate 75-4 (140 mg, 0.19 mmol) was dissolved in dichloromethane (2 mL), a solution of hydrogen chloride in ethanol (1.5 mL, 4 N) was added, and the reaction solution was stirred at room temperature for 3 h, and concentrated to give intermediate 75-5 (120 mg, crude) in the form of a yellow solid. LC-MS: $[M+H]^+$=581.

Step (6) Preparation of Intermediate 75-6 (N-(4-(N,N-bis(4-methoxybenzyl)sulfamoyl)-3-chloro-1-(4-fluorophenyl)-1H-indazol-6-yl)-2-(2-chlorophenyl)acetamide)

Intermediate 75-5 (120 mg, 0.21 mmol) and triethylamine (84 mg, 0.82 mmol) were dissolved in dichloromethane (3 mL), intermediate 44-10 (2-chlorophenylacetyl chloride)(78 mg, 0.41 mmol) was added dropwise, and the reaction solution was stirred at room temperature for 12 h, concentrated and purified by silica gel column chromatography (DCM/EA=4/1), and concentrated to give intermediate 75-6 (140 mg, 82.3% yield) in the form of a yellow oil. LC-MS: $[M+H]^+$=734.

Step (7) Preparation of Compound 75 (N-(3-chloro-1-(4-fluorophenyl)-4-sulfamoyl-1H-indazol-6-yl)-2-(2-chlorophenyl)acetamide)

Intermediate 75-6 (140 mg, 0.19 mmol) was dissolved in dichloromethane (2 mL), trifluoroacetic acid (2 mL) was added, and the reaction solution was stirred at room temperature for 6 h, concentrated and purified by preparative chromatography, and then separated by a chiral column (SP-120-10-C18-BIO-C18 250×50 mm, 10 μm (pH 8-10), flow rate: 12.5 g/min, mobile phase B: $CO_2$-EtOH (DEA)

(0.1% DEA), mobile phase A: ETOH (DEA), retention time: 13.41 min). The product was collected, concentrated and lyophilized to give a white solid (23.6 mg). LC-MS: $[M+H]^+$: 494.

$^1H$ NMR (400 MHz, $CDCl_3$) S 8.43 (d, J=1.6 Hz, 1H), 7.69 (d, J=1.7 Hz, 1H), 7.65-7.60 (m, 2H), 7.56 (s, 1H), 7.51-7.45 (m, 2H), 7.37-7.33 (m, 2H), 7.30-7.25 (m, 2H), 5.23 (s, 2H), 3.94 (s, 2H).

Example 83

Compound No. 83

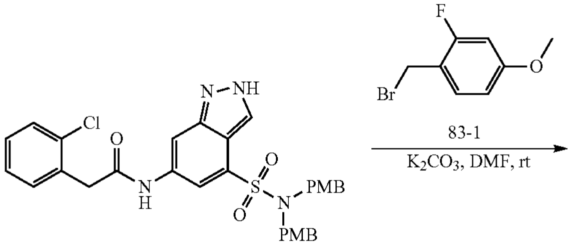

3-1

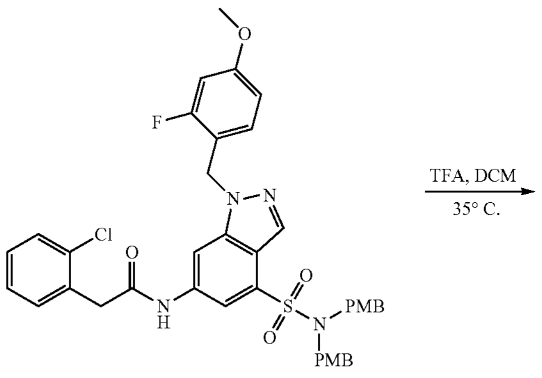

83-2

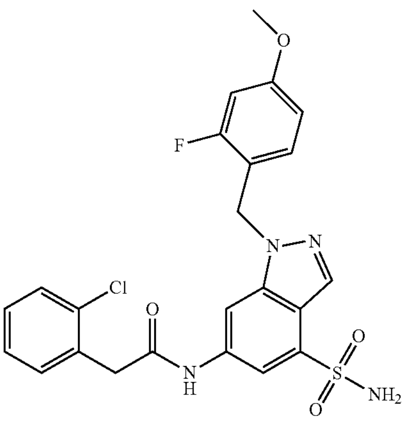

83

Step (1) Preparation of Intermediate 83-2 (N-(4-(N, N-bis(4-methoxybenzyl)sulfamoyl)-1-(2-fluoro-4-methoxybenzyl)-1H-indazol-6-yl)-2-(2-chlorophenyl)acetamide)

Intermediate 3-1 (700.0 mg, 1.16 mmol) was dissolved in DMF (15 mL), intermediate 83-1 (1-(bromomethyl)-2-fluoro-4-methoxybenzene) (380.1 mg, 1.74 mmol) and $K_2CO$; (319.8 mg, 2.31 mmol) were added, and the mixture was stirred at room temperature overnight. After the reaction starting material was completely reacted as detected by TLC (EA:PE=1:1), the reaction solution was diluted with 100 mL of water and extracted with EA (100 mL×3), the organic phases were combined, washed with saturated brine, and dried over anhydrous $Na_2SO_4$, and the solvent was concentrated by rotary evaporation to give intermediate 83-2 (750 mg) in the form of a yellow oil. LC-MS: $[M+H]^+$=743.

Step (2) Preparation of Compound 83 (2-(2-chlorophenyl)-N-(1-(2-fluoro-4-methoxybenzyl)-4-sulfamoyl-1H-indazol-6-yl)acetamide)

Intermediate 83-2 (580 mg, 780.36 μmol) was dissolved in DCM (8 mL), TFA (8 mL) was added, and the reaction mixture was stirred at 35° C. overnight. After the reaction starting material was completely reacted as detected by TLC (EA:PE=1:1), the reaction was stopped. The solvent was concentrated by rotary evaporation to give a crude product which was separated by prep-HPLC using a $H_2O$/ACN system and lyophilized to give compound 83 (51.3 mg, 95.924% purity) in the form of a beige solid. LC-MS (NB190102-34-02): $[M+H]^+$=502.95. $^1H$ NMR (NB190102-34-02):

$^1H$ NMR (400 MHz, DMSO) S (ppm): 10.75 (s, 1H), 8.41 (s, 1H), 8.29 (s, 1H), 7.78 (s, 1H), 7.61 (s, 2H), 7.52-7.45 (m, 2H), 7.40-7.32 (m, 2H), 7.14 (t, J=8.7 Hz, 1H), 6.84 (dd, J=12.1, 2.2 Hz, 1H), 6.75 (dd, J=8.5, 2.3 Hz, 1H), 5.58 (s, 2H), 3.93 (s, 2H), 3.74 (s, 3H).

Example 88

Compound 88, Compound 88A

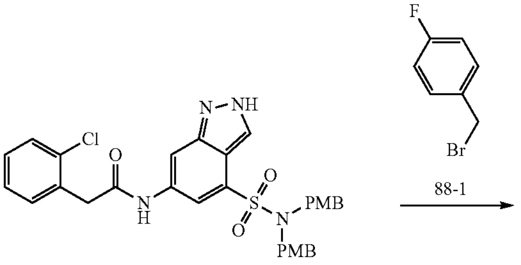

3-1

-continued

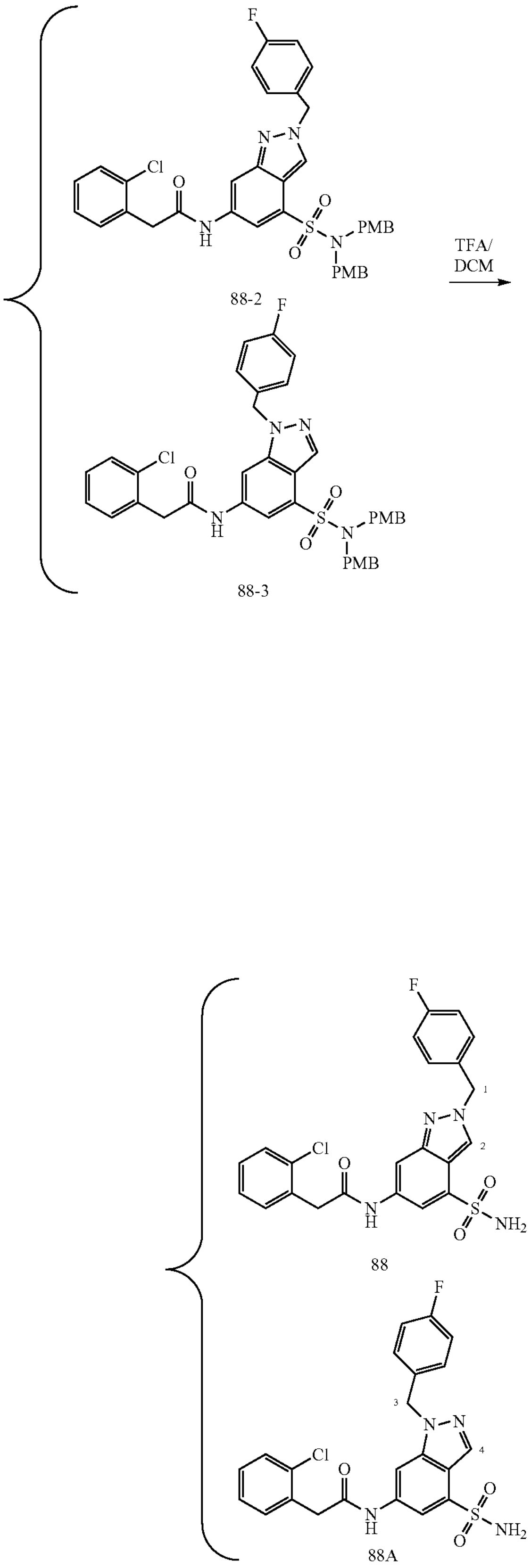

88-2

88-3

88

88A

Step (1) Preparation of Intermediate 88-2 (N-(4-(N,N-bis(4-methoxybenzyl)sulfamoyl)-2-(4-fluorobenzyl)-2H-indazol-6-yl)-2-(2-chlorophenyl)acetamide) and Intermediate 88-3 (N-(4-(N,N-bis(4-methoxybenzyl)sulfamoyl)-1-(4-fluorobenzyl)-1H-indazol-6-yl)-2-(2-chlorophenyl)acetamide)

Intermediate 3-1 (700 mg, 1.16 mmol), intermediate 88-1 (p-fluorobenzyl bromide) (330 mg, 1.74 mmol) and potassium carbonate (320 mg, 2.32 mmol) were dissolved in DMF, and the reaction mixture was stirred at room temperature overnight. After the reaction starting material was completely reacted as indicated by thin-layer chromatography, the reaction solution was added with water (10 mL) and extracted three times with EA, the EA phases were combined, washed with saturated brine, dried over sodium sulfate, and filtered, and the filtrate was concentrated to give a mixture of intermediate 88-2 and intermediate 88-3 (550 mg). LC-MS: $[M+H]^+$=713.

Step (2) Preparation of 2-(2-chlorophenyl)-N-(2-(4-fluorobenzyl)-4-sulfamoyl-2H-indazol-6-yl)acetamide and N-(4-(N,N-bis(4-methoxybenzyl)sulfamoyl)-1-(4-fluorobenzyl)-1H-indazol-6-yl)-2-(2-chlorophenyl)acetamide A mixture of intermediate 88-2 and intermediate 88-3 (500 mg, 0.7 mmol) was dissolved in DCM (5 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 88 (15 mg) and compound 88A (13 mg) in the form of white solids.

NOE Data and Description

NOE showed that the correlation signal between No. 1 hydrogen (δ=5.66) and No. 2 hydrogen (δ=7.73) was confirmed to be compound 88.

NOE showed that no correlation signal between hydrogen No. 3 (δ=5.63) and hydrogen No. 4 (δ=7.74) was confirmed to be compound 88A.

Compound 88: $^1H$ NMR (400 MHz, dmso) δ 10.53 (s, 1H), 8.59 (s, 1H), 8.23 (s, 1H), 7.73 (s, 1H), 7.50 (s, 2H), 7.47-7.40 (m, 4H), 7.34-7.28 (m, 2H), 7.20 (t, J=8.3 Hz, 2H), 5.66 (s, 2H), 3.88 (s, 2H).

Compound 88A: $^1H$ NMR (400 MHz, dmso) δ 10.71 (s, 1H), 8.31 (d, J=11.8 Hz, 2H), 7.74 (s, 1H), 7.60 (s, 2H), 7.44 (dd, J=8.6, 4.6 Hz, 2H), 7.32 (dd, J=4.7, 2.9 Hz, 2H), 7.25-7.06 (m, 4H), 5.63 (s, 2H), 3.89 (s, 2H).

Example 89
Compound Nos. 89+89A
Naming: Preparation of N-(2-(4-chlorobenzyl)-4-sulfamoyl-2H-indazol-6-yl)-2-(2-chlorophenyl)acetamide (Compound 89)/N-(1-(4-chlorobenzyl)-4-sulfamoyl-1H-indazol-6-yl)-2-(2-chlorophenyl) acetamide (Compound 89A)
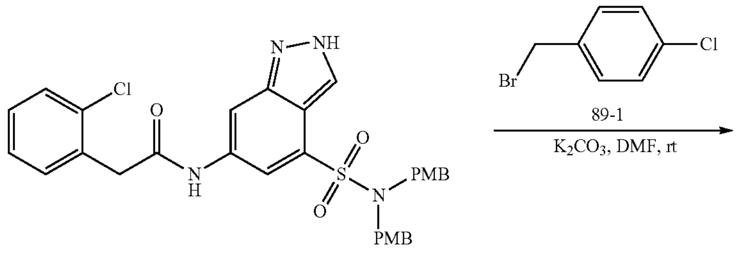
3-1
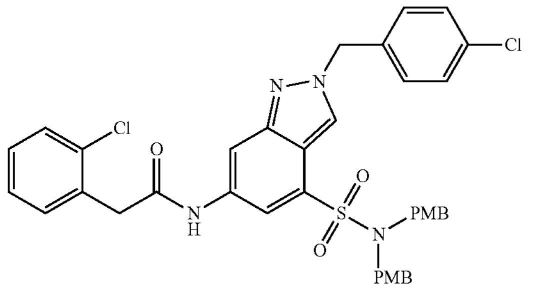
89-2
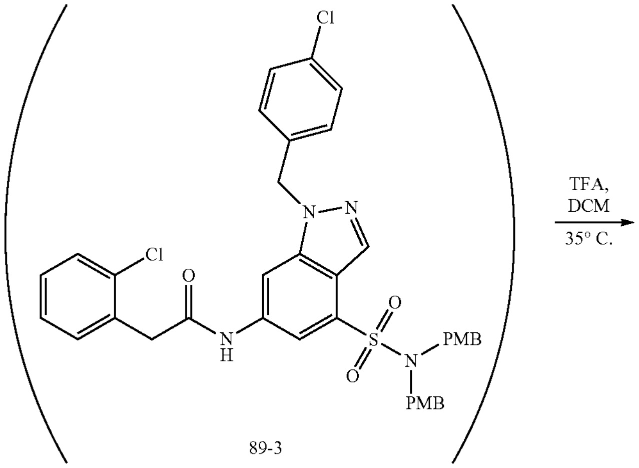
89-3
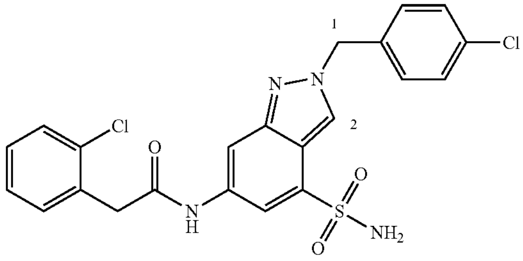
89
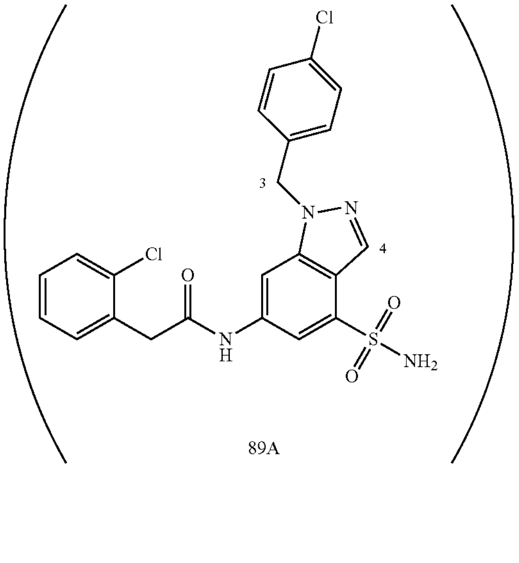
89A Step (1) Preparation of Intermediate 89-2 (1 N-(4-(N,N-bis(4-methoxybenzyl)sulfamoyl)-2-(4-chlorobenzyl)-2H-indazol-6-yl)-2-(2-chlorophenyl)acetamide) and Intermediate 89-3 (N-(4-(N,N-bis(4-methoxybenzyl)sulfamoyl)-1-(4-chlorobenzyl)-1H-indazol-6-yl)-2-(2-chlorophenyl)acetamide)

Intermediate 3-1 (600.0 mg, 991.56 μmol) was dissolved in DMF (15 mL), intermediate 89-1 (p-chlorobenzyl bromide) (305.6 mg, 1.49 mmol) and $K_2CO_3$ (274.1 mg, 1.98 mmol) were added, and the mixture was stirred at room temperature overnight. After the reaction starting material was completely reacted as detected by TLC (EA:PE=1:1), the reaction solution was diluted with 100 mL of water and extracted with EA (100 mL×3), the organic phases were combined, washed with saturated brine, and dried over anhydrous $Na_2SO_4$, and the solvent was concentrated by rotary evaporation to give a mixture of intermediate 89-2 and intermediate 89-3 (650 mg) in the form of a yellow oil. LC-MS: $[M+H]^+$=729.

Step (2) Preparation of N-(2-(4-chlorobenzyl)-4-sulfamoyl-2H-indazol-6-y)-2-(2-chlorophenyl)acetamide/N-(1-(4-chlorobenzyl)-4-sulfamoyl-1H-indazol-6-yl)-2-(2-chlorophenyl)acetamide A mixture (540.0 mg, 740.06 μmol) of intermediate 89-2 and intermediate 89-3 was dissolved in DCM (8 mL), TFA (8 mL) was added, and the reaction mixture was stirred at 35° C. overnight. After the reaction starting material was completely reacted as detected by TLC (EA:PE=1:1), the reaction was stopped. The solvent was concentrated by rotary evaporation to give a crude product which was separated by prep-HPLC using a $H_2O$/ACN system and lyophilized to give compound 89 (38.1 mg, 96.060% purity) in the form of a beige solid and compound 89A (15.0 mg, 96.679% purity) in the form of a beige solid.

LC-MS (NB190102-30-01): $[M+H]^+$=488.95. $^1$H NMR (NB190102-30-01);

LC-MS (NB190102-30-02): $[M+H]^+$=488.90.

NOE Data and Description

NOE showed that the correlation signal between No. 1 hydrogen (δ=5.58) and No. 2 hydrogen (δ=7.78) was confirmed to be compound 89.

NOE showed that no correlation signal between hydrogen No. 3 (δ=5.66) and hydrogen No. 4 (δ=7.76) was confirmed to be compound 89A.

Compound 89: $^1$H NMR (400 MHz, DMSO) δ (ppm): 10.75 (s, 1H), 8.41 (s, 1H), 8.29 (s, 1H), 7.78 (s, 1H), 7.61 (s, 2H), 7.52-7.45 (m, 2H), 7.40-7.32 (m, 2H), 7.14 (t, J=8.7 Hz, 1H), 6.84 (dd, J=12.1, 2.2 Hz, 1H), 6.75 (dd, J=8.5, 2.3 Hz, 1H), 5.58 (s, 2H), 3.93 (s, 2H), 3.74 (s, 3H).

Compound 89A: $^1$H NMR (NB190102-30-02): $^1$H NMR (400 MHz, dmso) δ 10.73 (s, 1H), 8.33 (s, 2H), 7.76 (d, J=1.1 Hz, 1H), 7.63 (s, 2H), 7.49-7.43 (m, 2H), 7.41-7.37 (m, 2H), 7.37-7.30 (m, 2H), 7.18 (d, J=8.4 Hz, 2H), 5.66 (s, 2H), 3.90 (s, 2H).

Example 90

Compound Nos. 90+90A

Preparation of 2-(2-chlorophenyl)-N-(4-sulfamoyl-2-(4-(trifluoromethyl)benzyl)-2H-indazol-6-yl)acetamide (Compound 90) and N-(4-(N,N-bis(4-methoxybenzyl)sulfamoyl)-1-(4-(trifluoromethyl)benzyl)-1H-indazol-6-yl)-2-(2-chlorophenyl)acetamide (Compound 90A)

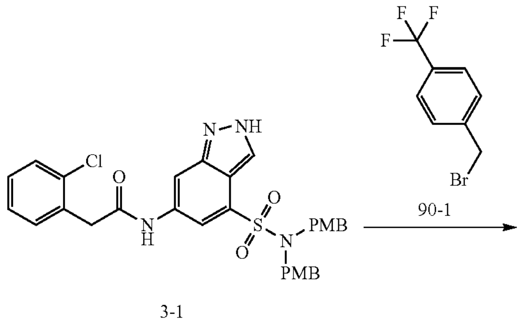

3-1

-continued

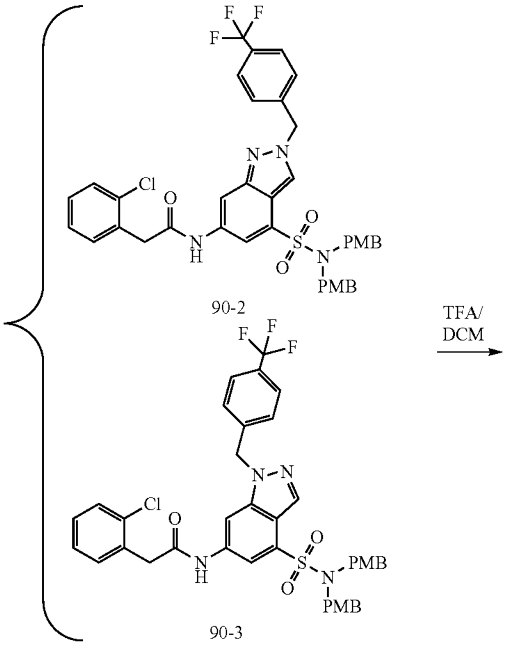

90-2

90-3

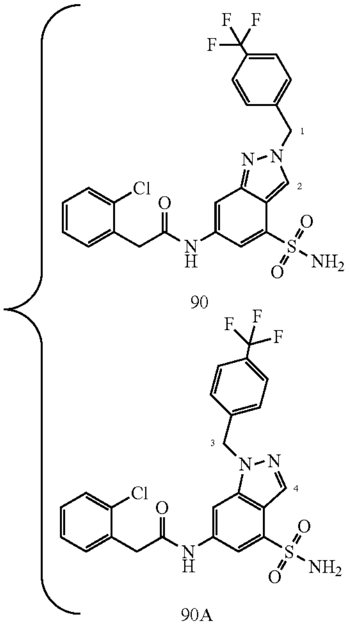

90

90A

Step (1) Preparation of N-(4-(N,N-bis(4-methoxybenzyl)sulfamoyl)-2-(4-(trifluoromethyl)benzyl)-2H-indazol-6-yl)-2-(2-chlorophenyl)acetamide (Intermediate 90-2) and N-(4-(N,N-bis(4-methoxybenzyl)sulfamoyl)-1-(4-(trifluoromethyl)benzyl)-1H-indazol-6-yl)-2-(2-chlorophenyl)acetamide (Intermediate 90-3)

Intermediate 3-1 (700 mg, 1.16 mmol), intermediate 90-1 (p-trifluoromethylbromobenzyl) (415 mg, 1.74 mmol) and potassium carbonate (320 mg, 2.32 mmol) were dissolved in DMF, and the reaction solution was stirred at room temperature overnight. After the reaction starting material was completely reacted as indicated by thin-layer chromatography, the reaction solution was added with water (10 mL) and extracted three times with EA, the EA phases were combined, washed with saturated brine, dried over sodium sulfate, and filtered, and the filtrate was concentrated to give a mixture of intermediate 90-2 and intermediate 90-3 (550 mg). LC-MS: $[M+H]^+=763$.

Step (2) Preparation of 2-(2-chlorophenyl)-N-(4-sulfamoyl-2-(4-(trifluoromethyl)benzyl)-2H-indazol-6-yl)acetamide (Compound 90) and N-(4-(N,N-bis(4-methoxybenzyl)sulfamoyl)-1-(4-(trifluoromethyl)benzyl)-1H-indazol-6-yl)-2-(2-chlorophenyl)acetamide (Intermediate 90A)

A mixture of intermediate 90-2 and intermediate 90-3 (500 mg, 0.7 mmol) was dissolved in DCM (5 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 90 (15 mg) and compound 90A (10 mg) in the form of white solids.

NOE Data and Description

NOE showed that the correlation signal between No. 1 hydrogen (δ=5.76) and No. 2 hydrogen (δ=7.71) was confirmed to be compound 90.

NOE showed that no correlation signal between hydrogen No. 3 (δ=5.80) and hydrogen No. 4 (δ=7.73) was confirmed to be compound 90A.

Compound 90: $^1$H NMR (400 MHz, dmso) δ 10.72 (s, 1H), 8.32 (d, J=11.0 Hz, 2H), 7.71 (dd, J=23.3, 8.4 Hz, 3H), 7.63 (s, 2H), 7.57 (d, J=17.8 Hz, 1H), 7.43 (s, 2H), 7.33 (d, J=6.2 Hz, 3H), 5.76 (s, 2H), 3.88 (s, 2H).

Compound 90A: $^1$H NMR (400 MHz, dmso) δ 10.55 (s, 1H), 8.65 (s, 1H), 8.23 (s, 1H), 7.73 (d, J=8.5 Hz, 3H), 7.52 (d, J=8.4 Hz, 4H), 7.44 (dd, J=9.2, 4.1 Hz, 2H), 7.33-7.29 (m, 2H), 5.80 (s, 2H), 3.88 (s, 2H).

Example 91
Compound Nos. 91+91A
Preparation of 2-(2-chlorophenyl)-N-(2-(4-cyanobenzyl)-4-sulfamoyl-2H-indazol-6-yl)acetamide (Compound 91) and N-(4-(N,N-bis(4-methoxybenzyl)sulfamoyl)-1-(4-cyanobenzyl)-1H-indazol-6-yl)-2-(2-chlorophenyl)acetamide (Compound 91A)
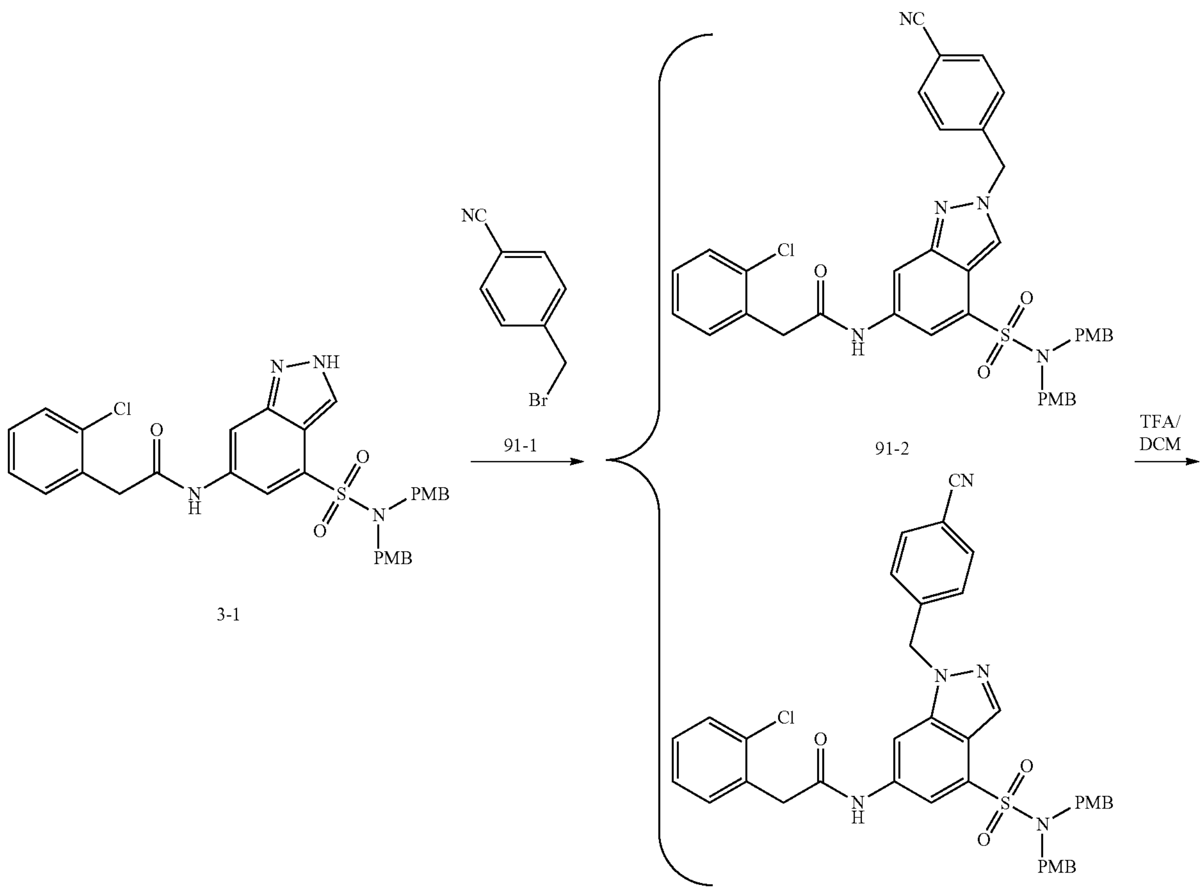
3-1
91-2
91-3

-continued

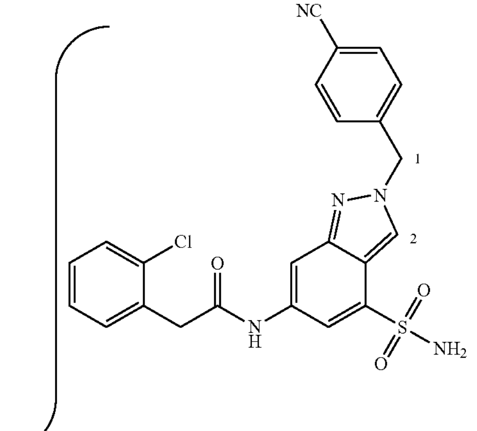

91

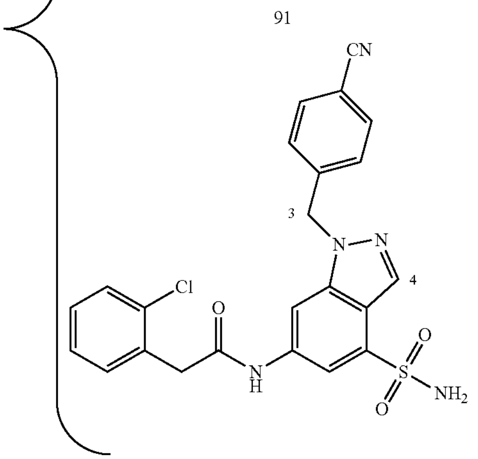

91A

Step (1) Preparation of N-(4-(N,N-bis(4-methoxybenzyl)sulfamoyl)-2-(4-cyanobenzyl)-2H-indazol-6-yl)-2-(2-chlorophenyl)acetamide (Intermediate 91-2) and N-(4-(N,N-bis(4-methoxybenzyl)sulfamoyl)-1-(4-cyanobenzyl)-1H-indazol-6-yl)-2-(2-chlorophenyl)acetamide (Intermediate 91-3)

Intermediate 3-1 (700 mg, 1.16 mmol), intermediate 91-1 (p-cyanobenzyl chloride) (263 mg, 1.74 mmol) and potassium carbonate (320 mg, 2.32 mmol) were dissolved in DMF, and the reaction solution was stirred at room temperature overnight. After the reaction starting material was completely reacted as indicated by thin-layer chromatography, the reaction solution was added with water (10 mL) and extracted three times with EA, the EA phases were combined, washed with saturated brine, dried over sodium sulfate, and filtered, and the filtrate was concentrated to give a mixture of intermediate 91-2 and intermediate 91-3 (550 mg). LC-MS: $[M+H]^+=720$.

Step (2) Preparation of 2-(2-chlorophenyl)-N-(2-(4-cyanobenzyl)-4-sulfamoyl-2H-indazol-6-yl)acetamide and N-(4-(N,N-bis(4-methoxybenzyl)sulfamoyl)-1-(4-cyanobenzyl)-1H-indazol-6-yl)-2-(2-chlorophenyl)acetamide A mixture of intermediate 91-2 and intermediate 91-3 (500 mg, 0.7 mmol) was dissolved in DCM (5 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 91 (16 mg) and compound 91A (14 mg) in the form of white solids.

NOE Data and Description

NOE showed that the correlation signal between No. 1 hydrogen (δ=5.78) and No. 2 hydrogen (δ=7.82) was confirmed to be compound 91.

NOE showed that no correlation signal between hydrogen No. 3 (δ=5.75) and hydrogen No. 4 (δ=7.82) was confirmed to be compound 91A.

Compound 91: $^1$H NMR (400 MHz, dmso) δ 10.53 (s, 1H), 8.63 (s, 1H), 8.21 (s, 1H), 7.82 (d, J=7.6 Hz, 2H), 7.73 (s, 1H), 7.49 (s, 2H), 7.46 (d, J=8.0 Hz, 2H), 7.44-7.39 (m, 2H), 7.36-7.24 (m, 2H), 5.78 (s, 2H), 3.86 (s, 2H).

Compound 91A: $^1$H NMR (400 MHz, dmso) δ 10.71 (s, 1H), 8.30 (d, J=12.6 Hz, 2H), 7.82-7.69 (m, 3H), 7.61 (s, 2H), 7.41 (dd, J=5.6, 3.7 Hz, 2H), 7.32-7.23 (m, 4H), 5.75 (s, 2H), 3.86 (s, 2H).

Example 92

Compound Nos. 92+92A

Preparation of 2-(2-chlorophenyl)-N-(2-(4-methylbenzyl)-4-sulfamoyl-2H-indazol-6-yl)acetamide (Compound 92) and 2-(2-chlorophenyl)-N-(1-(4-methylbenzyl)-4-sulfamoyl-1H-indazol-6-yl)acetamide (Compound 92A)

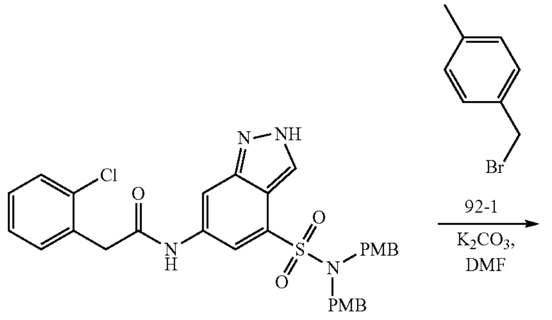

3-1

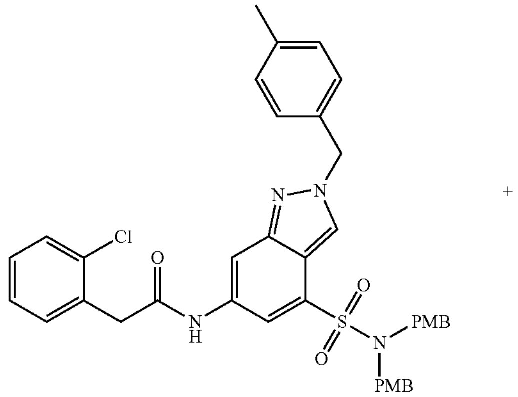

92-2

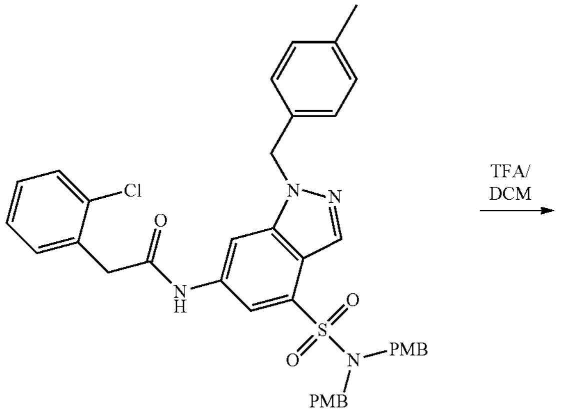

92-3

-continued

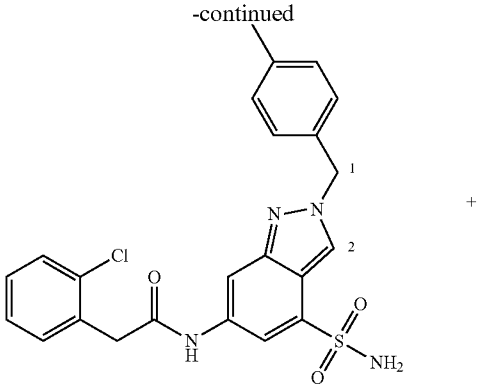

92

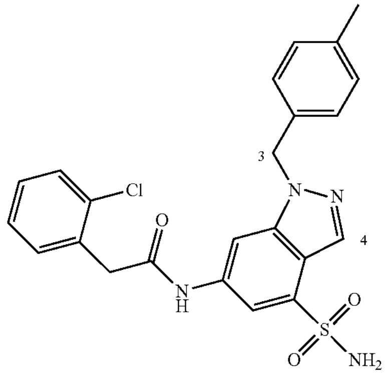

92A

Step (1) Preparation of N-(4-(N,N-bis (4-methoxybenzyl)sulfamoyl)-2-(4-methylbenzyl)-2H-indazol-6-yl)-2-(2-chlorophenyl)acetamide (Intermediate 92-2) and N-(4-(N,N-bis(4-methoxybenzyl)sulfamoyl)-1-(4-methylbenzyl)-1H-indazol-6-yl)-2-(2-chlorophenyl)acetamide (Intermediate 92-3)

Intermediate 3-1 (600 mg, 0.992 mmol) was dissolved in DMF (5 mL), intermediate 92-1 (202 mg, 1.09 mmol) and $K_2CO_3$ (205.6 mg, 1.49 mmol) were added, and the mixture was stirred at room temperature overnight. The reaction solution was poured into water (20 mL), the resulting solution was extracted with ethyl acetate (20 mL×3), and the organic phase was dried over anhydrous $Na_2SO_4$ and concentrated to dryness to give a mixture of intermediate 92-2 and intermediate 92-3 (450 mg, crude) in the form of a yellow oil. LC-MS: NB190032-64-02, ESI(+) m/z=709[M+1].

Step (2) Preparation of 2-(2-chlorophenyl)-N-(2-(4-methylbenzyl)-4-sulfamoyl-2H-indazol-6-yl)acetamide (Compound 92) and 2-(2-chlorophenyl)-N-(1-(4-methylbenzyl)-4-sulfamoyl-1H-indazol-6-yl) acetamide (Compound 92A)

A mixture of intermediate 92-2 and intermediate 92-3 (430 mg, 0.606 mmol) was dissolved in DCM (10 mL), followed by the addition of TFA (15 mL), and the mixture was stirred at room temperature overnight. The reaction starting material was reacted completely and a new spot was generated as detected by TLC (EA:PE=2:1), pH was adjusted to about 8, the reaction solution was extracted with DCM, and the organic phase was concentrated to dryness to give a crude product which was separated by prep-HPLC using a $H_2O$/ACN system and lyophilized to give compound 92 (29.4 mg, 99.672% purity) in the form of a white solid and compound 92A (20.6 mg, 99.640% purity) in the form of a white solid.

NOE Data and Description

NOE showed that the correlation signal between No. 1 hydrogen (δ=5.59) and No. 2 hydrogen (δ=7.71) was confirmed to be compound 92.

NOE showed that no correlation signal between hydrogen No. 3 (δ=5.56) and hydrogen No. 4 (δ=7.72) was confirmed to be compound 92A.

Compound 92: LC-MS: NB190032-70-01, ESI(+) m/z=460[M+1]. $^1$H NMR (400 MHz, dmso) δ 10.51 (s, 1H), 8.53 (s, 1H), 8.20 (s, 1H), 7.71 (s, 1H), 7.48 (s, 2H), 7.43 (dd, J=8.8, 3.6 Hz, 2H), 7.31 (dd, J=9.2, 5.2 Hz, 2H), 7.24 (d, J=7.6 Hz, 2H), 7.15 (d, J=7.6 Hz, 2H), 5.59 (s, 2H), 3.86 (s, 2H), 2.26 (s, 3H).

Compound 92A: LC-MS: NB190032-70-02, ESI(+) m/z=460[M+1]. $^1$H NMR (400 MHz, dmso) δ 10.69 (s, 1H), 8.28 (d, J=6.4 Hz, 2H), 7.72 (s, 1H), 7.58 (s, 2H), 7.42 (dd, J=9.2, 6.4 Hz, 2H), 7.34-7.27 (m, 2H), 7.06 (dd, J=20.4, 7.9 Hz, 4H), 5.56 (s, 2H), 3.87 (s, 2H), 2.21 (s, 3H).

Example 95

Compound Nos. 95+95A

Preparation of N-(2-(4-aminobenzyl)-4-sulfamoyl-2H-indazol-6-yl)-2-(2-chlorophenyl)acetamide (Compound 95) and N-(1-(4-aminobenzyl)-4-sulfamoyl-1H-indazol-6-yl)-2-(2-chlorophenyl)acetamide (Compound 95A)

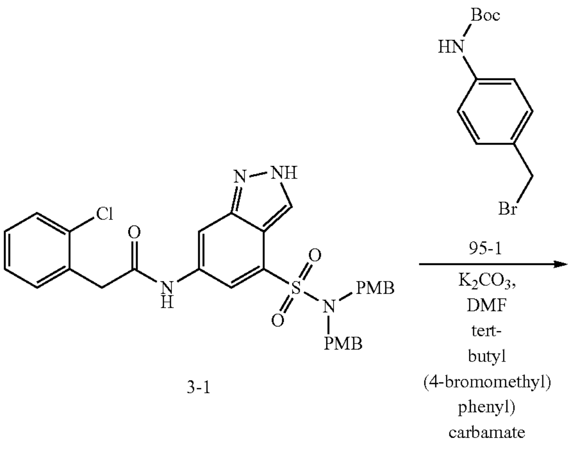

3-1

-continued

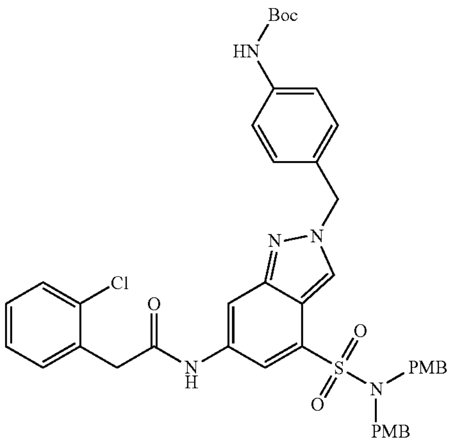

95-2

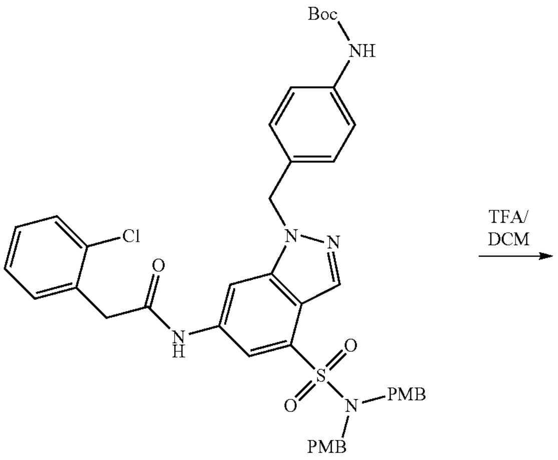

95-3

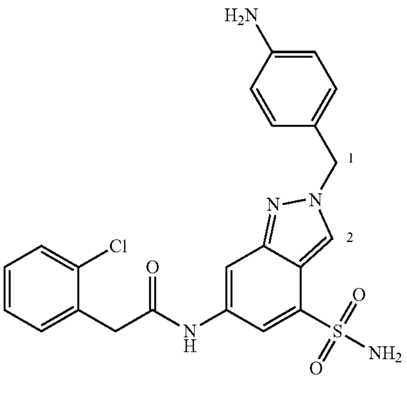

95

-continued

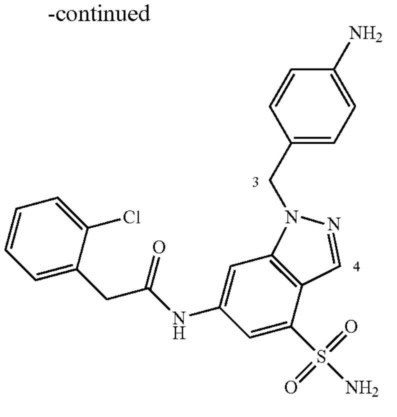

95A

Step (1) Preparation of tert-butyl (4-((4-(N,N-bis(4-methoxybenzyl)sulfamoyl)-6-(2-(2-chlorophenyl)acetamido)-2H-indazol-2-yl)methyl)phenyl)carbamate (Intermediate 95-2) and tert-butyl (4-((4-(N,N-bis(4-methoxybenzyl)sulfamoyl)-6-(2-(2-chlorophenyl)acetamido)-1H-indazol-1-yl)methyl)phenyl)carbamate (Intermediate 95-3)

Intermediate 3-1 (600 mg, 0.992 mmol) was dissolved in DMF (5 mL), intermediate 95-1 (ter-butyl (4-(bromomethyl)phenyl)carbamate) (312.1 mg, 1.09 mmol) and $K_2CO_3$ (205.6 mg, 1.49 mmol) were added, and the mixture was stirred at room temperature overnight. The reaction solution was poured into water (20 mL), the resulting solution was extracted with ethyl acetate (20 mL×3), and the organic phase was dried over anhydrous $Na_2SO_4$ and concentrated to dryness to give a mixture of intermediate 92-2 and intermediate 92-3 (800 mg, crude) in the form of a yellow oil. LC-MS: NB190032-66-02, ESI(+) m/z=810[M+1].

Step (2) Preparation of N-(2-(4-aminobenzyl)-4-sulfamoyl-2H-indazol-6-yl)-2-(2-chlorophenyl)acetamide (Compound 95) and N-(1-(4-aminobenzyl)-4-sulfamoyl-1H-indazol-6-yl)-2-(2-chlorophenyl)acetamide (Compound 95A)

A mixture of intermediate 95-2 and intermediate 95-3 (780 mg, 0.963 mmol) was dissolved in DCM (10 mL), followed by the addition of TFA (15 mL), and the mixture was stirred at room temperature overnight. The reaction starting material was reacted completely and a new spot was generated as detected by TLC (EA:PE=2:1), pH was adjusted to about 8, the reaction solution was extracted with DCM, and the organic phase was concentrated to dryness to give a crude product which was separated by prep-HPLC using a $H_2O$/ACN system and lyophilized to give compound 95 (15.8 mg, 98.277% purity) in the form of a white solid and compound 95A (17.1 mg, 98.855% purity) in the form of a white solid.

NOE Data and Description NOE showed that the correlation signal between No. 1 hydrogen (δ=5.40) and No. 2 hydrogen (δ=7.70) was confirmed to be compound 95.

NOE showed that no correlation signal between hydrogen No. 3 (δ=5.37) and hydrogen No. 4 (δ=7.72) was confirmed to be compound 95A.

Compound 95: LC-MS: NB190032-72-01, ESI(+) m/z=470[M+1].

$^1$H NMR (400 MHz, dmso) δ 10.49 (s, 1H), 8.42 (s, 1H), 8.20 (s, 1H), 7.70 (s, 1H), 7.52-7.37 (m, 4H), 7.30 (p, J=6.8 Hz, 2H), 7.07 (d, J=8.0 Hz, 2H), 6.51 (d, J=8.0 Hz, 2H), 5.40 (s, 2H), 5.12 (s, 2H), 3.86 (s, 2H).

Compound 95A: LC-MS: NB190032-72-02, ESI(+) m/z=470[M+1].

$^1$H NMR (400 MHz, dmso) δ 10.67 (s, 1H), 8.30 (s, 1H), 8.23 (s, 1H), 7.72 (s, 1H), 7.56 (s, 2H), 7.44 (dd, J=8.8, 4.4 Hz, 2H), 7.31 (dd, J=9.2, 4.9 Hz, 2H), 6.88 (d, J=8.0 Hz, 2H), 6.44 (d, J=8.0 Hz, 2H), 5.37 (s, 2H), 5.01 (s, 2H), 3.87 (d, J=6.4 Hz, 2H).

Example 101

Compounds 101, 101A

Preparation of N-(2-((6-aminopyridin-3-yl)methyl)-4-sulfamoyl-2H-indazol-6-yl)-2-(2-chlorophenyl)acetamide (Compound 101) and N-(1-((6-amino-pyridin-3-yl)methyl)-4-sulfamoyl-1H-indazol-6-yl)-2-(2-chlorophenyl)acetamide (Compound 101A)

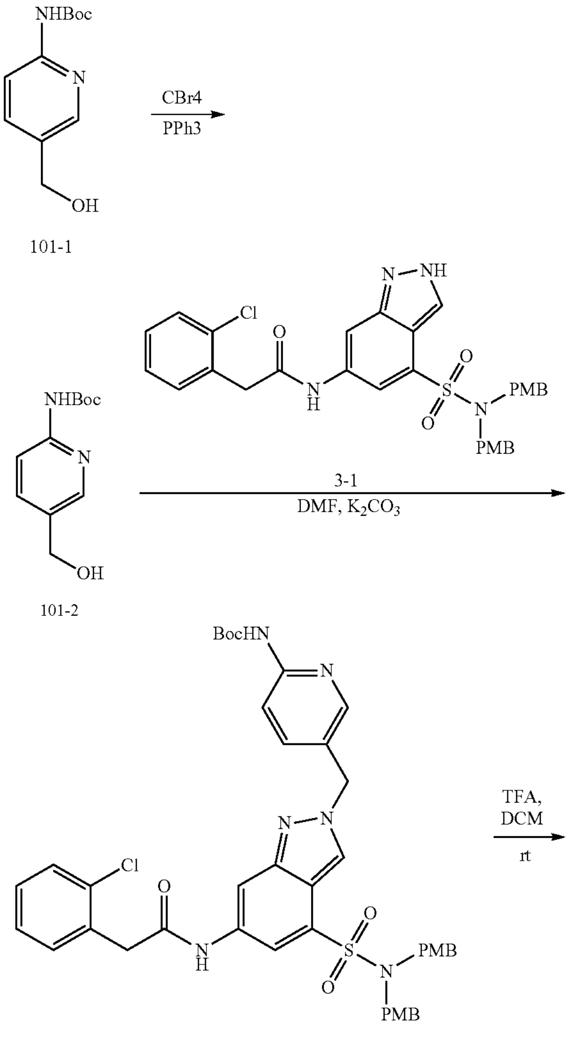

101-1

101-2

101-3

-continued

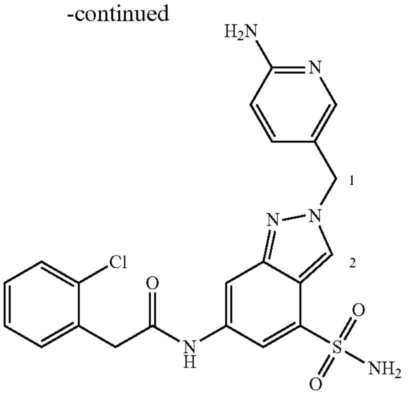

101

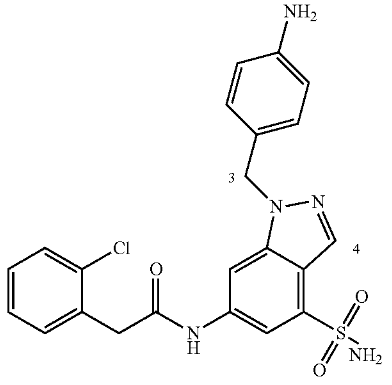

101A

Step (1) Preparation of tert-butyl (5-(bromomethyl) pyridin-2-yl)carbamate (Intermediate 101-2)

Intermediate 101-1 (tert-butyl (5-(hydroxymethyl)pyridin-2-yl)carbamate) (500 mg, 2.22 mmol) and carbon tetrabromide (880 mg, 2.88 mmol) were dissolved in DCM (10 mL) and stirred for 5 min, triphenylphosphine (870 mg, 3.33 mmol) was added at 0° C., and the reaction solution was stirred at room temperature for 2 h. After the reaction was completed as detected by TLC, the reaction solution was concentrated and purified by column chromatography to give intermediate 101-2 (410 mg, 71% yield) in the form of a white solid.

Step (2) Preparation of tert-butyl (5-((4-(N,N-bis(4-methoxybenzyl)sulfamoyl)-6-(2-(2-chlorophenyl) acetamido)-2H-indazol-2-yl)methyl)pyridin-2-yl) carbamate (Intermediate 101-3)

Intermediate 101-2 (430 mg, 1.5 mmol), intermediate 3-1 (600 mg, 1.0 mmol) and potassium carbonate (410 mg, 3.0 mmol) were dissolved in DMF (10 mL), and the reaction solution was stirred at room temperature for 3 h. After the reaction was completed as detected by TLC, the reaction solution was added with water (50 mL) and extracted twice with ethyl acetate (20 mL), the organic phases were combined, washed with saturated brine, dried over anhydrous sodium sulfate, and filtered, and the filtrate was concentrated under reduced pressure and then purified by column chromatography to give intermediate 101-3 (550 mg, yield 67.9%) in the form of a yellow solid.

Step (3) Preparation of N-(2-((6-aminopyridin-3-yl) methyl)-4-sulfamoyl-2H-indazol-6-yl)-2-(2-chlorophenyl)acetamide (Compound 101) and N-(1-((6-aminopyridin-3-yl)methyl)-4-sulfamoyl-1H-indazol-6-yl)-2-(2-chlorophenyl)acetamide (Compound 101A)

Intermediate 101-3 (550 mg, 0.67 mmol) was dissolved in DCM/TFA (15/15 mL) and stirred at 50° C. for 16 h. After the reaction was completed as detected by TLC, the reaction solution was concentrated under reduced pressure to give a crude product which was separated by prep-HPLC using a $H_2O$/CAN system and lyophilized to give compound 101 (30.8 mg, 98.31% purity, 9.8% yield) in the form of a white solid and compound 101A (68.9 mg, 99.40% purity, 17.6% yield) in the form of a white solid. LC-MS: $[M]^+$=471; LC-MS: $[M]^+$=471.

NOE Data and Description

NOE showed that the correlation signal between No. 1 hydrogen (δ=5.55) and No. 2 hydrogen (δ=8.07) was confirmed to be compound 101.

NOE showed that no correlation signal between hydrogen No. 3 (δ=5.51) and hydrogen No. 4 (δ=7.92) was confirmed to be compound 101A.

Compound 101: $^1$H NMR (400 MHz, DMSO) δ 10.53 (s, 1H), 8.57 (s, 1H), 8.23 (s, 1H), 8.07 (d, J=1.7 Hz, 1H), 7.85 (d, J=9.2 Hz, 2H), 7.70 (d, J=1.6 Hz, 1H), 7.49 (s, 2H), 7.44-7.39 (m, 2H), 7.36-7.24 (m, 2H), 6.87 (d, J=9.3 Hz, 1H), 5.55 (s, 2H), 3.86 (s, 2H).

Compound 101A: $^1$H NMR (400 MHz, DMSO) δ 10.74 (s, 1H), 8.44 (s, 1H), 8.28 (d, J=0.7 Hz, 1H), 7.92 (d, J=1.6 Hz, 1H), 7.82 (s, 2H), 7.68-7.64 (m, 2H), 7.62 (s, 2H), 7.48-7.39 (m, 2H), 7.36-7.26 (m, 2H), 6.84 (d, J=9.2 Hz, 1H), 5.51 (s, 2H), 3.89 (s, 2H).

Example 110

Compound Nos. 110+110A

Preparation of 2-(2-chlorophenyl)-N-(4-sulfamoyl-2-((tetrahydrofuran-3-yl)methyl)-2H-indazol-6-yl) acetamide (Compound 110) and 2-(2-chlorophenyl)-N-(4-sulfamoyl-1-((tetrahydrofuran-3-yl) methyl)-1H-indazol-6-yl)acetamide (Compound 110A)

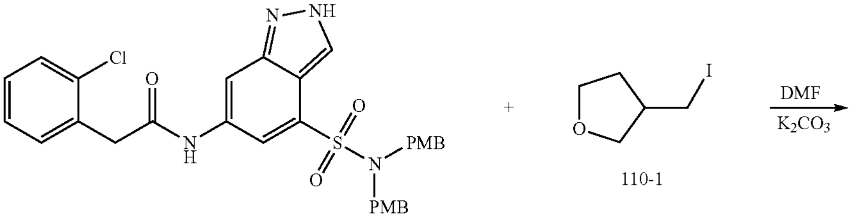

3-1

110-1

-continued

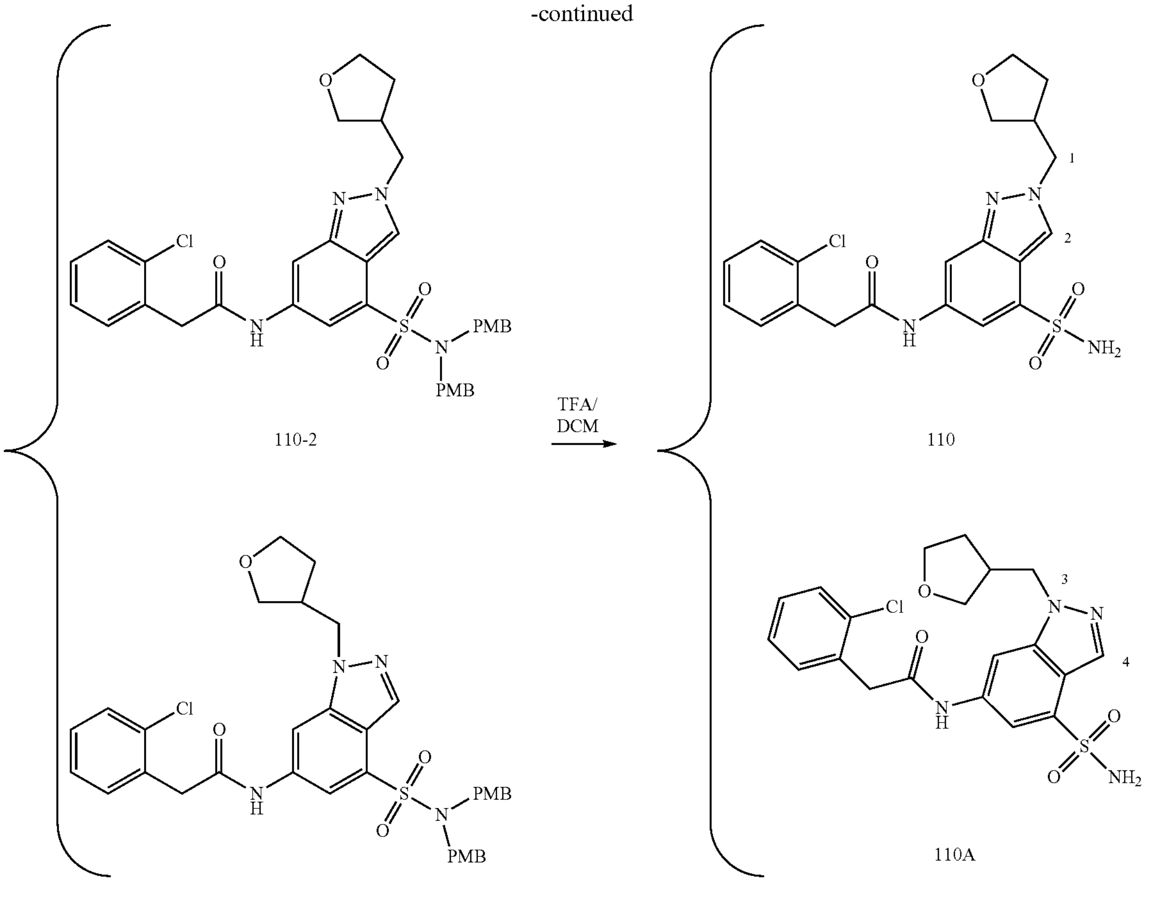

110-2

110-3

110

110A

Step (1) Preparation of N-(4-(N,N-bis(4-methoxy-benzyl)sulfamoyl)-2-((tetrahydrofuran-3-yl)methyl)-2H-indazol-6-yl)-2-(2-chlorophenyl)acetamide (Intermediate 110-2) and N-(4-(N,N-bis(4-methoxybenzyl)sulfamoyl)-1-((tetrahydrofuran-3-yl)methyl)-1H-indazol-6-yl)-2-(2-chlorophenyl)acetamide (Intermediate 110-3)

Intermediate 3-1 (375 mg, 0.62 mmol), intermediate 110-1 (3-(iodomethyl)tetrahydrofuran) (159 mg, 0.75 mmol) and potassium carbonate (172 mg, 1.24 mmol) were dissolved in DMF (5.0 mL), and the reaction solution was stirred at room temperature overnight. After a large amount of reaction starting material was completely reacted as indicated by thin-layer chromatography, the reaction solution was added with water (8 mL) and extracted three times with EA, the EA phases were combined, washed with saturated brine, dried over sodium sulfate, and filtered, and the filtrate was concentrated to give a mixture of intermediate 110-2 and intermediate 110-3 (220 mg). LC-MS: $[M+H]^+=689$.

Step (2) Preparation of 2-(2-chlorophenyl)-N-(4-sulfamoyl-2-((tetrahydrofuran-3-yl)methyl)-2H-indazol-6-yl)acetamide (Compound 110) and 2-(2-chlorophenyl)-N-(4-sulfamoyl-1-((tetrahydrofuran-3-yl)methyl)-1H-indazol-6-yl)acetamide (Compound 110A)

A mixture of intermediate 110-2 and intermediate 110-3 (200 mg, 0.29 mmol) was dissolved in DCM (3 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 110 (30 mg) and compound 110A (14 mg) in the form of white solids.

NOE Data and Description

NOE showed that the correlation signal between No. 1 hydrogen (δ=4.42) and No. 2 hydrogen (δ=7.70) was confirmed to be compound 110.

NOE showed that no correlation signal between hydrogen No. 3 (δ=4.34) and hydrogen No. 4 (δ=7.70) was confirmed to be compound 110A.

Compound 110: $^1$H NMR (400 MHz, dmso) δ 10.50 (s, 1H), 8.50 (s, 1H), 8.22 (s, 1H), 7.70 (s, 1H), 7.47 (s, 2H), 7.46-7.40 (m, 2H), 7.30 (p, J=7.0 Hz, 2H), 4.42 (d, J=7.5 Hz, 2H), 3.86 (s, 2H), 3.77 (dd, J=13.6, 7.8 Hz, 1H), 3.69-3.58 (m, 2H), 3.50 (dd, J=8.7, 5.4 Hz, 1H), 2.89-2.81 (m, 1H), 1.91 (dt, J=13.3, 7.9 Hz, 1H), 1.64 (dt, J=20.0, 6.5 Hz, 1H).

Compound 110A: $^1$H NMR (400 MHz, dmso) δ 10.72 (s, 1H), 8.34 (s, 1H), 8.24 (s, 1H), 7.70 (s, 1H), 7.58 (s, 2H), 7.43 (s, 2H), 7.29 (s, 2H), 4.34 (s, 2H), 3.89 (s, 2H), 3.75 (s, 1H), 3.57 (s, 2H), 3.48 (s, 1H), 2.76 (s, 1H), 1.88 (s, 1H), 1.61 (s, 1H).

Example 113

Compound No. 113

Preparation of 2-(3-chloropyridin-2-yl)-N-(2-(difluoromethyl)-4-sulfamoyl-2H-indazol-6-yl)acetamide

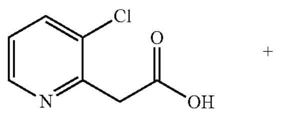

113-1

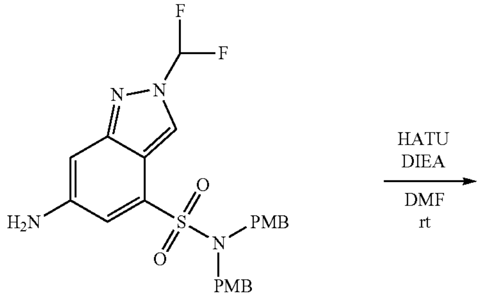

1-11

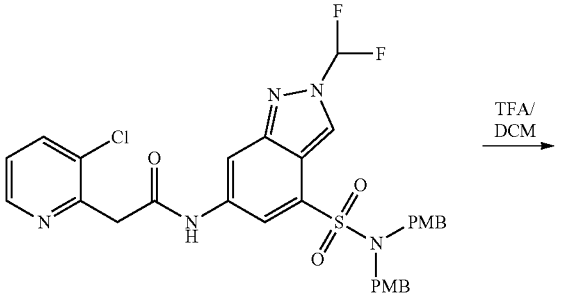

113-2

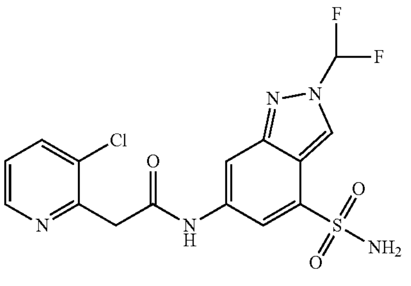

113

Step (1) Preparation of N-(4-(N,N-bis(methoxybenzyl)sulfamoyl)-2-(difluoromethyl)-2H-indazol-6-yl)-2-(3-chloropyridin-2-yl)acetamide (Intermediate 113-2)

Intermediate 113-1 (2-(3-chloropyridin-2-yl)acetic acid) (210 mg, 0.12 mmol), intermediate 1-11 (500 mg, 0.10 mmol), HATU (570 mg, 0.15 mmol) and DIEA (400 mg, 0.30 mmol) were dissolved in DMF and stirred at room temperature overnight. After the reaction starting material was completely reacted as indicated by thin-layer chromatography, the reaction solution was added with water (20 mL) and extracted three times with EA, the EA phases were combined, washed with saturated brine, dried over sodium sulfate, and filtered, and the filtrate was concentrated and separated and purified by column chromatography (PE/EA=5:1-1:2) to give the product (120 mg). LC-MS: $[M+H]^+$= 656.

Step (2) Preparation of 2-(3-chloropyridin-2-yl)-N-(2-(difluoromethyl)-4-sulfamoyl-2H-indazol-6-yl) acetamide Intermediate 113-2 (100 mg, 0.15 mmol) was dissolved in DCM (3 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 113 (6 mg) in the form of a white solid.

$^1$H NMR (400 MHz, dmso) δ 10.71 (s, 1H), 8.94 (s, 1H), 8.48 (d, J=4.7 Hz, 1H), 8.32 (s, 1H), 8.17 (s, 1H), 8.02 (s, 1H), 7.93 (d, J=8.1 Hz, 1H), 7.81 (s, 1H), 7.64 (s, 2H), 7.41-7.32 (m, 1H), 4.07 (s, 2H).

Example 115

Compound No. 115

Preparation of N-(2-(difluoromethyl)-4-sulfamoyl-2H-indazol-6-yl)-2-(2-methoxyphenyl)acetamide

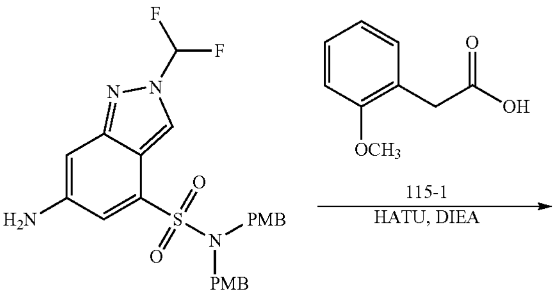

1-11

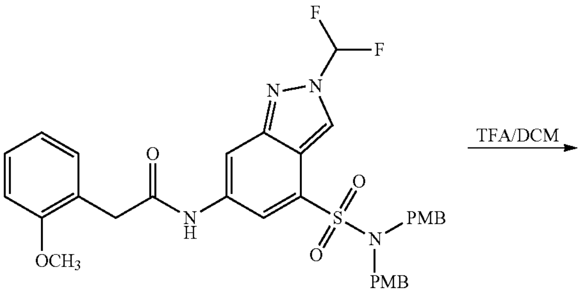

115-2

-continued

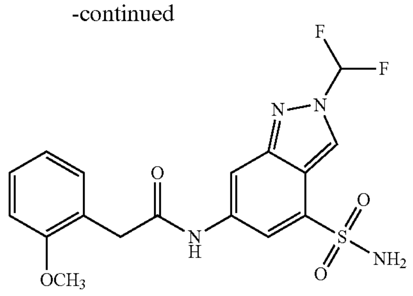

115

Step (1) Preparation of N-(4-(N,N-bis(4-methoxybenzyl)sulfamoyl)-2-(difluoromethyl)-2H-indazol-6-yl)-2-(2-methoxyphenyl)acetamide (Intermediate 115-2)

115-2

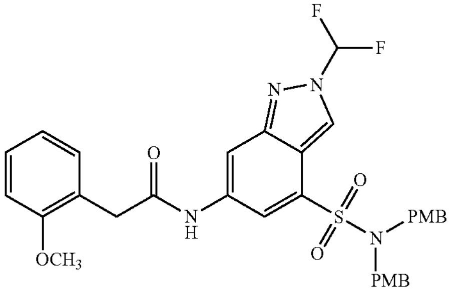

Intermediate 1-11 (300 mg, 0.6 mmol), intermediate 115-1 (o-methoxyphenylacetic acid) (120 mg, 0.72 mmol), HATU (342 mg, 0.9 mmol) and DIEA (232.2 mg, 1.8 mmol) were dissolved in DMF and stirred at room temperature overnight. After the reaction starting material was completely reacted as indicated by thin-layer chromatography, the reaction solution was added with water (10 mL) and extracted three times with EA, the EA phases were combined, washed with saturated brine, dried over sodium sulfate, and filtered, and the filtrate was concentrated to give the product (220 mg). LC-MS: $[M+H]^+$=651.

Step (2) Preparation of N-(2-(difluoromethyl)-4-sulfamoyl-2H-indazol-6-yl)-2-(2-methoxyphenyl) acetamide

115

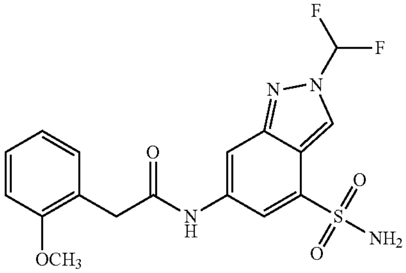

Intermediate 115-2 (200 mg, 0.31 mmol) was dissolved in DCM (3 mL), followed by the addition of an equal volume of TFA, and the mixture was stirred at room temperature overnight. After the reaction starting material was completely reacted as indicated by thin-layer chromatography, the reaction solution was concentrated by rotary evaporation, purified by preparative chromatography, and lyophilized to give compound 115 (17 mg) in the form of a yellow powdered solid.

$^1$H NMR (400 MHz, dmso) δ 10.53 (s, 1H), 8.94 (s, 1H), 8.35 (s, 1H), 8.18 (s, 1H), 8.03 (s, 1H), 7.85 (s, 1H), 7.65 (s, 2H), 7.24 (dd, J=7.6, 3.0 Hz, 2H), 6.99 (d, J=8.2 Hz, 1H), 6.92 (t, J=7.4 Hz, 1H), 3.77 (s, 3H), 3.69 (s, 2H).

Example 116

Compound No. 116

Preparation of N-(2-(difluoromethyl)-4-sulfamoyl-2H-indazol-6-yl)-2-(3-(2-methoxyethoxy)phenyl) acetamide

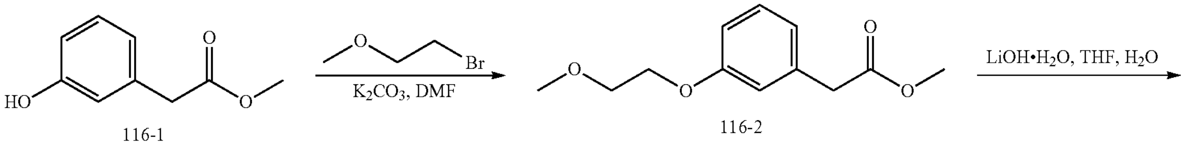

116-1

116-2

-continued

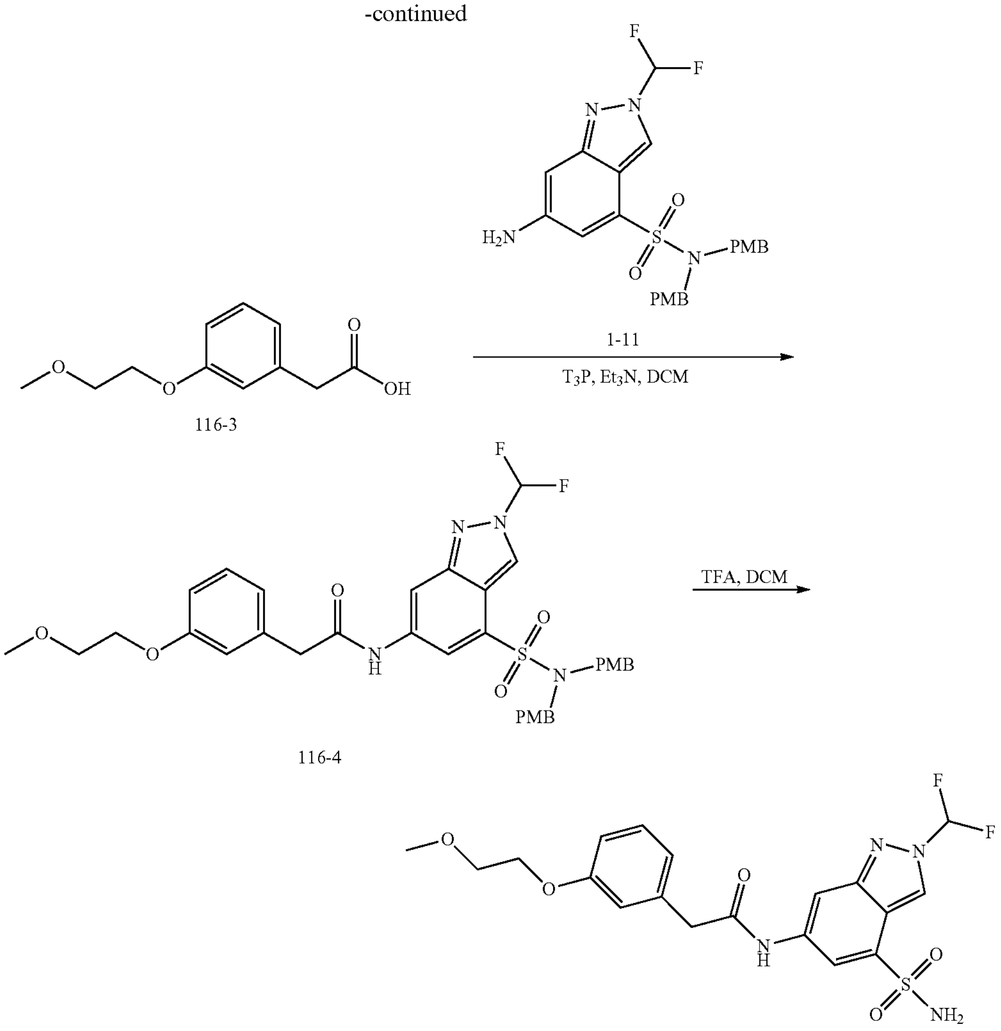

116-3

1-11

116-4

116

Step (1) Preparation of methyl 2-(3-(2-methoxyethoxy)phenyl)acetate(Intermediate 116-2)

To a reaction flask were added (1-bromo-2-methoxyethane) (1 g, 6.02 mmol), intermediate 116-1 (methyl 2-(3-hydroxyphenyl)acetate) (1 g, 7.22 mmol), $K_2CO_3$ (2.5 g, 18.05 mmol) and DMF (10 mL), and the mixture was stirred at 70° C. overnight. The reaction solution was poured into water, the resulting solution was extracted with ethyl acetate, and the organic phase was concentrated to dryness to give the product (900 mg) in the form of a colorless oil.

$^1$H NMR (400 MHz, $CDCl_3$) δ 8.00 (s, 1H), 7.24-7.18 (m, 1H), 6.84 (m, 3H), 4.10 (t, J=4.8 Hz, 2H), 3.73 (t, J=4.8, Hz, 2H), 3.67 (s, 3H), 3.58 (s, 2H), 3.44 (s, 3H).

Step (2) Preparation of 2-(3-(2-methoxyethoxy)phenyl)acetic acid (Intermediate 116-3)

Intermediate 116-2 (900 mg, 4.01 mmol) was dissolved in THF (10 mL) and $H_2O$ (5 mL), $LiOH{\cdot}H_2O$ (842 mg, 20.07 mmol) was added to the reaction flask, and the reaction solution was stirred at 30° C. for 8 h, then concentrated to remove THF, and poured into water (20 mL). The resulting solution was extracted three times with ethyl acetate, pH of the aqueous phase was adjusted to about 5 with 1 M HCl, the aqueous phase was extracted with EA, and the organic phase was concentrated to dryness to give the product (700 mg, 84.607% purity) in the form of a light yellow solid. LC-MS: NB190114-39-02, ESI(+) m/z=211[M+1].

Step (3) Preparation of N-(4-(N,N-bis(4-methoxybenzyl)sulfamoyl)-2-(difluoromethyl)-2H-indazol-6-yl)-2-(3-(2-methoxyethoxy)phenyl)acetamide (Intermediate 116-4)

Intermediate 116-4 (150 mg, 0.71 mmol) and intermediate 1-11 (359 mg, 0.71 mmol) were dissolved in DCM (10 mL), $Et_3N$ (217 mg, 2.14 mmol) and $T_3P$ (681 mg, 1.07 mmol) were added to the reaction flask, and the reaction solution was stirred at room temperature overnight and then poured into water. The resulting solution was extracted three times with ethyl acetate, and then the organic phase was concentrated and stirred with silica gel and purified by column chromatography to give the product (500 mg, 95.850% purity) in the form of a light yellow solid. LC-MS: NB190114-43-02, ESI(+) m/z=695[M+1].

Step (4) Preparation of N-(2-(difluoromethyl)-4-sulfamoyl-2H-indazol-6-yl)-2-(3-(2-methoxyethoxy)phenyl)acetamide (Compound 116)

Intermediate 116-4 (500 mg, 0.72 mmol) was dissolved in DCM (10 mL), TFA (10 mL) was added to the reaction flask, the reaction solution was stirred at 50° C. overnight, concentrated by rotary evaporation to dryness, and poured into water, pH was adjusted to about 8 with an aqueous sodium bicarbonate solution, the aqueous phase was extracted three times with ethyl acetate, and the organic phase was concentrated to dryness to give the product (72.3 mg, 99.955% purity) in the form of a white solid. LC-MS: NB190114-45-01, ESI(+) m/z=455[M+1].

$^1$H NMR (400 MHz, dmso) δ 10.58 (s, 1H), 8.93 (s, 1H), 8.33 (m, 1H), 8.09 (m, 1H), 7.80 (d, J=1.2 Hz, 1H), 7.62 (s, 2H), 7.22 (t, J=8.0 Hz, 1H), 6.91 (m, 2H), 6.82 (dd, J=8.4, 2.0 Hz, 1H), 4.10-4.03 (m, 2H), 3.66-3.61 (m, 4H), 3.28 (s, 3H).

Example 118

Compound Nos. 118+118A

Preparation of 2-(2-chlorophenyl)-N-(2-(2-morpholinoethyl)-4-sulfamoyl-2H-indazol-6-yl)acetamide (Compound 118) and 2-(2-chlorophenyl)-N-(1-(2-morpholinoethyl)-4-sulfamoyl-1H-indazol-6-yl)acetamide (Compound 118A)

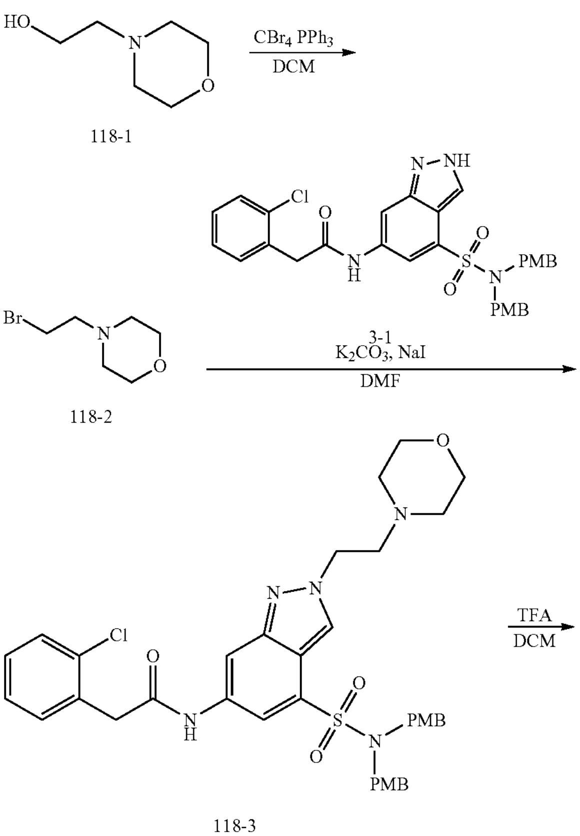

118-1

118-2

118-3

-continued

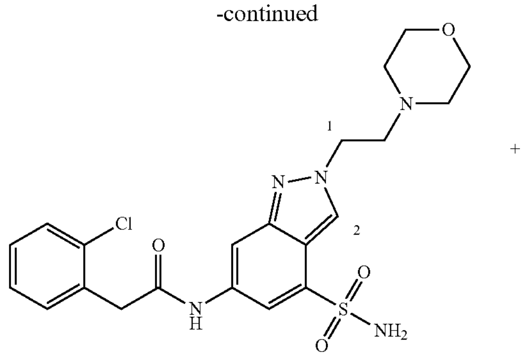

118

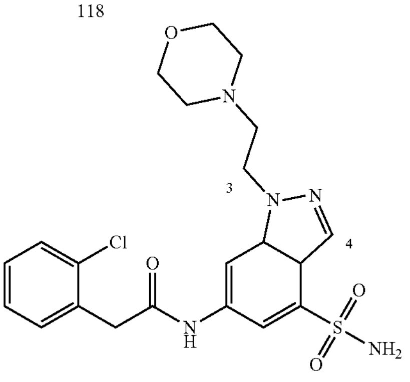

118A

Step (1) Preparation of Intermediate 118-2 (4-(2-bromoethyl)morpholine)

Intermediate 118-1 (2-morpholinoethan-1-ol) (1 g, 7.623 mmol) was weighed and dissolved in 30 mL of DCM, followed by the addition of $CBr_4$ (3.8 g, 11.435 mmol) and triphenylphosphine (2.4 g, 9.148 mmol), and the reaction solution was reacted at room temperature overnight. The reaction starting material was detected to be reacted completely and a product was generated, the reaction solution was concentrated by rotary evaporation and added with 50 mL of petroleum ether, then the solid was precipitated and filtered, and the filtrate was concentrated by rotary evaporation and stirred with silica gel and purified by column chromatography (PE/EA=3/1) to give the product (650 mg) in the form of a colorless transparent oily liquid.

Step (2) Preparation of Intermediate 118-3 (N-(4-(N,N-bis(4-methoxybenzyl)sulfamoyl)-2-(2-morpholinoethyl)-2H-indazol-6-yl)-2-(2-chlorophenyl)acetamide)

Intermediate 3-1 (500 mg, 0.826 mmol) was weighed and dissolved in 20 mL of DMF, intermediate 118-2 (241 mg, 1.239 mmol), $K_2CO_3$ (504 mg, 3.625 mmol) and NaI (38 mg, 0.248 mmol) were added sequentially, and the mixture was reacted at room temperature overnight. After the reaction starting material was reacted completely and a product was generated as detected by LCMS, the reaction solution was added with water and extracted with EA, and the organic phase was washed with water and saturated brine, dried over sodium sulfate, concentrated by rotary evaporation and slurried with PE to give the product (600 mg) in the form of a yellow oily liquid.

Step (3) Preparation of 2-(2-chlorophenyl)-N-(2-(2-morpholinoethyl)-4-sulfamoyl-2H-indazol-6-yl)acetamide (Compound 118) and 2-(2-chlorophenyl)-N-(1-(2-morpholinoethyl)-4-sulfamoyl-1H-indazol-6-yl)acetamide (Compound 118A)

Intermediate 118-3 (600 mg, 0.835 mmol) was weighed and dissolved in 10 mL of DCM, followed by the addition of 10 mL of TFA, and the reaction solution was reacted at 40° C. for 2 h. After the reaction starting material was reacted completely and a product was generated as detected by LCMS, the reaction solution was concentrated by rotary evaporation, purified by preparative chromatography, and purified by prep-HPLC to give compound 118 (50.3 mg) and compound 118A (29.3 mg) in the form of white solids.

NOE Data and Description

NOE showed that the correlation signal between No. 1 hydrogen (δ=4.48) and No. 2 hydrogen (δ=8.13) was confirmed to be compound 118.

NOE showed that no correlation signal between hydrogen No. 3 (δ=4.58) and hydrogen No. 4 (δ=8.13) was confirmed to be compound 118A.

Compound 118: LC-MS: $[M+H]^+$=478.00. 1H NMR (400 MHz, dmso) δ 10.72 (s, 1H), 8.37 (s, 1H), 8.25 (s, 1H), 8.13 (s, 1H), 7.71 (d, J=1.2 Hz, 1H), 7.60 (s, 2H), 7.48-7.43 (m, 2H), 7.36-7.30 (m, 2H), 4.48 (t, J=6.1 Hz, 2H), 3.91 (s, 2H), 3.48 (s, 4H), 2.75 (s, 2H), 2.42 (s, 4H).

Compound 118A: LC-MS: $[M+H]^+$=478.00. 1H NMR (400 MHz, dmso) δ 10.52 (s, 1H), 8.53 (s, 1H), 8.24 (s, 1H), 8.13 (s, 1H), 7.72 (d, J=1.3 Hz, 1H), 7.50 (s, 2H), 7.47-7.43 (m, 2H), 7.35-7.30 (m, 2H), 4.58 (s, 2H), 3.88 (s, 2H), 3.55 (s, 4H), 2.87 (s, 2H), 2.33 (s, 4H).

Example 120

Compound Nos. 120+120A

Preparation of 2-(2-chlorophenyl)-N-(4-sulfamoyl-2-((tetrahydrofuran-2-yl)methyl)-2H-indazol-6-yl)acetamide (120) and 2-(2-chlorophenyl)-N-(4-sulfamoyl-1-((tetrahydrofuran-2-yl)methyl)-1H-indazol-6-yl)acetamide (120A)

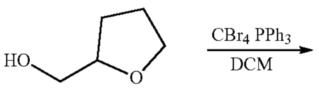

120-1

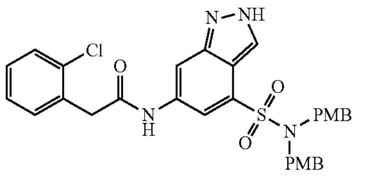

3-1

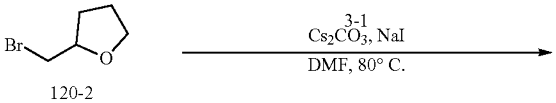

120-2

-continued

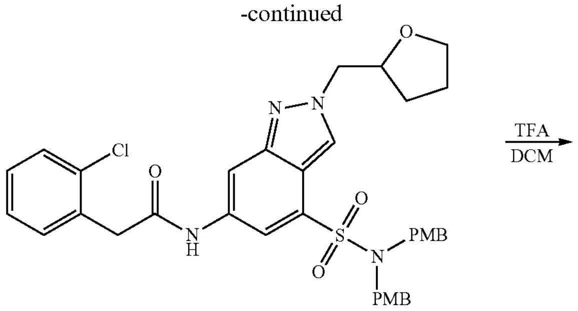

120-3

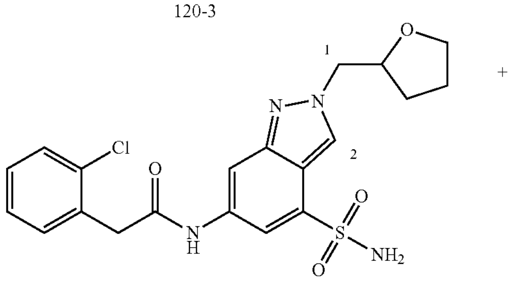

120

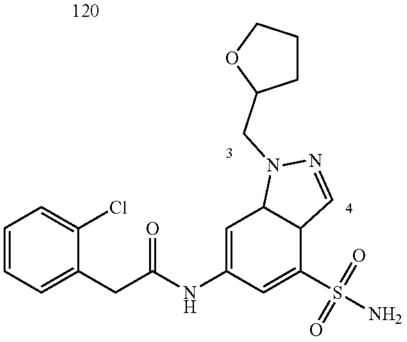

120A

Step (1) Preparation of Intermediate 120-2 (2-(bromomethyl)tetrahydrofuran)

Intermediate 120-1 (tetrahydrofuran-2-yl)methanol) (2 g, 19.583 mmol) was weighed and dissolved in 50 mL of DCM, $CBr_4$ (9.74 g, 29.374 mmol) and triphenylphosphine (6.16 g, 23.499 mmol) were added, and the mixture was reacted at room temperature overnight. The reaction starting material was detected to be reacted completely and a product was generated as detected by LCMS, the reaction solution was concentrated by rotary evaporation and stirred with silica gel and purified by column chromatography (PE/EA=30/1) to give the product (1.0 g) in the form of a colorless transparent oily liquid.

Step (2) Preparation of Intermediate 120-3 (N-(4-(N,N-bis(4-methoxybenzyl)sulfamoyl)-2-((tetrahydrofuran-2-yl)methyl)-2H-indazol-6-yl)-2-(2-chlorophenyl)acetamide)

Intermediate 3-1 (500 mg, 0.826 mmol) was weighed and dissolved in 20 mL of DMF, intermediate 120-2 (2-(bromomethyl)tetrahydrofuran) (205 mg, 1.239 mmol), $Cs_2CO_3$ (808 mg, 2.478 mmol) and NaI (124 mg, 0.826 mmol) were added sequentially, and the reaction solution was reacted at 80° C. overnight. After the reaction starting material was reacted completely and a product was generated as detected by LCMS, the reaction solution was cooled to room temperature, added with water and extracted with EA, and the organic phase was washed with water and saturated brine, dried over sodium sulfate and concentrated to give the product (700 mg, 80% purity) in the form of a yellow oily liquid.

Step (3) Preparation of (2-(2-chlorophenyl)-N-(4-sulfamoyl-2-((tetrahydrofuran-2-yl)methyl)-2H-indazol-6-yl)acetamide) and (2-(2-chlorophenyl)-N-(4-sulfamoyl-1-((tetrahydrofuran-2-yl)methyl)-1H-indazol-6-yl)acetamide)

Intermediate 120-3 (700 mg, 0.813 mmol) was weighed and dissolved in 10 mL of DCM, followed by the addition of 10 mL of TFA, and the reaction solution was reacted at 40° C. for 2 h. After the reaction starting material was reacted completely and a product was generated as detected by LCMS, the reaction solution was concentrated by rotary evaporation, purified by preparative chromatography, and purified by prep-HPLC to give compound 120 (19.0 mg) and compound 120A (17.1 mg) in the form of white solids.

NOE Data and Description

NOE showed that the correlation signal between No. 1 hydrogen (δ=4.51) and No. 2 hydrogen (δ=7.72) was confirmed to be compound 120.

NOE showed that no correlation signal between hydrogen No. 3 (δ=4.45) and hydrogen No. 4 (δ=7.74) was confirmed to be compound 120A.

Compound 120. LC-MS: [M+H]+=449.00. $^{1}$H NMR (400 MHz, dmso) δ 10.52 (s, 1H), 8.48 (s, 1H), 8.24 (s, 1H), 7.72 (d, J=1.3 Hz, 1H), 7.52 (s, 2H), 7.49-7.40 (m, 2H), 7.36-7.28 (m, 2H), 4.51 (dd, J=13.7, 4.2 Hz, 1H), 4.43 (dd, J=13.6, 7.2 Hz, 1H), 4.33 (dt, J=11.1, 6.8 Hz, 1H), 3.88 (s, 2H), 3.77 (dd, J=14.8, 6.8 Hz, 1H), 3.65 (dd, J=14.8, 6.9 Hz, 1H), 1.99 (dt, J=13.9, 7.1 Hz, 1H), 1.85-1.74 (m, 2H), 1.65 (dt, J=14.3, 7.5 Hz, 1H).

Compound 120A: LC-MS: $[M+H]^+$=449.00. $^{1}$H NMR (400 MHz, dmso) δ 10.70 (s, 1H), 8.33 (s, 1H), 8.25 (s, 1H), 7.74 (s, 1H), 7.58 (s, 2H), 7.50-7.43 (m, 2H), 7.36-7.28 (m, 2H), 4.45-4.33 (m, 2H), 4.25-4.17 (m, 1H), 3.91 (s, 2H), 3.66 (dd, J=14.2, 7.0 Hz, 1H), 3.55 (dd, J=14.1, 7.4 Hz, 1H), 1.98-1.89 (m, 1H), 1.79-1.63 (m, 3H).

Example 130

Compound No. 130

2-(2-chlorophenyl)-N-(2-(3-methyloxetan-3-yl)-7-sulfamoylisoindolin-5-yl)acetamide

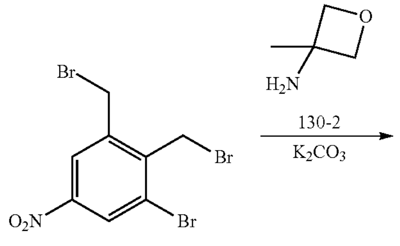

130-1

-continued

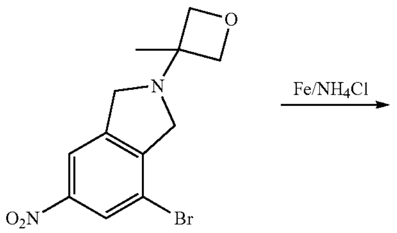

130-3

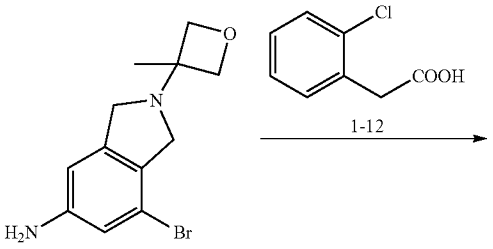

130-4

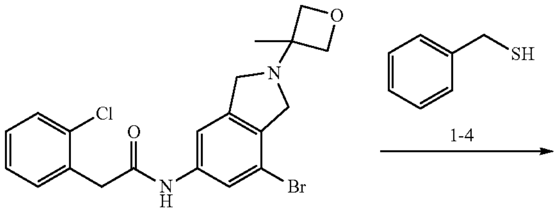

130-5

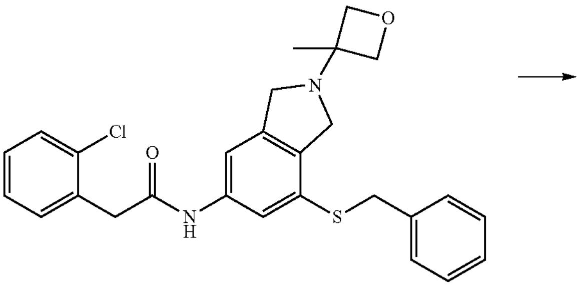

130-6

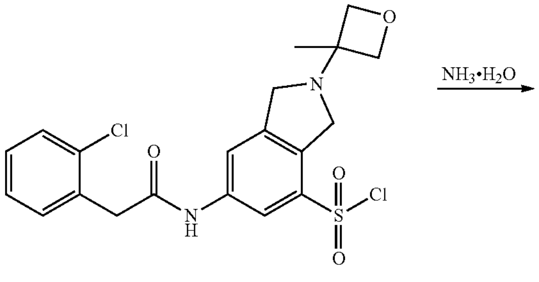

130-7

-continued

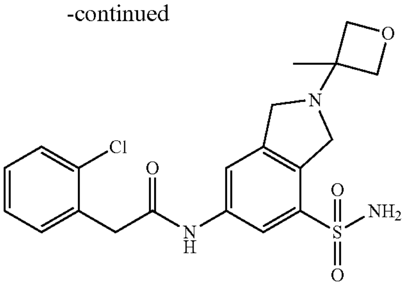

130

Step (1) Preparation of Intermediate 130-3 (4-bromo-2-(3-methyloxetan-3-yl)-6-nitroisoindoline)

Intermediate 130-2 (203 mg, 2.321 mmol) was weighed and dissolved in 20 mL of THF, potassium carbonate (641 mg, 4.642 mmol) was added and stirred at room temperature for 15 min, intermediate 130-1 (900 mg, 2.321 mmol) was added, and the reaction solution was reacted at room temperature overnight. After some reaction starting materials were not completely reacted as indicated by thin-layer chromatography, the extension time was invalid, then the reaction solution was added with water and extracted with EA, and the organic phase was washed with saturated saline, dried over sodium sulfate, and purified by column chromatography (PE/EA=5/1) to give a crude product (340 mg) in the form of a light yellow solid.

Step (2) Preparation of Intermediate 130-4 (7-bromo-2-(3-methyloxetan-3-yl)isoindolin-5-amine)

Intermediate 130-3 (340 mg, 1.086 mmol) was weighed and dissolved in 20 mL of ethanol and 5 mL of water, iron powder (305 mg, 5.429 mmol) and ammonium chloride (291 mg, 5.429 mmol) were added, and after the addition was completed, the mixture was reacted at 60° C. for 3 h. After the reaction starting material was completely reacted as indicated by thin-layer chromatography, the reaction solution was cooled to room temperature, concentrated by rotary evaporation, added with water, and extracted with EA, and the organic phase was washed with saturated brine, dried over sodium sulfate, and purified by column chromatography (PE/EA=3/1) to give a crude product (280 mg) in the form of a yellow oily liquid.

Step (3) Preparation of Intermediate 130-5 (N-(7-bromo-2-(3-methyloxetan-3-yl)isoindol-5-yl)-2-(2-chlorophenyl)acetamide)

2-chlorophenylacetic acid (202 mg, 1.187 mmol) was weighed and dissolved in 20 mL of DMF, HATU (565 mg, 1.484 mmol) and DIEA (384 mg, 2.967 mmol) were added, and after the addition was completed, the reaction solution was reacted at room temperature for 20 min, then added with intermediate 130-4 (280 mg, 0.989 mmol) and reacted at room temperature for 3 h. After the reaction starting material was completely reacted as indicated by thin-layer chromatography, the reaction solution was added with water and extracted with EA, the organic phase was washed with saturated brine, dried over sodium sulfate and purified by column chromatography (PE/EA=2/1) to give a crude product (300 mg) in the form of a light yellow solid.

Step (4) Preparation of Intermediate 130-6 (N-(7-(benzylsulfanyl)-2-(3-methyloxoazetidin-3-yl)isoindol-5-yl)-2-(2-chlorophenyl)acetamide)

Intermediate 130-5 (150 mg, 0.344 mmol) was weighed and dissolved in 10 mL of dioxane, $Pd_2(dba)_3$ (32 mg, 0.034 mmol), Xantphos (20 mg, 0.034 mmol), benzylthiol (65 mg, 0.516 mmol) and DIEA (134 mg, 1.033 mmol) were added sequentially, and after the addition was completed, the reaction solution was purged with $N_2$ and reacted at 100° C. overnight. After the reaction starting material was completely reacted as detected by LCMS, the reaction solution was cooled to room temperature, added with water, and extracted with EA, and the organic phase was washed with saturated brine, dried over sodium sulfate and purified by prep-TLC (PE/EA=1/1) to give the product (100 mg) in the form of a yellow oily liquid.

Step (5) Preparation of Intermediate 130-7 (6-(2-(2-chlorophenyl)acetamido)-2-(3-methyloxoazetidin-3-yl)isoindoline-4-sulfonyl chloride)

Intermediate 130-6 (50 mg, 0.104 mmol) was weighed and dissolved in 2 mL of acetonitrile, 0.3 mL of glacial acetic acid and 0.25 mL of water were added, and after the addition was completed, the reaction solution was cooled to 0° C., then added with 1,3-dichloro-5,5-dimethylhydantoin (52 mg, 0.261 mmol) and reacted for 0.5 h at 0° C., and then heated to room temperature and reacted for 1 h. After the reaction starting material was reacted completely and a product was generated as detected by LCMS, the reaction solution was directly used in the next step without treatment (The reason is that the sulfonyl chloride was unstable).

Step (6) Preparation of 2-(2-chlorophenyl)-N-(2-(3-methyloxetan-3-yl)-7-sulfamoylisoindolin-5-yl)acetamide At 0° C., the intermediate 130-7 reaction solution was added dropwise to 1 mL of aqueous ammonia and then reacted at 0° C. for 10 min. After a product was generated as detected by LCMS, the reaction solution was added with water and extracted with EA, and the organic phase was washed with saturated brine, dried over sodium sulfate, and purified by prep-HPLC (inseparable) and prep-TLC (PE/EA=1/1) to give the product (11.2 mg) in the form of a white solid. LC-MS: $[M+H]^+$=436.10.

$^1H$ NMR (400 MHz, dmso) δ 10.57 (s, 1H), 7.95 (s, 1H), 7.75 (s, 1H), 7.43 (ddd, J=9.3, 5.3, 2.2 Hz, 2H), 7.39 (s, 2H), 7.34-7.29 (m, 2H), 4.75 (d, J=6.2 Hz, 2H), 4.28 (d, J=6.2 Hz, 2H), 4.23 (s, 2H), 4.06 (s, 2H), 3.85 (s, 2H), 1.46 (s, 3H).

Example 131

Compound No. 131

2-(2-chlorophenyl)-N-(2-(4-fluorobenzoyl)-7-sulfamoylisoindolin-5-yl)acetamide

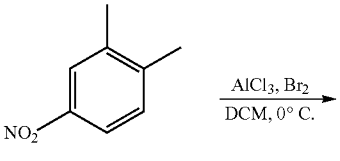

131-1

-continued
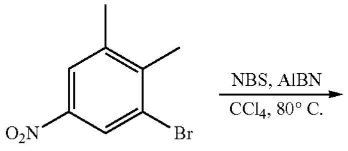
131-2
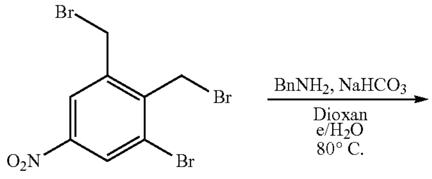
131-3
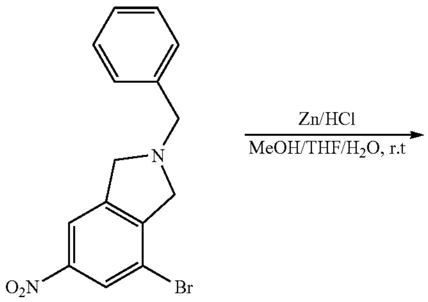
131-4
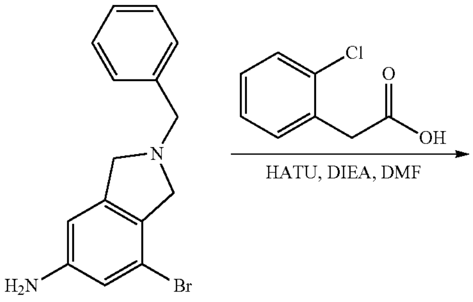
131-5
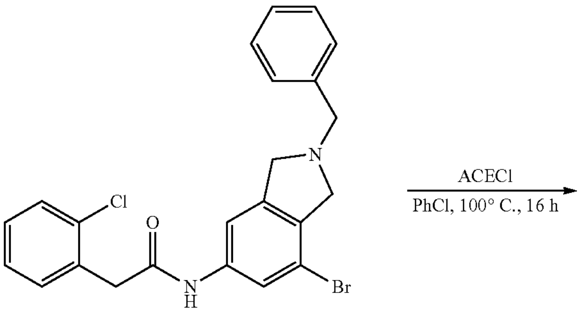
131-6
-continued
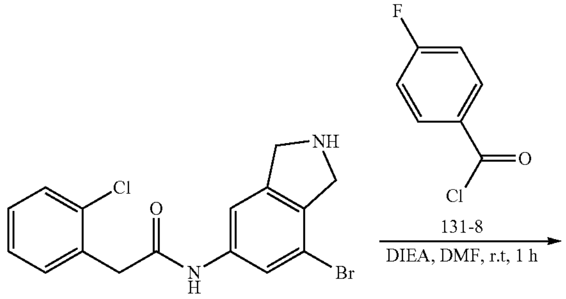
131-7
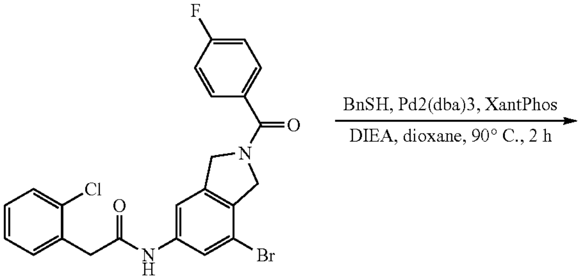
131-9
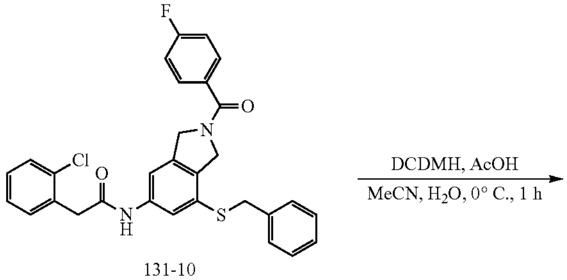
131-10
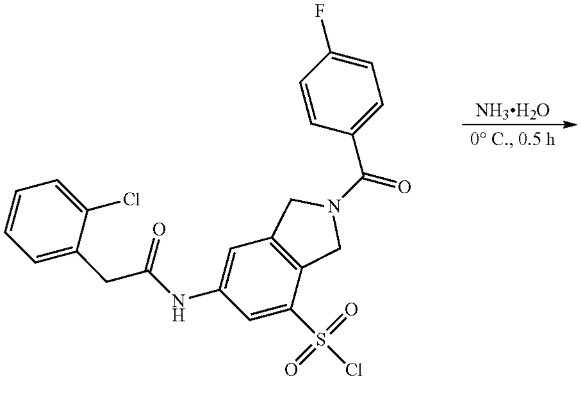
131-11

-continued

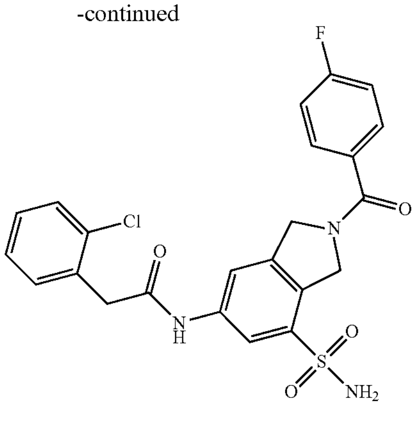

131

Step (1) Preparation of Intermediate 131-2 (1-bromo-2,3-dimethyl-5-nitrobenzene)

Intermediate 131-1 (1,2-dimethyl-4-nitrobenzene) (20 g, 0.132 mol) was dissolved in DCM (300 mL), $AlCl_3$ (44.1 g, 0.331 mol) was added and stirred at 0° C. for 1 h, the reaction solution was added dropwise with $Br_2$ (31.7 g, 0.198 mol), and after the dropwise addition was completed, the reaction solution was stirred at room temperature for 16 h, (wherein all operations were performed under nitrogen atmosphere). After the reaction was completed, the reaction solution was added to saturated aqueous $Na_2SO_3$ solution (300 mL) at 0° C., and the resulting solution was extracted with DCM (200 mL×3). The organic phase was concentrated by rotary evaporation to give a crude product which was purified by column chromatography ($SiO_2$, washed with petroleum ether) to give intermediate 131-2 (25 g, 82% yield) in the form of a light yellow solid.

Step (2) Preparation of Intermediate 131-3 (1-bromo-2,3-bis(bromomethyl)-5-nitrobenzene)

Intermediate 131-2 (10 g, 43.5 mmol) was dissolved in $CCl_4$ (200 mL), AIBN (713 mg, 4.35 mmol) and NBS (27.1 g, 152 mmol) were added, the reaction solution was stirred at 80° C. for 16 h under $N_2$ atmosphere, and after the reaction was completed, the reaction solution was washed with water (300 mL) and extracted with EtOAc (100 mL×3). The organic phase was concentrated by rotary evaporation to give a crude product which was purified by column chromatography ($SiO_2$, petroleum ether/ethyl acetate=1/0-20/1) to give intermediate 131-3 (10 g, 59% yield) in the form of a light yellow oil.

Step (3) Preparation of Intermediate 131-4 (2-benzyl-4-bromo-6-nitroisoindoline)

Intermediate 131-3 (10 g, 25.8 mmol) was dissolved in a mixed solution of dioxane (150 mL) and $H_2O$ (30 mL), then benzylamine (2.76 g, 25.8 mmol) and $NaHCO_3$ (4.33 g, 51.6 mmol) were added sequentially, and the mixture was stirred at 80° C. for 2 h. After the reaction was completed, the reaction solution was added to water (300 mL), the resulting solution was extracted with ethyl acetate (200 mL×3), and the organic phase was concentrated by rotary evaporation to give a crude product which was purified by silica gel column chromatography (petroleum ether/ethyl acetate=1/0-20/1) to give intermediate 131-4 (5 g, 58% yield) in the form of a brown oil. LCMS: NB190125-87-03, ESI(+) m/z=-(no product mass) $[M+1]^+$.

Step (4) Preparation of Intermediate 131-5 (2-benzyl-7-bromoisoindoline-5-amine)

Intermediate 131-4 (5 g, 15.0 mmol) was dissolved in a mixed solution of MeOH (60 mL) and THF (40 mL), then zinc powder (9.75 g, 150 mmol) and HCl (6 M in $H_2O$, 15 mL) were added sequentially, and the reaction solution was stirred at 25° C. for 2 h. After the reaction was completed, the reaction solution was added to water (300 mL), pH was adjusted to 8 with saturated aqueous $NaHCO_3$ solution, the resulting solution was extracted with ethyl acetate (200 mL×3), and the organic phase was concentrated by rotary evaporation to give a crude product which was purified by silica gel column chromatography (petroleum ether/ethyl acetate=20/1-0/1) to give intermediate 131-5 (3.2 g, 70% yield) in the form of a brown oil. LCMS: NB190125-88-01, ESI(+) m/z=303.00 $[M+1]^+$.

$^1$H NMR (400 MHz, DMSO-$d_6$) δ 7.35 (s, 4H), 7.27 (s, 1H), 6.57 (s, 1H), 6.40 (s, 1H), 5.23 (s, 2H), 3.81 (s, 4H), 3.65 (s, 2H).

Step (5) Preparation of Intermediate 131-6 (N-(2-benzyl-7-bromoisoindolin-5-yl)-2-(2-chlorophenyl) acetamide)

Intermediate 131-5 (3.2 g, 10.6 mmol), intermediate 1-12 (2-chlorophenylacetic acid) (2.7 g, 14.4 mmol), HATU (6.02 g, 14.4 mmol) and DIEA (2.72 g, 21.1 mmol) were sequentially dissolved in DMF (32 mL) and stirred at room temperature for 12 h. After the reaction was completed, the reaction solution was diluted with water (100 mL) and extracted with ethyl acetate (80 mL×3). The organic phases were combined, washed with saturated brine, dried over anhydrous sodium sulfate, and filtered, and the filtrate was concentrated under reduced pressure to give a crude product which was purified by silica gel column chromatography (PE/EA=100/1-0/1) to give intermediate 131-6 (3.5 g, 72.7% yield) in the form of a black solid. LCMS: NB190124-29-08, ESI(+) m/z=456.9 $[M+1]^+$.

Step (6) Preparation of Intermediate 131-7 (N-(7-bromoisoindolin-5-yl)-2-(2-chlorophenyl)acetamide)

Intermediate 131-6 (400 mg, 0.877 mmol) was dissolved in PhCl (10 mL), ACECl (376 mg, 2.63 mmol) and a 4A molecular sieves (5 g) were added, and the reaction solution was stirred at 100° C. for 16 h, added with MeOH (5 mL), then stirred at room temperature for 10 min, and filtered. The filtrate was washed with water (50 mL) and extracted once with ethyl acetate (30 mL), the organic phase was discarded, the aqueous phase was adjusted to pH=9 with $NaHCO_3$, and then extracted with ethyl acetate, and the organic phase was concentrated by rotary evaporation to give intermediate 131-7 (100 mg, 31% yield) in the form of an oil. LCMS: NB190125-96-05, ESI(+) m/z=366.95 $[M+1]^+$.

Step (7) Preparation of Intermediate 131-9 (N-(7-bromo-2-(4-fluorobenzoyl)isoindolin-5-yl)-2-(2-chlorophenyl)acetamide)

Intermediate 131-7 (100 mg, 0.273 mmol) was dissolved in DMF (2 mL), DIEA and intermediate 131-8 (p-fluorobenzoyl chloride) were added sequentially, and the mixture was stirred at room temperature for 1 h. The reaction solution was poured into water (50 mL), the resulting solution was extracted with ethyl acetate (40 mL×3), and the organic phase was concentrated by rotary evaporation to give a crude product which was purified by column chromatography ($SiO_2$, petroleum ether/ethyl acetate=10/1-1/1) to give intermediate 131-9 (100 mg, 75% yield) in the form of a white solid. LCMS: NB190125-97-01, ESI(+) m/z=488.95 $[M+1]^+$.

$^1H$ NMR (400 MHz, DMSO-$d_6$) δ 10.44 (d, J=7.2 Hz, 1H), 8.03-8.97 (m, 1H), 7.74-7.67 (m, 2H), 7.48-7.37 (m, 3H), 7.36-7.26 (m, 4H), 4.91 (d, J=24.0 Hz, 2H), 4.71 (d, J=29.6 Hz, 2H), 3.84 (d, J=6.8 Hz, 2H).

Step (8) Preparation of Intermediate 131-10 (N-(7-(benzylthio)-2-(4-fluorobenzoyl)isoindolin-5-yl)-2-(2-chlorophenyl)acetamide)

Intermediate 131-9 (100 mg, 0.205 mmol) and benzyl mercaptan (50.8 mg, 0.410 mmol) were dissolved in dioxane (2 mL), then $Pd_2(dba)_3$, XantPhos and DIEA were added, and the mixture was stirred at 90° C. for 2 h under $N_2$ atmosphere. The reaction solution was poured into water (50 mL), the resulting solution was extracted with ethyl acetate (40 mL×3), and the organic phase was concentrated by rotary evaporation to give a crude product which was purified by column chromatography ($SiO_2$, petroleum ether/ethyl acetate=20/1-1/1) to give intermediate 131-10 (80 mg, 73% yield) in the form of a white solid. LCMS: NB190125-98-01, ESI(+) m/z=531.15 $[M+1]^+$.

Step (9) Preparation of Compound 131 (2-(2-chlorophenyl)-N-(2-(4-fluorobenzoyl)-7-sulfamoylisoindolin-5-yl)acetamide)

Intermediate 131-10 (75 mg, 0.141 mmol) was dissolved in MeCN (0.5 mL), then AcOH (42.3 mg, 0.705 mmol) and $H_2O$ (0.1 mL) were added, finally 1,3-dichloro-5,5-dimethylhydantoin (27.8 mg, 0.424 mmol) was added, and the reaction solution was stirred at room temperature for 1 h and then added dropwise to aqueous ammonia (2 mL) with stirring, and after the dropwise addition was completed, the resulting solution was stirred at room temperature for 0.5 h. After the reaction was completed, the reaction solution was added to water (50 mL), the resulting solution was extracted with ethyl acetate (40 mL×3), and the organic phase was concentrated by rotary evaporation to give a crude product which was purified by preparative reverse phase chromatography to give compound 131 (15.7 mg, 23% yield) in the form of a white solid. LCMS: NB190103-38-04, ESI(+) m/z=488.05 $[M+1]^+$.

$^1H$ NMR (400 MHz, DMSO-$d_6$) δ 10.47 (d, J=11.2 Hz, 1H), 8.04 (d, J=12.4 Hz, 1H), 7.86 (s, 1H), 7.74-7.65 (m, 2H), 7.49-7.24 (m, 6H), 5.08 (s, 1H), 4.95 (s, 1H), 4.90 (s, 1H), 4.82 (s, 1H), 3.85 (s, 2H).

Example 132

Compound No. 132

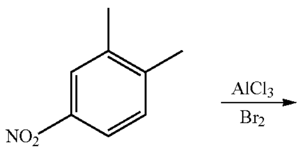

131-1

-continued

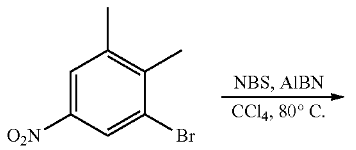

131-2

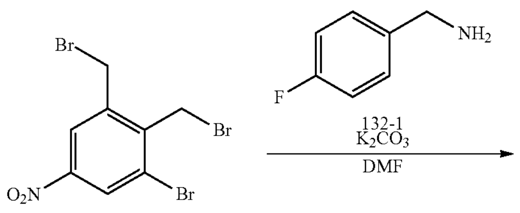

132-1

131-3

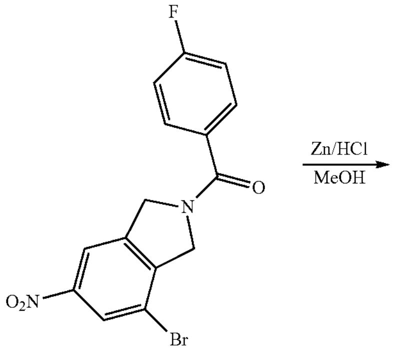

132-2

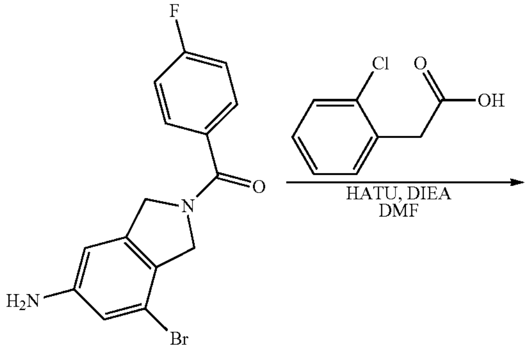

132-3

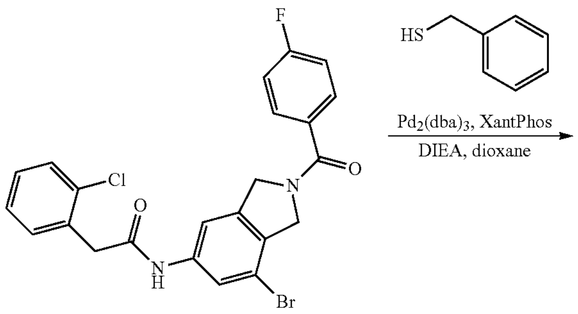

132-4

-continued

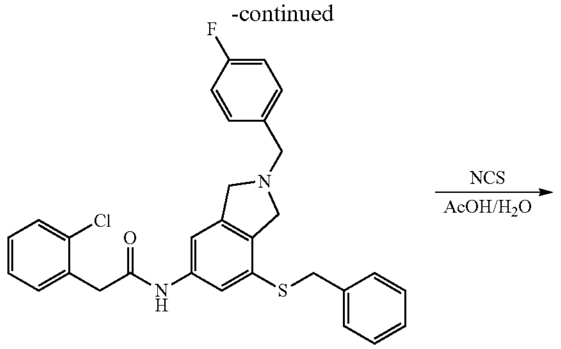

132-5

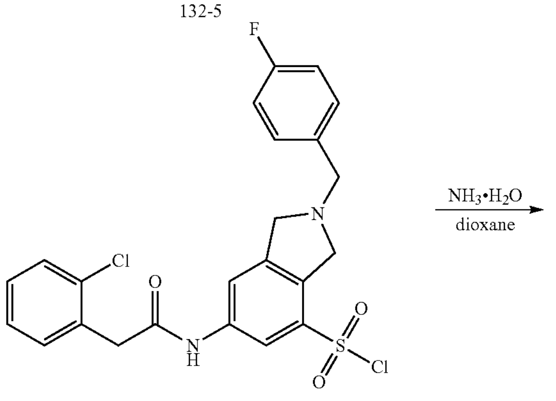

132-6

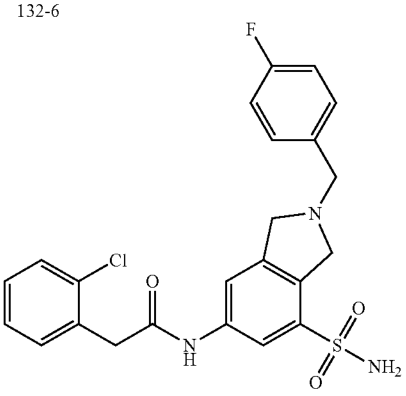

132

Step (1) Preparation of Intermediate 132-2 (4-bromo-2-(4-fluorophenylmethyl)-6-nitroisoindoline)

Intermediate 131-3 (2.5 g, 6.44 mmol) and intermediate 132-1 (4-fluorobenzylamine) (1.21 g, 9.66 mmol) were dissolved in DMF (50 mL), then $K_2CO_3$ (1.78 g, 12.9 mmol) was added, and the reaction solution was stirred at room temperature for 2 h. After the reaction was completed as detected by thin-layer chromatography (petroleum ether: ethyl acetate=10:1), the reaction solution was washed with water (200 mL) and extracted with EA (100 mL×3), and the organic phase was washed with saturated brine and subjected to rotary evaporation to give a crude product which was purified by silica gel column chromatography (petroleum ether:ethyl acetate=0:1-20:1) to give intermediate 132-2 (500 mg, 22% yield) in the form of a light yellow solid. LCMS: NB190125-80-02, ESI(+) m/z=350.95 $[M+1]^+$.

Step (2) Preparation of Intermediate 132-3 (7-bromo-2-(4-fluorobenzyl)isoindol-5-amine)

Intermediate 132-2 (400 mg, 1.14 mmol), Zn (744.68 mg, 11.40 mmol) and HCl (1153.52 mg, 11.40 mmol) were dissolved in MeOH (3.5 mL). The reaction solution was stirred at room temperature for 2 h. After the reaction was completed as detected by thin-layer chromatography (PE: EA=5:1, Rf=0.2, 254 nm), pH was adjusted to 8 with saturated $NaHCO_3$, the reaction solution was extracted with EA, and the organic phase was washed with saturated brine and subjected to rotary evaporation to give intermediate 132-3 (350 mg, 95.6% yield, crude) in the form of a light yellow solid.

Step (3) Preparation of Intermediate 132-4 (N-(7-bromo-2-(4-fluorobenzyl)isoindol-5-yl)-2-(2-chlorophenyl)acetamide)

Intermediate 132-3 (350 mg, 934.02 μmol), intermediate 1-12 (2-chlorophenylacetic acid) (278.84 mg, 278.84 μmol), HATU (621.53 mg, 1.63 mmol) and DIEA (281.68 mg, 2.18 mmol) were dissolved in DMF (3.5 mL). The reaction solution was stirred at room temperature for 12 h. After the reaction was completed as detected by thin-layer chromatography (PE:EA=1:1, Rf=0.4, 254 nm), the reaction solution was added with water and extracted with EA, and the organic phase was washed with saturated brine, dried, and concentrated by rotary evaporation to give intermediate 132-4 (420 mg, 88.6% yield, crude) in the form of a light yellow solid.

Step (4) Preparation of Intermediate 132-5 (N-(7-(benzylthio)-2-(4-fluorobenzyl)isoindol-5-yl)-2-(2-chlorophenyl)acetamide)

Intermediate 132-4 (370 mg, 886.51 μmol), $Pd_2(dba)_3$ (243.54 mg, 265.95 μmol), XantPhos (153.89 mg, 265.95 μmol), intermediate 1-4 (benzylthiol) (330.31 mg, 2.66 mmol) and DIEA (229.16 mg, 1.77 mmol) were dissolved in dioxane (5 mL) and stirred at 90° C. for 3 h. After the reaction was completed as detected by thin-layer chromatography (PE:EA=2:1, Rf=0.5, 254 nm), the reaction solution was added with water and then extracted with EA, and the organic phase was washed with saturated brine, dried, and concentrated by rotary evaporation to give intermediate 132-5 (280 mg, 69.3% yield, light yellow).

Step (5) Preparation of Intermediate 132-6 (6-(2-(2-chlorophenyl)acetamide)-2-(4-fluorobenzyl)isoindole-4-sulfonyl chloride)

Intermediate 132-5 (230 mg, 444.82 μmol) and NCS (64.56 mg, 2.21 mmol) were added to AcOH (3 mL) and $H_2O$ (1 mL). The reaction solution was stirred at room temperature for 13 h. After the reaction was completed as detected by thin-layer chromatography (DCM:MeOH=10:1, Rf=0.7, 254 nm), the reaction solution was directly used in the next step without treatment to give intermediate 132-6 (216 mg).

Step (6) Preparation of Compound 132 (2-(2-chlorophenyl)-N-(2-(4-fluorobenzyl)-7-sulfamoyliodo-5-yl)acetamide)

Intermediate 132-6 (216 mg, 444.82 μmol) was added to $NH_3 \cdot H_2O$ (40 mL) and dioxane (80 mL). The reaction solution was stirred at room temperature for 1 h. After the reaction was completed as detected by thin-layer chromatography (DCM:MeOH=10:1, Rf=0.4, 254 nm), the reaction solution was added with water and extracted with EA, and the organic phase was washed with saturated brine, dried, and concentrated by rotary evaporation to give compound 132 (8.2 mg, 3.9% yield, 95.559% purity) in the form of a white solid. LCMS: NB190046-23-01, ESI(+) m-z=474.00 $[M+1]^+$. HPLC: NB190046-23-01, $^1$H NMR (400 MHz, DMSO) δ10.98 (s, 1H), 10.69 (s, 1H), 8.05 (s, 1H), 7.89 (s, 1H), 7.66 (d, J=23.20 Hz, 4H), 7.43 (s, 2H), 7.43-7.33 (m, 4H), 4.87-4.66 (m, 6H), 3.87 (s, 2H).

Example 133

Compound No. 133

2-(2-chlorophenyl)-N-(2-(1,1-difluoropropyl)-4-sulfamoyl-2H-indazol-6-yl)acetamide

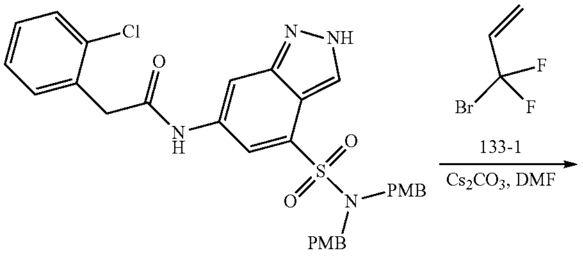

3-1

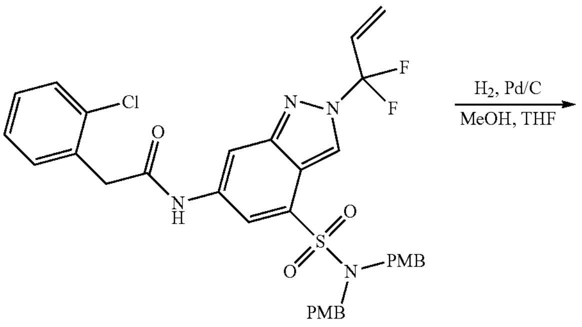

133-2

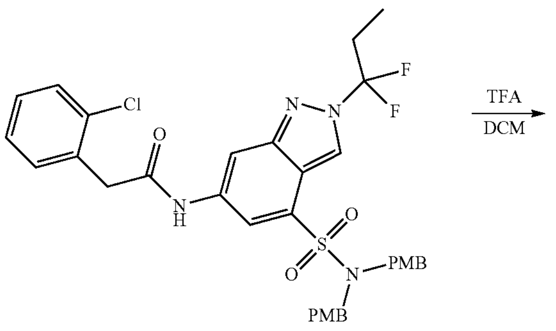

133-3

-continued

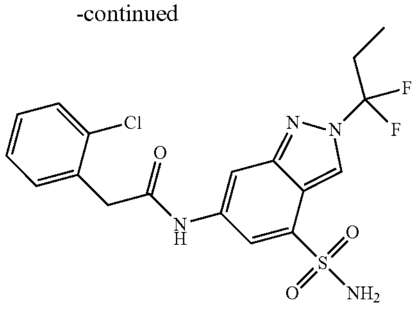

133

Step (1) Preparation of Intermediate 133-2 (N-(4-(N,N-bis(4-methoxybenzyl)sulfamoyl)-2-(1,1-difluoroallyl)-2H-indazol-6-yl)-2-(2-chlorophenyl)acetamide)

Intermediate 3-1 (500 mg, 0.8 mmol) was dissolved in DMF (5 mL), intermediate 133-1 (named) (188 mg, 1.2 mmol) and cesium carbonate (520 mg, 1.6 mmol) were added, and the reaction solution was reacted at room temperature for 2 h. After the reaction was completed as detected by TLC, the reaction solution was added with water and extracted with ethyl acetate, dried and concentrated, and the crude product was purified by column chromatography to give intermediate 133-2 (120 mg, 21.6% yield) in the form of a yellow oil. LC-MS: $[M+H]^+$=681.15.

Step (2) Preparation of Intermediate 133-3 (N-(4-(N,N-bis(4-methoxybenzyl)sulfamoyl)-2-(1,1-difluoropropyl)-2H-indazol-6-yl)-2-(2-chlorophenyl)acetamide)

Intermediate 133-2 (300 mg) was dissolved in a mixed solvent of MeOH (15 mL)/THF (3 mL), Pd/C (40 mg) was added, and the reaction solution was stirred at room temperature overnight under $H_2$ atmosphere, filtered and concentrated by rotary evaporation to give 230 mg of a yellow solid. LC-MS: $[M+H]^+$=683.20.

Step (3) Preparation of 2-(2-chlorophenyl)-N-(2-(1,1-difluoropropyl)-4-sulfamoyl-2H-indazol-6-yl)acetamide Intermediate 133-3 (150 mg) was dissolved in DCM (2 mL), TFA (2 mL) was added, and the reaction solution was reacted at 40° C. for 4 h and concentrated to give 20 mg of a crude product which was purified by preparative chromatography to give 6.2 mg of a white solid. LC-MS: $[2M+H]^+$=885.10.

$^1$H NMR (400 MHz, dmso) δ 10.51 (s, 2H), 8.51 (d, J=10.4 Hz, 1H), 8.22 (s, 2H), 7.71 (d, J=1.5 Hz, 2H), 7.51-7.38 (m, 4H), 7.33-7.25 (m, 2H), 6.36-6.28 (m, 1H), 6.17 (t, J=4.3 Hz, 1H), 6.06-6.01 (m, 1H), 4.60 (t, J=7.0 Hz, 2H), 3.86 (s, 2H).

Example 134

Compound No. 134

2-(2-chlorophenyl)-N-(2-(1,1-difluoroallyl)-4-sulfamoyl-2H-indazol-6-yl)acetamide

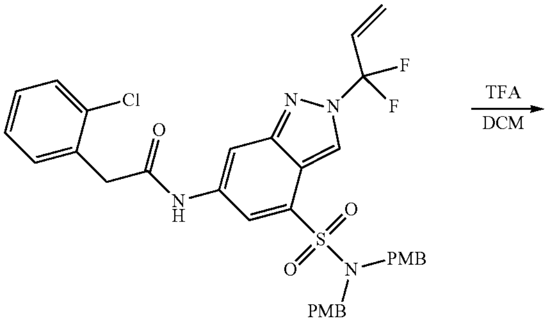

133-2

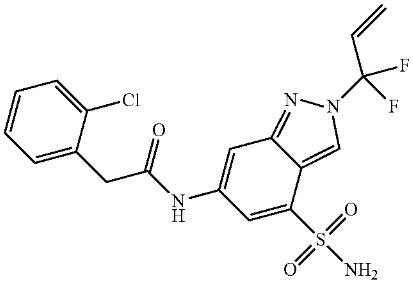

134

Step (1) Preparation of 2-(2-chlorophenyl)-N-(2-(1,1-difluoroallyl)-4-sulfamoyl-2H-indazol-6-yl)acetamide Intermediate 133-2 (60 mg, 0.088 mmol) was dissolved in DCM (2 mL), TFA (2 mL) was added, and the reaction solution was reacted at 55° C. for 3 h and concentrated to give 80 mg of a crude product which was separated by prep-HPLC using a $H_2O$/CAN system and lyophilized to give compound 134 (12.5 mg, 99.44% purity, 31.5% yield) in the form of a white solid. LC-MS: $[M]^+$=441.

$^1$H NMR (400 MHz, dmso) δ 10.51 (s, 1H), 8.52 (s, 1H), 8.22 (s, 1H), 7.72 (s, 1H), 7.49 (s, 2H), 7.45-7.40 (m, 2H), 7.33-7.26 (m, 2H), 5.22-5.04 (m, 3H), 3.86 (s, 2H).

Example 136

Compound No. 136

N-(2-(difluoromethyl)-4-sulfamoyl-2H-indazol-6-yl)-2-(2-hydroxycyclohexyl)acetamide

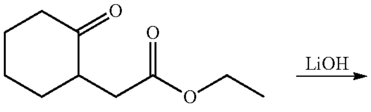

136-1

-continued

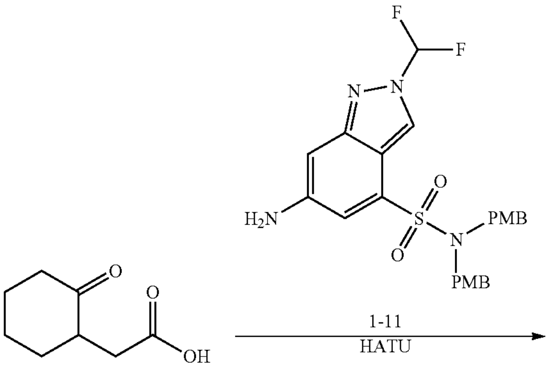

136-2

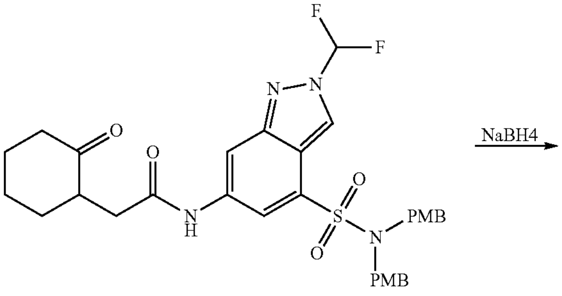

136-3

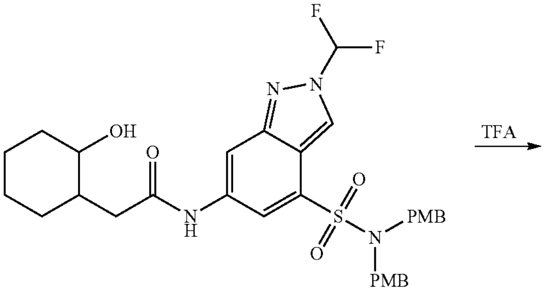

136-4

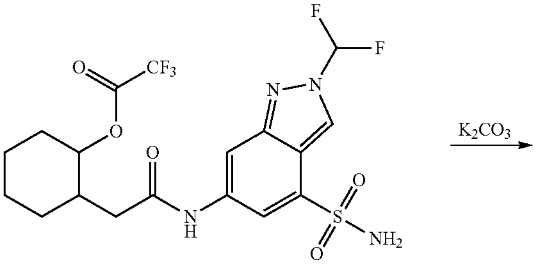

136-5

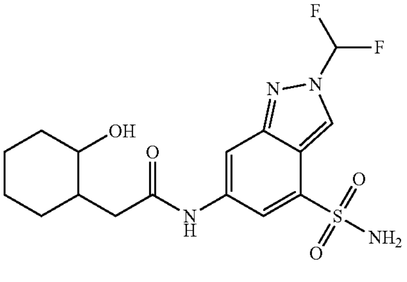

136

Step (1) Preparation of Intermediate 136-2 (2-(2-carbonylcyclohexyl)acetic acid)

Intermediate 136-1 (ethyl 2-(2-carbonylcyclohexyl)acetate) (500 mg, 2.71 mmol) was dissolved in THF/$H_2O$ (10/10 mL), LiOH (650 mg, 27.1 mmol) was added, the reaction solution was stirred at 60° C. for 24 h, concentrated, and added with water, pH was adjusted to about 5 with 1 M hydrochloric acid, the reaction solution was extracted twice with DCM, the organic phases were combined, washed with saturated brine, dried over anhydrous sodium sulfate, and filtered, and the filtrate was concentrated to give intermediate 136-2 (420 mg, 90% yield, crude) in the form of a light yellow oil.

Step (2) Preparation of Intermediate 136-3 (N-(4-(N,N-bis(4-methoxybenzyl)sulfamoyl)-2-(difluoromethyl)-2H-indazol-6-yl)-2-(2-carbonylcyclohexyl)acetamide)

Intermediate 136-2 (420 mg, 2.1 mmol), intermediate 1-11 (200 mg, 0.2 mmol), HATU (1.1 g, 3.1 mmol) and DIEA (820 mg, 6.3 mmol) were dissolved in DMF (5 mL) and stirred at room temperature for 7 h. After the reaction was completed as detected by TLC, the reaction solution was added with water (30 mL) and extracted twice with ethyl acetate (10 mL), the organic phases were combined, washed with saturated brine, dried over anhydrous sodium sulfate, and filtered, and the filtrate was concentrated under reduced pressure and then purified by column chromatography to give intermediate 136-3 (110 mg, 42% yield) in the form of a yellow oil.

Step (3) Preparation of Intermediate 136-4 (N-(4-(N,N-bis(4-methoxybenzyl)sulfamoyl)-2-(difluoromethyl)-2H-indazol-6-yl)-2-(2-hydroxycyclohexyl)acetamide)

Intermediate 136-3 (90 mg, 0.14 mmol) was dissolved in THF (1 mL), and sodium borohydride (10.4 mg, 0.28 mmol) was added at 0° C. under $N_2$ atmosphere and stirred for 2 h. After the reaction was completed as detected by TLC, the reaction solution was added with water (5 mL) and extracted twice with ethyl acetate (2 mL), the organic phases were combined, washed with saturated brine, dried over anhydrous sodium sulfate, and filtered, and the filtrate was concentrated under reduced pressure to give intermediate 136-4 (110 mg, 100% yield) in the form of a yellow oil.

Step (4) Preparation of Intermediate 136-5 (2-(2-((2-(difluoromethyl)-4-sulfamoyl-2H-indazol-6-yl)amino)-2-carbonylethyl)cyclohexyl 2,2,2-trifluoroacetate)

Intermediate 136-4 (110 mg, 0.17 mmol) was dissolved in DCM (5 mL), followed by the addition of TFA (5 mL), and the reaction solution was stirred at 55° C. for 16 h. After the reaction was completed as detected by TLC, the reaction solution was concentrated under reduced pressure to give intermediate 136-5 (180 mg, crude) in the form of a yellow oil which was directly used in the next step without purification.

Step (5) Preparation of N-(2-(difluoromethyl)-4-sulfamoyl-2H-indazol-6-yl)-2-(2-hydroxycyclohexyl)acetamide Intermediate 136-5 (180 mg, 0.36 mmol) was dissolved in methanol (5 mL), followed by the addition of potassium carbonate (100 mg, 0.72 mmol), and the mixture was stirred at 40° C. for 16 h. After the reaction was completed as detected by LCMS, the reaction solution was filtered and concentrated to give a crude product which was then separated by prep-HPLC using a $H_2O$/CAN system and lyophilized to give compound 136 (10.6 mg, 99.09% purity, 18.3% yield) in the form of a white solid. LC-MS: $[M+1]^+$=403.

$^1H$ NMR (400 MHz, DMSO) δ 10.29 (d, J=6.7 Hz, 1H), 8.91 (s, 1H), 8.35 (s, 1H), 8.31 (s, 1H), 8.16 (s, 1H), 8.01 (s, 1H), 7.81 (d, J=1.4 Hz, 1H), 7.61 (s, 2H), 3.09-2.98 (m, 1H), 2.83 (dd, J=14.3, 3.8 Hz, 1H), 2.08-1.97 (m, 1H), 1.83 (d, J=8.6 Hz, 1H), 1.68 (dd, J=27.9, 13.6 Hz, 3H), 1.54 (d, J=11.8 Hz, 1H), 1.25-1.07 (m, 3H), 1.02-0.93 (m, 1H).

Example 137

Compound 137

2-(2-chlorophenyl)-N-(2-(4-methoxybenzyl)-4-(S-methylsulfonylimino)-2H-indazol-6-yl)acetamide

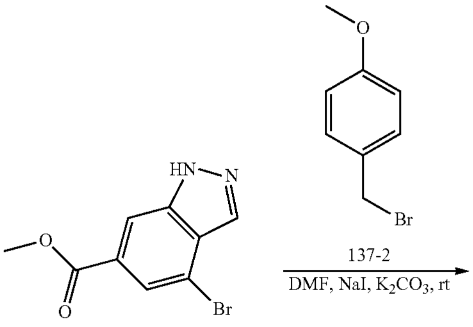

137-1

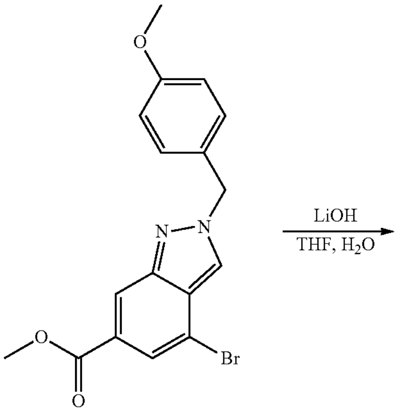

137-3

-continued

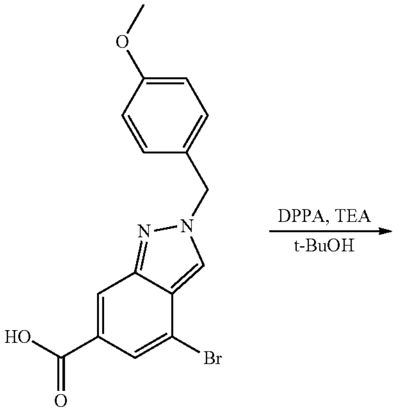

137-4

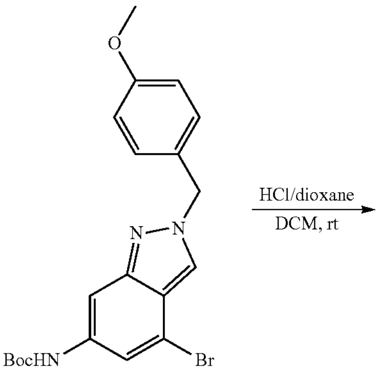

137-5

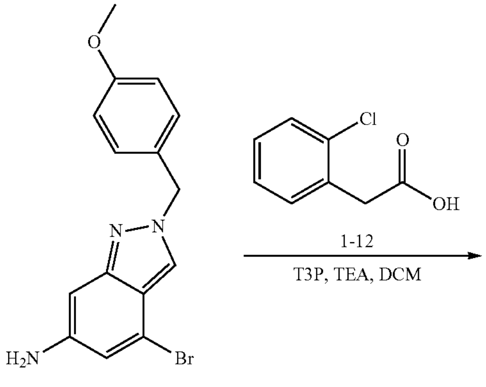

1-12

137-6

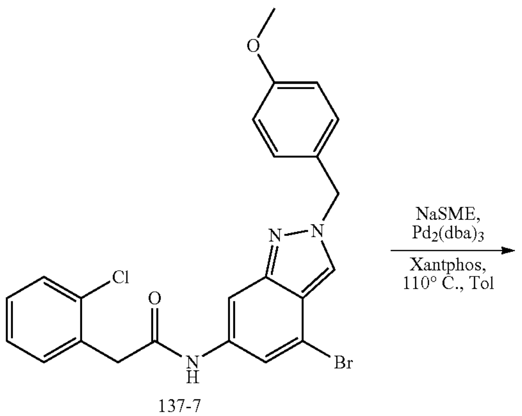

137-7

-continued

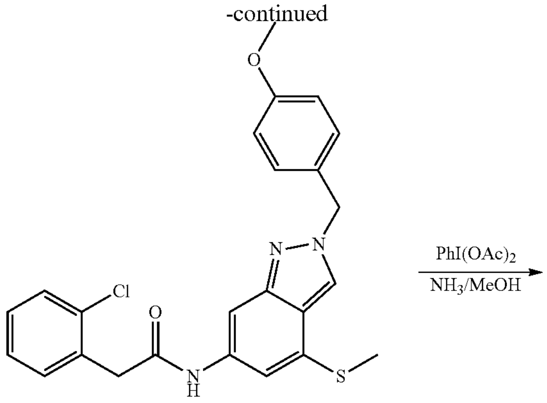

137-8

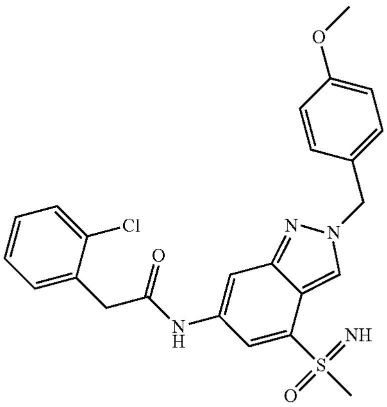

137

Step (1) Preparation of Intermediate 137-3 (methyl 4-bromo-2-(4-methoxybenzyl)-2H-indazole-6-carboxylate)

Intermediate 137-1 (2.50 g) was dissolved in DMF (30 mL), NaI (1.47 g), $K_2CO_3$ (2.03 g) and intermediate 137-2 (2.30 g) were added, and the reaction solution was stirred at room temperature for 3 h. After the reaction starting material was completely reacted as detected by TLC (EA:PE=1:5), the reaction solution was diluted with 50 mL of water and extracted with ethyl acetate (50 mL×3), the organic phases were combined, and the solvent was concentrated by rotary evaporation and separated by column chromatography (EA:PE=1:10). LC-MS: $[M+H]^+$=375.

Step (2) Preparation of Intermediate 67-4 (4-bromo-2-(4-methoxybenzyl)-2H-indazole-6-carboxylic acid)

LiOH (510.6 mg, 21.32 mmol) was dissolved in $H_2O$ (4 mL) to prepare a solution which was added dropwise to a solution of intermediate 137-3 (1.60 g) in THF (12 mL), and the reaction solution was stirred at room temperature for 4 h. After the reaction starting material was completely reacted as detected by TLC (EA:PE=1:2), pH was adjusted to 3 with HCl (aq) (12 M), the system was extracted with DCM (30 mL×3), and the organic phases were combined and concentrated by rotary evaporation. LC-MS: $[M+H]^+$=361.

Step (3) Preparation of Intermediate 137-5 (tert-butyl (4-bromo-2-(4-methoxybenzyl)-2H-indazol-6-yl)carbamate)

Intermediate 137-4 (1.50 g, 4.15 mmol) was dissolved in tert-BuOH (15 mL), DPPA (1.71 g, 6.23 mmol) and triethylamine (840.5 mg, 8.31 mmol) were added, and after the addition was completed, the reaction solution was heated to 80° C. and stirred overnight. After the reaction starting material was completely reacted as detected by TLC (EA:PE=1:2), the reaction was stopped, the solvent was concentrated by rotary evaporation and separated by column chromatography (EA:PE=1:3) to give 700.0 mg of a beige solid. LC-MS: $[M+H]^+$=432.

$^1$H NMR (400 MHz, DMSO-$d_6$) δ (ppm): 9.45 (s, 1H), 8.37 (s, 1H), 7.69 (s, 1H), 7.40 (d, J=1.2 Hz, 1H), 7.34-7.30 (m, 2H), 6.93-6.89 (m, 2H), 5.49 (s, 2H), 3.72 (s, 3H), 1.48 (s, 9H).

Step (4) Preparation of Intermediate 137-6 (4-bromo-2-(4-methoxybenzyl)-2H-indazol-6-amine)

Intermediate 137-5 (670.0 mg, 1.55 mmol) was dissolved in DCM (7 mL), followed by the addition of HCl/dioxane (3 mL, 12.0 mmol), and the reaction solution was stirred at room temperature for 1 h. After the reaction starting material was completely reacted as detected by TLC (EA:PE=1:2), the solvent was concentrated by rotary evaporation, pH was adjusted to 8 with saturated $NaHCO_3$ (aq), and the system was diluted with 50 mL of water and 50 mL of dichloromethane, followed by liquid separation. The organic phase was collected and concentrated by rotary evaporation to give 200.0 mg of a beige solid. LC-MS: $[M+H]^+$=332.

Step (5) Preparation of Intermediate 137-7 (N-(4-bromo-2-(4-methoxybenzyl)-2H-indazol-6-yl)-2-(2-chlorophenyl)acetamide)

Intermediate 1-12 (170.0 mg, 511.74 μmol) was dissolved in DCM (10 mL), intermediate 137-6 (131.0 mg, 767.61 μmol), T3P (244.2 mg, 767.61 μmol) and triethylamine (103.6 mg, 1.02 mmol) were added, and the reaction solution was stirred at room temperature for 3 h. After the reaction starting material was completely reacted as detected by TLC (EA:PE=1:1), the reaction solution was diluted with 50 mL of water and 50 mL of dichloromethane, followed by liquid separation, and the organic phase was collected, concentrated by rotary evaporation, and separated by column chromatography (EA:PE=1:3) to give 250 mg of a beige solid. LC-MS: $[M+H]^+$=484.

Step (6) Preparation of Intermediate 137-8 (2-(2-chlorophenyl)-N-(2-(4-methoxybenzyl)-4-(methylthio)-2H-indazol-6-yl)acetamide)

Intermediate 137-7 (200.0 mg, 412.56 μmol) was dissolved in toluene (20 mL), NaSMe (86.8 mg, 1.24 mmol), $Pd_2(dba)_3$ (37.8 mg, 41.26 μmol), Xantphos (37.8 mg, 41.26 μmol) and $K_2CO_3$ (114.0 mg, 825.12 μmol) were added, and the mixture was heated to 110° C. and stirred overnight under nitrogen atmosphere. After the reaction starting material was completely reacted as detected by TLC (EA:PE=1:1), the solvent was concentrated by rotary evaporation and separated by column chromatography (EA:PE=1:2) to give 190 mg of a beige solid. LC-MS: $[M+H]^+$=452.

Step (7) Preparation of 2-(2-chlorophenyl)-N-(2-(4-methoxybenzyl)-4-(S-methylsulfonylimino)-2H-indazol-6-yl)acetamide Intermediate 137-8 (160.0 mg, 354.0 μmol) was dissolved in MeOH (1.8 mL) to prepare 0.2 M solution A, $PhI(OAc)_2$ (228.0 mg, 708.02 mmol) was dissolved in MeOH (1.8 mL) to prepare 0.4 M solution B, and $NH_3$/MeOH (7 mol/L) (0.2 mL) was diluted with MeOH (3.3 mL) to prepare 0.4 M solution C. To a flash were added solution A (1.8 mL), solution B (1.8 mL) and solution C (1.8 mL) at 0° C. at the same time, and the reaction solution was stirred at 0° C. for 15 min. After the reaction starting material was completely reacted as detected by TLC (EA:PE=1:2), the solvent was concentrated by rotary evaporation and separated by preparative liquid chromatography using a formic acid and acetonitrile/water system to give 40 mg of a beige solid. LC-MS: $[M+H]^+$=483.00.

$^1$H NMR (400 MHz, DMSO-$d_6$) δ (ppm): 10.56 (s, 1H), 8.64 (s, 1H), 8.30 (s, 1H), 7.77 (d, J=1.6 Hz, 1H), 7.48-7.42 (m, 2H), 7.38-7.34 (m, 2H), 7.33-7.28 (m, 2H), 6.93-6.89 (m, 2H), 5.58 (s, 2H), 4.41 (s, 1H), 3.88 (s, 2H), 3.72 (s, 3H), 3.10 (s, 3H).

Example 138

Corresponding Compound Nos. 138+138A (S)-2-(2-chlorophenyl)-N-(2-(4-fluorophenylmethyl)-4-(S-methylsulfonimidoyl)-2H-indazol-6-yl) acetamide (Compound 138) and (R)-2-(2-chlorophenyl)-N-(2-(4-fluorophenylmethyl)-4-(S-methylsulfonimidoyl)-2H-indazol-6-yl)acetamide (Compound 138A)

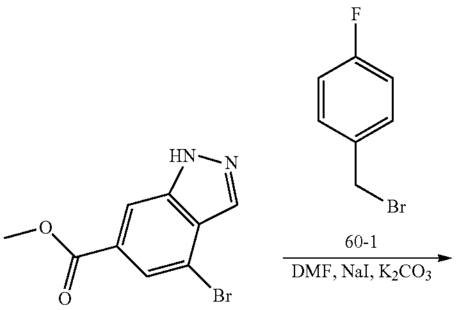

1-1

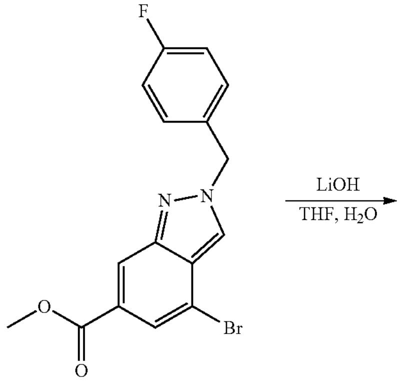

138-1

-continued

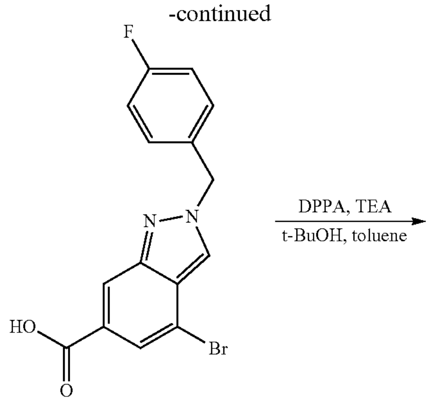

138-2

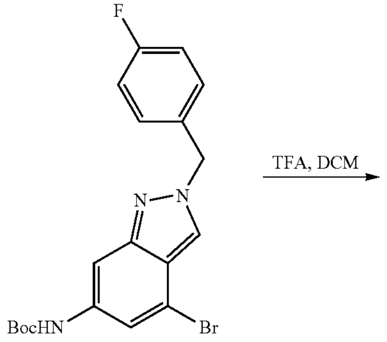

138-3

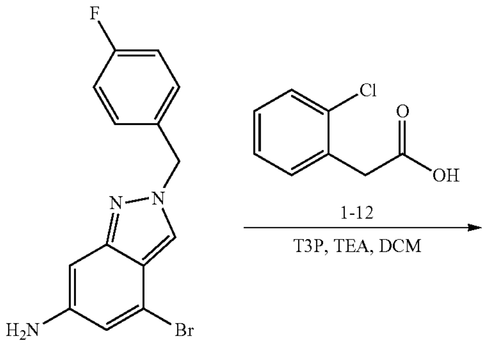

138-4

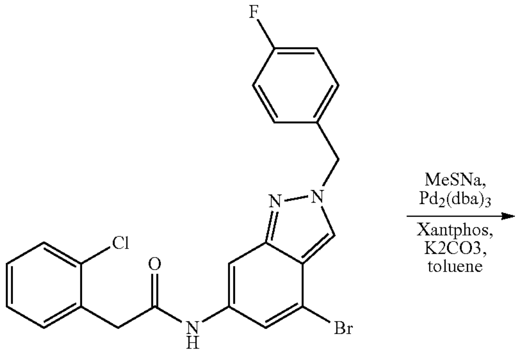

138-5

-continued

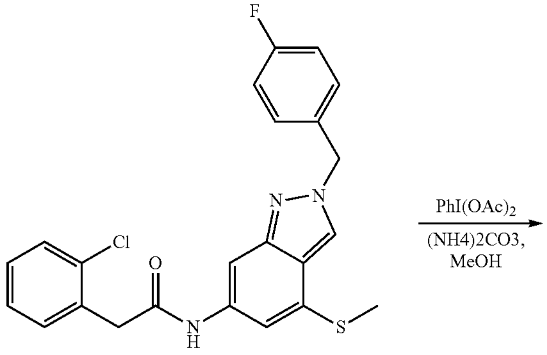

138-6

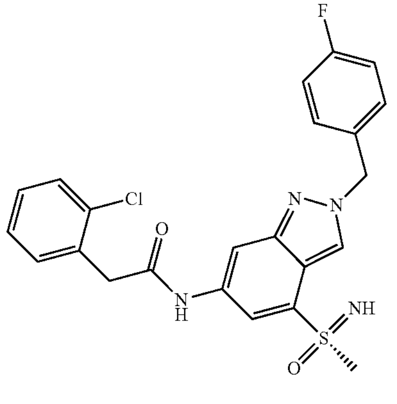

138

+

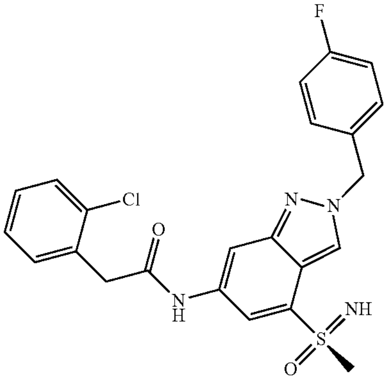

138A

Step (1) Preparation of Intermediate 138-1 (methyl 4-bromo-2-(4-fluorophenylmethyl)-2H-indazole-6-carboxylate)

To the reaction flask were added intermediate 1-1 (9.2 g, 44.06 mmol), intermediate 88-1 (8.18 g, 43.29 mmol), NaI (5.41 g, 44.06 mmol), $K_2CO_3$ (7.48 g, 54.1 mmol) and DMF (90 mL), and the reaction solution was stirred at room temperature for 3 h and poured into water, the resulting solution was extracted with EA, and the organic phase was concentrated and stirred with silica gel and purified by column chromatography to give intermediate 138-1 (5.5 g) in the form of a yellow solid. The product was confirmed by TLC (PE/EA=6/1).

Step (2) Preparation of Intermediate 138-2 (4-bromo-2-(4-fluorophenylmethyl)-2H-indazole-6-carboxylic acid)

To a reaction flask were added intermediate 138-1 (4.4 g, 12.11 mmol), LIOH·$H_2O$ (2.54 g, 60.57 mmol), THF (40 mL) and $H_2O$ (10 mL), and the reaction solution was stirred at room temperature overnight, adjusted to pH=5 with an aqueous HCl solution, and extracted with EA. The organic phase was concentrated to dryness to give intermediate 138-2 (4.1 g) in the form of a light yellow solid. LC-MS: NB190044-31-02, ESI(+) m/z=351 [M+1].

Step (3) Preparation of Intermediate 138-3 (tert-butyl (4-bromo-2-(4-fluorophenylmethyl)-2H-indazol-6-yl)carbamate)

Intermediate 138-2 (4.1 g, 11.74 mmol) was dissolved in tert-BuOH (40 mL) and toluene (80 mL), DPPA (4.8 g, 17.61 mmol) and TEA (2.38 g, 23.48 mmol) were added to the reaction flask, and the reaction solution was stirred at 80° C. overnight under $N_2$ atmosphere and poured into water, the resulting solution was extracted with EA, the organic phase was concentrated and stirred with silica gel and purified by column chromatography to give intermediate 138-3 (680 mg) in the form of a yellow solid, LC-MS: NB190044-34-01, ESI(+) m/z=422 [M+1].

Step (4) Preparation of Intermediate 138-4 (4-bromo-2-(4-fluorophenylmethyl)-2H-indazol-6-amine)

Intermediate 138-3 (680 mg, 1.62 mmol) was dissolved in DCM (6 mL), TFA (3 mL) was added to the reaction flask, and the reaction solution was stirred at room temperature for 1.5 h. pH was adjusted to about 8 with an aqueous sodium bicarbonate solution, the reaction solution was extracted with EA, and the organic phase was concentrated to dryness to give intermediate 138-4 (500 mg) in the form of a tan solid. LC-MS:ESI(+) m/z=320 [M+1].

Step (5) Preparation of Intermediate 138-5 (N-(4-bromo-2-(4-fluorophenylmethyl)-2H-indazol-6-yl)-2-(2-chlorophenyl)acetamide)

To a reaction flask were added intermediate 138-4 (240 mg, 0.75 mmol), intermediate 1-12 (153 mg, 0.90 mmol), T3P (716 mg, 1.12 mmol), Et3N (228 mg, 2.25 mmol) and DCM (4 mL), and the reaction solution was stirred at room temperature for 2 h and poured into water, the resulting solution was extracted with DCM, and the organic phase was concentrated and stirred with silica gel and purified by column chromatography to give intermediate 138-5 (270 mg) in the form of a yellow solid, LC-MS: NB190044-39-02, ESI(+) m/z=474 [M+1].

Step (6) Preparation of Intermediate 138-6 (2-(2-chlorophenyl)-N-(2-(4-fluorophenylmethyl)-4-(methylthio)-2H-indazol-6-yl)acetamide)

To a reaction flask were added intermediate 138-5 (250 mg, 0.529 mmol), MeSNa (44 mg, 0.635 mmol), $K_2CO_3$ (146 mg, 1.06 mmol) and toluene (4 mL), $Pd_2(dba)_3$ (48 mg, 0.0529 mmol) and Xantphos (31 mg, 0.0529 mmol) were added in the reaction flask, and the reaction solution was purged with $N_2$ for 3 min. The flask was capped, the reaction solution was stirred at 110° C. overnight and poured into water, and the resulting solution was extracted with EA. The organic phase was concentrated and stirred with silica gel and purified by column chromatography to give intermediate 138-6 (150 mg) in the form of a yellow solid, LC-MS: NB190044-42-02, ESI(+) m/z=440 [M+1].

Step (7) Preparation of (S)-2-(2-chlorophenyl)-N-(2-(4-fluorophenylmethyl)-4-(S-methylsulfonimidoyl)-2H-indazol-6-yl)acetamide (138) and (R)-2-(2-chlorophenyl)-N-(2-(4-fluorophenylmethyl)-4-(S-methylsulfonimidoyl)-2H-indazol-6-yl)acetamide (138A)

Intermediate 138-6 (80 mg, 0.182 mmol) was dissolved in MeOH (5 mL), $(NH_4)_2CO_3$ (52 mg, 0.546 mmol) and PhI(OAc)$_2$ (117 mg, 0.364 mmol) were added sequentially to the reaction flask at 0° C., and the reaction solution was stirred at 0° C. for 20 min and then stirred at room temperature. The reaction solution was added with an aqueous sodium sulfite solution to quench the reaction, and extracted with EA, and the organic phase was concentrated to dryness and purified by preparative chromatography to give compound 138 (8.6 mg) in the form of a white solid and compound 138A (12.0 mg) in the form of a white solid.

NOE Data and Description

Compound 138: LC-MS: NB190044-49-01, ESI(+) m/z=471 [M+1]. $^1$H NMR (400 MHz, dmso) δ 10.53 (s, 1H), 8.65 (s, 1H), 8.25 (s, 1H), 7.79 (s, 1H), 7.35 (s, 4H), 7.23 (s, 2H), 7.09 (t, J=8.4 Hz, 2H), 5.57 (s, 2H), 3.79 (s, 2H), 3.23 (s, 3H).

Compound 138A: LC-MS: NB190044-49-02, ESI(+) m/z=471 [M+1]. $^1$H NMR (400 MHz, dmso) δ 10.51 (s, 1H), 8.63 (s, 1H), 8.22 (s, 1H), 7.76 (s, 1H), 7.33 (s, 4H), 7.21 (s, 2H), 7.07 (t, J=8.4 Hz, 2H), 5.55 (s, 2H), 3.77 (s, 2H), 3.20 (s, 3H).

Example 139

Corresponding Compound Nos. 139+139A

Preparation of (S)—N-(2-(4-fluorophenylmethyl)-4-(S-methylsulfonimidoyl)-2H-indazol-6-yl)-2-(o-phenylmethyl)acetamide (Compound 139) and (R)—N-(2-(4-methylbenzyl)-4-(S-methylsulfonimidoyl)-2H-indazol-6-yl)-2-(o-phenylmethyl)acetamide (Compound 139A)

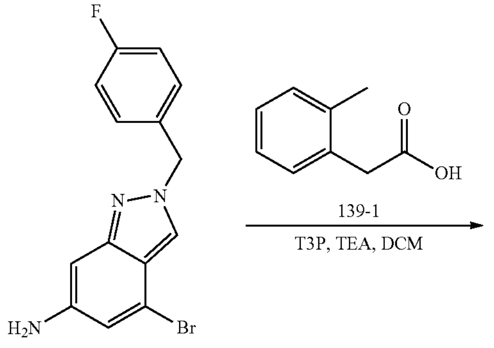

78-4

-continued

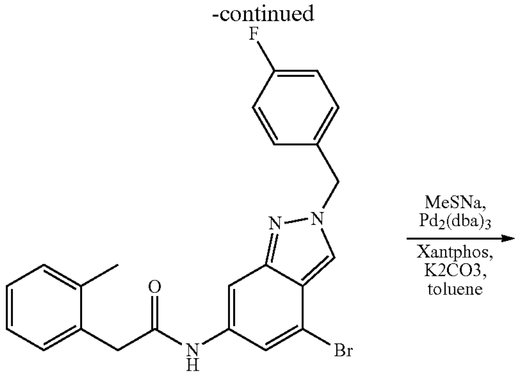

139-2

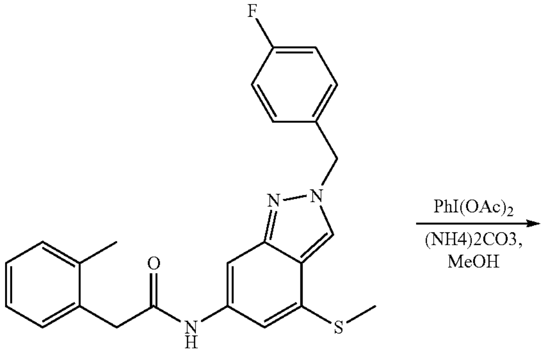

139-3

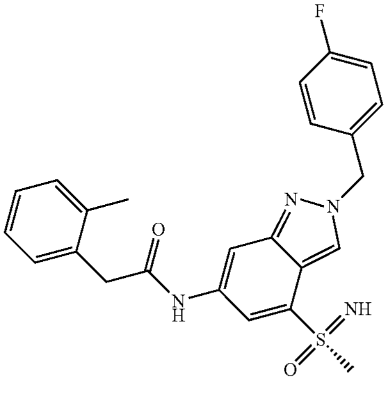

139

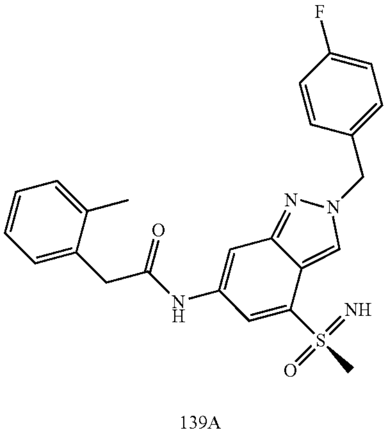 [SMILES: C[S@@](=N)(=O)c1cc(NC(=O)Cc2ccccc2Cl)cc2nn(Cc3ccc(F)cc3)cc12]

139A

Step (1) Preparation of Intermediate 139-2 (N-(4-bromo-2-(4-fluorophenylmethyl)-2H-indazol-6-yl)-2-(o-benzyl)acetamide)

To a reaction flask were added intermediate 138-4 (120 mg, 0.375 mmol), intermediate 139-1 (68 mg, 0.45 mmol), T3P (358 mg, 0.56 mmol), Et3N (114 mg, 1.12 mmol) and DCM (2 mL), and the reaction solution was stirred at room temperature overnight and poured into water, the resulting solution was extracted with DCM, and the organic phase was concentrated and stirred with silica gel and purified by column chromatography to give intermediate 139-2 (140 mg) in the form of a yellow solid, LC-MS: NB190044-41-02, ESI(+) m-z=454 [M+1].

Step (2) Preparation of Intermediate 139-3 (N-(2-(4-fluorophenylmethyl)-4-(methylthio)-2H-indazol-6-yl)-2-(o-benzyl)acetamide)

To a reaction flask were added intermediate 139-2 (130 mg, 0.287 mmol), MeSNa (101 mg, 1.44 mmol), $K_2CO_3$ (79 mg, 0.575 mmol) and toluene (4 mL), $Pd_2(dba)_3$ (26 mg, 0.0287 mmol) and Xantphos (17 mg, 0.0287 mmol) were added to the reaction flask, and the reaction solution was purged with $N_2$ for 3 min. The flask was capped, the reaction solution was stirred at 110° C. overnight and poured into water, the resulting solution was extracted with EA, and the organic phase was concentrated and stirred with silica gel and purified by column chromatography to give intermediate 139-3 (80 mg) in the form of a yellow solid. The product was confirmed by TLC (PE/EA=3/1).

Step (3) Preparation of (S)—N-(2-(4-fluorophenylmethyl)-4-(S-methylsulfonimidoyl)-2H-indazol-6-yl)-2-(o-phenylmethyl)acetamide and (R)—N-(2-(4-methylbenzyl)-4-(S-methylsulfonimidoyl)-2H-indazol-6-yl)-2-(o-phenylmethyl)acetamide Intermediate 139-3 (70 mg, 0.167 mmol) was dissolved in MeOH (2 mL), $(NH_4)_2CO_3$ (48 mg, 0.501 mmol) and $PhI(OAc)_2$ (107 mg, 0.334 mmol) were added sequentially to the reaction flask at 0° C., and the reaction solution was stirred at 0° C. for 20 min and then stirred at room temperature. The reaction solution was added with an aqueous sodium sulfite solution to quench the reaction, and extracted with EA, and the organic phase was concentrated to dryness and purified by preparative chromatography to give compound 139 (4.4 mg) in the form of a white solid and compound 139A (2.8 mg) in the form of a white solid.

Compound 139: LC-MS: NB190044-50-01, ESI(+) m/z=451 [M+1]. $^1$H NMR (400 MHz, dmso) δ 10.49 (s, 1H), 8.70 (d, J=0.8 Hz, 1H), 8.32 (s, 1H), 7.79 (d, J=1.6 Hz, 1H), 7.45-7.40 (m, 2H), 7.26-7.22 (m, 1H), 7.21-7.03 (m, 6H), 5.64 (s, 2H), 3.70 (s, 2H), 3.16 (s, 3H), 2.28 (s, 3H).

Compound 139A: LC-MS: NB190044-50-02, ESI(+) m/z=451 [M+1]. $^1$H NMR (400 MHz, dmso) δ 10.50 (s, 1H), 8.71 (d, J=0.8 Hz, 1H), 8.33 (s, 1H), 7.81 (d, J=1.6 Hz, 1H), 7.45-7.40 (m, 2H), 7.26-7.23 (m, 1H), 7.20-7.07 (m, 6H), 5.64 (s, 2H), 3.70 (s, 2H), 3.21 (s, 3H), 2.28 (s, 3H).

Example 140

Compound No. 140

Naming: N-(2-(4-fluorophenylmethyl)-4-(S-methylsulphonimidoyl)-2H-indazol-6-y)-2-(2-methoxyphenyl)acetamide

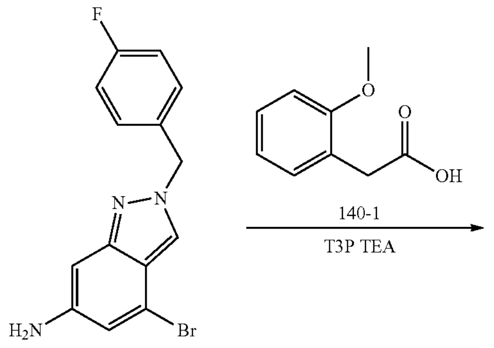

138-4

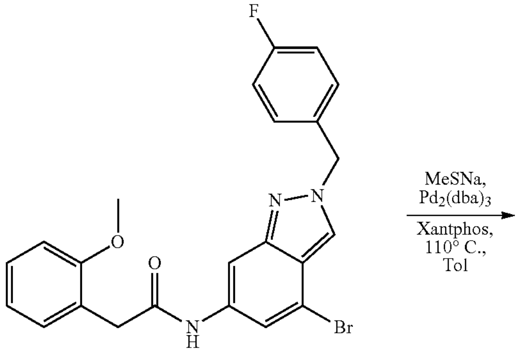

140-2

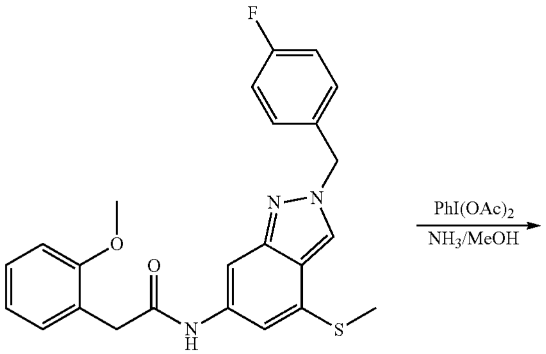

140-3

-continued

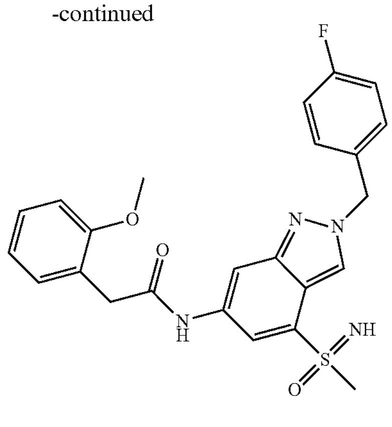

140

Step (1) Preparation of Intermediate 140-2 (N-(4-bromo-2-(4-fluorophenylmethyl)-2H-indazol-6-yl)-2-(2-methoxyphenyl)acetamide)

Intermediate 138-4 (130 mg, 0.4 mmol), intermediate 140-1 (100 mg, 0.6 mmol), T3P (190 mg, 0.6 mmol) and TEA (120 mg, 1.2 mmol) were dissolved in DCM (2 mL) and stirred at room temperature for 2 h. After the reaction was completed as detected by TLC, the reaction solution was concentrated under reduced pressure and purified by column chromatography to give intermediate 140-2 (138 mg, 73.7% yield) in the form of a yellow oil. LC-MS: $[M]^+$=468.

Step (2) Preparation of Intermediate 140-3 (N-(2-(4-fluorophenylmethyl)-4-(methylthio)-2H-indazol-6-yl)-2-(2-methoxyphenyl)acetamide)

Intermediate 140-2 (138 mg, 0.3 mmol) was dissolved in toluene (10 mL), sodium thiomethoxide (63 mg, 0.9 mmol), $K_2CO_3$ (83 mg, 0.6 mmol), $Pd_2(dba)_3$ (27.4 mg, 0.02 mmol) and Xantphos (17.4 mg, 0.03 mmol) were added and reacted at 110° C. overnight under $N_2$ atmosphere. After the reaction was completed as detected by TLC, the reaction solution was added with water, extracted with ethyl acetate, concentrated and purified by column chromatography to give intermediate 140-3 (100 mg, 82.6% yield) in the form of a yellow oil, LC-MS: [M+1]=436.

Step (3) Preparation of N-(2-(4-fluorophenylmethyl)-4-(S-methylsulfonimidoyl)-2H-indazol-6-yl)-2-(2-methoxyphenyl)acetamide Intermediate 140-3 (100 mg, 0.23 mmol) was dissolved in methanol (3 mL), ammonium carbonate (66 mg, 0.69 mmol) was added at 0° C., then iodobenzene acetate (148 mg, 0.46 mmol) was added in portions, and after the addition was completed, the reaction solution was reacted at this temperature for 20 min and then stirred at room temperature for 3 h. After the reaction was completed as detected by TLC, the reaction solution was concentrated under reduced pressure to give a crude product which was separated by prep-HPLC using a $H_2O$/CAN system and lyophilized to give compound 140 (7.3 mg, 97.16% purity, 10.6% yield) in the form of a white solid. LC-MS: $[M+1]^+$=467.

$^1$H NMR (400 MHz, dmso) δ 10.28 (s, 1H), 8.58 (s, 1H), 8.19 (s, 1H), 7.67 (s, 1H), 7.32 (s, 2H), 7.08 (dd, J=20.8, 7.2 Hz, 4H), 6.90-6.75 (m, 2H), 5.54 (s, 2H), 4.29 (s, 1H), 3.64 (s, 3H), 3.54 (s, 2H), 2.99 (s, 3H).

Example 141
Compound Nos. 141+141A
Naming: 2-(2-chlorophenyl)-N-(4-sulfamoyl-2-((tetrahydro-2H-pyran-4-yl)methyl)-2H-indazol-6-yl) acetamide and 2-(2-chlorophenyl)-N-(4-sulfamoyl-1-((tetrahydro-2H-pyran-4-yl)methyl)-1H-indazol-6-yl)acetamide
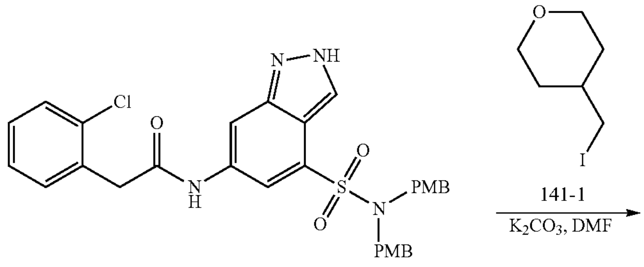
3-1
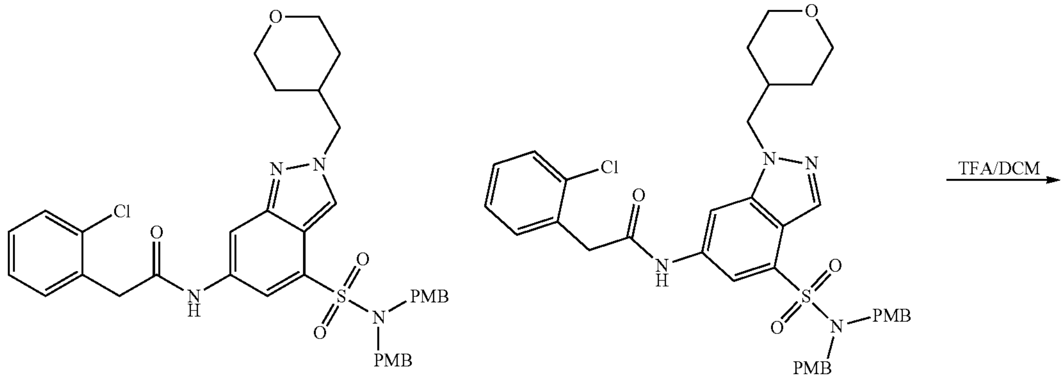
141-2
141-3
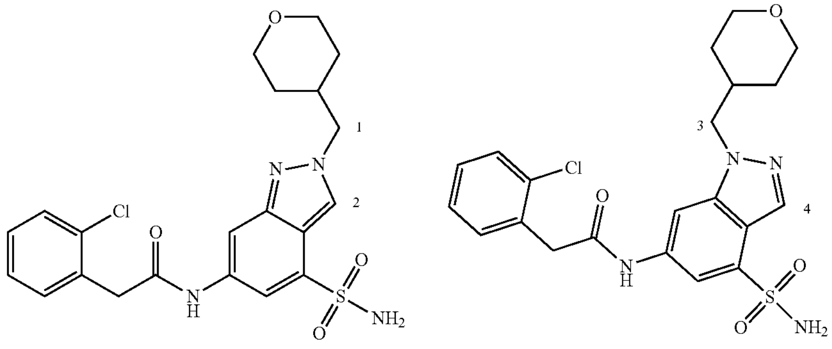
141
141A Step (1) Preparation of Intermediate 141-2 (N-(4-(N,N-bis(4-methoxybenzyl)sulfamoyl)-2-((tetrahydro-2H-pyran-4-yl)methyl)-2H-indazol-6-yl)-2-(2-chlorophenyl)acetamide) and Intermediate 141-3 (N-(4-(N,N-bis(4-methoxybenzyl)sulfamoyl)-1-((tetrahydro-2H-pyran-4-yl)methyl)-1H-indazol-6-yl)-2-(2-chlorophenyl)acetamide)

Intermediate 3-1 (600 mg, 0.992 mmol) was dissolved in DMF (4 mL), intermediate 141-1 (4-(iodomethyl)tetrahydro-2H-pyran) (336.2 mg, 1.49 mmol) and $K_2CO_3$ (411 mg, 2.97 mmol) were added, and the reaction solution was stirred at 80° C. overnight and then poured into water, the resulting solution was extracted with ethyl acetate, and the organic phase was concentrated to dryness to give a mixture of intermediate 141-2 and intermediate 141-3 (710 mg, crude) in the form of a yellow oil. LC-MS: NB190114-58-02, ESI(+) m/z=703[M+1].

Step (2) Preparation of 2-(2-chlorophenyl)-N-(4-sulfamoyl-2-((tetrahydro-2H-pyran-4-yl)methyl)-2H-indazol-6-yl)acetamide and 2-(2-chlorophenyl)-N-(4-sulfamoyl-1-((tetrahydro-2H-pyran-4-yl)methyl)-1H-indazol-6-yl)acetamide A mixture of intermediate 141-2 and intermediate 141-3 (710 mg, 1.01 mmol) was dissolved in DCM (3 mL), TFA (6 mL) was added to the reaction flask, and the reaction solution was stirred at 30° C. for 3 h. pH was adjusted to about 8, the reaction solution was extracted with DCM, and the organic phase was concentrated to dryness to give a crude product which was separated by prep-HPLC using a $H_2O$/ACN system and lyophilized to give compound 141 (78.7 mg, 98.419% purity) in the form of a light yellow solid and compound 141A (151.6 mg, 98.780% purity) in the form of a white solid.

NOE Data and Description

NOE showed that the correlation signal between No. 1 hydrogen (δ=4.32) and No. 2 hydrogen (δ=7.70) was confirmed to be compound 141.

NOE showed that no correlation signal between hydrogen No. 3 (δ=4.25) and hydrogen No. 4 (δ=7.69) was confirmed to be compound 141A.

Compound 141: LC-MS: NB190114-62-01, ESI(+) m/z=463[M+1]. $^1$H NMR (400 MHz, dmso) δ 10.50 (s, 1H), 8.45 (s, 1H), 8.22 (s, 1H), 7.70 (d, J=1.6 Hz, 1H), 7.48 (s, 2H), 7.46-7.41 (m, 2H), 7.34-7.27 (m, 2H), 4.32 (d, J=7.2 Hz, 2H), 3.86 (s, 2H), 3.80 (dd, J=11.2, 2.4 Hz, 2H), 3.28-3.17 (m, 2H), 2.27-2.12 (m, 1H), 1.41-1.23 (m, 4H).

Compound 141A: LC-MS: NB190114-62-02, ESI(+) m/z=463[M+1]. $^1$H NMR (400 MHz, dmso) δ 10.70 (s, 1H), 8.33 (s, 1H), 8.24 (s, 1H), 7.69 (d, J=1.2 Hz, 1H), 7.57 (s, 2H), 7.47-7.40 (m, 2H), 7.35-7.27 (m, 2H), 4.25 (d, J=7.2 Hz, 2H), 3.89 (s, 2H), 3.81-3.72 (m, 2H), 3.24-3.13 (m, 2H), 2.16-2.07 (m, 1H), 1.39-1.17 (m, 4H).

Biological Experiments

Example A: In Vitro Evaluation of Biological Activity

The antagonist property of the compounds disclosed herein was determined using the FLIPR (fluorescence imaging plate reader) method, wherein the compounds are inhibitors for the intracellular calcium increase induced by activation of hP2X4 (human purinergic P2X receptor subtype 4, accession No. NM_001256796.2) expressed in HEK293 cells (human renal epithelial cell line, ATCC).

HEK293 cells stably expressing hP2X4 were cultured in DMEM high glucose medium containing 10% FBS (fetal bovine serum, Biosera, FB-1058/500), 1% penicillin-streptomycin (Gibco, 15140-122) and 1 mg/mL G418 (CABIOCHE, 345810) in a cell incubator (37° C., 5% humidity). Cells at 400,000 cells/mL were seeded into a 384-well plate (10,000 cells/well) 18-24 h prior to the FLIPR experiment and then incubated overnight in a cell incubator. On the day of the experiment, the medium was discarded and the cells were washed in an FLIPR buffer (0.3 mL of probenecid (Thermo, P36400), 0.6 mL of 1 M HEPES (Invitrogen, 15630080) and 29.1 mL of HBSS (Invitrogen, 14065056) per 30 mL of the buffer). Each well was added with 20 μL of 0.5× Calcium 6 fluorescent dye (Molecular Devices, R8190) and then the cells were subjected to dye-loading incubation at 37° C. for 1.5 h. Each well was added with 10 μL of respective test compound (dissolved in DMSO at a concentration of 10 mM and serially diluted with buffer) or vehicle and the mixture was equilibrated for 30 min at room temperature. The cell plate was then placed in the FLIPR for baseline fluorescence measurements (excitation at 485 nm and emission at 525-535 nm). An agonist (BZ-ATP (Sigma, B6396) at a final concentration of 2.5 μM) or a vehicle (ultrapure water) was then added at 10 μL/well, fluorescence values were measured for 2 min at 1-second intervals, and finally the output fluorescence counts were analyzed. $IC_{50}$ values obtained using the above method are shown in Table 1.

TABLE 1

$IC_{50}$ values of compounds of Examples 1-56 for P2X4 receptor

| Compound | P2X4 $IC_{50}$ (nM) | Compound | P2X4 $IC_{50}$ (nM) |
|---|---|---|---|
| Compound 1 | 29.1 | Compound 2 | 5.4 |
| Compound 3-A | 4.9 | Compound 3-B | 6.3 |
| Compound 4-A | A | Compound 4-B | A |
| Compound 5-A | 5.24 | Compound 5-B | 2.2 |
| Compound 6-A | 1.16 | Compound 6-B | B |
| Compound 7-A | 4.8 | Compound 7-B | 2.33 |
| Compound 8-A | 13.85 | Compound 8-B | 0.38 |
| Compound 9 | A | Compound 10 | B |
| Compound 11 | A | Compound 12-A | 31 |
| Compound 12-B | 21.8 | Compound 13 | B |
| Compound 14-A | A | Compound 14-B | A |
| Compound 15-A | 119.4 | Compound 15-B | B |
| Compound 16-A | B | Compound 16-B | A |
| Compound 17 | B | Compound 18 | B |
| Compound 19 | B | Compound 20 | B |
| Compound 21 | B | Compound 22 | B |
| Compound 23 | B | Compound 24-A | 1.6 |
| Compound 24-B | A | Compound 25 | B |
| Compound 26-A | 6.1 | Compound 26-B | D |
| Compound 27-A | D | Compound 27-B | C |
| Compound 28 | B | Compound 29 | B |
| Compound 30 | B | Compound 31-A | A |
| Compound 31-B | A | Compound 32-A | A |
| Compound 32-B | B | Compound 33 | A |
| Compound 34 | B | Compound 35-A | B |
| Compound 35-B | B | Compound 36-A | B |
| Compound 36-B | B | Compound 37-A | B |
| Compound 37-B | B | Compound 38 | B |
| Compound 39 | B | Compound 40-A | B |
| Compound 40-B | A | Compound 41 | B |
| Compound 42-A | B | Compound 42-B | D |
| Compound 43 | B | Compound 44 | 36.8 |
| Compound 45 | B | Compound 46 | B |
| Compound 47 | 16.99 | Compound 48-A | D |

TABLE 1-continued

| IC$_{50}$ values of compounds of Examples 1-56 for P2X4 receptor | | | |
|---|---|---|---|
| Compound | P2X4 IC$_{50}$ (nM) | Compound | P2X4 IC$_{50}$ (nM) |
| Compound 48-B | D | Compound 49 | 89.53 |
| Compound 50 | C | Compound 51 | 934 |
| Compound 52 | D | Compound 53 | D |
| Compound 54 | D | Compound 55 | B |
| Compound 56 | B | Compound 108 | C |
| Compound 58 | D | Compound 110 | C |
| Compound 59 | D | Compound 110A | D |
| Compound 75 | D | Compound 113 | D |
| Compound 82 | A | Compound 115 | D |
| Compound 83 | A | Compound 116 | D |
| Compound 85 | A | Compound 118 | D |
| Compound 86 | A | Compound 118A | D |
| Compound 87 | A | Compound 120 | C |
| Compound 88 | A | Compound 120A | C |
| Compound 88A | A | Compound 130 | D |
| Compound 89 | A | Compound 131 | B |
| Compound 89A | A | Compound 132 | D |
| Compound 90 | A | Compound 133 | B |
| Compound 90A | A | Compound 134 | B |
| Compound 91 | A | Compound 135 | C |
| Compound 91A | A | Compound 136 | D |
| Compound 92 | A | Compound 137 | D |
| Compound 92A | A | Compound 138 | D |
| Compound 93 | A | Compound 138A | D |
| Compound 94 | A | Compound 139 | D |
| Compound 95 | A | Compound 139A | D |
| Compound 95A | A | Compound 140 | D |
| Compound 101 | B | Compound 141 | C |
| Compound 101A | B | Compound 141A | C |
| Compound 25A | B | | |

A: IC$_{50}$ ≤ 10 nM,
B: 10 < IC$_{50}$ ≤ 50 nM,
C: 50 < IC$_{50}$ ≤ 200 nM,
D: 200 < IC$_{50}$ ≤ 5000 nM.

As can be seen from the data in Table 1, the compounds disclosed herein have good P2X4 inhibitory activity. Preferred are compounds with IC$_{50}$<500 nM, and more preferred are compounds with IC$_{50}$<100 nM.

Example B: Activity Test in Citric Acid Only Cough Models

Male Dunkin Hartley guinea pigs (300-350 g) were placed in an animal atomization box, and then the door of the atomization box was closed while the ultrasonic atomizer (Guangdong Yuehua) was turned on. 17.5% citric acid gas was introduced into the atomization box at a maximum atomization rate (about 2 mL/min) for 20 s, and coughs of the animals within 10 min were continuously observed from the time of the start of atomization. During the 10-min observation, coughs of the animals needed to be counted manually, and the number of coughs were judged according to cough postures of the guinea pigs, such as abdominal twitching, mouth opening, and head inclining downward abruptly. The number of coughs during the first 5 min and that during 10 min were recorded, and the cough latency of the guinea pigs, namely the time from the initiation of citric acid induction to the appearance of the 1st cough, was also recorded.

Cough inhibition rate Vs vehicle represents the percentage of reduction $$\text{(Cough inhibition rate } Vs \text{ vehicle} = \frac{\text{Number of coughs in vehicle group} - \text{Number of coughs in each administration group}}{\text{Number of coughs in vehicle group}} \times 100\ \%)$$

in the number of coughs in the administration group compared to the vehicle group upon citric acid challenge; Cough inhibition rate Vs baseline represents the percentage of reduction $$\text{(Cough inhibition rate } Vs \text{ baseline} = \frac{\text{Number of coughs before administration} - \text{Number of coughs after administration}}{\text{Number of coughs before administration}} \times 100\ \%)$$

in the number of coughs in the administration group before and after administration.

TABLE 2

The number of coughs and inhibition rates obtained in vivo for some of the compounds

| | Vehicle group | | Dextromethorphan (60 mg/kg) | | Compound 1 (20 mg/kg) | | Compound 1 (60 mg/kg) | |
|---|---|---|---|---|---|---|---|---|
| | Before administration | After administration | Before administration | After administration | Before administration | After administration | Before administration | After administration |
| Mean number of coughs | 18.5 | 19.25 | 18.57 | 12.71 | 18.57 | 15.29 | 18.50 | 10.25 |
| Cough inhibition rate Vs vehicle (%) | / | | 33.95 | | 20.59 | | 46.75 | |
| Cough inhibition rate Vs baseline (%) | / | | 31.54 | | 17.69 | | 44.59 | |
| Cough latency (s) | 83.63 | 63.13 | 73.43 | 154.29 | 94.29 | 214.29 | 84.88 | 221.75 |

The above experiment was performed using compound 1 and the results in Table 2 show that, compared with a blank vehicle group or the administration group before administration, compound 1 at the dosage of 20 mg/kg and 60 mg/kg can reduce the number of coughs and prolong the cough latency in a dose-dependent manner, and the group at the dosage of 60 mg/kg has a significant improvement effect, and has no significant difference in the drug effect compared with the positive compound dextromethorphan at the same dosage, which indicates that compound 1 has the effects of reducing the number of coughs and improving the cough latency and is comparable to the positive compound.

Example C: In Vitro Cytotoxicity Assay

In vitro cytotoxicity assay for the compounds disclosed herein was performed in HepG2 cells using the CCK-8 method. HepG2 cells (Beina Bio) in the logarithmic growth phase were collected, the concentration of cell suspension was adjusted, and then the cells were plated on a 96-well cell culture plate at 50,000 cells/well. The cells were then incubated overnight in a cell incubator (5%/humidity, 37° C.), and after 80-90% cell confluence was achieved, test compounds or vehicle (DMSO) at various concentration gradients were added after medium change. The resulting mixture was incubated in the cell incubator (5% humidity, 37° C.) for 48 h. After the treatment, the medium in the plate was discarded. The plate was washed twice with PBS, added with CCK-8 working solution (Beyotime) at 100 μL per well, and then incubated at 37° C. for 1.5 h away from the light. Absorbance at $OD_{450\ nm}$ was measured for each well on a microplate reader, and $CC_{50}$ value of each compound was analyzed and calculated.

$CC_{50}$ values obtained using the above method are shown in Table 3.

TABLE 3

$CC_{50}$ values obtained for some of the compounds

| Compound | HepG2 $CC_{50}$ (μM) | Compound | HepG2 $CC_{50}$ (μM) |
|---|---|---|---|
| Compound 1 | >200 | Compound 2 | >200 |
| Compound 5-A | >200 | Compound 5-B | >200 |
| Compound 6 | >200 | Compound 7-B | 150.18 |
| Compound 8-A | >200 | Compound 8-B | >200 |
| Compound 12-A | >200 | Compound 24-B | >200 |
| Compound 26-A | >200 | Compound 35-A | >200 |
| Compound 35-B | >200 | Compound 47 | >200 |
| Compound 88 | >200 | Compound 91 | >200 |
| Compound 91A | >200 | Compound 133 | >100 |

As can be seen from the data in Table 3, most of the compounds disclosed herein exhibit relatively good safety, and the $CC_{50}$ ranges are all more than 30 μM, which satisfies the requirement for in vitro cytotoxicity of general compounds. Preferred are compounds with $CC_{50}$>30 μM, and more preferred are compounds with $CC_{50}$>100 μM.

Example D: Test of In Vitro Metabolic Stability

The in vitro metabolic stability of the compounds disclosed herein was determined through incubation of liver microsomes of various species. A proper amount of test compound was added into a liver microsome reaction system (1 mg/mL liver microsome protein, 25 U/mL glucose-6 phosphate dehydrogenase, 1 mM NADP, 6 mM D-glucose 6-phosphate and 5 mM $MgCl_2$), and then the mixture was incubated in a water bath kettle at 37° C. to start the reaction. At each time point, 100 μL of the reaction system was added into a centrifuge tube containing 400 μL of internal standard working solution (containing a 200 ng/mL solution of dexamethasone, diclofenac, tolbutamide and labetalol in acetonitrile) precooled at 0° C. so as to stop the reaction, and the mixture was then centrifuged at 10,000 g for 10 min at 4° C. The supernatant was collected for LC-MS assay so as to obtain the values of in vitro metabolic half-life of the test compounds in liver microsomes of various species.

$T_{1/2}$ values obtained using the above method are shown in Table 4.

TABLE 4

$T_{1/2}$ values obtained for some of the compounds

| Compound | $T_{1/2}$ in human liver microsome min | $T_{1/2}$ in rat liver microsome min | $T_{1/2}$ in guinea pig liver microsome min |
|---|---|---|---|
| Compound 1 | 692.79 | 362.05 | 154.5 |
| Compound 2 | 154.05 | 48.52 | 212.58 |
| Compound 3-A | 6341.77 | | |
| Compound 3-B | 154.75 | | |
| Compound 4-B | 73.59 | / | / |
| Compound 5-A | 357.89 | 142.01 | 5.87 |
| Compound 5-B | 65.64 | / | / |
| Compound 6 | 36.79 | / | / |
| Compound 7-A | 59.27 | / | / |
| Compound 7-B | 32.48 | / | / |
| Compound 8-A | 35.04 | / | / |
| Compound 8-B | 26.93 | / | / |
| Compound 10 | 24.46 | | |
| Compound 12-A | NA | / | / |
| Compound 12-B | 18.06 | / | / |
| Compound 14-B | 96.58 | / | / |
| Compound 24-A | 64.85 | | |
| Compound 24-B | 110.56 | 46.06 | 144.45 |
| Compound 26-A | 125.38 | / | / |
| Compound 31-A | 44.89 | / | / |
| Compound 35-A | 372.69 | / | / |
| Compound 35-B | 279.88 | / | / |
| Compound 36-A | 86.33 | / | / |
| Compound 36-B | 57.70 | / | / |
| Compound 37-A | 79.25 | / | / |
| Compound 44 | 305.09 | 91.67 | 71.81 |
| Compound 47 | 784.52 | / | / |
| Compound 53 | 227.67 | 45.20 | 9.26 |
| Compound 88 | 512.69 | 124.09 | 120 |
| Compound 91 | 193.85 | 110.48 | 48.57 |
| Compound 91A | 100.96 | 125.14 | 85.45 |
| Compound 101 | 111.34 | / | / |
| Compound 101A | 71.15 | / | / |
| Compound 110 | 430.96 | 68.86 | / |
| Compound 110A | 52.9 | 20.09 | / |
| Compound 120 | 63.4 | 13.56 | / |
| Compound 120A | 22.24 | 8.23 | / |
| Compound 133 | 1501.57 | 135.84 | / |
| Compound 134 | 824.67 | 193.37 | / |
| Compound 141 | 64.32 | 13.56 | |

Note:
NA indicates essentially not metabolized;
"/" indicates not detected.

As can be seen from the data in Table 4, the compounds disclosed herein have a relatively good metabolic stability in human, rat and guinea pig. Preferred are compounds with $T_{1/2}$>30 min in human liver microsome, and more preferred are compounds with $T_{1/2}$>90 min in human liver microsome.

Although examples of the disclosure are illustrated and described above, it will be appreciated that the above examples are exemplary and not to be construed as limiting the disclosure, and that changes, modifications, substitutions and alterations can be made to the above examples by those of ordinary skilled in the art within the scope of the disclosure.

The invention claimed is:

1. A compound containing a benzene ring represented by formula I, or a pharmaceutically acceptable salt thereof, a stereoisomer thereof, a tautomer thereof, an isotope compound thereof, a crystalline form thereof, a nitrogen oxide thereof or a solvate thereof, or a solvate of a pharmaceutically acceptable salt thereof;

I

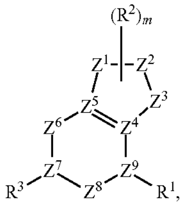

wherein,

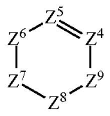

is a benzene ring;

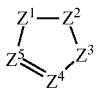

is a "5 membered heteroaryl ring containing 1, 2 or 3 heteroatoms selected from one or more of N, O and S" or a "5 membered heteroalkenyl ring containing 1, 2 or 3 heteroatoms selected from one or more of N, O and S";

$R^1$ is

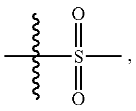, 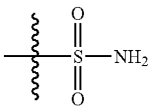 or 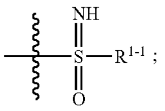;

$R^{1-1}$ is $C_1$-$C_6$ alkyl, $R^3$ is

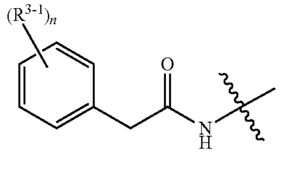 or 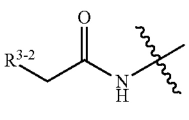;

n is 0, 1, 2 or 3;

$R^{3-1}$ is independently halogen, hydroxyl, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, "5-6 membered heterocycloalkyl containing 1, 2 or 3 heteroatoms selected from one or more of N, O and S" substituted with one or more $R^{3-2-2}$, or "5-6 membered heteroaryl containing 1, 2 or 3 heteroatoms selected from one or more of N, O and S" substituted with one or more $R^{3-2-3}$;

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or $C_1$-$C_6$ alkoxy substituted with $C_1$-$C_6$ alkoxy;

m is 0, 1 or 2;

$R^2$ is oxo, halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-7}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl, phenyl substituted with one or more $R^{2-4}$, "5-6 membered heteroaryl containing 1, 2 or 3 heteroatoms selected from one or more of N, O and S", "5-6 membered heteroaryl containing 1, 2 or 3 heteroatoms selected from one or more of N, O and S" substituted with one or more $R^{2-5}$, or —(C═O)-$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, "4-6 membered heterocycloalkyl containing 1, 2 or 3 heteroatoms selected from one or more of N, O and S", "4-6 membered heterocycloalkyl containing 1, 2 or 3 heteroatoms selected from one or more of N, O and S" substituted with one or more $R^{2-1-7}$, phenyl, phenyl substituted with one or more $R^{2-1-1}$, "5-6 membered heteroaryl containing 1, 2 or 3 heteroatoms selected from one or more of N, O and S", "5-6 membered heteroaryl containing 1, 2 or 3 heteroatoms selected from one or more of N, O and S" substituted with one or more $R^{2-1-6}$, —$OR^{2-1-2}$, —$N(R^{2-1-3})(R^{2-1-4})$, or —$S(═O)_2$-$R^{2-1-5}$;

$R^{2-1-1}$, $R^{2-1-6}$, $R^{2-1-7}$ and $R^{2-1-8}$ are independently oxo, hydroxyl, amino, carboxyl, halogen, —CN, $C_1$-$C_6$ alkyl, $C_1$-$C_6$ alkyl substituted with one or more halogen, —$OR^{2-1-1-1}$, or —$N(R^{2-1-1-2})(R^{2-1-1-3})$;

$R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ and $R^{2-6}$ are independently $C_1$-$C_6$ alkyl;

$R^{2-4}$ and $R^{2-5}$ are independently halogen, hydroxyl, —$N(R^{2-4-1})(R^{2-4-2})$ or $C_1$-$C_6$ alkoxy; $R^{2-4-1}$ and $R^{2-4-2}$ are independently hydrogen, $C_1$-$C_6$ alkyl or $C_3$-$C_6$ cycloalkyl;

$R^{2-7}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

2. The compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof according to claim 1, characterized in that

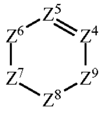

is a benzene ring and/or,

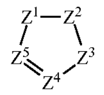

is a "5 membered heteroaryl ring containing 1 or 2 heteroatoms selected from one or more of N, O and S" or a "5 membered heteroalkenyl ring containing 1 or 2 heteroatoms selected from one or more of N, O and S";

and/or, $R^1$ is

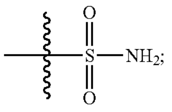 [SMILES: *S(N)(=O)=O]

and/or, $R^3$ is

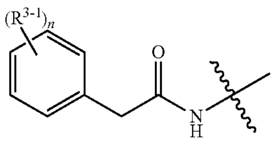

or

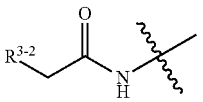

;

n is 1; $R^{3-1}$ is halogen, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy; $R^{3-2}$ is $C_3$-$C_6$ cycloalkyl substituted with one or more $R^{3-2-1}$, or "5-6 membered heteroaryl containing 1, 2 or 3 heteroatoms selected from one or more of N, O and S" substituted with one or more $R^{3-2-3}$; $R^{3-2-1}$ and $R^{3-2-3}$ are independently halogen or hydroxyl;

and/or, $R^2$ is halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-7}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl substituted with one or more $R^{2-4}$, or —(C═O)-$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, "4-6 membered heterocycloalkyl containing 1, 2 or 3 heteroatoms selected from one or more of N, O and S", phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —$N(R^{2-1-3})(R^{2-1-4})$, or —$S(═O)_2$-$R^{2-1-5}$; $R^{2-1-1}$, $R^{2-1-6}$ and $R^{2-1-8}$ are independently hydroxyl, amino, halogen, —CN, $C_1$-$C_6$ alkyl, $C_1$-$C_6$ alkyl substituted with one or more halogen, —$OR^{2-1-1-1}$, or —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl; $R^{2-1-2}$ is independently $C_1$-$C_6$ alkyl or $C_3$-$C_6$ cycloalkyl; $R^{2-1-3}$ and $R^{2-1-4}$ are independently hydrogen, $C_1$-$C_6$ alkyl or $C_3$-$C_6$ cycloalkyl; $R^{2-1-5}$ is independently $C_{1-6}$ alkyl or $C_3$-$C_6$ cycloalkyl; $R^{2-3}$ and $R^{2-6}$ are independently $C_1$-$C_6$ alkyl; $R^{2-4}$ is independently halogen; $R^{2-7}$ is independently halogen; $R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen.

3. The compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof according to claim 2, characterized in that is

I

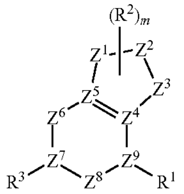

is

I-1

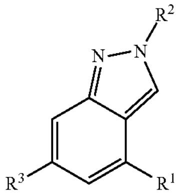

or

I-2

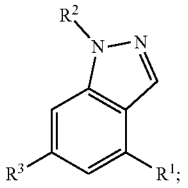

and/or, $R^3$ is

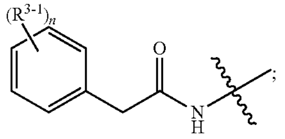

n is 1; $R^{3-1}$ is halogen;

and/or, $R^2$ is $C_1$-$C_{10}$ alkyl, $C_1$-$C_{10}$ alkyl substituted with one $R^{2-1}$, or $C_3$-$C_6$ cycloalkyl; $R^{2-1}$ is independently halogen, $C_3$-$C_6$ cycloalkyl, phenyl substituted with one or more $R^{2-1-1}$, "5-6 membered heteroaryl containing 1, 2 or 3 heteroatoms selected from one or more of N, O and S" substituted with one or more $R^{2-1-6}$, or —$OR^{2-1-2}$; $R^{2-1-1}$ and $R^{2-1-6}$ are independently amino, halogen, —CN, $C_1$-$C_6$ alkyl, $C_1$-$C_6$ alkyl substituted with one or more halogen, or —$OR^{2-1-1-1}$; $R^{2-1-1-1}$ is independently $C_1$-$C_6$ alkyl; $R^{2-1-2}$ is $C_1$-$C_6$ alkyl.

4. The compound containing a benzene ring represented by formula I, or the pharmaceutically acceptable salt thereof, the stereoisomer thereof, the tautomer thereof, the isotopic compound thereof, the crystalline form thereof, the nitrogen oxide or the solvate thereof, or the solvate of the pharmaceutically acceptable salt thereof according to claim 1, characterized in that

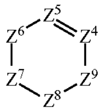

is a benzene ring;

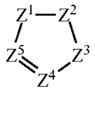

is a “5 membered heteroaryl ring containing 1, 2 or 3 heteroatoms selected from one or more of N, O and S” or a “5 membered heteroalkenyl ring containing 1, 2 or 3 heteroatoms selected from one or more of N, O and S”;

$R^1$ is

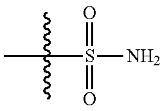

or

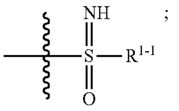

;

$R^{1-1}$ is-$C_1$-$C_6$ alkyl, $R^3$ is

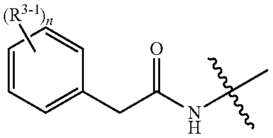

or

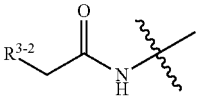

;

n is 0, 1, 2 or 3;

$R^{3-1}$ is independently halogen, hydroxyl, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, “5-6 membered heterocycloalkyl containing 1, 2 or 3 heteroatoms selected from one or more of N, O and S” substituted with one or more $R^{3-2-2}$, or “5-6 membered heteroaryl containing 1, 2 or 3 heteroatoms selected from one or more of N, O and S” substituted with one or more $R^{3-2-3}$;

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or $C_1$-$C_6$ alkoxy substituted with $C_1$-$C_6$ alkoxy;

m is 0 or 1;

$R^2$ is oxo, cyano, $C_1$-$C_{10}$ alkyl, $C_1$-$C_{10}$ alkyl substituted with one or more $R^{2-1}$, $C_3$-$C_6$ cycloalkyl, $C_3$-$C_6$ cycloalkyl substituted with one or more $R^{2-3}$, “5-6 membered heterocycloalkyl containing 1, 2 or 3 heteroatoms selected from one or more of N, O and S”, phenyl, phenyl substituted with one or more $R^{2-4}$, “5-6 membered heteroaryl containing 1, 2 or 3 heteroatoms selected from one or more of N, O and S”, “5-6 membered heteroaryl containing 1, 2 or 3 heteroatoms selected from one or more of N, O and S” substituted with one or more $R^{2-5}$, or —(C═O)-$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, “4-6 membered heterocycloalkyl containing 1, 2 or 3 heteroatoms selected from one or more of N, O and S”, “4-6 membered heterocycloalkyl containing 1, 2 or 3 heteroatoms selected from one or more of N, O and S” substituted with one or more $R^{2-1-7}$, phenyl, phenyl substituted with one or more $R^{2-1-1}$, “5-6 membered heteroaryl containing 1, 2 or 3 heteroatoms selected from one or more of N, O and S”, “5-6 membered heteroaryl containing 1, 2 or 3 heteroatoms selected from one or more of N, O and S” substituted with one or more $R^{2-1-6}$, —$OR^{2-1-2}$, —N($R^{2-1-3}$)($R^{2-1-4}$), or —S(═O)$_2$-$R^{2-1-5}$;

$R^{2-1-1}$, $R^{2-1-6}$, $R^{2-1-7}$ and $R^{2-1-8}$ are independently oxo, hydroxyl, amino, carboxyl, halogen, —CN, $C_1$-$C_6$ alkyl, $C_1$-$C_6$ alkyl substituted with one or more halogen, —$OR^{2-1-1-1}$, or —N($R^{2-1-1-2}$)($R^{2-1-1-3}$);

$R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ and $R^{2-5}$ are independently halogen, hydroxyl, —N($R^{2-4-1}$)($R^{2-4-2}$) or $C_1$-$C_6$ alkoxy; $R^{2-4-1}$ and $R^{2-4-2}$ are independently hydrogen, $C_1$-$C_6$ alkyl or $C_3$-$C_6$ cycloalkyl;

$R^{2-2}$ is $C_1$-$C_6$ alkyl, $C_3$-$C_6$ cycloalkyl, phenyl or phenyl substituted with one or more $R^{2-2-1}$, $R^{2-2-1}$ is independently halogen.

5. The compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof according to claim 1, characterized in that the compound containing a benzene ring represented by formula I is a compound represented by scheme 1, scheme 2, scheme 3, scheme 4, scheme 5, or scheme 6: scheme 1:

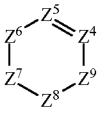

is a benzene ring;

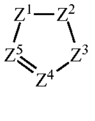

is a “5 membered heteroaryl ring containing 1 or 2 heteroatoms selected from one or more of N, O and S”;

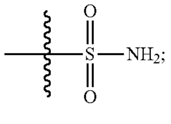

$R^1$ is $R^3$ is

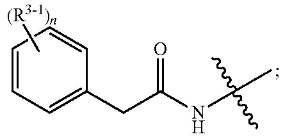

n is 1;

$R^{3-1}$ is halogen;

m is 0 or 1;

$R^2$ is cyano, $C_1$-$C_{10}$ alkyl, $C_1$-$C_{10}$ alkyl substituted with one or more $R^{2-1}$, $C_3$-$C_6$ cycloalkyl, $C_3$-$C_6$ cycloalkyl substituted with one or more $R^{2-3}$, phenyl substituted with one or more $R^{2-4}$, or (C═O)-$R^{2-2}$;

$R^{2-1}$ is independently hydroxyl, halogen, $C_3$-$C_6$ cycloalkyl, phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —N($R^{2-1-3}$)($R^{2-1-4}$), or —S(═O)$_2$-$R^{2-1-5}$;

$R^{2-1-1}$ and $R^{2-1-6}$ are independently hydroxyl, halogen, —$OR^{2-1-1-1}$, or —N($R^{2-1-1-2}$)($R^{2-1-1-3}$); $R^{2-1-1-1}R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen;

scheme 2:

I-1

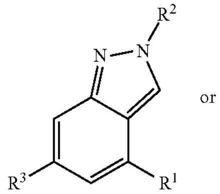

or

I-2

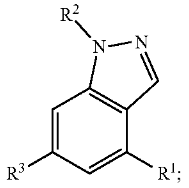

$R^1$ is

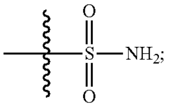 [SMILES: *S(N)(=O)=O]

$R^3$ is

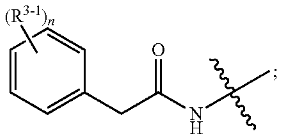

n is 1;

$R^{3-1}$ is halogen;

$R^2$ is $C_1$-$C_{10}$ alkyl, $C_1$-$C_{10}$ alkyl substituted with one $R^{2-1}$, or $C_3$-$C_6$ cycloalkyl;

$R^{2-1}$ is independently halogen, $C_3$-$C_6$ cycloalkyl, phenyl substituted with one or more $R^{2-1-1}$, or —$OR^{2-1-2}$; $R^{2-1-1}$ is halogen; $R^{2-1-2}$ is $C_1$-$C_6$ alkyl;

scheme 3:

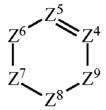

is a benzene ring;

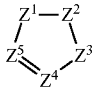

is a "5 membered heteroaryl ring containing 1 or 2 heteroatoms selected from one or more of N, O and S" or a "5 membered heteroalkenyl ring containing 1 or 2 heteroatoms selected from one or more of N, O and S";

$R^1$ is

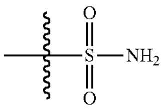

or

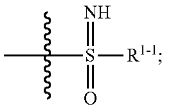

$R^{1-1}$ is $C_1$-$C_6$ alkyl;

$R^3$ is

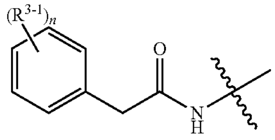

or

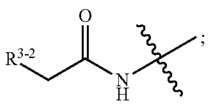

n is 1;

$R^{3-1}$ is halogen, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, or "5-6 membered heteroaryl containing 1, 2 or 3 heteroatoms selected from one or more of N, O and S" substituted with one or more $R^{3-2-3}$, $R^{3-2-1}$ and $R^{3-2-3}$ are independently halogen or hydroxyl;

m is 0, 1 or 2;

$R^2$ is halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-7}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl substituted with one or more $R^{2-4}$, or —(C═O)-$R^{2-2}$;

$R^{2-1}$ is independently hydroxyl, halogen, $C_3$-$C_6$ cycloalkyl, "4-6 membered heterocycloalkyl containing 1, 2 or 3 heteroatoms selected from one or more of N, O and S", phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —N($R^{2-1-3}$)($R^{2-1-4}$), or —S(═O)$_2$-$R^{2-1-5}$;

$R^{2-1-1}$ and $R^{2-1-6}$ are independently hydroxyl, amino, halogen, —CN, $C_1$-$C_6$ alkyl, $C_1$-$C_6$ alkyl substituted with one or more halogen, —$OR^{2-1-1-1}$, or —N($R^{2-1-1-2}$)($R^{2-1-1-3}$); $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ and $R^{2-6}$ are independently $C_1$-$C_6$ alkyl;

$R^{2-4}$ is independently halogen;

$R^{2-7}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen;

scheme 4:

I-1

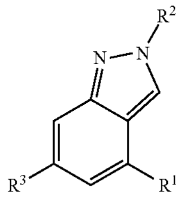

or

I-2

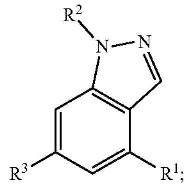

$R^1$ is

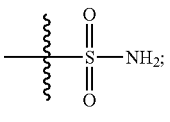 [SMILES: *S(N)(=O)=O]

$R^3$ is

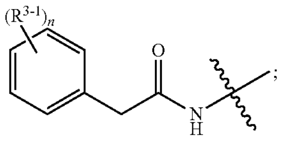

n is 1;

$R^{3-1}$ is halogen;

$R^2$ is $C_1$-$C_{10}$ alkyl, $C_1$-$C_{10}$ alkyl substituted with one $R^{2-1}$, or $C_3$-$C_6$ cycloalkyl;

$R^{2-1}$ is independently halogen, $C_3$-$C_6$ cycloalkyl, phenyl substituted with one or more $R^{2-1-1}$, or —$OR^{2-1-2}$; $R^{2-1-1}$ is independently amino, halogen, —CN, $C_1$-$C_6$ alkyl, $C_1$-$C_6$ alkyl substituted with one or more halogen or —$OR^{2-1-1-1}$; $R^{2-1-1-1}$ is independently $C_1$-$C_6$ alkyl; $R^{2-1-2}$ is $C_1$-$C_6$ alkyl;

scheme 5:

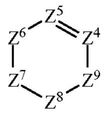

is a benzene ring;

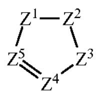

is a "5 membered heteroaryl ring containing 1 or 2 heteroatoms selected from one or more of N, O and S" or a "5 membered heteroalkenyl ring containing 1 or 2 heteroatoms selected from one or more of N, O and S";

$R^1$ is

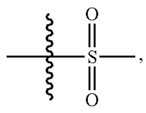

,

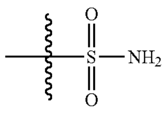

or

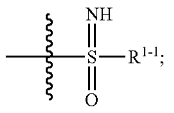

$R^{1-1}$ is $C_1$-$C_6$ alkyl;

$R^3$ is

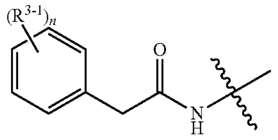

or

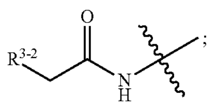

n is 1;

$R^{3-1}$ is halogen, $C_1$-$C_6$ alkyl, $C_1$-$C_6$ alkoxy, $C_3$-$C_6$ cycloalkyl, or $C_1$-$C_6$ alkoxy substituted with $C_1$-$C_6$ alkoxy;

$R^{3-2}$ is $C_3$-$C_6$ cycloalkyl substituted with one or more $R^{3-2-1}$, or "5-6 membered heteroaryl containing 1, 2 or 3 heteroatoms selected from one or more of N, O and S" substituted with one or more $R^{3-2-3}$;

$R^{3-2-1}$ and $R^{3-2-3}$ are independently halogen or hydroxyl;

$R^2$ is halogen, cyano, $C_1$-$C_{10}$ alkyl, $C_1$-$C_{10}$ alkyl substituted with one or more $R^{2-1}$, $C_2$-$C_6$ alkenyl, $C_2$-$C_6$ alkenyl substituted with one or more $R^{2-7}$, $C_3$-$C_6$ cycloalkyl, $C_3$-$C_6$ cycloalkyl substituted with one or more $R^{2-3}$, "5-6 membered heterocycloalkyl containing 1, 2 or 3 heteroatoms selected from one or more of N, O and S", "4 membered heterocycloalkyl containing 1 heteroatom selected from one of N, O and S", "4-6 membered heterocycloalkyl containing 1, 2 or 3 heteroatoms selected from one or more of N, O and S" substituted with one or more $R^{2-6}$, phenyl substituted with one or more $R^{2-4}$, or —(C═O)-$R^{2-2}$;

$R^{2-1}$ is independently hydroxyl, halogen, $C_3$-$C_6$ cycloalkyl, $C_3$-$C_6$ cycloalkyl substituted with one or more $R^{2-1-8}$, "4-6 membered heterocycloalkyl containing 1, 2 or 3 heteroatoms selected from one or more of N, O and S", phenyl substituted with one or more $R^{2-1-1}$, "5-6 membered heteroaryl containing 1, 2 or 3 heteroatoms selected from one or more of N, O and S" substituted with one or more $R^{2-1-6}$, —$OR^{2-1-2}$, —N($R^{2-1-3}$)($R^{2-1-4}$), or —S(═O)$_2$-$R^{2-1-5}$;

$R^{2-1-1}$, $R^{2-1-6}$ and $R^{2-1-8}$ are independently hydroxyl, amino, halogen, —CN, $C_1$-$C_6$ alkyl, $C_1$-$C_6$ alkyl substituted with one or more halogen, —$OR^{2-1-1-1}$, or —N($R^{2-1-1-2}$)($R^{2-1-1-3}$); $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ and $R^{2-6}$ are independently $C_1$-$C_6$ alkyl;

$R^{2-4}$ is independently halogen;

$R^{2-7}$ is independently halogen;

$R^{2-2}$ is $C_1$-$C_6$ alkyl, $C_3$-$C_6$ cycloalkyl, phenyl or phenyl substituted with one or more $R^{2-2-1}$; $R^{2-2-1}$ is independently halogen;

scheme 6:

I-1

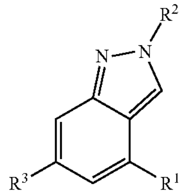

or

I-2

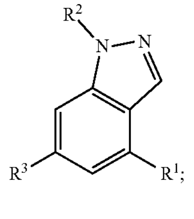

;

$R^1$ is

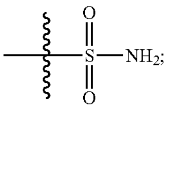 [SMILES: *S(N)(=O)=O]

;

$R^3$ is

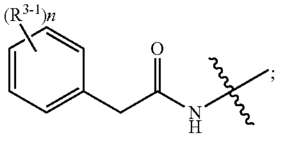

;

n is 1;

$R^{3-1}$ is halogen;

$R^2$ is $C_1$-$C_{10}$ alkyl, $C_1$-$C_{10}$ alkyl substituted with one $R^{2-1}$, or $C_3$-$C_6$ cycloalkyl;

$R^{2-1}$ is independently halogen, $C_3$-$C_6$ cycloalkyl, phenyl substituted with one or more $R^{2-1-1}$, "5-6 membered heteroaryl containing 1, 2 or 3 heteroatoms selected from one or more of N, O and S" substituted with one or more $R^{2-1-6}$, or —$OR^{2-1-2}$; $R^{2-1-1}$ and $R^{2-1-6}$ are independently amino, halogen, —CN, $C_1$-$C_6$ alkyl, $C_1$-$C_6$ alkyl substituted with one or more halogen, or —$OR^{2-1-1-1}$; $R^{2-1-1-1}$ is independently $C_1$-$C_6$ alkyl; $R^{2-1-2}$ is $C_1$-$C_6$ alkyl.

6. The compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof according to claim 1, characterized in that, when

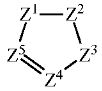

is a "5 membered heteroaryl ring containing 1 or 2 heteroatoms selected from one or more of N, O and S", the "5 membered heteroaryl ring containing 1 or 2 heteroatoms selected from one or more of N, O and S" is a "5 membered heteroaryl ring containing 1 or 2 heteroatoms selected from N"; and/or, when

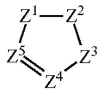

is a "5 membered heteroalkenyl ring containing 1, 2 or 3 heteroatoms selected from one or more of N, O and S", the "5 membered heteroalkenyl ring containing 1, 2 or 3 heteroatoms selected from one or more of N, O and S" is a "5 membered heteroalkenyl ring containing 1 or 2 heteroatoms selected from N";

and/or, when $R^{1-1}$ is $C_1$-$C_6$ alkyl, the $C_1$-$C_6$ alkyl is $C_1$-$C_4$ alkyl;

and/or, when n is 1 or 2, $R^{3-1}$ is independently located in the ortho-, meta-or para-position relative to

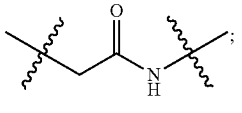 [SMILES: *CC(=O)N*]

;

and/or, when $R^{3-1}$ is independently halogen, the halogen is fluorine, chlorine, bromine or iodine;

and/or, when $R^{3-1}$ is $C_1$-$C_6$ alkyl, the $C_1$-$C_6$ alkyl is $C_1$-$C_4$ alkyl;

and/or, when $R^{3-1}$ is $C_1$-$C_6$ alkoxy, the $C_1$-$C_6$ alkoxy is $C_1$-$C_4$ alkoxy;

and/or, when $R^{3-1}$ is $C_1$-$C_6$ alkoxy substituted with $C_1$-$C_6$ alkoxy, the $C_1$-$C_6$ alkoxy is $C_1$-$C_4$ alkoxy;

and/or, when $R^{3-2}$ is $C_3$-$C_6$ cycloalkyl substituted with one or more $R^{3-2-1}$, the $C_3$-$C_6$ cycloalkyl is cyclopropyl, cyclobutyl, cyclopentyl or cyclohexyl;

and/or, when $R^{3-2-3}$ is halogen, the halogen is fluorine, chlorine, bromine or iodine;

and/or, when $R^{3-2}$ is "5-6 membered heteroaryl containing 1, 2 or 3 heteroatoms selected from one or more of N, O and S" substituted with one or more $R^{3-2-3}$, the "5-6 membered heteroaryl containing 1, 2 or 3 heteroatoms selected from one or more of N, O and S" is "5-6 membered heteroaryl containing 1 or 2 heteroatoms selected from N";

and/or, when $R^2$ is halogen, the halogen is fluorine, chlorine, bromine or iodine;

and/or, when $R^2$ is $C_1$-$C_{10}$ alkyl, the $C_1$-$C_{10}$ alkyl is $C_1$-$C_6$ alkyl;

and/or, when $R^2$ is $C_1$-$C_{10}$ alkyl substituted with one or more $R^{2-1}$, the $C_1$-$C_{10}$ alkyl is $C_1$-$C_6$ alkyl;

and/or, when $R^{2-1}$ is independently halogen, the halogen is fluorine, chlorine, bromine or iodine;

and/or, when $R^{2-1}$ is independently $C_3$-$C_6$ cycloalkyl, the $C_3$-$C_6$ cycloalkyl is cyclopropyl, cyclobutyl, cyclopentyl or cyclohexyl;

and/or, when $R^{2-1}$ is $C_3$-$C_6$ cycloalkyl substituted with one or more $R^{2-1-8}$, the $C_3$-$C_6$ cycloalkyl is cyclopropyl, cyclobutyl, cyclopentyl or cyclohexyl;

and/or, when $R^{2-1}$ is "4-6 membered heterocycloalkyl containing 1, 2 or 3 heteroatoms selected from one or more of N, O and S", the "4-6 membered heterocycloalkyl containing 1, 2 or 3 heteroatoms selected from one or more of N, O and S" is "5 or 6 membered heterocycloalkyl containing 1 or 2 heteroatoms selected from one or more of N, O and S";

and/or, when $R^{2-1}$ is independently "5-6 membered heteroaryl containing 1, 2 or 3 heteroatoms selected from one or more of N, O and S" substituted with one or more $R^{2-1-6}$, the "5-6 membered heteroaryl containing 1, 2 or 3 heteroatoms selected from one or more of N, O and S" is "5-6 membered heteroaryl containing 1 heteroatom selected from one or more of N, O and S";

and/or, $R^{2-1-1}$ is independently located in the ortho-, meta-or para-position relative to phenyl;

and/or, $R^{2-1-6}$ is independently located in the ortho-, meta-or para-position relative to 6 membered heteroaryl;

and/or, $R^{2-1-6}$ is independently located in the ortho-or meta-position relative to 5 membered heteroaryl;

and/or, when $R^{2-1-1}$ is independently halogen, the halogen is fluorine, chlorine, bromine or iodine;

and/or, when $R^{2-1-1}$ is $C_1$-$C_6$ alkyl, the $C_1$-$C_6$ alkyl is $C_1$-$C_4$ alkyl;

and/or, when $R^{2-1-1}$ is $C_1$-$C_6$ alkyl substituted with one or more halogen, the halogen is fluorine, chlorine, bromine or iodine;

and/or, when $R^{2-1-1}$ is $C_1$-$C_6$ alkyl substituted with one or more halogen, the $C_1$-$C_6$ alkyl is $C_1$-$C_4$ alkyl;

and/or, when $R^{2-1-6}$ is independently halogen, the halogen is fluorine, chlorine, bromine or iodine;

and/or, when $R^{2-1-1-1}$, $R^{2-1-1-2}$ and $R^{2-1-1-3}$ are independently $C_1$-$C_6$ alkyl, the $C_1$-$C_6$ alkyl is $C_1$-$C_4$ alkyl;

and/or, when $R^{2-1-2}$ is independently $C_1$-$C_6$ alkyl, the $C_1$-$C_6$ alkyl is $C_1$-$C_4$ alkyl;

and/or, when $R^{2-1-2}$ is independently $C_3$-$C_6$ cycloalkyl, the $C_3$-$C_6$ cycloalkyl is cyclopropyl, cyclobutyl, cyclopentyl or cyclohexyl;

and/or, when $R^{2-1-3}$ and $R^{2-1-4}$ are independently $C_1$-$C_6$ alkyl, the $C_1$-$C_6$ alkyl is $C_1$-$C_4$ alkyl;

and/or, when $R^{2-1-3}$ and $R^{2-1-4}$ are independently $C_3$-$C_6$ cycloalkyl, the $C_3$-$C_6$ cycloalkyl is cyclopropyl, cyclobutyl, cyclopentyl or cyclohexyl;

and/or, when $R^{2-1-5}$ is independently $C_1$-$C_6$ alkyl, the $C_1$-$C_6$ alkyl is $C_1$-$C_4$ alkyl;

and/or, when $R^{2-1-5}$ is independently $C_3$-$C_6$ cycloalkyl, the $C_3$-$C_6$ cycloalkyl is cyclopropyl, cyclobutyl, cyclopentyl or cyclohexyl;

and/or, when $R^2$ is $C_3$-$C_6$ cycloalkyl, the $C_3$-$C_6$ cycloalkyl is cyclopropyl, cyclobutyl, cyclopentyl or cyclohexyl;

and/or, when $R^2$ is $C_3$-$C_6$ cycloalkyl substituted with one or more $R^{2-3}$, the $C_3$-$C_6$ cycloalkyl is cyclopropyl, cyclobutyl, cyclopentyl or cyclohexyl;

and/or, when $R^{2-3}$ is independently $C_1$-$C_6$ alkyl, the $C_1$-$C_6$ alkyl is $C_1$-$C_4$ alkyl;

and/or, when $R^2$ is $C_2$-$C_6$ alkenyl, the $C_2$-$C_6$ alkenyl is $C_2$-$C_4$ alkenyl;

and/or, when $R^2$ is $C_2$-$C_6$ alkenyl substituted with one or more $R^{2-7}$, the $C_2$-$C_6$ alkenyl is $C_2$-$C_4$ alkenyl;

and/or, when $R^{2-7}$ is halogen, the halogen is fluorine, chlorine, bromine or iodine;

and/or, when $R^2$ is "4 membered heterocycloalkyl containing 1 heteroatom selected from one of N, O and S", the "4 membered heterocycloalkyl containing 1 heteroatom selected from one of N, O and S" is oxetanyl;

and/or, when $R^{2-6}$ is $C_1$-$C_6$ alkyl, the $C_1$-$C_6$ alkyl is $C_1$-$C_4$ alkyl;

and/or, when $R^2$ is "4-6 membered heterocycloalkyl containing 1, 2 or 3 heteroatoms selected from one or more of N, O and S" substituted with one or more $R^{2-6}$, the "4-6 membered heterocycloalkyl containing 1, 2 or 3 heteroatoms selected from one or more of N, O and S" is "4-6 membered heterocycloalkyl containing 1 heteroatom selected from one of N, O and S";

and/or, $R^{2-4}$ is independently located in the ortho-, meta-or para-position relative to phenyl;

and/or, when $R^{2-4}$ is independently halogen, the halogen is fluorine, chlorine, bromine or iodine;

and/or, when $R^{2-2}$ is independently $C_1$-$C_6$ alkyl, the $C_1$-$C_6$ alkyl is $C_1$-$C_4$ alkyl;

and/or, when $R^{2-2}$ is $C_3$-$C_6$ cycloalkyl, the $C_3$-$C_6$ cycloalkyl is cyclopropyl, cyclobutyl, cyclopentyl or cyclohexyl;

and/or, $R^{2-2-1}$ is independently located in the ortho-, meta-or para-position relative to phenyl;

and/or, when $R^{2-2-1}$ is independently halogen, the halogen is fluorine, chlorine, bromine or iodine.

7. The compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof according to claim 6, wherein, when

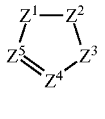

is a “5 membered heteroaryl ring containing 1 or 2 heteroatoms selected from one or more of N, O and S”, the “5 membered heteroaryl ring containing 1 or 2 heteroatoms selected from one or more of N, O and S” is a pyrrole ring, a pyrazole ring or an imidazole ring; and/or, when

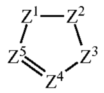

is a “5 membered heteroalkenyl ring containing 1, 2 or 3 heteroatoms selected from one or more of N, O and S”, the “5 membered heteroalkenyl ring containing 1, 2 or 3 heteroatoms selected from one or more of N, O and S” is a 2,5-dihydropyrrole ring;

and/or, when $R^{1-1}$ is $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^{3-1}$ is independently halogen, the halogen is chlorine;

and/or, when n is 1 or 2, $R^{3-1}$ is independently located in the ortho-position relative to

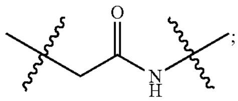 [SMILES: *CC(=O)N*]
;

and/or, when $R^{3-1}$ is $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^{3-1}$ is $C_1$-$C_6$ alkoxy, the $C_1$-$C_6$ alkoxy is methoxy, ethoxy, n-propoxy, isopropoxy, n-butoxy, isobutoxy, sec-butoxy or tert-butoxy;

and/or, when $R^{3-1}$ is $C_1$-$C_6$ alkoxy substituted with $C_1$-$C_6$ alkoxy, the $C_1$-$C_6$ alkoxy is methoxy, ethoxy, n-propoxy, isopropoxy, n-butoxy, isobutoxy, sec-butoxy or tert-butoxy;

and/or, when $R^{3-2}$ is $C_3$-$C_6$ cycloalkyl substituted with one or more $R^{3-2-1}$, the $C_3$-$C_6$ cycloalkyl substituted with one $R^{3-2-1}$ is

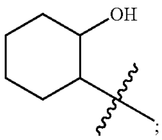 [SMILES: *C1CCCCC1O]
;

and/or, when $R^{3-2-3}$ is halogen, the halogen is chlorine;

and/or, when $R^{3-2}$ is “5-6 membered heteroaryl containing 1, 2 or 3 heteroatoms selected from one or more of N, O and S” substituted with one or more $R^{3-2-3}$, the “5-6 membered heteroaryl containing 1, 2 or 3 heteroatoms selected from one or more of N, O and S” is pyridinyl;

and/or, when $R^2$ is halogen, the halogen is chlorine;

and/or, when $R^2$ is $C_1$-$C_{10}$ alkyl, the $C_1$-$C_{10}$ alkyl is $C_1$-$C_5$ alkyl;

and/or, when $R^2$ is $C_1$-$C_{10}$ alkyl substituted with one or more $R^{2-1}$, the $C_1$-$C_{10}$ alkyl is $C_1$-$C_4$ alkyl;

and/or, when $R^{2-1}$ is independently halogen, the halogen is fluorine;

and/or, when $R^{2-1}$ is “4-6 membered heterocycloalkyl containing 1, 2 or 3 heteroatoms selected from one or more of N, O and S”, the “4-6 membered heterocycloalkyl containing 1, 2 or 3 heteroatoms selected from one or more of N, O and S” is tetrahydrofuranyl, morpholinyl or tetrahydropyranyl;

and/or, when $R^{2-1}$ is independently “5-6 membered heteroaryl containing 1, 2 or 3 heteroatoms selected from one or more of N, O and S” substituted with one or more $R^{2-1-6}$, the “5-6 membered heteroaryl containing 1, 2 or 3 heteroatoms selected from one or more of N, O and S” is pyridinyl;

and/or, when $R^{2-1-1}$ is independently halogen, the halogen is fluorine;

and/or, when $R^{2-1-1}$ is $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^{2-1-1}$ is $C_1$-$C_6$ alkyl substituted with one or more halogen, the halogen is fluorine;

and/or, when $R^{2-1-1}$ is $C_1$-$C_6$ alkyl substituted with one or more halogen, the $C_1$-$C_6$ alkyl is methyl, ethyl, n-propyl, isopropyl, n-butyl, isobutyl, sec-butyl or tert-butyl;

and/or, when $R^{2-1-6}$ is independently halogen, the halogen is fluorine;

and/or, when $R^{2-1-1-1}$, $R^{2-1-1-2}$ and $R^{2-1-1-3}$ are independently $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^{2-1-2}$ is independently $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^{2-1-2}$ is independently $C_3$-$C_6$ cycloalkyl, the $C_3$-$C_6$ cycloalkyl is cyclopropyl;

and/or, when $R^{2-1-3}$ and $R^{2-1-4}$ are independently $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^{2-1-3}$ and $R^{2-1-4}$ are independently $C_3$-$C_6$ cycloalkyl, the $C_3$-$C_6$ cycloalkyl is cyclopropyl;

and/or, when $R^{2-1-5}$ is independently $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^{2-1-5}$ is independently $C_3$-$C_6$ cycloalkyl, the $C_3$-$C_6$ cycloalkyl is cyclopropyl;

and/or, when $R^2$ is $C_3$-$C_6$ cycloalkyl, the $C_3$-$C_6$ cycloalkyl is cyclopropyl;

and/or, when $R^2$ is $C_3$-$C_6$ cycloalkyl substituted with one or more $R^{2-3}$, the $C_3$-$C_6$ cycloalkyl is cyclopropyl;

and/or, when $R^{2-3}$ is independently $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^2$ is $C_2$-$C_6$ alkenyl, the $C_2$-$C_6$ alkenyl is vinyl or propenyl;

and/or, when $R^2$ is $C_2$-$C_6$ alkenyl substituted with one or more $R^{2-7}$, the $C_2$-$C_6$ alkenyl is vinyl or propenyl;

and/or, when $R^{2-7}$ is halogen, the halogen is fluorine;

and/or, when $R^2$ is “4 membered heterocycloalkyl containing 1 heteroatom selected from one of N, O and S”, the “4 membered heterocycloalkyl containing 1 heteroatom selected from one of N, O and S” is oxetan-3-yl;

and/or, when $R^{2-6}$ is $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^2$ is “4-6 membered heterocycloalkyl containing 1, 2 or 3 heteroatoms selected from one or more of N, O and S” substituted with one or more $R^{2-6}$, the "4-6 membered heterocycloalkyl containing 1, 2 or 3 heteroatoms selected from one or more of N, O and S" is oxetan-3-yl;

and/or, when $R^{2-4}$ is independently halogen, the halogen is fluorine or chlorine;

and/or, when $R^{2-2}$ is independently $C_1$-$C_6$ alkyl, the $C_1$-$C_6$ alkyl is methyl, ethyl, n-propyl, isopropyl, n-butyl, isobutyl, sec-butyl or tert-butyl;

and/or, when $R^{2-2}$ is $C_3$-$C_6$ cycloalkyl, the $C_3$-$C_6$ cycloalkyl is cyclopropyl;

and/or, when $R^{2-2-1}$ is independently halogen, the halogen is fluorine.

8. The compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof according to claim 7, characterized in that,

I

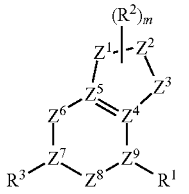

is

I-1

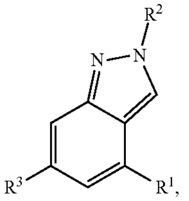

I-2

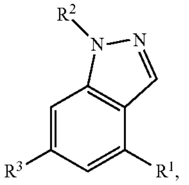

I-3

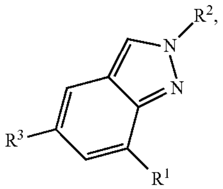

I-4

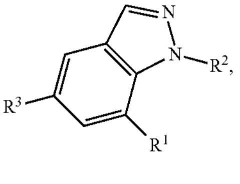

-continued

I-5

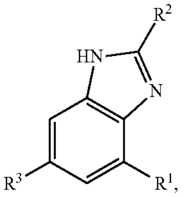

I-6

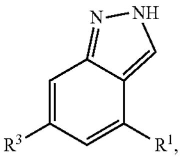

I-7

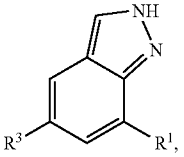

I-8

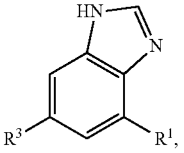

I-9

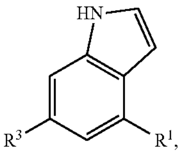

I-10

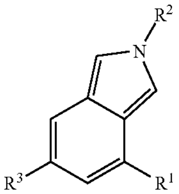

or

I-11

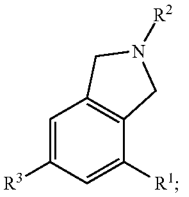

and/or, when $R^{3-1}$ is $C_1$-$C_6$ alkoxy substituted with $C_1$-$C_6$ alkoxy, the $C_1$-$C_6$ alkoxy substituted with $C_1$-$C_6$ alkoxy is

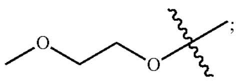 [SMILES: *OCCOC]

and/or, when $R^{3-2}$ is "5-6 membered heteroaryl containing 1, 2 or 3 heteroatoms selected from one or more of N, O and S" substituted with one or more $R^{3-2-3}$, the "5-6 membered heteroaryl containing 1, 2 or 3 heteroatoms selected from one or more of N, O and S" substituted with one $R^{3-2-3}$ is

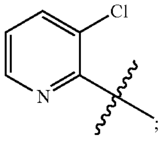 [SMILES: *c1ncccc1Cl];

and/or,

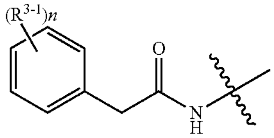

is

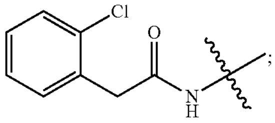 [SMILES: *NC(=O)Cc1ccccc1Cl];

and/or, when $R^2$ is $C_1$-$C_{10}$ alkyl, the $C_1$-$C_{10}$ alkyl is methyl, ethyl, n-propyl, isopropyl, n-butyl, isobutyl, sec-butyl, tert-butyl, n-pentyl, isopentyl or

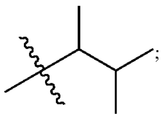 [SMILES: *C(C)C(C)C];

and/or, when $R^2$ is $C_1$-$C_{10}$ alkyl substituted with one or more $R^{2-1}$, the $C_1$-$C_{10}$ alkyl is methyl, ethyl, n-propyl, isopropyl, n-butyl, isobutyl, sec-butyl or tert-butyl;

and/or, when $R^{2-1}$ is "4-6 membered heterocycloalkyl containing 1, 2 or 3 heteroatoms selected from one or more of N, O and S", the "4-6 membered heterocycloalkyl containing 1, 2 or 3 heteroatoms selected from one or more of N, O and S" is tetrahydrofuran-2-yl, tetrahydrofuran-3-yl, morpholin-1-yl or tetrahydropyran-4-yl;

and/or, when $R^{2-1}$ is independently "5-6 membered heteroaryl containing 1, 2 or 3 heteroatoms selected from one or more of N, O and S" substituted with one or more $R^{2-1-6}$, the "5-6 membered heteroaryl containing 1, 2 or 3 heteroatoms selected from one or more of N, O and S" is pyridin-3-yl or pyridin-4-yl;

and/or, when $R^{2-1-1}$ is $C_1$-$C_6$ alkyl, the $C_1$-$C_6$ alkyl is methyl or isopropyl;

and/or, when $R^{2-1-1}$ is $C_1$-$C_6$ alkyl substituted with one or more halogen, the $C_1$-$C_6$ alkyl substituted with a plurality of halogen is trifluoromethyl;

and/or, when $R^{2-1-1-1}$, $R^{2-1-1-2}$ and $R^{2-1-1-3}$ are independently $C_1$-$C_6$ alkyl, the $C_1$-$C_6$ alkyl is methyl;

and/or, when $R^{2-1-2}$ is independently $C_1$-$C_6$ alkyl, the $C_1$-$C_6$ alkyl is methyl or isopropyl;

and/or, when $R^{2-1-3}$ and $R^{2-1-4}$ are independently $C_1$-$C_6$ alkyl, the $C_1$-$C_6$ alkyl is methyl or isopropyl;

and/or, when $R^{2-1-5}$ is independently $C_1$-$C_6$ alkyl, the $C_1$-$C_6$ alkyl is methyl or isopropyl;

and/or, when $R^{2-3}$ is independently $C_1$-$C_6$ alkyl, the $C_1$-$C_6$ alkyl is methyl, ethyl or isopropyl;

and/or, when $R^{2-6}$ is $C_1$-$C_6$ alkyl, the $C_1$-$C_6$ alkyl is methyl;

and/or, when $R^{2-2}$ is independently $C_1$-$C_6$ alkyl, the $C_1$-$C_6$ alkyl is isopropyl.

9. The compound containing a benzene ring represented by formula I, or the pharmaceutically acceptable salt thereof, the stereoisomer thereof, the tautomer thereof, the isotopic compound thereof, the crystalline form thereof, the nitrogen oxide thereof or the solvate thereof, or the solvate of the pharmaceutically acceptable salt thereof according to claim 1, characterized in that, the compound containing a benzene ring represented by formula I is any one of the following compounds:

1

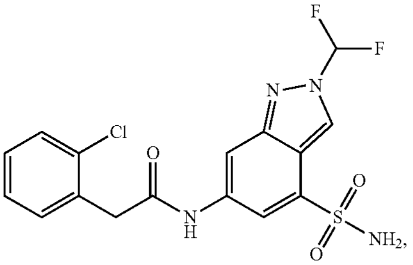

2

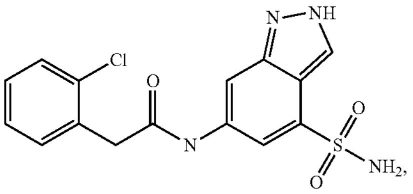

3-A

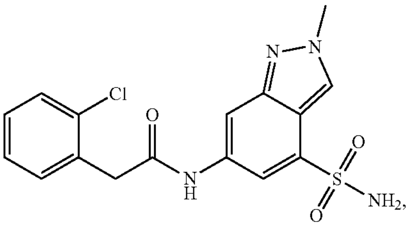

3-B

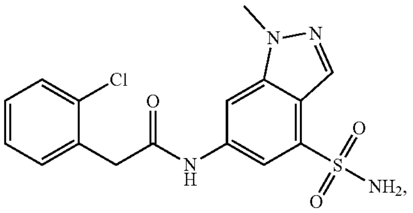

4-A

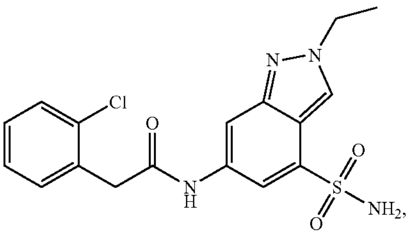

-continued
4-B
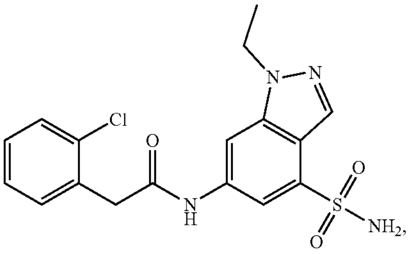
5-A
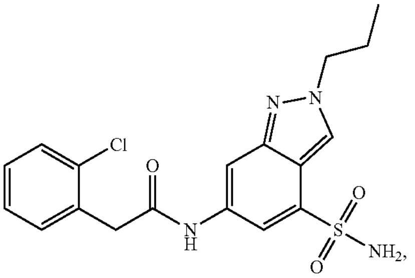
5-B
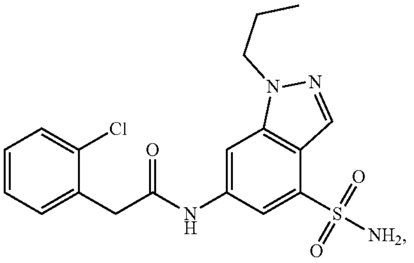
6-A
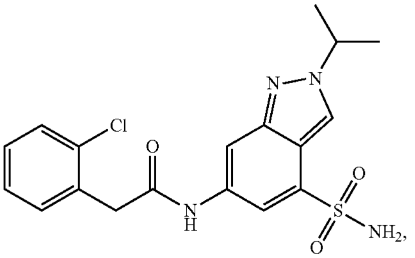
6-B
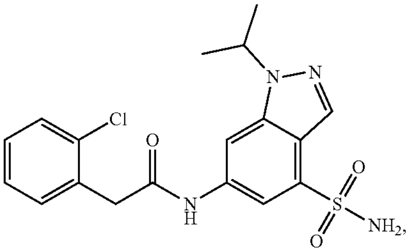
7-A
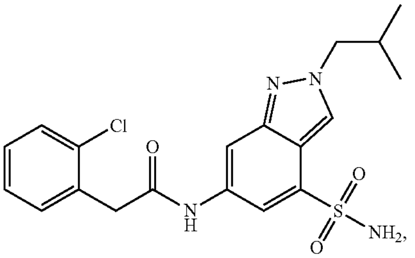
-continued
7-B
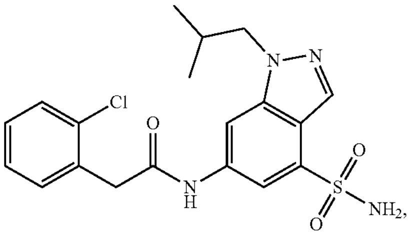
8-A
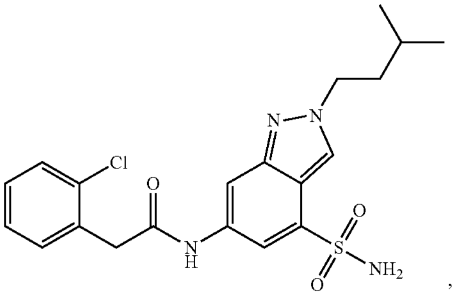
,
8-B
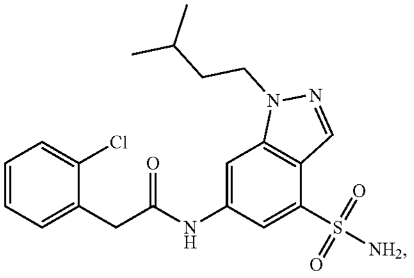
9
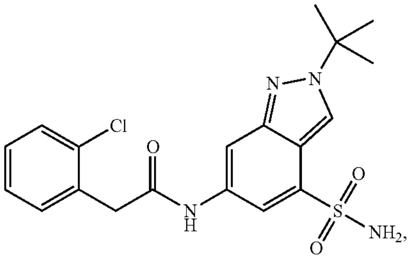
10
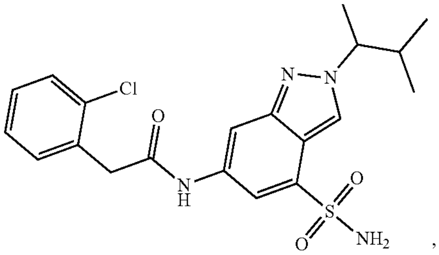
,
11
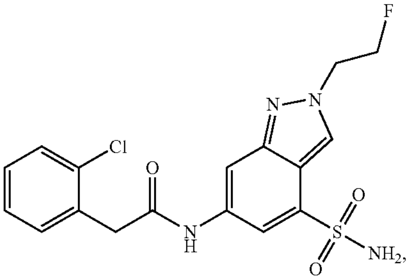

-continued
12-A
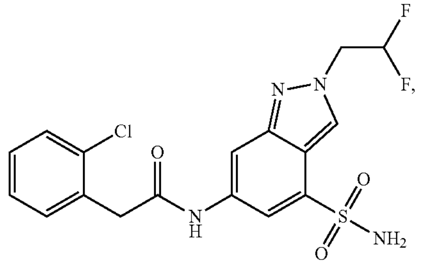
12-B
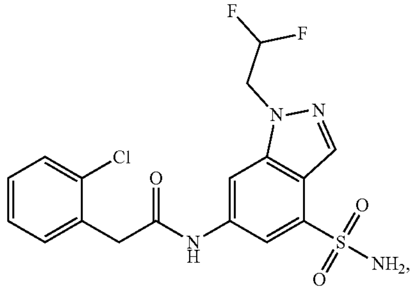
13
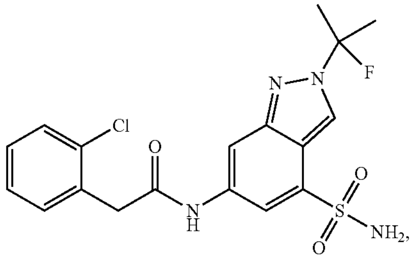
14-A
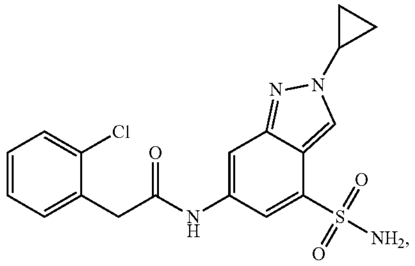
14-B
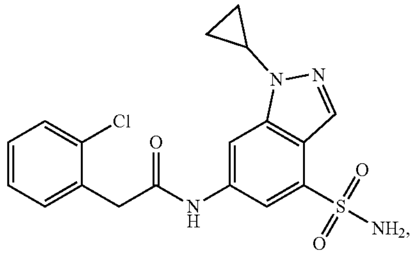
15-A
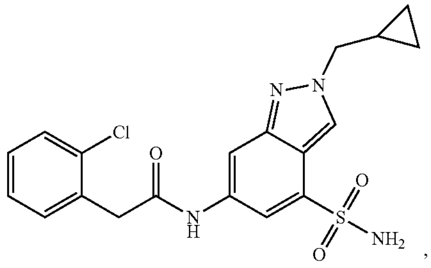
,
-continued
15-B
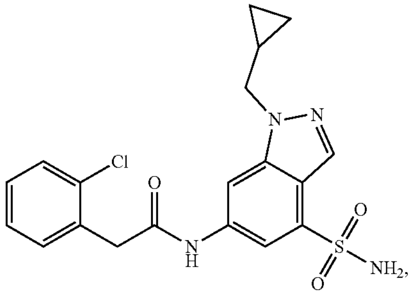
16-A
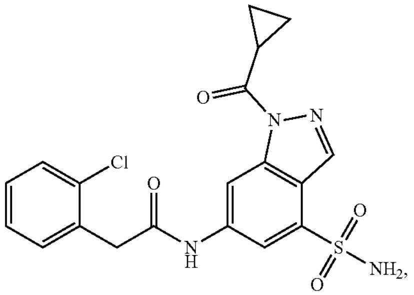
16-B
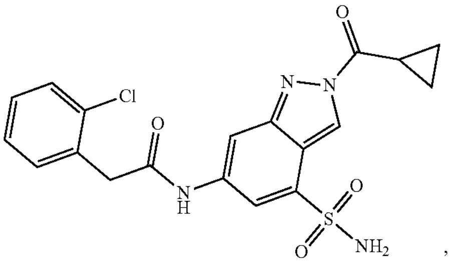
,
17
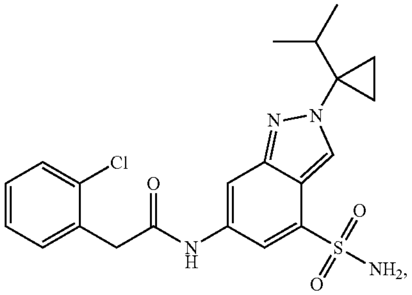
18
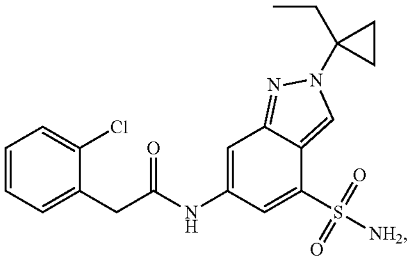

-continued
19
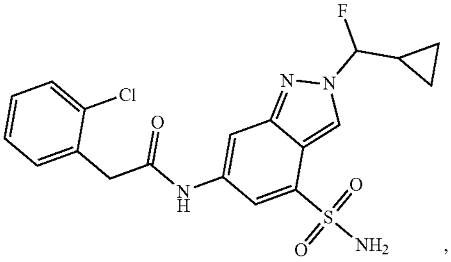
,
20
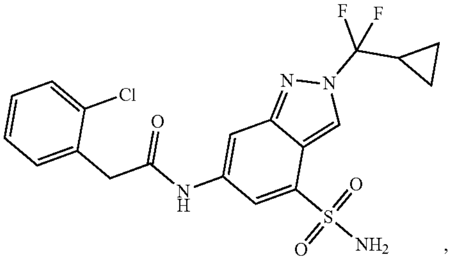
,
21
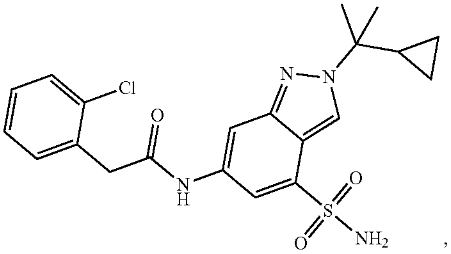
,
22
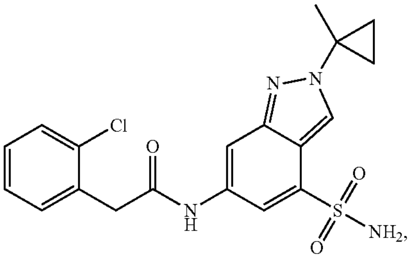
23
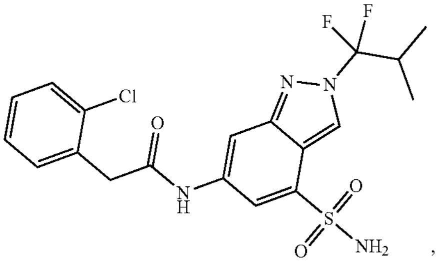
,
24-A
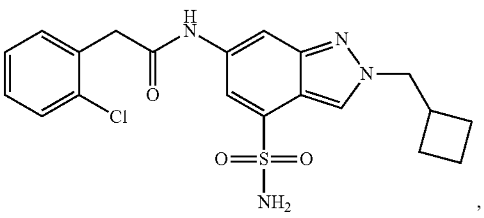
,
-continued
24-B
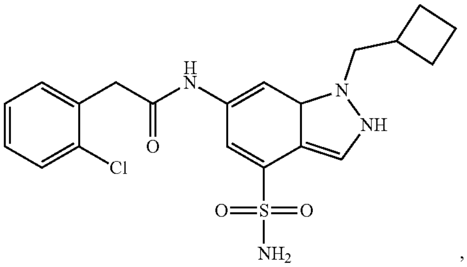
,
25
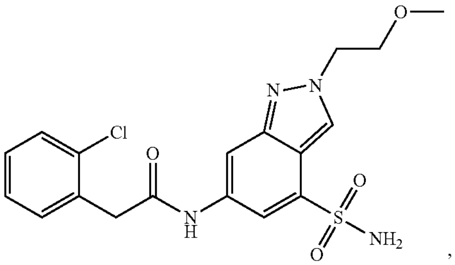
,
25A
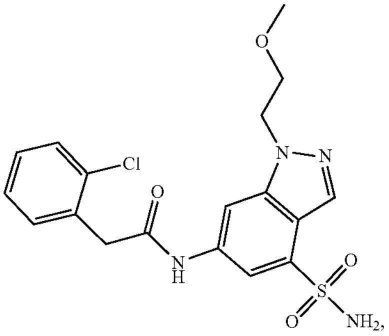
26-A
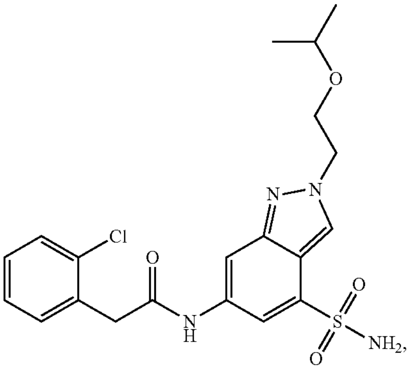
26-B
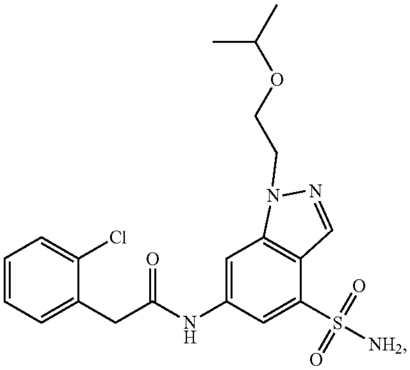

-continued
27-A
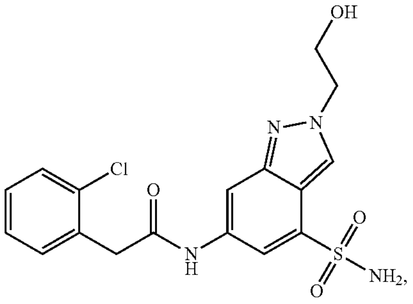
27-B
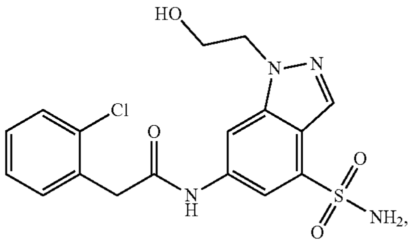
28
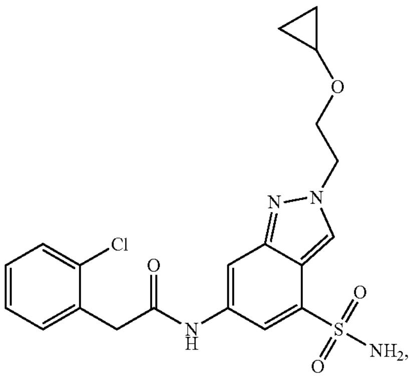
29
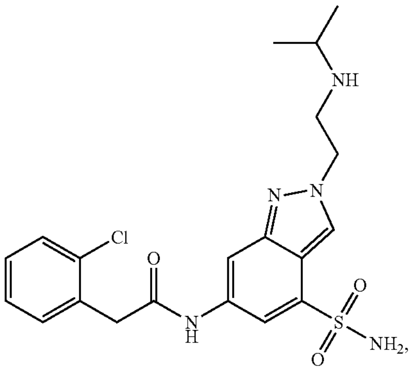
30
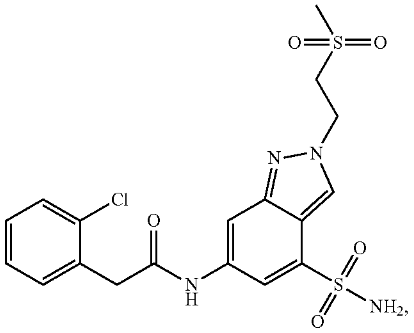
-continued
31-A
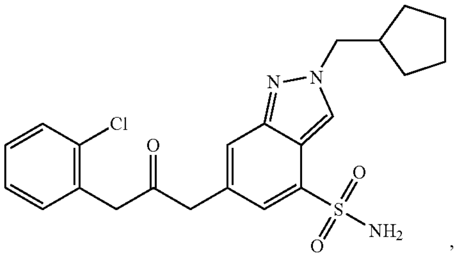
,
31-B
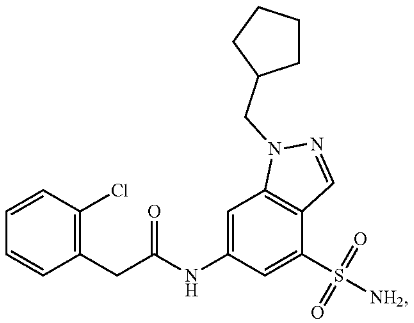
32-A
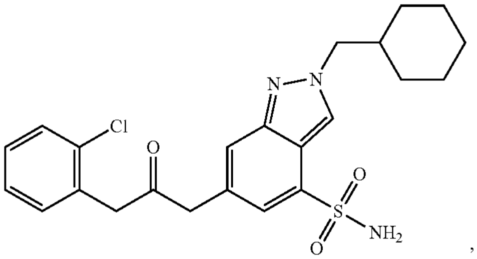
,
32-B
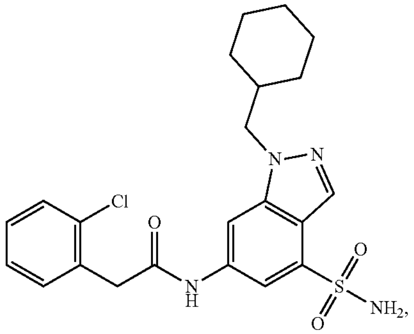
33
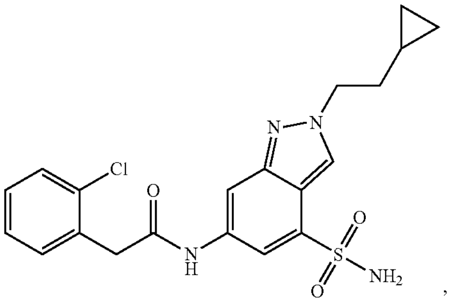
, -continued
34
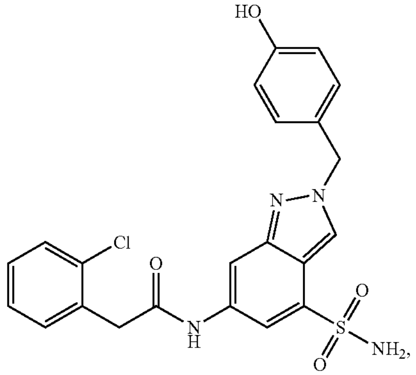
35-A
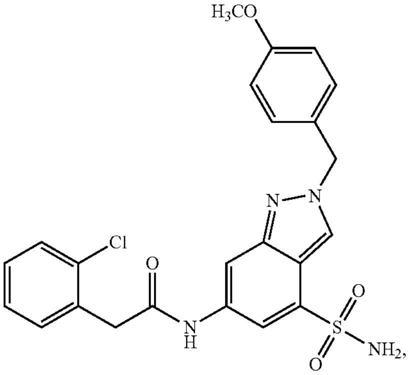
35-B
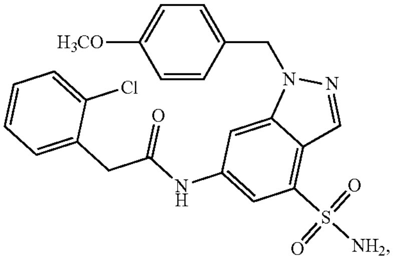
36-A
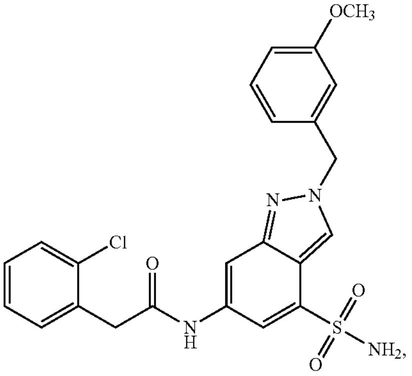
-continued
36-B
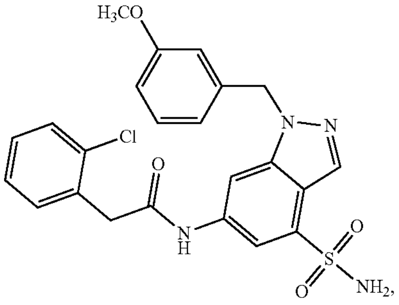
37-A
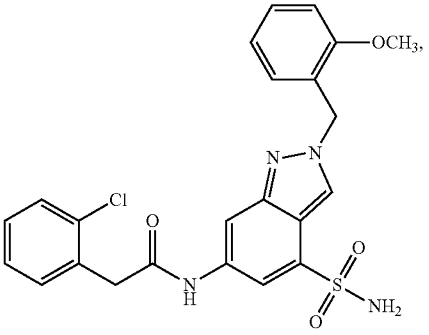
37-B
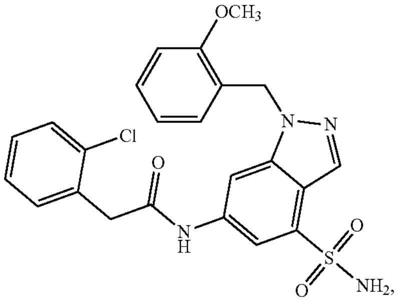
38
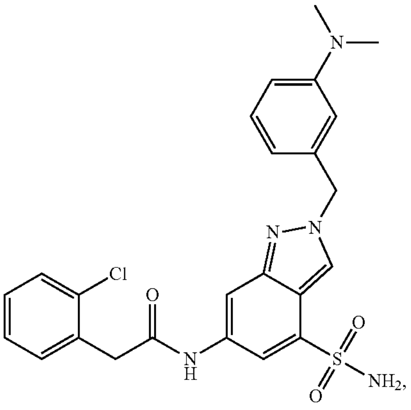

-continued
39
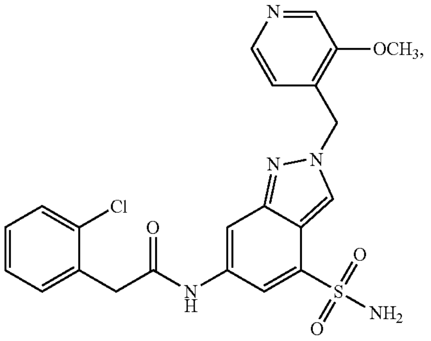
40-A
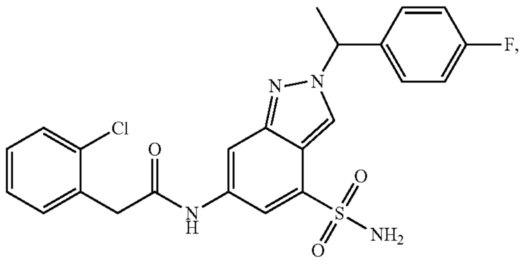
40-B
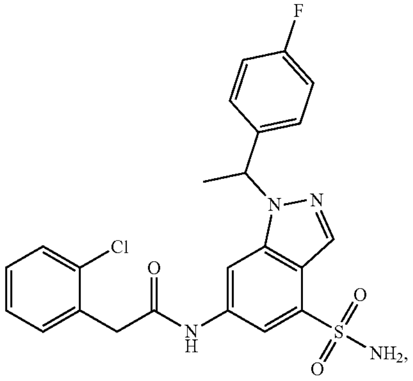
41
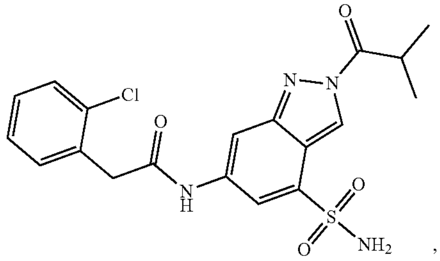
,
-continued
42-A
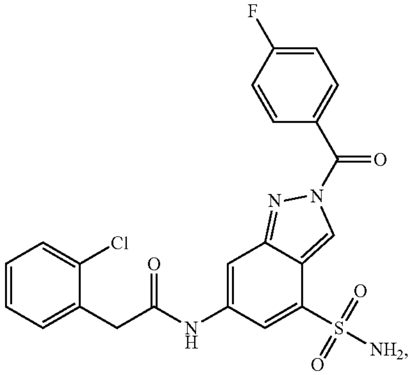
42-B
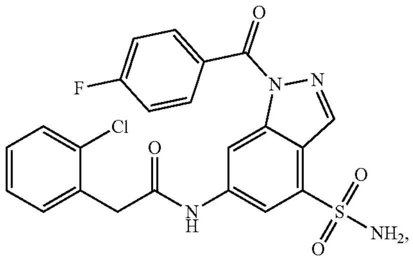
43
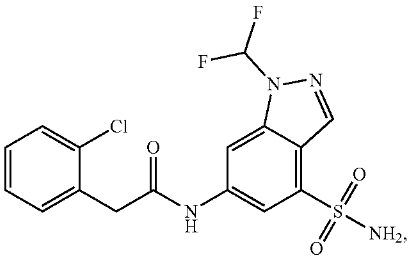
44
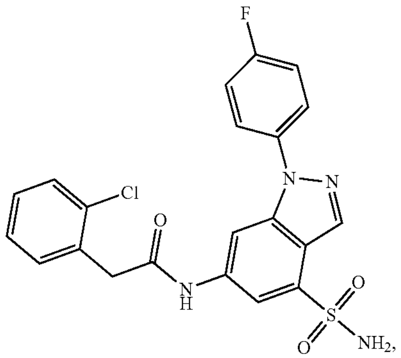
45
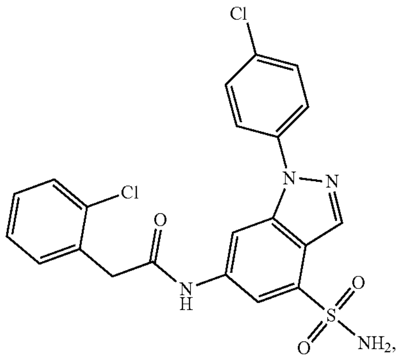

-continued
46
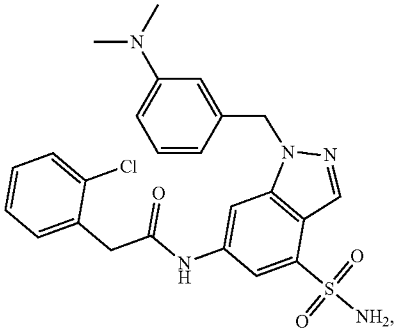
47
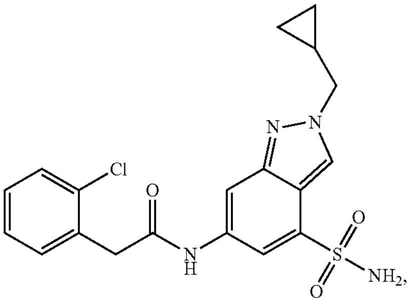
48-A
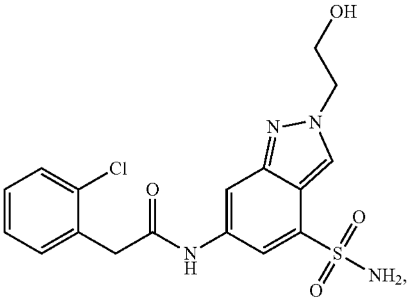
48-B
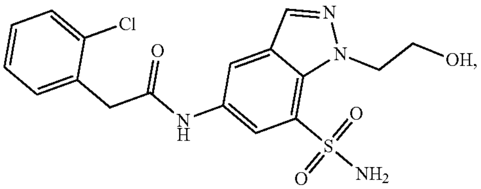
49
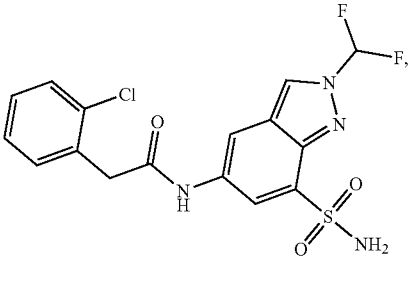
50
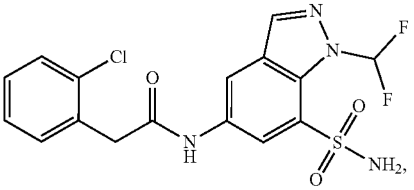
51
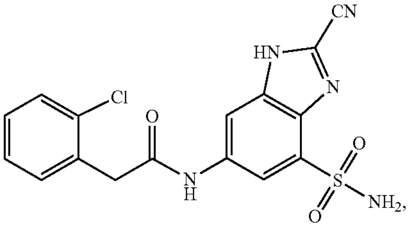
52
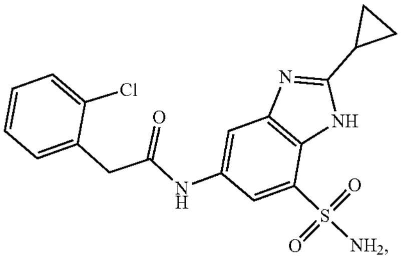
53
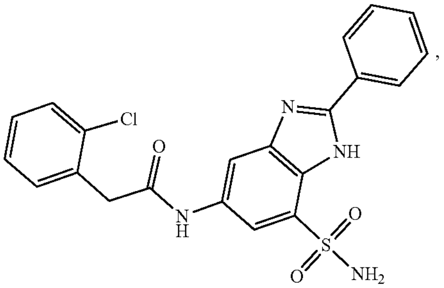
55
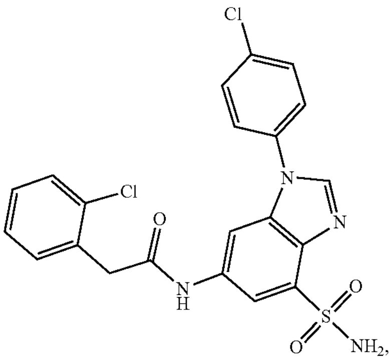

-continued
54
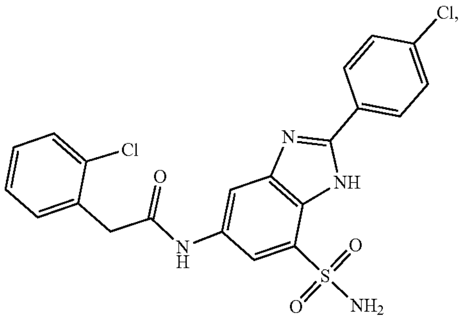
56
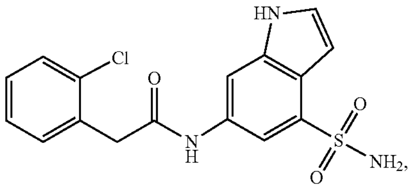
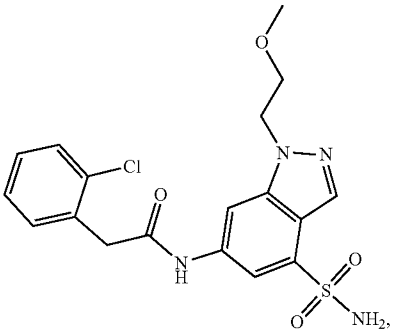
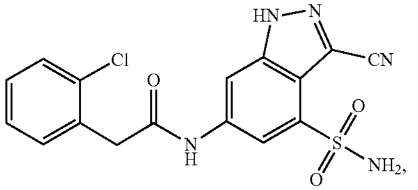
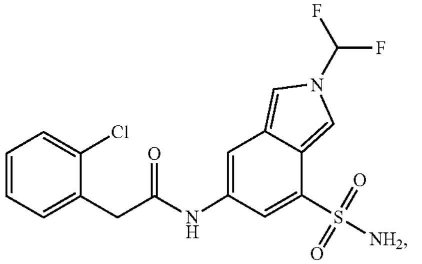
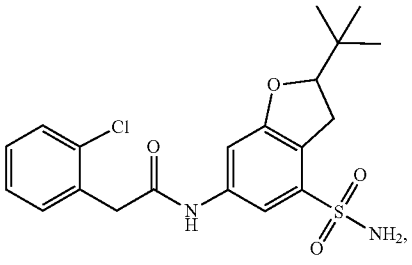
-continued
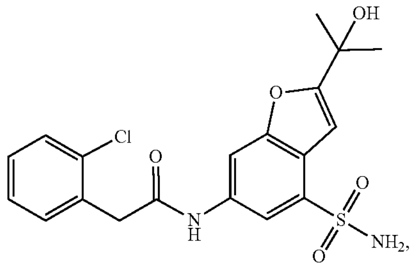
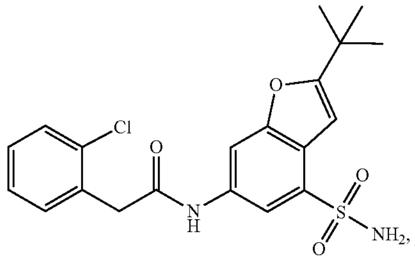
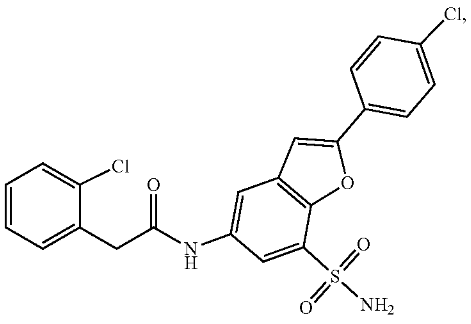
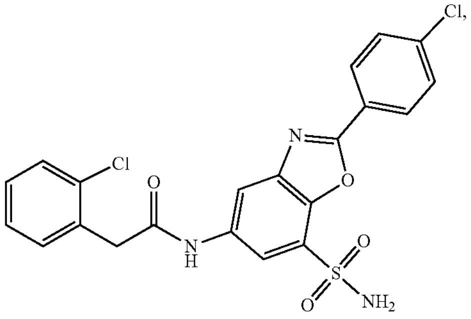
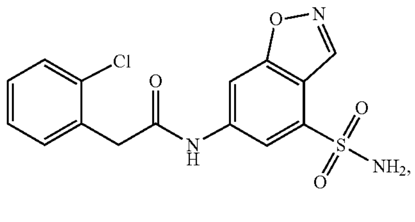
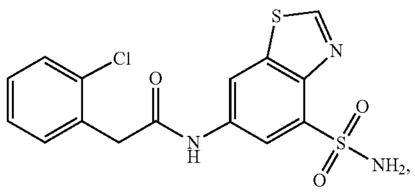

-continued
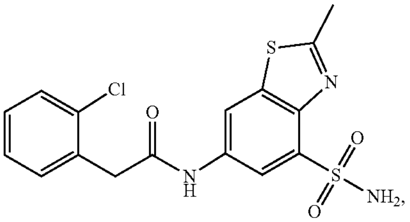
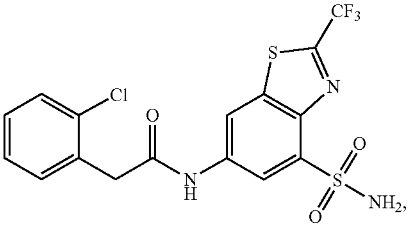
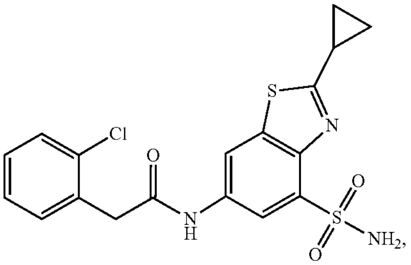
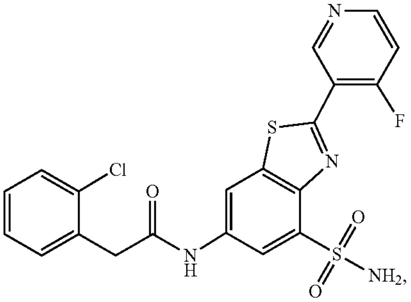
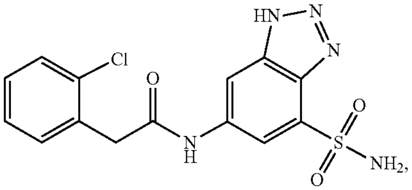
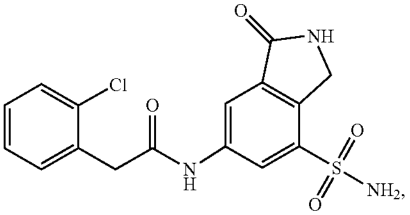
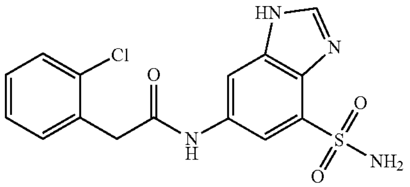
-continued
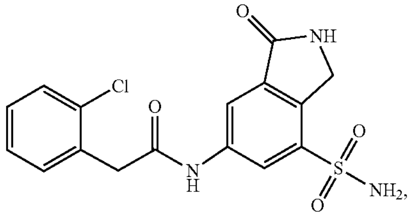
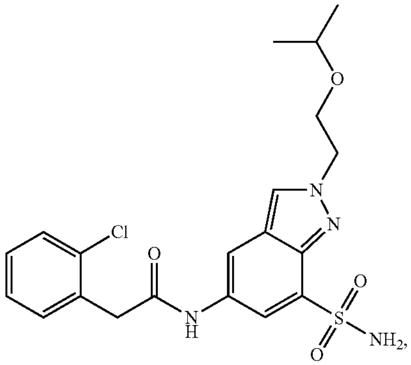
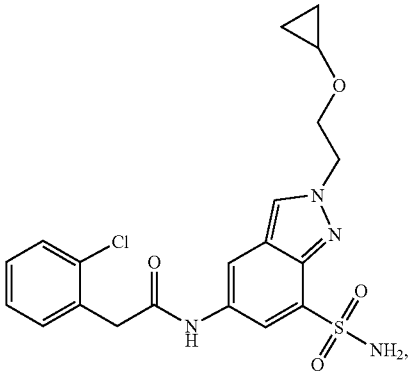
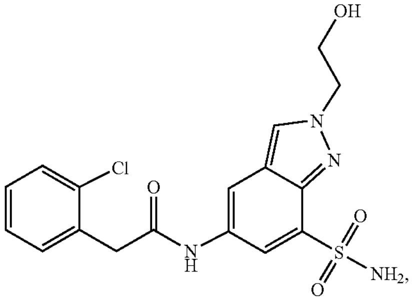
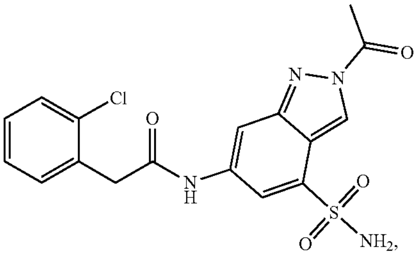

-continued
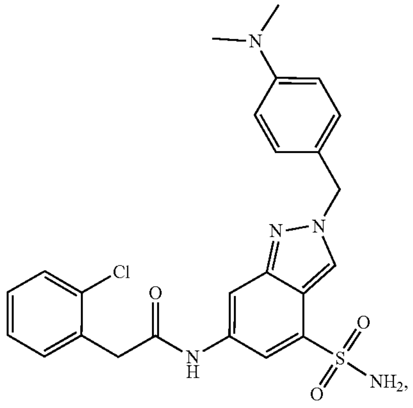
,
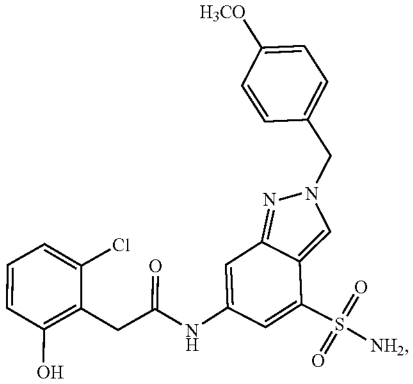
,
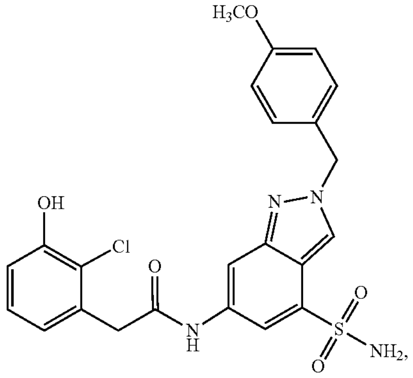
,
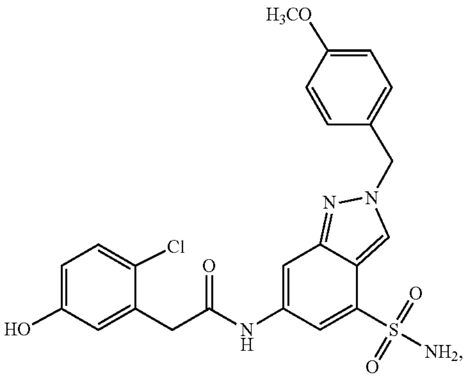
,
-continued
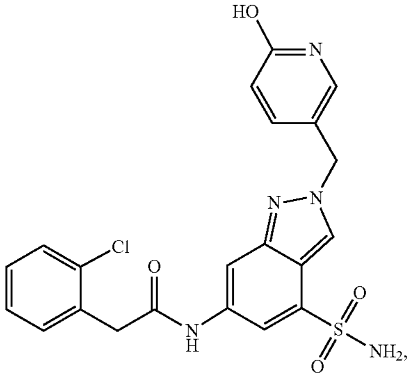
,
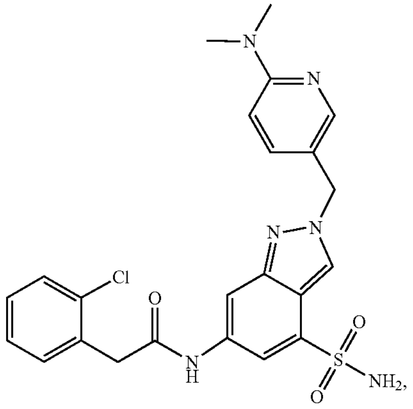
,
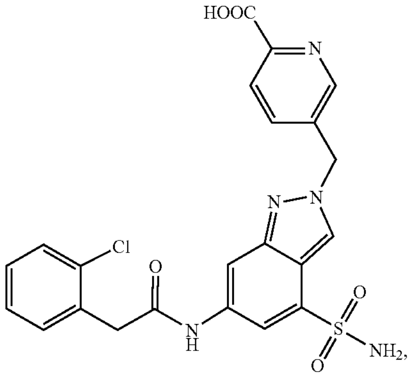
,
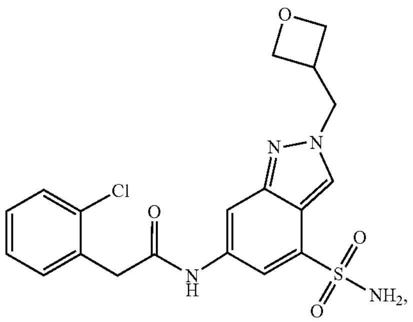
, -continued
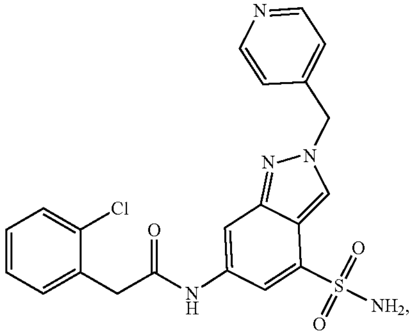
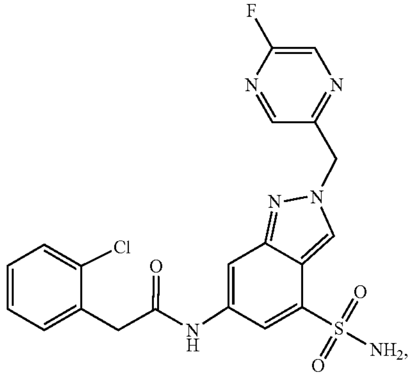
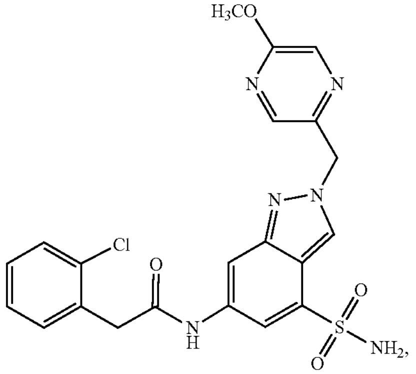
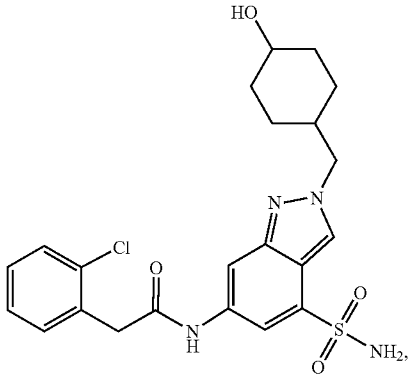
-continued
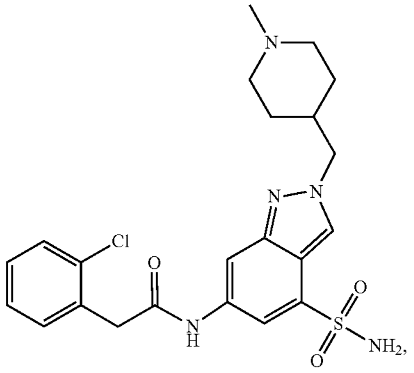
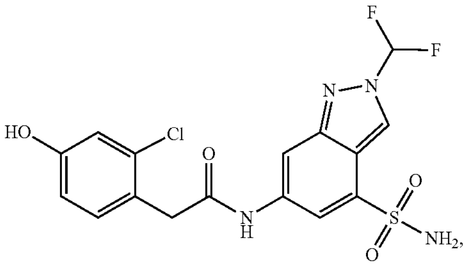
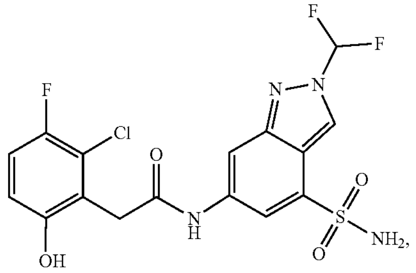
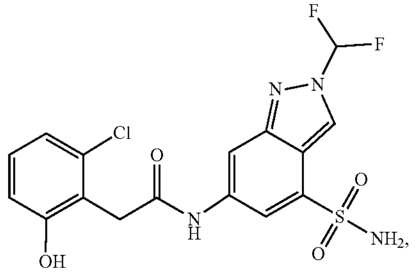
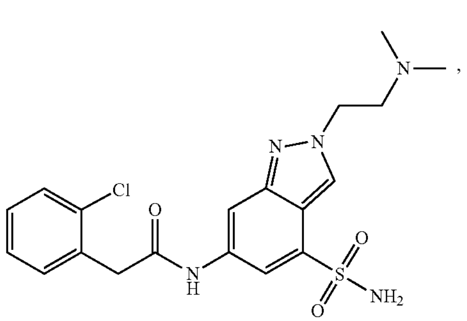

-continued
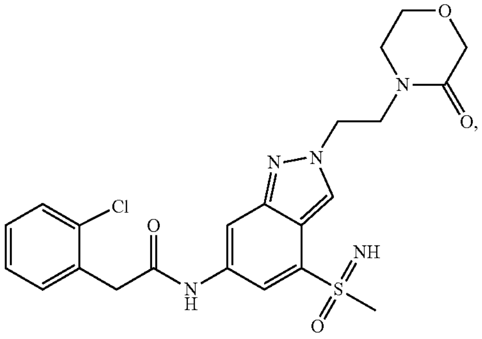
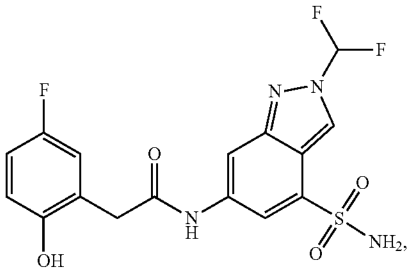
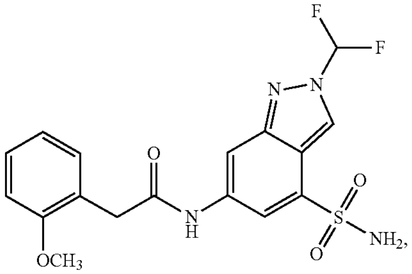
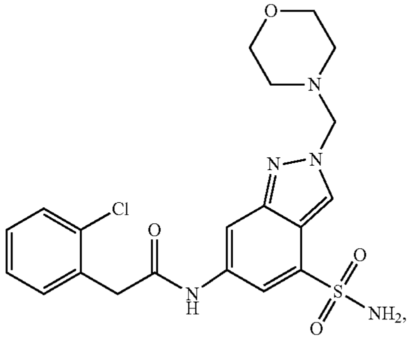
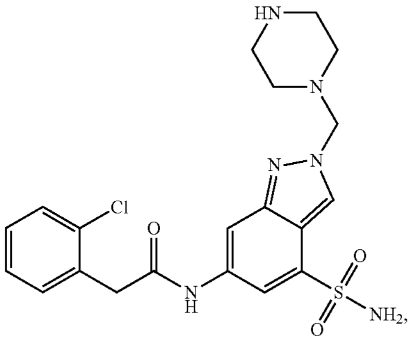
-continued
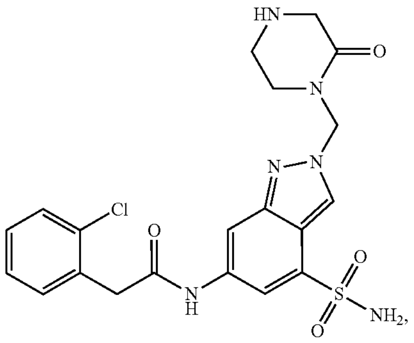
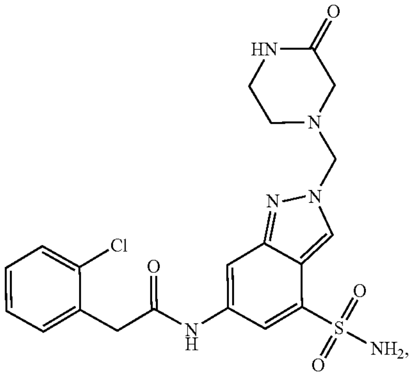
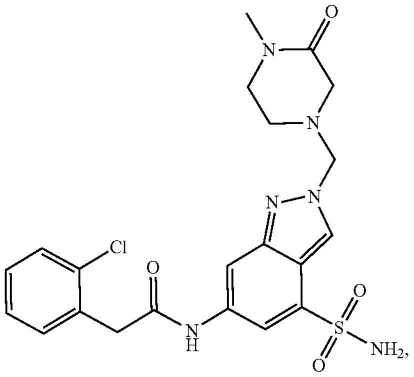
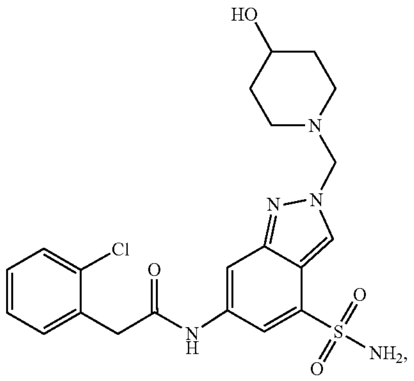

-continued
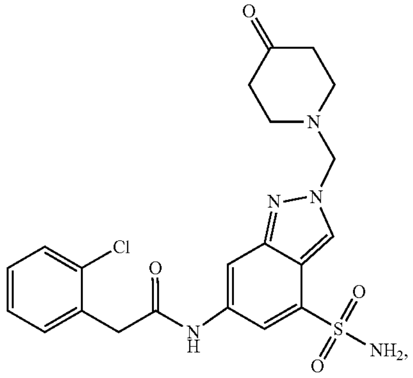
58
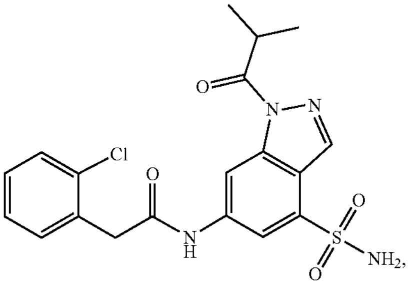
59
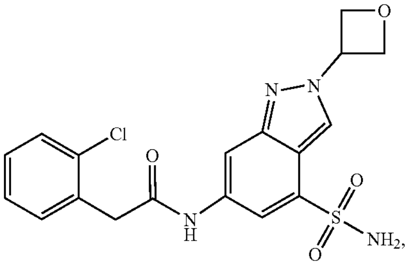
75
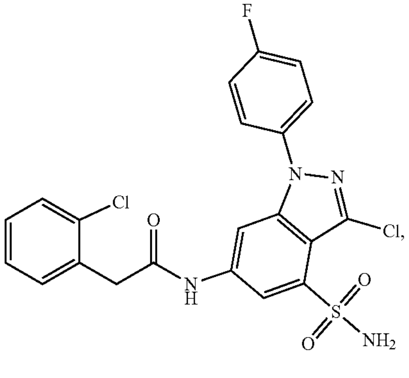
-continued
83
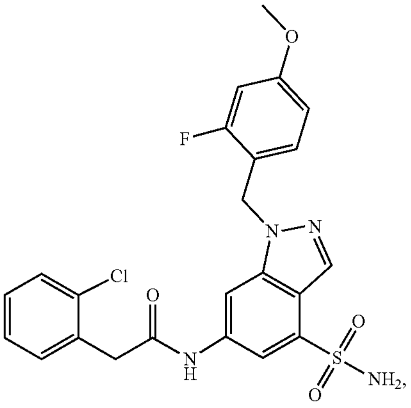
88
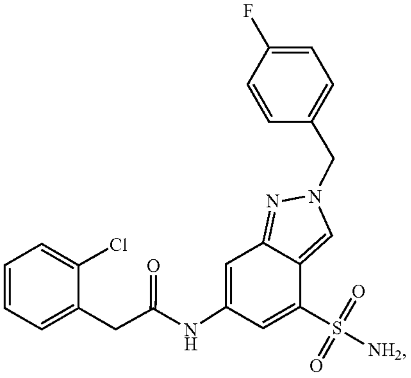
88A
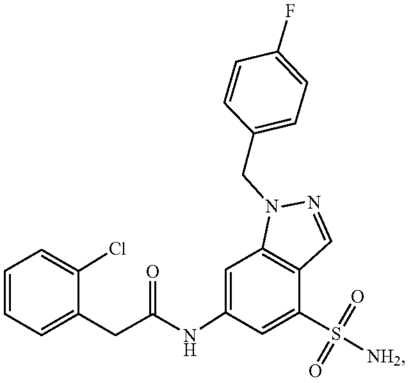
89
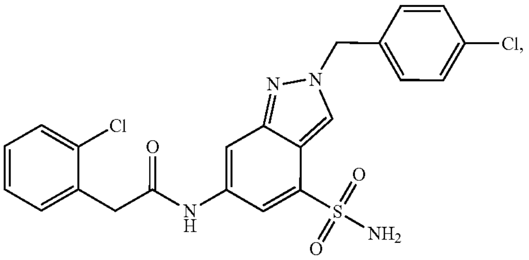

-continued
89A
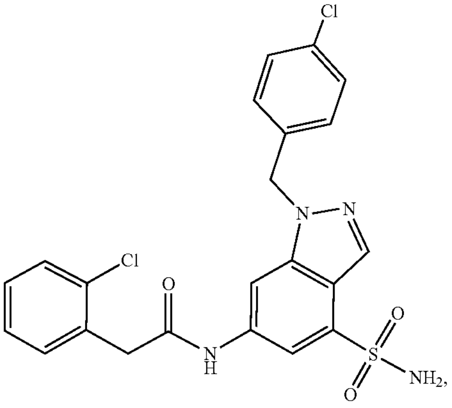
90
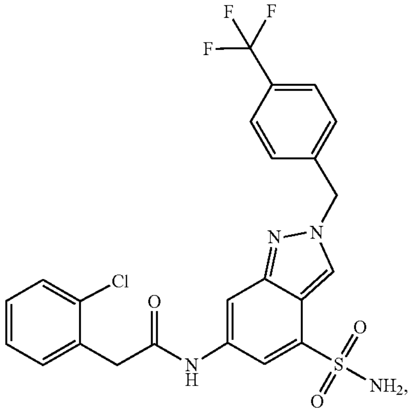
90A
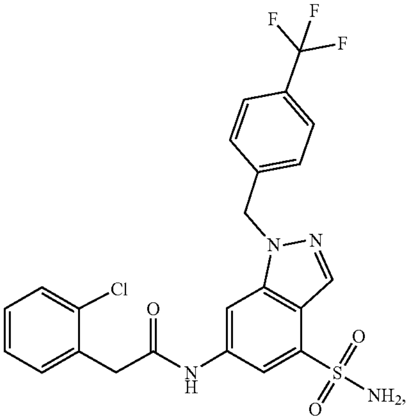
91
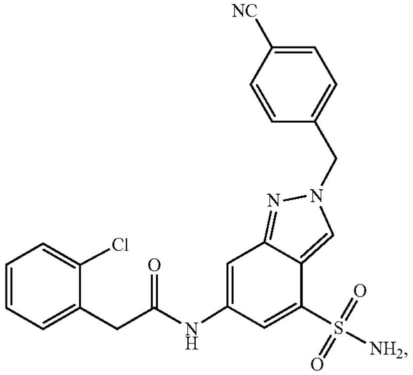
-continued
91A
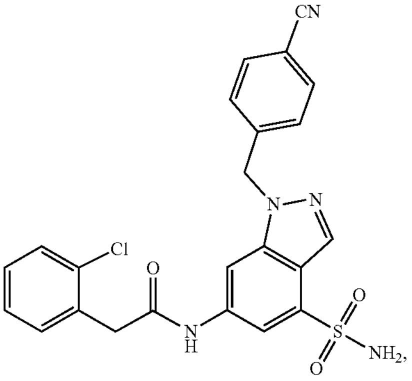
92
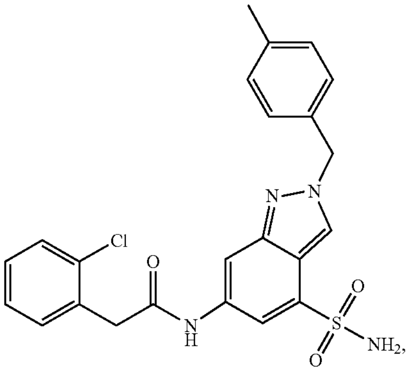
92A
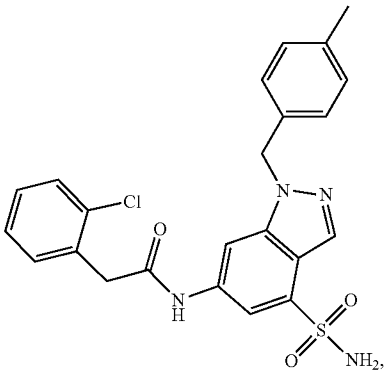
95
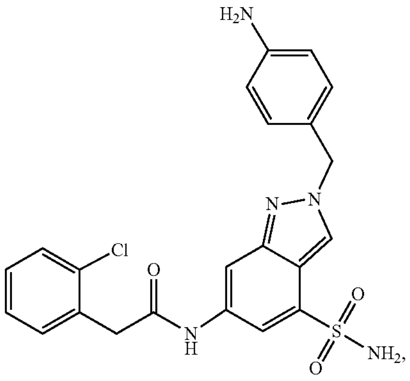

-continued
95A
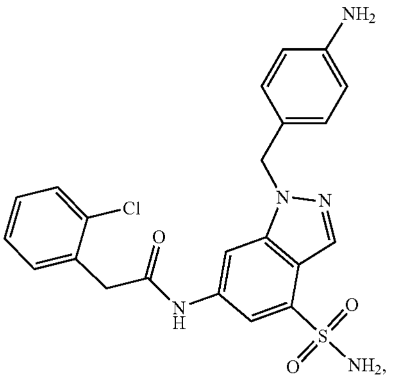
101
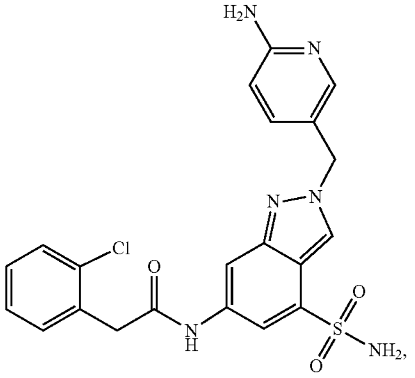
101A
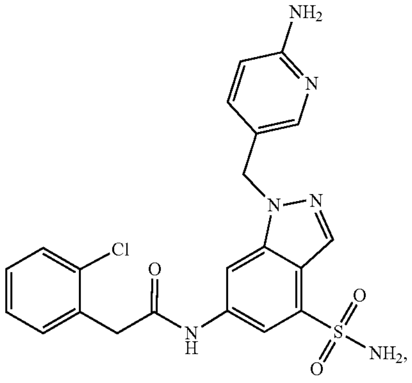
110
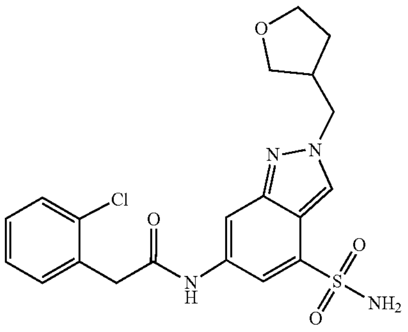
-continued
110A
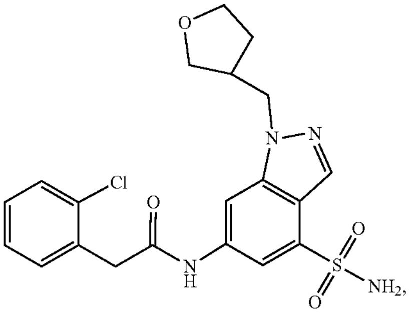
113
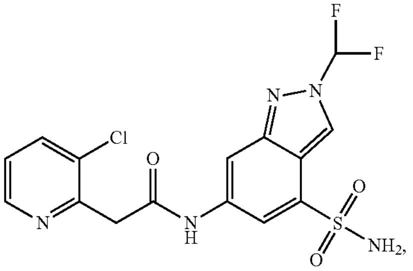
115
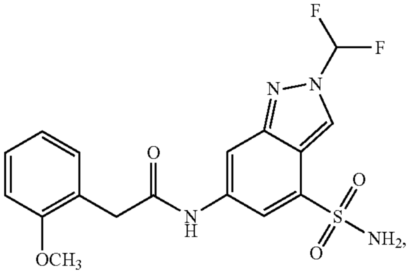
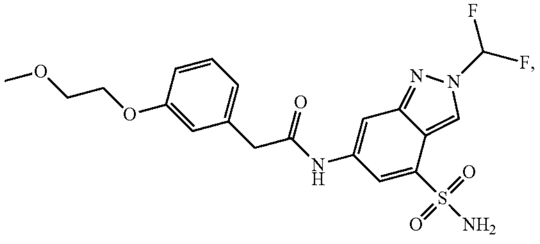
118
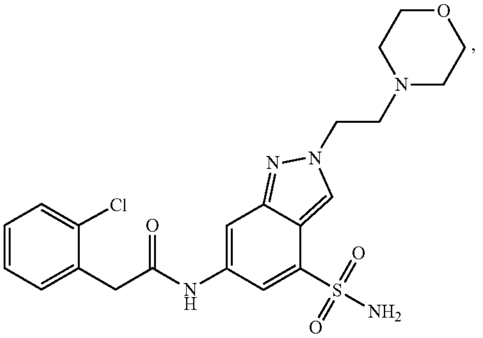

-continued
118A
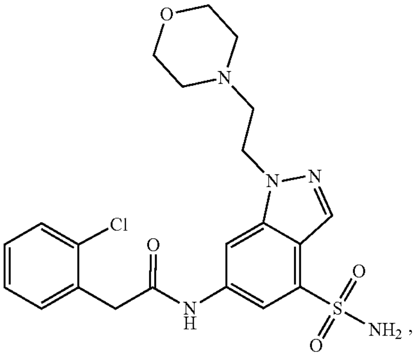
120
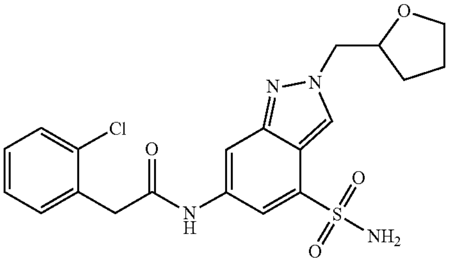
,
120A
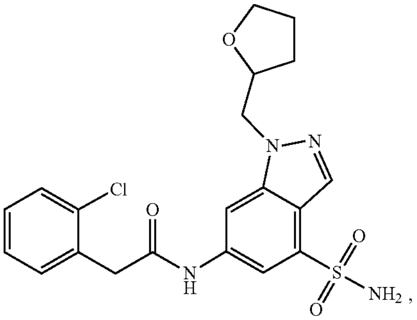
130
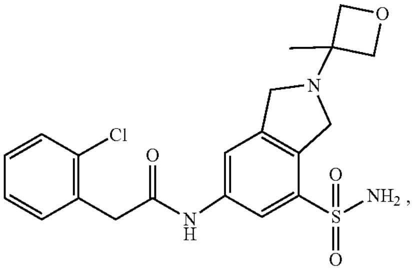
131
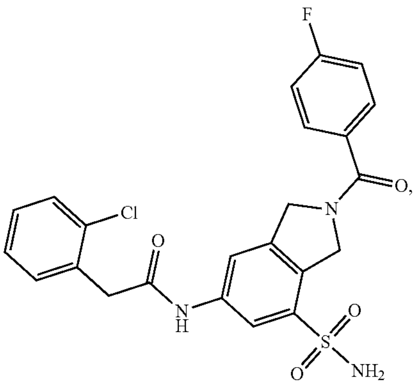
-continued
132
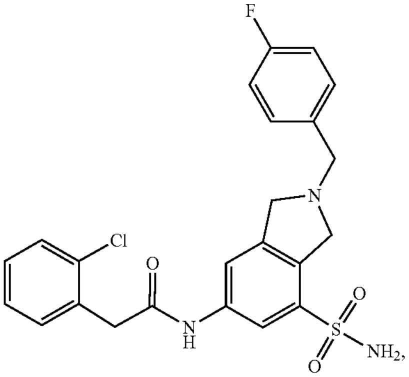
133
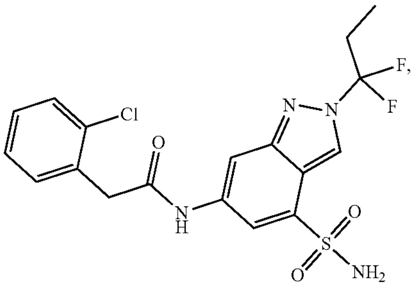
134
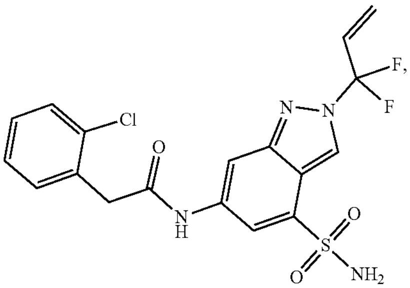
136
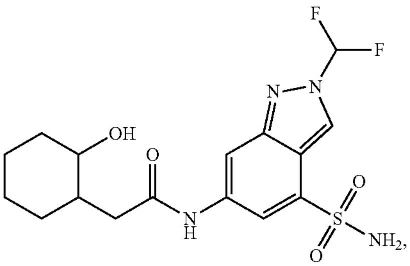
137
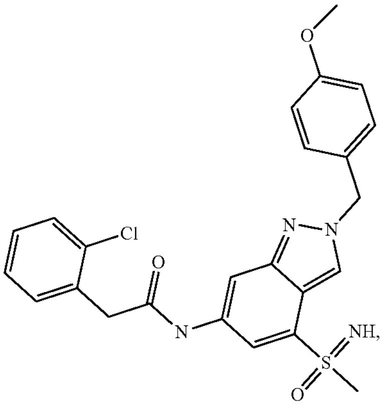

138
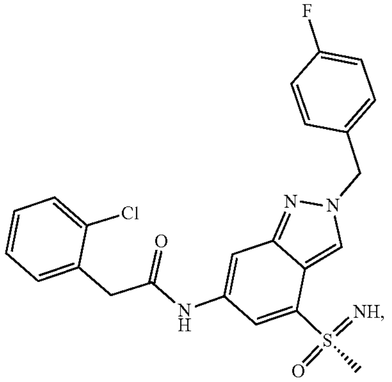
138A
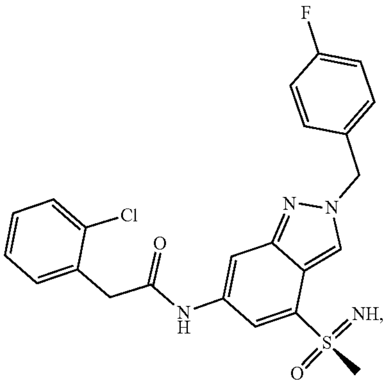
139
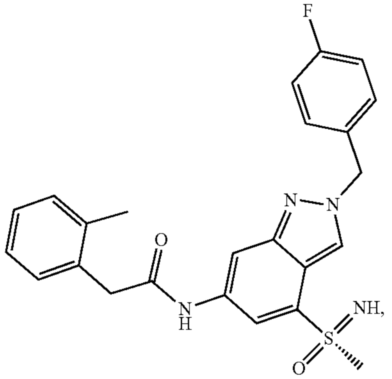
139A
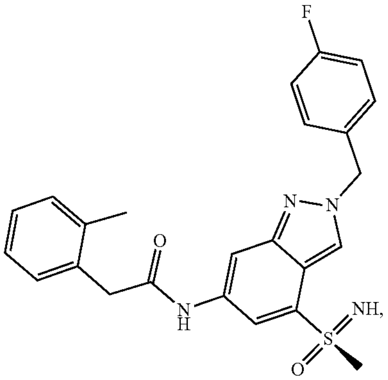
140
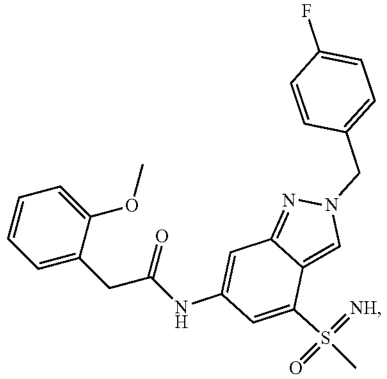
141
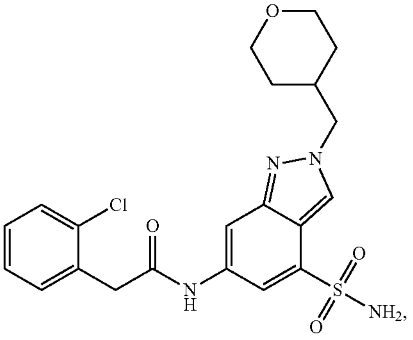
141A
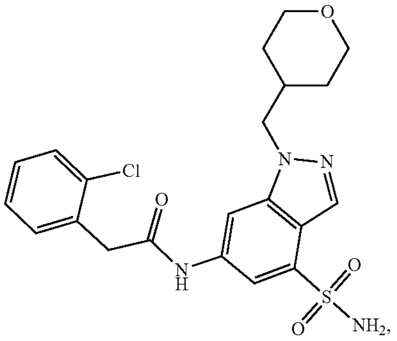
82
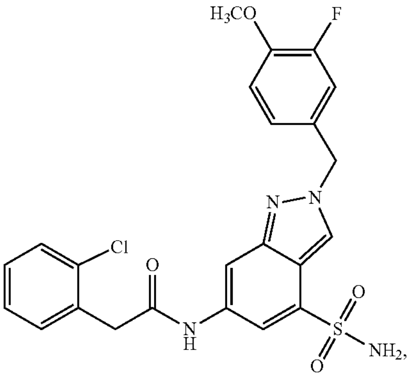

-continued

85

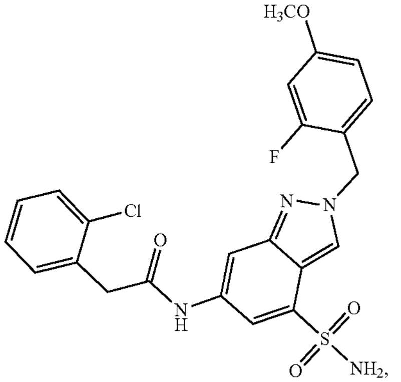

86

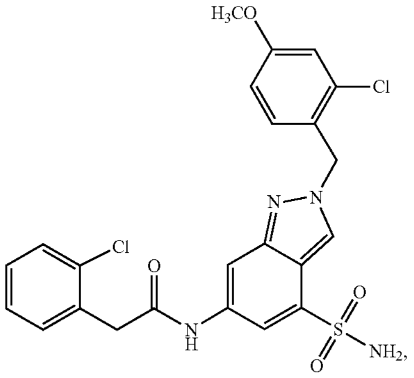

87

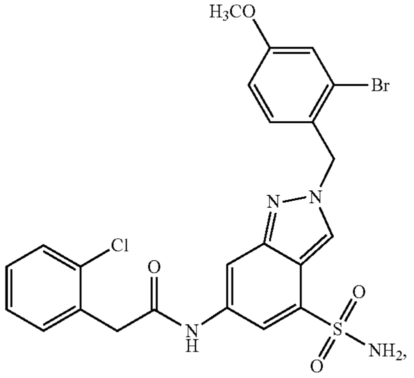

93

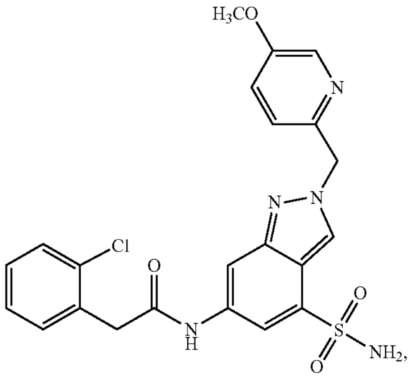

-continued

94

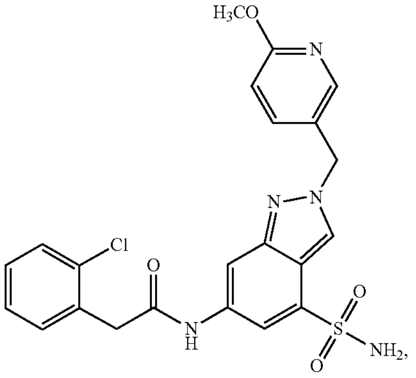

108

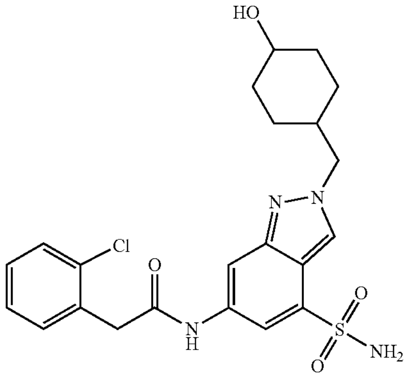

and

135

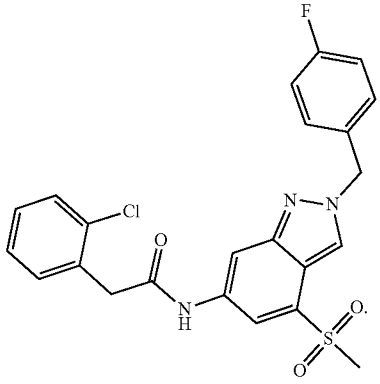

10. A pharmaceutical composition, comprising substance A and at least one pharmaceutically acceptable excipient; wherein substance A is the compound containing a benzene ring represented by formula I, or the pharmaceutically acceptable salt thereof, the stereoisomer thereof, the tautomer thereof, the isotope compound thereof, the crystalline form thereof, the nitrogen oxide thereof or the solvate thereof, or the solvate of the pharmaceutically acceptable salt thereof according to claim 1.

* * * * *